US010513519B2

(12) United States Patent
Chen et al.

(10) Patent No.: US 10,513,519 B2
(45) Date of Patent: Dec. 24, 2019

(54) SOLID FORMS OF (1S,4S)-4-(2-(((3S,4R)-3-FLUOROTETRAHYDRO-2H-PYRAN-4-YL)AMINO)-8-((2,4,6-TRICHLOROPHENYL)AMINO)-9H-PURIN-9-YL)-1-METHYLCYCLOHEXANE-1-CARBOXAMIDE AND METHODS OF THEIR USE

(71) Applicant: Signal Pharmaceuticals, LLC, San Diego, CA (US)

(72) Inventors: Zheng Chen, Westfield, NJ (US); Paul F. Fernandez, Roseland, NJ (US); Tracy L. Gaebele, Green Brook, NJ (US); Lianfeng Huang, Basking Ridge, NJ (US); Matthew J. Jackson, Watchung, NJ (US); Matthew M. Kreilein, Hillsborough, NJ (US); Xiaoling Lu, Whippany, NJ (US); Wenju Wu, Warren, NJ (US); Jean Xu, Warren, NJ (US)

(73) Assignee: Signal Pharmaceuticals, LLC, San Diego, CA (US)

(*) Notice: Subject to any disclaimer, the term of this patent is extended or adjusted under 35 U.S.C. 154(b) by 0 days.

(21) Appl. No.: 16/027,503

(22) Filed: Jul. 5, 2018

(65) Prior Publication Data
US 2018/0362529 A1 Dec. 20, 2018

Related U.S. Application Data

(62) Division of application No. 15/475,836, filed on Mar. 31, 2017, now Pat. No. 10,047,090.

(60) Provisional application No. 62/317,468, filed on Apr. 1, 2016.

(51) Int. Cl.
*C07D 473/32* (2006.01)

(52) U.S. Cl.
CPC ........ *C07D 473/32* (2013.01); *C07B 2200/13* (2013.01)

(58) Field of Classification Search
CPC .................. C07B 2200/13; C07D 473/32
See application file for complete search history.

(56) References Cited

U.S. PATENT DOCUMENTS

| 4,810,643 A | 3/1989 | Souza |
| 4,999,291 A | 3/1991 | Souza |
| 5,229,496 A | 7/1993 | Deeley et al. |
| 5,391,485 A | 2/1995 | Deeley et al. |
| 5,393,870 A | 2/1995 | Deeley et al. |
| 5,580,755 A | 12/1996 | Souza |
| 5,582,823 A | 12/1996 | Souza |
| 5,858,968 A | 1/1999 | Weiner et al. |
| 7,521,446 B2 | 4/2009 | Albers et al. |
| 7,723,340 B2 | 5/2010 | Albers et al. |
| 7,759,342 B2 | 7/2010 | Bennett et al. |
| 8,101,588 B2 | 1/2012 | Albers et al. |
| 8,158,635 B2 | 4/2012 | Beauchamps et al. |
| 8,324,225 B2 | 12/2012 | Brain et al. |
| 8,440,661 B2 | 5/2013 | Bennett et al. |
| 8,491,930 B2 | 7/2013 | Fernandez De Gatta Garcia et al. |
| 8,603,527 B2 | 12/2013 | Bhat et al. |
| 8,680,076 B2 | 3/2014 | Bennett et al. |
| 9,187,479 B2 | 11/2015 | Clareen et al. |
| 9,198,866 B2 | 12/2015 | Bhat et al. |
| 9,512,124 B2 | 12/2016 | Alexander et al. |
| 2009/0312320 A1 | 12/2009 | Albers et al. |
| 2012/0115890 A1 | 5/2012 | Beauchamps et al. |
| 2013/0034495 A1 | 2/2013 | Beauchamps et al. |
| 2013/0191086 A1 | 7/2013 | Temple, III |
| 2014/0093566 A1 | 4/2014 | Bhat et al. |
| 2014/0206697 A1 | 7/2014 | Clareen et al. |
| 2016/0039822 A1 | 2/2016 | Clareen et al. |
| 2017/0042902 A1 | 2/2017 | Alexander et al. |
| 2017/0281633 A1 | 10/2017 | Boylan et al. |

FOREIGN PATENT DOCUMENTS

| WO | WO 1999/015155 A1 | 4/1999 | |
| WO | WO 2006/076595 A1 | 7/2006 | |
| WO | WO 2007/062338 A2 | 5/2007 | |
| WO | WO 2007/127382 A1 | 11/2007 | |
| WO | WO 2008/057252 A2 | 5/2008 | |
| WO | WO 2011/071491 A1 | 6/2011 | |
| WO | WO 2014/172616 A2 | 10/2014 | |
| WO | WO 2015/086505 A1 | 6/2015 | |
| WO | WO 2016/057370 * | 4/2016 | ........... C07D 473/40 |

OTHER PUBLICATIONS

Alcorn et al., "c-Jun N-Terminal Kinase 1 Is Required for the Development of Pulmonary Fibrosis," *Am. J. Respir. Cell Mol. Biol.*, 40:422-432 (2009).
Aljaberi et al., "Functional performance of silicified microcrystalline cellulose versus microcrystalline cellulose: a case study," Drug Development and Industrial Pharmacy 35(9): 1066-1071 (2009).
Bollag et al., "Vemurafenib: the first drug approved for BRAF-mutant cancer," *Nat. Rev. Drug Discov.*, 11(11):873-866 (2012).
Cheson et al., "Revised response criteria for malignant lymphoma," *J. Clin. Oncol.*, 25(9):579-586 (2007).
Corcoran et al., "EGFR-mediated re-activation of MAPK signaling contributes to insensitivity of BRAF mutant colorectal cancers to RAF inhibition with vemurafenib," *Cancer Discov.*, 2(3):227-235 (2012).
Davis, "Signal transduction by the JNK group of MAP kinases," Cell, 203:239-252 (2000).
Durie et al, "International uniform response criteria for multiple myeloma," *Leukemia*, 20:1467-1473 (2006).
Edge et al., "Polysaccharide engineering: Silicified microcrystalline cellulose as a novel high-functionality pharmaceutical material", in: *Polysaccharide Applications: Cosmetics and Pharmaceuticals*, American Chemical Society Symposium Series 737, Chapter 7, pp. 98-112 (1999).
Eisenhauer et al., "New response evaluation criteria in solid tumours: revised RECIST guideline (version 1.1)," *Eur. J. Cancer*, 45(2):228-247 (2009).

(Continued)

*Primary Examiner* — Erich A Leeser
(74) *Attorney, Agent, or Firm* — Jones Day

(57) ABSTRACT

Provided herein are formulations, solid forms and methods of use relating to (1s,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexane-1-carboxamide.

30 Claims, 157 Drawing Sheets

(56) References Cited

OTHER PUBLICATIONS

Emens et al., "Chemotherapy: friend of foe to cancer vaccines," Curr. Opin. Mol. Ther., 3(1):77-84 (2001).
Hallek et al., "Guidelines for the diagnosis and treatment of chronic lymphocytic leukemia: a report from the InternationalWorkshop on Chronic Lymphocytic Leukemia updating the National Cancer Institute—Working Group 1996 guidelines," *Blood*, 111(12):5446-5456 (2008).
Kluwe et al., "Modulation of hepatic fibrosis by c-Jun-N-terminal kinase inhibition," *Gastroenterology*, 138:347-359 (2010).
Lee et al., "Bleomycin induces alveolar epithelial cell death through JNK-dependent activation of the mitochondrial death pathway," *Am. J. Physiol. Lung Cell Mol. Physiol.*, 289:L521-1528 (2005).
Lin et al., "Connective tissue growth factor induces collagen I expression in human lung fibroblasts through the Rac1/MLK3/JNK/AP-1 pathway," *Biochim. Biophys. Acta*, 1833:2823-2833 (2013).
Penichet et al., "Antibody-cytokine fusion proteins for the therapy of cancer," J. Immunol. Methods, 284:91-101 (2001).
Roitt et al., Immunology, Third Edition, Mosby, St. Louis, MO, 17.1-17.12 (1993).
Therasse et al., "New guidelines to evaluate the response to treatment in solid tumors," J. Natl. Cancer Inst., 92(3):205-216 (2000).
Tobyn et al., "Physiochemical comparison between microcrystalline cellulose and silicified microcrystalline cellulose," International Journal of Pharmaceutics 169(2):183-194 (1998).
Wen et al., "Updated response assessment criteria for high-grade gliomas: response assessment in neuro-oncology working group," *J. Clin. Oncol.*, 28(11):1963-1972 (2010).
Wilen et al., "Strategies in optical resolutions," *Tetrahedron*, 33:2725-2736 (1977).
Wilen, Tables of Resolving Agents and Optical Resolutions, (E.L. Eliel, Ed.), University of Notre Dame Press, Notre Dame, IN, p. 268 (1972).
Yoshida et al., "MAP kinase activation and apoptosis in lung tissues from patients with idiopathic pulmonary fibrosis," J. Pathol., 198:388-396 (2002).

* cited by examiner

| | Target % P/Po | Change In Mass (%) - ref | | |
|---|---|---|---|---|
| | | Sorption | Desorption | Hysteresis |
| Cycle 1 | 0.0 | 0.000 | 0.109 | |
| | 10.0 | 0.147 | 3.203 | 3.055 |
| | 20.0 | 0.589 | 3.379 | 2.789 |
| | 30.0 | 3.276 | 3.521 | 0.245 |
| | 40.0 | 3.428 | 3.716 | 0.288 |
| | 50.0 | 3.601 | 4.291 | 0.690 |
| | 60.0 | 3.798 | 4.403 | 0.604 |
| | 70.0 | 4.013 | 4.497 | 0.484 |
| | 80.0 | 4.410 | 4.588 | 0.178 |
| | 90.0 | 4.672 | 4.672 | |

|  | Target | Change In Mass (%) - ref | | |
|---|---|---|---|---|
|  | % P/Po | Sorption | Desorption | Hysteresis |
| Cycle 1 | 0.0 | 0.000 | 0.060 |  |
|  | 10.0 | 1.040 | 1.780 | 0.740 |
|  | 20.0 | 1.738 | 2.846 | 1.108 |
|  | 30.0 | 2.358 | 3.700 | 1.342 |
|  | 40.0 | 2.945 | 4.401 | 1.456 |
|  | 50.0 | 3.574 | 5.041 | 1.468 |
|  | 60.0 | 4.219 | 5.538 | 1.319 |
|  | 70.0 | 4.894 | 6.014 | 1.121 |
|  | 80.0 | 5.576 | 6.379 | 0.804 |
|  | 90.0 | 6.421 | 6.800 | 0.379 |
|  | 95.0 | 6.876 | 6.876 |  |

| | Target | Change In Mass (%) - ref | | |
|---|---|---|---|---|
| | % P/Po | Sorption | Desorption | Hysteresis |
| Cycle 1 | 0.0 | 0.000 | 0.023 | |
| | 10.0 | 0.185 | 0.200 | 0.015 |
| | 20.0 | 0.349 | 0.347 | -0.002 |
| | 30.0 | 0.538 | 0.515 | -0.023 |
| | 40.0 | 0.648 | 0.662 | 0.014 |
| | 50.0 | 0.797 | 0.868 | 0.071 |
| | 60.0 | 0.941 | 1.076 | 0.134 |
| | 70.0 | 1.172 | 1.321 | 0.148 |
| | 80.0 | 1.567 | 1.583 | 0.016 |
| | 90.0 | 2.135 | 2.135 | |

| | Target | Change In Mass (%) - ref | | |
|---|---|---|---|---|
| | % P/Po | Sorption | Desorption | Hysteresis |
| Cycle 1 | 0.0 | 0.001 | -0.197 | |
| | 10.0 | 0.237 | 0.107 | -0.131 |
| | 20.0 | 0.459 | 0.373 | -0.086 |
| | 30.0 | 0.625 | 0.577 | -0.048 |
| | 40.0 | 0.774 | 0.739 | -0.035 |
| | 50.0 | 0.905 | 0.878 | -0.027 |
| | 60.0 | 1.027 | 1.014 | -0.013 |
| | 70.0 | 1.144 | 1.148 | 0.004 |
| | 80.0 | 1.268 | 1.274 | 0.006 |
| | 90.0 | 1.447 | 1.447 | |

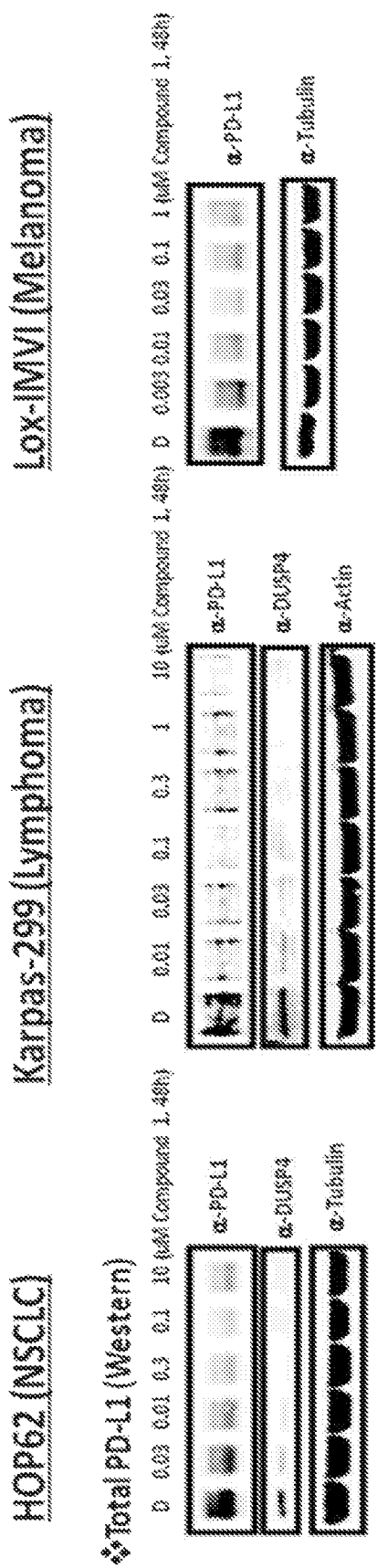
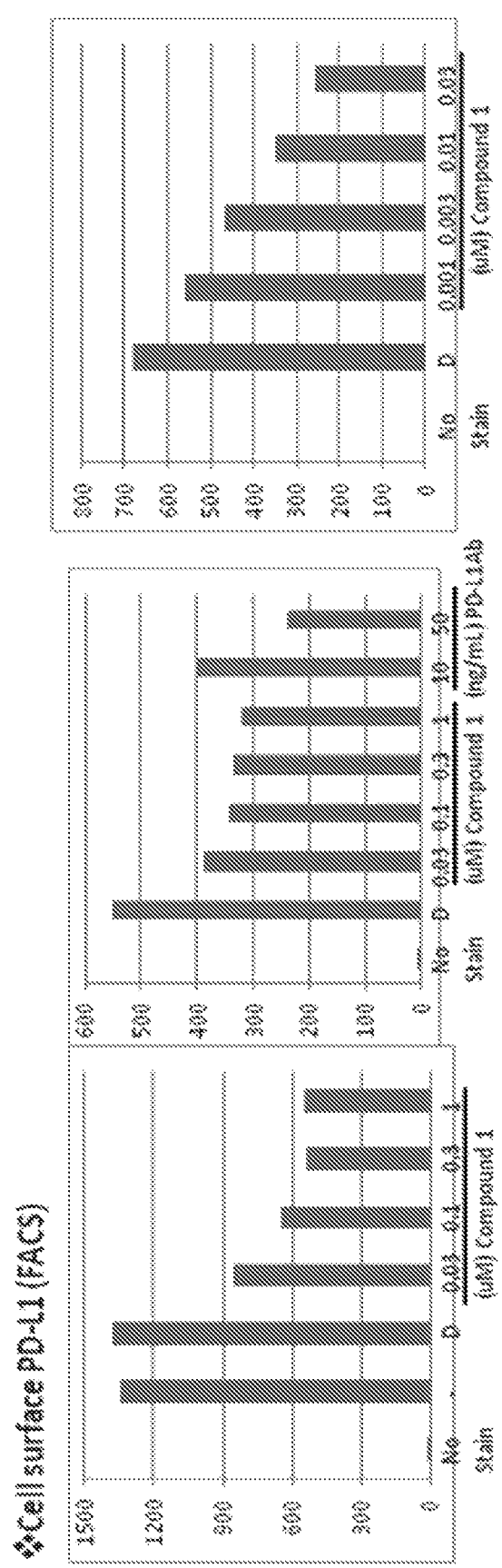
FIG. 191A
FIG. 191B

Human Bronchial Epithelial cell gene expression at 24hrs

SOLID FORMS OF (1S,4S)-4-(2-(((3S,4R)-3-FLUOROTETRAHYDRO-2H-PYRAN-4-YL)AMINO)-8-((2,4,6-TRICHLOROPHENYL)AMINO)-9H-PURIN-9-YL)-1-METHYLCYCLOHEXANE-1-CARBOXAMIDE AND METHODS OF THEIR USE

CROSS-REFERENCE TO RELATED APPLICATIONS

This application is a divisional of U.S. patent application Ser. No. 15/475,836, filed Mar. 31, 2017, currently allowed, which claims priority to U.S. Provisional Patent Application No. 62/317,468, filed Apr. 1, 2016, each of which is incorporated herein by reference in its entirety and for all purposes.

FIELD

Provided herein are solid forms of cis-4-[2-{[(3S,4R)-3-fluorooxan-4-yl]amino}-8-(2,4,6-trichloroanilino)-9H-purin-9-yl]-1-methylcyclohexane-1-carboxamide, alternatively named (1s,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexane-1-carboxamide, and methods of their use for the treatment of cancer.

BACKGROUND

The identification and selection of a solid form of a pharmaceutical compound are complex, given that a change in solid form may affect a variety of physical and chemical properties, which may provide benefits or drawbacks in processing, formulation, stability, bioavailability, storage, handling (e.g., shipping), among other important pharmaceutical characteristics. Useful pharmaceutical solids include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Whether crystalline or amorphous, solid forms of a pharmaceutical compound include single-component and multiple-component solids. Single-component solids consist essentially of the pharmaceutical compound or active ingredient in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., *Solid State Chemistry of Drugs*, (1999) SSCI, West Lafayette). The importance of discovering polymorphs was underscored by the case of Ritonavir™, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (see S. R. Chemburkar et al., *Org. Process Res. Dev.*, (2000) 4:413-417).

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*:3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable and marketable pharmaceutical product.

The connection between abnormal protein phosphorylation and the cause or consequence of diseases has been known for over 20 years. Accordingly, protein kinases have become a very important group of drug targets. (See Cohen, *Nature*, 1:309-315 (2002), Gaestel et al. *Curr. Med. Chem.*14: 2214-223 (2007); Grimminger et al. *Nat. Rev. Drug Disc.* 9(12):956-970 (2010)). Various protein kinase inhibitors have been used clinically in the treatment of a wide variety of diseases, such as cancer and chronic inflammatory diseases, including rheumatoid arthritis and psoriasis. (See Cohen, *Eur. J. Biochem.*, 268:5001-5010 (2001); Protein Kinase Inhibitors for the Treatment of Disease: The Promise and the Problems, *Handbook of Experimental Pharmacology*, Springer Berlin Heidelberg, 167 (2005)).

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance (Roitt, I., Brostoff, J and Kale, D., Immunology, 17.1-17.12 (3rd ed., Mosby, St. Louis, Mo., 1993)).

Cancers figure among the leading causes of death worldwide, accounting for 8.2 million deaths in 2012. It is expected that annual cancer cases will rise from 14 million in 2012 to 22 million within the next two decades (See Cancer Fact sheet No. 297, World Health Organization, February 2014, retrieved 10 Jun. 2014 and Globocan 2012, IARC).

The current drugs used in cancer treatment are highly toxic and often non-specific. Current anticancer therapy strategies are typically focused on rapid proliferating cells, which can shrink primary and metastatic tumors, but such effects are usually transient and tumor relapse of most metastatic cancers frequently occur. One possible reason for failure is the existence of cancer stem cells. Unlike most cells within the tumor, cancer stem cells are resistant to well-defined chemotherapy, and after treatment, they can regenerate all the cell types in the tumor through their stem cell-like behavior of largely quiescent nature and their abundant expression of drug transporters.

There is an enormous variety of cancers which are described in detail in the medical literature. The incidence of cancer continues to climb as the general population ages, as new cancers develop, and as susceptible populations (e.g., people infected with AIDS or excessively exposed to sunlight) grow. However, options for the treatment of cancer are limited. A tremendous demand therefore exists for new methods and compositions that can be used to treat patients with cancer.

Citation or identification of any reference in Section of this application is not to be construed as an admission that the reference is prior art to the present application.

Accordingly, there remains a need for cancer therapies, for example, modulators, and in particular solid forms.

SUMMARY

Provided herein are solid forms of Compound 1:

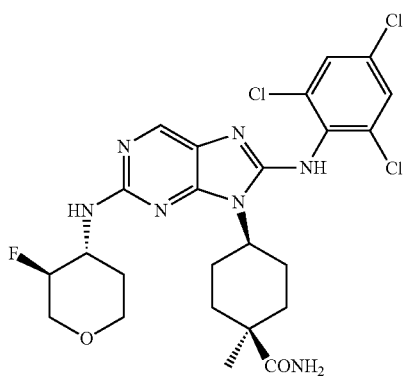

having the name cis-4-[2-{[(3S,4R)-3-fluorooxan-4-yl]amino}-8-(2,4,6-trichloroanilino)-9H-purin-9-yl]-1-methyl-cyclohexane-1-carboxamide, alternatively named (1s,4s)-4-(2-(((3S,4R)-3-fluorotetrahydro-2H-pyran-4-yl)amino)-8-((2,4,6-trichlorophenyl)amino)-9H-purin-9-yl)-1-methylcyclohexane-1-carboxamide, including tautomers thereof.

Also provided are methods of preparing, isolating, and characterizing the solid forms.

In certain aspects, the solid forms of Compound 1 described herein are useful for treating or preventing one or more diseases or conditions, such as for example, cancer.

Provided herein are methods of treating a cancer, in particular a solid tumor or a hematological cancer. The solid forms of Compound 1 described herein provided herein can be used in the methods for treating or preventing a cancer, in particular a solid tumor or a hematological cancer, as described herein. The methods comprise administering to a subject in need thereof an effective amount of a solid form of Compound 1 described herein. Also provided herein are methods for treating and preventing cancer metastasis, comprising administering to a subject in need thereof an effective amount of a solid form of Compound 1 described herein. The solid forms of Compound 1 described herein provided herein can be used in the methods for treating and preventing cancer metastasis. Additionally, provided herein are methods of eradicating cancer stem cells in a subject, comprising administering to a subject in need thereof an effective amount of a solid form of Compound 1 described herein. The solid forms of Compound 1 described herein provided herein can be used in the methods of eradicating cancer stem cells in a subject. Also provided are methods of inducing differentiation in cancer stem cells in a subject, comprising administering to a subject in need thereof an effective amount of a solid form of Compound 1 described herein. The solid forms of Compound 1 described herein provided herein can be used in the methods of inducing differentiation in cancer stem cells in a subject. In another aspect, provided are methods of inducing cancer stem cell death in a subject, comprising administering to a subject in need thereof an effective amount of a solid form of Compound 1 described herein. The solid forms of Compound 1 described herein provided herein can be used in the methods of inducing cancer stem cell death in a subject.

Compounds useful in the methods disclosed herein include solid forms of Compound 1 described herein, or a pharmaceutically acceptable salt, tautomer, stereoisomer, enantiomer, or isotopologue thereof.

The present embodiments can be understood more fully by reference to the detailed description and examples, which are intended to exemplify non-limiting embodiments.

BRIEF DESCRIPTION OF THE DRAWINGS

FIG. 62A illustrates XRPD before compression. FIG. 62B illustrates XRPD after compression.

FIG. 189A illustrates proteins extracted from treated cells and analyzed by Western blot using antibodies against DUSP4, DUSP6, cyclin D1, c-Myc, YAP or β-actin. FIGS. 189B-189C illustrate RNAs extracted using Cell-To-CT kit and quantitative PCR was performed with probes specific for DUSP4, DUSP6, SPRY2, c-Myc and cyclin D1. Specific probes for β-actin were used for normalization. FIGS. 189D-189I illustrate Compound 1 Treatment modulates MAPK-driven mRNA levels in Colo 205 (mut BRAFV600E) and HT-29 (mut BRAFV600E) Cells. Colo 205 or HT-29 cells were treated with DMSO or 0.3 or 1 µM Compound 1 for 6 h. mRNA was extracted using MagMAX Total RNA Isolation kit and quantitative PCR was performed.

FIGS. 191A-191B illustrate Compound 1 down-regulates PD-L1 level in multiple cancer cell lines. FIG. 191A illustrates Western blotting of total PD-L1 in Hop66, Karpas-299, and LOX-IMVI. Cells were cultured in presence or absence of Compound 1 for indicated time before expression levels of PD-L1, DUSP4 and α-tubulin or α-actin were measured by Western blot. FIG. 191B illustrates surface staining of PD-L1 with the Fluorescence-Activated Cell Sorter (FACS). Cells were treated with DMSO or Compound 1 at indicated concentrations for 48 h and cell surface expression of PD-L1 was detected using the FACS analysis with an APC-labeled antibody to PD-L1 (clone 29E.1A3.; BioLegend, San Diego, Calif.). Geometric mean of PD-L1 positive cells was determined by FlowJo 10 (Treestar, Ashland, Oreg.).

FIG. 197A illustrates tumor volume as a function of time. FIG. 197B illustrates individual tumor volume on the last study day, day 40. Percent inhibition is calculated relative to the vehicle control on the last study day and is in parentheses next to the respective tumor volume for the treatment groups. Dotted line is the tumor volume at the initiation of dosing. Camp=camptosar.

FIGS. 206A-206C show that cell lines containing BRAF and CTNNB1 mutations are more sensitive to treatment with Compound 1 than cell lines with wild type BRAF and CTNNB1. FIG. 206D and FIG. 206E show that cell lines with mutations in RB and the PI3K/PTEN pathway are associated with resistance to Compound 1 treatment in vitro.

FIG. 210A shows inhibition of colony formation of SW48 (colo) cells. FIG. 210B shows inhibition of colony formation of HCT-116 (colo) cells. FIG. 210C shows inhibition of colony formation of AGS (gastric) cells. FIG. 210D shows inhibition of colony formation of Hep3B (HCC) cells.

DETAILED DESCRIPTION

Definitions

Figure 1:
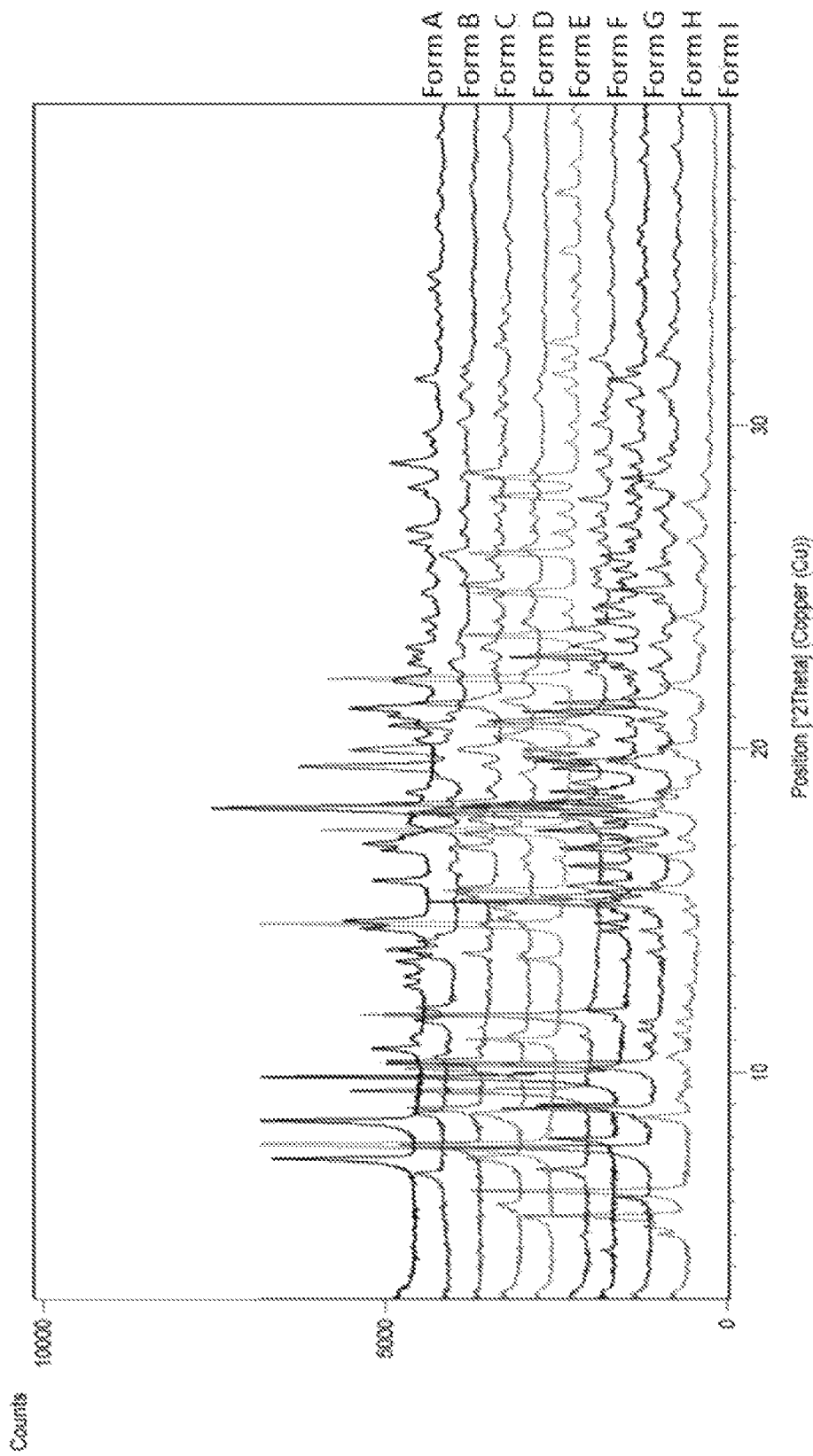
FIG. 1 depicts a XRPD Stack Plot of Free Base Crystalline Forms A-I.

As used herein, and in the specification and the accompanying claims, the indefinite articles "a" and "an" and the definite article "the" include plural as well as single referents, unless the context clearly indicates otherwise.

As used herein, and unless otherwise specified, the terms "about" and "approximately," when used in connection with doses, amounts, or weight percent of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, IR or Raman spectroscopy or XRPD; indicate that the value or range of values may deviate to an extent deemed reasonable to one of ordinary skill in the art while still describing the solid form. Techniques for characterizing crystal forms and amorphous solids include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of an XRPD peak position may vary by up to ±0.1° 2θ (or ±0.2° 2θ) while still describing the particular XRPD peak.

As used herein, and unless otherwise specified, a crystalline that is "pure," i.e., substantially free of other crystalline or amorphous solids, contains less than about 10% by weight of one or more other crystalline or amorphous solids, less than about 5% by weight of one or more other crystalline or amorphous solids, less than about 3% by weight of one or more other crystalline or amorphous solids, or less than about 1% by weight of one or more other crystalline or amorphous solids.

As used herein, and unless otherwise specified, a solid form that is "substantially physically pure" is substantially free from other solid forms. In certain embodiments, a crystal form that is substantially physically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

Unless otherwise specified, the terms "solvate" and "solvated," as used herein, refer to a solid form of a substance which contains solvent. The terms "hydrate" and "hydrated" refer to a solvate wherein the solvent is water. "Polymorphs of solvates" refer to the existence of more than one solid form for a particular solvate composition. Similarly, "polymorphs of hydrates" refer to the existence of more than one solid form for a particular hydrate composition. The term "desolvated solvate," as used herein, refers to a solid form of a substance which can be made by removing the solvent from a solvate. The terms "solvate" and "solvated," as used herein, can also refer to a solvate of a salt, cocrystal, or molecular complex. The terms "hydrate" and "hydrated," as used herein, can also refer to a hydrate of a salt, cocrystal, or molecular complex.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

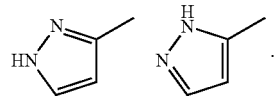

As readily understood by one skilled in the art, a wide variety of functional groups and other structures may exhibit tautomerism and all tautomers of Compound 1 are within the scope of the present invention.

Unless otherwise specified, the term "composition" as used herein is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," it is meant a diluent, excipient, or carrier in a formulation must be compatible with the other ingredient(s) of the formulation and not deleterious to the recipient thereof.

The term "solid form" refers to a physical form which is not predominantly in a liquid or a gaseous state. The terms "solid type" and "type" are used interchangeably herein with "solid form". As used herein and unless otherwise specified, the term "solid form," when used herein to refer to Compound 1, refers to a physical form comprising Compound 1 which is not predominantly in a liquid or a gaseous state. A solid form may be a crystalline form or a mixture thereof. In certain embodiments, a solid form may be a liquid crystal. In certain embodiments, the term "solid forms comprising Compound 1" includes crystal forms comprising Compound 1. In certain embodiments, the solid form of Compound 1 is Form A, Form B, Form C, Form D, Form E, Form F, Form G, Form H, Form I, the amorphous solid, or a mixture thereof. In one embodiment, the solid form of Compound 1 is a citrate salt Form Y or citrate salt form Z. In certain embodiments, the solid form of Compound 1 is HCl Salt Form 1, HCl Salt Form 2, HCl Salt Form 3, HCl Salt Form 4, HCl Salt Form 5, HCl Salt Form 6, HCl Salt Form 7, HCl Salt Form 8, the amorphous solid, or a mixture thereof.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, 23$^{rd}$ ed., 1843-1844 (1995).

The term "crystal form" or "crystalline form" refers to a solid form that is crystalline. In certain embodiments, a crystal form of a substance may be substantially free of amorphous solids and/or other crystal forms. In certain embodiments, a crystal form of a substance may contain less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, or less than about 50% by weight of one or more amorphous solids and/or other crystal forms. In certain embodiments, a crystal form of a substance may be physically and/or chemically pure. In certain embodiments, a crystal form of a substance may be about 99%, about 98%, about 97%, about 96%, about 95%, about 94%, about 93%, about 92%, about 91%, or about 90% physically and/or chemically pure.

Unless otherwise specified, the term "amorphous" or "amorphous solid" means that the substance, component, or product in question is not substantially crystalline as determined by X-ray diffraction. In particular, the term "amorphous solid" describes a disordered solid form, i.e., a solid form lacking long range crystalline order. In certain embodiments, an amorphous solid of a substance may be substantially free of other amorphous solids and/or crystal forms. In certain embodiments, an amorphous solid of a substance may contain less than about 1%, less than about 2%, less than about 3%, less than about 4%, less than about 5%, less than about 10%, less than about 15%, less than about 20%, less than about 25%, less than about 30%, less than about 35%, less than about 40%, less than about 45%, or less than about 50% by weight of one or more other amorphous solids and/or crystal forms on a weight basis. In certain embodiments, an amorphous solid of a substance may be physically and/or chemically pure. In certain embodiments, an amorphous solid of a substance be about 99%, about 98%, about 97%, about 96%, about 95%, about 94%, about 93%, about 92%, about 91%, or about 90% physically and/or chemically pure.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a cancer, in particular, a solid tumor or hematological cancer. In some embodiments, "treating" means an alleviation, in whole or in part, of a cancer, or symptoms associated with a cancer, in particular, a solid tumor or hematological cancer, or a slowing, or halting of further progression or worsening of those symptoms.

"Preventing" as used herein, means a method of delaying and/or precluding the onset, recurrence or spread, in whole or in part, of a cancer, in particular, a solid tumor or hematological cancer; barring a subject from acquiring a cancer, in particular, a solid tumor or hematological cancer; or reducing a subject's risk of acquiring a cancer, in particular, a solid tumor or hematological cancer.

The term "effective amount" in connection with a solid form of Compound 1 means an amount capable of treating or preventing a disorder, disease or condition, or symptoms thereof, disclosed herein. An effective amount refers to an amount capable of treating or preventing a cancer, in particular, a solid tumor or hematological cancer, or symptoms thereof, as disclosed herein. The effective amount of a solid form of Compound 1 described herein, for example in a pharmaceutical composition, may be at a level that will exercise the desired effect; for example, about 0.005 mg/kg of a subject's body weight to about 100 mg/kg of a patient's body weight in unit dosage for parenteral administration. As will be apparent to those skilled in the art, it is to be expected that the effective amount of a solid form of Compound 1 described herein may vary depending on the severity of the indication being treated.

"Patient" or "subject" as used herein include an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having cancer, in particular, a solid tumor or hematological cancer, or symptoms thereof. In one embodiment, a patient is a human having histologically or cytologically-confirmed solid tumor or hematological cancer, including subjects who have progressed on (or not been able to tolerate) standard anticancer therapy or for whom no standard anticancer therapy exists.

As used herein, and unless otherwise specified, the terms "cancer" refers to or describes the physiological condition in mammals that is typically characterized by unregulated cell growth. Examples of cancer include solid tumors and hematological cancer. In some embodiments, the cancer is a primary cancer, in others, the cancer is metastasized.

As used herein "solid tumors" includes, but is not limited to, bladder cancer (including, but not limited to, superficial bladder cancer), breast cancer (including, but not limited to, luminal B type, ER+, PR+ and Her2+ breast cancer), central nervous system cancer (including, but not limited to, glioblastoma multiforme (GBM), glioma, medulloblastoma, and astrocytoma), colorectal cancer, gastrointestinal cancer (including, but not limited to, stomach cancer, esophageal cancer, and rectum cancer), endocrine cancer (including, but not limited to, thyroid cancer, and adrenal gland cancer), eye cancer (including, but not limited to, retinoblastoma), female genitourinary cancer (including, but not limited to, cancer of the placenta, uterus, vulva, ovary, cervix), head and neck cancer (including, but not limited to, cancer of the pharynx, esophageal, and tongue), liver cancer, lung cancer (including, but not limited to, non-small cell lung cancer (NSCLC), small cell lung cancer (SCLC), mucoepidermoid, bronchogenic, squamous cell carcinoma (SQCC), and anal-plastic/NSCLC), skin cancer (including, but not limited to, melanoma, and SQCC), soft tissue cancer (including but not limited to, sarcoma, Ewing's sarcoma, and rhabdomyosarcoma), bone cancer (including, but not limited to, sarcoma, Ewing's sarcoma, and osteosarcoma), squamous cell cancer (including, but not limited to, lung, esophageal, cervical, and head and neck cancer), pancreas cancer, kidney cancer (including, but not limited to, renal Wilm's tumor and renal cell carcinoma), and prostate cancer. In one embodiment, the solid tumor is not triple negative breast cancer (TNBC). In some embodiments, the solid tumor is breast cancer, colon cancer, lung cancer or bladder cancer. In one such embodiment, the solid tumor is superficial bladder cancer. In another, the solid tumor is lung squamous cell carcinoma. In yet another embodiment, the solid tumor is luminal B type breast cancer.

As used herein "hematological cancer" includes, but is not limited to, leukemia (including, but not limited to, acute lymphocytic leukemia (ALL), chronic myeloid leukemia (CML), acute T-cell leukemia, B cell precursor leukemia, acute promyelocytic leukemia (APML), plasma cell leukemia, myelomonoblastic/T-ALL, B myelomonocytic leukemia, erythroleukemia, and acute myeloid leukemia (AML)), lymphoma (including but not limited to Hodgkin's lymphoma, non-Hodgkin's lymphoma (NHL), Burkitt's lymphoma (BL), B cell lymphoma, lymphoblastic lymphoma, follicular lymphoma (FL), diffuse large B-cell lymphoma (DLBCL), large cell immunoblastic lymphoma), and multiple myeloma.

In the context of a cancer, inhibition may be assessed by inhibition of disease progression, inhibition of tumor growth, reduction of primary tumor, relief of tumor-related symptoms, inhibition of tumor secreted factors (including tumor secreted hormones, such as those that contribute to carcinoid syndrome), delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP as used herein means the time from treatment onset until tumor progression; TTP does not include deaths. As used herein, PFS means the time from treatment onset until tumor progression or death. In one embodiment, PFS rates will be computed using the Kaplan-Meier estimates. In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of lymphoma may be assessed by the International Workshop Criteria (IWC) for non-Hodgkin lymphoma (NHL) (see Cheson B D, Pfistner B, Juweid, M E, et. al. Revised Response Criteria for Malignant Lymphoma. J. Clin. Oncol: 2007: (25) 579-586), using the response and endpoint definitions shown below:

| Response | Definition | Nodal Masses | Spleen, liver | Bone Marrow |
|---|---|---|---|---|
| CR | Disappearance of all evidence of disease | (a) FDG-avid or PET positive prior to therapy; mass of any size permitted if PET negative (b) Variably FDG-avid or PET negative; regression to normal size on CT | Not palpable, nodules disappeared | Infiltrate cleared on repeat biopsy; if indeterminate by morphology, immunohistochemistry should be negative |
| PR | Regression of measurable disease and no new sites | ≥50% decrease in SPD of up to 6 largest dominant masses; no increase in size of other nodes (a) FDG-avid or PET positive prior to therapy; one or more PET positive at previously involved site (b) Variably FDG-avid or PET negative; regression on CT | ≥50% decrease in SPD of nodules (for single nodule in greatest transverse diameter); no increase in size of liver or spleen | Irrelevant if positive prior to therapy; cell type should be specified |

| Response | Definition | Nodal Masses | Spleen, liver | Bone Marrow |
|---|---|---|---|---|
| SD | Failure to attain CR/PR or PD | (a) FDG-avid or PET positive prior to therapy; PET positive at prior sites of disease and no new sites on CT or PET (b) Variably FDG-avid or PET negative; no change in size of previous lesions on CT | | |
| PD or relapsed disease | Any new lesion or increase by ≥50% of previously involved sites from nadir | Appearance of a new lesion(s) ≥1.5 cm in any axis, ≥50% increase in SPD of more than one node, or ≥50% increase in longest diameter of a previously identified node ≥1 cm in short axis Lesions PET positive if FDG-avid lymphoma or PET positive prior to therapy | ≥50% increase from nadir in the SPD of any previous lesions | New or recurrent involvement |

Abbreviations:
CR, complete remission;
FDG, [$^{18}$F]fluorodeoxyglucose;
PET, positron emission tomography;
CT, computed tomography;
PR, partial remission;
SPD, sum of the product of the diameters;
SD, stable disease;
PD, progressive disease.

| End point | Patients | Definition | Measured from |
|---|---|---|---|
| Primary | | | |
| Overall survival | All | Death as a result of any cause | Entry onto study |
| Progression-free survival | All | Disease progression or death as a result of any cause | Entry onto study |
| Secondary | | | |
| Event-free survival | All | Failure of treatment or death as result of any cause | Entry onto study |
| Time to progression | All | Time to progression or death as a result of lymphoma | Entry onto study |
| Disease-free survival | In CR | Time to relapse or death as a result of lymphoma or acute toxicity of treatment | Documentation of response |
| Response duration | In CR or PR | Time to relapse or progression | Documentation of response |
| Lymphoma-specific survival | All | Time to death as a result of lymphoma | Entry onto study |
| Time to next treatment | All | Time to new treatment | End of primary treatment |

Abbreviations:
CR: complete remission;
PR: partial remission.

In one embodiment, the end point for lymphoma is evidence of clinical benefit. Clinical benefit may reflect improvement in quality of life, or reduction in patient symptoms, transfusion requirements, frequent infections, or other parameters. Time to reappearance or progression of lymphoma-related symptoms can also be used in this end point.

In certain embodiments, the treatment of CLL may be assessed by the International Workshop Guidelines for CLL (see Hallek M, Cheson B D, Catovsky D, et al. Guidelines for the diagnosis and treatment of chronic lymphocytic leukemia: a report from the International Workshop on Chronic Lymphocytic Leukemia updating the National Cancer Institute-Working Group 1996 guidelines. Blood, 2008; (111) 12: 5446-5456) using the response and endpoint definitions shown therein and in particular:

| Parameter | CR | PR | PD |
|---|---|---|---|
| Group A | | | |
| Lymphadenopathy[†] | None >1.5 cm | Decrease ≥50% | Increase ≥50% |
| Hepatomegaly | None | Decrease ≥50% | Increase ≥50% |
| Splenomegaly | None | Decrease ≥50% | Increase ≥50% |
| Blood lymphocytes | <4000/μL | Decrease ≥50% from baseline | Increase ≥50% over baseline |
| Marrow[‡] | Normocellular, <30% lymphocytes, no B-lymphoid nodules. Hypocellular marrow defines CRi (5.1.6). | 50% reduction in marrow infiltrate, or B-lymphoid nodules | |
| Group B | | | |
| Platelet count | >100 000/μL | >100000/μL or increase ≥50% over baseline | Decrease of ≥50% from baseline secondary to CLL |
| Hemoglobin | >11.0 g/dL | >11 g/dL or increase ≥50% over baseline | Decrease of >2 g/dL from baseline secondary to CLL |
| Neutrophils[‡] | >1500/μL | >1500/μL or >50% improvement over baseline | |

Group A criteria define the tumor load; Group B criteria define the function of the hematopoietic system (or marrow).
CR (complete remission): all of the criteria have to be met, and patients have to lack disease-related constitutional symptoms;
PR (partial remission): at least two of the criteria of group A plus one of the criteria of group B have to be met;
SD is absence of progressive disease (PD) and failure to achieve at least a PR;
PD: at least one of the above criteria of group A or group B has to be met.
Sum of the products of multiple lymph nodes (as evaluated by CT scans in clinical trials, or by physical examination in general practice). These parameters are irrelevant for some response categories.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7), using the response and endpoint definitions shown below:

| Response Subcategory | Response Criteria[a] |
|---|---|
| sCR | CR as defined below plus<br>Normal FLC ratio and<br>Absence of clonal cells in bone marrow[b] by immunohistochemistry or immunofluorescence[c] |
| CR | Negative immunofixation on the serum and urine and<br>Disappearance of any soft tissue plasmacytomas and<br><5% plasma cells in bone marrow[b] |
| VGPR | Serum and urine M-protein detectable by immunofixation but not on electrophoresis or 90% or greater reduction in serum M-protein plus urine M-protein level <100 mg per 24 h |
| PR | ≥50% reduction of serum M-protein and reduction in 24-h urinary M-protein by ≥90% or to <200 mg per 24 h<br>If the serum and urine M-protein are unmeasurable,[d] a ≥50% decrease in the difference between involved and uninvolved FLC levels is required in place of the M-protein criteria<br>If serum and urine M-protein are unmeasurable, and serum free light assay is also unmeasurable, ≥50% reduction in plasma cells is required in place of M-protein, provided baseline bone marrow plasma cell percentage was ≥30%<br>In addition to the above listed criteria, if present at baseline, a ≥50% reduction in the size of soft tissue plasmacytomas is also required |
| SD (not recommended for use as an indicator of response; stability of disease is best | Not meeting criteria for CR, VGPR, PR or progressive disease |

-continued

| Response Subcategory | Response Criteria[a] |
|---|---|
| described by providing the time to progression estimates) | |

Abbreviations:
CR, complete response;
FLC, free light chain;
PR, partial response;
SD, stable disease;
sCR, stringent complete response;
VGPR, very good partial response;
[a]All response categories require two consecutive assessments made at any time before the institution of any new therapy; all categories also require no known evidence of progressive or new bone lesions if radiographic studies were performed. Radiographic studies are not required to satisfy these response requirements;
[b]Confirmation with repeat bone marrow biopsy not needed;
[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2.
[d]Measurable disease defined by at least one of the following measurements: Bone marrow plasma cells ≥30%; Serum M-protein ≥1 g/dl (≥10 gm/l)[10 g/l]; Urine M-protein ≥200 mg/24 h; Serum FLC assay: Involved FLC level ≥10 mg/dl (≥100 mg/l); provided serum FLC ratio is abnormal.

In certain embodiments, the treatment of a cancer may be assessed by Response Evaluation Criteria in Solid Tumors (RECIST 1.1) (see Thereasse P., et al. New Guidelines to Evaluate the Response to Treatment in Solid Tumors. J. of the National Cancer Institute; 2000; (92) 205-216 and Eisenhauer E. A., Therasse P., Bogaerts J., et al. New response evaluation criteria in solid tumors: Revised RECIST guideline (version 1.1). European J. Cancer; 2009; (45) 228-247). Overall responses for all possible combinations of tumor responses in target and non-target lesions with our without the appearance of new lesions are as follows:

| Target lesions | Non-target lesions | New lesions | Overall response |
|---|---|---|---|
| CR | CR | No | CR |
| CR | Incomplete response/SD | No | PR |
| PR | Non-PD | No | PR |
| SD | Non-PD | No | SD |
| PD | Any | Yes or no | PD |
| Any | PD | Yes or no | PD |
| Any | Any | Yes | PD |

CR = complete response;
PR = partial response;
SD = stable disease; and
PD = progressive disease.

With respect to the evaluation of target lesions, complete response (CR) is the disappearance of all target lesions, partial response (PR) is at least a 30% decrease in the sum of the longest diameter of target lesions, taking as reference the baseline sum longest diameter, progressive disease (PD) is at least a 20% increase in the sum of the longest diameter of target lesions, taking as reference the smallest sum longest diameter recorded since the treatment started or the appearance of one or more new lesions and stable disease (SD) is neither sufficient shrinkage to qualify for partial response nor sufficient increase to qualify for progressive disease, taking as reference the smallest sum longest diameter since the treatment started.

With respect to the evaluation of non-target lesions, complete response (CR) is the disappearance of all non-target lesions and normalization of tumor marker level; incomplete response/stable disease (SD) is the persistence of one or more non-target lesion(s) and/or the maintenance of tumor marker level above the normal limits, and progressive disease (PD) is the appearance of one or more new lesions and/or unequivocal progression of existing non-target lesions.

The procedures, conventions, and definitions described below provide guidance for implementing the recommendations from the Response Assessment for Neuro-Oncology (RANO) Working Group regarding response criteria for high-grade gliomas (Wen P., Macdonald, D R., Reardon, D A., et al. Updated response assessment criteria for high-grade gliomas: Response assessment in neuro-oncology working group. J Clin Oncol 2010; 28: 1963-1972). Primary modifications to the RANO criteria for Criteria for Time Point Responses (TPR) can include the addition of operational conventions for defining changes in glucocorticoid dose, and the removal of subjects' clinical deterioration component to focus on objective radiologic assessments. The baseline MRI scan is defined as the assessment performed at the end of the post-surgery rest period, prior to initiating or re-initiating compound treatment. The baseline MRI is used as the reference for assessing complete response (CR) and partial response (PR). Whereas, the smallest SPD (sum of the products of perpendicular diameters) obtained either at baseline or at subsequent assessments will be designated the nadir assessment and utilized as the reference for determining progression. For the 5 days preceding any protocol-defined MRI scan, subjects receive either no glucocorticoids or are on a stable dose of glucocorticoids. A stable dose is defined as the same daily dose for the 5 consecutive days preceding the MRI scan. If the prescribed glucocorticoid dose is changed in the 5 days before the baseline scan, a new baseline scan is required with glucocorticoid use meeting the criteria described above. The following definitions will be used.

Measurable Lesions: Measurable lesions are contrast-enhancing lesions that can be measured bi-dimensionally. A measurement is made of the maximal enhancing tumor diameter (also known as the longest diameter, LD). The greatest perpendicular diameter is measured on the same image. The cross hairs of bi-dimensional measurements should cross and the product of these diameters will be calculated.

Minimal Diameter: T1-weighted image in which the sections are 5 mm with 1 mm skip. The minimal LD of a measurable lesion is set as 5 mm by 5 mm. Larger diameters may be required for inclusion and/or designation as target lesions. After baseline, target lesions that become smaller than the minimum requirement for measurement or become no longer amenable to bi-dimensional measurement will be recorded at the default value of 5 mm for each diameter below 5 mm. Lesions that disappear will be recorded as 0 mm by 0 mm.

Multicentric Lesions: Lesions that are considered multicentric (as opposed to continuous) are lesions where there is normal intervening brain tissue between the two (or more) lesions. For multicentric lesions that are discrete foci of enhancement, the approach is to separately measure each enhancing lesion that meets the inclusion criteria. If there is no normal brain tissue between two (or more) lesions, they will be considered the same lesion.

Nonmeasurable Lesions: All lesions that do not meet the criteria for measurable disease as defined above will be considered non-measurable lesions, as well as all non-enhancing and other truly nonmeasurable lesions. Nonmeasurable lesions include foci of enhancement that are less than the specified smallest diameter (i.e., less than 5 mm by 5 mm), non-enhancing lesions (e.g., as seen on T1-weighted post-contrast, T2-weighted, or fluid-attenuated inversion recovery (FLAIR) images), hemorrhagic or predominantly cystic or necrotic lesions, and leptomeningeal tumor. Hemorrhagic lesions often have intrinsic T1-weighted hyperintensity that could be misinterpreted as enhancing tumor, and for this reason, the pre-contrast T1-weighted image may be examined to exclude baseline or interval sub-acute hemorrhage.

At baseline, lesions will be classified as follows: Target lesions: Up to 5 measurable lesions can be selected as target lesions with each measuring at least 10 mm by 5 mm, representative of the subject's disease; Non-target lesions: All other lesions, including all nonmeasurable lesions (including mass effects and T2/FLAIR findings) and any measurable lesion not selected as a target lesion. At baseline, target lesions are to be measured as described in the definition for measurable lesions and the SPD of all target lesions is to be determined. The presence of all other lesions is to be documented. At all post-treatment evaluations, the baseline classification of lesions as target and non-target lesions will be maintained and lesions will be documented and described in a consistent fashion over time (e.g., recorded in the same order on source documents and eCRFs). All measurable and nonmeasurable lesions must be assessed using the same technique as at baseline (e.g., subjects should be imaged on the same MRI scanner or at least with the same magnet strength) for the duration of the study to reduce difficulties in interpreting changes. At each evaluation, target lesions will be measured and the SPD calculated. Non-target lesions will be assessed qualitatively and new lesions, if any, will be documented separately. At each evaluation, a time point response will be determined for target lesions, non-target lesions, and new lesion. Tumor progression can be established even if only a subset of lesions is assessed. However, unless progression is observed, objective status (stable disease, PR or CR) can only be determined when all lesions are assessed.

Confirmation assessments for overall time point responses of CR and PR will be performed at the next scheduled assessment, but confirmation may not occur if scans have an interval of <28 days. Best response, incorporating confirmation requirements, will be derived from the series of time points.

Compound 1

The solid forms, formulations and methods of use provided herein relate to solid forms (e.g., polymorphs) of Compound 1:

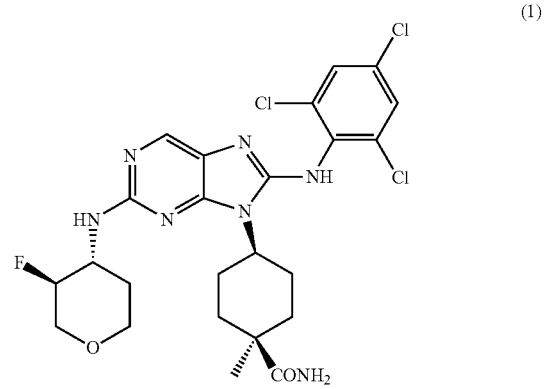 [SMILES: C[C@]1(C(N)=O)CC[C@@H](n2c(Nc3c(Cl)cc(Cl)cc3Cl)nc3cnc(N[C@@H]4CCOC[C@H]4F)nc32)CC1]

(1)

having the name (1s,4s)-4-(8-((2,4,6-trichlorophenyl)amino)-2-(((3S,4R)-3-fluorotetrahydro-2H-pyran-4-yl)amino)-9H-purin-9-yl)-1-methylcyclohexane-1-carboxamide, alternatively named cis-4-[2-{[(3S,4R)-3-fluorooxan-4-yl]amino}-8-(2,4,6-trichloroanilino)-9H-purin-9-yl]-1-methylcyclohexane-1-carboxamide, including tautomers thereof.

Solid Forms of Compound 1

In certain embodiments, provided herein are solid forms of Compound 1. In certain embodiments, the solid form is crystalline. In certain embodiments, the solid form is a single-component solid form. In certain embodiments, the solid form is a hydrate. In certain embodiments, the solid form is an anhydrate. In certain embodiments, the solid form is an HCl salt of Compound 1. In certain embodiments, the solid form is a citrate salt of Compound 1. In certain embodiments, the solid form is a mesylate salt. In certain embodiments, the solid form is a sulfate salt. In certain embodiments, the solid form is a solvate.

While not intending to be bound by any particular theory, certain solid forms are characterized by physical properties, e.g., stability, solubility and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

The solid forms provided herein (e.g., Form A, Form B, Form C, Form D, Form E, Form F, Form G, Form H, Form I, and the amorphous solid of Compound 1, and HCl salt Form 1, HCl Salt Form 2, HCl Salt Form 3, HCl Salt Form 4, HCl Salt Form 5, HCl Salt Form 6, HCl Salt Form 7, HCl Salt Form 8, and the HCl salt amorphous solid of Compound 1, and citrate salt Form Y, Form Z and the citrate salt amorphous solid of Compound 1) may be characterized using a number of methods known to a person skilled in the art, including, but not limited to, single crystal X-ray diffraction, X-ray powder diffraction (XRPD), microscopy (e.g., scanning electron microscopy (SEM)), thermal analysis (e.g., differential scanning calorimetry (DSC), dynamic vapor sorption (DVS), thermal gravimetric analysis (TGA), and hot-stage microscopy), spectroscopy (e.g., infrared, Raman, and solid-state nuclear magnetic resonance), ultra-high performance liquid chromatography (UHPLC), and proton nuclear magnetic resonance ($^1$H NMR) spectrum. The particle size and size distribution of the solid form provided herein may be determined by conventional methods, such as laser light scattering technique.

The purity of the solid forms provided herein may be determined by standard analytical methods, such as thin layer chromatography (TLC), gel electrophoresis, gas chromatography, ultra-high performance liquid chromatography (UHPLC), and mass spectrometry (MS).

It should be understood that the numerical values of the peaks of an X-ray powder diffraction pattern may vary slightly from one machine to another or from one sample to another, and so the values quoted are not to be construed as absolute, but with an allowable variability, such as ±0.2° 2θ or ±0.1° 2θ (see United State Pharmacopoeia, page 2228 (2003)).

In certain embodiments, provided herein are methods for making a solid form of Compound 1, comprising 1) obtaining a slurry of Compound 1 in a solvent; 2) stirring the slurry for a period of time (e.g., about 24 h) at a certain temperature (e.g., about 25° C. or about 50° C.); and 3) collecting solids from the slurry by filtration and optionally drying, where the solids can be Form A. In certain embodiments, provided herein are methods for making a solid form of Compound 1, comprising 1) obtaining a slurry of Compound 1 in a solvent; 2) stirring the slurry for about 24 h at about 25° C. or about 50° C.; and 3) collecting solids from the slurry by filtration, for example through a 0.45 μm PTFE syringe filter and optionally air drying, where the solids can be Form A. In certain embodiments, the methods for making a solid form of Compound 1 are equilibration experiments, such as slurry experiments.

In certain embodiments, provided herein are methods for making a solid form of Compound 1, comprising 1) dissolving Compound 1 in a solvent to yield a solution; 2) filtering the solution if the compound does not dissolve completely; and 3) evaporating the solution under certain air pressure (e.g., about 1 atm) at a certain temperature (e.g., about 25° C. or about 50° C.) to yield a solid that is optionally Form A. In certain embodiments, provided herein are methods for making a solid form of Form A, comprising 1) dissolving Compound 1 in a solvent to yield a solution; 2) filtering the solution (for example, through a 0.45 μm PTFE syringe filter) if Form A does not dissolve completely; and 3) evaporating the solution under about 1 atm air pressure at about 25° C. or about 50° C. under nitrogen to yield a solid. In certain embodiments, the methods for making a solid form of Compound 1 are evaporation experiments.

In certain embodiments, provided herein are methods for making a solid form of Compound 1, comprising 1) obtaining a saturated solution of Form A in a solvent at a first temperature (e.g., about 60° C.); 2) stirring the solution at the first temperature for a period of time (e.g., 10 minutes); 3) filtering the solution; 4) cooling the solution slowly to a second temperature (e.g., about −5° C. to about 15° C.); and 5) isolating solids from the solution and optionally drying. In certain embodiments, provided herein are methods for making a solid form of Compound 1, comprising 1) obtaining a saturated solution of Form A in a solvent at about 60° C.; 2) stirring the solution at about 60° C. for 10 minutes; 3) filtering the solution (for example through a 0.45 μm PTFE syringe filter); 4) cooling the solution slowly to about 5° C.; and 5) isolating solids from the solution and optionally air-drying. In certain embodiments, the methods for making a solid form of Compound 1 are cooling recrystallization experiments.

In certain embodiments, provided herein are methods for making a solid form of Compound 1, comprising 1) obtaining a saturated solution of Form A in a solvent at a first temperature (e.g., about 60° C.); 2) adding an anti-solvent into the saturated solution at the first temperature; 3) cooling down to a second temperature (e.g., about −5° C. to about 15° C.); and 4) collecting a solid if there is precipitation, and evaporating the solvent to collect a solid if there is no precipitation; and 5) optionally drying. In certain embodiments, provided herein are methods for making a solid form of Compound 1, comprising 1) obtaining a saturated solution of Form A in a solvent at about 60° C.; 2) adding an anti-solvent into the saturated solution at about 60° C.; 3) cooling down to about 5° C.; and 4) collecting a solid if there is precipitation, and evaporating the solvent to collect a solid if there is no precipitation; and 5) optionally air drying. In certain embodiments, the ratio by volume of solvent and anti-solvent is about 1:9. In certain embodiments, the methods for making a solid form of Compound 1 are anti-solvent recrystallization experiments.

In certain embodiments, the solvent is acetone, DCM, EtOAc, EtOH, EtOH/H$_2$O (about 1:1), H$_2$O, heptane, IPA, ACN, ACN/H$_2$O (about 1:1), MEK, MeOH, MTBE, n-BuOH, THF, THF/H$_2$O (about 1:1), toluene or sulfolane.

In certain embodiments, the anti-solvent is ACN, heptane, MTBE, or water.

Form A

In certain embodiments, provided herein is Form A.

In one embodiment, Form A is a solid form of Compound 1. In one embodiment, Form A is a monohydrate. In one embodiment, Form A is a non-stoichiometric channel hydrate solid form of Compound 1. In one embodiment, Form A is a free base form of Compound 1. In another embodiment, Form A is crystalline.

In certain embodiments, Form A provided herein is obtained by equilibration experiments, evaporation experiments and anti-solvent recrystallization experiments (see Table 6, Table 7, and Table 9). In certain embodiments, Form A is obtained from certain solvent systems including heptane/water, heptanes, water, toluene, MeCN, MeCN/water, EtOH, EtOH/H$_2$O (about 1:1), THF/water (about 1:1), and IPA.

In one embodiment, a method of preparing Form A comprises the steps of contacting Compound 1 (e.g., a crystalline form of Compound 1 such as Form B, Form C, or Form H) with ambient conditions comprising greater than about 10%-20% relative humidity (RH).

In one embodiment, a method of preparing Form A comprises the steps of cooling Compound 1 in a solvent to a temperature less than about 50° C. and collecting solids.

Figure 2:
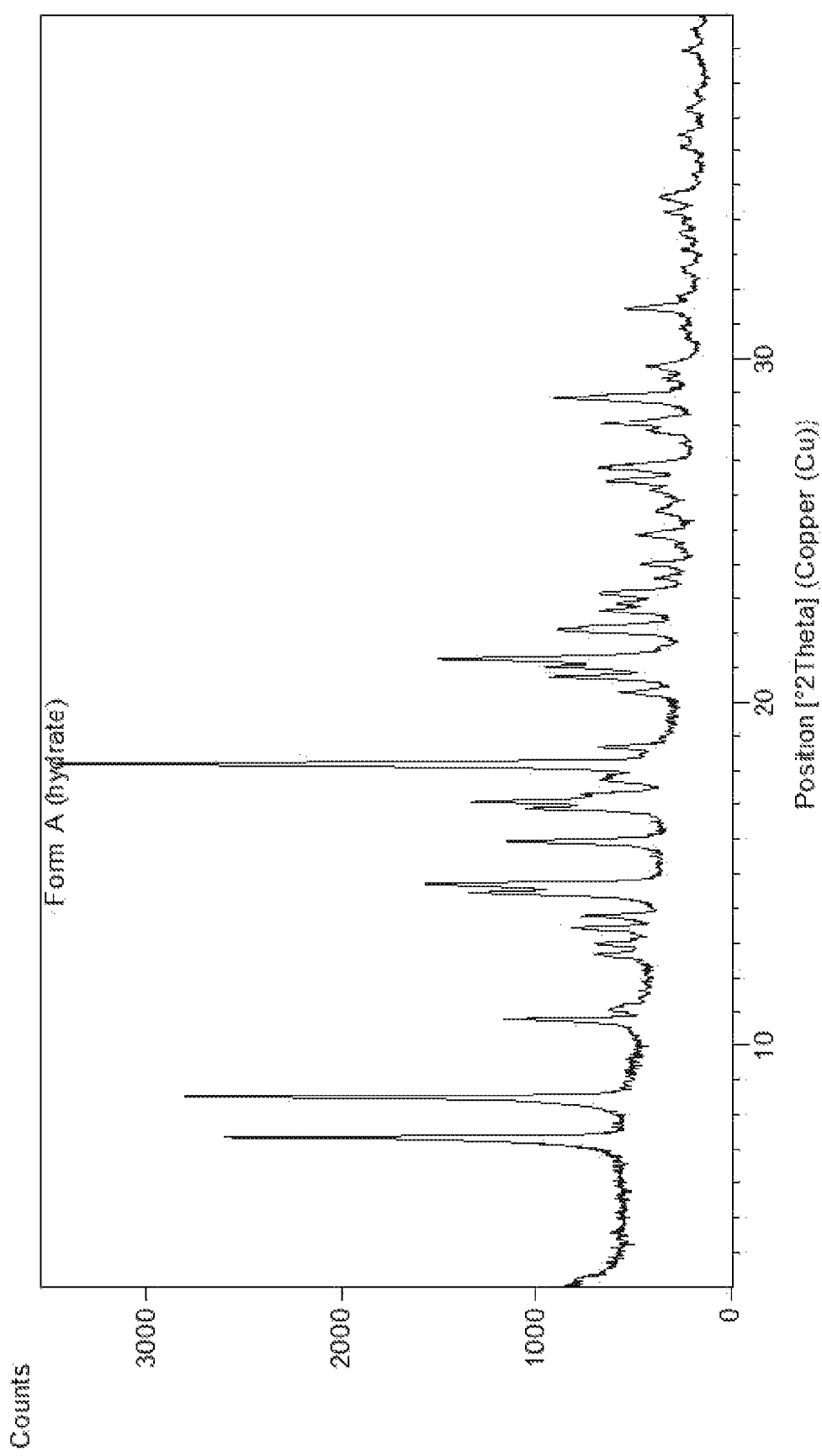
FIG. 2 depicts a XRPD Pattern of Free Base Form A.

In certain embodiments, a solid form provided herein, e.g., Form A, is the free base of Compound 1, and is substantially crystalline, as indicated by, e.g., X-ray powder diffraction measurements. In one embodiment, is an X-ray powder diffraction pattern (XRPD) substantially as shown in FIG. 2 (e.g. Form A). In one embodiment, a solid form provided herein, e.g., Form A, has one or more characteristic X-ray powder diffraction peaks at approximately 3.2, 7.3, 8.5, 10.7, 11.1, 12.7, 13.0, 13.4, 13.8, 14.5, 14.7, 15.9, 16.9, 17.1, 17.3, 17.7, 18.2, 18.7, 20.3, 20.7, 21.0, 21.3, 22.1, 22.7, 22.9, 23.2, 23.6, 24.0, 24.8, 25.5, 26.1, 26.4, 26.8, 27.9, 28.1, 28.8, 29.4, 29.8, 31.4, 31.8, 32.6, 33.1, 33.6, 33.9, 34.2, 34.7, 36.1, 36.5, 37.2, 37.7, 38.9, or 39.5,° 2θ (±0.2° 2θ) or (±0.1° 2θ) as depicted in FIG. 2. In a specific embodiment, a solid form provided herein has one, two, three, four, five, six, seven, eight, nine, ten, eleven, or twelve characteristic X-ray powder diffraction peaks at approximately 7.3, 8.5, 10.8, 14.5, 14.7, 15.9, 16.9, 17.1, 18.2, 21.0, 21.3, or 28.8° 2θ (±0.2° 2θ). In embodiments, the solid form is Form A. In another embodiment, a solid form provided herein has one, two, three or four characteristic X-ray powder diffraction peaks at approximately 7.3, 8.5, 18.2, or 21.3° 2θ (±0.2° 2θ). In another embodiment, Form A has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, or fifty-two characteristic X-ray powder diffraction peaks as set forth in Table 12.

Figure 3:
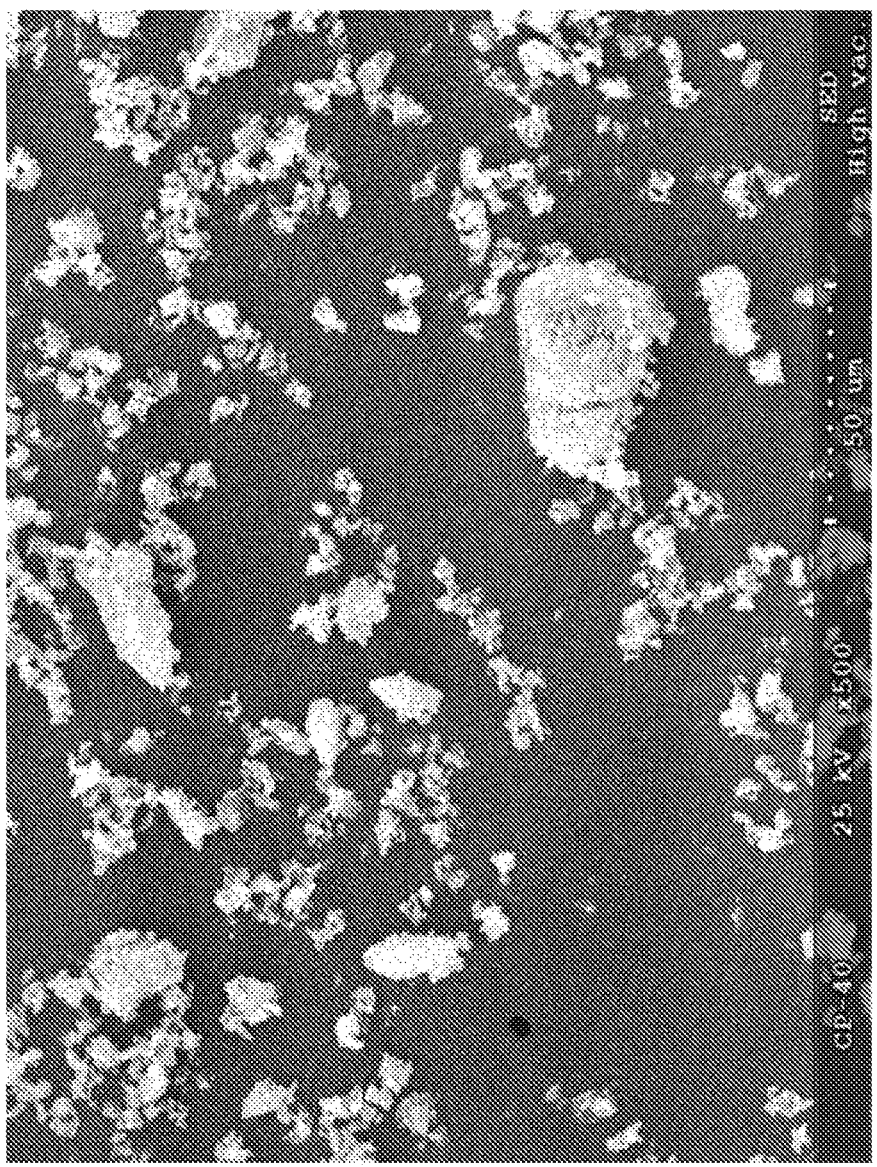
FIG. 3 depicts a SEM Picture of Free Base Form A.

In one embodiment, a solid form provided herein, e.g. Form A, has a SEM image substantially as shown in FIG. 3.

Figure 4:
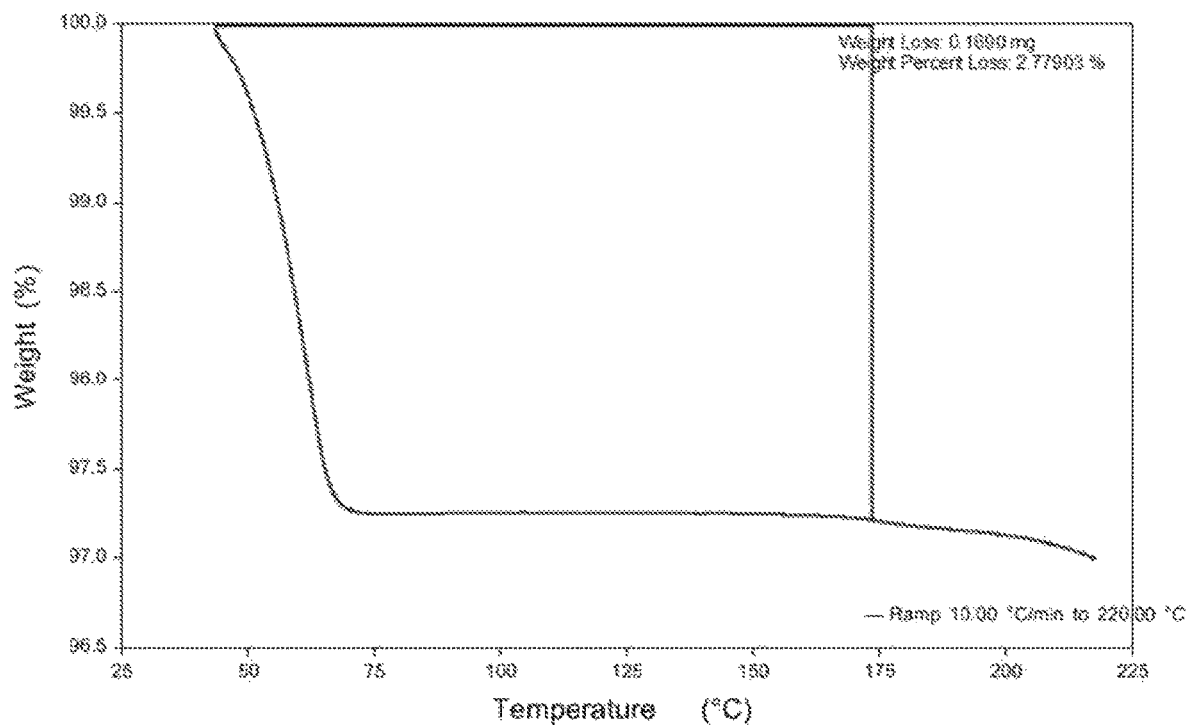
FIG. 4 depicts a TGA Thermogram of Free Base Form A.

In one embodiment, provided herein is a solid form, e.g. Form A, having a TGA thermograph corresponding substantially to the representative TGA thermogram as depicted in FIG. 4. In certain embodiments, the crystalline form exhibits a TGA thermogram comprising a total mass loss of approximately 2.8% of the total mass of the sample between approximately 50° C. and approximately 175° C. when heated from approximately 50° C. to approximately 220° C. Thus, in certain embodiments, the crystalline form loses about 2.8% its total mass when heated from about ambient temperature to about 220° C.

Figure 5:
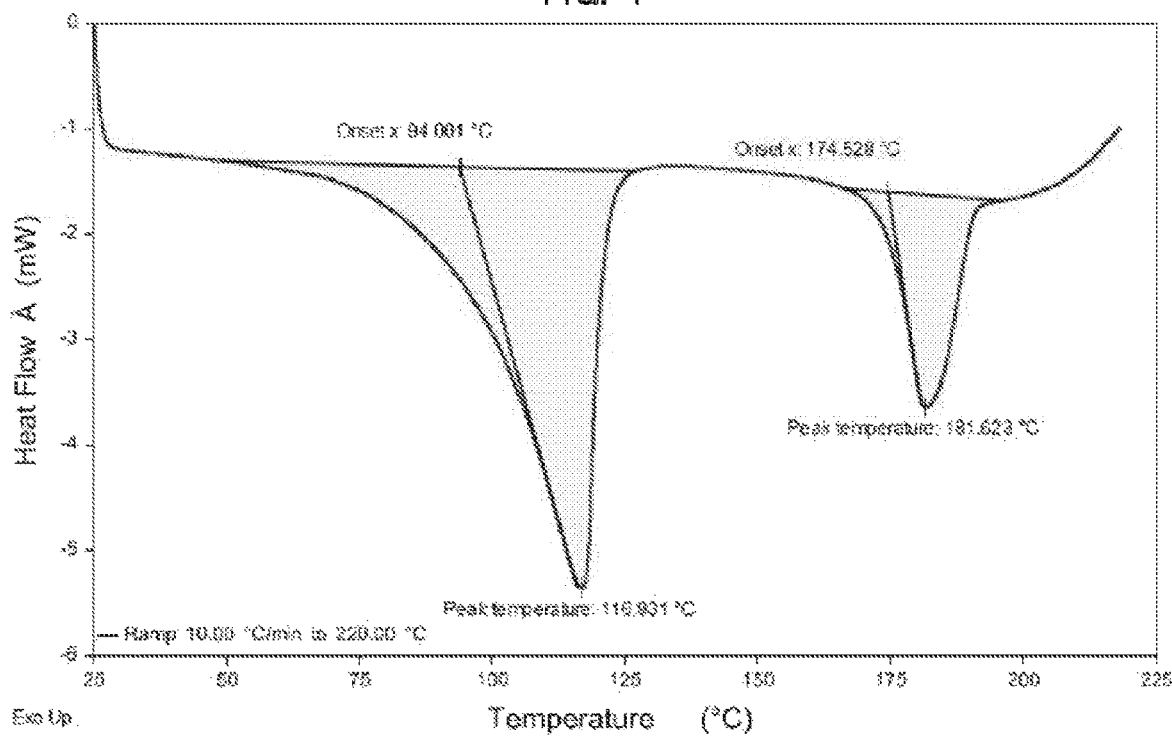
FIG. 5 depicts a DSC Thermogram of Free Base Form A.

In one embodiment, provided herein is a solid form, e.g. Form A, having a DSC thermogram substantially as depicted in FIG. 5 comprising an endothermic event with an onset temperature of about 94° C. and a peak maximum temperature of about 117° C. In one embodiment, provided herein is a solid form, e.g. Form A, having a DSC thermogram substantially as depicted in FIG. 5 comprising an endothermic event with an onset temperature of about 174° C. and a peak maximum temperature of about 182° C. when heated from approximately 25° C. to approximately 220° C.

Figures 6A, 6B:
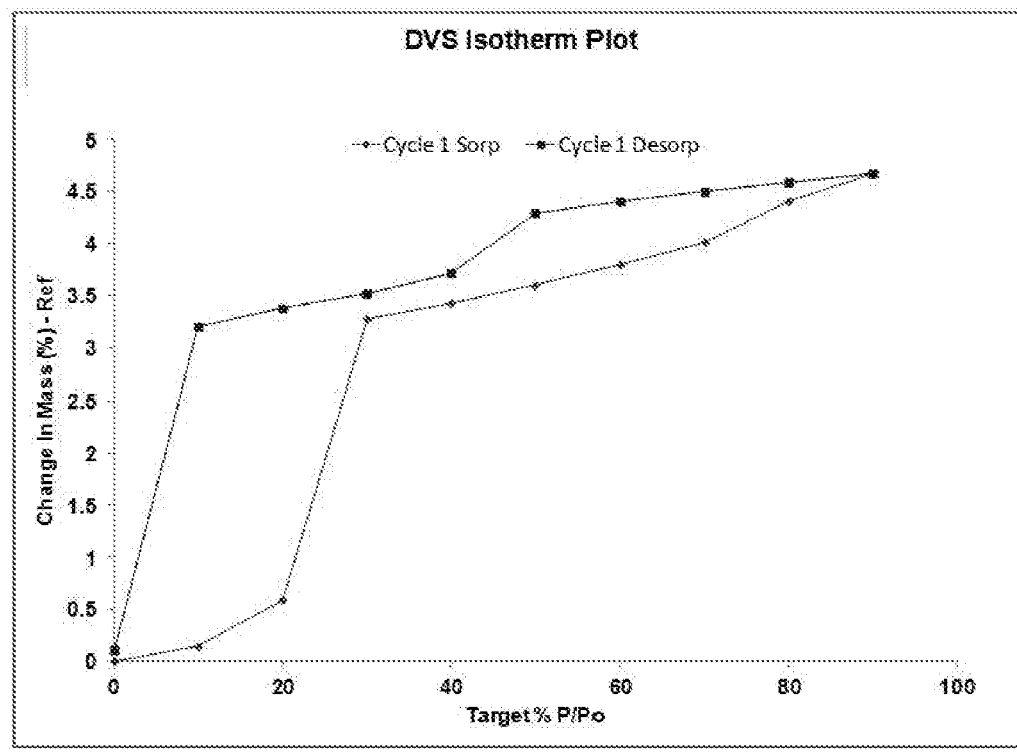
FIG. 6A depicts a DVS Isotherm Plot of Free Base Form A.
FIG. 6B depicts the values of the Isotherm Plot of FIG. 6A.

In one embodiment, provided herein is a solid form, e.g. Form A, having a DVS isotherm plot substantially as depicted in FIG. 6A.

Figure 7:
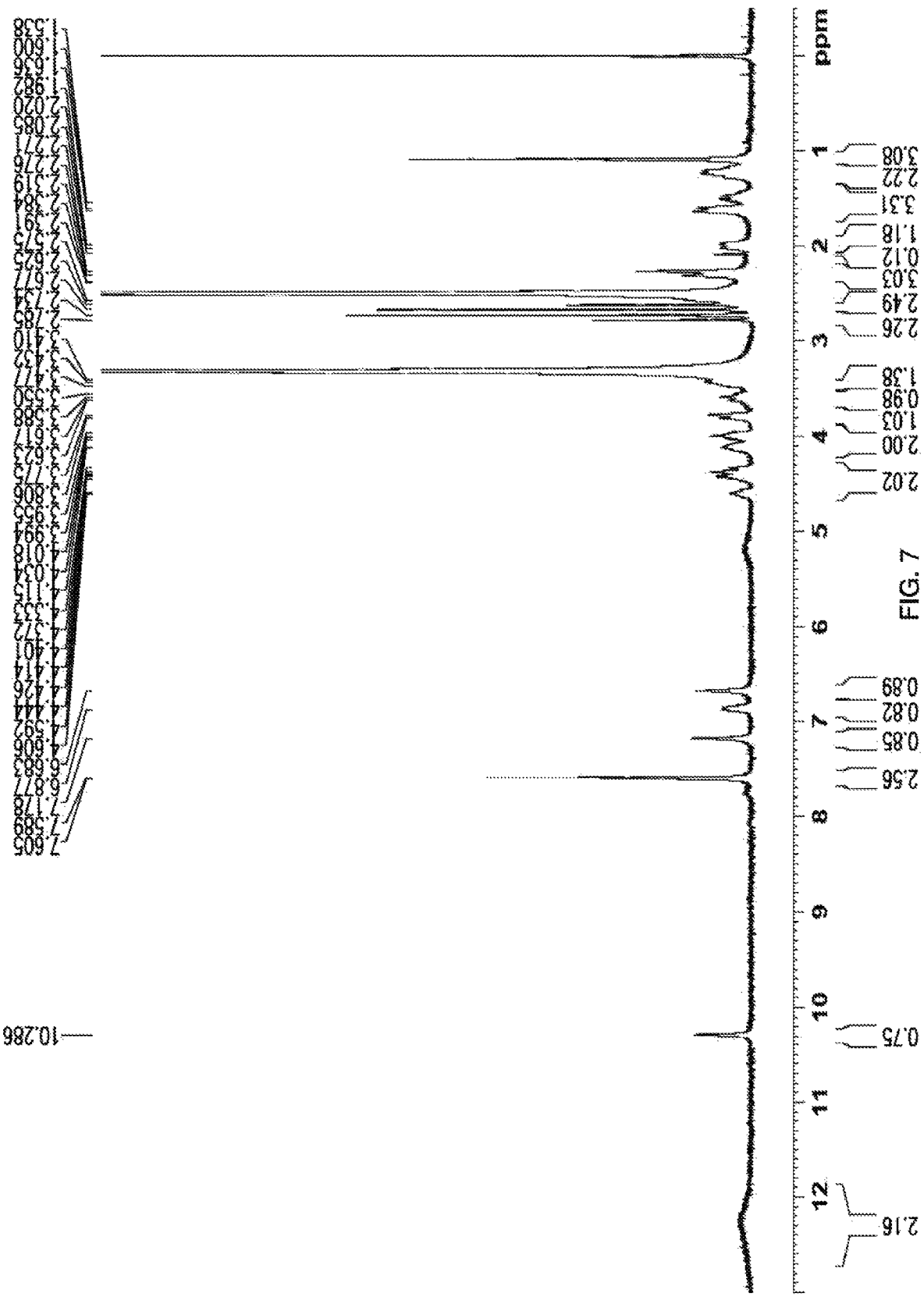
FIG. 7 depicts a $^1$H NMR Spectrum of Free Base Form A.

In one embodiment, provided herein is Form A having a $^1$H NMR spectrum substantially as depicted in FIG. 7.

In still another embodiment, Form A is substantially pure. In certain embodiments, the substantially pure Form A is substantially free of other solid forms, e.g., amorphous solid. In certain embodiments, the substantially pure Form A is substantially free of Form B, Form C, or Form H. In certain embodiments, the purity of the substantially pure Form A is no less than about 95%, no less than about 96%, no less than about 97%, no less than about 98%, no less than about 98.5%, no less than about 99%, no less than about 99.5%, or no less than about 99.8%.

Form B

In certain embodiments, provided herein is Form B.

In one embodiment, Form B is a solid form of Compound 1. In another embodiment, Form B is crystalline. In one embodiment, Form B is an anhydrate form of Compound 1.

In certain embodiments, Form B provided herein is obtained by equilibration experiments, evaporation experiments and anti-solvent recrystallization experiments (see Table 6, Table 7, and Table 9). In certain embodiments, Form B is obtained from certain solvent systems including heptane/water, heptanes, water, toluene, MeCN, MeCN/water, EtOH, EtOH/H$_2$O (about 1:1), THF/water (about 1:1), and IPA. In certain embodiments, Form B is obtained by drying or reducing the RH subjected to Form A to less than about 10%.

Figure 8:
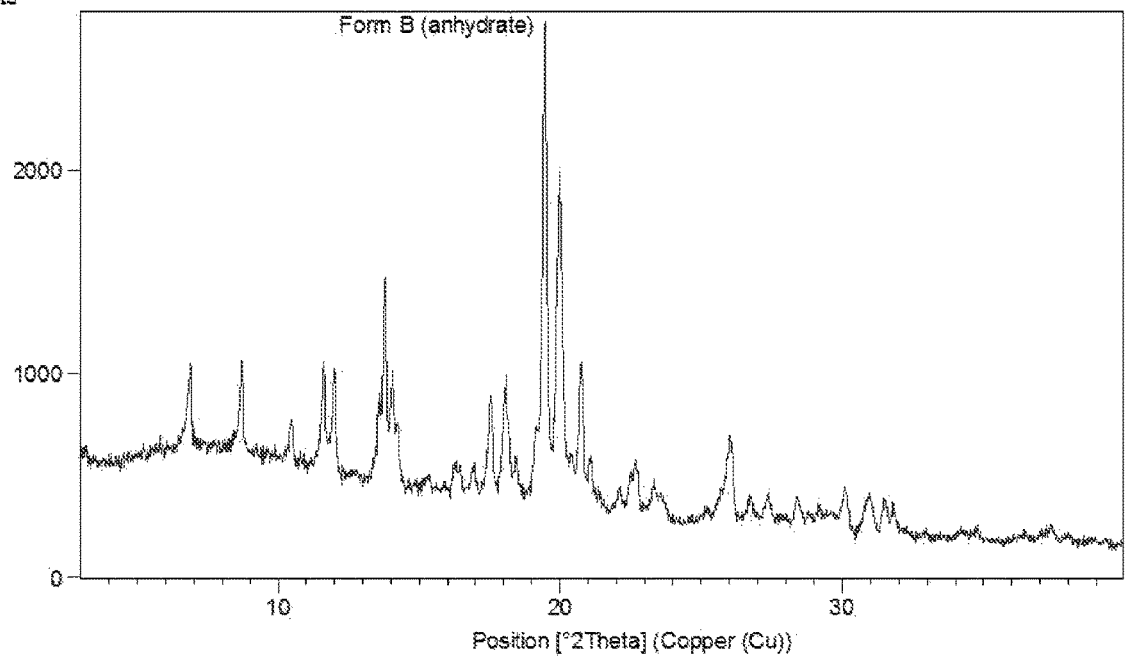
FIG. 8 depicts a XRPD Pattern of Free Base Form B.

In certain embodiments, a solid form provided herein, e.g., Form B, is substantially crystalline, as indicated by, e.g., X-ray powder diffraction measurements. In one embodiment, Form B has an X-ray powder diffraction pattern substantially as shown in FIG. 8. In one embodiment, a solid form provided herein, e.g. Form B, has one or more characteristic X-ray powder diffraction peaks at approximately 6.9, 8.7, 10.5, 11.6, 12.0, 13.6, 13.8, 14.1, 14.2, 16.3, 16.9, 17.5, 18.0, 18.4, 19.1, 19.5, 20.0, 20.8, 21.1, 22.1, 22.7, 23.3, 25.2, 26.0, 26.7, 27.4, 28.4, 28.8, 29.2, 30.1, 31.0, 31.5, or 31.8° 2θ (±0.2° 2θ) or (±0.1° 2θ) as depicted in FIG. 8. In a specific embodiment, a solid form provided herein has one, two, three, four, five, six, seven, eight, nine, or ten characteristic X-ray powder diffraction peaks at approximately 8.7, 11.6, 12.0, 13.8, 14.1, 17.5, 18.0, 19.5, 20.0, or 20.8° 2θ (±0.2° 2θ). In a specific embodiment, a solid form provided herein has one, two, three, or four characteristic X-ray powder diffraction peaks at approximately 13.8, 19.5, 20.0, or 20.8° 2θ (±0.2° 2θ). In one embodiment, the solid form is Form B. In another embodiment, Form B has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, or thirty-three characteristic X-ray powder diffraction peaks as set forth in Table 13.

Figure 9:
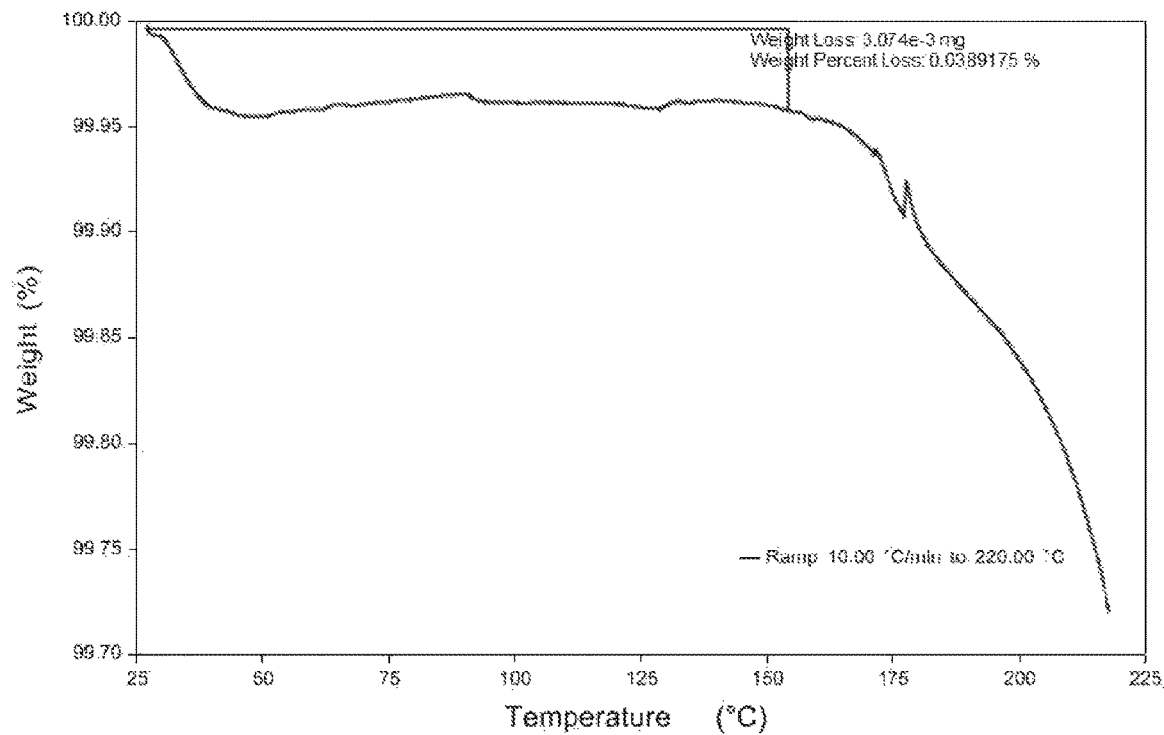
FIG. 9 depicts a TGA Thermogram of Free Base Form B.

In one embodiment, provided herein is a crystalline form of Compound 1, e.g. Form B, having a TGA thermograph corresponding substantially to the representative TGA thermogram as depicted in FIG. 9. In certain embodiments, the crystalline form exhibits a TGA thermogram comprising a total mass loss of approximately 0.1% of the total mass of the sample between approximately 30° C. and approximately 155° C. when heated from approximately 25° C. to approximately 220° C. Thus, in certain embodiments, the crystalline form loses about 0.1% of its total mass when heated from about ambient temperature to about 220° C. In certain embodiments, the crystalline form is an anhydrate of Compound 1 and corresponds to Form B.

Figure 10:
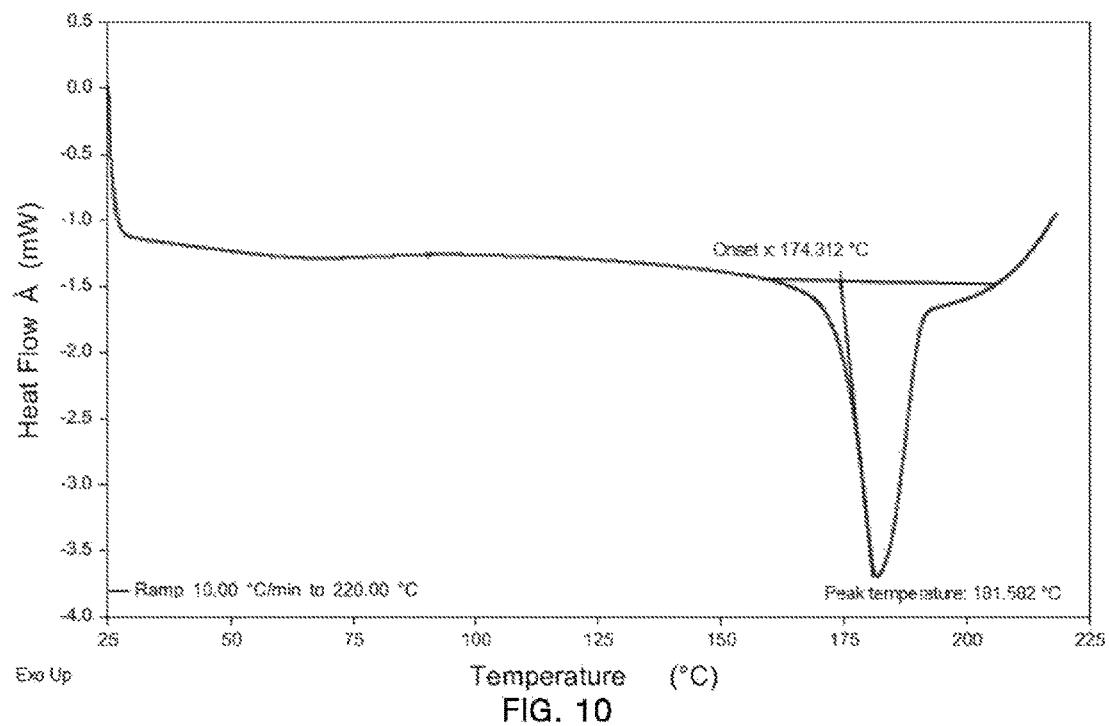
FIG. 10 depicts a DSC Thermogram of Free Base Form B.

In one embodiment, provided herein is a crystalline form of Compound 1 having a DSC thermogram as depicted in FIG. 10 comprising an endothermic event with on onset temperature at about 174° C. and a peak maximum temperature at about 182° C. when heated from approximately 25° C. to approximately 220° C.

In still another embodiment, Form B is substantially pure. In certain embodiments, the substantially pure Form B is substantially free of other solid forms, e.g., amorphous solid. In another embodiment, Form B is substantially free of Form A. In certain embodiments, the purity of the substantially pure Form B is no less than about 95%, no less than about 96%, no less than about 97%, no less than about 98%, no less than about 98.5%, no less than about 99%, no less than about 99.5%, or no less than about 99.8%.

Form C

In certain embodiments, provided herein is Form C.

In one embodiment, Form C is a solid form of Compound 1. In another embodiment, Form C is crystalline. In one embodiment, Form C is a solvated form of Compound 1. In one embodiment, Form C is an acetonitrile (MeCN) solvated form of Compound 1.

In certain embodiments, Form C provided herein is obtained by equilibration experiments, evaporation experiments, cooling recrystallization experiments and anti-solvent recrystallization experiments (see Table 6, Table 7, and Table 9). In certain embodiments, Form C is obtained from certain solvent systems including MeCN or MeCN/$H_2O$ (about 1:1). In certain embodiments, Form C is obtained from certain solvent systems including MeCN or MeCN/$H_2O$ (about 1:1) at a temperature of about 50° C. In another embodiment, Form C is obtained from a solution of 2-MeTHF/$H_2O$ (about 1:1) distilled under vacuum at constant volume with addition of MeCN.

Figure 11:
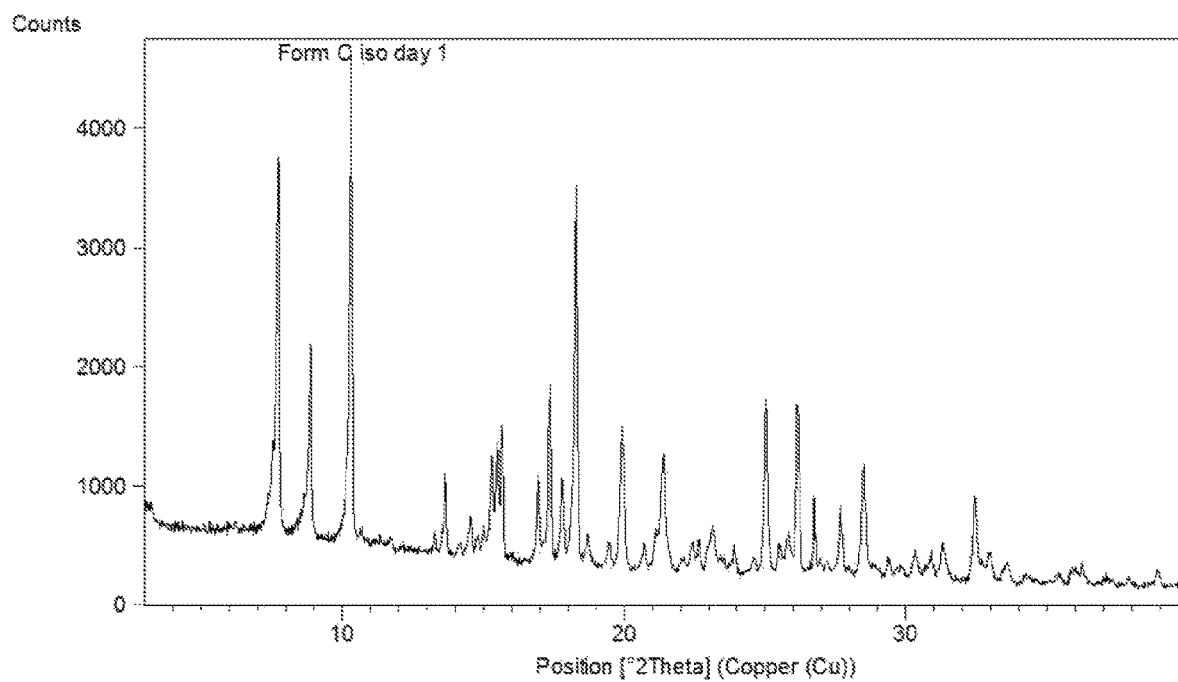
FIG. 11 depicts a XRPD Pattern of Free Base Form C.

In certain embodiments, a solid form provided herein, e.g., Form C, is substantially crystalline, as indicated by, e.g., X-ray powder diffraction measurements. In one embodiment, Form C has an X-ray powder diffraction pattern substantially as shown in FIG. 11. In one embodiment, a solid form provided herein, e.g. Form C, has one or more characteristic X-ray powder diffraction peaks at approximately 3.1, 7.7, 8.9, 10.3, 13.3, 13.7, 14.2, 14.6, 14.8, 15.0, 15.3, 15.5, 15.7, 16.9, 17.4, 17.8, 18.3, 18.7, 19.5, 19.9, 20.7, 21.1, 21.4, 22.1, 22.4, 22.7, 23.1, 23.9, 24.6, 25.0, 25.5, 25.8, 26.1, 26.7, 26.9, 27.2, 27.7, 28.5, 29.4, 29.8, 30.3, 30.9, 31.3, 32.4, 33.0, 33.6, 34.3, 35.4, 35.9, 36.2, 37.1, 37.9, or 38.9° 2θ (±0.2° 2θ) or (±0.1° 2θ) as depicted in FIG. 11. In a specific embodiment, a solid form provided herein has one, two, three, four, five, six, seven, eight, or nine characteristic X-ray powder diffraction peaks at approximately 7.7, 8.9, 10.3, 15.3, 17.4, 18.3, 19.9, 21.4, or 28.5° 2θ (±0.2° 2θ). In one embodiment, the solid form is Form C. In another embodiment, a solid form provided herein, e.g. Form C, has one, two, three or four characteristic X-ray powder diffraction peaks at approximately 7.7, 8.9, 10.3, or 18.3° 2θ (±0.2° 2θ). In another embodiment, Form C has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, or fifty-three characteristic X-ray powder diffraction peaks as set forth in Table 14.

Figure 12:
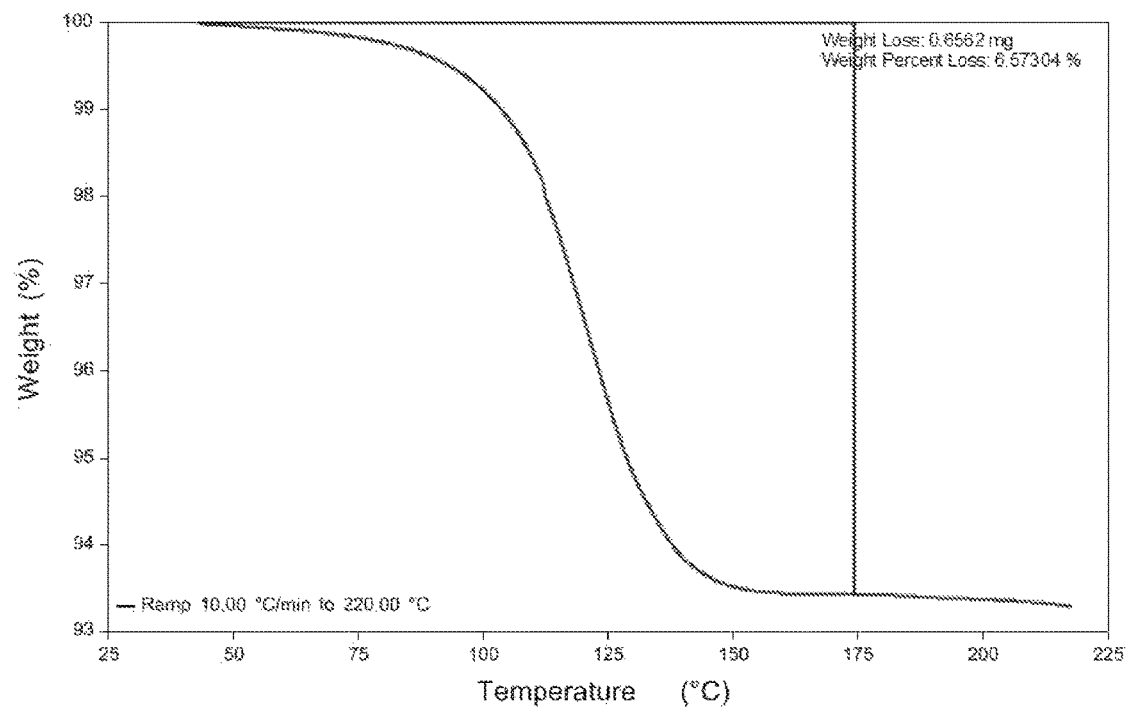
FIG. 12 depicts a TGA Thermogram of Free Base Form C.

In one embodiment, provided herein is a crystalline form of Compound 1 having a TGA thermograph corresponding substantially to the representative TGA thermogram as depicted in FIG. 12. In certain embodiments, the crystalline form exhibits a TGA thermogram comprising a total mass loss of approximately 6.6% of the total mass of the sample between approximately 50° C. and approximately 175° C. when heated from approximately 25° C. to approximately 220° C. Thus, in certain embodiments, the crystalline form loses about 6.6% of its total mass when heated from about ambient temperature to about 220° C. The theoretical MeCN content of MeCN mono-solvate of Compound 1 is 6.7% by weight, matching the TGA weight loss observed.

Figure 13:
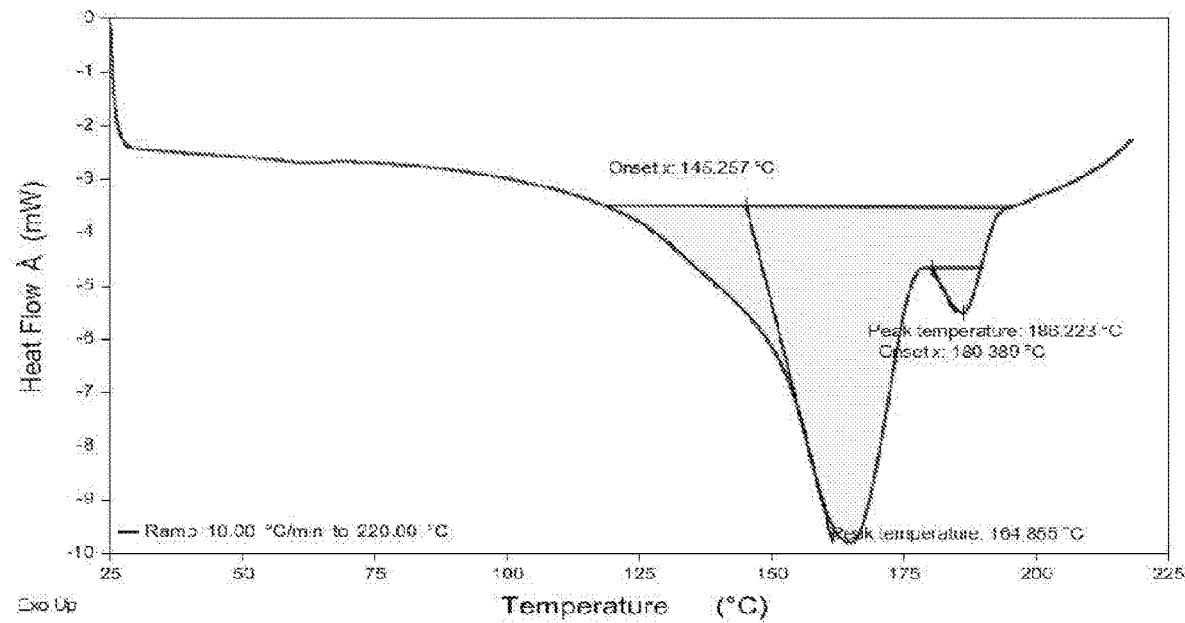
FIG. 13 depicts a DSC Thermogram of Free Base Form C.

In one embodiment, provided herein is a crystalline form of Compound 1 having a DSC thermogram as depicted in FIG. 13 comprising an endothermic event with a maximum at about 165° C. when heated from approximately 25° C. to approximately 300° C. In another embodiment, provided herein is a crystalline form of Compound 1 having a DSC thermogram as depicted in FIG. 13 further comprising an endothermic event with a maximum at about 186° C. when heated from approximately 25° C. to approximately 300° C.

Figure 14:
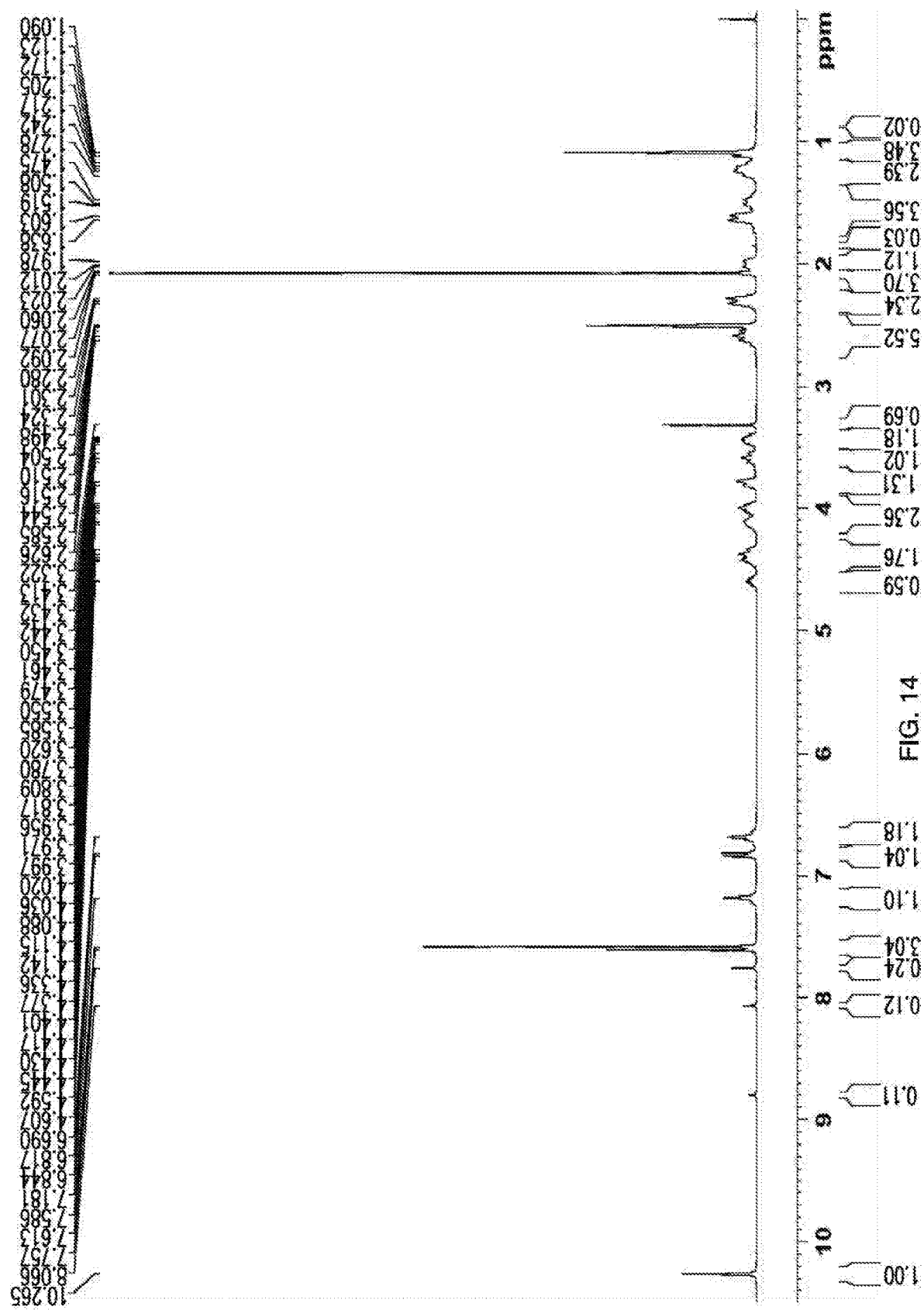
FIG. 14 depicts a $^1$H NMR Spectrum of Free Base Form C.

In one embodiment, provided herein is a solid form, e.g. Form C, having a $^1H$ NMR spectrum substantially as depicted in FIG. 14.

In still another embodiment, Form C is substantially pure. In certain embodiments, the substantially pure Form C is substantially free of other solid forms, e.g., amorphous solid. In certain embodiments, the purity of the substantially pure Form C is no less than about 95%, no less than about 96%, no less than about 97%, no less than about 98%, no less than about 98.5%, no less than about 99%, no less than about 99.5%, or no less than about 99.8%.

Form D

In certain embodiments, provided herein is Form D.

In one embodiment, Form D is a solid form of Compound 1. In another embodiment, Form D is crystalline. In one embodiment, Form D is a solvated form of Compound 1. In one embodiment, Form D is an IPA solvated form of Compound 1.

In certain embodiments, Form D provided herein is obtained by equilibration experiments, evaporation experiments, cooling recrystallization experiments and anti-solvent recrystallization experiments (see Table 6, Table 7, and Table 9). In certain embodiments, Form D is obtained from certain solvent systems including IPA at room temperature.

Figure 15:
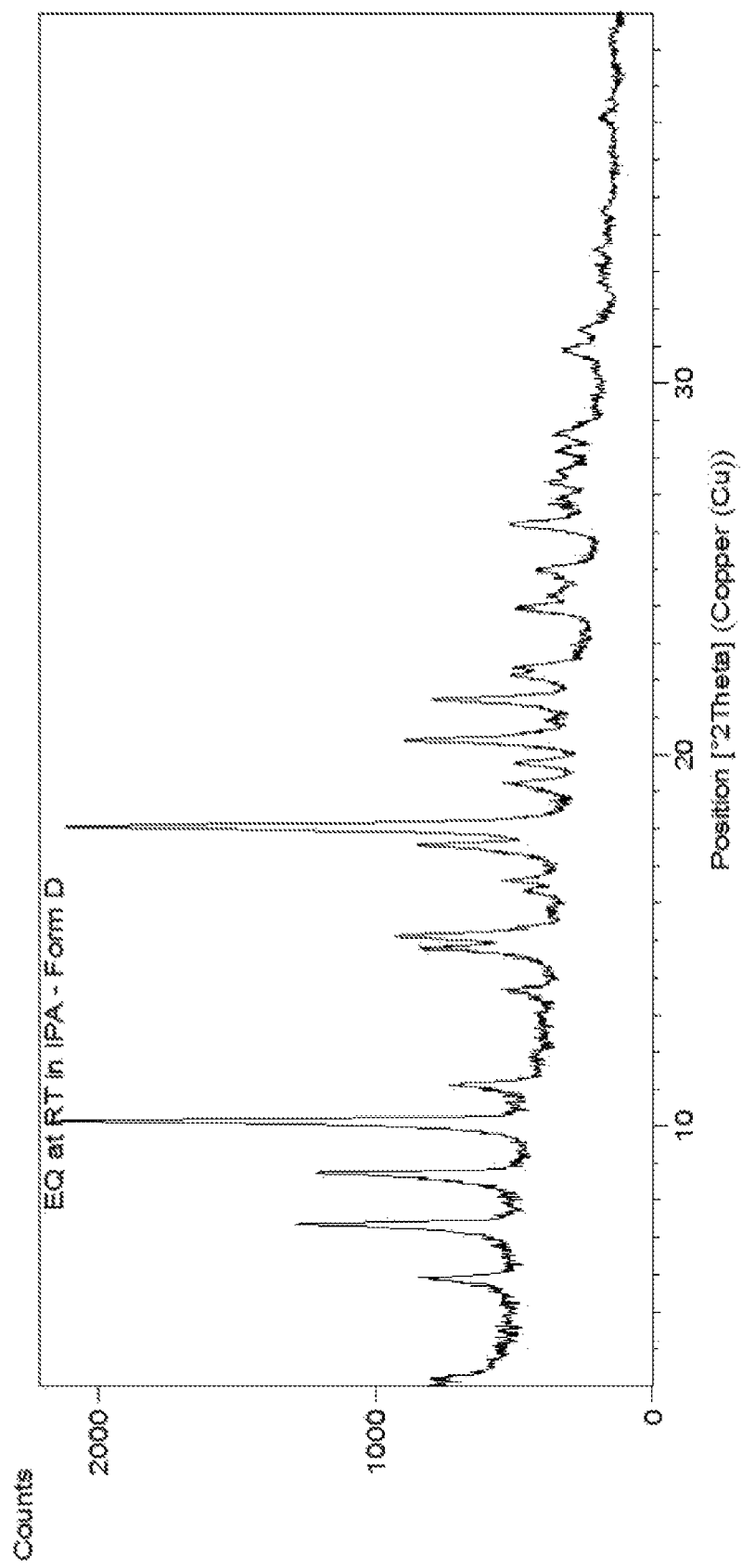
FIG. 15 depicts a XRPD Pattern of Free Base Form D.

In certain embodiments, a solid form provided herein, e.g., Form D, is substantially crystalline, as indicated by, e.g., X-ray powder diffraction measurements. In one embodiment, Form D has an X-ray powder diffraction pattern substantially as shown in FIG. 15. In one embodiment, a solid form provided herein, e.g. Form D, has one or more characteristic X-ray powder diffraction peaks at approximately 3.1, 5.9, 7.4, 8.7, 10.1, 11.1, 13.7, 14.8, 15.1, 16.3, 16.6, 17.6, 18.1, 19.2, 19.8, 20.4, 21.5, 22.1, 22.3, 24.0, 24.3, 25.0, 26.2, 26.9, 27.3, 27.6, 28.2, 28.6, 30.9, 31.4, 32.9, 33.6, 34.6, or 37.2° 2θ (±0.2° 2θ) or (±0.1° 2θ) as depicted in FIG. 15. In a specific embodiment, a solid form provided herein has one, two, three, or four characteristic X-ray powder diffraction peaks at approximately 7.4, 8.7, 10.1, or 18.1° 2θ (±0.2° 2θ). In one embodiment, the solid form is Form D. In another embodiment, Form D has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, or thirty-four characteristic X-ray powder diffraction peaks as set forth in Table 15.

Figure 16:
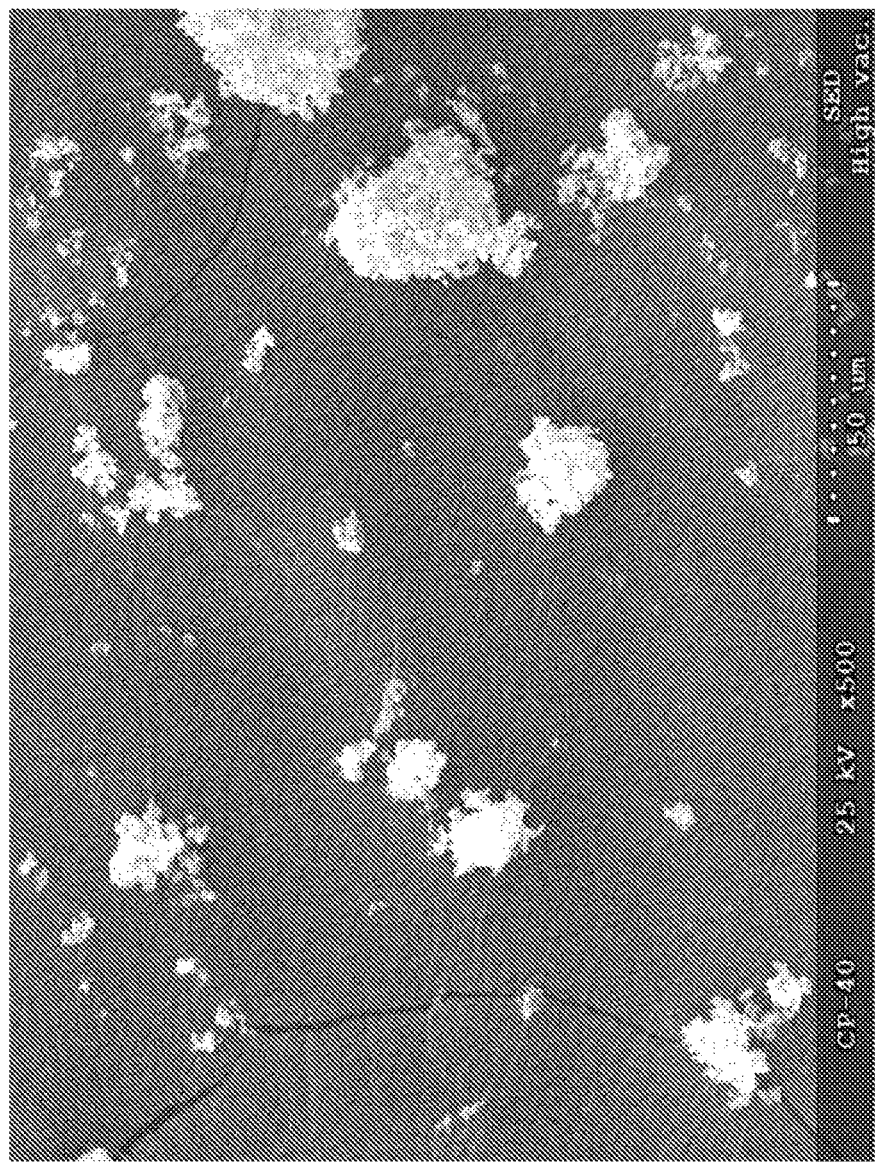
FIG. 16 depicts a SEM Picture of Free Base Form D.

In one embodiment, a solid form provided herein, e.g. Form D has a SEM image substantially as shown in FIG. 16.

Figure 17:
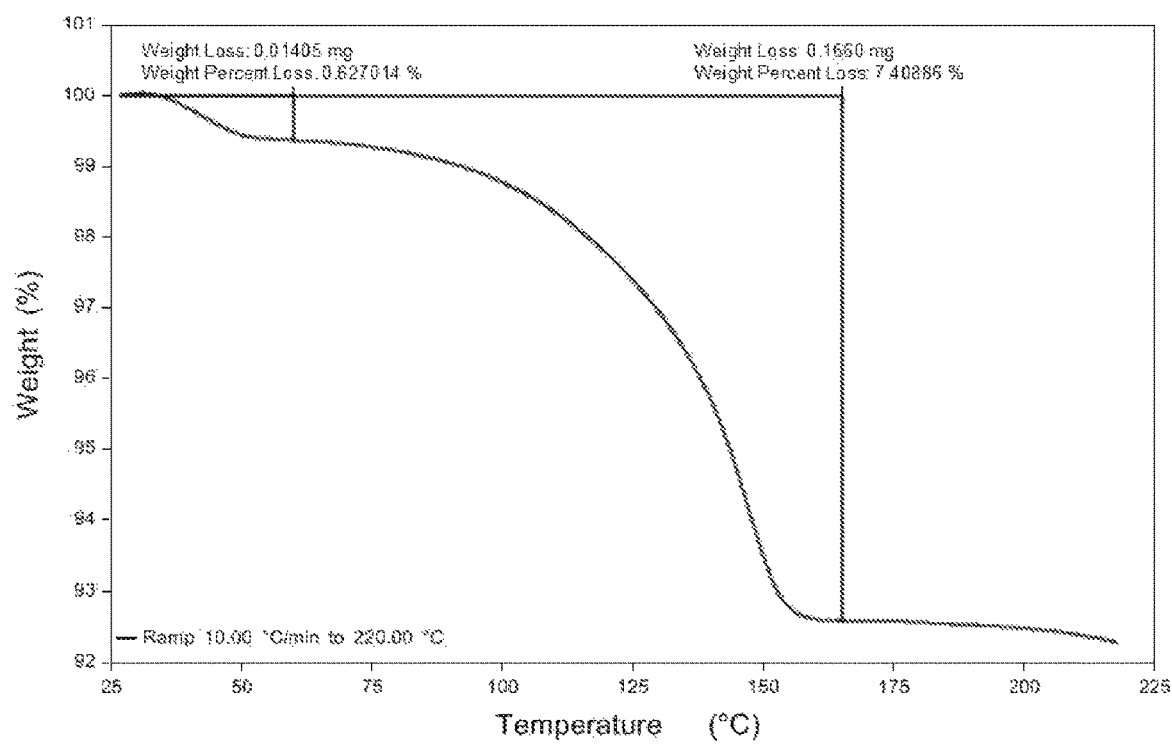
FIG. 17 depicts a TGA Thermogram of Free Base Form D.

In one embodiment, provided herein is a crystalline form of Compound 1 having a TGA thermograph corresponding substantially to the representative TGA thermogram as depicted in FIG. 17. In certain embodiments, the crystalline form exhibits a TGA thermogram comprising a total mass loss of approximately 7.4% of the total mass of the sample between approximately 100° C. and approximately 160° C. when heated from approximately 25° C. to approximately 220° C. Thus, in certain embodiments, the crystalline form loses about 7.4% of its total mass when heated from about ambient temperature to about 220° C.

Figure 18:
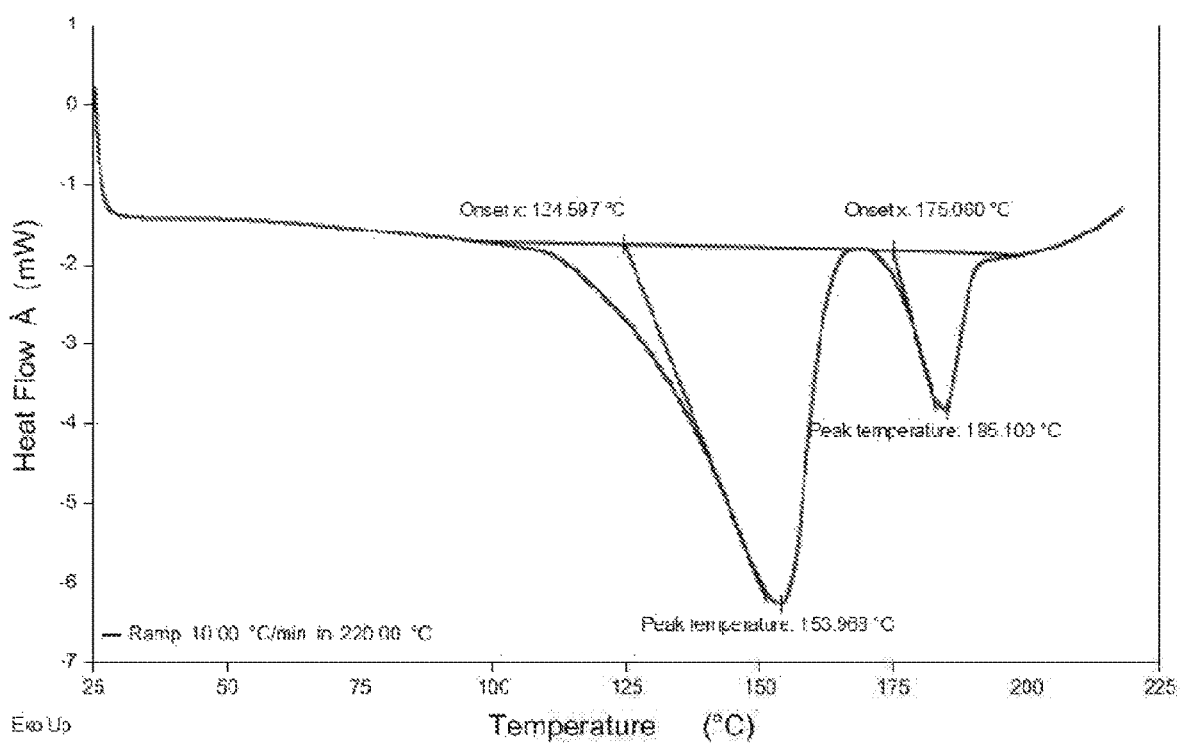
FIG. 18 depicts a DSC Thermogram of Free Base Form D.

In one embodiment, provided herein is a crystalline form of Compound 1 having a DSC thermogram as depicted in FIG. 18 comprising an endothermic event with an onset temperature at about 125° C. and a peak maximum temperature at about 154° C. when heated from approximately 25° C. to approximately 220° C. In one embodiment, provided herein is a crystalline form of Compound 1 having a DSC thermogram as depicted in FIG. 18 further comprising an endothermic event with an onset temperature at about 175° C. and a peak maximum temperature at about 185° C. when heated from approximately 25° C. to approximately 220° C.

Figure 19:
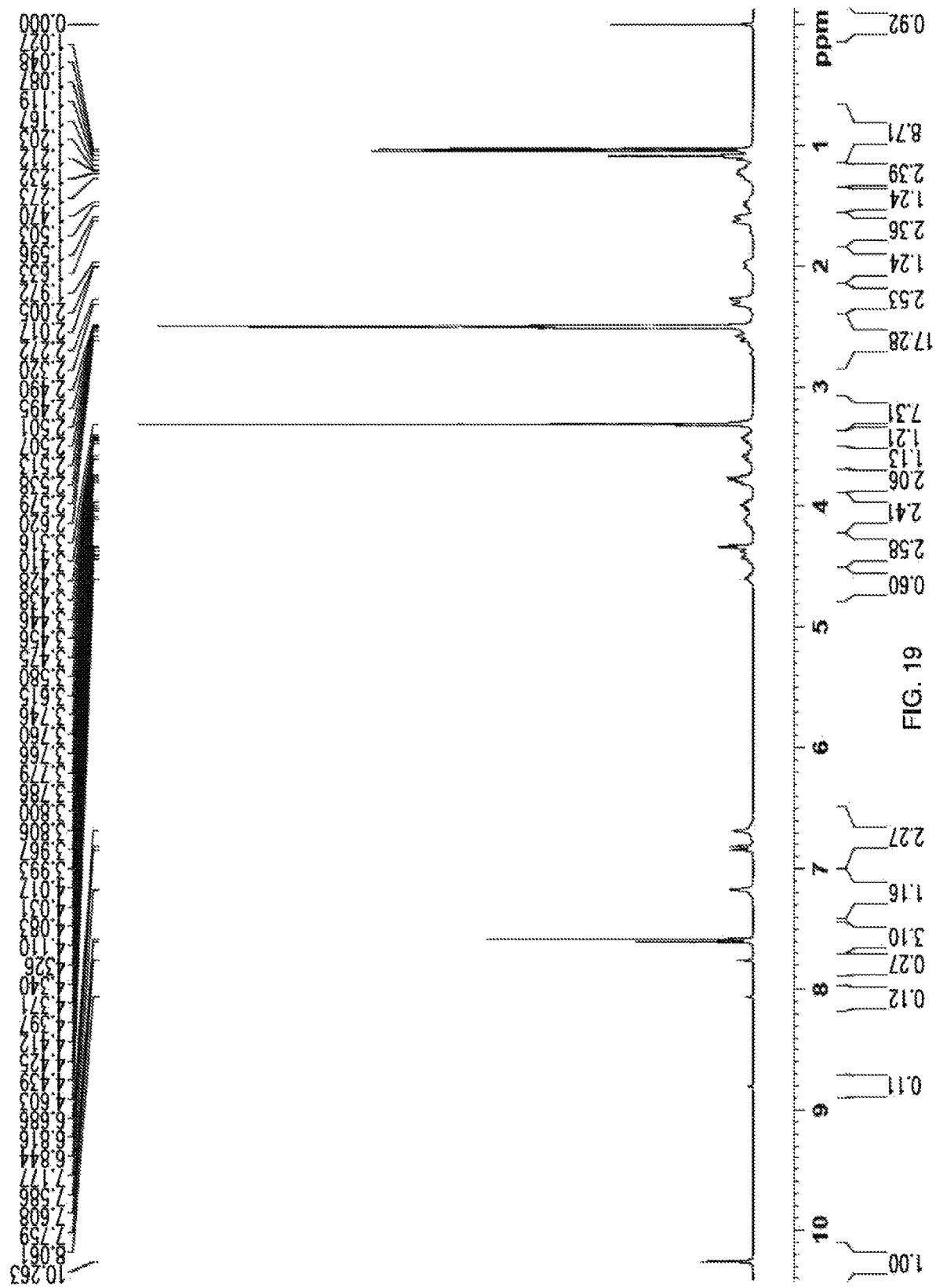
FIG. 19 depicts a $^1$H NMR Spectrum of Free Base Form D

In one embodiment, provided herein is a solid form provided herein, e.g. Form D, having a $^1$H NMR spectrum substantially as depicted in FIG. 19.

In still another embodiment, Form D is substantially pure. In certain embodiments, the substantially pure Form D is substantially free of other solid forms, e.g., amorphous solid. In certain embodiments, the purity of the substantially pure Form D is no less than about 95%, no less than about 96%, no less than about 97%, no less than about 98%, no less than about 98.5%, no less than about 99%, no less than about 99.5%, or no less than about 99.8%.

Form E

In certain embodiments, provided herein is Form E.

In one embodiment, Form E is a solid form of Compound 1. In another embodiment, Form E is crystalline. In one embodiment, Form E is a solvated form of Compound 1. Form E can be an ethanol solvate where the solvate optionally contains water.

In certain embodiments, Form E provided herein is obtained by equilibration experiments and evaporation experiments (see Table 6, Table 7, and Table 9). In certain embodiments, Form E is obtained from certain solvent systems including EtOH or EtOH/water (about 1:1). In certain embodiments, Form E is obtained from certain solvent systems including EtOH or EtOH/water (about 1:1) at a temperature of about 50° C.

Figure 20:
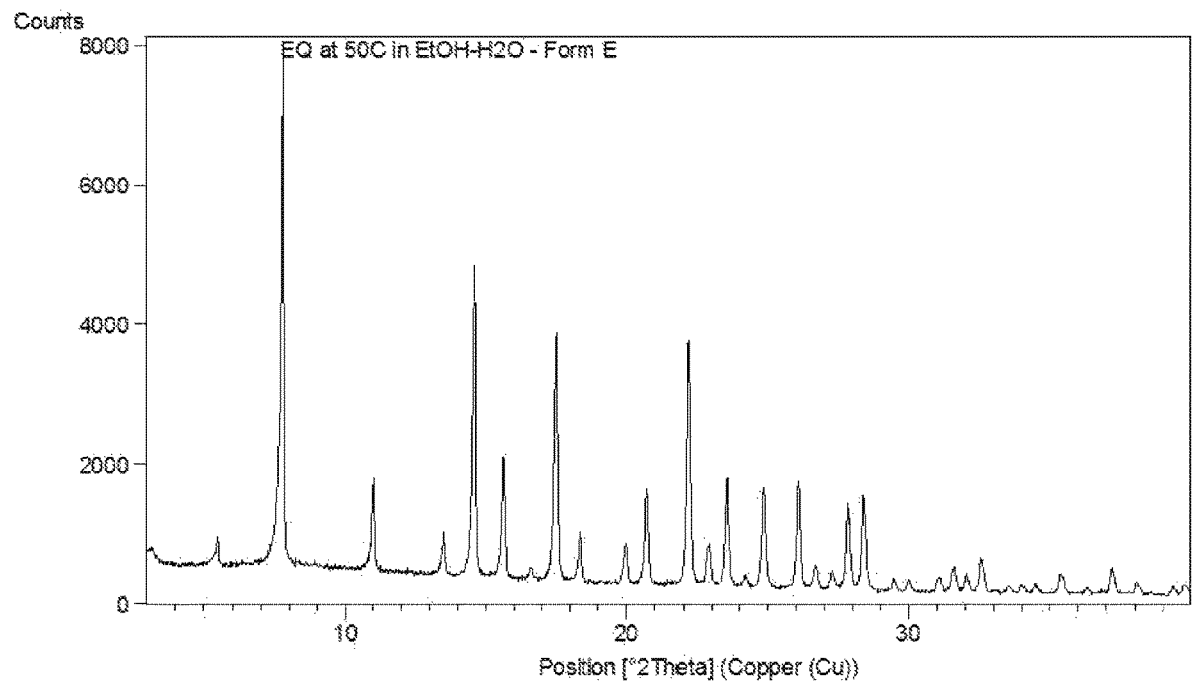
FIG. 20 depicts a XRPD Pattern of Free Base Form E.

In certain embodiments, a solid form provided herein, e.g., Form E, is substantially crystalline, as indicated by, e.g., X-ray powder diffraction measurements. In one embodiment, Form E has an X-ray powder diffraction pattern substantially as shown in FIG. 20. In one embodiment, a solid form provided herein, e.g. Form E, has one or more characteristic X-ray powder diffraction peaks at approximately 3.1, 5.5, 7.8, 11.0, 13.5, 14.6, 15.6, 16.6, 17.5, 18.4, 20.0, 20.7, 22.2, 22.9, 23.5, 24.2, 24.8, 26.1, 26.7, 27.3, 27.8, 28.4, 29.5, 30.0, 31.1, 31.6, 32.1, 32.6, 33.6, 34.0, 34.5, 35.4, 36.3, 37.2, 38.1, 39.4, or 39.8° 2θ (±0.2° 2θ) or (±0.1° 2θ) as depicted in FIG. 20. In a specific embodiment, a solid form provided herein has one, two, three, four, five, six, or seven characteristic X-ray powder diffraction peaks at approximately 7.8, 14.6, 15.6, 17.5, 22.2, 23.5, or 26.1° 2θ (±0.2° 2θ). In one embodiment, the solid form is Form E. In another embodiment, a solid form provided herein, e.g. Form E, has one, two, three or four characteristic X-ray powder diffraction peaks at approximately 7.8, 14.6, 17.5, or 22.2° 2θ (±0.2° 2θ). In another embodiment, Form E has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, or thirty-seven characteristic X-ray powder diffraction peaks as set forth in Table 16.

Figure 21:
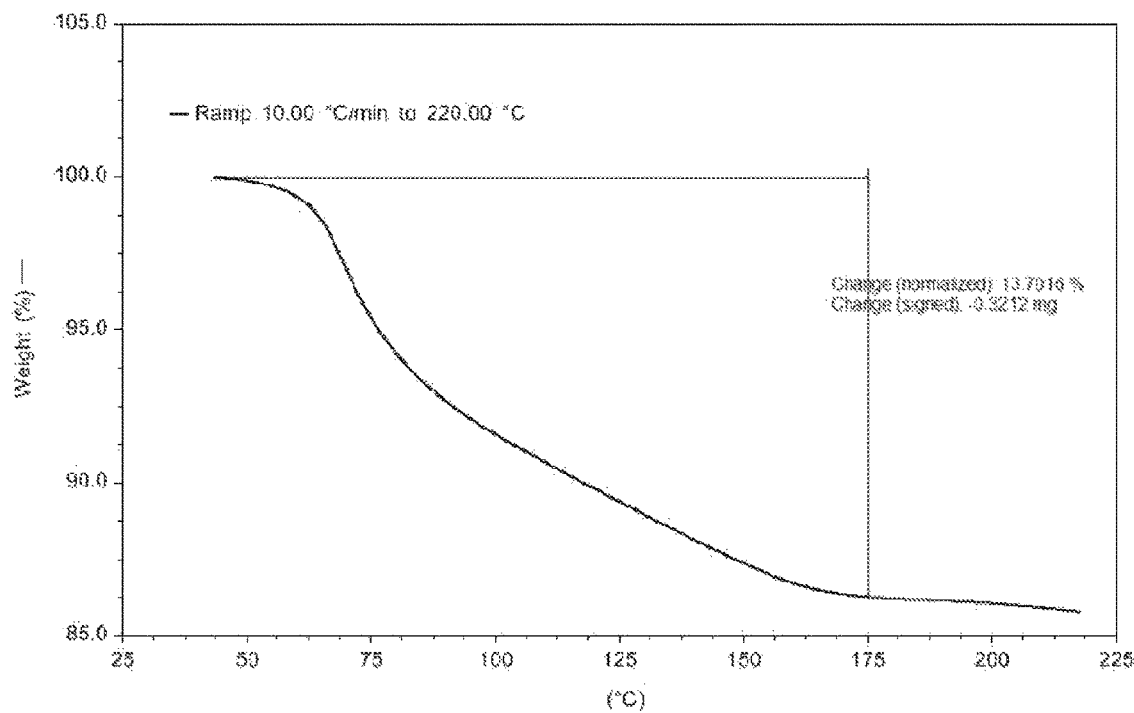
FIG. 21 depicts a TGA Thermogram of Free Base Form E.

In one embodiment, provided herein is a crystalline form of Compound 1 having a TGA thermograph corresponding substantially to the representative TGA thermogram as depicted in FIG. 21. In certain embodiments, the crystalline form exhibits a TGA thermogram comprising a total mass loss of approximately 13.7% of the total mass of the sample between approximately 35° C. and approximately 175° C. when heated from approximately 35° C. to approximately 220° C. Thus, in certain embodiments, the crystalline form loses about 13.7% of its total mass when heated from about ambient temperature to about 220° C.

Figure 22:
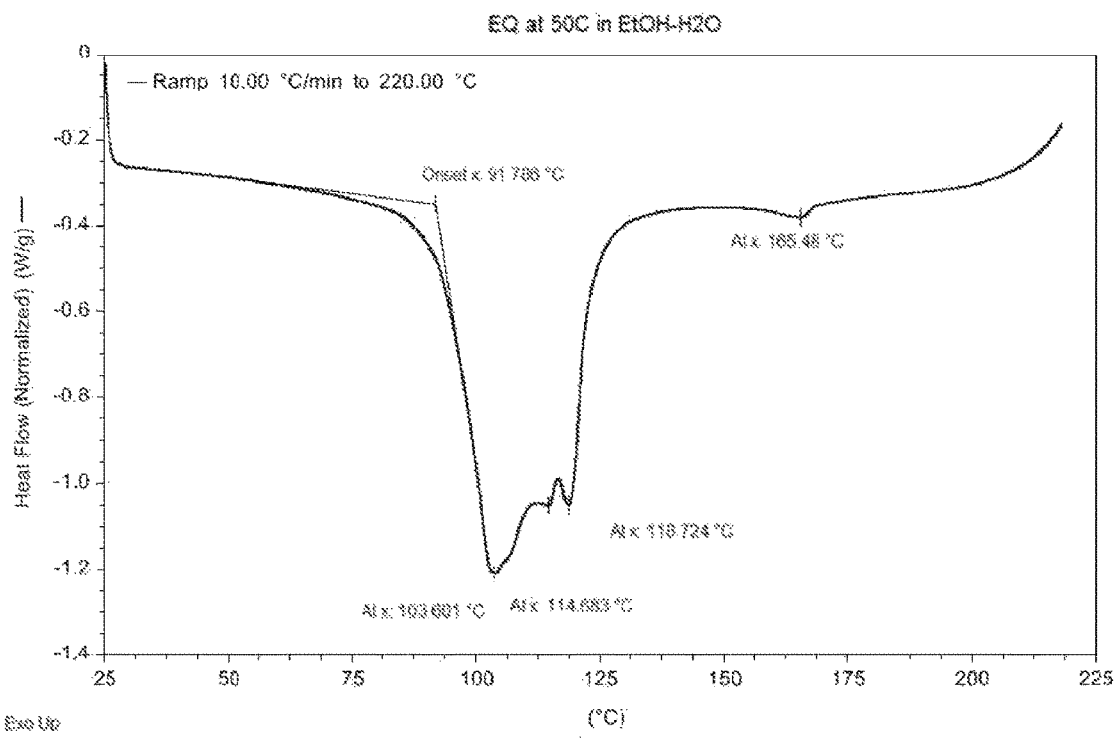
FIG. 22 depicts a DSC Thermogram of Free Base Form E.

In one embodiment, provided herein is a crystalline form of Compound 1 having a DSC thermogram as depicted in FIG. 22 comprising a broad endothermic event with and onset temperature at about 92° C. and a maximum at about 104° C. when heated from approximately 25° C. to approximately 220° C.

In still another embodiment, Form E is substantially pure. In certain embodiments, the substantially pure Form E is substantially free of other solid forms, e.g., amorphous solid. In certain embodiments, the purity of the substantially pure Form E is no less than about 95%, no less than about 96%, no less than about 97%, no less than about 98%, no less than about 98.5%, no less than about 99%, no less than about 99.5%, or no less than about 99.8%.

Form F

In certain embodiments, provided herein is Form F.

In one embodiment, Form F is a solid form of Compound 1. In another embodiment, Form F is crystalline. In one embodiment, Form F is a solvated form of Compound 1. In one embodiment, Form F is an IPA solvated form of Compound 1.

In certain embodiments, Form F provided herein is obtained by equilibration experiments (see Table 6, Table 7, and Table 9). In certain embodiments, Form F is obtained from certain solvent systems including IPA or IPA/water at about 50° C.

Figure 23:
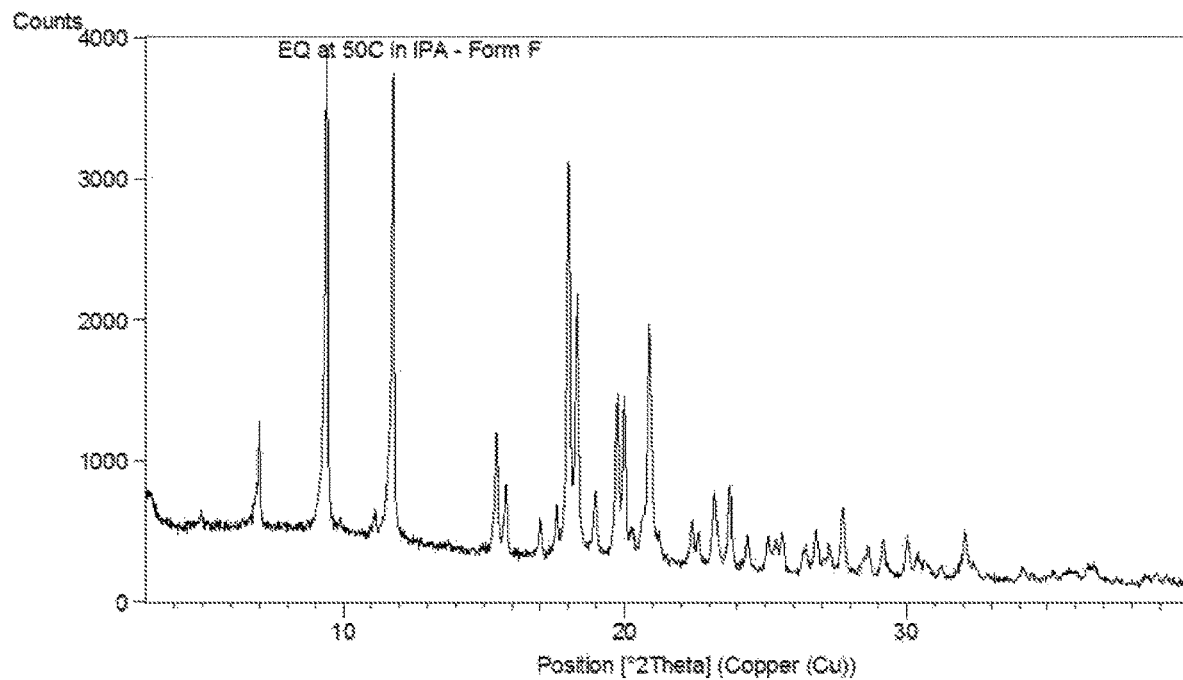
FIG. 23 depicts a XRPD Pattern of Free Base Form F.

In certain embodiments, a solid form provided herein, e.g., Form F, is substantially crystalline, as indicated by, e.g., X-ray powder diffraction measurements. In one embodiment, Form F has an X-ray powder diffraction pattern substantially as shown in FIG. 23. In one embodiment, a solid form provided herein, e.g. Form F, has one or more characteristic X-ray powder diffraction peaks at approximately 4.9, 7.0, 9.4, 11.1, 11.8, 15.5, 15.8, 17.0, 17.6, 18.0, 18.3, 19.0, 19.7, 20.0, 20.3, 20.9, 22.4, 22.6, 23.2, 23.7, 24.4, 25.1, 25.4, 25.6, 26.4, 26.8, 27.3, 27.7, 28.6, 29.2, 30.0, 30.4, 30.7, 31.2, 32.1, 34.1, 34.4, 35.2, 35.8, 36.5, 38.5, 38.8, or 39.2° 2θ (±0.2° 2θ) or (±0.1° 2θ) as depicted in FIG. 23. In a specific embodiment, a solid form provided herein, e.g. Form F, has one, two, three, four, five, six, seven, eight, or nine characteristic X-ray powder diffraction peaks at approximately 7.0, 9.4, 11.8, 15.5, 18.0, 18.3, 19.7, 20.0, or 20.9° 2θ (±0.2° 2θ). In another embodiment, a solid form provided herein has one, two, three or four characteristic X-ray powder diffraction peaks at approximately 9.4, 11.8, 18.0, or 18.3° 2θ (±0.2° 2θ). In one embodiment, the solid form is Form F. In another embodiment, Form F has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, or forty-three characteristic X-ray powder diffraction peaks as set forth in Table 17.

Figure 24:
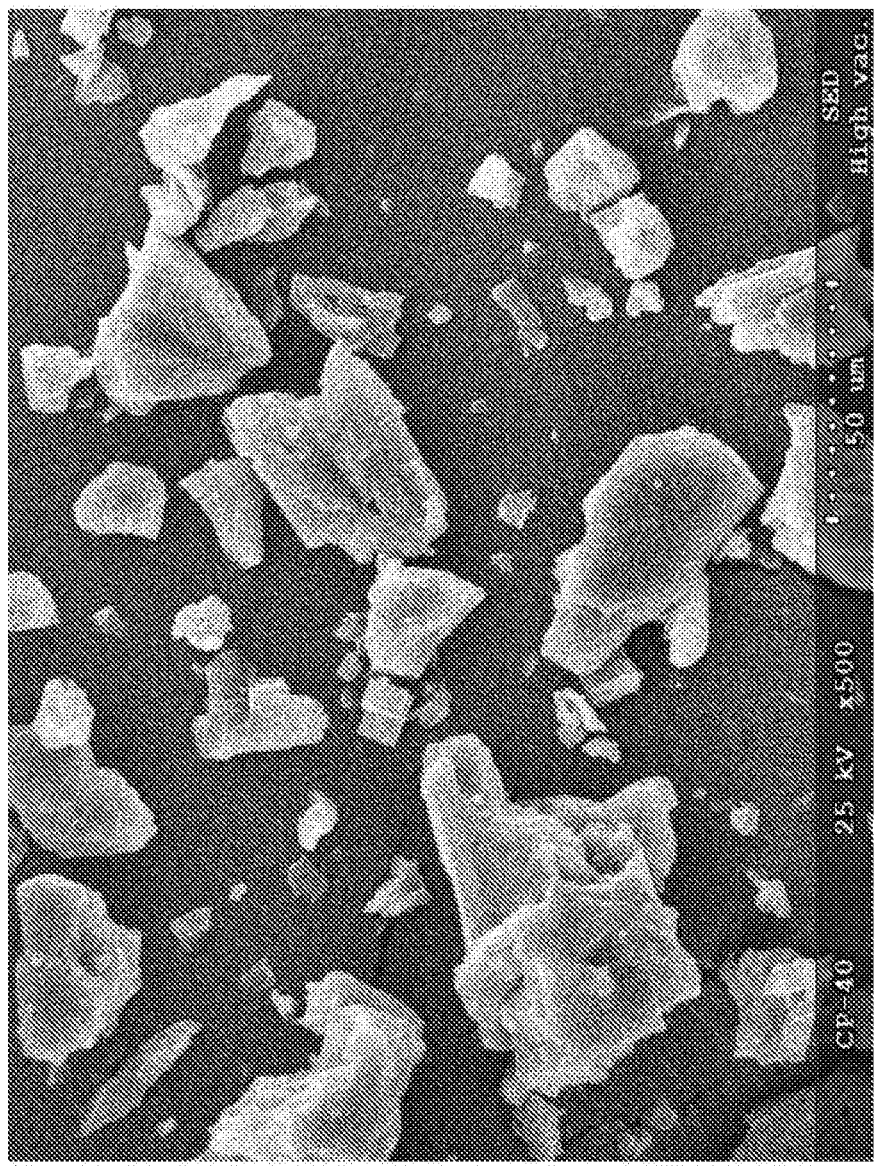
FIG. 24 depicts a SEM of Free Base Form F.

In one embodiment, a solid form provided herein, e.g. Form F has a SEM image substantially as shown in FIG. 24.

Figure 25:
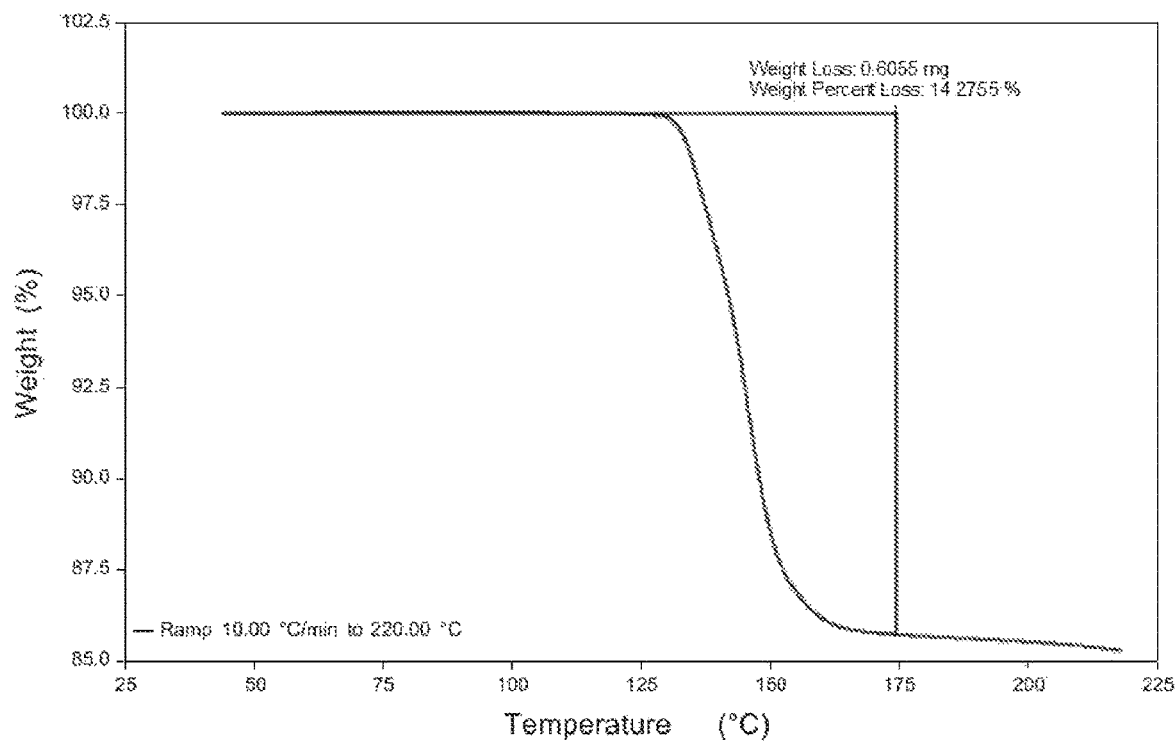
FIG. 25 depicts a TGA Thermogram of Free Base Form F.

In one embodiment, provided herein is a crystalline form of Compound 1 having a TGA thermograph corresponding substantially to the representative TGA thermogram as depicted in FIG. 25. In certain embodiments, the crystalline form exhibits a TGA thermogram comprising a total mass loss of approximately 14.3% of the total mass of the sample between approximately 50° C. and approximately 175° C. when heated from approximately 50° C. to approximately 220° C. Thus, in certain embodiments, the crystalline form loses about 14.3% of its total mass when heated from about ambient temperature to about 220° C.

Figure 26:
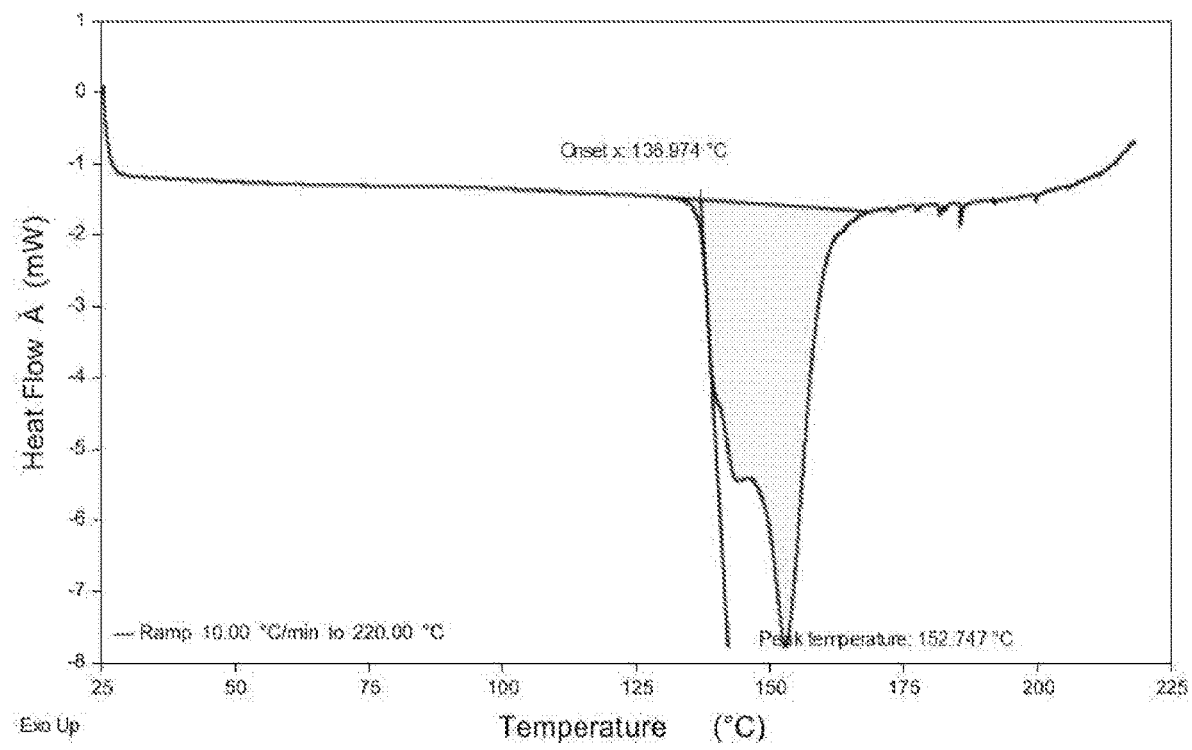
FIG. 26 depicts a DSC Thermogram of Free Base Form F.

In one embodiment, provided herein is a crystalline form of Compound 1 having a DSC thermogram as depicted in FIG. 26 comprising an endothermic event with an onset temperature at about 137° C. and a peak maximum temperature at about 152° C. when heated from approximately 25° C. to approximately 220° C.

Figure 27:
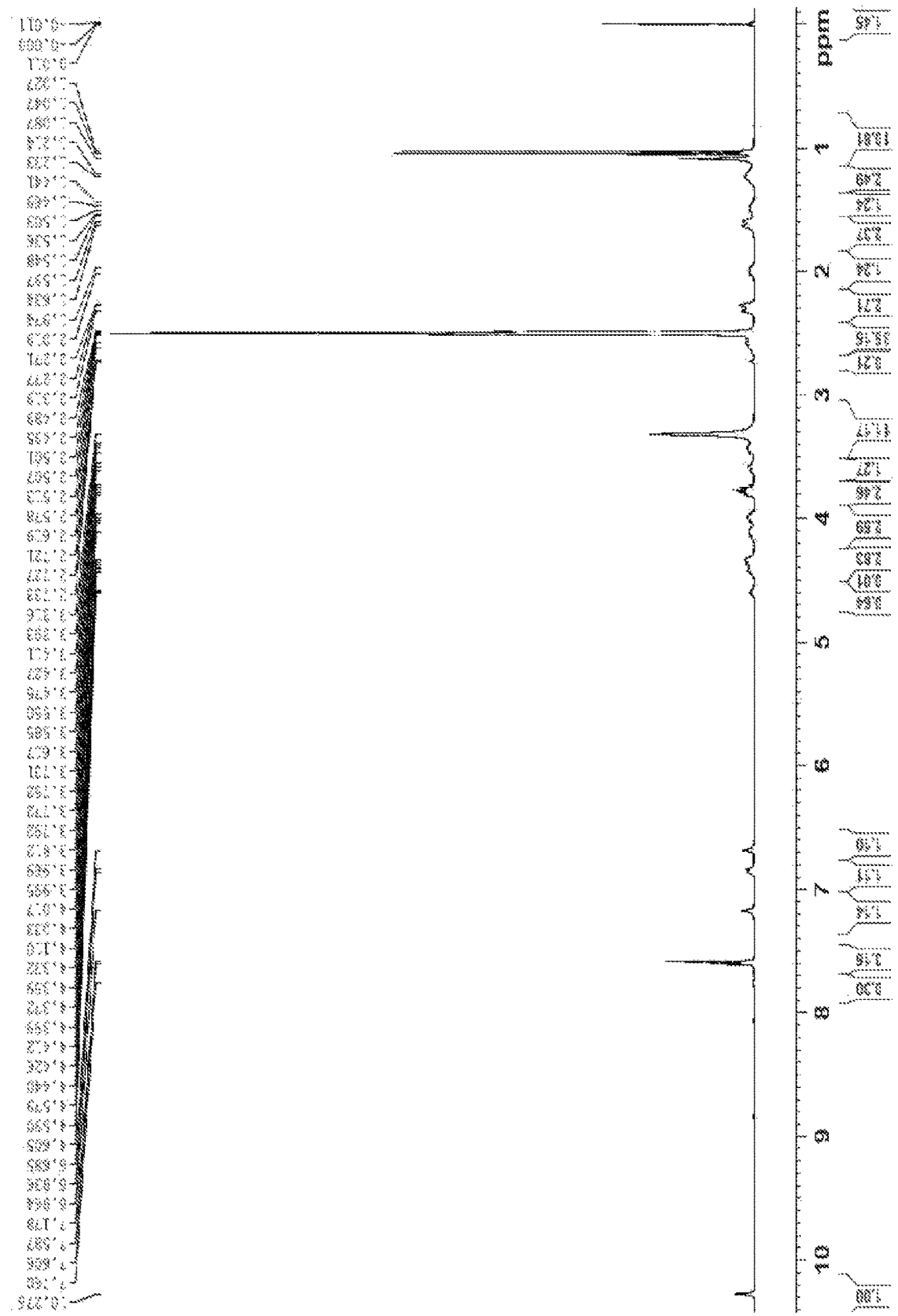
FIG. 27 depicts a $^1$H NMR Spectrum of Free Base Form F.

In one embodiment, provided herein is a solid form provided herein, e.g. Form F, having a $^1$H NMR spectrum substantially as depicted in FIG. 27.

In still another embodiment, Form F is substantially pure. In certain embodiments, the substantially pure Form F is substantially free of other solid forms, e.g., amorphous solid. In certain embodiments, the purity of the substantially pure Form F is no less than about 95%, no less than about 96%, no less than about 97%, no less than about 98%, no less than about 98.5%, no less than about 99%, no less than about 99.5%, or no less than about 99.8%.

Form G

In certain embodiments, provided herein is Form G.

In one embodiment, Form G is a solid form of Compound 1. In another embodiment, Form G is crystalline. In one embodiment, Form G is a solvated form of Compound 1. In one embodiment, Form G is a MTBE solvated form of Compound 1.

In certain embodiments, Form G provided herein is obtained by equilibration experiments, evaporation experiments and anti-solvent recrystallization experiments (see Table 6, Table 7, and Table 9). In certain embodiments, Form G is obtained from certain solvent systems including MTBE. In certain embodiments, Form G is obtained from certain solvent systems including MTBE at a temperature of 50° C.

Figure 28:
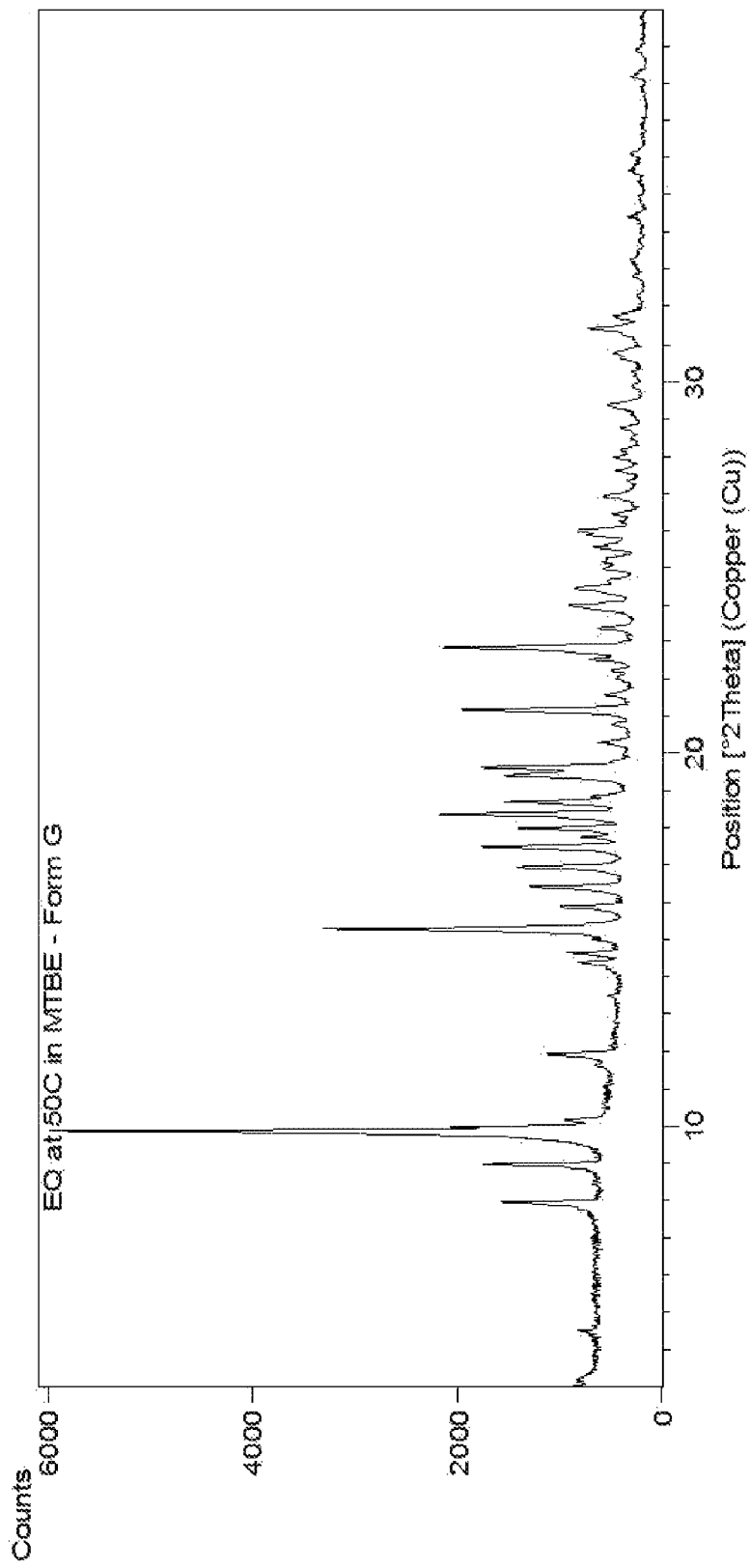
FIG. 28 depicts a XRPD Pattern of Free Base Form G.

In certain embodiments, a solid form provided herein, e.g., Form G, is substantially crystalline, as indicated by, e.g., X-ray powder diffraction measurements. In one embodiment, Form G has an X-ray powder diffraction pattern substantially as shown in FIG. 28. In one embodiment, Form G has one or more characteristic X-ray powder diffraction peaks at approximately 4.5, 8.0, 9.0, 9.9, 10.0, 10.2, 11.6, 11.9, 13.5, 14.4, 14.6, 15.3, 15.9, 16.4, 16.9, 17.5, 17.7, 18.0, 18.4, 18.7, 18.8, 19.4, 19.6, 20.3, 20.8, 21.2, 21.6, 22.0, 22.2, 22.5, 22.9, 23.4, 24.0, 24.5, 24.6, 25.0, 25.2, 25.6, 25.9, 26.0, 26.4, 26.9, 27.3, 27.6, 28.0, 28.2, 28.8, 29.4, 29.9, 30.2, 30.8, 31.4, 31.8, 32.8, 33.2, 34.4, 34.9, 35.7, 36.1, 38.2, or 38.9° 2θ (±0.2° 2θ) or (±0.1° 2θ). In a specific embodiment, a solid form provided herein, e.g. Form G, has one, two, three, four, five, six, seven, eight, nine, ten, or eleven characteristic X-ray powder diffraction peaks at approximately 9.0, 9.9, 10.0, 15.3, 17.5, 18.4, 18.7, 19.4, 19.6, 21.2, or 22.9° 2θ (±0.2° 2θ). In another embodiment, a solid form provided herein has one, two, three, or four characteristic X-ray powder diffraction peaks at approximately 9.9, 15.3, 18.4, or 22.9° 2θ (±0.2° 2θ). In one embodiment, the solid form is Form G. In another embodiment, Form G has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, or sixty-one characteristic X-ray powder diffraction peaks as set forth in Table 18.

Figure 29:
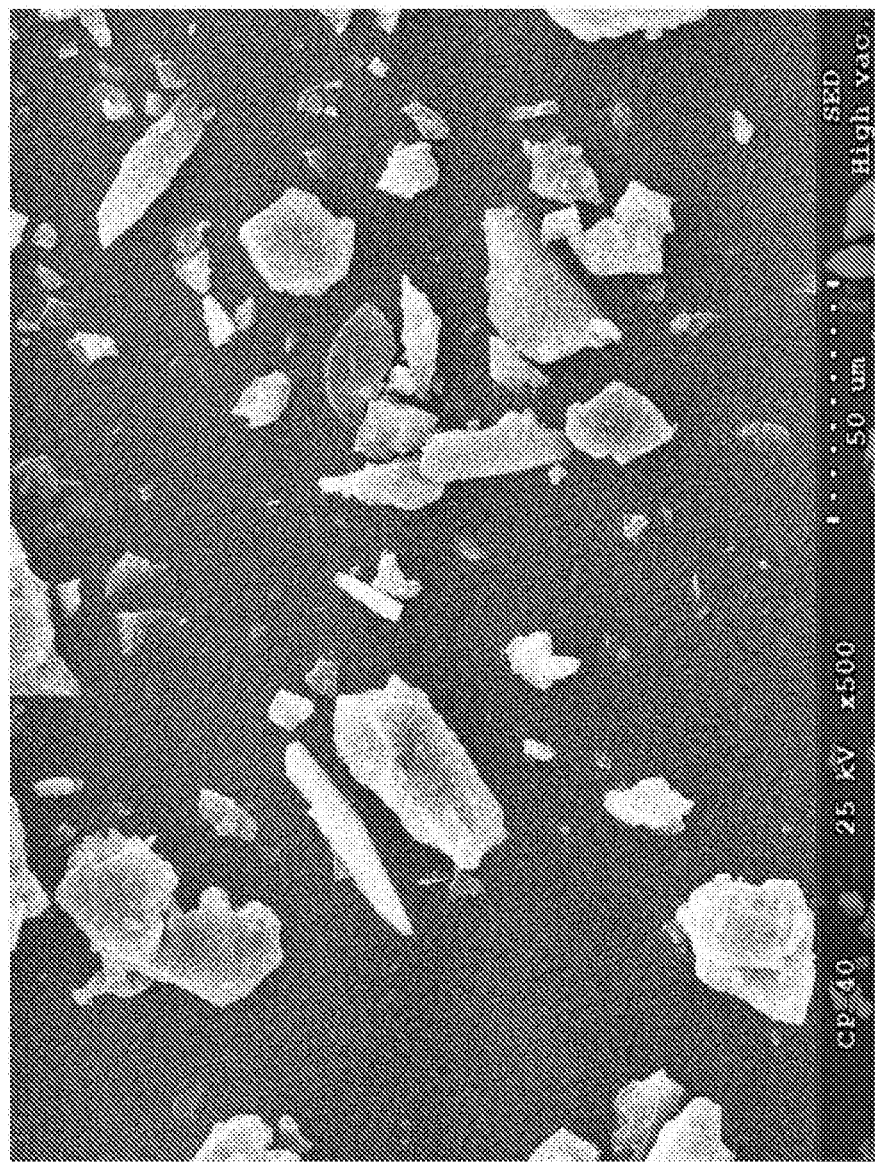
FIG. 29 depicts a SEM Picture of Free Base Form G.

In one embodiment, Form G has a SEM image substantially as shown in FIG. 29.

Figure 30:
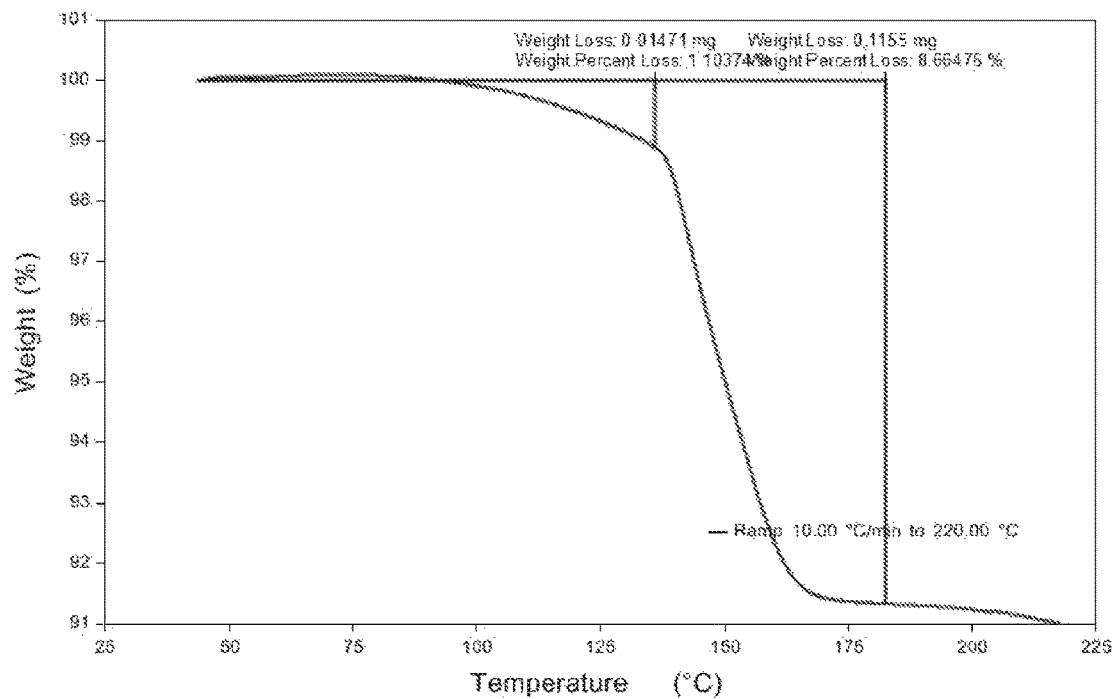
FIG. 30 depicts a TGA Thermogram of Free Base Form G.

In one embodiment, provided herein is a crystalline form of Compound 1 having a TGA thermograph corresponding substantially to the representative TGA thermogram as depicted in FIG. 30. In certain embodiments, the crystalline form exhibits a TGA thermogram comprising a total mass loss of approximately 1.1% of the total mass of the sample between approximately 50° C. and approximately 140° C. In certain embodiments, the crystalline form exhibits a TGA thermogram comprising a total mass loss of approximately 8.7% of the total mass of the sample between approximately 50° C. and approximately 180° C. when heated from approximately 25° C. to approximately 220° C. Thus, in certain embodiments, the crystalline form loses about 8.7% of its total mass when heated from about ambient temperature to about 220° C.

Figure 31:
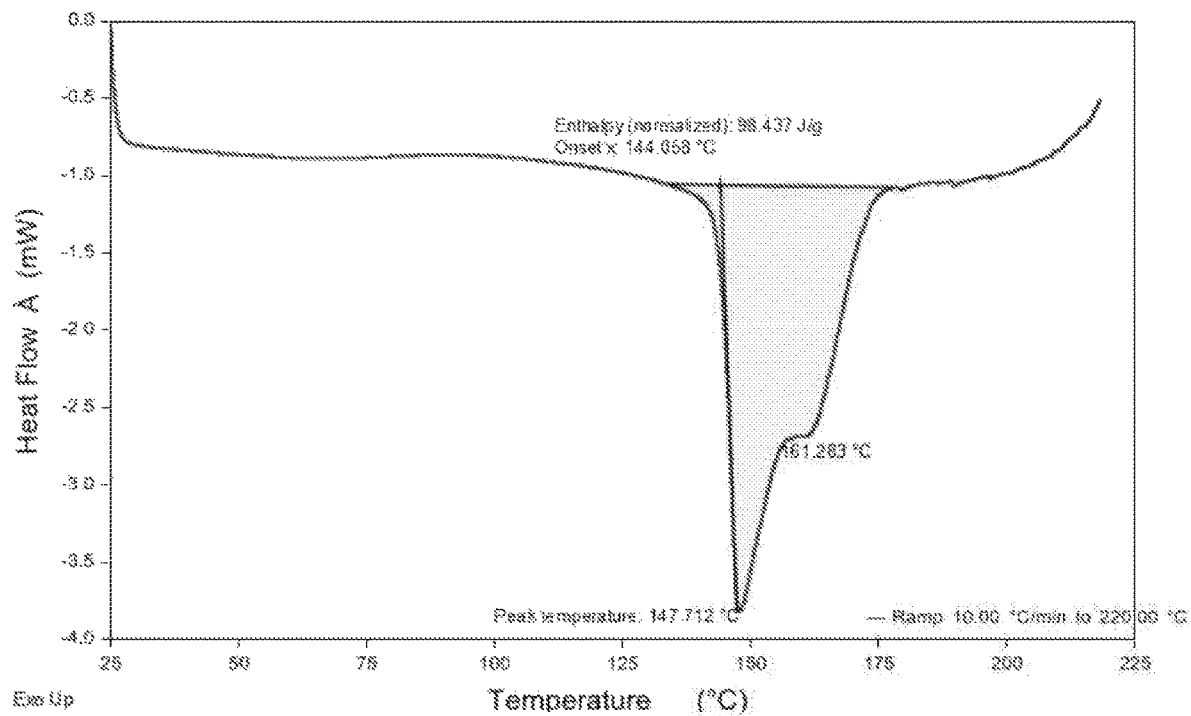
FIG. 31 depicts a DSC of Free Base Form G.

In one embodiment, provided herein is a crystalline form of Compound 1 having a DSC thermogram as depicted in FIG. 31 comprising an endothermic event with an onset temperature at about 144° C. and a peak maximum temperature at about 148° C. when heated from approximately 25° C. to approximately 220° C.

In one embodiment, provided herein is a crystalline form of Compound 1 having a DSC thermogram as depicted in FIG. 31 comprising an endothermic event with a maximum at about 161° C. when heated from approximately 25° C. to approximately 220° C.

Figure 32:
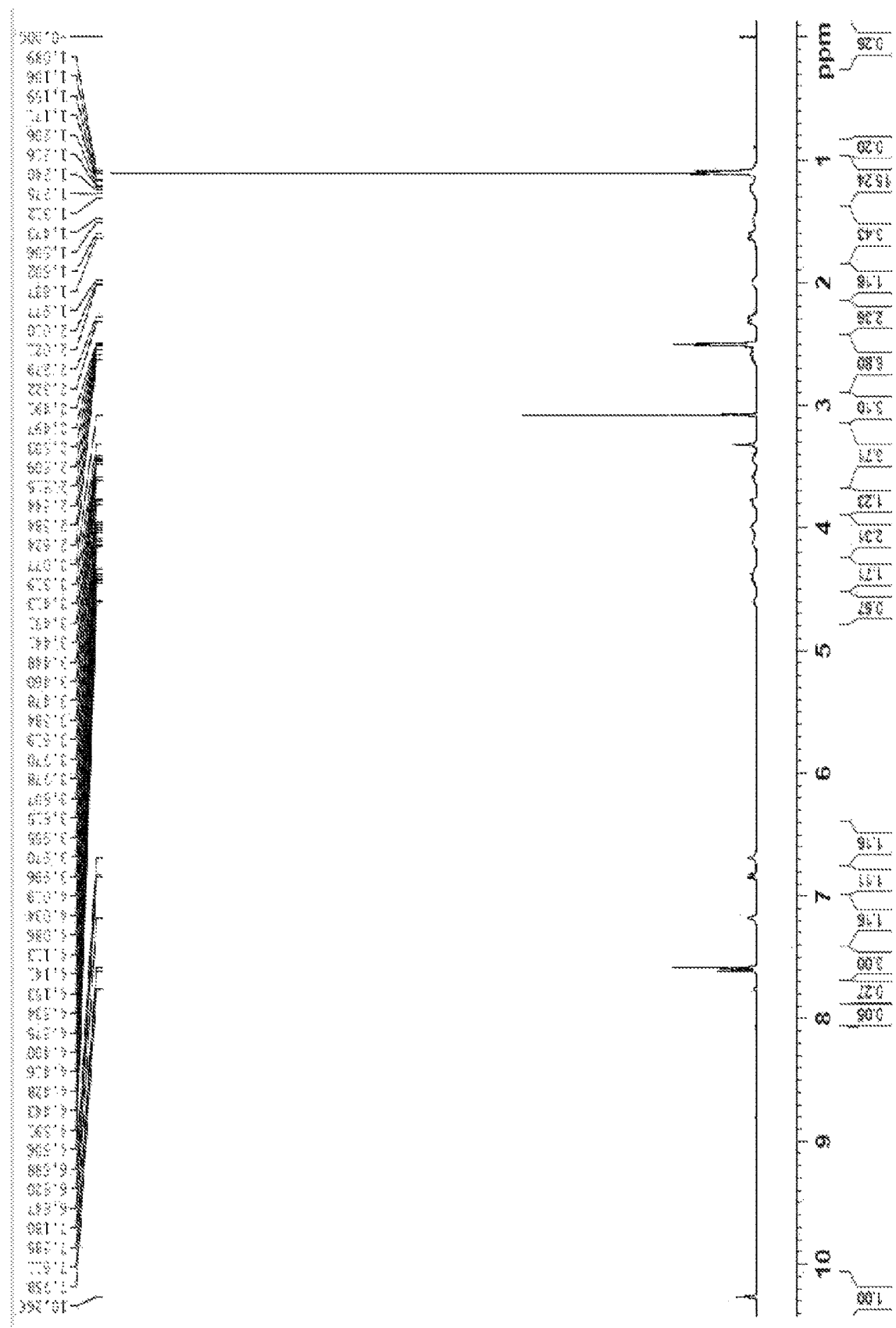
FIG. 32 depicts a $^1$H NMR Spectrum of Free Base Form G.

In one embodiment, provided herein is a solid form provided herein, e.g. Form G, having a $^1$H NMR spectrum substantially as depicted in FIG. 32. In one embodiment, the $^1$H NMR spectrum of Form G shows Form G contains a significant amount of MBTE.

In still another embodiment, Form G is substantially pure. In certain embodiments, the substantially pure Form G is substantially free of other solid forms, e.g., amorphous solid. In certain embodiments, the purity of the substantially pure Form G is no less than about 95%, no less than about 96%, no less than about 97%, no less than about 98%, no less than about 98.5%, no less than about 99%, no less than about 99.5%, or no less than about 99.8%.

Form H

In certain embodiments, provided herein is Form H.

In one embodiment, Form H is a solid form of Compound 1. In another embodiment, Form H is crystalline. In one embodiment, Form H is a solvated form of Compound 1. In one embodiment, Form H is an EtOH solvated form of Compound 1. In certain embodiments, Form H can be converted to Form A by contact with an environment comprising at least 20% RH.

In certain embodiments, Form H provided herein is obtained by equilibration experiments, evaporation experiments and anti-solvent recrystallization experiments (see Table 6, Table 7, and Table 9). In certain embodiments, Form H is obtained from certain solvent systems including EtOH, EtOH/water (about 1:1), or EtOAc. In certain embodiments, Form H is obtained from certain solvent systems including EtOH, EtOH/water (about 1:1), or EtOAc at a temperature of 50° C.

Figure 33:
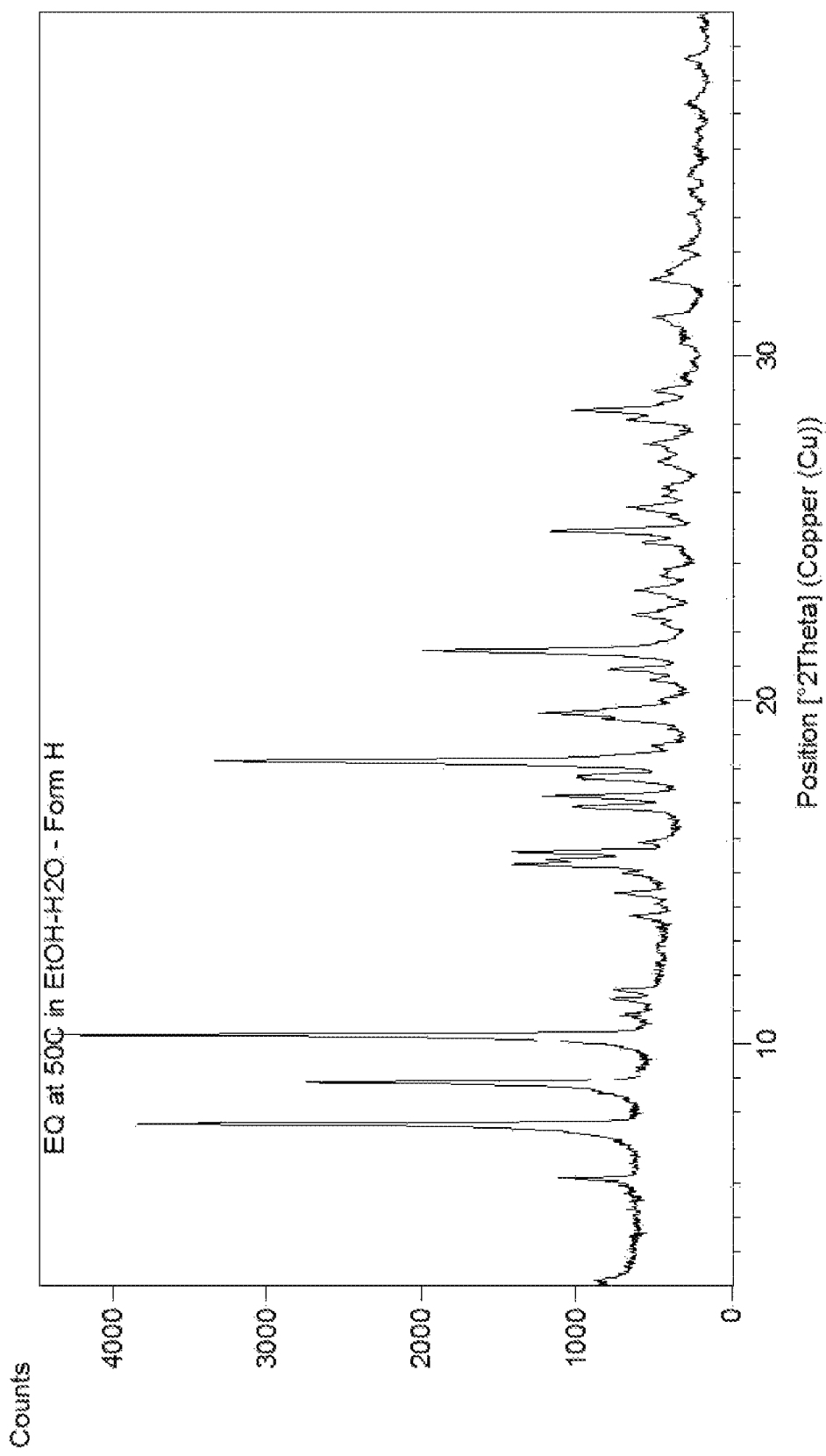
FIG. 33 depicts a XRPD Pattern of Free Base Form H.

In certain embodiments, a solid form provided herein, e.g., Form H, is substantially crystalline, as indicated by, e.g., X-ray powder diffraction measurements. In one embodiment, Form H has an X-ray powder diffraction pattern substantially as shown in FIG. 33. In one embodiment, a solid form provided herein, e.g. Form H, has one or more characteristic X-ray powder diffraction peaks at approximately 6.1, 7.7, 8.9, 10.3, 10.9, 11.3, 11.6, 13.7, 14.4, 15.0, 15.2, 15.4, 15.6, 15.9, 16.9, 17.2, 17.7, 18.2, 18.7, 19.4, 19.6, 20.6, 20.9, 21.4, 22.5, 23.2, 23.7, 24.6, 24.9, 25.6, 25.9, 26.2, 26.9, 27.4, 28.1, 28.4, 29.0, 29.4, 31.1, 32.2, 33.1, 34.1, 34.7, 35.3, 37.3, or 38.6° 2θ (±0.2° 2θ) or (±0.1° 2θ) as depicted in FIG. 33. In a specific embodiment, a solid form provided herein, e.g. Form H, has one, two, three, four, five, six, seven, eight, nine, ten, or eleven characteristic X-ray powder diffraction peaks at approximately 7.7, 8.9, 10.3, 15.2, 15.4, 15.6, 17.2, 18.2, 19.6, 21.4, or 24.9° 2θ (±0.2° 2θ). In another embodiment, a solid form provided herein has one, two, three, or four characteristic X-ray powder diffraction peaks at approximately 7.7, 8.9, 10.3, or 18.2° 2θ (±0.2° 2θ). In one embodiment, the solid form is Form H. In another embodiment, Form H has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, or forty-six characteristic X-ray powder diffraction peaks as set forth in Table 19.

Figure 34:
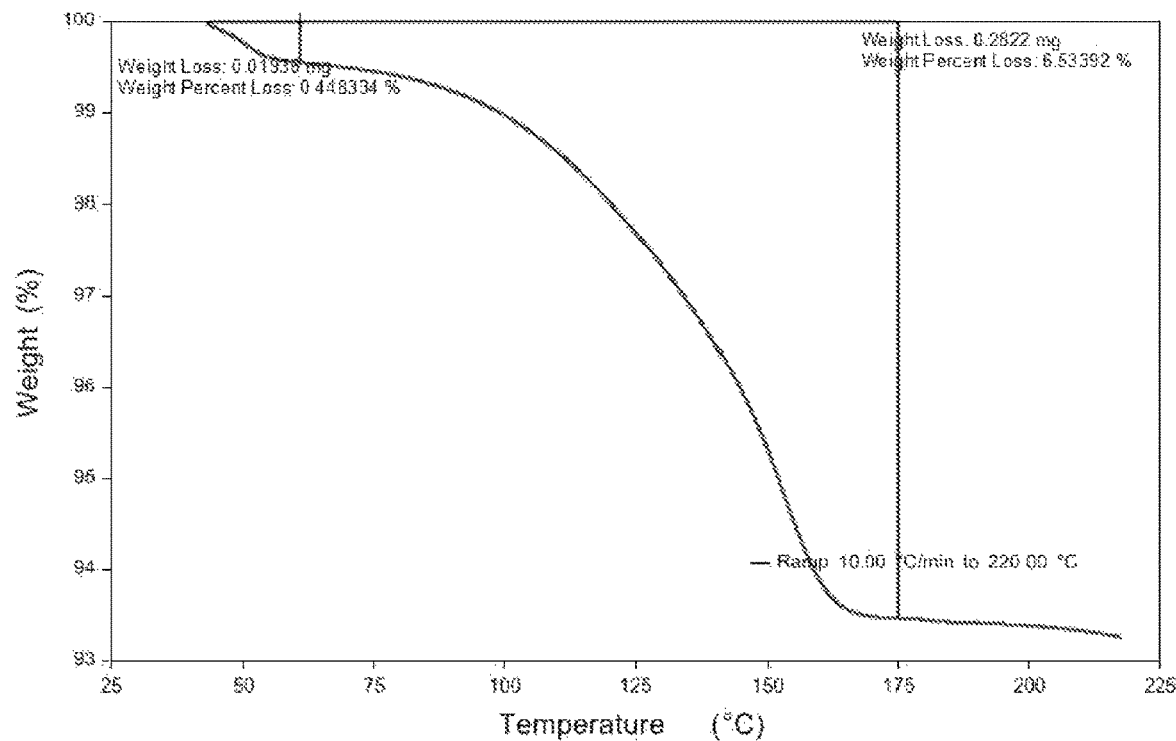
FIG. 34 depicts a TGA Thermogram of Free Base Form H.

In one embodiment, provided herein is a crystalline form of Compound 1 having a TGA thermograph corresponding substantially to the representative TGA thermogram as depicted in FIG. 34. In certain embodiments, the crystalline form exhibits a TGA thermogram comprising a total mass loss of approximately 6.5% of the total mass of the sample between approximately 50° C. and approximately 175° C. when heated from approximately 50° C. to approximately 220° C. Thus, in certain embodiments, the crystalline form loses about 6.5% of its total mass when heated from about ambient temperature to about 220° C.

Figure 35:
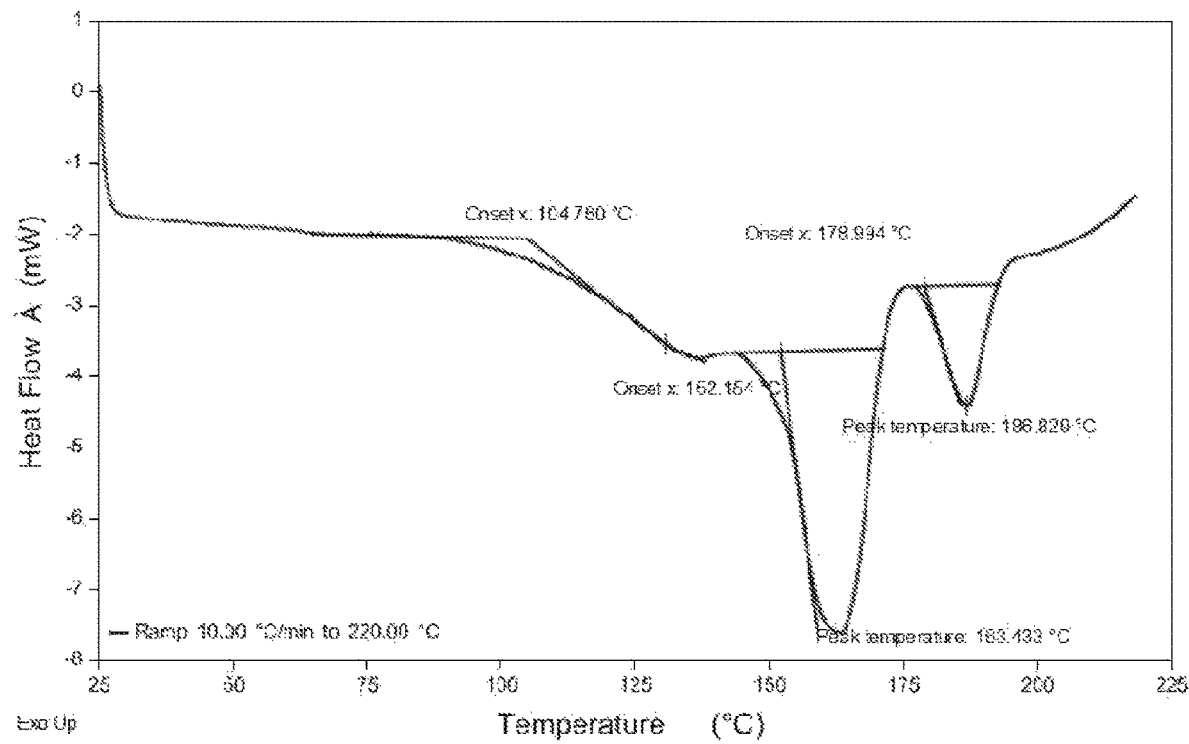
FIG. 35 depicts a DSC Thermogram of Free Base Form H.

In one embodiment, provided herein is a crystalline form of Compound 1 having a DSC thermogram as depicted in FIG. 35 comprising an endothermic event with a peak maximum at about 163° C. when heated from approximately 25° C. to approximately 220° C.

In one embodiment, provided herein is a crystalline form of Compound 1 having a DSC thermogram as depicted in FIG. 35 comprising an endothermic event with an onset temperature at about 179° C. and a peak maximum temperature at about 187° C. when heated from approximately 25° C. to approximately 220° C.

In still another embodiment, Form H is substantially pure. In certain embodiments, the substantially pure Form H is substantially free of other solid forms, e.g., amorphous solid. In certain embodiments, the purity of the substantially pure Form H is no less than about 95%, no less than about 96%, no less than about 97%, no less than about 98%, no less than about 98.5%, no less than about 99%, no less than about 99.5%, or no less than about 99.8%.

Form I

In certain embodiments, provided herein is Form I.

In one embodiment, Form I is a solid form of Compound 1. In another embodiment, Form I is crystalline. In one embodiment, Form I is a solvated form of Compound 1. In one embodiment, Form I is a MeCN solvated form of Compound 1.

In certain embodiments, Form I provided herein is obtained by cooling recrystallization experiments and anti-solvent recrystallization experiments. In certain embodiments, Form I is obtained from certain solvent systems including MeCN. In certain embodiments, Form I can convert to Form C in a MeCN slurry at room temperature.

Figure 36:
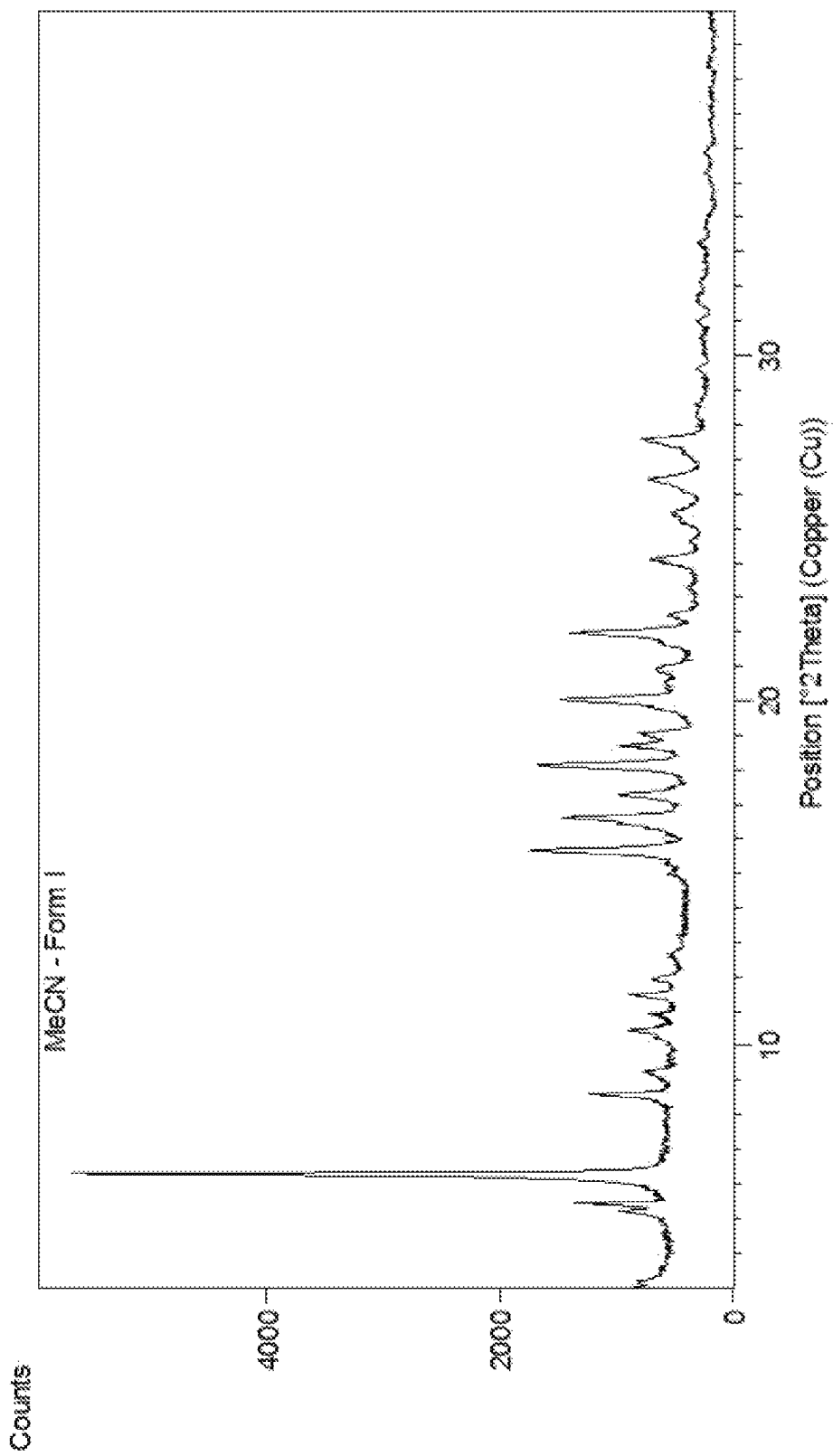
FIG. 36 depicts a XRPD Pattern of Free Base Form I.

In certain embodiments, a solid form provided herein, e.g., Form I, and is substantially crystalline, as indicated by, e.g., X-ray powder diffraction measurements. In one embodiment, Form I has an X-ray powder diffraction pattern substantially as shown in FIG. 36. In one embodiment, a solid form provided herein, e.g. Form I, has one or more characteristic X-ray powder diffraction peaks at approximately 5.2, 5.5, 6.3, 8.6, 9.3, 10.4, 10.9, 11.5, 11.9, 12.6, 15.7, 16.6, 17.3, 18.1, 18.7, 19.0, 20.0, 20.9, 22.0, 22.5, 23.3, 24.1, 24.6, 25.4, 26.4, 27.6, 28.4, 29.6, 31.0, 31.6, 32.1, 33.2, 33.9, 35.3, 35.9, or 38.5° 2θ (±0.2° 2θ) or (±0.1° 2θ) as depicted in FIG. 36. In a specific embodiment, a solid form provided herein has one, two, three, or four characteristic X-ray powder diffraction peaks at approximately 6.3, 15.7, 18.1, or 20.0° 2θ (±0.2° 2θ). In one embodiment, the solid form is Form I. In another embodiment, Form I has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, or thirty-six characteristic X-ray powder diffraction peaks as set forth in Table 20.

Figure 38:
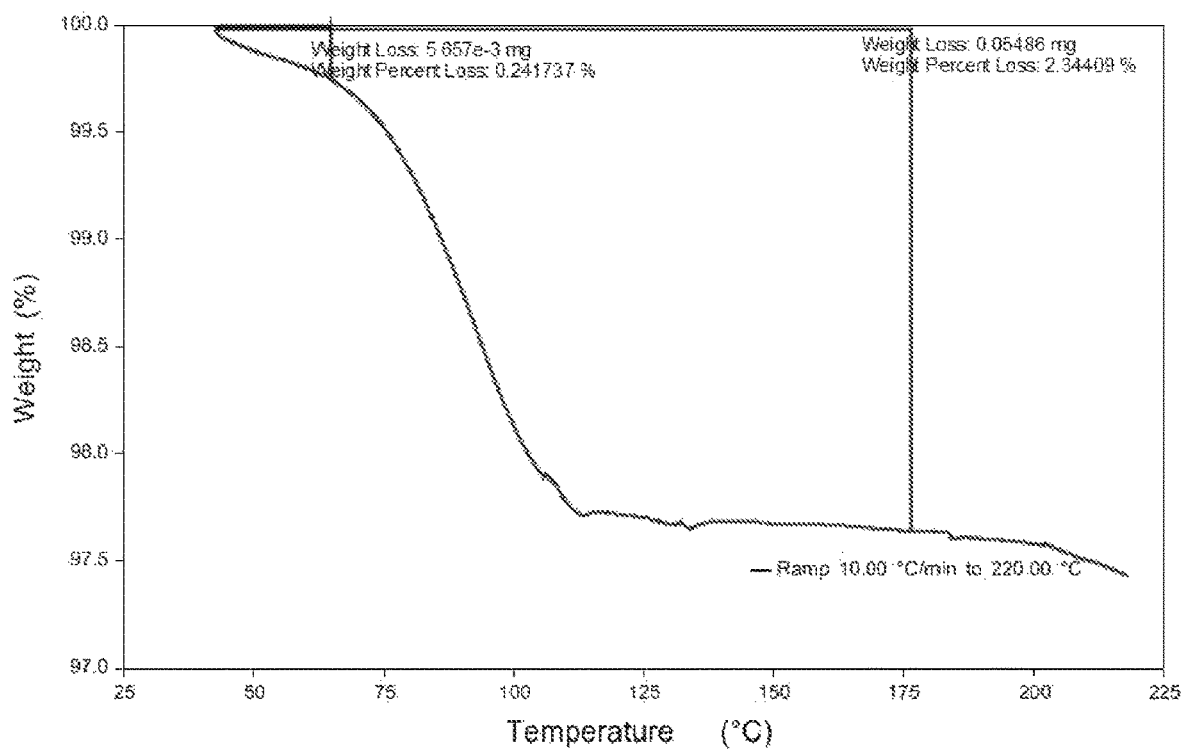
FIG. 38 depicts a TGA Thermogram of Free Base Form I.

In one embodiment, provided herein is a crystalline form of Compound 1 having a TGA thermograph corresponding substantially to the representative TGA thermogram as depicted in FIG. 38. In certain embodiments, the crystalline form exhibits a TGA thermogram comprising a total mass loss of approximately 2.3% of the total mass of the sample between approximately 50° C. and approximately 180° C. when heated from approximately 50° C. to approximately 220° C. Thus, in certain embodiments, the crystalline form loses about 2.3% of its total mass when heated from about ambient temperature to about 220° C.

Figure 39:
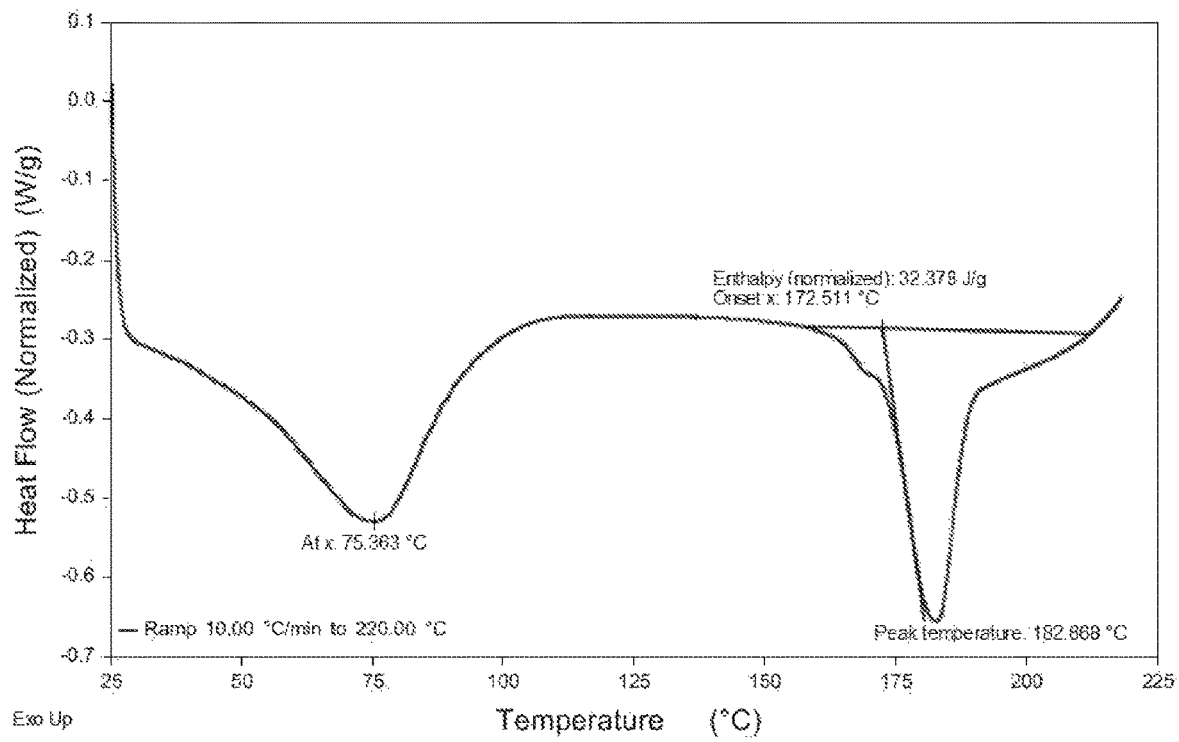
FIG. 39 depicts a DSC Thermogram of Free Base Form I.

In one embodiment, provided herein is a crystalline form of Compound 1 having a DSC thermogram as depicted in FIG. 39 comprising an endothermic event with a peak maximum at about 75° C. when heated from approximately 25° C. to approximately 220° C.

In one embodiment, provided herein is a crystalline form of Compound 1 having a DSC thermogram as depicted in FIG. 39 comprising an endothermic event with an onset temperature of about 173° C. and a peak maximum temperature at about 183° C. when heated from approximately 25° C. to approximately 220° C.

Figure 37:
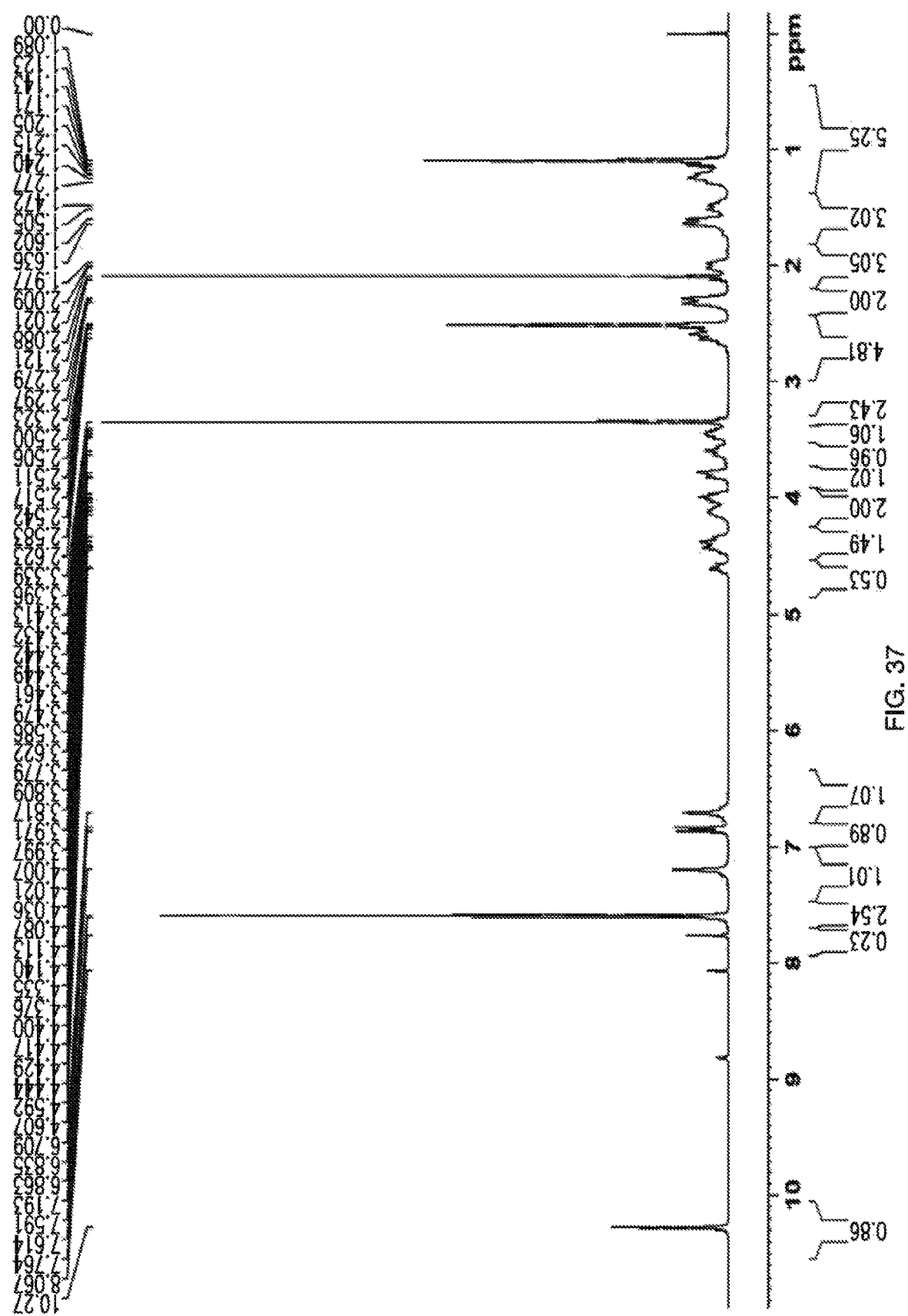
FIG. 37 depicts a $^1$H NMR Spectrum of Free Base Form I.

In one embodiment, provided herein is a solid form provided herein, e.g. Form I, having a $^1$H NMR spectrum substantially as depicted in FIG. 37.

In still another embodiment, Form I is substantially pure. In certain embodiments, the substantially pure Form I is substantially free of other solid forms, e.g., amorphous solid. In certain embodiments, the purity of the substantially pure Form I is no less than about 95%, no less than about 96%, no less than about 97%, no less than about 98%, no less than about 98.5%, no less than about 99%, no less than about 99.5%, or no less than about 99.8%.

Amorphous Solid

In certain embodiments, provided herein is an amorphous solid of Compound 1.

In certain embodiments, the amorphous solid provided herein is obtained by evaporation and/or heat treatment of Form A.

Figure 40:
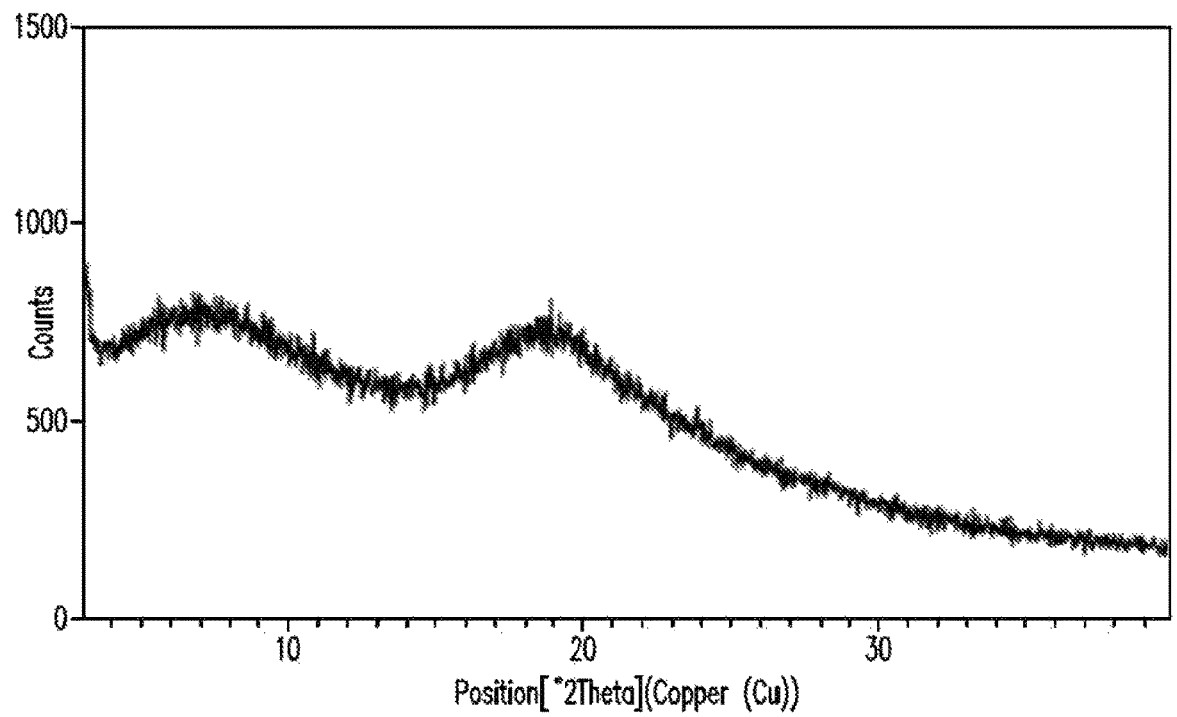
FIG. 40 depicts a XRPD Pattern of Amorphous Material.

In one embodiment, the amorphous solid has an X-ray powder diffraction spectrum substantially as shown in FIG. 40.

Figure 41:
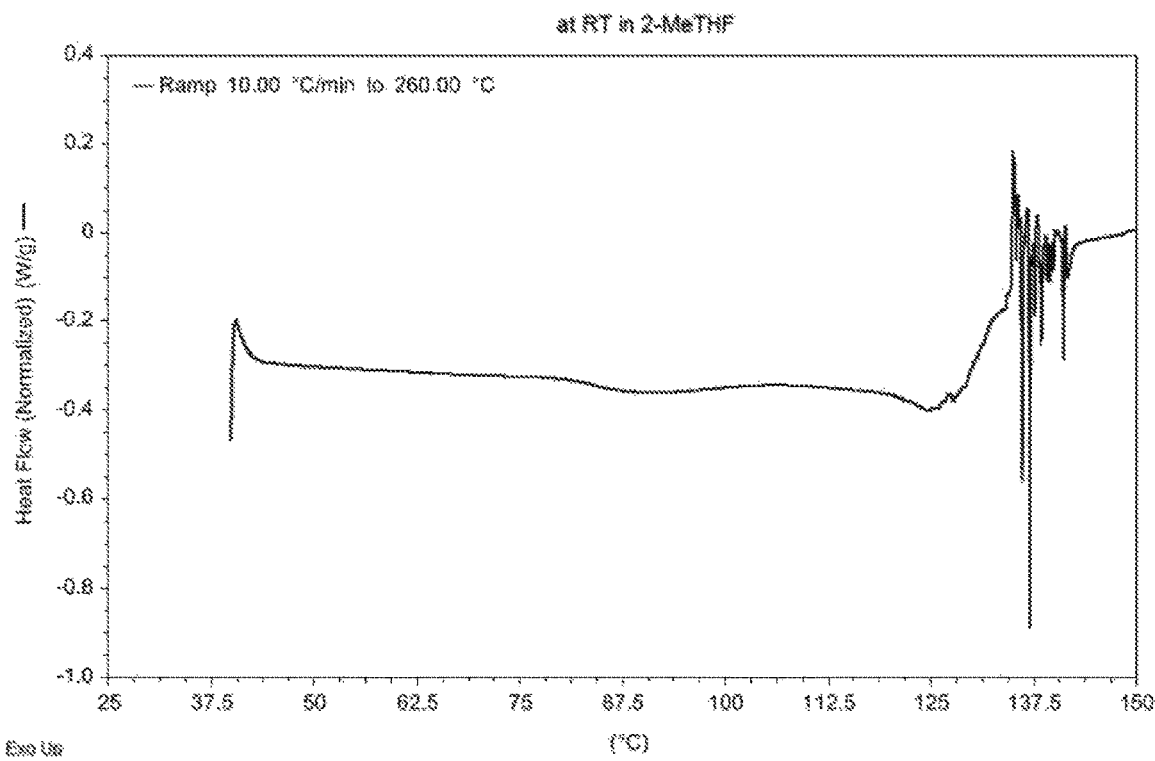
FIG. 41 depicts a DSC Thermogram of Amorphous Material.

In one embodiment, provided herein is an amorphous solid of Compound 1 having a DSC thermogram as depicted in FIG. 41 comprising a glass transition temperature of 84° C. when heated from approximately 40° C. to approximately 260° C.

Figure 42:
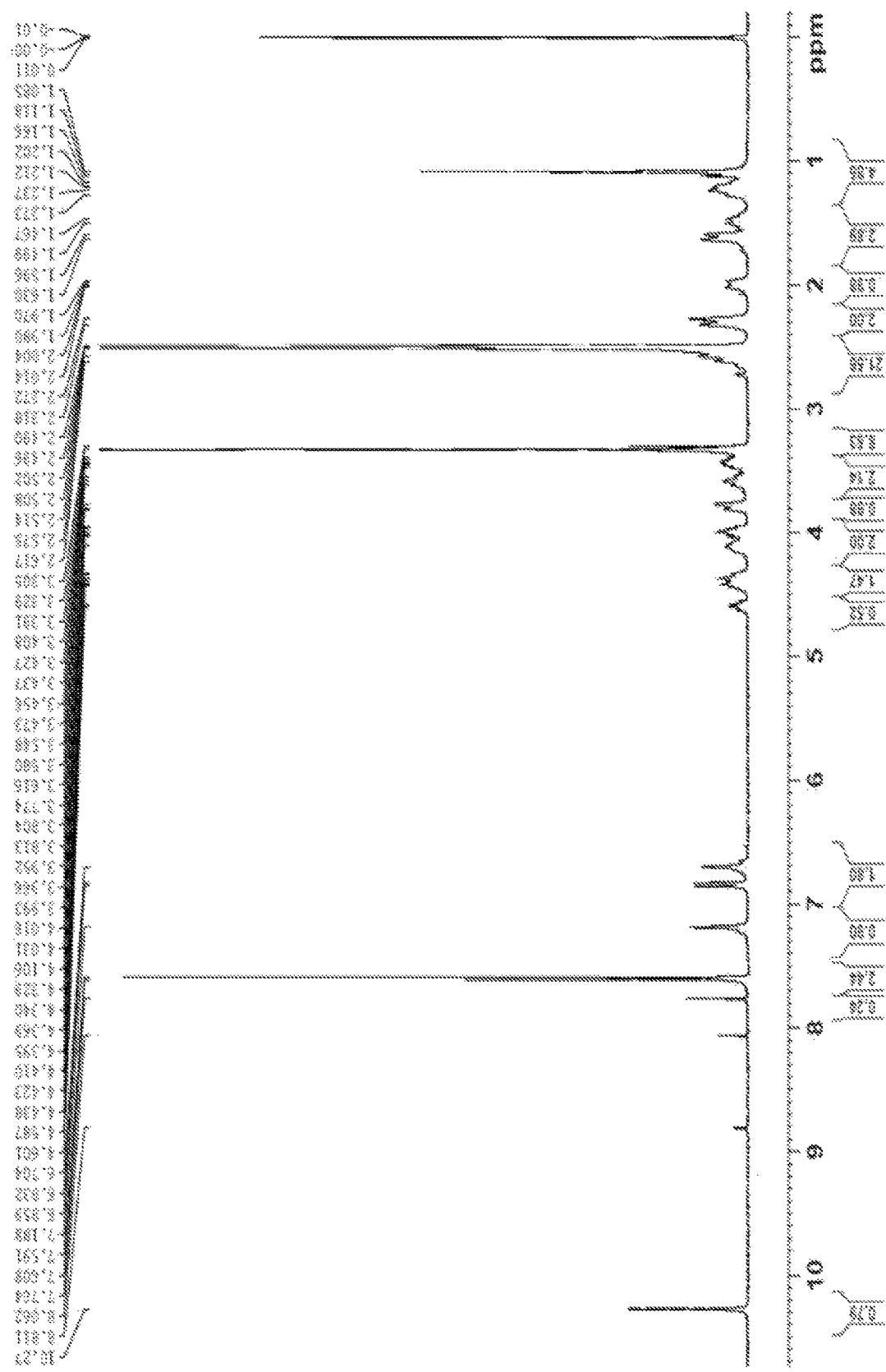
FIG. 42 depicts a $^1$H NMR Spectrum of Amorphous Material.

In one embodiment, provided herein is an amorphous solid of Compound 1 having a $^1$H NMR spectrum substantially as depicted in FIG. 42.

Figures 43A, 43B:
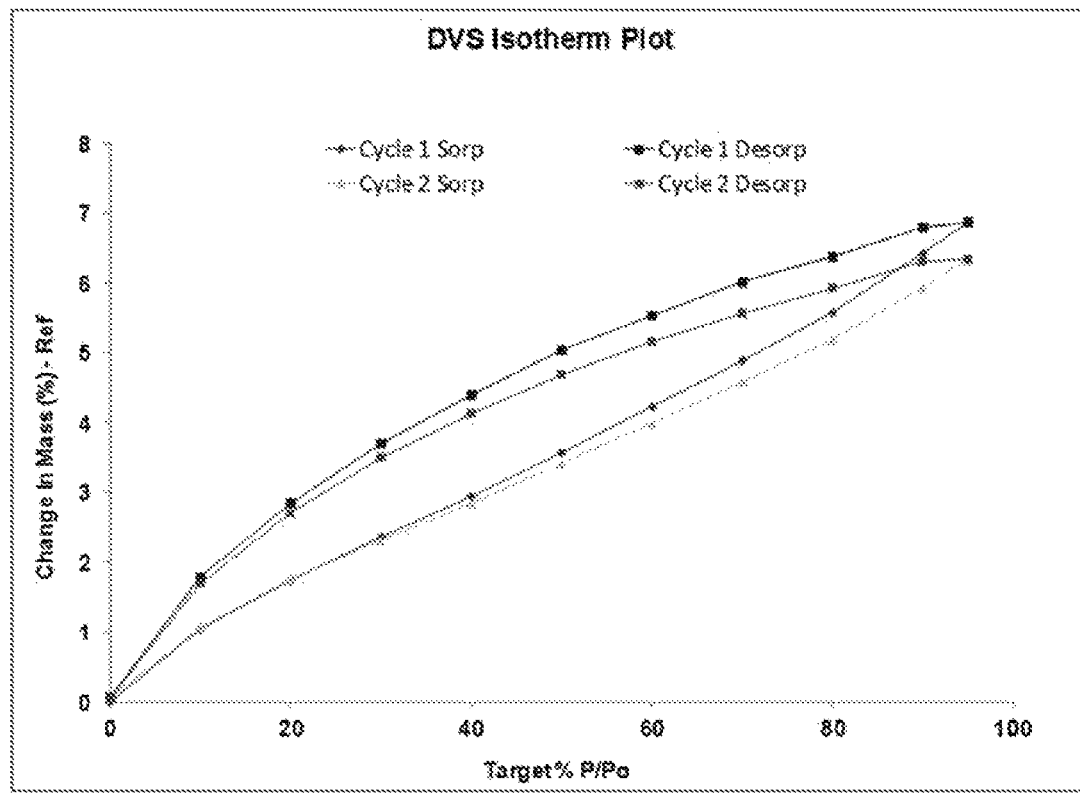
FIG. 43A depicts a DVS Isotherm Plot of Amorphous Material.
FIG. 43B depicts the values of the DVS Isotherm Plot of FIG. 43A.

In one embodiment, provided herein is an amorphous solid of Compound 1 having a DVS isotherm plot substantially as depicted in FIG. 43A.

In still another embodiment, the amorphous solid of Compound 1 is substantially pure. In certain embodiments, the substantially pure amorphous solid of Compound 1 is substantially free of other solid forms, e.g., Form A, Form B, Form C, Form D, Form E, Form F, Form G, Form H, and Form I. In certain embodiments, the purity of the substantially pure amorphous solid is no less than about 95%, no less than about 96%, no less than about 97%, no less than about 98%, no less than about 98.5%, no less than about 99%, no less than about 99.5%, or no less than about 99.8%.

Citrate Salt Form Y

Also provided herein are solid forms of Compound 1 that include citrate salts.

In certain embodiments, provided herein is citrate salt Form Y.

In one embodiment, the citrate salt Form Y is a solid form of Compound 1. In another embodiment, the citrate salt Form Y is crystalline. In another embodiment, the citrate salt Form Y is an anhydrate.

In certain embodiments, the citrate salt Form Y provided herein is obtained by equilibration experiments, evaporation experiments and anti-solvent recrystallization experiments (see Table 23, Table 24, and Table 25). In certain embodiments, the citrate salt Form Y is obtained from certain solvent systems including acetone, MeCN, n-butanol, EtOH, EtOH/water (about 1:1), EtOAc, heptanes, IPA, DCM, MeOAc, MTBE, MEK, toluene, THF, THF/water (about 1:1), 1,4-dioxane, MIBK, IPAc, and 2-MeTHF. In certain embodiments, the citrate salt Form Y is obtained from certain solvent systems including acetone, MeCN, n-butanol, EtOH, EtOH/water (about 1:1), EtOAc, heptanes, IPA, DCM, MeOAc, MTBE, MEK, toluene, THF, THF/water (about 1:1), 1,4-dioxane, MIBK, IPAc, and 2-MeTHF at 50° C. In one embodiment, the citrate salt Form Y is an EtOH solvate.

In one embodiment, a method of preparing the citrate salt Form Y comprises the steps of cooling to a temperature less than about 50° C. in THF or THF/water and collecting solids.

Figure 45:
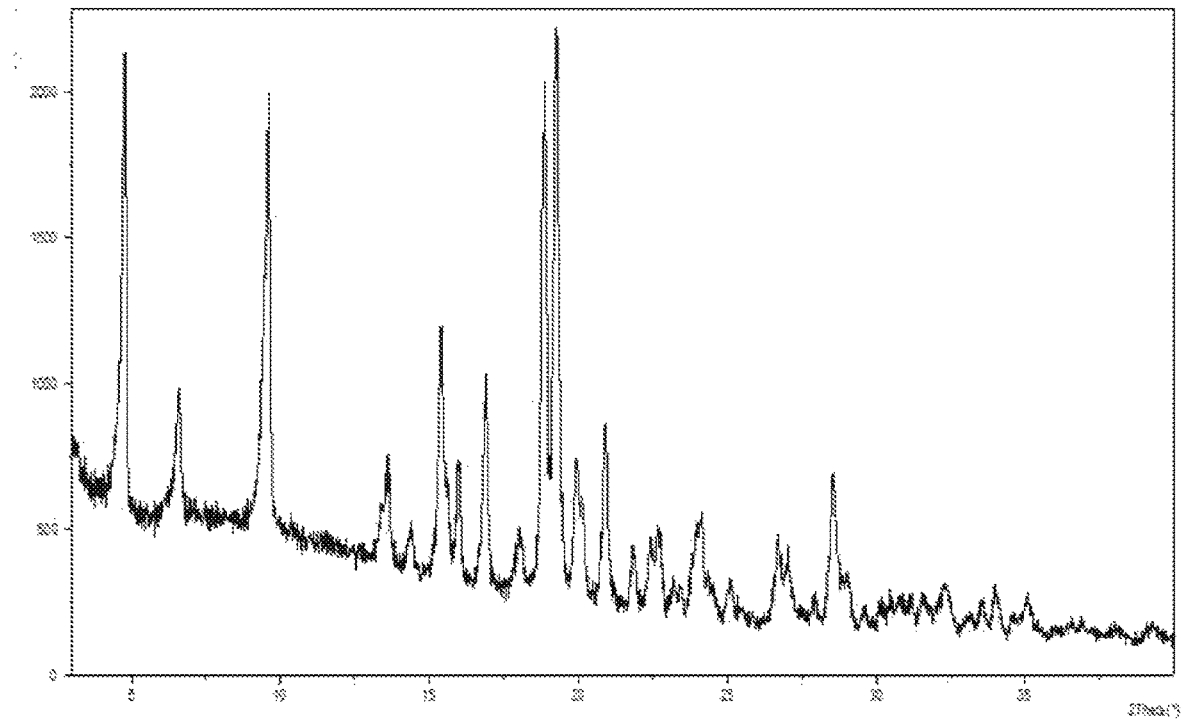
FIG. 45 depicts a XRPD Pattern of Citrate Form Y.

In certain embodiments, a solid form provided herein, e.g., Form Y is a citrate salt of Compound 1, and is substantially crystalline, as indicated by, e.g., X-ray powder diffraction measurements. In one embodiment, a solid form provided herein, e.g., Form Y, has an X-ray powder diffraction pattern (XRPD) substantially as shown in FIG. 45. In one embodiment, a solid form provided herein, e.g., Form Y, has one or more characteristic X-ray powder diffraction peaks at approximately 4.8, 6.6, 9.6, 13.6, 14.4, 15.4, 16.0, 16.9, 18.0, 18.9, 19.2, 19.9, 20.1, 20.9, 21.8, 22.4, 22.7, 23.2, 23.4, 24.0, 24.1, 24.3, 25.1, 26.7, 27.0, 27.9, 28.5, 29.0, 29.6, 30.2, 30.4, 30.8, 31.1, 31.6, 32.3, 33.1, 33.5, 34.0, 34.6, or 35.1° 2θ (±0.2° 2θ) or (±0.1° 2θ) as depicted in FIG. 45. In a specific embodiment, a solid form provided herein, e.g., Form Y, has one, two, three, four, five, six, seven, eight, nine, ten, or eleven characteristic X-ray powder diffraction peaks at approximately 4.8, 6.6, 9.6, 15.4, 16.0, 16.9, 18.9, 19.2, 19.9, 20.9, or 28.5° 2θ (±0.2° 2θ). In another embodiment, a solid form provided herein has one, two, three, or four characteristic X-ray powder diffraction peaks at approximately 4.8, 9.6, 18.9, or 19.2° 2θ (±0.2° 2θ). In one embodiment, the solid form is citrate salt Form Y. In another embodiment, the citrate salt Form Y has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, or forty characteristic X-ray powder diffraction peaks as set forth in Table 27.

Figure 46:
FIG. 46 depicts a SEM Picture of Citrate Form Y.

In one embodiment, a solid form provided herein, e.g., Form Y, has a SEM image substantially as shown in FIG. 46.

Figure 47:
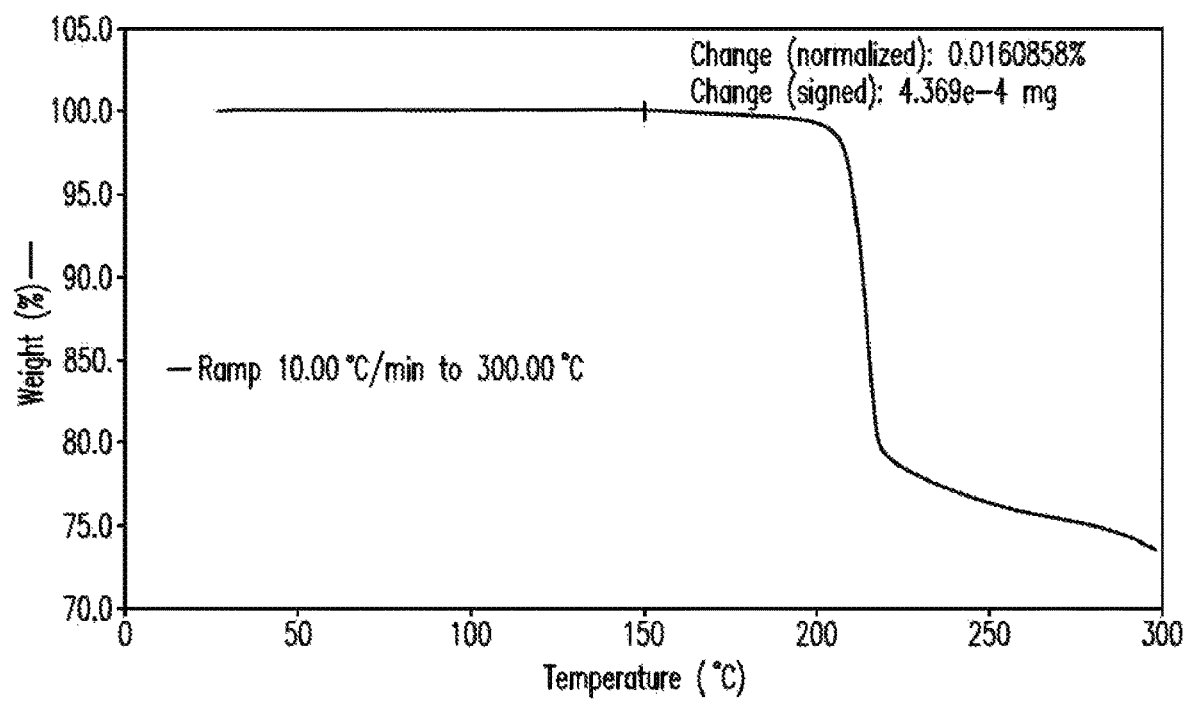
FIG. 47 depicts a TGA Thermogram of Citrate Form Y.

In one embodiment, provided herein is a crystalline citrate salt of Compound 1 having a TGA thermograph corresponding substantially to the representative TGA thermogram as depicted in FIG. 47. In certain embodiments, the crystalline form exhibits a TGA thermogram comprising a total mass loss of approximately 0.1% of the total mass of the sample between approximately 50° C. and approximately 150° C. when heated from approximately 50° C. to approximately 220° C.

Figure 48:
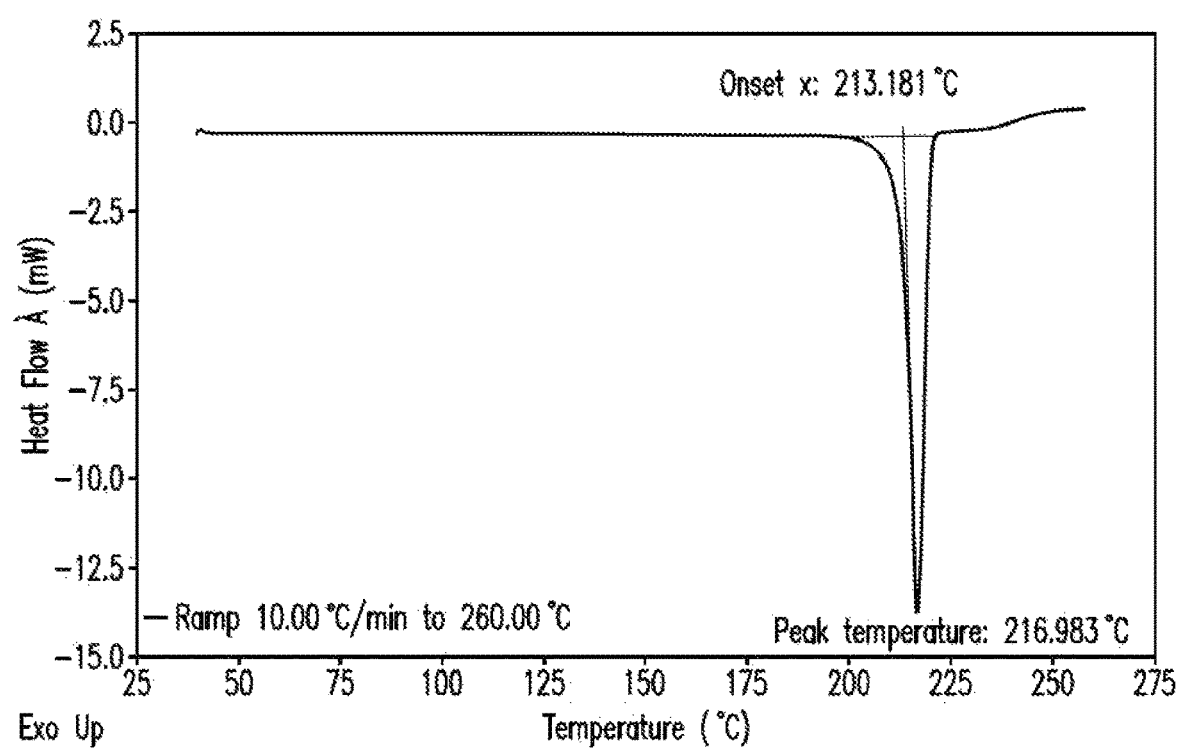
FIG. 48 depicts a DSC Thermogram of Citrate Form Y.

In one embodiment, provided herein is a crystalline citrate salt of Compound 1 having a DSC thermogram substantially as depicted in FIG. 48 comprising an endothermic event with an onset temperature of about 213° C. and a peak maximum temperature at about 217° C. when heated from approximately 25° C. to approximately 260° C.

Figures 49A, 49B:
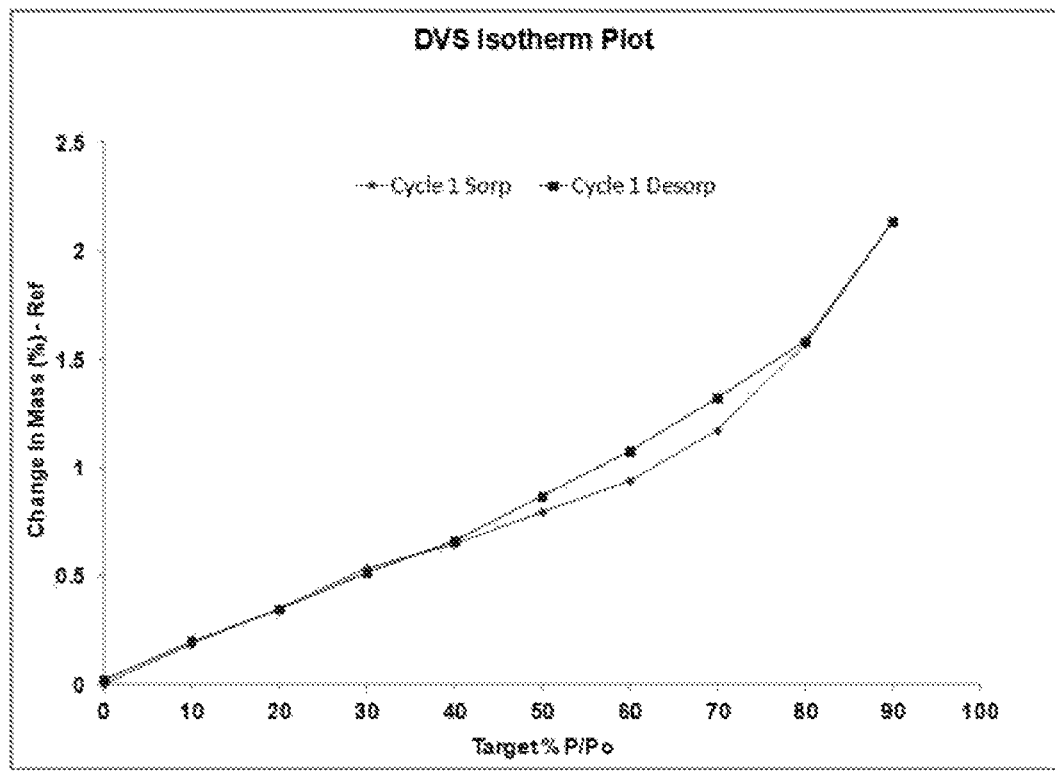
FIG. 49A depicts a DVS Isotherm Plot Citrate Form Y.
FIG. 49B depicts the values of the Isotherm Plot of FIG. 49A.

In one embodiment, provided herein is a solid form, e.g., Form Y, having a DVS isotherm plot substantially as depicted in FIG. 49A.

Figure 50:
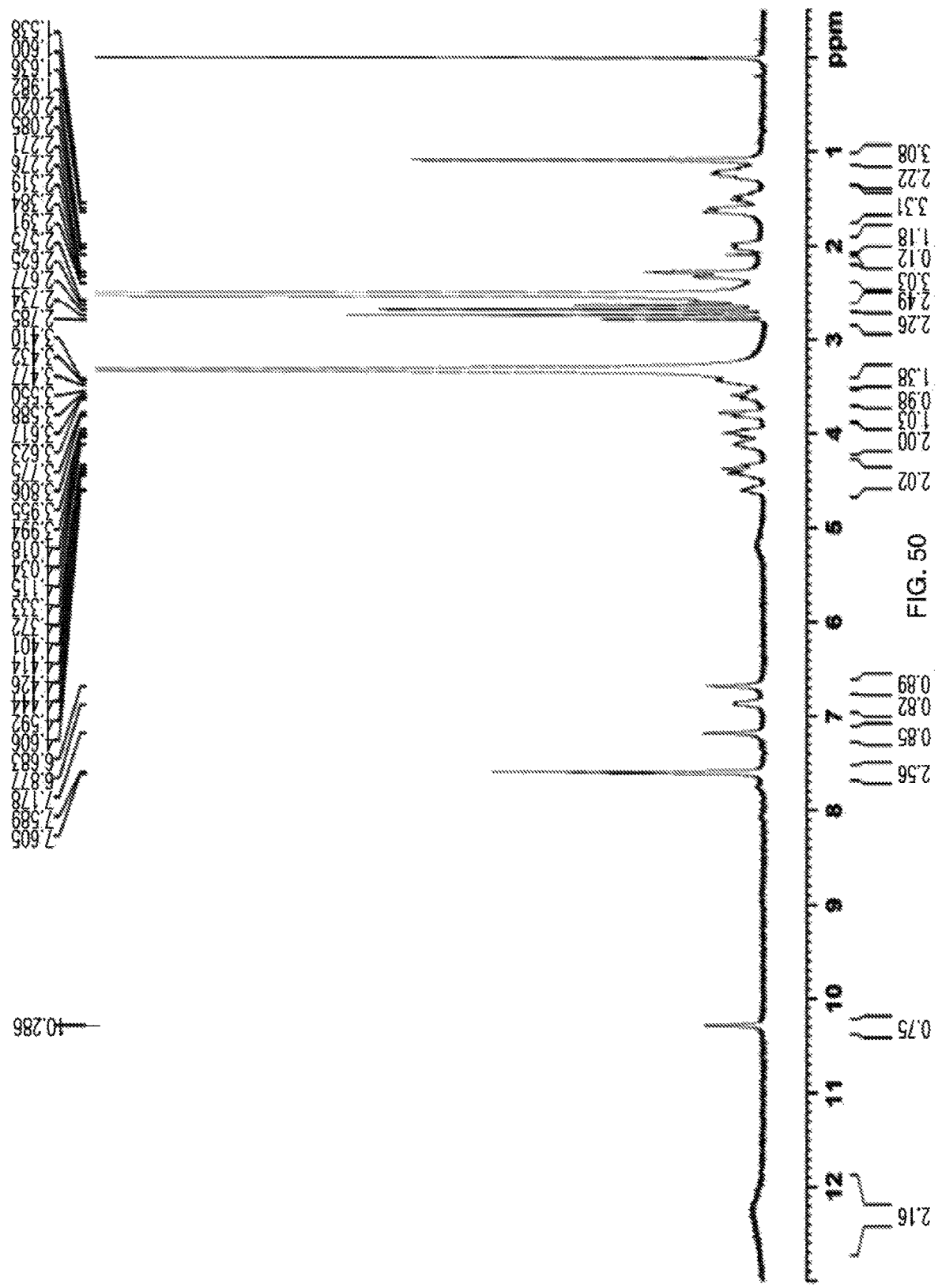
FIG. 50 depicts a $^1$H NMR Spectrum of Citrate Form Y.

In one embodiment, provided herein a solid form, e.g., Form Y, having a ¹H NMR spectrum substantially as depicted in FIG. 50.

In still another embodiment, the citrate salt Form Y is substantially pure. In certain embodiments, the substantially pure citrate salt Form Y is substantially free of other solid forms, e.g., amorphous solid. In certain embodiments, the purity of the substantially pure citrate salt Form Y is no less than about 95%, no less than about 96%, no less than about 97%, no less than about 98%, no less than about 98.5%, no less than about 99%, no less than about 99.5%, or no less than about 99.8%.

Citrate Salt Form Z

In certain embodiments, provided herein is a citrate salt Form Z.

In one embodiment, the citrate salt Form Z is a solid form of Compound 1. In another embodiment, the citrate salt Form Z is crystalline. In another embodiment, the citrate salt Form Z is an anhydrate. In another embodiment, the citrate salt Form Z is a hydrate. In one embodiment, the citrate salt Form Z is a non-stoichiometric hydrate. In still another embodiment, the citrate salt Form Z is a channel hydrate. In still another embodiment, the citrate salt Form Z is a non-stoichiometric channel hydrate. In still another embodiment, the citrate salt Form Z is a solvate.

In certain embodiments, Form Z is obtained by equilibration experiments, evaporation experiments and anti-solvent recrystallization experiments (see Table 23, Table 24, and Table 25). In certain embodiments, the citrate salt Form Z is obtained from certain solvent systems including MeCN/water (about 1:1), EtOH, EtOH/water (about 1:1), or MeOH. In certain embodiments, the citrate salt Form Z is obtained from certain solvent systems including MeCN/water (about 1:1), EtOH, EtOH/water (about 1:1), or MeOH at a temperature of about 50° C.

Figure 53:
FIG. 53 depicts a SEM Picture of Citrate Form Z.

In one embodiment, a solid form provided herein, e.g., Form Z, has a SEM image substantially as shown in FIG. 53.

Figure 52:
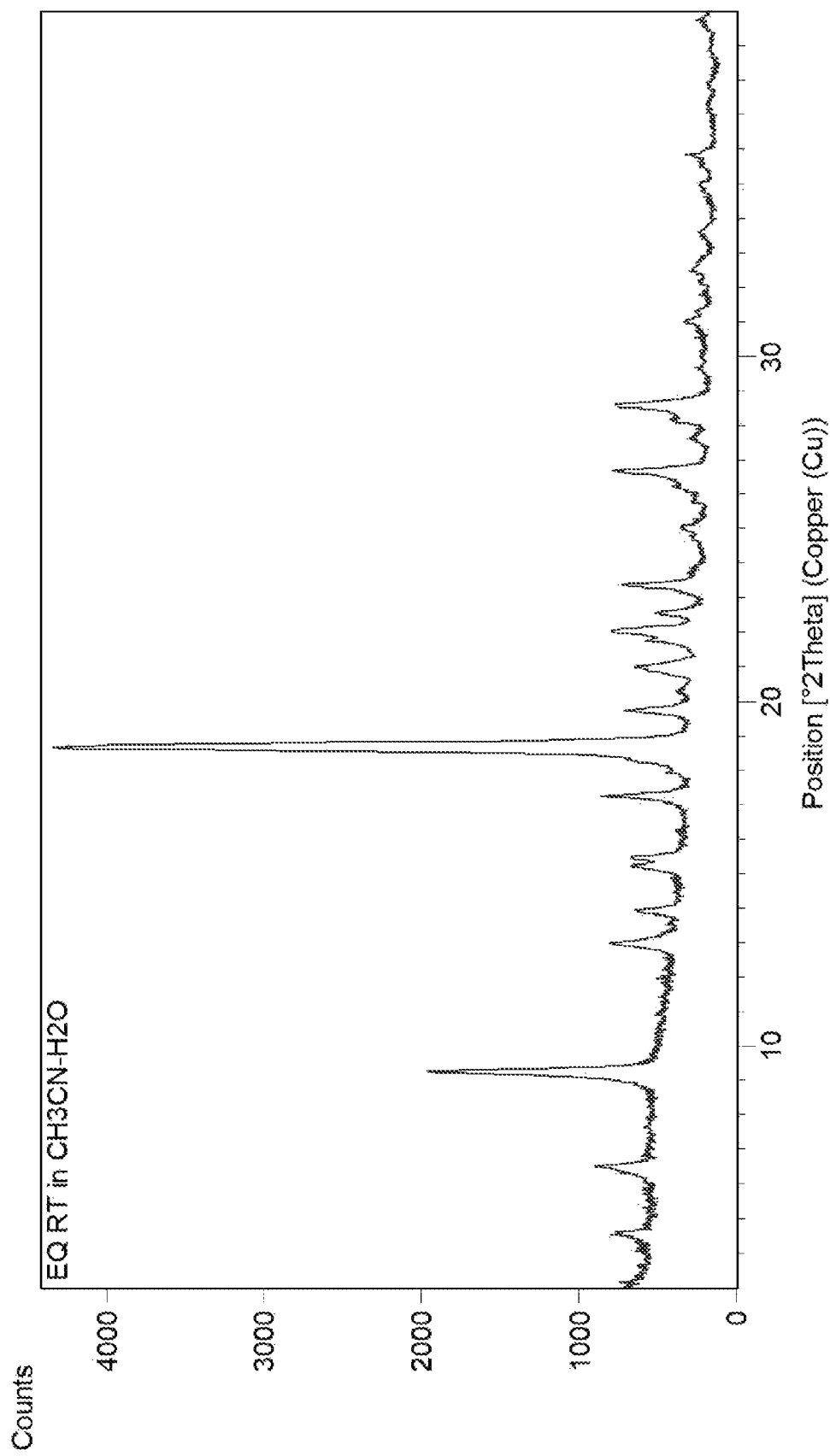
FIG. 52 depicts a XRPD Pattern of Citrate Form Z.

In certain embodiments, a solid form provided herein, e.g., Form Z, is substantially crystalline, as indicated by, e.g., X-ray powder diffraction measurements. In one embodiment, a solid form provided herein, e.g., Form Z, has an X-ray powder diffraction pattern substantially as shown in FIG. 52. In one embodiment, a solid form provided herein, e.g., Form Z, has one or more characteristic X-ray powder diffraction peaks at approximately 4.6, 6.6, 9.4, 13.1, 14.1, 15.3, 15.6, 17.4, 18.8, 19.0, 19.9, 20.4, 21.1, 21.9, 22.2, 22.7, 23.5, 23.9, 25.2, 26.3, 26.8, 27.8, 28.3, 28.7, 29.8, 31.2, 31.9, 32.6, 33.7, 35.1, 35.9, 37.4, or 38.0° 2θ (±0.2° 2θ) or (±0.1° 2θ) as depicted in FIG. 52. In a specific embodiment, a solid form provided herein has one, two, three, or four characteristic X-ray powder diffraction peaks at approximately 9.4, 18.8, 19.0, or 28.7° 2θ (±0.2° 2θ). In one embodiment, the solid form is citrate salt Form Z. In another embodiment, the citrate salt Form Z has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, or thirty-three characteristic X-ray powder diffraction peaks as set forth in Table 30.

Figure 54:
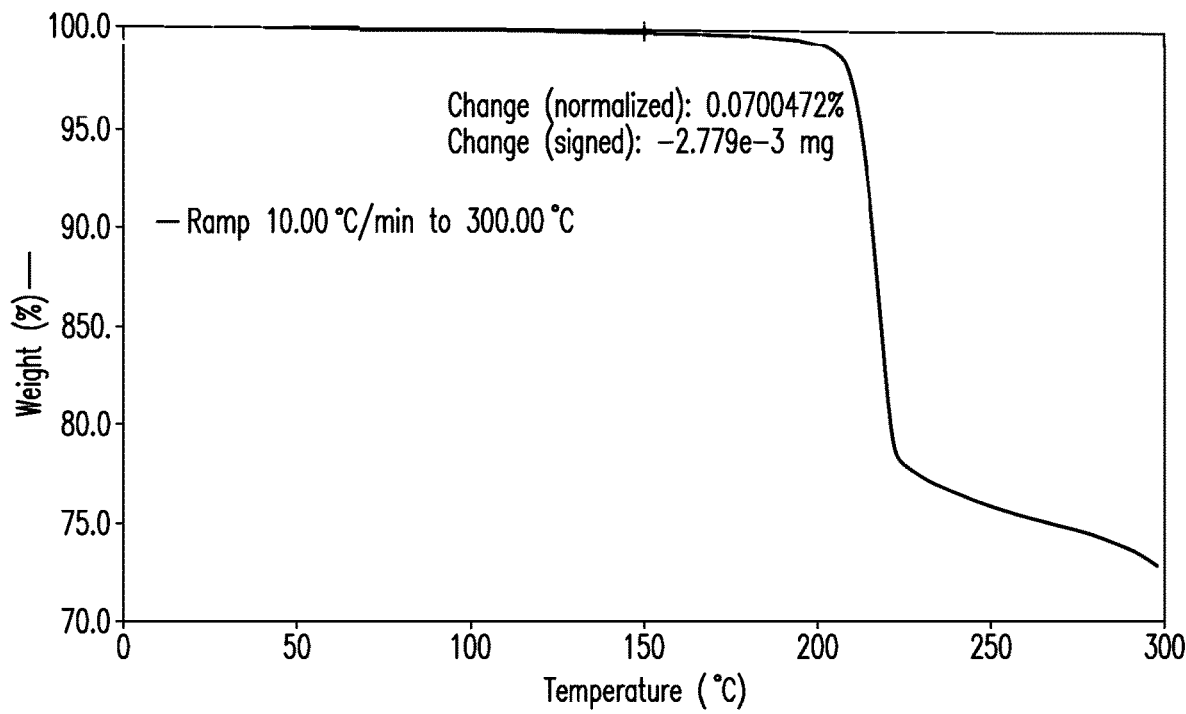
FIG. 54 depicts a TGA Thermogram of Citrate Form Z.

In one embodiment, provided herein is a crystalline citrate salt of Compound 1 having a TGA thermograph corresponding substantially to the representative TGA thermogram as depicted in FIG. 54. In certain embodiments, the crystalline form exhibits a TGA thermogram comprising a total mass loss of approximately 0.1% of the total mass of the sample between approximately 50° C. and approximately 150° C. when heated from approximately 25° C. to approximately 300° C. In certain embodiments, the crystalline form is an anhydrate of Compound 1.

Figure 55:
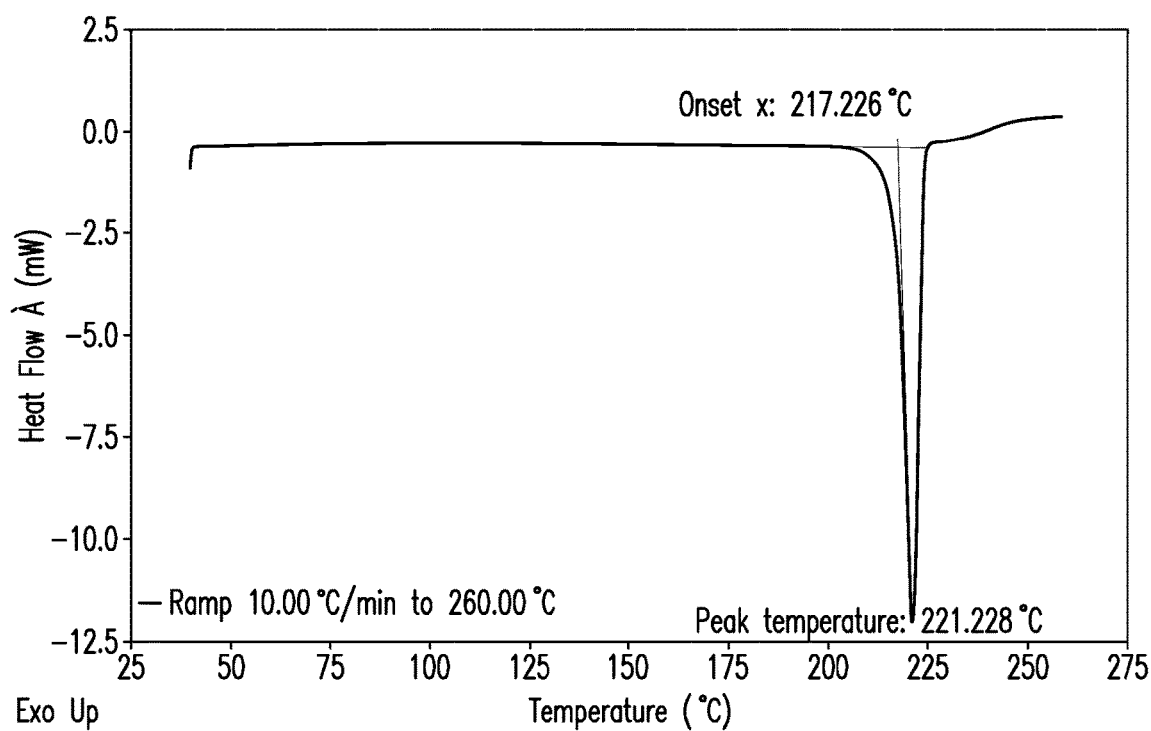
FIG. 55 depicts a DSC Thermogram of Citrate Form Z.

In one embodiment, provided herein is a crystalline citrate salt Form of Compound 1 having a DSC thermogram as depicted in FIG. 55 comprising an endothermic event with an onset temperature at about 217° C. and a peak maximum temperature at about 221° C. when heated from approximately 25° C. to approximately 260° C.

Figures 56A, 56B:
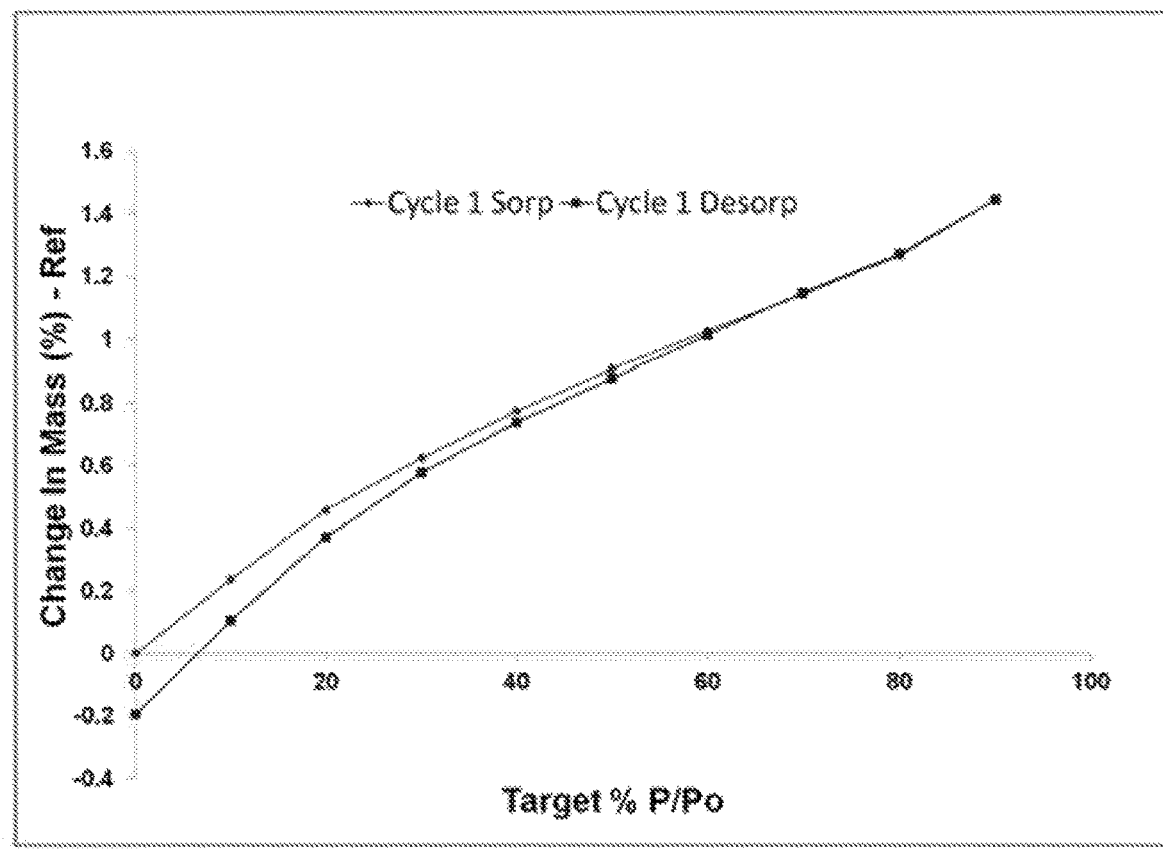
FIG. 56A depicts a DVS Isotherm Plot Citrate Form Z.
FIG. 56B depicts the values of the Isotherm Plot of FIG. 56A

In one embodiment, provided herein is a solid form, e.g., Form Y, having a DVS isotherm plot substantially as depicted in FIG. 56A.

Figure 57:
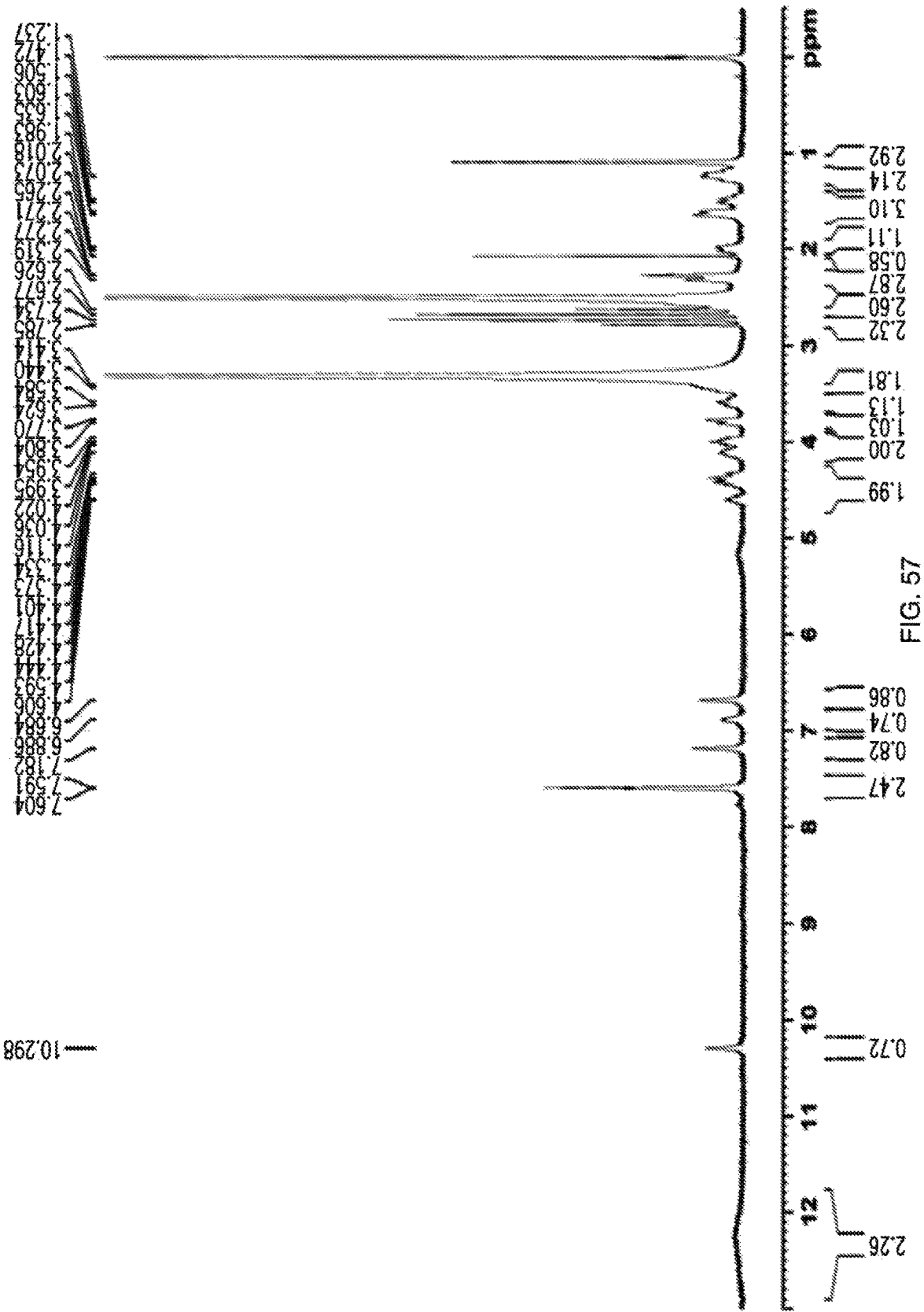
FIG. 57 depicts a $^1$H NMR Spectrum of Citrate Form Z.

In one embodiment, provided herein is a solid form provided herein, e.g., Form Z, having a ¹H NMR spectrum substantially as depicted in FIG. 57.

Figure 58:
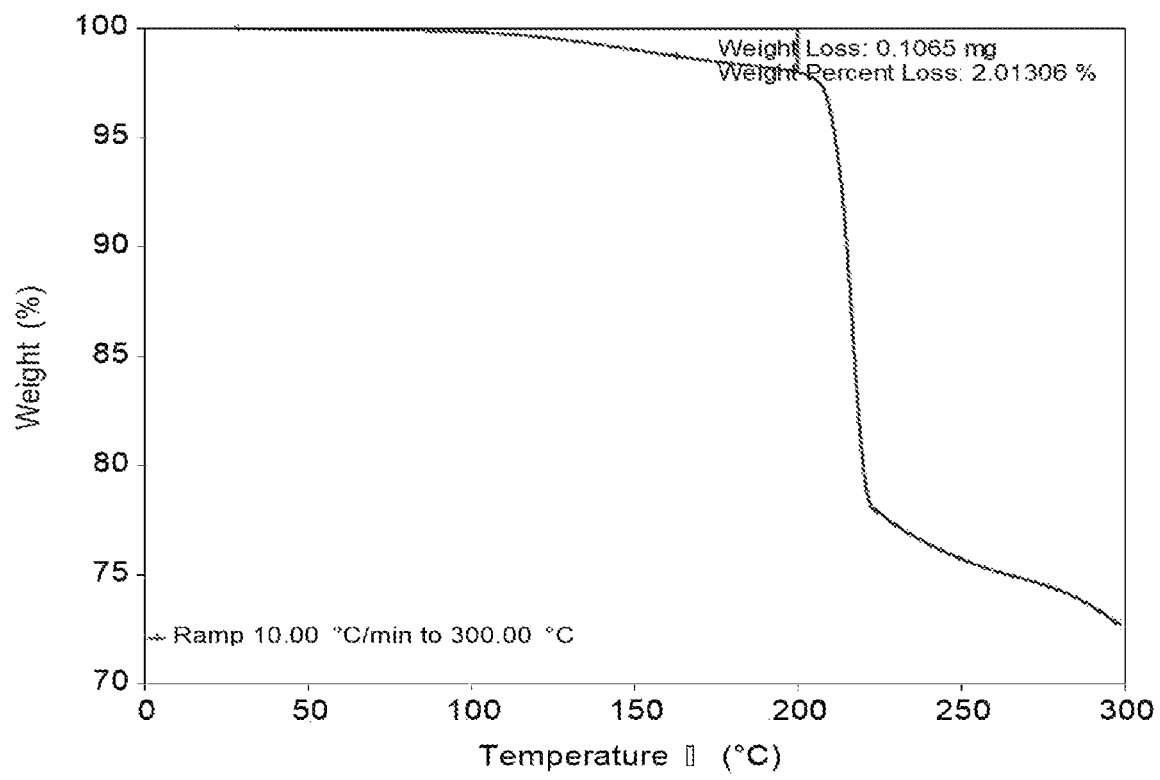
FIG. 58 depicts a TGA Thermogram of a hydrate form of Citrate Form Z.

In one embodiment, provided herein is a hydrate of the citrate salt of Compound 1 having a TGA thermograph corresponding substantially to the representative TGA thermogram as depicted in FIG. 58. In certain embodiments, the hydrate exhibits a TGA thermogram comprising a total mass loss of approximately 2% of the total mass of the sample between approximately 25° C. and approximately 200° C. when heated from approximately 25° C. to approximately 300° C. In certain embodiments, the crystalline form is a hydrate of the Citrate form of Compound 1.

Figure 59:
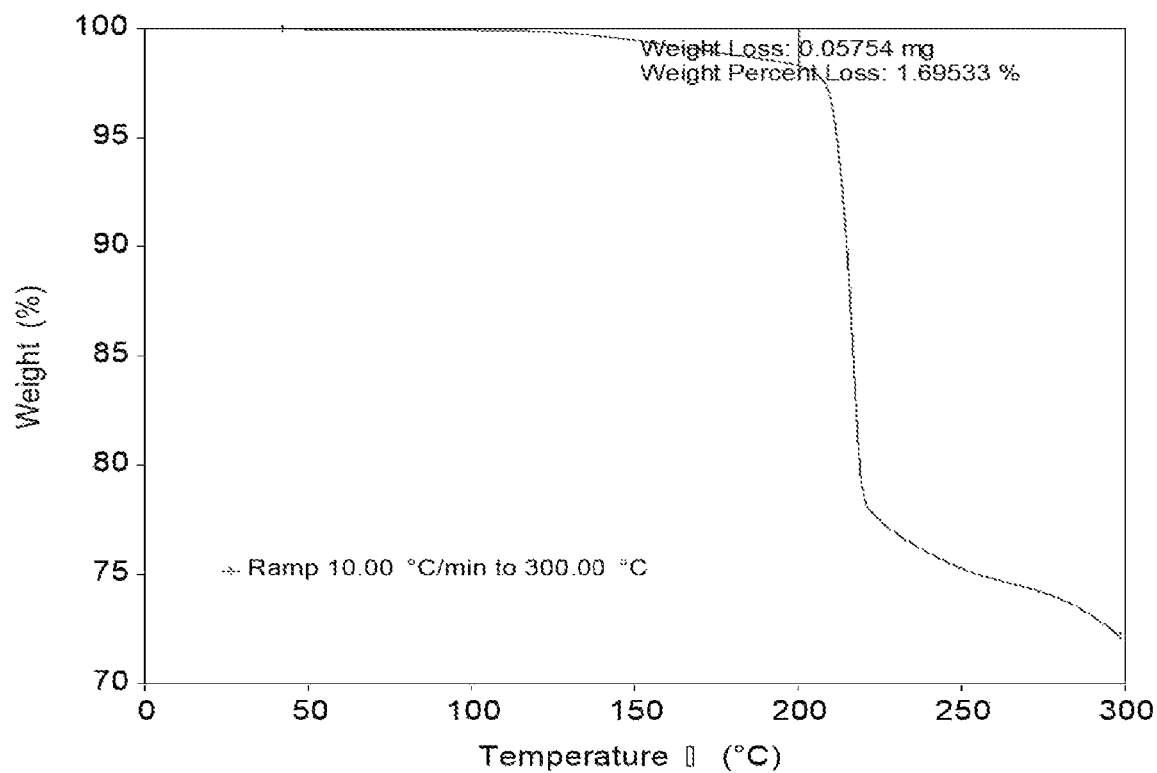
FIG. 59 depicts a TGA Thermogram of a non-stoichiometric form of Citrate Form Z.

In one embodiment, provided herein is a non-stoichiometric hydrate of the citrate salt of Compound 1 having a TGA thermograph corresponding substantially to the representative TGA thermogram as depicted in FIG. 59. In certain embodiments, the non-stoichiometric hydrate form exhibits a TGA thermogram comprising a total mass loss of approximately 1.7% of the total mass of the sample between approximately 50° C. and approximately 200° C. when heated from approximately 50° C. to approximately 300° C. In certain embodiments, the crystalline form is a non-stoichiometric hydrate of the Citrate form of Compound 1.

Figure 60:
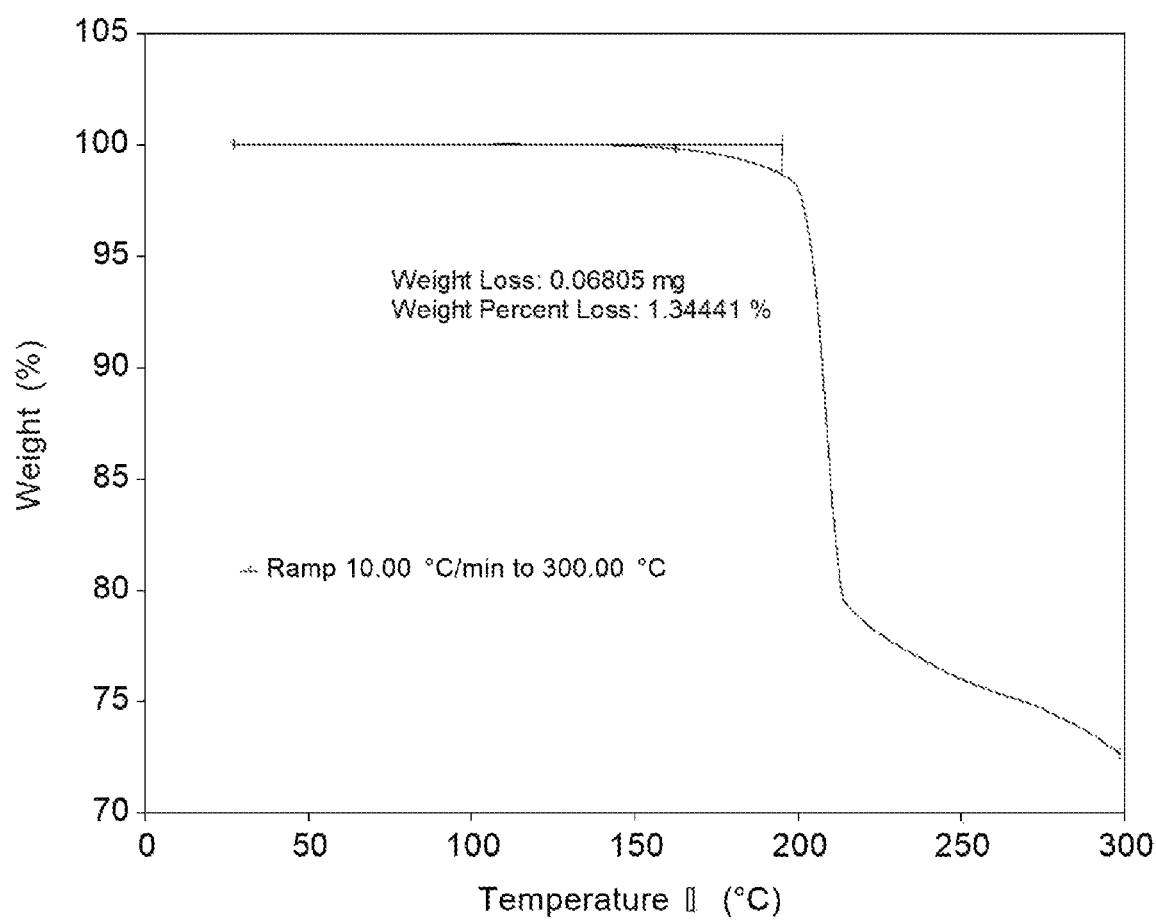
FIG. 60 depicts a TGA Thermogram of a solvate form of Citrate Form Z.

In one embodiment, provided herein is a solvate of the citrate salt of Compound 1 having a TGA thermograph corresponding substantially to the representative TGA thermogram as depicted in FIG. 60. In certain embodiments, the solvate exhibits a TGA thermogram comprising a total mass loss of approximately 1.3% of the total mass of the sample between approximately 25° C. and approximately 200° C. when heated from approximately 25° C. to approximately 300° C. In certain embodiments, the crystalline form is a solvate of the Citrate form of Compound 1.

Figure 61:
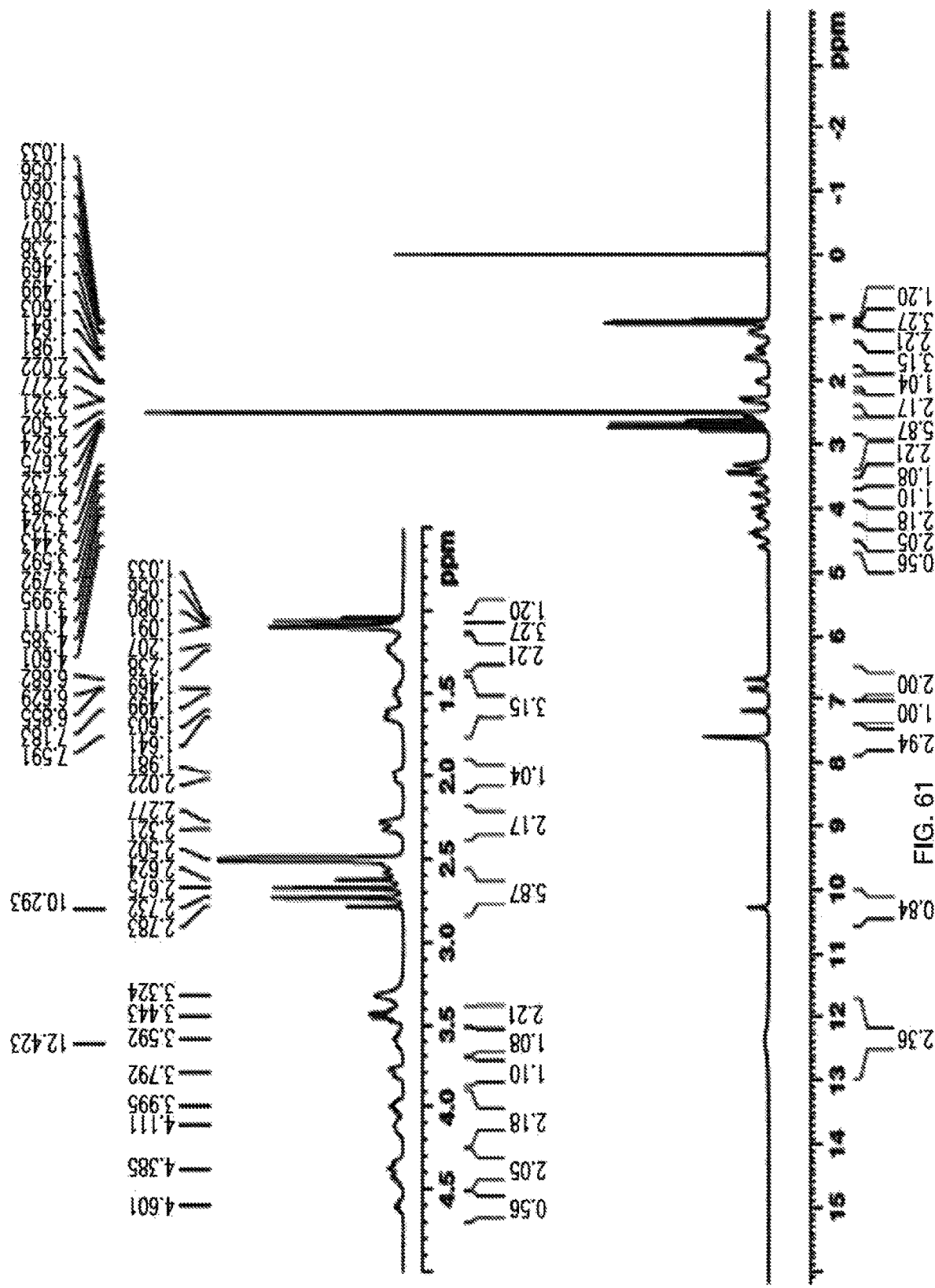
FIG. 61 depicts $^1$H NMR Spectrum of a solvate form of Citrate Form Z.

In one embodiment, provided herein is a solid form provided herein, e.g., solvate of Form Z, having a ¹H NMR spectrum substantially as depicted in FIG. 61.

In still another embodiment, the citrate salt Form Z is substantially pure. In certain embodiments, the substantially pure citrate salt Form Z is substantially free of other solid forms, e.g., amorphous solid. In certain embodiments, the purity of the substantially pure citrate salt Form Z is no less than about 95%, no less than about 96%, no less than about 97%, no less than about 98%, no less than about 98.5%, no less than about 99%, no less than about 99.5%, or no less than about 99.8%.

HCl Salt Forms

In certain embodiments provided herein is a starting material HCl salt Form. In one embodiment, the starting material HCl salt Form is a solid form of Compound 1. In another embodiment, the starting material HCl salt Form is an anhydrate.

In one embodiment, is the starting material HCl salt Form is obtained by dissolving Compound 1 in MeOH (e.g., about 10 Vol.) at a temperature of about 25° C. to about 30° C. HCl in MeOH (~1.25 M, 1.10 eq) is added to obtain the HCl salt Form starting material of Compound 1. The solution can be vacuum distilled and the solvent changed from MeOH to EtOAc (e.g., about 30-35 Vol.), where the temperature is optionally maintained at about 25° C. to about 35° C. The slurry can be filtered and the cake washed with EtOAc (e.g., about 5 Vol.). The cake can be dried in a vacuum oven at 50° C.

Figure 63:
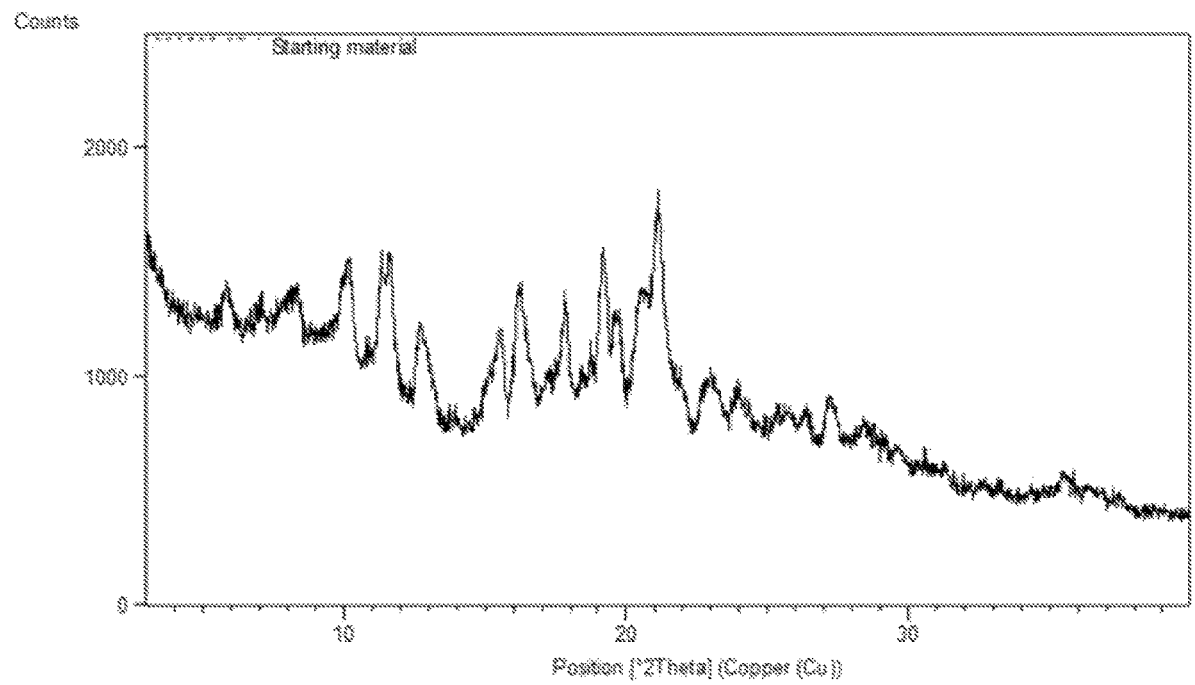
FIG. 63 depicts a XRPD Pattern of HCl Salt starting material.

In certain embodiments, a solid form provided herein, e.g., a starting material HCl salt Form, is substantially crystalline, as indicated by, e.g., X-ray powder diffraction measurements. In one embodiment, a solid form provided herein, e.g., a starting material HCl salt Form, has an X-ray powder diffraction pattern substantially as shown in FIG. 63. In one embodiment, a solid form provided herein, e.g., a starting material HCl salt Form, has one or more characteristic X-ray powder diffraction peaks at approximately 5.8, 7.1, 8.3, 10.1, 11.3, 11.6, 12.7, 15.5, 16.1, 17.8, 19.2, 19.7, 20.5, 21.1, 23.0, 24.0, 25.5, 26.3, 27.2, 28.4, 31.0, or 35.6° 2θ (±0.2° 2θ) or (±0.1° 2θ) as depicted in FIG. 63. In a specific embodiment, a solid form provided herein has one, two, three, or four characteristic X-ray powder diffraction peaks at approximately 21.1, 19.2, 20.5, 17.8° 2θ (±0.2° 2θ) as depicted in FIG. 63. In one embodiment, the solid form is a starting material HCl salt Form. In another embodiment, the starting material HCl salt Form has one, two, three, four, five, six, seven, eight, nine, ten, eleven, twelve, thirteen, fourteen, fifteen, sixteen, seventeen, eighteen, nineteen, twenty, twenty-one, or twenty-two, characteristic X-ray powder diffraction peaks as set forth in Table 42.

Figure 64:
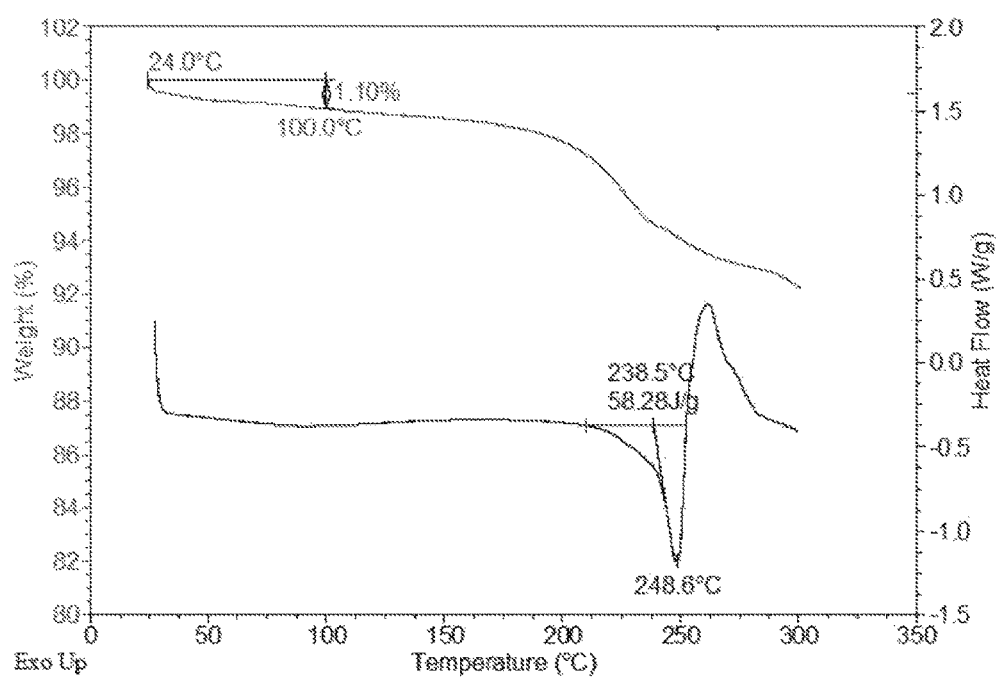
FIG. 64 depicts a TGA and DSC Thermogram of HCl Salt starting material.

In one embodiment, provided herein is a starting material HCl salt Form of Compound 1 having a TGA thermograph corresponding substantially to the representative TGA thermogram as depicted in FIG. 64. In certain embodiments, the starting material HCl salt Form exhibits a TGA thermogram comprising a total mass loss of approximately 1.1% of the total mass of the sample between approximately 24° C. and approximately 100° C. when heated from approximately 24° C. to approximately 300° C. In certain embodiments, the crystalline form is an anhydrate of Compound 1.

In one embodiment, provided herein is a starting material HCl salt Form of Compound 1 having a DSC thermogram as depicted in FIG. 64 comprising an endothermic event with an onset temperature at about 239° C. and a peak maximum temperature at about 249° C. when heated from approximately 24° C. to approximately 300° C.

Figure 65:
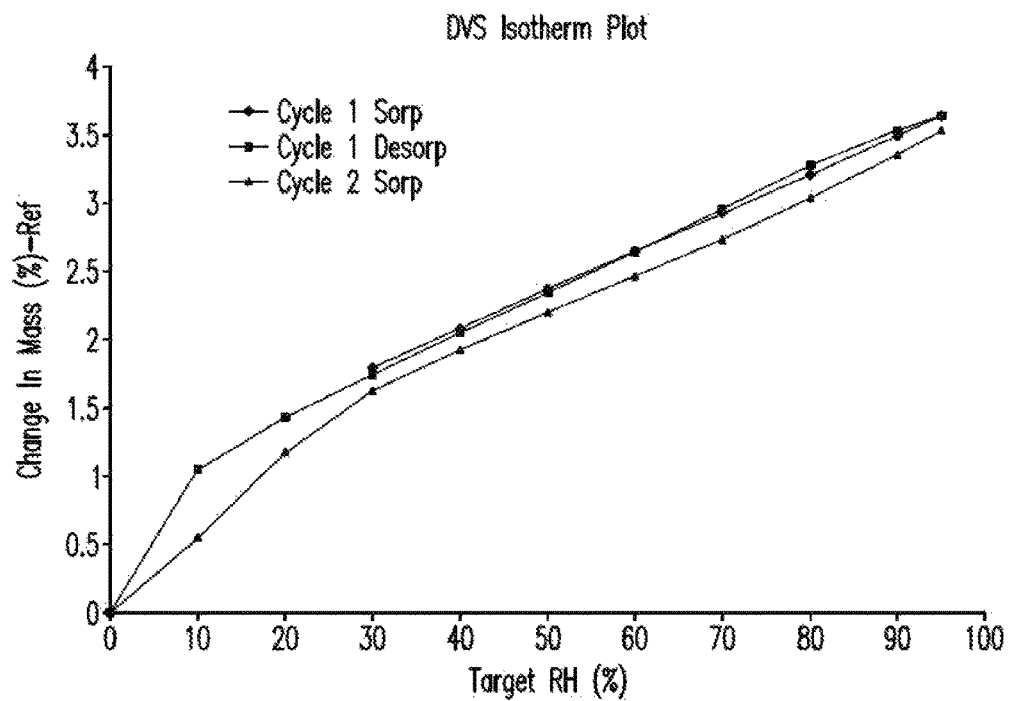
FIG. 65 depicts a DVS Isotherm Plot of HCl Salt starting material.

In one embodiment, provided herein is a solid form, e.g., a starting material HCl salt Form, having a DVS isotherm plot substantially as depicted in FIG. 65.

In still another embodiment, the starting material HCl salt Form is substantially pure. In certain embodiments, the substantially pure starting material HCl salt Form is substantially free of other solid forms, e.g., amorphous solid. In certain embodiments, the purity of the substantially pure starting material HCl salt Form is no less than about 95%, no less than about 96%, no less than about 97%, no less than about 98%, no less than about 98.5%, no less than about 99%, no less than about 99.5%, or no less than about 99.8%.

HCl Salt Form 1

In certain embodiments, provided herein is an HCl salt Form 1 of Compound 1.

In one embodiment, the HCl salt Form 1 is a solid form of Compound 1. In one embodiment, the HCl salt Form 1 is a solvate. In one embodiment, the HCl salt Form 1 is an IPA solvate form of Compound 1. In another embodiment, the HCl salt Form 1 is crystalline.

In certain embodiments, the HCl salt Form 1 provided herein is obtained by equilibration experiments, evaporation experiments and anti-solvent recrystallization experiments (see see Table 23, Table 24, and Table 25). In certain embodiments, the HCl salt Form 1 is obtained from certain solvent systems including IPA.

In one embodiment, a method of preparing the HCl salt Form 1 comprises the steps of dissolving Compound 1 in IPA and slowly evaporating the IPA and collecting solids.

Figure 66:
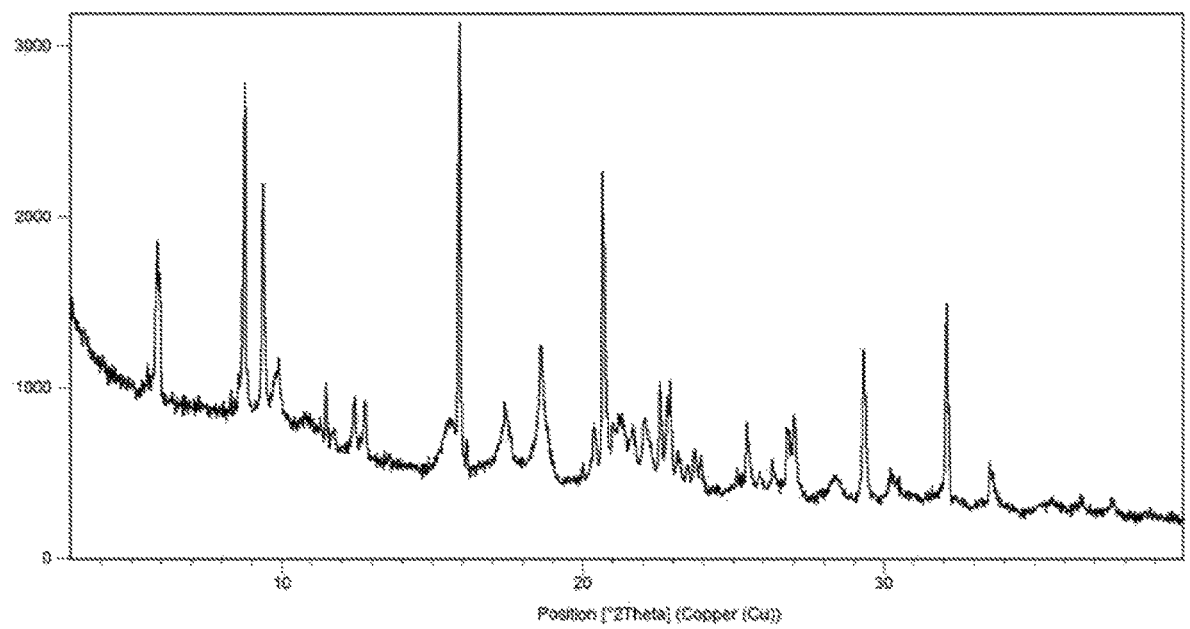
FIG. 66 depicts a XRPD Pattern of HCl Salt Form 1.

In certain embodiments, a solid form provided herein, e.g., HCl salt Form 1, is an HCl salt of Compound 1, and is substantially crystalline, as indicated by, e.g., X-ray powder diffraction measurements. In one embodiment, a solid form provided herein, e.g., HCl salt Form 1, has an X-ray powder diffraction pattern (XRPD) substantially as shown in FIG. 66. In one embodiment, a solid form provided herein, e.g., HCl salt Form 1, has one or more characteristic X-ray powder diffraction peaks at approximately 5.5, 5.9, 5.9, 8.8, 9.4, 9.9, 11.5, 12.4, 12.8, 15.6, 15.9, 16.2, 17.4, 18.6, 20.4, 20.7, 21.0, 21.3, 21.7, 22.1, 22.6, 22.8, 22.9, 23.2, 23.5, 23.7, 23.9, 25.5, 25.8, 26.3, 26.8, 27.0, 28.4, 29.3, 30.3, 32.1, 32.2, 33.5, 35.5, 36.6, or 37.6° 2θ (±0.2° 2θ) or (±0.1° 2θ) as depicted in FIG. 66. In a specific embodiment, a solid form provided herein has one, two, three, four, five, six, seven, eight, nine, ten, eleven, twelve, or thirteen characteristic X-ray powder diffraction peaks at approximately 5.5 5.9, 8.8, 9.4, 15.9, 18.6, 20.7, 22.6, 22.8, 22.9, 29.3, 32.1, or 32.2° 2θ (±0.2° 2θ). In one embodiment, the solid form is HCl Salt Form 1. In another embodiment, a solid form provided herein has one, two, three or four characteristic X-ray powder diffraction peaks at approximately 8.8, 9.4, 15.9, or 20.7° 2θ (±0.2° 2θ). In another embodiment, HCl Salt Form 1 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, or forty-one characteristic X-ray powder diffraction peaks as set forth in Table 34.

Figure 67:
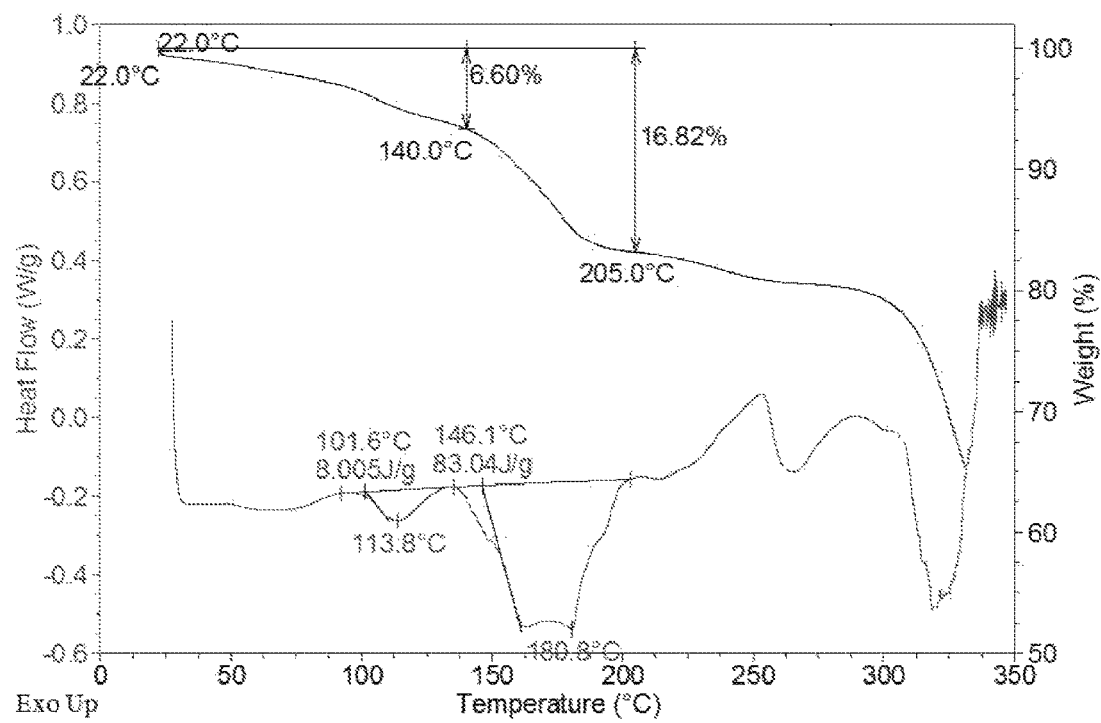
FIG. 67 depicts a TGA and DSC Thermogram of HCl Salt Form 1.

In one embodiment, provided herein is crystalline form HCl salt of Compound 1 having a TGA thermograph corresponding substantially to the representative TGA thermogram as depicted in FIG. 67. In certain embodiments, crystalline form HCl salt of Compound 1 exhibits a TGA thermogram comprising a total mass loss of approximately 6.6% of the total mass of the sample between approximately 20° C. and approximately 140° C. when heated from approximately 20° C. to approximately 325° C.

In certain embodiments, a solid form provided herein exhibits a TGA thermogram comprising a total mass loss of approximately 10% of the total mass of the sample between approximately 150° C. and approximately 200° C. when heated from approximately 20° C. to approximately 325° C. Thus, in certain embodiments, the crystalline form HCl salt of Compound 1 loses about 17% of its total mass when heated from about ambient temperature to about 325° C.

In one embodiment, provided herein is crystalline form HCl salt of Compound 1 having a DSC thermogram substantially as depicted in FIG. 67 comprising an endothermic event with an onset temperature at about 102° C. and a peak maximum temperature at about 114° C. when heated from approximately 25° C. to approximately 350° C.

In one embodiment, provided herein is a crystalline form HCl salt of Compound 1 having a DSC thermogram substantially as depicted in FIG. 67 comprising an endothermic event with an onset temperature at about 146° C. and a peak maximum temperature at about 181° C. when heated from approximately 25° C. to approximately 350° C.

In still another embodiment, provided herein is a crystalline form HCl salt of Compound 1 having a DSC thermogram substantially as depicted in FIG. 67 comprising multiple endothermic events each having a maximum greater than 250° C. when heated from approximately 25° C. to approximately 350° C.

In still another embodiment, HCl salt Form 1 is substantially pure. In certain embodiments, the substantially pure HCl salt Form 1 is substantially free of other solid forms, e.g., amorphous solid. In certain embodiments, the purity of the substantially pure HCl salt Form 1 is no less than about 95%, no less than about 96%, no less than about 97%, no less than about 98%, no less than about 98.5%, no less than about 99%, no less than about 99.5%, or no less than about 99.8%.

HCl Salt Form 2

In certain embodiments, provided herein is the HCl salt Form 2.

In one embodiment, the HCl salt Form 2 is a solid form of Compound 1. In another embodiment, HCl Salt Form 2 is crystalline. In one embodiment, HCl Salt Form 2 is an anhydrate form of Compound 1. In one embodiment, HCl salt Form 2 is solvated form of Compound 1. In one embodiment, HCl salt Form 2 is an IPA solvated form of Compound 1. In one embodiment, HCl salt Form 2 is a toluene solvated form of Compound 1.

In certain embodiments, HCl salt Form 2 provided herein is obtained by equilibration experiments, evaporation experiments and anti-solvent recrystallization experiments. In certain embodiments, HCl salt Form 2 is obtained from certain solvent systems including IPA/toluene (about 1:1).

Figure 68:
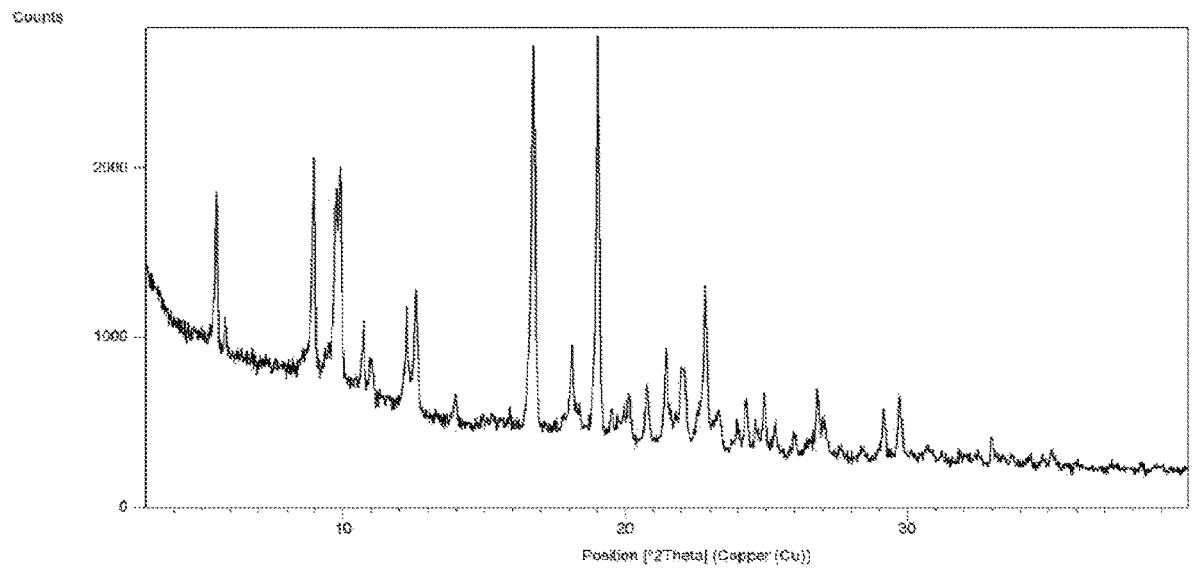
FIG. 68 depicts a XRPD Pattern of HCl Salt Form 2.

In certain embodiments, a solid form provided herein, e.g., HCl salt Form 2, is substantially crystalline, as indicated by, e.g., X-ray powder diffraction measurements. In one embodiment, HCl salt Form 2 has an X-ray powder diffraction pattern substantially as shown in FIG. 68. In one embodiment, a solid form provided herein, e.g., HCl salt Form 2, has one or more characteristic X-ray powder diffraction peaks at approximately 5.5, 5.8, 9.0, 9.8, 9.9, 10.7, 11.0, 12.3, 12.6, 14.0, 16.7, 18.1, 19.0, 19.5, 19.9, 20.1, 20.8, 21.5, 21.8, 22.0, 22.8, 23.3, 24.0, 24.3, 24.6, 24.9, 25.3, 26.0, 26.5, 26.8, 27.0, 27.6, 28.4, 29.2, 29.7, 30.7, 33.0, or 35.1° 2θ (±0.2° 2θ) or (±0.1° 2θ) as depicted in FIG. 68. In a specific embodiment, a solid form provided herein, e.g., HCl salt Form 2, has one, two, three, four, five, six, seven, eight, nine, ten, or eleven characteristic X-ray powder diffraction peaks at approximately 5.5, 9.0, 9.8, 9.9, 12.3, 12.6, 16.7, 18.1, 19.0, 21.5, or 22.8° 2θ (±0.2° 2θ). In another embodiment, a solid form provided herein has one, two, three, or four characteristic X-ray powder diffraction peaks at approximately 9.0, 9.8, 9.9, or 16.7° 2θ (±0.2° 2θ). In one embodiment, the solid form is HCl salt Form 2. In another embodiment, HCl Salt Form 2 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, or thirty-eight characteristic X-ray powder diffraction peaks as set forth in Table 35.

Figure 69:
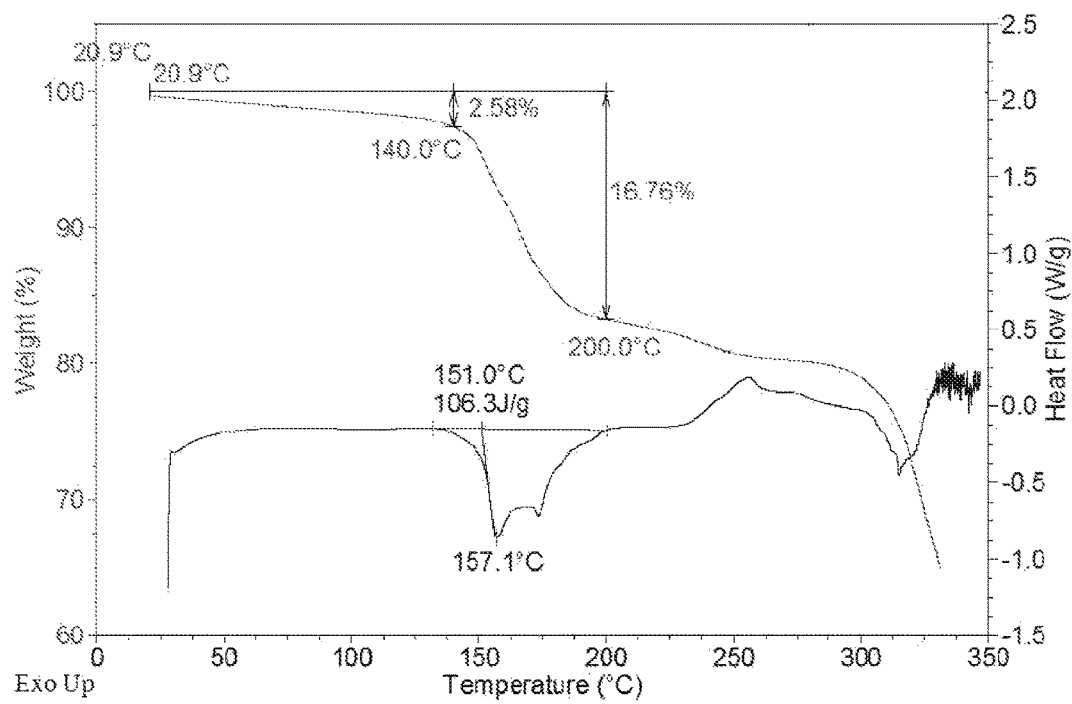
FIG. 69 depicts a TGA and DSC Thermogram of HCl Salt Form 2.

In one embodiment, provided herein is a crystalline form HCl salt of Compound 1 having a TGA thermograph corresponding substantially to the representative TGA thermogram as depicted in FIG. 69. In certain embodiments, the crystalline form, HCl salt Form 2, exhibits a TGA thermogram comprising a total mass loss of approximately 2.6% of the total mass of the sample between approximately 20° C. and approximately 140° C. when heated from approximately 20° C. to approximately 325° C.

In one embodiment, provided herein is a crystalline form HCl salt of Compound 1 having a TGA thermograph corresponding substantially to the representative TGA thermogram as depicted in FIG. 69, where the crystalline form HCl salt of Compound 1 exhibits a TGA thermogram comprising a total mass loss of approximately 14% of the total mass of the sample between approximately 140° C. and approximately 200° C. when heated from approximately 20° C. to approximately 325° C. Thus, in certain embodiments, the crystalline form HCl salt of Compound 1 loses about 17% of its total mass when heated from about ambient temperature to about 325° C.

In one embodiment, provided herein is a crystalline form HCl salt of Compound 1 having a DSC thermogram as depicted in FIG. 69 comprising an endothermic event with an onset temperature at about 151° C. and a peak maximum temperature at about 157° C. when heated from approximately 25° C. to approximately 350° C.

In still another embodiment, HCl salt Form 2 is substantially pure. In certain embodiments, the substantially pure HCl salt Form 2 is substantially free of other solid forms, e.g., amorphous solid. In certain embodiments, the purity of the substantially pure HCl salt Form 2 is no less than about 95%, no less than about 96%, no less than about 97%, no less than about 98%, no less than about 98.5%, no less than about 99%, no less than about 99.5%, or no less than about 99.8%.

HCl Salt Form 3

In certain embodiments, provided herein is HCl salt Form 3.

In one embodiment, HCl salt Form 3 is a solid form of Compound 1. In another embodiment, HCl Salt Form 3 is crystalline. In one embodiment, HCl salt Form 3 is a solvated form of Compound 1. In one embodiment, HCl salt Form 3 is an n-butanol solvated form of Compound 1. In one embodiment, HCl salt Form 3 is a heptane solvated form of Compound 1. In one embodiment, HCl salt Form 3 is an n-butanol/heptane solvated form of Compound 1. In one embodiment, HCl salt Form 3 is a hydrated form of Compound 1. In one embodiment, HCl salt Form 3 is an anhydrate form of Compound 1.

In certain embodiments, HCl salt Form 3 provided herein is obtained by equilibration experiments, evaporation experiments, cooling recrystallization experiments and anti-solvent recrystallization experiments. In certain embodiments, HCl salt Form 3 is obtained from certain solvent systems including n-butanol, toluene, or n-butanol/toluene (about 1:1).

Figure 70:
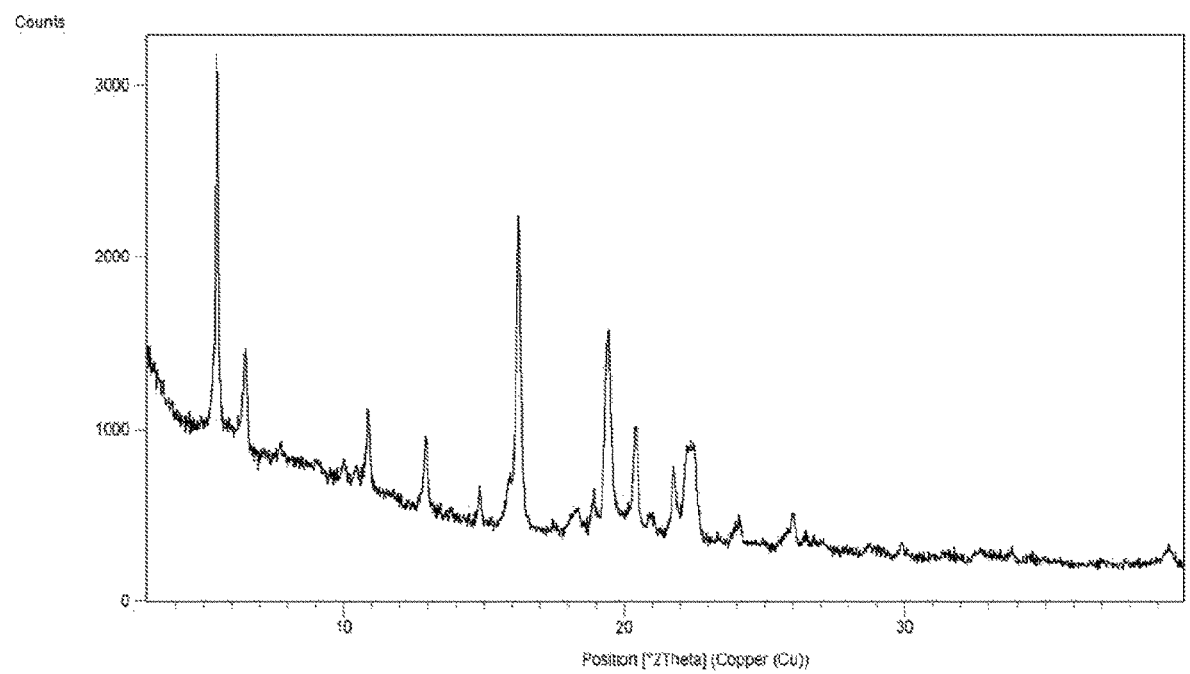
FIG. 70 depicts a XRPD Pattern of HCl Salt Form 3.

In certain embodiments, a solid form provided herein, e.g., HCl salt Form 3, is substantially crystalline, as indicated by, e.g., X-ray powder diffraction measurements. In one embodiment, the HCl salt Form 3 has an X-ray powder diffraction pattern substantially as shown in FIG. 70. In one embodiment, a solid form provided herein, e.g., HCl salt Form 3, has one or more characteristic X-ray powder diffraction peaks at approximately 5.5, 6.5, 7.7, 10.0, 10.5, 10.9, 12.9, 14.8, 15.9, 16.2, 18.3, 18.9, 19.4, 20.4, 21.0, 21.8, 22.2, 22.5, 24.1, 26.0, 28.8, 29.9, 32.7, or 39.4° 2θ (±0.2° 2θ) or (±0.1° 2θ) as depicted in FIG. 70. In a specific embodiment, a solid form provided herein, e.g., HCl salt Form 3, has one, two, three, four, five, six, seven, or eight characteristic X-ray powder diffraction peaks at approximately 5.5, 6.5, 10.9, 16.2, 19.4, 20.4, 22.2, or 22.5° 2θ (±0.2° 2θ). In another embodiment, a solid form provided herein has one, two, three, or four characteristic X-ray powder diffraction peaks at approximately 5.5, 16.2, 19.4, or 20.4° 2θ (±0.2° 2θ). In one embodiment, the solid form is HCl Salt Form 3. In another embodiment, the HCl salt Form 3 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four characteristic X-ray powder diffraction peaks as set forth in Table 36.

Figure 71:
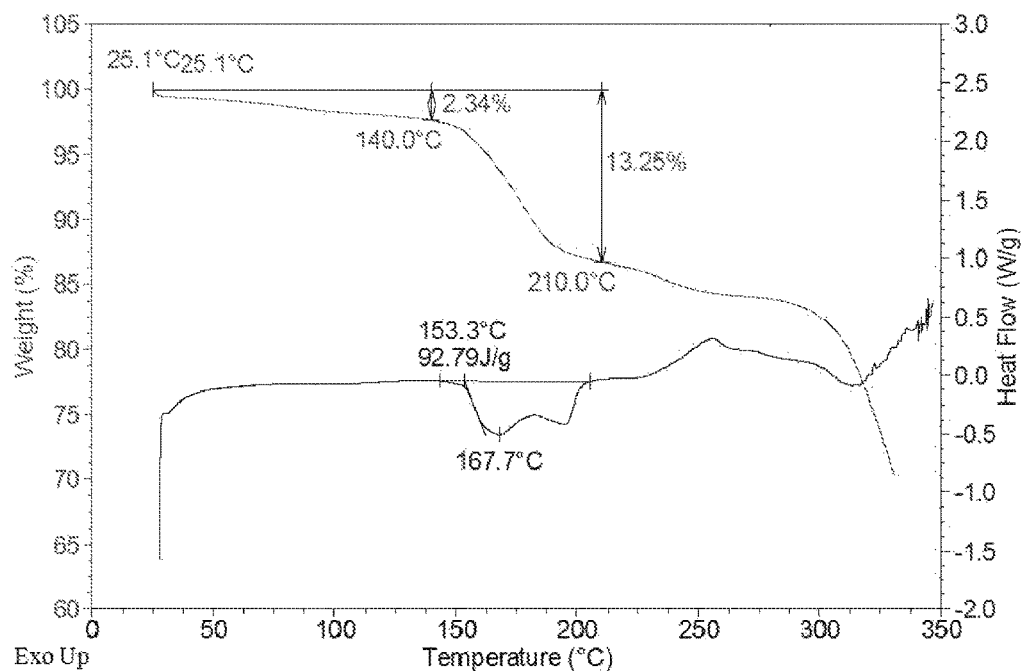
FIG. 71 depicts a TGA and DSC Thermogram of HCl Salt Form 3.

In one embodiment, provided herein is a crystalline form HCl salt of Compound 1 having a TGA thermograph corresponding substantially to the representative TGA thermogram as depicted in FIG. 71. In certain embodiments, the crystalline form HCl salt of Compound 1, exhibits a TGA thermogram comprising a total mass loss of approximately 2.3% of the total mass of the sample between approximately 50° C. and approximately 175° C. when heated from approximately 25° C. to approximately 140° C. In certain embodiments, the crystalline form HCl salt of Compound 1, exhibits a TGA thermogram comprising a total mass loss of approximately 11% of the total mass of the sample between approximately 140° C. and approximately 210° C. when heated from approximately 25° C. to approximately 140° C. Thus, in certain embodiments, the crystalline form HCl salt of Compound 1 loses about 13% of its total mass when heated from about ambient temperature to about 220° C.

In one embodiment, provided herein is a crystalline form HCl salt of Compound 1 having a DSC thermogram as depicted in FIG. 71 comprising an endothermic event with an onset temperature at about 153° C. and a peak maximum temperature at about 168° C. when heated from approximately 25° C. to approximately 350° C.

In still another embodiment, HCl salt Form 3 is substantially pure. In certain embodiments, the substantially pure HCl salt Form 3 is substantially free of other solid forms, e.g., amorphous solid. In certain embodiments, the purity of the substantially pure HCl salt Form 3 is no less than about 95%, no less than about 96%, no less than about 97%, no less than about 98%, no less than about 98.5%, no less than about 99%, no less than about 99.5%, or no less than about 99.8%.

HCl Salt Form 4

In certain embodiments, provided herein is HCl salt Form 4.

In one embodiment, HCl salt Form 4 is a solid form of Compound 1. In another embodiment, HCl salt Form 4 is crystalline. In one embodiment, HCl salt Form 4 is a solvated form of Compound 1. In one embodiment, HCl salt Form 4 is a methanol solvated form of Compound 1. In one embodiment, HCl salt Form 4 is an IPAc solvated form of Compound 1. In one embodiment, HCl salt Form 4 is a MeOH/IPAc solvated form of Compound 1.

In certain embodiments, HCl salt Form 4 provided herein is obtained by equilibration experiments, evaporation experiments, cooling recrystallization experiments and anti-solvent recrystallization experiments. In certain embodiments, HCl salt Form 4 is obtained from certain solvent systems including MeOH/IPAc.

Figure 72:
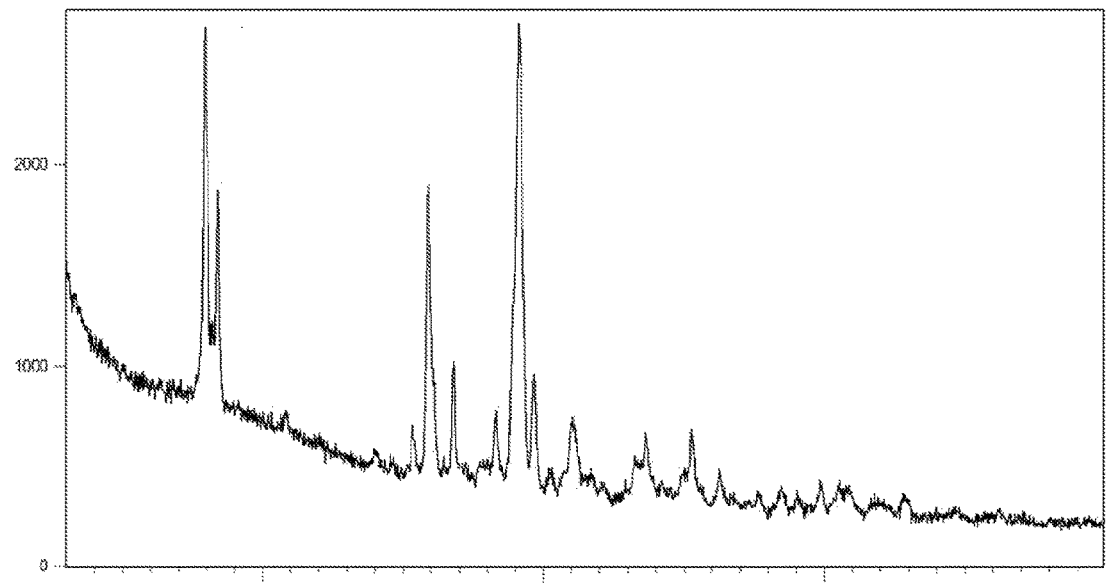
FIG. 72 depicts a XRPD Pattern of HCl Salt Form 4.

In certain embodiments, a solid form provided herein, e.g., HCl salt Form 4, is substantially crystalline, as indicated by, e.g., X-ray powder diffraction measurements. In one embodiment, a solid form provided herein, e.g., HCl salt Form 4, has an X-ray powder diffraction pattern substantially as shown in FIG. 72. In one embodiment, a solid form provided herein, e.g., HCl salt Form 4, has one or more characteristic X-ray powder diffraction peaks at approximately 7.9, 8.1, 8.2, 8.4, 10.8, 14.0, 15.3, 15.9, 16.4, 16.8, 17.8, 18.3, 18.9, 19.1, 19.7, 20.3, 21.0, 21.6, 22.1, 23.3, 23.6, 24.9, 25.3, 26.3, 27.6, 28.5, 29.1, 29.9, 30.6, 30.9, 31.9, 32.8, 34.6, or 36.2° 2θ (±0.2° 2θ) or (±0.1° 2θ) as depicted in FIG. 72. In a specific embodiment, a solid form provided herein, e.g., HCl salt Form 4, has one, two, three, four, five, six, seven or eight characteristic X-ray powder diffraction peaks at approximately 7.9, 8.1, 8.4, 15.9, 16.8, 18.9, 19.1, or 19.7° 2θ (±0.2° 2θ). In another embodiment, a solid form provided herein has one, two, three, or four characteristic X-ray powder diffraction peaks at approximately 7.9, 8.1, 8.4, or 15.9° 2θ (±0.2° 2θ). In one embodiment, the solid form is HCl Salt Form 4. In another embodiment, HCl salt Form 4 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, or thirty-four characteristic X-ray powder diffraction peaks as set forth in Table 37.

Figure 73:
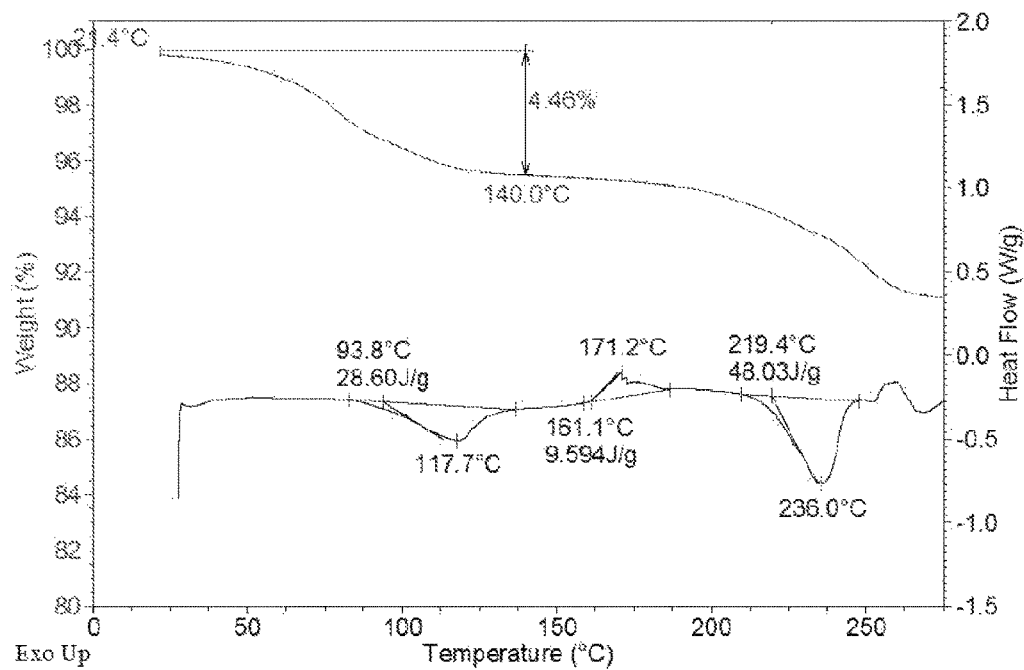
FIG. 73 depicts a TGA and DSC Thermogram of HCl Salt Form 4.

In one embodiment, provided herein is a crystalline form HCl salt of Compound 1 having a TGA thermograph corresponding substantially to the representative TGA thermogram as depicted in FIG. 73. In certain embodiments, the crystalline form HCl salt of Compound 1 exhibits a TGA thermogram comprising a total mass loss of approximately 4.5% of the total mass of the sample between approximately 20° C. and approximately 140° C. when heated from approximately 20° C. to approximately 275° C. Thus, in certain embodiments, the crystalline form HCl salt of Compound 1 loses about 4.5% of its total mass when heated from about ambient temperature to about 275° C.

In one embodiment, provided herein is a crystalline form HCl salt of Compound 1 having a DSC thermogram as depicted in FIG. 73 comprising an endothermic event with an onset temperature at about 94° C. and a peak maximum temperature at about 118° C. when heated from approximately 25° C. to approximately 275° C. In one embodiment, provided herein is a crystalline form HCl salt of Compound 1 having a DSC thermogram as depicted in FIG. 73 further comprising an endothermic event with an onset temperature at about 219° C. and a peak maximum temperature at about 236° C. when heated from approximately 25° C. to approximately 275° C.

In still another embodiment, HCl salt Form 4 is substantially pure. In certain embodiments, the substantially pure HCl salt Form 4 is substantially free of other solid forms, e.g., amorphous solid. In certain embodiments, the purity of the substantially pure HCl salt Form 4 is no less than about 95%, no less than about 96%, no less than about 97%, no less than about 98%, no less than about 98.5%, no less than about 99%, no less than about 99.5%, or no less than about 99.8%.

HCl Salt Form 5

In certain embodiments, provided herein is HCl salt Form 5.

In one embodiment, HCl salt Form 5 is a solid form of Compound 1. In another embodiment, HCl salt Form 5 is crystalline. In one embodiment, HCl salt Form 5 is a solvated form of Compound 1. In one embodiment, HCl salt Form 5 is a DMF solvated form of Compound 1.

In certain embodiments, HCl salt Form 5 provided herein is obtained by equilibration experiments, vapor diffusion, and evaporation experiments. In certain embodiments, HCl salt Form 5 is obtained from certain solvent systems including DMF.

Figure 74:
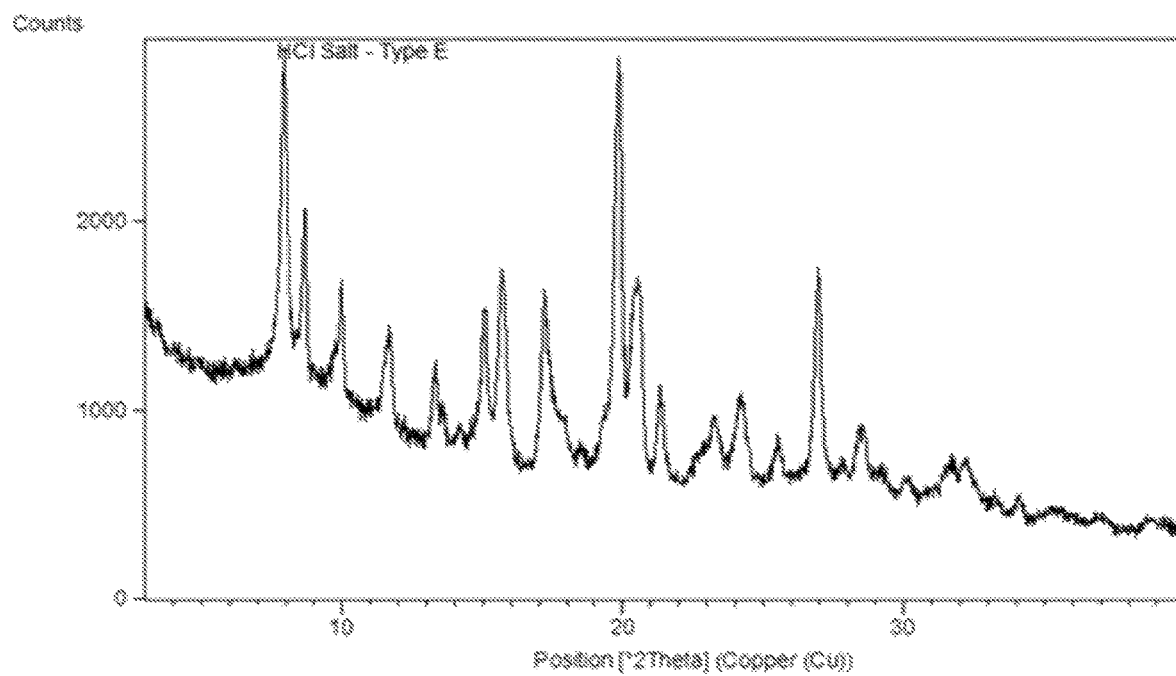
FIG. 74 depicts a XRPD Pattern of HCl Salt Form 5.

In certain embodiments, a solid form provided herein, e.g., HCl salt Form 5, is substantially crystalline, as indicated by, e.g., X-ray powder diffraction measurements. In one embodiment, a solid form provided herein, e.g., HCl salt Form 5, has an X-ray powder diffraction pattern substantially as shown in FIG. 74. In one embodiment, a solid form provided herein, e.g., HCl salt Form 5, has one or more characteristic X-ray powder diffraction peaks at approximately 7.9, 8.7, 10.0, 11.7, 13.3, 13.6, 15.1, 15.7, 17.2, 17.9, 19.9, 20.6, 21.3, 23.3, 24.2, 25.5, 27.0, 28.5, 29.3, 30.1, 31.7, 32.2, 34.1, 35.4, 37.0, or 38.8° 2θ (±0.2° 2θ) or (±0.1° 2θ) as depicted in FIG. 74. In a specific embodiment, a solid form provided herein, e.g., HCl salt Form 5, has one, two, three, four, five, six, seven, eight, nine, ten, eleven, or twelve characteristic X-ray powder diffraction peaks at approximately 7.9, 8.7, 10.0, 11.7, 15.1, 15.7, 17.2, 19.9, 20.6, 21.3, 24.2, or 27.0° 2θ (±0.2° 2θ). In another embodiment, a solid form provided herein has one, two, three, or four characteristic X-ray powder diffraction peaks at approximately 7.9, 19.9, 20.6, or 27.0° 2θ (±0.2° 2θ). In one embodiment, the solid form is HCl Salt Form 5. In another embodiment, HCl salt Form 5 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, or twenty-six characteristic X-ray powder diffraction peaks as set forth in Table 38.

Figure 75:
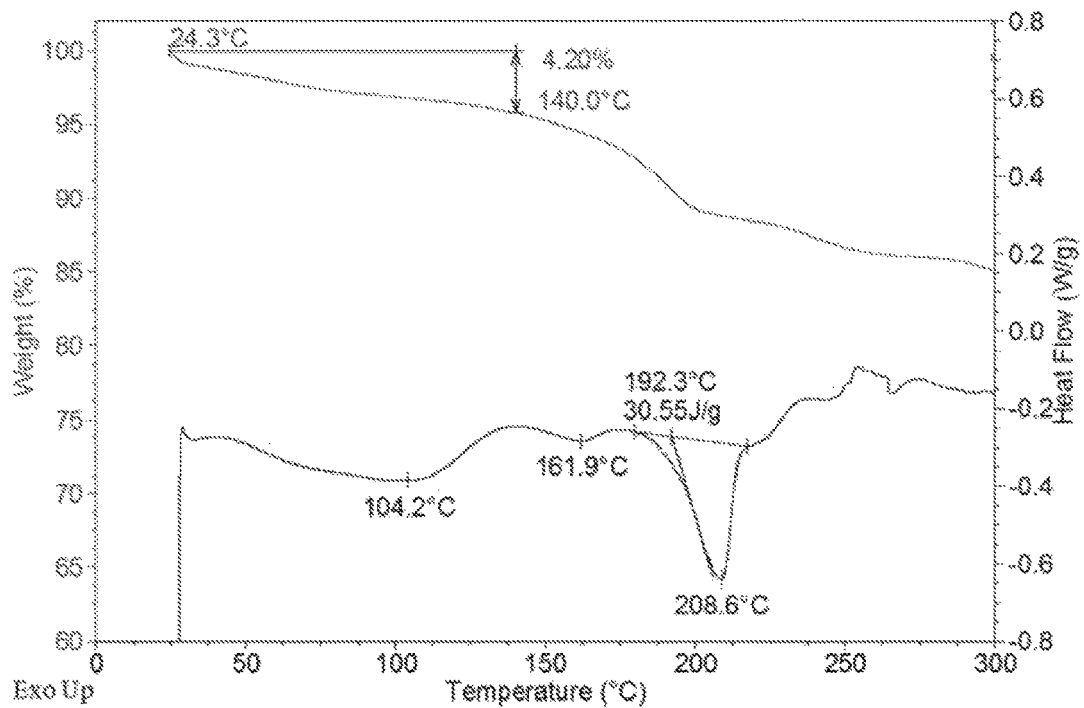
FIG. 75 depicts a TGA and DSC Thermogram of HCl Salt Form 5.

In one embodiment, provided herein is a crystalline form HCl salt of Compound 1 having a TGA thermograph corresponding substantially to the representative TGA thermogram as depicted in FIG. 75. In certain embodiments, the crystalline form HCl salt of Compound 1 exhibits a TGA thermogram comprising a total mass loss of approximately 4.2% of the total mass of the sample between approximately 25° C. and approximately 140° C. when heated from approximately 25° C. to approximately 300° C. Thus, in certain embodiments, the crystalline form HCl salt of Compound 1 loses about 4.2% of its total mass when heated from about ambient temperature to about 300° C.

In one embodiment, provided herein is a crystalline form of Compound 1 having a DSC thermogram as depicted in FIG. 75 comprising an endothermic event with a maximum at about 104° C. when heated from approximately 25° C. to approximately 220° C.

In one embodiment, provided herein is a crystalline form of Compound 1 having a DSC thermogram as depicted in FIG. 75 comprising an endothermic event with an onset temperature at about 192° C. and a peak maximum temperature at about 209° C. when heated from approximately 25° C. to approximately 220° C.

In still another embodiment, HCl salt Form 5 is substantially pure. In certain embodiments, the substantially pure HCl salt Form 5 is substantially free of other solid forms, e.g., amorphous solid. In certain embodiments, the purity of the substantially pure HCl salt Form 5 is no less than about 95%, no less than about 96%, no less than about 97%, no less than about 98%, no less than about 98.5%, no less than about 99%, no less than about 99.5%, or no less than about 99.8%.

HCl Salt Form 6

In certain embodiments, provided herein is HCl salt Form 6.

In one embodiment, HCl salt Form 6 is a solid form of Compound 1. In another embodiment, HCl salt Form 6 is crystalline. In one embodiment, HCl salt Form 6 is a hydrate of Compound 1. In one embodiment, HCl salt Form 6 is a pentahydrate of Compound 1.

In certain embodiments, HCl salt Form 6 provided herein is obtained by equilibration experiments. In certain embodiments, HCl salt Form 6 is obtained from certain solvent systems including 0.1N HCl in water.

Figure 76:
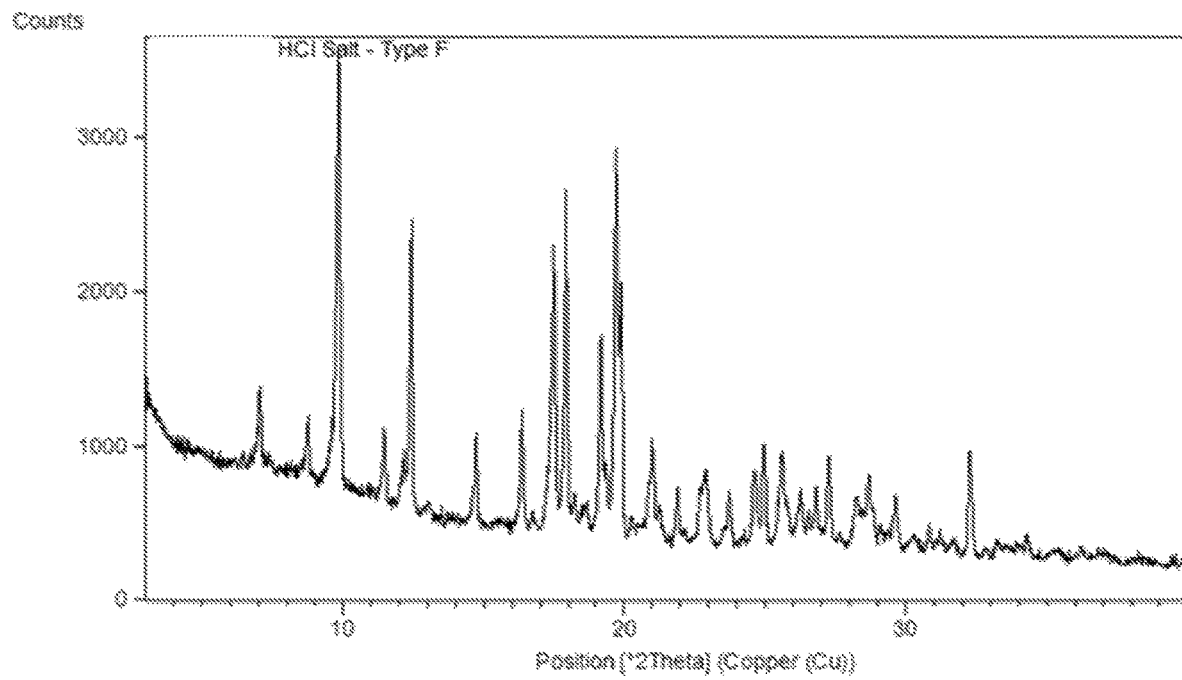
FIG. 76 depicts a XRPD Pattern of HCl Salt Form 6.

In certain embodiments, a solid form provided herein, e.g., the HCl salt Form 6, is substantially crystalline, as indicated by, e.g., X-ray powder diffraction measurements. In one embodiment, a solid form provided herein, e.g., the HCl salt Form 6, has an X-ray powder diffraction pattern substantially as shown in FIG. 76. In one embodiment, a solid form provided herein, e.g., the HCl salt Form 6, has one or more characteristic X-ray powder diffraction peaks at approximately 7.0, 8.8, 9.9, 11.5, 12.2, 12.4, 14.7, 16.3, 16.7, 17.5, 17.9, 18.2, 18.6, 19.2, 19.4, 19.7, 19.9, 20.3, 21.0, 21.2, 21.9, 22.7, 22.9, 23.7, 24.6, 25.0, 25.6, 26.3, 26.5, 26.8, 27.2, 27.6, 28.2, 28.7, 29.1, 29.6, 30.3, 30.8, 31.2, 31.7, 32.3, 32.8, 33.3, 34.0, 34.3, 35.3, 36.2, or 37.0° 2θ (±0.2° 2θ) or (±0.1° 2θ) as depicted in FIG. 76. In a specific embodiment, a solid form provided herein, e.g., the HCl salt Form 6, has one, two, three, four, five, six, seven, eight, nine, ten, eleven, or twelve characteristic X-ray powder diffraction peaks at approximately 9.9, 12.4, 16.3, 17.5, 19.2, 19.7, 19.9, 21.0, 25.0, 25.6, 27.2, or 32.3° 2θ (±0.2° 2θ). In another embodiment, a solid form provided herein has one, two, three, or four characteristic X-ray powder diffraction peaks at approximately 9.9, 12.4, 17.9, or 19.7° 2θ (±0.2° 2θ). In one embodiment, the solid form is HCl Salt Form 6. In another embodiment, HCl salt Form 6 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, or forty-eight characteristic X-ray powder diffraction peaks as set forth in Table 39.

Figure 77:
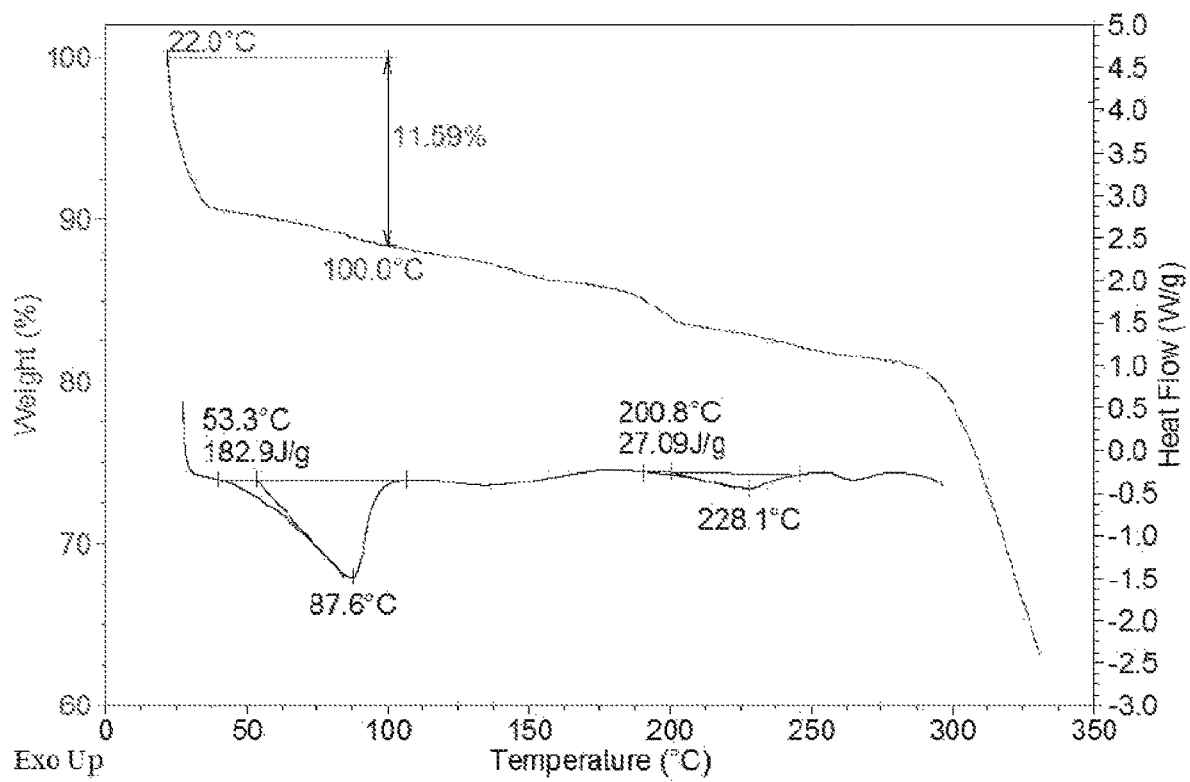
FIG. 77 depicts a TGA and DSC Thermogram of HCl Salt Form 6.

In one embodiment, provided herein is a crystalline form HCl salt of Compound 1 having a TGA thermograph corresponding substantially to the representative TGA thermogram as depicted in FIG. 77. In certain embodiments, the crystalline form HCl salt of Compound 1 exhibits a TGA thermogram comprising a total mass loss of approximately 11.6% of the total mass of the sample between approximately 25° C. and approximately 100° C. when heated from approximately 20° C. to approximately 300° C.

Figure 78:
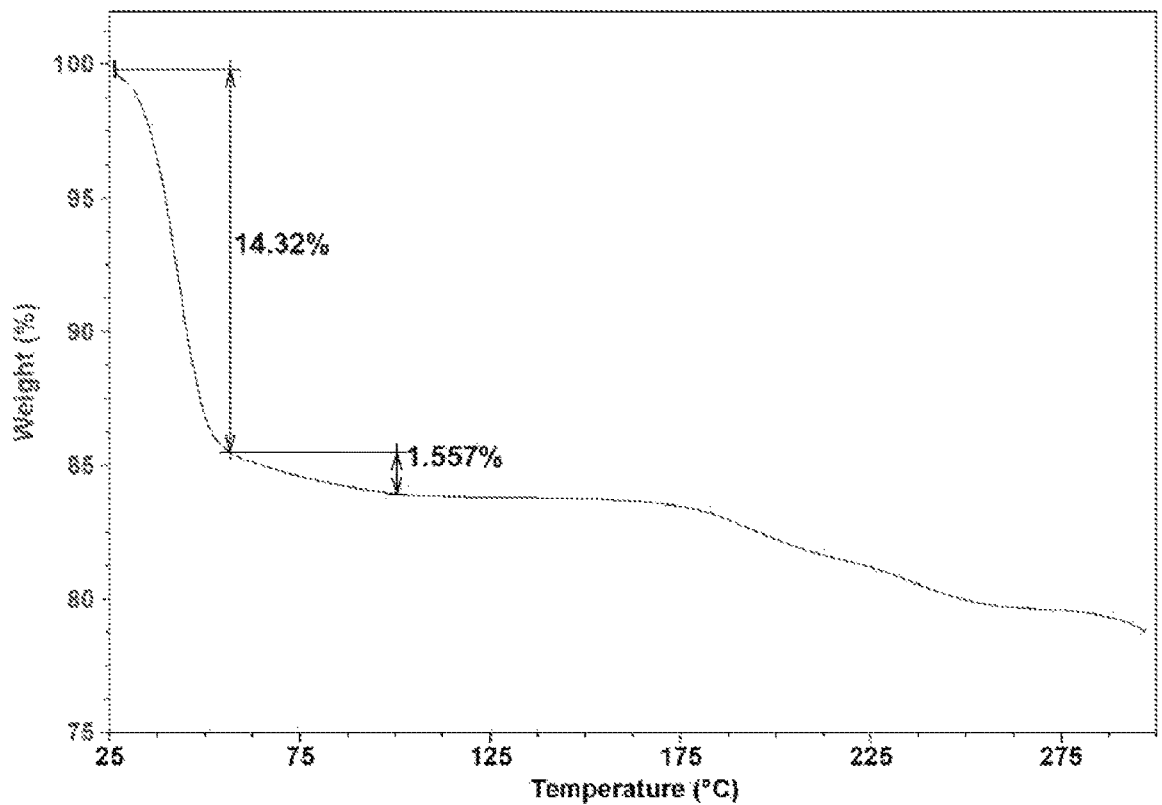
FIG. 78 depicts a TGA Thermogram of HCl Salt Form 6.

In one embodiment, provided herein is a crystalline form HCl salt of Compound 1 having a TGA thermograph corresponding substantially to the representative TGA thermogram as depicted in FIG. 78. In certain embodiments, the crystalline form HCl salt of Compound 1 exhibits a TGA thermogram comprising a total mass loss of approximately 14.3% of the total mass of the sample between approximately 25° C. and approximately 60° C. when heated from approximately 20° C. to approximately 300° C.

In certain embodiments, the crystalline form HCl salt of Compound 1 exhibits a TGA thermogram comprising a total mass loss of approximately 1.6% of the total mass of the sample between approximately 60° C. and approximately 125° C. when heated from approximately 20° C. to approximately 300° C. Thus, in certain embodiments, the crystal crystalline form HCl salt of Compound 1 loses about 15.9% of its total mass when heated from about ambient temperature to about 100° C.

In one embodiment, provided herein is a crystalline form HCl salt of Compound 1 having a DSC thermogram as depicted in FIG. 77 comprising an endothermic event with an onset temperature at about 53° C. and a peak maximum temperature at about 88° C. when heated from approximately 25° C. to approximately 325° C. In one embodiment, provided herein is a crystalline form HCl salt of Compound 1 having a DSC thermogram as depicted in FIG. 77 comprising an endothermic event with an onset temperature at about 201° C. and a peak maximum temperature at about 228° C. when heated from approximately 25° C. to approximately 325° C.

Figure 79:
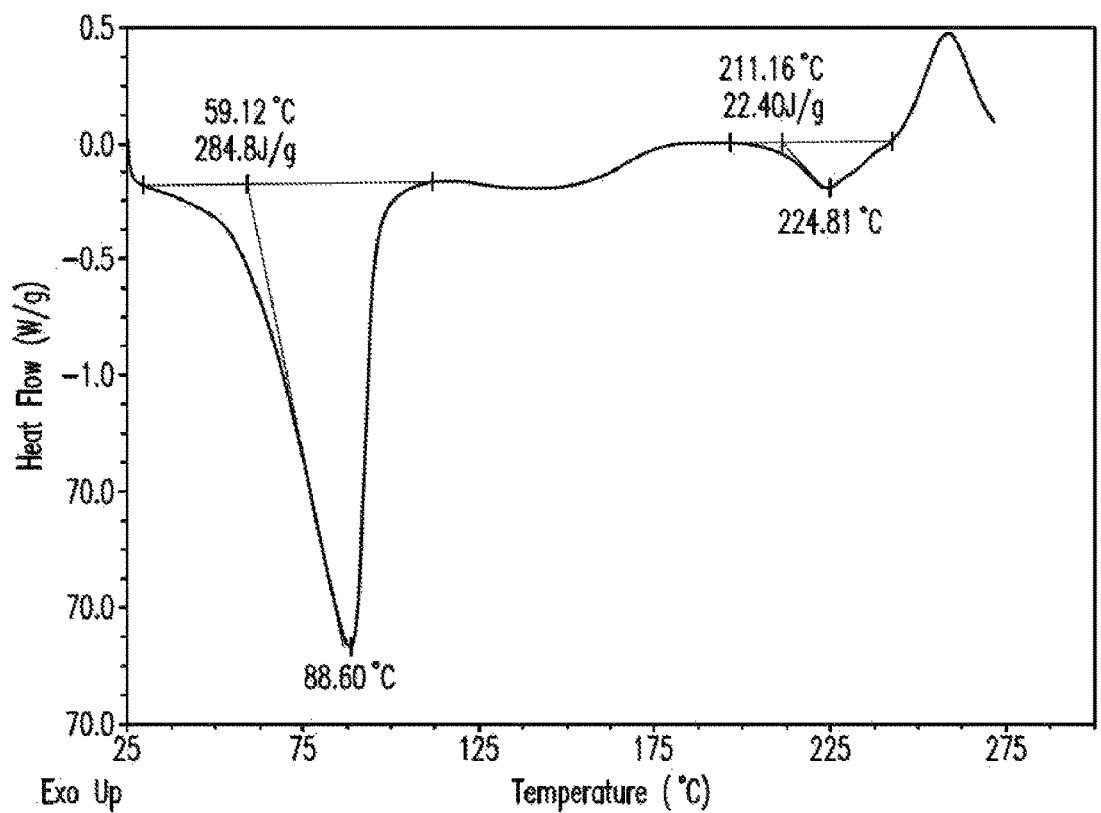
FIG. 79 depicts a DSC Thermogram of HCl Salt Form 6.

In one embodiment, provided herein is a crystalline form HCl salt of Compound 1 having a DSC thermogram as depicted in FIG. 79 comprising an endothermic event with an onset temperature at about 59° C. and a peak maximum temperature at about 89° C. when heated from approximately 25° C. to approximately 325° C. In one embodiment, provided herein is a crystalline form HCl salt of Compound 1 having a DSC thermogram as depicted in FIG. 79 comprising an endothermic event with an onset temperature at about 211° C. and a peak maximum temperature at about 225° C. when heated from approximately 25° C. to approximately 325° C.

In still another embodiment, HCl salt Form 6 is substantially pure. In certain embodiments, the substantially pure HCl salt Form 6 is substantially free of other solid forms, e.g., amorphous solid. In certain embodiments, the purity of the substantially pure HCl salt Form 6 is no less than about 95%, no less than about 96%, no less than about 97%, no less than about 98%, no less than about 98.5%, no less than about 99%, no less than about 99.5%, or no less than about 99.8%.

HCl Salt Form 7

In certain embodiments, provided herein is HCl salt Form 7.

In one embodiment, HCl salt Form 7 is a solid form of Compound 1. In another embodiment, HCl salt Form 7 is crystalline. In one embodiment, HCl salt Form 7 is a hydrate of Compound 1. In one embodiment, HCl salt Form 7 is a monohydrate of Compound 1.

In certain embodiments, HCl salt Form 7 provided herein is obtained by equilibration experiments, evaporation experiments and anti-solvent recrystallization experiments. In certain embodiments, HCl salt Form 7 is obtained from certain solvent systems including water at room temperature.

Figure 80:
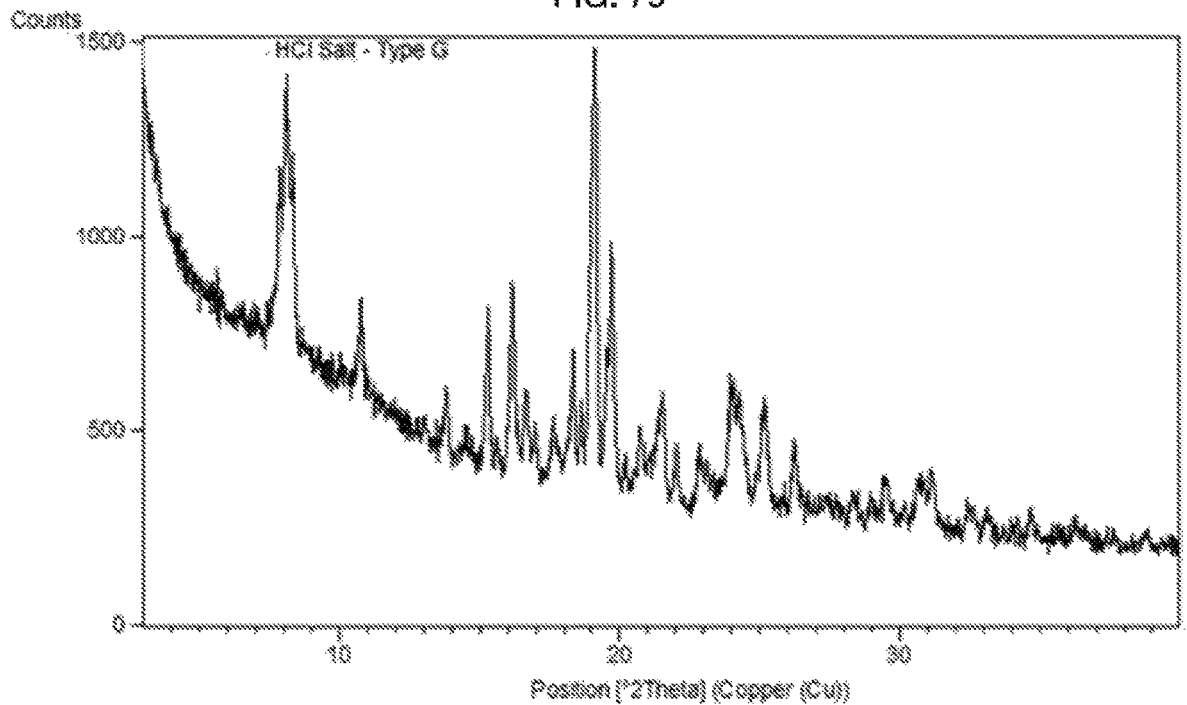
FIG. 80 depicts a XRPD Pattern of HCl Salt Form 7.

In certain embodiments, a solid form provided herein, e.g., HCl salt Form 7, is substantially crystalline, as indicated by, e.g., X-ray powder diffraction measurements. In one embodiment, a solid form provided herein, e.g., HCl salt Form 7, has an X-ray powder diffraction pattern substantially as shown in FIG. 80. In one embodiment, a solid form provided herein, e.g., HCl salt Form 7, has one or more characteristic X-ray powder diffraction peaks at approximately 7.9, 8.1, 8.3, 10.8, 13.8, 14.5, 15.3, 15.6, 16.2, 16.6, 17.0, 17.6, 18.3, 18.6, 19.1, 19.6, 19.7, 20.2, 20.7, 21.5, 22.0, 22.9, 24.0, 24.3, 25.2, 26.2, 28.4, 29.0, 29.5, 30.2, 30.8, 31.2, 32.5, 33.1, 34.7, or 36.3° 2θ (±0.2° 2θ) or (±0.1° 2θ) as depicted in FIG. 80. In a specific embodiment, a solid form provided herein, e.g., HCl salt Form 7, has one, two, three, four, five, six, seven, eight, nine, ten, eleven, twelve, thirteen, or fourteen characteristic X-ray powder diffraction peaks at approximately 7.9, 8.1, 8.3, 10.8, 15.3, 16.2, 18.3, 19.1, 19.6, 19.7, 21.5, 24.0, 24.3, or 25.2° 2θ (±0.2° 2θ). In another embodiment, a solid form provided herein has one, two, three, or four characteristic X-ray powder diffraction peaks at approximately 8.1, 8.3, 19.1, or 19.7° 2θ (±0.2° 2θ). In one embodiment, the solid form is HCl Salt Form 7. In another embodiment, HCl salt Form 7 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, or thirty-six characteristic X-ray powder diffraction peaks as set forth in Table 40.

Figure 81:
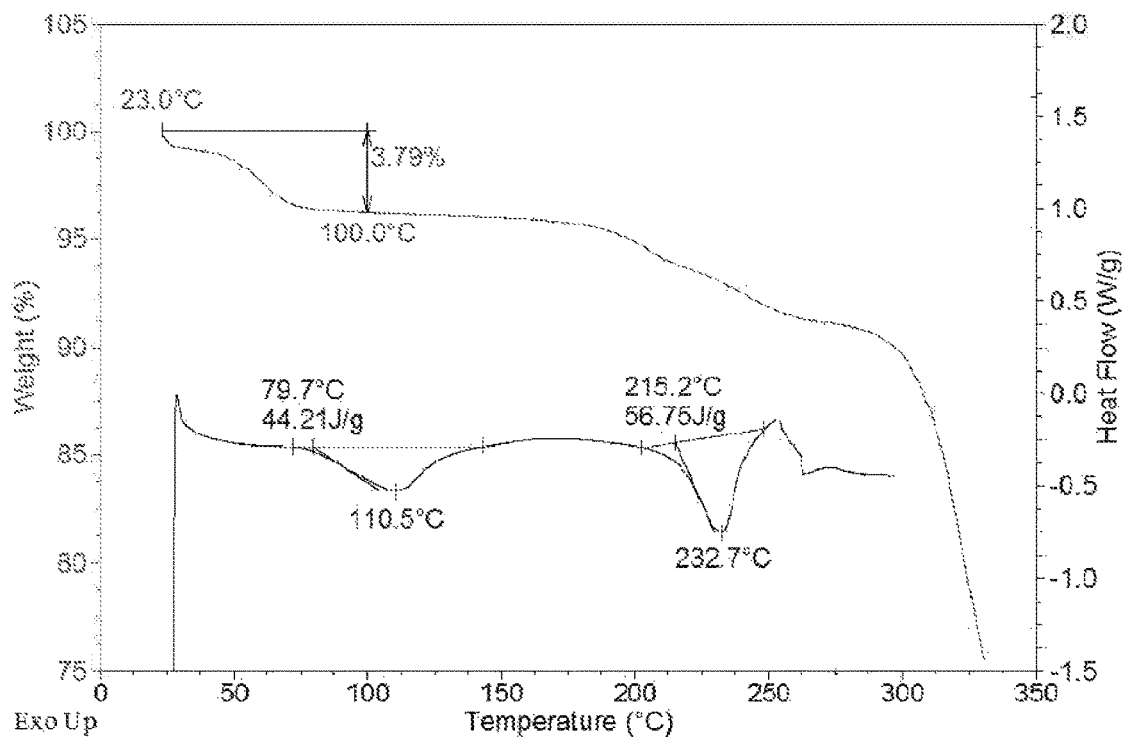
FIG. 81 depicts a TGA and DSC Thermogram of HCl Salt Form 7.

In one embodiment, provided herein is a crystalline form HCl salt of Compound 1 having a TGA thermograph corresponding substantially to the representative TGA thermogram as depicted in FIG. 81. In certain embodiments, the crystalline form HCl salt of Compound 1 exhibits a TGA thermogram comprising a total mass loss of approximately 3.8% of the total mass of the sample between approximately 25° C. and approximately 100° C. when heated from approximately 25° C. to approximately 300° C. Thus, in certain embodiments, the crystalline form HCl salt of Compound 1 loses about 3.8% of its total mass when heated from about ambient temperature to about 300° C.

Figure 83:
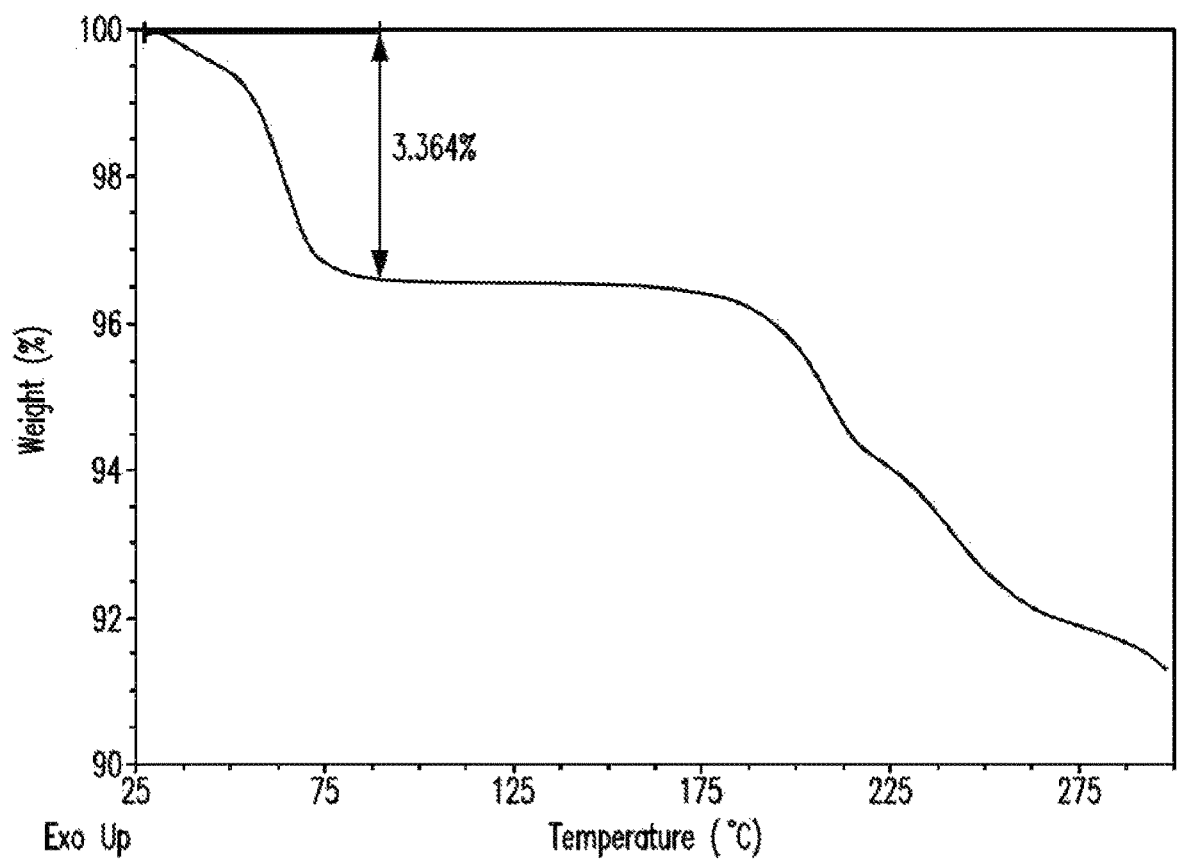
FIG. 83 depicts a TGA Thermogram of HCl Salt Form 7.

In one embodiment, provided herein is a crystalline form HCl salt of Compound 1 having a TGA thermograph corresponding substantially to the representative TGA thermogram as depicted in FIG. 83. In certain embodiments, the crystalline form HCl salt of Compound 1 exhibits a TGA thermogram comprising a total mass loss of approximately 3.4% of the total mass of the sample between approximately 25° C. and approximately 100° C. when heated from approximately 25° C. to approximately 300° C. Thus, in certain embodiments, the crystalline form HCl salt of Compound 1 loses about 3.4% of its total mass when heated from about ambient temperature to about 300° C.

In one embodiment, provided herein is a crystalline form HCl salt of Compound 1 having a DSC thermogram as depicted in FIG. 81 comprising an endothermic event with an onset temperature at about 80° C. and a peak maximum temperature at about 111° C. when heated from approximately 25° C. to approximately 300° C. In one embodiment, provided herein is a crystalline form HCl salt of Compound 1 having a DSC thermogram as depicted in FIG. 81 comprising an endothermic event with an onset temperature at about 215° C. and a peak maximum temperature at about 233° C. when heated from approximately 25° C. to approximately 300° C.

Figure 82:
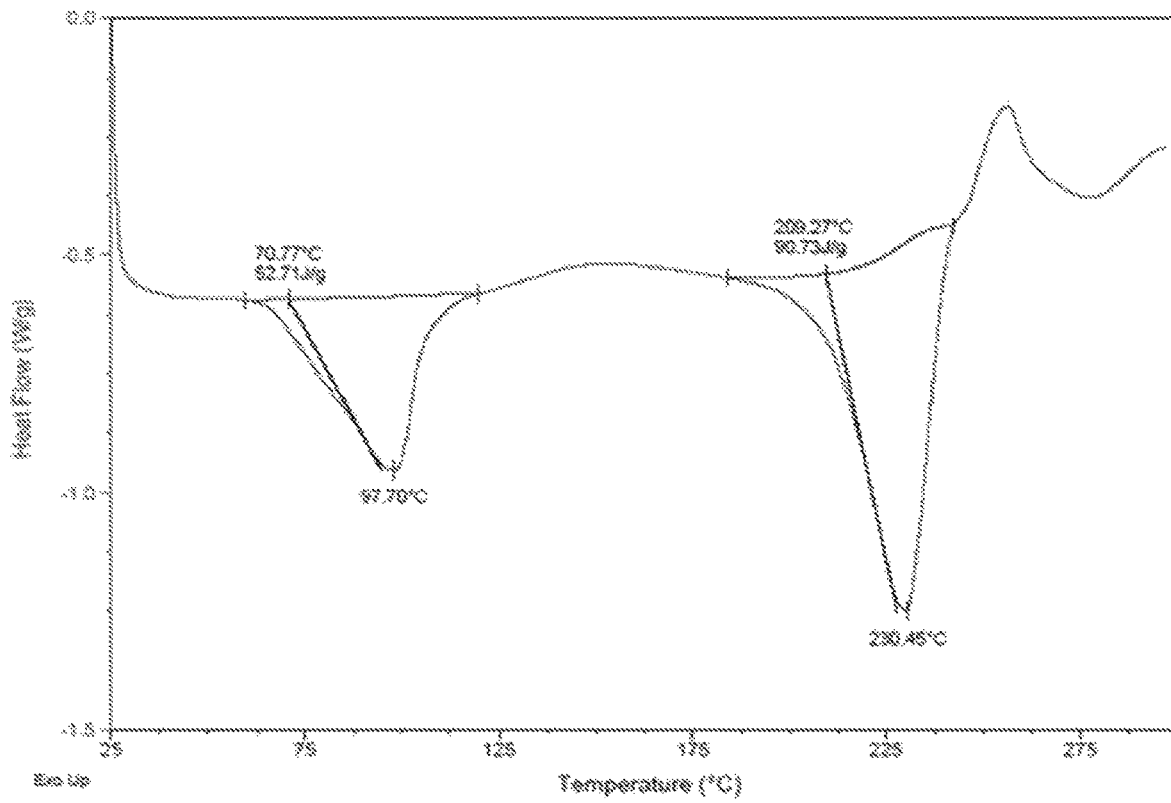
FIG. 82 depicts a DSC Thermogram of HCl Salt Form 7.

In one embodiment, provided herein is a crystalline form HCl salt of Compound 1 having a DSC thermogram as depicted in FIG. 82 comprising an endothermic event with an onset temperature at about 71° C. and a peak maximum temperature at about 98° C. when heated from approximately 25° C. to approximately 300° C. In one embodiment, provided herein is a crystalline form HCl salt of Compound 1 having a DSC thermogram as depicted in FIG. 82 comprising an endothermic event with an onset temperature at about 209° C. and a peak maximum temperature at about 230° C. when heated from approximately 25° C. to approximately 300° C.

Figure 84:
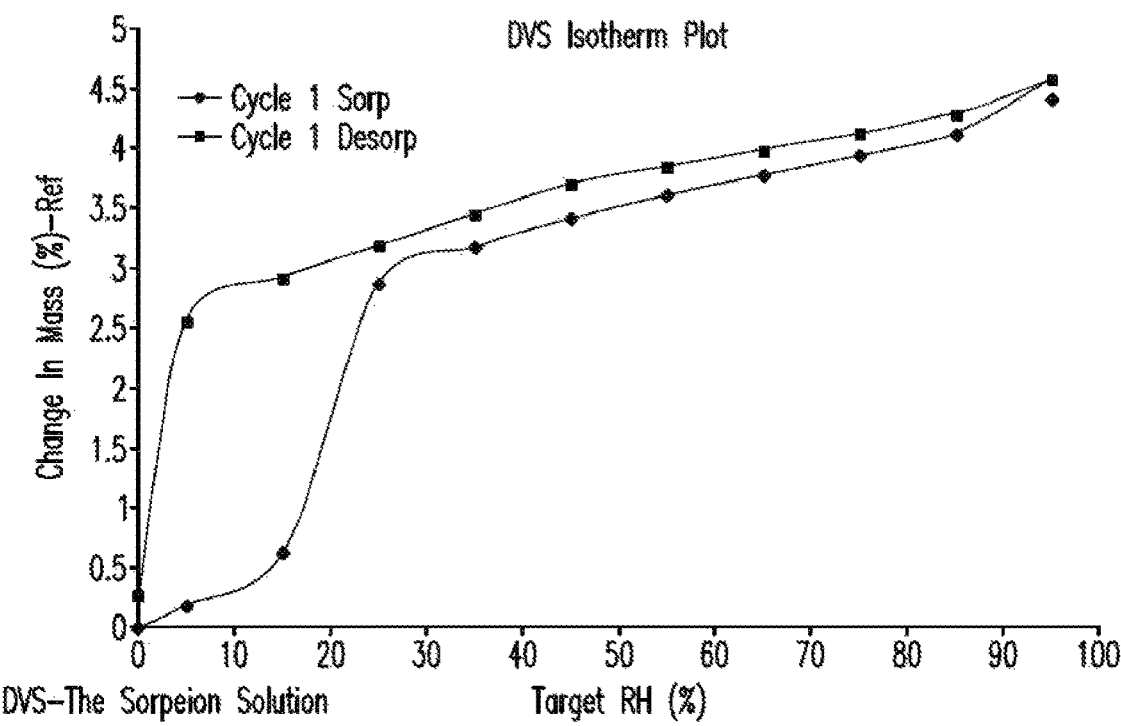
FIG. 84 depicts a DVS Isotherm Plot of HCl Salt Form 7.

In one embodiment, provided herein is a solid form, e.g., a starting material HCl salt Form, having a DVS isotherm plot substantially as depicted in FIG. 84.

In still another embodiment, HCl salt Form 7 is substantially pure. In certain embodiments, the substantially pure HCl salt Form 7 is substantially free of other solid forms, e.g., amorphous solid. In certain embodiments, the purity of the substantially pure HCl salt Form 7 is no less than about 95%, no less than about 96%, no less than about 97%, no less than about 98%, no less than about 98.5%, no less than about 99%, no less than about 99.5%, or no less than about 99.8%.

HCl Salt Form 8

In certain embodiments, provided herein is HCl salt Form 8.

In one embodiment, HCl salt Form 8 is a solid form of Compound 1. In another embodiment, HCl salt Form 8 is crystalline. In one embodiment, HCl salt Form 8 is a hydrate of Compound 1. In one embodiment, HCl salt Form 8 is a monohydrate of Compound 1.

In certain embodiments, HCl salt Form 8 provided herein is obtained by equilibration experiments, evaporation experiments and anti-solvent recrystallization experiments. In certain embodiments, HCl salt Form 8 is obtained from certain solvent systems including water at 50° C.

Figure 85:
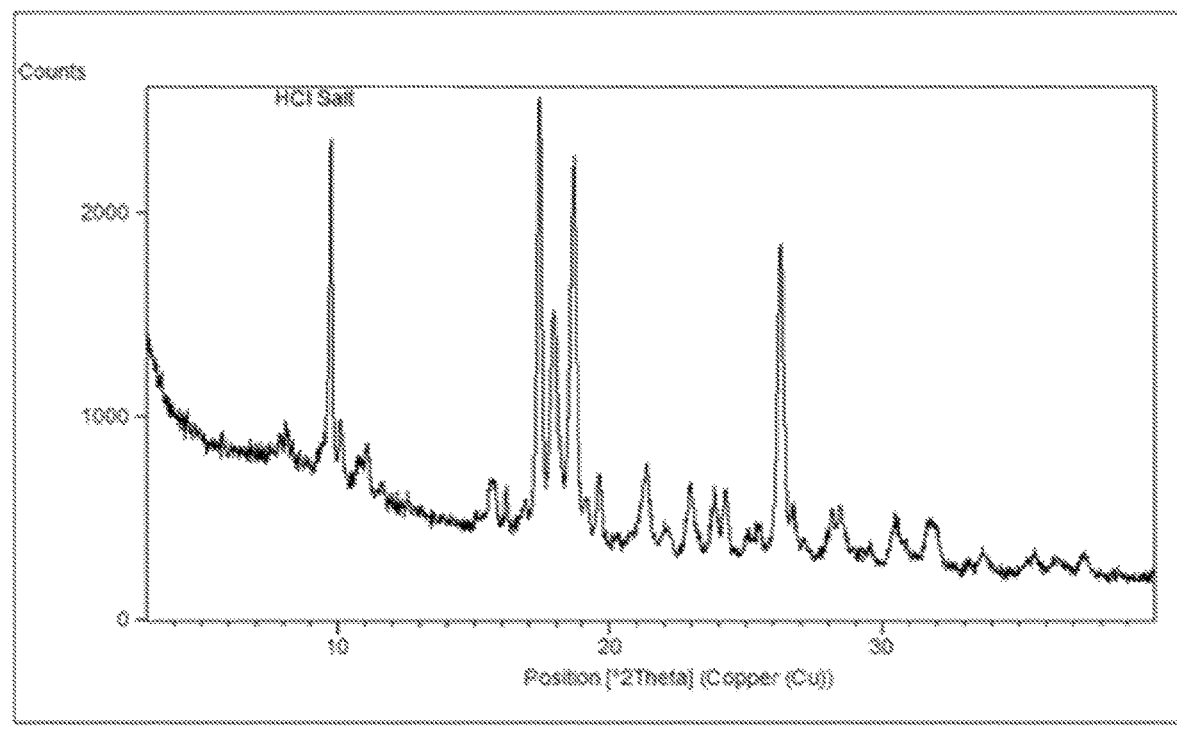
FIG. 85 depicts a XRPD Pattern of HCl Salt Form 8.

In certain embodiments, a solid form provided herein, e.g., HCl salt Form 8, is substantially crystalline, as indicated by, e.g., X-ray powder diffraction measurements. In one embodiment, a solid form provided herein, e.g., HCl salt Form 8, has an X-ray powder diffraction pattern substantially as shown in FIG. 85. In one embodiment, a solid form provided herein, e.g., HCl salt Form 8 has one or more characteristic X-ray powder diffraction peaks at approximately 8.1, 9.8, 10.1, 10.8, 11.1, 11.6, 15.7, 16.2, 16.9, 17.4, 18.0, 18.7, 19.2, 19.6, 21.4, 22.1, 22.9, 23.8, 24.2, 25.1, 25.5, 26.2, 26.7, 28.2, 28.4, 29.6, 30.5, 31.7, 32.0, 33.7, 35.6, 36.4, or 37.4° 2θ (±0.2° 2θ) or (±0.1° 2θ) as depicted in FIG. 85. In a specific embodiment, a solid form provided herein has one, two, three, or four characteristic X-ray powder diffraction peaks at approximately 9.8, 17.4, 18.7, or 26.2° 2θ (±0.2° 2θ). In one embodiment, the solid form is HCl Salt Form 8. In another embodiment, HCl salt Form 8 has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, or thirty-three characteristic X-ray powder diffraction peaks as set forth in Table 41.

Figure 86:
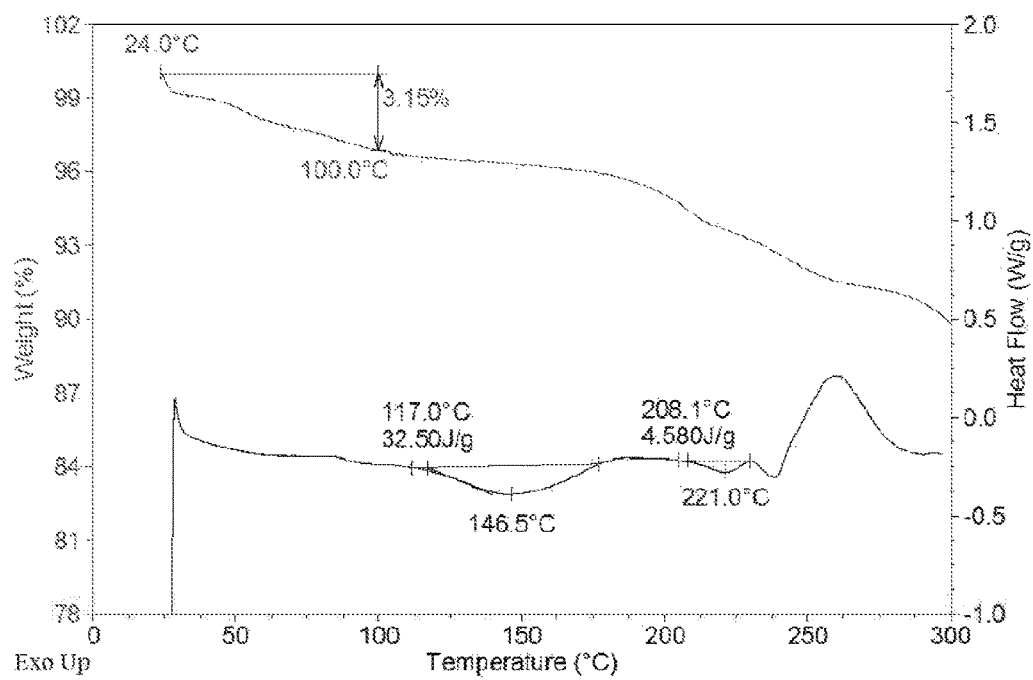
FIG. 86 depicts a TGA and DSC Thermogram of HCl Salt Form 8.
Figure 87:
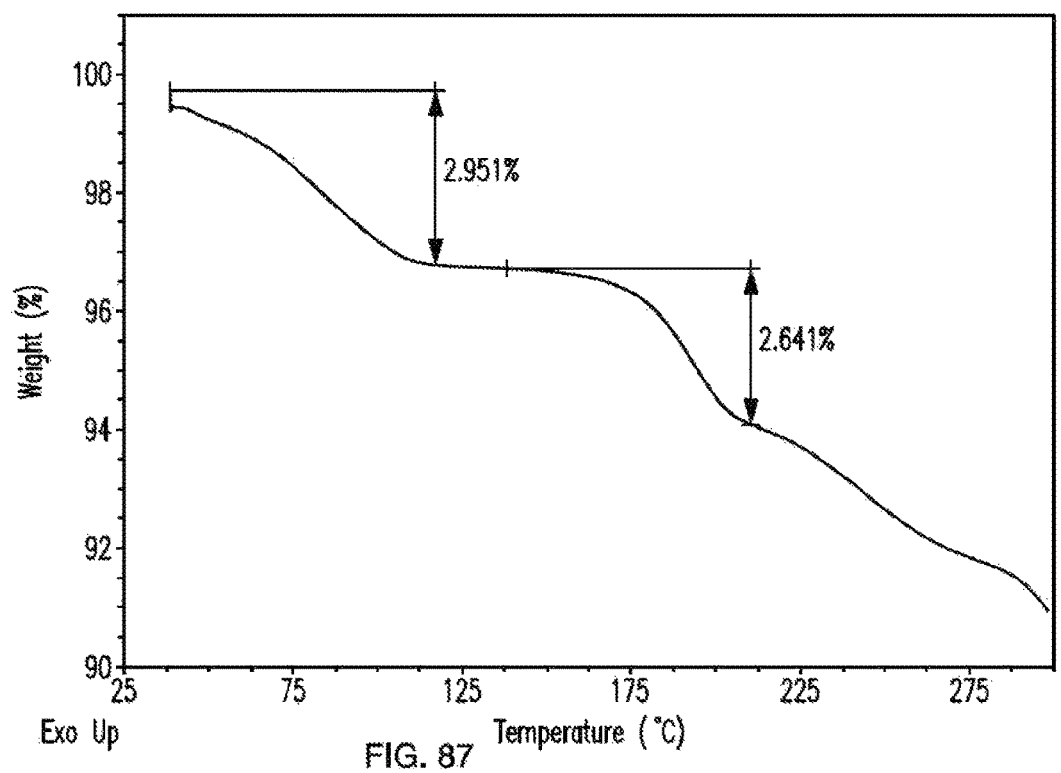
FIG. 87 depicts a TGA Thermogram of HCl Salt Form 8.

In one embodiment, provided herein is a crystalline form HCl salt of Compound 1 having a TGA thermograph corresponding substantially to the representative TGA thermogram as depicted in FIG. 86. In certain embodiments, the crystalline form HCl salt of Compound 1 exhibits a TGA thermogram comprising a total mass loss of approximately 3.1% of the total mass of the sample between approximately 25° C. and approximately 100° C. when heated from approximately 25° C. to approximately 300° C. In one embodiment, provided herein is a crystalline form HCl salt of Compound 1 having a TGA thermograph corresponding substantially to the representative TGA thermogram as depicted in FIG. 87. In certain embodiments, the crystalline form HCl salt of Compound 1 exhibits a TGA thermogram comprising a total mass loss of approximately 3.0% of the total mass of the sample between approximately 30° C. and approximately 120° C. when heated from approximately 25° C. to approximately 300° C.

In certain embodiments, the crystalline form HCl salt of Compound 1 exhibits a TGA thermogram comprising a total mass loss of approximately 2.6% of the total mass of the sample between approximately 125° C. and approximately 215° C. when heated from approximately 30° C. to approximately 300° C. Thus, in certain embodiments, the crystalline form HCl salt of Compound 1 loses about 5.6% of its total mass when heated from about ambient temperature to about 220° C. The theoretical water content for the monohydrate HCl salt Form 8 is 2.9% and matches the percent total mass lost by the sample in the above TGA thermogram.

In one embodiment, provided herein is a crystalline form HCl salt of Compound 1 having a DSC thermogram as depicted in FIG. 86 comprising an endothermic event with an onset temperature at about 117° C. and a peak maximum temperature at about 148° C. when heated from approximately 25° C. to approximately 300° C. In one embodiment, provided herein is a crystalline form HCl salt of Compound 1 having a DSC thermogram as depicted in FIG. 86 comprising an endothermic event with an onset temperature at about 208° C. and a peak maximum temperature at about 221° C. when heated from approximately 25° C. to approximately 300° C.

Figure 88:
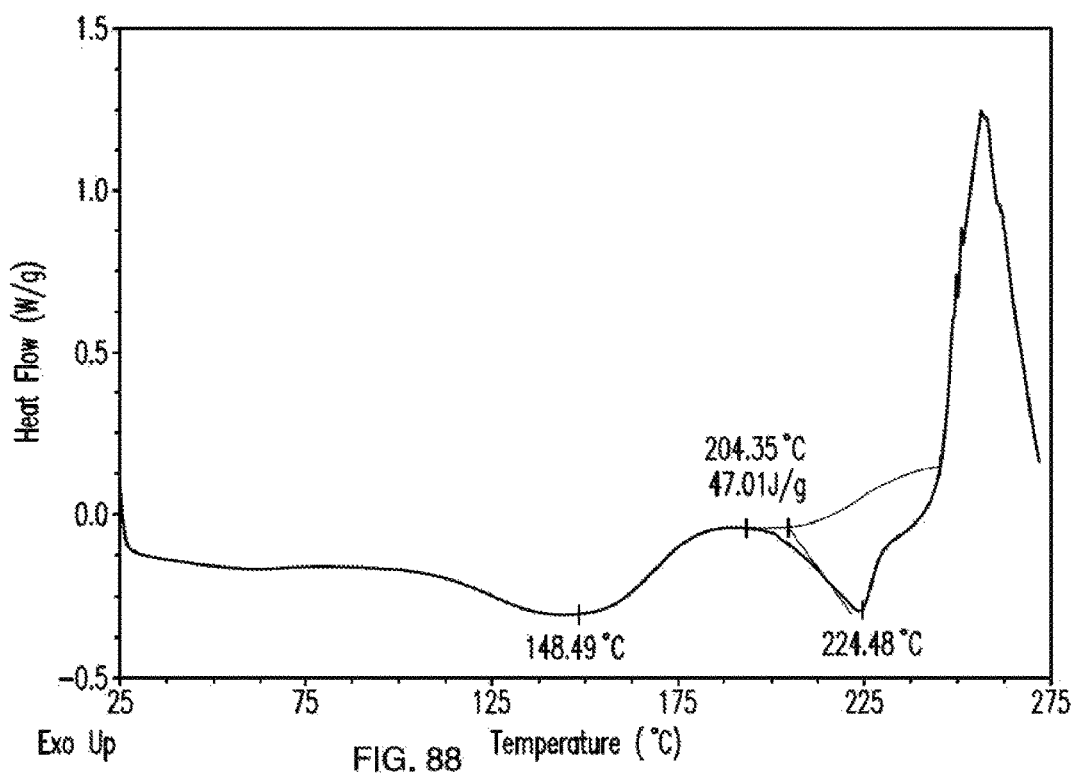
FIG. 88 depicts a DSC Thermogram of HCl Salt Form 8.

In one embodiment, provided herein is a crystalline form HCl salt of Compound 1 having a DSC thermogram as depicted in FIG. 88 comprising an endothermic event with a maximum at about 148° C. when heated from approximately 25° C. to approximately 275° C. In one embodiment, provided herein is a crystalline form HCl salt of Compound 1 having a DSC thermogram as depicted in FIG. 88 comprising an endothermic event with an onset temperature at about 204° C. and a peak maximum temperature at about 224° C. when heated from approximately 25° C. to approximately 300° C.

In still another embodiment, HCl salt Form 8 is substantially pure. In certain embodiments, the substantially pure HCl salt Form 8 is substantially free of other solid forms, e.g., amorphous solid. In certain embodiments, the purity of the substantially pure HCl salt Form 8 is no less than about 95%, no less than about 96%, no less than about 97%, no less than about 98%, no less than about 98.5%, no less than about 99%, no less than about 99.5%, or no less than about 99.8%.

Methods of Use

The solid forms of Compound 1 described herein have utility as pharmaceuticals to treat, prevent or improve conditions in animals or humans. Accordingly, provided herein are solid forms of Compound 1 described herein that can be used in all the methods as provided herein. Particularly, the solid forms of Compound 1 as provided herein are for uses in the treatment or prevention of a cancer. The methods provided herein comprise the administration of an effective amount of one or more solid forms of Compound 1 described herein to a subject in need thereof. It is to be understood that the methods described herein also include treatment with a pharmaceutical composition, such as those provided below, where the pharmaceutical composition includes a solid form of Compound 1 described herein and optionally at least one pharmaceutically acceptable excipient.

In another aspect, provided herein are methods for treating or preventing a cancer, comprising administering to a subject in need thereof an effective amount of a solid form of Compound 1 a solid form of Compound 1, as described herein. In some embodiments, the cancer is a solid tumor or a hematological tumor. In some embodiments, the cancer is not melanoma.

In some embodiments, the solid tumor is melanoma, colorectal cancer, stomach cancer, head and neck cancer, thyroid cancer, bladder cancer, CNS cancer, lung cancer, pancreatic cancer, and soft tissue cancer. In one embodiment, the solid tumor is endocrine cancer, bladder cancer, breast cancer, cervix cancer, colon cancer, duodenum cancer, glioma, head and d neck cancer, kidney cancer, liver cancer, lung cancer (e.g. non-small cell lung cancer NSCLC), esophageal cancer, thyroid cancer, or pancreatic cancer.

In other embodiment, the cancer is bladder cancer, breast cancer (for example Her positive, Her negative, or EGFR positive), CNS cancer (including neuroblastoma, and glioma), colon cancer, gastrointestinal cancer (for example, stomach cancer, and colon cancer), endocrine cancer (for example, thyroid cancer, or adrenal gland cancer), female genitoureal cancer (for example, cervix cancer, ovary clear cell cancer, vulva cancer, uterus cancer, or ovary cancer), head and neck cancer, hematopoietic cancer (for example, leukemia or myeloma), kidney cancer, liver cancer, lung cancer (for example, NSCLC, or SCLC), melanoma, pancreas cancer, prostate cancer, or soft tissue cancer (for example, sarcoma, or osteosarcoma).

In another embodiment, the cancer is bladder cancer, breast cancer (for example Her positive, Her negative, or EGFR positive), CNS cancer (for example, glioma, or neuroblastoma), colon cancer, gastrointestinal cancer (for example, stomach cancer), endocrine cancer (for example, thyroid cancer or adrenal gland cancer), female genitoureal cancer (for example, cancer of the uterus, cervix, ovary clear cell, or vulva), head and neck cancer, hematopoietic cancer (for example, leukemia or myeloma), kidney cancer, liver cancer, lung cancer (for example, NSCLC, or SCLC), melanoma, pancreas cancer, prostate cancer, or soft tissue cancer (for example, sarcoma or osteosarcoma).

In still another embodiment, the cancer is a cancer set forth in Table 44.

Also provided herein are methods for treating or preventing hepatocellular carcinoma (HCC), comprising administering to a subject in need thereof an effective amount of a solid form of Compound 1, as described herein.

Also provided herein are methods for treating or preventing colorectal cancer (CRC), melanoma, gastric cancer, HCC, lung cancer, pancreatic cancer, leukemia, or multiple myeloma, comprising administering to a subject in need thereof an effective amount of a solid form of Compound 1 as described herein or a pharmaceutical composition thereof, as described herein. In one embodiment, the CRC, gastric, or HCC is a cancer characterized by a β-catenin mutation. Also provided herein are methods for treating or preventing colorectal cancer (CRC), gastric cancer, HCC, lung cancer, pancreatic cancer, leukemia, and multiple myeloma, comprising administering to a subject in need thereof an effective amount of a solid form of Compound 1 as described herein, as described herein.

In another embodiment provided herein are methods of treating leukemia comprising administering a solid form of Compound 1 as described herein or a pharmaceutical composition thereof. The leukemia can be chronic myelogenous leukemia (CML). In another embodiment, the leukemia is acute myelogenous leukemia (AML). In one embodiment, the leukemia is FLT-3 mutated AML.

In another embodiment provided herein are methods of treating lymphoma comprising administering a solid form of Compound 1 as described herein or a pharmaceutical composition thereof. The lymphoma can be Burkitt's lymphoma. In one embodiment, the leukemia is Hodgkin's lymphoma. In another embodiment, the leukemia is a B-cell lymphoma. In another embodiment, the leukemia is a T-cell lymphoma. In still another embodiment, the lymphoma is primary effusion lymphoma (PEL).

The solid forms of Compound 1) show anti-proliferative activity in a variety of cancer cell lines. (Table 44) Anti-proliferative activity in these cancer cell lines indicates that the solid forms of Compound 1 are useful in the treatment of cancers, including hematopoietic and solid tumors. In one embodiment, the hematopoietic and solid tumors are selected from bladder cancer, breast cancer, CNS cancer (for example, neuroblastoma, medulloblastoma and glioma), colon cancer, duodenum cancer, endocrine cancer (for example, thyroid cancer and adrenal gland cancer), female genitourinary cancer (for example, uterus cancer, cervix cancer, ovary cancer and vulva cancer), head and neck cancer (for example, esophageal cancer), hematopoietic and lymphoid cancer (for example, lymphoma, leukemia, and myeloma), kidney cancer, liver cancer, lung cancer (for example, NSCLC and SCLC), pancreas cancer, prostate cancer, skin cancer (for example, melanoma and carcinoma), soft tissue cancer (for example, sarcoma and osteosarcoma), stomach cancer, and testis cancer. In one embodiment, the hematopoietic and solid tumors are selected from bladder cancer, breast cancer, CNS cancer (for example, neuroblastoma, medulloblastoma and glioma), colon cancer, duodenum cancer, endocrine cancer (for example, thyroid cancer and adrenal gland cancer), female genitourinary cancer (for example, uterus cancer, cervix cancer, and vulva cancer), head and neck cancer, hematopoietic and lymphoid cancer (for example, lymphoma, leukemia, and myeloma), kidney cancer, liver cancer, lung cancer (for example, NSCLC and SCLC), pancreas cancer, prostate cancer, skin cancer (for example, melanoma and carcinoma), soft tissue cancer (for example, sarcoma and osteosarcoma), stomach cancer, and testis cancer.

In another embodiment, the solid forms of Compound 1 described herein induce apoptosis in a variety of cancer cell lines. Induction of apoptosis indicates that the solid forms of Compound 1 described herein are useful in the treatment of cancers, including hematopoietic and solid tumors. In one embodiment, the hematopoietic and solid tumors are selected from bladder cancer, breast cancer, CNS cancer (for example, neuroblastoma, and glioma), colon cancer, duodenum cancer, endocrine cancer (for example, thyroid cancer and adrenal gland cancer), female genitourinary cancer (for example, uterus cancer, cervix cancer, ovary cancer and vulva cancer), head and neck cancer (for example, esophageal cancer), hematopoietic and lymphoid cancer (for example, lymphoma, leukemia, and myeloma), kidney cancer, liver cancer, lung cancer (for example, NSCLC and SCLC), pancreas cancer, prostate cancer, skin cancer (for example, melanoma and carcinoma), soft tissue cancer (for example, sarcoma and osteosarcoma), stomach cancer, and testis cancer. In one embodiment, the hematopoietic and solid tumors are selected from bladder cancer, breast cancer, CNS cancer (for example, neuroblastoma, and glioma), colon cancer, duodenum cancer, endocrine cancer (for example, thyroid cancer and adrenal gland cancer), female genitourinary cancer (for example, vulva cancer), head and neck cancer (for example, esophageal cancer), hematopoietic and lymphoid cancer (for example, lymphoma, and leukemia), kidney cancer, liver cancer, lung cancer (for example, NSCLC and SCLC), pancreas cancer, prostate cancer, skin cancer (for example, melanoma), soft tissue cancer (for example, sarcoma and osteosarcoma), stomach cancer, and testis cancer. In one embodiment, the hematopoietic and solid tumors are selected from bladder cancer, breast cancer, CNS cancer (for example, medulloblastoma, neuroblastoma, and glioma), colon cancer, duodenum cancer, endocrine cancer (for example, thyroid cancer and adrenal gland cancer), female genitourinary cancer (for example, placenta cancer, uterus cancer, cervix cancer, ovary cancer and vulva cancer), head and neck cancer (for example, esophageal cancer), hematopoietic and lymphoid cancer (for example, lymphoma, leukemia, and myeloma), kidney cancer, liver cancer, lung cancer (for example, NSCLC and SCLC), pancreas cancer, prostate cancer, skin cancer (for example, melanoma and carcinoma), soft tissue cancer (for example, sarcoma and osteosarcoma), stomach cancer, and testis cancer. In still another embodiment, the cases is a cancer set forth in Table 44.

Also provided herein are methods for treating or preventing a cancer characterized by a BRAF mutation and/or a beta-catenin mutation (alternatively referred to as CTNNB1 mutation), comprising administering to a subject in need thereof an effective amount of a solid form of Compound 1, as described herein. In some such embodiments, the cancer is characterized by a BRAF mutation. In another embodiment, the cancer is characterized by a beta-catenin mutation. In yet another embodiment, the cancer is characterized by an activated beta-catenin pathway. In some such embodiments, the cancer is CRC or melanoma characterized by a BRAF mutation. In other embodiments, the cancer is CRC characterized by a beta-catenin mutation, additionally comprising an EGFR mutation or increased EGFR activity (for example, CRC characterized by an activated beta-catenin pathway and an EGFR mutation, or CRC characterized by an activated beta-catenin pathway and increased EGFR activity). In still other embodiments, the cancer is gastric cancer characterized by a beta-catenin mutation, additionally comprising a KRAS mutation (i.e. gastric cancer characterized by an activated beta-catenin pathway and a KRAS mutation). In another embodiment the cancer is HCC, characterized by an activated beta-catenin pathway. In some such embodiments, the BRAF mutation is BRAF V660E. In some such embodiments, the BRAF mutation is BRAF V600E. In some such embodiments, the BRAF mutation is one or more of BRAF V600E, BRAF T119S, or BRAF G596R. In some such embodiments, the beta-catenin mutation is one or more of beta-catenin S33Y, G34E, S45del, or S33C. In some such embodiments, the EGFR mutation is one or more of EGFR E282K, G719S, P753S, or V1011M. In some such embodiments, the KRAS mutation is A146T, G12C, G12D, G12V, G13D, or Q61L.

Also provided herein are methods for treating or preventing a cancer expressing PD-L1, comprising administering to a subject in need thereof an effective amount of a solid form of Compound 1, as described herein. In some such embodiments, the PD-L1 expressing cancer is melanoma, lung cancer, renal cell carcinoma (RCC), or HCC.

Also provided herein are methods for treating or preventing a cancer characterized by a BRAF mutation, comprising administering to a subject in need thereof an effective amount of a solid form of Compound 1, as described herein. In some such embodiments, the cancer characterized by a BRAF mutation is CRC, thyroid cancer, melanoma or lung cancer. In some such embodiments, the cancer characterized by a BRAF mutation is CRC, thyroid cancer, or lung cancer. In some such embodiments, the BRAF mutation is BRAF V660E. In some such embodiments, the BRAF mutation is BRAF V600E. In other embodiments, the BRAF mutation is one or more of BRAF V600E, BRAF T119S, or BRAF G596R.

Also provided herein are methods for treating or preventing a cancer characterized by an NRAS mutation, comprising administering to a subject in need thereof an effective amount of a solid form of Compound 1, as described herein. In some such embodiments, the cancer characterized by an NRAS mutation is melanoma.

Also provided herein are methods for treating or preventing a cancer characterized by a KRAS mutation, comprising administering to a subject in need thereof an effective amount of a solid form of Compound 1, as described herein. In some such embodiments, the cancer characterized by a KRAS mutation is CRC, pancreas cancer or lung cancer.

Also provided herein are methods for treating or preventing a cancer characterized by a beta-catenin mutation, comprising administering to a subject in need thereof an effective amount of a solid form of Compound 1, as described herein. Also provided herein are methods for treating or preventing a cancer characterized by an activated beta-catenin pathway, comprising administering to a subject in need thereof an effective amount of a solid form of Compound 1, as described herein. In some such embodiments, the cancer characterized by a beta-catenin mutation is CRC, stomach cancer, HCC or sarcoma. In some such embodiments, the cancer characterized by an activated beta-catenin pathway is CRC, stomach cancer, HCC or sarcoma.

Also provided herein are methods for treating or preventing hepatocellular carcinoma (HCC), comprising administering to a subject in need thereof an effective amount of a solid form of Compound 1, as described herein. In some such embodiments, the HCC is characterized by a beta-catenin mutation and/or increased YAP expression. In some such embodiments, the HCC is characterized by an activated beta-catenin pathway and/or increased YAP amplification expression. In some embodiments, the increased YAP expression is due to amplification or a mutation.

Also provided herein are methods for treating or preventing colorectal cancer (CRC), comprising administering to a subject in need thereof an effective amount of a solid form of Compound 1, as described herein. In some such embodiments, the CRC is characterized by a BRAF mutation and/or beta-catenin mutation. In some such embodiments, the CRC is characterized by a BRAF mutation and/or an activated beta-catenin pathway.

Also provided herein are methods for treating or preventing gastric cancer, comprising administering to a subject in need thereof an effective amount of a solid form of Compound 1, as described herein. In some such embodiments, the gastric cancer is characterized by a beta-catenin mutation. In some such embodiments, the gastric cancer is characterized by an activated beta-catenin pathway.

Also provided herein are methods for treating or preventing melanoma, comprising administering to a subject in need thereof an effective amount of a solid form of Compound 1, as described herein. In some such embodiments, the melanoma is characterized by a BRAF mutation and/or NRAS mutation.

Further provided herein are methods for predicting response to treatment with a solid form of Compound 1 described herein in a patient having a cancer characterized by a gene mutation, the method comprising: a) obtaining a biological test sample from the patient's cancer; b) obtaining the gene sequence of one or more genes selected from BRAF, NRAS, KRAS, and/or CTNNB1 in said biological test sample; c) comparing said gene sequence(s) to the gene sequence(s) of a biological wild-type sample; wherein the presence of a mutation indicates an increased likelihood of response to a solid form of Compound 1 described herein treatment of said patient's cancer. In some such embodiments, the method additionally comprises administering an effective amount of a solid form of Compound 1, as described herein.

Further provided herein are methods for predicting therapeutic efficacy of a solid form of Compound 1 described herein for treatment of a patient having a cancer characterized by a gene mutation, the method comprising: a) obtaining a biological test sample from the patient's cancer; b) obtaining the gene sequence(s) of one or more genes selected from BRAF, NAS, KRAS, and/or CTNNB1 in said biological test sample; c) comparing said gene sequence(s) to the gene sequence(s) of a biological wild-type sample; wherein the presence of a mutation indicates an increased likelihood of therapeutic efficacy of said treatment with a solid form of Compound 1 described herein for said patient. In some such embodiments, the method additionally comprises administering an effective amount of a solid form of Compound 1, as described herein.

In some embodiments, provided herein are methods for treating and preventing cancer metastasis, comprising administering to a subject in need thereof an effective amount of a solid form of Compound 1, as described herein. In some embodiments, the cancer is a metastatic cancer, in particular, a metastatic solid tumor or metastatic hematologic cancer, wherein the solid tumor and hematologic cancer is as described herein. In other embodiments, provided herein are methods of treating and preventing cancer metastasis, comprising administering to a subject in need thereof an effective amount of a solid form of Compound 1, as described herein. In yet another aspect, provided herein is methods of eradicating cancer stem cells in a subject, comprising administering to a subject in need thereof an effective amount of a solid form of Compound 1, as described herein. In other embodiments, provided herein are methods of inducing differentiation in cancer stem cells in a subject, comprising administering to a subject in need thereof an effective amount of a solid form of Compound 1, as described herein. In other embodiments, provided herein are methods of inducing cancer stem cell death in a subject, comprising administering to a subject in need thereof an effective amount of a solid form of Compound 1, as described herein. In some such embodiments, the cancer is a solid tumor or a hematological cancer, as described herein.

In one embodiment, provided herein are methods for achieving a Response Evaluation Criteria in Solid Tumors (RECIST 1.1) of complete response, partial response or stable disease in a patient comprising administering an effective amount of a solid form of Compound 1 described herein to a patient having a cancer, in particular a solid tumor as described herein. In another embodiment, provided herein are methods to increase Progression Free Survival rates, as determined by Kaplan-Meier estimates.

In one embodiment, provided herein are methods for preventing or delaying a Response Evaluation Criteria in Solid Tumors (RECIST 1.1) of progressive disease in a patient, comprising administering an effective amount of a solid form of Compound 1 described herein to a patient having a solid tumor as described herein. In one embodiment the prevention or delaying of progressive disease is characterized or achieved by a change in overall size of the target lesions, of for example, between −30% and +20% compared to pre-treatment. In another embodiment, the change in size of the target lesions is a reduction in overall size of more than 30%, for example, more than 50% reduction in target lesion size compared to pre-treatment. In another, the prevention is characterized or achieved by a reduction in size or a delay in progression of non-target lesions compared to pre-treatment. In one embodiment, the prevention is achieved or characterized by a reduction in the number of target lesions compared to pre-treatment. In another, the prevention is achieved or characterized by a reduction in the number or quality of non-target lesions compared to pre-treatment. In one embodiment, the prevention is achieved or characterized by the absence or the disappearance of target lesions compared to pre-treatment. In another, the prevention is achieved or characterized by the absence or the disappearance of non-target lesions compared to pre-treatment. In another embodiment, the prevention is achieved or characterized by the prevention of new lesions compared to pre-treatment. In yet another embodiment, the prevention is achieved or characterized by the prevention of clinical signs or symptoms of disease progression compared to pre-treatment, such as cancer-related cachexia or increased pain. In one embodiment, the cases is a cancer set forth in Table 44.

In certain embodiments, provided herein are methods for decreasing the size of target lesions in a patient compared to pre-treatment, comprising administering an effective amount of a solid form of Compound 1 described herein to a patient having a cancer, in particular a solid tumor as described herein.

In certain embodiments, provided herein are methods for decreasing the size of a non-target lesion in a patient compared to pre-treatment, comprising administering an effective amount of a solid form of Compound 1 described herein to a patient having a cancer, in particular a solid tumor as described herein.

In certain embodiments, provided herein are methods for achieving a reduction in the number of target lesions in a patient compared to pre-treatment, comprising administering an effective amount of a solid form of Compound 1 described herein to a patient having a cancer, in particular a solid tumor as described herein.

In certain embodiments, provided herein are methods for achieving a reduction in the number of non-target lesions in a patient compared to pre-treatment, comprising administering an effective amount a solid form of Compound 1 described herein to a patient having a cancer, in particular a solid tumor as described herein.

In certain embodiments, provided herein are methods for achieving a disappearance of all target lesions in a patient, comprising administering an effective amount of a solid form of Compound 1 described herein to a patient having a cancer, in particular a solid tumor as described herein.

In certain embodiments, provided herein are methods for achieving a disappearance of all non-target lesions in a patient, comprising administering an effective amount of a solid form of Compound 1 described herein to a patient having a cancer, in particular a solid tumor as described herein.

In certain embodiments, provided herein are methods for treating a cancer, in particular a solid tumor as described herein, the methods comprising administering an effective amount of a solid form of Compound 1 described herein to a patient having a cancer, in particular a solid tumor, wherein the treatment results in a complete response, partial response or stable disease, as determined by Response Evaluation Criteria in Solid Tumors (RECIST 1.1).

In certain embodiments, provided herein are methods for treating a cancer, in particular a solid tumor as described herein, the methods comprising administering an effective amount of a solid form of Compound 1 described herein to a patient having a cancer, in particular a solid tumor as described herein, wherein the treatment results in a reduction in target lesion size, a reduction in non-target lesion size and/or the absence of new target and/or non-target lesions, compared to pre-treatment. In one embodiment, the cases is a cancer set forth in Table 44.

In certain embodiments, provided herein are methods for treating a cancer, in particular a solid tumor as described herein, the methods comprising administering an effective amount a solid form of Compound 1 described herein to a patient having a cancer, in particular a solid tumor as described herein, wherein the treatment results in prevention or retarding of clinical progression, such as cancer-related cachexia or increased pain.

In another embodiment, provided herein are methods for inducing a therapeutic response characterized with the International Workshop Criteria (IWC) for NHL (see Cheson B D, Pfistner B, Juweid, M E, et. al. Revised Response Criteria for Malignant Lymphoma. J. Clin. Oncol: 2007: (25) 579-586) of a patient, comprising administering an effective amount a solid form of Compound 1 described herein to a patient having a cancer, in particular hematological cancers such as lymphoma, as described herein. In another embodiment, provided herein are methods for achieving complete remission, partial remission or stable disease, as determined by the International Workshop Criteria (IWC) for NHL in a patient, comprising administering an effective amount of a solid form of Compound 1 described herein to a patient having a cancer, in particular hematological cancers such as lymphoma, as described herein. In another embodiment, provided herein are methods for achieving an increase in overall survival, progression-free survival, event-free survival, time to progression, disease-free survival or lymphoma-free survival as determined by the International Workshop Criteria (IWC) for NHL in a patient, comprising administering an effective amount of a solid form of Compound 1 described herein to a patient having a cancer, in particular hematological cancers such as lymphoma, as described herein.

In another embodiment, provided herein are methods for inducing a therapeutic response assessed with the International Uniform Response Criteria for Multiple Myeloma (IURC) (see Durie B G M, Harousseau J-L, Miguel J S, et al. International uniform response criteria for multiple myeloma. Leukemia, 2006; (10) 10: 1-7) of a patient, comprising administering an effective amount of a solid form of Compound 1 to a patient having a cancer, in particular multiple myeloma. In another embodiment, provided herein are methods for achieving a stringent complete response, complete response, very good partial response, or partial response, as determined by the International Uniform Response Criteria for Multiple Myeloma (IURC) in a patient, comprising administering an effective amount of a solid form of Compound 1 described herein to a patient having a cancer, in particular multiple myeloma. In another embodiment, provided herein are methods for achieving an increase in overall survival, progression-free survival, event-free survival, time to progression, or disease-free survival in a patient, comprising administering an effective amount of a solid form of Compound 1 described herein to a patient having a cancer, in particular multiple myeloma.

In another embodiment, provided herein are methods for inducing a therapeutic response assessed with the Response Assessment for Neuro-Oncology (RANO) Working Group for GBM (see Wen P., Macdonald, D R., Reardon, D A., et al. Updated response assessment criteria for high-grade gliomas: Response assessment in neuro-oncology working group. J. Clin. Oncol. 2010; 28: 1963-1972) of a patient, comprising administering an effective amount of a solid form of Compound 1 described herein to a patient having a cancer, in particular glioblastoma multiforme (GBM). In one embodiment, RANO will be used to establish the proportion of subjects progression-free at 6 months from Day 1 of treatment relative to efficacy evaluable subjects in the GBM type.

In another embodiment, provided herein are methods for improving the Eastern Cooperative Oncology Group Performance Status (ECOG) of a patient, comprising administering an effective amount a solid form of Compound 1 described herein to a patient having a cancer, in particular a solid tumor or hematological cancer as described herein.

In another embodiment, provided herein are methods for inducing a therapeutic response assessed by Positron Emission Tomography (PET) outcome of a patient, comprising administering an effective amount of a solid form of Compound 1 described herein to a patient having a cancer, in particular a solid tumor or hematological cancer as described herein. In certain embodiments, provided herein are methods for treating a cancer, in particular a solid tumor or hematological cancer as described herein, the methods comprising administering an effective amount of a solid form of Compound 1 described herein to a patient having a cancer, in particular a solid tumor or hematological cancer as described herein, wherein the treatment results in a reduction in tumor metabolic activity, for example, as measured by PET imaging.

Further provided herein are methods for treating patients who have been previously treated for a cancer, in particular a solid tumor or a hematological cancer as described herein, as well as those who have not previously been treated. Such methods include administration of a solid form of Compound 1 described herein. Because patients with a cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with a cancer.

Biomarkers

In one embodiment, provided herein are methods for modulating the levels of a biomarker in a subject having a cancer as described herein, comprising administering an effective amount of a solid form of Compound 1 described herein, to said subject. In some such embodiments, the modulation of the biomarker is assessed in a biological sample of the subject, such as in circulating blood, skin biopsies, tumor biopsies, circulating tumor cells, hair, and/or urine. In one embodiment, the biological sample is peripheral blood mononuclear cells (PBMC). In such embodiments, the amount of biomarker modulation is assessed by comparison of the amount of biomarker before and after administration of the solid form of Compound 1 described herein or pharmaceutical composition thereof. In some embodiments, the modulation in biomarker is a reduction of about 10%, 20%, 25%, 30%, 40%, 50%, 60%, 70%, 75%, 80%, 90%, 95%, 99%, or about 100% compared to baseline levels. In some other embodiments, the modulation in biomarker is an increase of about 10%, 20%, 25%, 30%, 40%, 50%, 60%, 70%, 75%, 80%, 90%, 95%, 99%, or about 100% compared to baseline levels.

In some embodiments, the biomarker is ERK, RSK1, DUSP4, DUSP5, DUSP6, BMF, EFNA1, EGR1, ETV5, FOS, FOSL1, GJA1, IL-8, cMyc, Cyclin D1, YAP, SPRY2, SPRY4, Axin2, CTGF, AREG, CYR61, CXCL1, HAS2, HES1, MAFF, CITED2, ELF3, or PD-L1. In some such embodiments, the modulation is measured by measurement of the reduction of phosphorylation levels of one or more of ERK and RSK1. In some embodiments, the modulation in biomarker is a reduction of about 10%, 20%, 25%, 30%, 40%, 50%, 60%, 70%, 75%, 80%, 90%, 95%, 99%, or about 100% compared to baseline levels. In some other embodiments, the modulation in biomarker is an increase of about 10%, 20%, 25%, 30%, 40%, 50%, 60%, 70%, 75%, 80%, 90%, 95%, 99%, or about 100% compared to baseline levels.

In some embodiments, the biomarker is one or more of DUSP4, DUSP6, cyclin D1, c-Myc, SPRY2, and YAP. In some such embodiments, the modulation is measured by measurement of the reduction in mRNA and/or protein expression levels of one or more of DUSP4, DUSP6, cyclin D1, c-Myc, and YAP. In some such embodiments, the modulation is measured by measurement of the reduction in mRNA and/or protein expression levels of one or more of DUSP4, DUSP6, SPRY2, c-Myc and cyclin D1. In some embodiments, the modulation in biomarker is a reduction of about 10%, 20%, 25%, 30%, 40%, 50%, 60%, 70%, 75%, 80%, 90%, 95%, 99%, or about 100% compared to baseline levels.

In some embodiments, the biomarker is one or more of DUSP4, DUSP6, cyclin D1, c-Myc, SPRY2, and YAP. In some such embodiments, the modulation is measured by measurement of the reduction in mRNA and/or protein expression levels of one or more of DUSP4, DUSP6, cyclin D1, c-Myc, and YAP. In some such embodiments, the modulation is measured by measurement of the reduction in mRNA and/or protein expression levels of one or more of DUSP4, DUSP6, SPRY2, c-Myc and cyclin D1. In some embodiments, the modulation in biomarker is a reduction of about 10%, 20%, 25%, 30%, 40%, 50%, 60%, 70%, 75%, 80%, 90%, 95%, 99%, or about 100% compared to baseline levels.

In some embodiments, the biomarker is one or more of DUSP5, DUSP6, EGR1, ETV5, FOS, FOSL1, IL8, SPRY2, and SPRY4. In some such embodiments, the modulation is measured by measurement of the reduction in mRNA and/or protein expression levels of one or more of DUSP5, DUSP6, EGR1, ETV5, FOS, FOSL1, IL8, SPRY2, and SPRY4. In some embodiments, the modulation in biomarker is a reduction of about 10%, 20%, 25%, 30%, 40%, 50%, 60%, 70%, 75%, 80%, 90%, 95%, 99%, or about 100% compared to baseline levels.

In some embodiments, the biomarker is one or more of BMF and EFNA. In some such embodiments, the modulation is measured by measurement of the increase in mRNA and/or protein expression levels of one or more of BMF and EFNA1. In some embodiments, the modulation in biomarker is an increase of about 10%, 20%, 25%, 30%, 40%, 50%, 60%, 70%, 75%, 80%, 90%, 95%, 99%, or about 100% compared to baseline levels.

In some embodiments, the biomarker is GJA1. In some such embodiments, the modulation is measured by measurement of the modulation in mRNA and/or protein expression levels of one or more of GJA1. In some such embodiments, the modulation in biomarker is a reduction of about 10%, 20%, 25%, 30%, 40%, 50%, 60%, 70%, 75%, 80%, 90%, 95%, 99%, or about 100% compared to baseline levels. In some embodiments, the modulation in biomarker is an increase of about 10%, 20%, 25%, 30%, 40%, 50%, 60%, 70%, 75%, 80%, 90%, 95%, 99%, or about 100% compared to baseline levels.

In some embodiments, the biomarker is one or more of Axin2, CTGF, Cur61 and AREG. In some such embodiments, the modulation is measured by measurement of the reduction in mRNA and/or protein expression levels of one or more of Axin2, CTGF, and AREG. In some embodiments, the modulation in biomarker is a reduction of about 10%, 20%, 25%, 30%, 40%, 50%, 60%, 70%, 75%, 80%, 90%, 95%, 99%, or about 100% compared to baseline levels.

In some embodiments, the biomarker is one or more of CYR61, CXCL1, HAS2, HES1 and MAFF. In some such embodiments, the modulation is measured by measurement of the reduction in mRNA and/or protein expression levels of one or more of CYR61, CXCL1, HAS2, HES1 and MAFF. In some embodiments, the modulation in biomarker is a reduction of about 10%, 20%, 25%, 30%, 40%, 50%, 60%, 70%, 75%, 80%, 90%, 95%, 99%, or about 100% compared to baseline levels.

In some embodiments, the biomarker is one or more of CITED2 and ELF3. In some such embodiments, the modulation is measured by measurement of the increase in mRNA and/or protein expression levels of one or more of CITED2 and ELF3. In some embodiments, the modulation in biomarker is an increase of about 10%, 20%, 25%, 30%, 40%, 50%, 60%, 70%, 75%, 80%, 90%, 95%, 99%, or about 100% compared to baseline levels.

In some embodiments, the biomarker is PD-L1. In some embodiments, the modulation in the levels of biomarker is a reduction in cell surface expression levels of PD-L1. In some embodiments, the modulation in biomarker is a reduction of about 10%, 20%, 25%, 30%, 40%, 50%, 60%, 70%, 75%, 80%, 90%, 95%, 99%, or about 100% compared to baseline levels.

In another embodiment, the biomarker is IFNγ or IL-2. In some such embodiments, the modulation in the levels of biomarker is an increase in mRNA and/or protein expression levels of IFNγ or IL-2. In some such embodiments, the modulation in mRNA and/or protein expression levels of IFNγ or IL-2 is an increase of about 10%, 20%, 25%, 30%, 40%, 50%, 60%, 70%, 75%, 80%, 90%, 95%, 99%, or about 100% compared to baseline levels.

In another embodiment, the biomarker is IL-8. In some such embodiments, the modulation in the levels of biomarker is a decrease in mRNA and/or protein expression levels of IL-8. In some such embodiments, the modulation in mRNA and/or protein expression levels of IL-8 is an decrease of about 10%, 20%, 25%, 30%, 40%, 50%, 60%, 70%, 75%, 80%, 90%, 95%, 99%, or about 100% compared to baseline levels.

In one embodiment, provided herein are methods for inhibiting phosphorylation of ERK and/or RSK1 in a subject having a cancer as described herein, comprising administering an effective amount of a solid form of Compound 1 as described herein to said subject. In some such embodiments, the inhibition of phosphorylation is assessed in a biological sample of the subject, such as in circulating blood and/or tumor cells, skin biopsies and/or tumor biopsies or aspirate. In such embodiments, the amount of inhibition of phosphorylation is assessed by comparison of the amount of phospho-ERK and/or RSK1 before and after administration of the solid form of Compound 1 provided herein. In certain embodiments, provided herein are methods for measuring inhibition of phosphorylation of ERK and/or RSK1, in a subject having a cancer as described herein, comprising administering an effective amount of a solid form of Compound 1 provided herein to said subject, measuring the amount of phosphorylated ERK and/or RSK1 in said subject, and comparing said amount of phosphorylated ERK and/or RSK to that of said subject prior to administration of an effective amount of the solid form of Compound 1 provided herein. In some embodiments, the biological sample is a tumor biopsy. In another embodiment, the biological sample is PBMC. In still another embodiment, the biological sample is circulating tumor cells.

In certain embodiments, provided herein are methods for inhibiting phosphorylation of ERK and/or RSK1 in a biological sample of a subject having a cancer as described herein, comprising administering an effective amount of a solid form of Compound 1 provided herein to said subject and comparing the amount of phosphorylated ERK and/or RSK1 in a biological sample of a subject obtained prior to and after administration of said solid form of Compound 1 provided herein, wherein less phosphorylated ERK and/or RSK1 in said biological sample obtained after administration of said solid form of Compound 1 provided herein relative to the amount of phosphorylated ERK and/or RSK1 in said biological sample obtained prior to administration of said solid form of Compound 1 provided herein indicates inhibition. In some embodiments, the biological sample is a tumor biopsy. In another embodiment, the biological sample is PBMC. In still another embodiment, the biological sample is circulating tumor cells.

Further provided herein are methods for determining whether a patient is sensitive to a solid form of Compound 1 described herein, comprising administering said patient said solid form of Compound 1 described herein and determining whether or not ERK and/or RSK1 phosphorylation is inhibited in said patient by measuring the amount of phosphorylated ERK and/or RSK1 in a biological sample from said patient prior to and after the administration of a solid form of Compound 1 described herein to said patient, wherein inhibition of ERK and/or RSK1 phosphorylation indicates that said patient is sensitive to said solid form of Compound 1 described herein. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for determining the effective amount of a solid form of Compound 1 described herein for the treatment of a cancer treatable by inhibition of phosphorylation of ERK and/or RSK1 in a patient, comprising administering said patient varying doses of said a solid form of Compound 1 described herein and determining the amount of ERK and/or RSK1 phosphorylation inhibition in said patient resulting from each dose of said a solid form of Compound 1 described herein by measuring the amount of phosphorylated ERK and/or RSK1 in a biological sample from said patient prior to and after the administration of each dose of a solid form of Compound 1 described herein to said patient, wherein inhibition of ERK and/or RSK1 phosphorylation by at least about 10%, about 20%, about 30%, about 40%, about 50% or greater than about 50%, corresponds to an effective amount of a solid form of Compound 1 described herein. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for predicting response to treatment with a solid form of Compound 1 described herein in a patient having a cancer, the method comprising: a) obtaining a biological test sample from the patient's cancer; b) obtaining the mRNA and/or protein expression levels of one or more of DUSP4, DUSP5, DUSP6, EGR1, ETV5, FOS, FOSL1, IL-8, cMyc, Cyclin D1, YAP, SPRY2, SPRY4, Axin2, CTGF, AREG, CYR61, CXCL1, HAS2, HES1, and MAFF in said biological test sample; c) comparing said mRNA and/or protein expression levels to the mRNA and/or protein expression levels of a biological wild-type sample; wherein a reduction in mRNA and/or protein expression levels in said patient's biological test sample relative to said biological wild-type sample, indicates an increased likelihood of response to treatment with a solid form of Compound 1 described herein of said patient's cancer. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for predicting therapeutic efficacy of treatment with a solid form of Compound 1 described herein of a patient having a cancer, the method comprising: a) obtaining a biological test sample from the patient's cancer; b) obtaining the mRNA and/or protein expression levels of one or more of DUSP4, DUSP5, DUSP6, EGR1, ETV5, FOS, FOSL1, IL-8, cMyc, Cyclin D1, YAP, SPRY2, SPRY4, Axin2, CTGF, AREG, CYR61, CXCL1, HAS2, HES1, and MAFF in said biological test sample; c) comparing said mRNA and/or protein expression levels to the mRNA and/or protein expression levels of a biological wild-type sample; wherein a reduction in mRNA and/or protein expression levels indicates an increased likelihood of therapeutic efficacy of said treatment with a solid form of Compound 1 described herein for said patient. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for determining whether a patient is sensitive to a solid form of Compound 1 described herein, comprising administering said patient said solid form of Compound 1 described herein and determining whether or not mRNA and/or protein expression levels of one or more of DUSP4, DUSP5, DUSP6, EGR1, ETV5, FOS, FOSL1, IL-8, cMyc, Cyclin D1, YAP, SPRY2, SPRY4, Axin2, CTGF, AREG, CYR61, CXCL1, HAS2, HES1, and MAFF, are inhibited in said patient, by measuring the amount of mRNA and/or protein expression levels of one or more of DUSP4, DUSP5, DUSP6, EGR1, ETV5, FOS, FOSL1, IL-8, cMyc, Cyclin D1, YAP, SPRY2, SPRY4, Axin2, CTGF, AREG, CYR61, CXCL1, HAS2, HES1, and MAFF in a biological sample from said patient, prior to and after the administration of a solid form of Compound 1 described herein to said patient. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for determining the effective amount of a solid form of Compound 1 described herein for the treatment of a cancer treatable by inhibition of mRNA and/or protein expression levels of one or more of DUSP4, DUSP5, DUSP6, EGR1, ETV5, FOS, FOSL1, IL-8, cMyc, Cyclin D1, YAP, SPRY2, SPRY4, Axin2, CTGF, AREG, CYR61, CXCL1, HAS2, HES1, and MAFF in a patient, comprising administering said patient varying doses of said solid form of Compound 1 described herein and determining the amount of mRNA and/or protein expression levels of one or more of DUSP4, DUSP5, DUSP6, EGR1, ETV5, FOS, FOSL1, IL-8, cMyc, Cyclin D1, YAP, SPRY2, SPRY4, Axin2, CTGF, AREG, CYR61, CXCL1, HAS2, HES1, and MAFF inhibition in said patient, resulting from each dose of said solid form of Compound 1 described herein by measuring the amount of mRNA and/or protein expression levels of one or more of DUSP4, DUSP5, DUSP6, EGR1, ETV5, FOS, FOSL1, IL-8, cMyc, Cyclin D1, YAP, SPRY2, SPRY4, Axin2, CTGF, AREG, CYR61, CXCL1, HAS2, HES1, and MAFF in a biological sample from said patient, prior to and after the administration of each dose of a solid form of Compound 1 described herein to said patient. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for predicting response to treatment with a solid form of Compound 1 described herein in a patient having a cancer, the method comprising: a) obtaining a biological test sample from the patient's cancer; b) obtaining the mRNA and/or protein expression levels of one or more of BMF, EFNA1, CITED2, and ELF3 in said biological test sample; c) comparing said mRNA and/or protein expression levels to the mRNA and/or protein expression levels of a biological wild-type sample; wherein an increase in mRNA and/or protein expression levels in said patient's biological test sample relative to said biological wild-type sample, indicates an increased likelihood of response to treatment with a solid form of Compound 1 described herein of said patient's cancer. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for predicting therapeutic efficacy of treatment with a solid form of Compound 1 described herein of a patient having a cancer, the method comprising: a) obtaining a biological test sample from the patient's cancer; b) obtaining the mRNA and/or protein expression levels of one or more of BMF, EFNA1, CITED2, and ELF3 in said biological test sample; c) comparing said mRNA and/or protein expression levels to the mRNA and/or protein expression levels of a biological wild-type sample; wherein an increase in mRNA and/or protein expression levels indicates an increased likelihood of therapeutic efficacy of said solid form of Compound 1 described herein treatment for said patient. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for determining whether a patient is sensitive to a solid form of Compound 1 described herein, comprising administering said patient said solid form of Compound 1 described herein and determining whether or not mRNA and/or protein expression levels of one or more of BMF, EFNA1, CITED2, and ELF3 are increased in said patient, by measuring the amount of mRNA and/or protein expression levels of one or more of BMF, EFNA1, CITED2, and ELF3 in a biological sample from said patient, prior to and after the administration of a solid form of Compound 1 described herein to said patient. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for determining the effective amount of a solid form of Compound 1 described herein for the treatment of a cancer treatable by an increase of mRNA and/or protein expression levels of one or more of BMF, EFNA1, CITED2, and ELF3 in a patient, comprising administering said patient varying doses of said solid form of Compound 1 described herein, and determining the amount of mRNA and/or protein expression levels of one or more of BMF, EFNA1, CITED2, and ELF3 increase in said patient resulting from each dose of said solid form of Compound 1 described herein by measuring the amount of mRNA and/or protein expression levels of one or more of BMF, EFNA1, CITED2, and ELF3 in a biological sample from said patient, prior to and after the administration of each dose of a solid form of Compound 1 described herein to said patient. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for predicting response to treatment with a solid form of Compound 1 described herein in a patient having a cancer, the method comprising: a) obtaining a biological test sample from the patient's cancer; b) obtaining the mRNA and/or protein expression levels of GJA1 in said biological test sample; c) comparing said mRNA and/or protein expression levels to the mRNA and/or protein expression levels of a biological wild-type sample; wherein a reduction in mRNA and/or protein expression levels in said patient's biological test sample relative to said biological wild-type sample, indicates an increased likelihood of response to treatment with a solid form of Compound 1 described herein of said patient's cancer. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for predicting therapeutic efficacy of treatment with a solid form of Compound 1 described herein of a patient having a cancer, the method comprising: a) obtaining a biological test sample from the patient's cancer; b) obtaining the mRNA and/or protein expression levels of GJA1 in said biological test sample; c) comparing said mRNA and/or protein expression levels to the mRNA and/or protein expression levels of a biological wild-type sample; wherein a reduction in mRNA and/or protein expression levels indicates an increased likelihood of therapeutic efficacy of said treatment with a solid form of Compound 1 described herein for said patient. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for determining whether a patient is sensitive to a solid form of Compound 1 described herein, comprising administering said patient said solid form of Compound 1 described herein and determining whether or not mRNA and/or protein expression levels of GJA1 are inhibited in said patient, by measuring the amount of mRNA and/or protein expression levels of GJA1 in a biological sample from said patient, prior to and after the administration of a solid form of Compound 1 described herein to said patient. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for determining the effective amount of a solid form of Compound 1 described herein for the treatment of a cancer treatable by inhibition of mRNA and/or protein expression levels of GJA1 in a patient, comprising administering said patient varying doses of said solid form of Compound 1 described herein and determining the amount of mRNA and/or protein expression levels of GJA1 inhibition in said patient, resulting from each dose of said solid form of Compound 1 described herein by measuring the amount of mRNA and/or protein expression levels of GJA1 in a biological sample from said patient, prior to and after the administration of each dose of a solid form of Compound 1 described herein to said patient. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for predicting response to treatment with a solid form of Compound 1 described herein in a patient having a cancer, the method comprising: a) obtaining a biological test sample from the patient's cancer; b) obtaining the mRNA and/or protein expression levels of GJA1 in said biological test sample; c) comparing said mRNA and/or protein expression levels to the mRNA and/or protein expression levels of a biological wild-type sample; wherein an increase in mRNA and/or protein expression levels in said patient's biological test sample relative to said biological wild-type sample, indicates an increased likelihood of response to a solid form of Compound 1 described herein treatment of said patient's cancer. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for predicting therapeutic efficacy of treatment with a solid form of Compound 1 described herein of a patient having a cancer, the method comprising: a) obtaining a biological test sample from the patient's cancer; b) obtaining the mRNA and/or protein expression levels of GJA1 in said biological test sample; c) comparing said mRNA and/or protein expression levels to the mRNA and/or protein expression levels of a biological wild-type sample; wherein an increase in mRNA and/or protein expression levels indicates an increased likelihood of therapeutic efficacy of said treatment with a solid form of Compound 1 described herein for said patient. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for determining whether a patient is sensitive to a solid form of Compound 1, comprising administering said patient said a solid form of Compound 1 described herein and determining whether or not mRNA and/or protein expression levels of GJA1 are increased in said patient, by measuring the amount of mRNA and/or protein expression levels of GJA1 in a biological sample from said patient, prior to and after the administration of a solid form of Compound 1 described herein to said patient. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for determining the effective amount of a solid form of Compound 1 for the treatment of a cancer treatable by an increase of mRNA and/or protein expression levels of GJA1 in a patient, comprising administering said patient varying doses of said solid form of Compound 1 described herein, and determining the amount of mRNA and/or protein expression levels of GJA1 increase in said patient resulting from each dose of said solid form of Compound 1 described herein by measuring the amount of mRNA and/or protein expression levels of GJA1 in a biological sample from said patient, prior to and after the administration of each dose of a solid form of Compound 1 described herein to said patient. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for predicting response to treatment with a solid form of Compound 1 described herein in a patient having a cancer, the method comprising: a) obtaining a biological test sample from the patient's cancer; b) obtaining the cell surface expression levels of PD-L1 in said biological test sample; c) comparing said cell surface expression levels of PD-L1 to the cell surface expression levels of PD-L1 of a biological wild-type sample; wherein a reduction in cell surface expression levels of PD-L1 indicates an increased likelihood of response to a solid form of Compound 1 described herein treatment of said patient's cancer. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for predicting therapeutic efficacy of treatment with a solid form of Compound 1 described herein of a patient having a cancer, the method comprising: a) obtaining a biological test sample from the patient's cancer; b) obtaining the cell surface expression levels of PD-L1 in said biological test sample; c) comparing said cell surface expression levels of PD-L1 to the cell surface expression levels of PD-L1 of a biological wild-type sample; wherein a reduction in cell surface expression levels of PD-L1 indicates an increased likelihood of therapeutic efficacy of said treatment with a solid form of Compound 1 described herein for said patient. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for determining whether a patient is sensitive to a solid form of Compound 1, comprising administering said patient said a solid form of Compound 1 described herein and determining whether or not cell surface expression levels of PD-L1 are inhibited in said patient by measuring the amount of cell surface expression levels of PD-L1 in a biological sample from said patient prior to and after the administration of a solid form of Compound 1 described herein to said patient. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Further provided herein are methods for determining the effective amount of a solid form of Compound 1 described herein for the treatment of a cancer treatable by cell surface expression levels of PD-L1 in a patient, comprising administering said patient varying doses of said solid form of Compound 1 described herein and determining the amount of cell surface expression levels of PD-L1 inhibition in said patient resulting from each dose of said solid form of Compound 1 described herein by measuring the amount of cell surface expression levels of PD-L1 in a biological sample from said patient prior to and after the administration of each dose of a solid form of Compound 1 described herein to said patient. In some such embodiments, the method additionally comprises administering an effective amount of a solid form of Compound 1, as described herein. In some embodiments, the biological sample is a tumor biopsy. In another embodiment, the biological sample is PBMC. In still another embodiment, the biological sample is circulating tumor cells.

Combination Therapy

Solid forms of Compound 1 provided herein can also be combined or used in combination with other therapeutic agents useful in the treatment and/or prevention of cancer described herein.

In one embodiment, provided herein is a method of treating, preventing, or managing cancer, comprising administering to a patient a solid form of Compound 1 provided herein in combination with one or more second active agents, and optionally in combination with radiation therapy, blood transfusions, or surgery. Examples of second active agents are disclosed herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a solid form of Compound 1 provided herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of a solid form of Compound 1 provided herein and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of a solid form of Compound 1 described herein is independent of the route of administration of a second therapy. Thus, in accordance with these embodiments, a solid form of Compound 1 described herein is administered intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, a solid form of Compound 1 described herein and a second therapy are administered by the same mode of administration, for example, orally. In another embodiment, a solid form of Compound 1 described herein is administered by one mode of administration, e.g., orally, whereas the second agent (an anticancer agent) is administered by another mode of administration, e.g., IV.

In one embodiment, the second active agent is administered, for example, orally, intravenously or subcutaneously, and once or twice daily in an amount of from about 1 to about 1000 mg, from about 5 to about 500 mg, from about 10 to about 350 mg, from about 50 to about 200 mg, from about 1 to about 100 mg, from about 1 to about 200 mg, from about 1 to about 300 mg, from about 1 to about 400 mg, or from about 1 to about 500 mg. The specific amount of the second active agent will depend on the specific agent used, the type of disease being treated or managed, the severity and stage of disease, and the amount of a solid form of Compound 1 described herein described herein and any optional additional active agents concurrently administered to the patient.

One or more second active ingredients or agents can be used together with a solid form of Compound 1 described herein in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins. Proteins that are particularly useful in the methods and compositions provided herein include proteins that stimulate the survival and/or proliferation of hematopoietic precursor cells lymphopoietic cells in vitro or in vivo. Other useful proteins stimulate the division and differentiation of committed hematopoietic progenitors in cells in vitro or in vivo. Particular proteins include, but are not limited to: interleukins, such as IL-2 (including recombinant IL-2 ("rIL2") and canarypox IL-2), IL-10, IL-12, and IL-18; interferons, such as interferon alfa-2a, interferon alfa-2b, interferon alfa-n1, interferon alfa-n3, interferon beta-Ia, and interferon gamma-I b; GM-CF and GM-CSF; and EPO.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

Particular proteins that can be used in the methods and compositions include, but are not limited to: filgrastim, sargramostim, and recombinant EPO.

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; the entireties of which are incorporated herein by reference.

Also provided for use in combination with a solid form of Compound 1 described herein are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with a solid form of Compound 1 described herein include monoclonal and polyclonal antibodies. Examples of antibodies include, but are not limited to, trastuzumab, rituximab, bevacizumab, pertuzumab, tositumomab, edrecolomab, and G250. Solid forms of Compound 1 described herein can also be combined with, or used in combination with, anti-TNF-α antibodies, and/or anti-EGFR antibodies, such as, for example, cetuximab or panitumumab.

Antibodies that can be used in combination with a solid form of Compound 1 described herein include immune checkpoint inhibitors, such as, anti-CTLA4, anti-PD1, anti-PD-L1, anti-Tim-3, anti-Lag-3 antibodies. In some such embodiments, the PD-1 or PD-L1 antibodies are, for example, avelumab, durvalumab, MEDI0680, atezolizumab, BMS-936559, nivolumab, pembrolizumab, pidilizumab, or PDR-001. In one such embodiment, the anti-Lag-3 antibody is BMS-986016.

Additional antibodies that can be used in combination with a solid form of Compound 1 described herein include anti-RSPO antibodies.

Large molecule active agents may be administered in the form of anti-cancer vaccines. For example, vaccines that secrete, or cause the secretion of, cytokines such as IL-2, G-CSF, and GM-CSF can be used in the methods and pharmaceutical compositions provided. See, e.g., Emens, L. A., et al., *Curr. Opinion Mol. Ther.* 3(1):77-84 (2001).

Second active agents that are small molecules can also be used to alleviate adverse effects associated with the administration of a solid form of Compound 1 described herein. However, like some large molecules, many are believed to be capable of providing an additive or synergistic effect when administered with (e.g., before, after or simultaneously) a solid form of Compound 1 described herein. Examples of small molecule second active agents include, but are not limited to, anti-cancer agents, antibiotics, immunosuppressive agents, and steroids.

In certain embodiments, the second agent is a BRAF inhibitor, an HSP inhibitor, a proteasome inhibitor, a FLT3 inhibitor, a MEK inhibitor, a PI3K inhibitor, an EGFR inhibitor, an immunomodulatory compound, or a TOR kinase inhibitor. In some such embodiments, the BRAF inhibitor is sorafenib, dabrafenib, encorafenib, or vemurafenib. In some such embodiment, the HSP inhibitor is geldanamycin, gamitrinib, luminespib, or radicicol. In some embodiments, the proteasome inhibitor is bortezomib, carfilzomib, ixazomib, disulfiram, oprozomib, delanzomib, or ixazomib. In other embodiments, the FLT3 inhibitor is quizartinib, midostaurin, sorafenib, sunitinib, or lestaurtinib. In some such embodiments, the MEK inhibitor is trametinib, cobimetinib, binimetinib, selumetinib, PD-325901, CI-1040 (PD184352) or TAK-733. In some other embodiments, the PI3K inhibitor is AT7867, AZD 8055, BX-912, silmitasertib, pictilisib, MK-2206, or pilaralisib. In another embodiment, the EGFR inhibitor is gefitinib, erlotinib, afatinib, osimertinib (TAGRISSO), rociletinib, or lapatinib. In some other embodiments, the TOR kinase inhibitor is CC-115, CC-223, OSI-027, AZD8055, sapanisertib, dactolisib, BGT226, voxtalisib (SAR-245409), apitolisib, omipalisib (GSK-2126458), PF-04691502, gedatolisib or PP242. In some embodiments, the immunomodulatory compound is thalidomide, lenalidomide, pomalidomide, CC-220, or CC-122.

Examples of additional anti-cancer agents to be used within the methods or compositions described herein include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; clofarabine; crisnatol mesylate; cyclophosphamide; arabinoxylcytosine; dacarbazine; dabrafenib; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; omacetaxine; ormaplatin; oxisuran; paclitaxel; paclitaxel protein-bound particles for injectable suspension, albumin bound (ABRAXANE®); pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sorafenib; sparfosate sodium; sparsomycin; spirogermanium hydrochloride; spiromustine; spiroplatin; streptonigrin; streptozocin; sulofenur; talisomycin; tecogalan sodium; docetaxel; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; vemurafenib; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs to be included within the methods or compositions include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogens, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; j asplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; cetuximab, human chorionic gonadotrophin; monophosphoryl lipid A+*mycobacterium* cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen; O$^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; paclitaxel protein-bound particles for injectable suspension, albumin bound (ABRAXANE®); palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; sarmustine; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents particularly useful in the methods or compositions include, but are not limited to, rituximab, oblimersen, infliximab, docetaxel, celecoxib, melphalan, dexamethasone, steroids, gemcitabine, cisplatinum, temozolomide, etoposide, cyclophosphamide, temodar, carboplatin, procarbazine, carmustine, tamoxifen, topotecan, methotrexate, gefitinib, paclitaxel, fluorouracil, leucovorin, irinotecan, capecitabine, interferon alpha, pegylated interferon alpha, cisplatin, thiotepa, fludarabine, carboplatin, liposomal daunorubicin, cytarabine, vinblastine, IL-2, GM-CSF, dacarbazine, vinorelbine, zoledronic acid, palmitronate, clarithormycin, busulphan, prednisone, bisphosphonate, arsenic trioxide, vincristine, doxorubicin, ganciclovir, estramustine sodium phosphate, clinoril, and etoposide.

Other specific second active agents particularly useful in the methods or compositions include, but are not limited to, sorafenib, dabrafenib, vemurafenib, trametinib, cobimetinib, binimetinib, selumetinib, PD-325901, CI-1040 (PD184352), TAK-733, AT7867, AZD 8055, BX-912, silmitasertib, pictilisib, MK-2206, pilaralisib, gefitinib, erlotinib, lapatinib, osimertinib, CC-115, CC-223, OSI-027, AZD8055, sapanisertib, dactolisib, BGT226, voxtalisib, apitolisib, omipalisib, PF-04691502, gedatolisib, PP242, lenalidomide, pomalidomide, or CC-122.

Other specific second active agents particularly useful in the methods or compositions include, but are not limited to, avelumab, durvalumab, MEDI0680, atezolizumab, BMS-936559, nivolumab, pembrolizumab, pidilizumab, PDR-001, sorafenib, cetuximab, panatumumab, erlotinib, trametinib, trastuzumab, CC-223, CC-122 or lapatinib.

In certain embodiments of the methods provided herein, use of a second active agent in combination with a solid form of Compound 1 described herein may be modified or delayed during or shortly following administration of a solid form of Compound 1 described herein as deemed appropriate by the practitioner of skill in the art. In certain embodiments, subjects being administered a solid form of Compound 1 described herein alone or in combination with other therapies may receive supportive care including antiemetics, myeloid growth factors, and transfusions of blood products, when appropriate. In some embodiments, subjects being administered a solid form of Compound 1 described herein may be administered a growth factor as a second active agent according to the judgment of the practitioner of skill in the art.

In certain embodiments, a solid form of Compound 1 described herein is administered with gemcitabine, cisplatinum, 5-fluorouracil, mitomycin, methotrexate, vinblastine, doxorubicin, carboplatin, thiotepa, paclitaxel, paclitaxel protein-bound particles for injectable suspension-albumin bound (ABRAXANE®), or docetaxel to patients with locally advanced or metastatic urothelial carcinoma.

In certain embodiments, a solid form of Compound 1 described herein is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temozolomide to patients with recurrent or progressive meningioma, malignant meningioma, hemangiopericytoma, multiple brain metastases, relapsed brain tumors, or newly diagnosed glioblastoma multiforme; irinotecan to patients with recurrent glioblastoma; carboplatin to pediatric patients with brain stem gliomas; procarbazine to pediatric patients with progressive malignant gliomas; cyclophosphamide to patients with poor prognosis malignant brain tumors, newly diagnosed or recurrent glioblastoma multiforms; carmustine for high grade recurrent malignant gliomas; temozolomide and tamoxifen for anaplastic astrocytoma; or topotecan for gliomas, glioblastoma, anaplastic astrocytoma or anaplastic oligodendroglioma.

In certain embodiments, a solid form of Compound 1 described herein is administered with methotrexate, cyclophosphamide, 5-fluorouracil, everolimus, paclitaxel, paclitaxel protein-bound particles for injectable suspension-albumin bound (ABRAXANE®), lapatinib, trastuzumab, pamidronate disodium, eribulin mesylate, everolimus, gemcitabine, palbociclib, ixabepilone, ado-trastuzumab emtansine, pertuzumab, thiotepa, aromatase inhibitors, exemestane, selective estrogen modulators, estrogen receptor antagonists, anthracyclines, emtansine, and/or pexidartinib to patients with metastatic breast cancer.

In certain embodiments, a solid form of Compound 1 described herein is administered with temozolomide, doxorubicin, everolimus, fluorouracil, 5-fluorouracil, or streptozocin to patients with neuroendocrine tumors.

In certain embodiments, a solid form of Compound 1 described herein is administered with methotrexate, gemcitabine, cisplatin, cetuximab, 5-fluorouracil, bleomycin, docetaxel or carboplatin to patients with recurrent or metastatic head or neck cancer. In one embodiment, a solid form of Compound 1 as described herein provided herein is administered with cetuximab, to patients with head or neck cancer.

In certain embodiments, a solid form of Compound 1 described herein is administered with gemcitabine, paclitaxel, paclitaxel protein-bound particles for injectable suspension-albumin bound (ABRAXANE®), 5-fluorouracil, everolimus, irinotecan, mitomycin C, sunitinib or erlotinib to patients with pancreatic cancer.

In certain embodiments, a solid form of Compound 1 described herein is administered to patients with colon cancer in combination with getfitinib, erlotinib, oxaliplatin, 5-fluorouracil, irinotecan, capecitabine, cetuximab, ramucirumab, panitumumab, bevacizumab, leucovorin calcium, LONSURF, regorafenib, ziv-aflibercept, trametinib, paclitaxel, paclitaxel protein-bound particles for injectable suspension-albumin bound (ABRAXANE®), and/or docetaxel. In certain embodiments, a solid form of Compound 1 as described herein provided herein is administered to patients with colon cancer in combination with bevacizumab, irinotecan hydrochloride, capecitabine, cetuximab, ramucirumab, oxaliplatin, cetuximab, fluorouracil, leucovorin calcium, trifluridine and tipiracil hydrochloride, panitumumab, regorafenib, or ziv-aflibercept. In some embodiments, a solid form of Compound 1 as described herein provided herein is administered to patients with colon cancer in combination with an EGFR inhibitor (for example cetuximab or erlotinib) and/or a BRAF inhibitor (for example, sorafenib, dabrafenib, or vemurafenib).

In certain embodiments, a solid form of Compound 1 described herein is administered with capecitabine, cetuximab, erlotinib, trametinib, and/or vemurafenib to patients with refractory colorectal cancer or patients who fail first line therapy or have poor performance in colon or rectal adenocarcinoma. In some embodiments, a solid form of Compound 1 as described herein provided herein is administered to patients with refractory colorectal cancer or patients who fail first line therapy or have poor performance in colon or rectal adenocarcinoma in combination with an EGFR inhibitor (for example cetuximab or erlotinib) and a BRAF inhibitor (for example, sorafenib, dabrafenib, or vemurafenib). In some embodiments, a solid form of Compound 1 as described herein provided herein is administered to patients with refractory colorectal cancer or patients who fail first line therapy or have poor performance in colon or rectal adenocarcinoma in combination with an anti-RSPO antibody.

In certain embodiments, a solid form of Compound 1 described herein is administered in combination with fluorouracil, leucovorin, trametinib and/or irinotecan to patients with Stage IIIa to IV colorectal cancer or to patients who have been previously treated for metastatic colorectal cancer. In some embodiments, a solid form of Compound 1 as described herein provided herein is administered to patients with Stage IIIa to IV colorectal cancer or to patients who have been previously treated for metastatic colorectal cancer, in combination with an EGFR inhibitor (for example cetuximab or erlotinib) and a BRAF inhibitor (for example, sorafenib, dabrafenib, or vemurafenib). In certain embodiments, a solid form of Compound 1 as described herein provided herein is administered to patients with refractory colorectal cancer in combination with capecitabine, xeloda, trametinib, oxaliplatin and/or irinotecan. In some embodiments, a solid form of Compound 1 as described herein provided herein is administered to patients with refractory colorectal cancer, in combination with an EGFR inhibitor (for example cetuximab or erlotinib) and a BRAF inhibitor (for example, sorafenib, dabrafenib, or vemurafenib). In certain embodiments, a solid form of Compound 1 as described herein provided herein is administered with capecitabine, trametinib, and/or irinotecan to patients with refractory colorectal cancer or to patients with unresectable or metastatic colorectal carcinoma. In some embodiments, a solid form of Compound 1 as described herein provided herein is administered to patients with refractory colorectal cancer or to patients with unresectable or metastatic colorectal carcinoma, in combination with an EGFR inhibitor (for example cetuximab or erlotinib) and a BRAF inhibitor (for example, sorafenib, dabrafenib, or vemurafenib).

In certain embodiments, a solid form of Compound 1 described herein is administered alone or in combination with interferon alpha, 5-fluorouracil/leucovorin or capecitabine to patients with unresectable or metastatic hepatocellular carcinoma; or with cisplatin and thiotepa, or with sorafenib to patients with primary or metastatic liver cancer. In certain embodiments, a solid form of Compound 1 as described herein provided herein is administered alone or in combination with sorafenib, sunitinib, erlotinib, and/or sirolimus, to patients with unresectable or metastatic hepatocellular carcinoma; or with sorafenib, sunitinib, erlotinib, and/or rapamycin to patients with primary or metastatic liver cancer. In some embodiments, a solid form of Compound 1 as described herein provided herein is administered to patients with primary, unresectable, or metastatic liver cancer, in combination with an immune checkpoint inhibitor (for example, an anti-CTLA4, anti-PD1, anti-PD-L1, anti-Tim-3, or anti-Lag-3 antibody) or a BRAF inhibitor (for example, sorafenib, dabrafenib, or vemurafenib). In some such embodiments, the anti-PD-1 or anti-PD-L1 antibody is avelumab, durvalumab, MEDI0680, atezolizumab, BMS-936559, nivolumab, pembrolizumab, pidilizumab, or PDR-001. In certain embodiments, a solid form of Compound 1 as described herein provided herein is administered alone or in combination with lenalidomide, pomalidomide or CC-122 to patients with primary, unresectable or metastatic hepatocellular carcinoma. In certain embodiments, a solid form of Compound 1 as described herein provided herein is administered alone or in combination CC-223 to patients with primary, unresectable or metastatic hepatocellular carcinoma.

In certain embodiments, a solid form of Compound 1 described herein is administered in combination with cisplatin/5-fluorouracil, ramucirumab, docetaxel, doxorubicin hydrochloride, fluorouracil injection, trastuzumab, and/or mitomycin C to patients with gastric (stomach) cancer.

In certain embodiments, a solid form of Compound 1 described herein is administered in combination with an immune checkpoint inhibitor (for example, an anti-CTLA4, anti-PD1, anti-PD-L1, anti-Tim-3, or anti-Lag-3 antibody) and/or a BRAF inhibitor (for example, sorafenib, dabrafenib, or vemurafenib) to patients with various types or stages of melanoma. In some embodiments, a solid form of Compound 1 as described herein provided herein is administered in combination with aldesleukin, cobimetinib, dabrafenib, dacarbazine, IL-2, talimogene laherparepvec, recombinant interferon alfa-2b, ipilimumab, pembrolizumab, lapatinib, trametinib, nivolumab, peginterferon alfa-2b, aldesleukin, dabrafenib, and/or vemurafenib to patients with various types or stages of melanoma.

In certain embodiments, a solid form of Compound 1 described herein is administered in combination with doxorubicin, paclitaxel, paclitaxel protein-bound particles for injectable suspension-albumin bound (ABRAXANE®), vinblastine or pegylated interferon alpha to patients with Kaposi's sarcoma.

In certain embodiments, a solid form of Compound 1 described herein is administered in combination with methotrexate, mechlorethamine hydrochloride, afatinib dimaleate, pemetrexed, bevacizumab, carboplatin, cisplatin, ceritinib, crizotinib, ramucirumab, pembrolizumab, docetaxel, vinorelbine tartrate, gemcitabine, paclitaxel, paclitaxel protein-bound particles for injectable suspension-albumin bound (ABRAXANE®), erlotinib, geftinib, and/or irinotecan to patients with non-small cell lung cancer.

In certain embodiments, a solid form of Compound 1 described herein is administered in combination with carboplatin and irinotecan to patients with non-small cell lung cancer.

In certain embodiments, a solid form of Compound 1 described herein is administered with docetaxel to patients with non-small cell lung cancer who have been previously treated with carboplatin/etoposide and radiotherapy.

In certain embodiments, a solid form of Compound 1 described herein is provided herein is administered in combination with carboplatin and/or docetaxel, or in combination with carboplatin, paclitaxel, paclitaxel protein-bound particles for injectable suspension-albumin bound (ABRAXANE®), and/or thoracic radiotherapy to patients with non-small cell lung cancer.

In certain embodiments, a solid form of Compound 1 described herein is administered in combination with docetaxel to patients with stage IIIB or IV non-small cell lung cancer.

In certain embodiments, a solid form of Compound 1 described herein is administered in combination with oblimersen, methotrexate, mechlorethamine hydrochloride, etoposide, topotecan or doxorubicin to patients with small cell lung cancer.

In certain embodiments, a solid form of Compound 1 described herein and doxetaxol are administered to patients with small cell lung cancer who were previously treated with carbo/VP 16 and radiotherapy.

In certain embodiments, a solid form of Compound 1 described herein is administered to patients with various types or stages of ovarian cancer such as peritoneal carcinoma, papillary serous carcinoma, refractory ovarian cancer or recurrent ovarian cancer, in combination with carboplatin, doxorubicin, gemcitabine, cisplatin, capecitabine, paclitaxel, paclitaxel protein-bound particles for injectable suspension-albumin bound (ABRAXANE®), dexamethasone, avastin, cyclophosphamide, topotecan, olaparib, thiotepa, or a combination thereof.

In certain embodiments, a solid form of Compound 1 described herein is administered to patients with various types or stages of prostate cancer, in combination with capecitabine, 5-fluorouracil plus leucovorin, gemcitabine, irinotecan plus gemcitabine, cyclophosphamide, vincristine, dexamethasone, GM-CSF, celecoxib, ganciclovir, paclitaxel, paclitaxel protein-bound particles for injectable suspension-albumin bound (ABRAXANE®), docetaxel, estramustine, denderon, abiraterone, bicalutamide, cabazitaxel, degarelix, enzalutamide, goserelin, leuprolide acetate, mitoxantrone hydrochloride, prednisone, sipuleucel-T, radium 223 dichloride, or a combination thereof.

In certain embodiments, a solid form of Compound 1 described herein is administered to patients with various types or stages of renal cell cancer, in combination with capecitabine, IFN, tamoxifen, IL-2, GM-CSF, celecoxib, or a combination thereof.

In certain embodiments, a solid form of Compound 1 described herein is administered to patients with various types or stages of gynecologic, uterus or soft tissue sarcoma cancers in combination with IFN, dactinomycin, doxorubicin, imatinib mesylate, pazopanib, hydrochloride, trabectedin, a COX-2 inhibitor such as celecoxib, and/or sulindac.

In certain embodiments, a solid form of Compound 1 described herein is administered to patients with various types or stages of solid tumors in combination with celecoxib, etoposide, cyclophosphamide, docetaxel, apecitabine, IFN, tamoxifen, IL-2, GM-CSF, or a combination thereof.

In certain embodiments, a solid form of Compound 1 described herein is administered alone or in combination with vinorelbine to patients with malignant mesothelioma, or stage IIIB non-small cell lung cancer with pleural implants or malignant mesothelioma syndrome.

In certain embodiments, a solid form of Compound 1 described herein is administered in combination with A navitoclax, venetoclax and/or obatoclax to patients with lymphoma and other blood cancers.

In certain embodiments, a solid form of Compound 1 described herein is administered in combination with arsenic trioxide, fludarabine, carboplatin, daunorubicin, cyclophosphamide, cytarabine, doxorubicin, idarubicin, mitoxantrone hydrochloride, thioguanine, vincristine, and/or topotecan to patients with acute myeloid leukemia, including refractory or relapsed or high-risk acute myeloid leukemia.

In certain embodiments, a solid form of Compound 1 described herein is administered in combination with liposomal daunorubicin, topotecan and/or cytarabine to patients with unfavorable karotype acute myeloblastic leukemia.

In certain embodiments, a solid form of Compound 1 described herein is administered alone or in combination with a second active ingredient such as vinblastine or fludarabine, chlorambucil, bleomycin, brentuximab vedotin, carmustine, chlorambucil, cyclophosphamide, dacarbazine, doxorubicin, lomustine, mechlorethamine hydrochloride, prednisone, procarbazine hydrochloride or vincristine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, a solid form of Compound 1 described herein is administered to patients with various types or stages of multiple myeloma in combination with dexamethasone, zoledronic acid, pamitronate, GM-CSF, clarithromycin, vinblastine, melphalan, busulphan, cyclophosphamide, IFN, prednisone, bisphosphonate, celecoxib, arsenic trioxide, peginterferon alfa-2b, vincristine, carmustine, bortezomib, carfilzomib, doxorubicin, panobinostat, lenalidomide, pomalidomide, thalidomide, plerixafor or a combination thereof.

In certain embodiments, a solid form of Compound 1 described herein is administered to patients with various types or stages of multiple myeloma in combination with chimeric antigen receptor (CAR) T-cells.

In certain embodiments, a solid form of Compound 1 described herein is administered to patients with relapsed or refractory multiple myeloma in combination with doxorubicin, vincristine and/or dexamethasone.

In certain embodiments, a solid form of Compound 1 described herein is administered to patients with scleroderma or cutaneous vasculitis in combination with celecoxib, etoposide, cyclophosphamide, docetaxel, capecitabine, IFN, tamoxifen, IL-2, GM-CSF, or a combination thereof.

Also encompassed herein is a method of increasing the dosage of an anti-cancer drug or agent that can be safely and effectively administered to a patient, which comprises administering to the patient (e.g., a human) a solid form of Compound 1 described herein. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of a solid form of Compound 1 described herein alleviates or reduces adverse effects which are of such severity that it would otherwise limit the amount of anti-cancer drug.

In one embodiment, a solid form of Compound 1 described herein is administered daily in an amount ranging from about 0.1 to about 150 mg, from about 1 to about 100 mg, from about 2 to about 50 mg, or from about 1 to about 10 mg prior to, during, or after the occurrence of the adverse effect associated with the administration of an anti-cancer drug to a patient. In certain embodiments, a solid form of Compound 1 described herein is administered in combination with specific agents such as heparin, aspirin, coumadin, anti-Factor Xa, or G-CSF to avoid adverse effects that are associated with anti-cancer drugs such as but not limited to thromboembolism, neutropenia or thrombocytopenia.

In one embodiment, a solid form of Compound 1 described herein is administered to patients with diseases and disorders associated with or characterized by, undesired angiogenesis in combination with additional active ingredients, including, but not limited to, anti-cancer drugs, anti-inflammatories, antihistamines, antibiotics, and steroids.

In another embodiment, encompassed herein is a method of treating, preventing and/or managing cancer, which comprises administering a solid form of Compound 1 described herein in conjunction with (e.g. before, during, or after) conventional therapy including, but not limited to, surgery, immunotherapy, biological therapy, radiation therapy, or other non-drug based therapy presently used to treat, prevent or manage cancer. The combined use of the compound provided herein and conventional therapy may provide a unique treatment regimen that is unexpectedly effective in certain patients. Without being limited by theory, it is believed that a solid form of Compound 1 described herein may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. A solid form of Compound 1 as provided herein and other active ingredient can be administered to a patient prior to, during, or after the occurrence of the adverse effect associated with conventional therapy.

Cycling Therapy

In certain embodiments, the prophylactic or therapeutic agents provided herein are cyclically administered to a patient. Cycling therapy involves the administration of an active agent for a period of time, followed by a rest for a period of time, and repeating this sequential administration. Cycling therapy can reduce the development of resistance to one or more of the therapies, avoid, or reduce the side effects of one of the therapies, and/or improves the efficacy of the treatment.

Consequently, in certain embodiments, a solid form of Compound 1 provided herein is administered daily in a single or divided dose in a four to six week cycle with a rest period of about a week or two weeks. In certain embodiments, a solid form of Compound 1 provided herein is administered daily in a single or divided doses for one to ten consecutive days of a 28 day cycle, then a rest period with no administration for rest of the 28 day cycle. The cycling method further allows the frequency, number, and length of dosing cycles to be increased. Thus, encompassed herein in certain embodiments is the administration of a solid form of Compound 1 provided herein for more cycles than are typical when it is administered alone. In certain embodiments, a solid form of Compound 1 provided herein is administered for a greater number of cycles that would typically cause dose-limiting toxicity in a patient to whom a second active ingredient is not also being administered.

In one embodiment, a solid form of Compound 1 provided herein is administered daily and continuously for three or four weeks at a dose of from about 0.1 to about 150 mg/day followed by a break of one or two weeks.

In another embodiment, a solid form of Compound 1 provided herein is administered intravenously and a second active ingredient is administered orally, with administration of a solid form of Compound 1 described herein occurring 30 to 60 minutes prior to a second active ingredient, during a cycle of four to six weeks. In certain embodiments, the combination of a solid form of Compound 1 provided herein and a second active ingredient is administered by intravenous infusion over about 90 minutes every cycle. In certain embodiments, one cycle comprises the administration from about 0.1 to about 150 mg/day of a solid form of Compound 1 provided herein and from about 50 to about 200 mg/m$^2$/day of a second active ingredient daily for three to four weeks and then one or two weeks of rest. In certain embodiments, the number of cycles during which the combinatorial treatment is administered to a patient is ranging from about one to about 24 cycles, from about two to about 16 cycles, or from about four to about three cycles.

Pharmaceutical Compositions and Routes of Administration

Solid forms of Compound 1 described herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrrolidone or aluminum stearate), a dispersing agent (e.g., hydroxypropylmethylcellulose), a diluent (e.g., water), and base wax (e.g., cocoa butter, white petrolatum or polyethylene glycol). The effective amount of the solid forms of Compound 1 described herein in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of a solid form of Compound 1 to be administered to a subject is rather widely variable and can be subject to the judgment of a health-care practitioner. In general, the solid forms of Compound 1 can be administered one to four times a day in a dose of about 0.005 mg/kg of a subject's body weight to about 10 mg/kg of a subject's body weight in a subject, but the above dosage may be properly varied depending on the age, body weight and medical condition of the subject and the type of administration. In one embodiment, the dose is about 0.01 mg/kg of a subject's body weight to about 10 mg/kg of a subject's body weight, about 0.1 mg/kg of a subject's body weight to about 10 mg/kg of a subject's body weight, about 1 mg/kg of a subject's body weight to about 10 mg/kg of a subject's body weight or about 1 mg/kg of a subject's body weight to about 5 mg/kg of a subject's body weight. In one embodiment, one dose is given per day. In any given case, the amount of the solid form of Compound 1 administered will depend on such factors as the solubility of the active component, the formulation used and the route of administration. In one embodiment, application of a topical concentration provides intracellular exposures or concentrations of about 0.01-10 M.

In another embodiment, provided herein are methods for the treatment or prevention of a disease or disorder comprising the administration of about 1 mg/day to about 1000 mg/day, about 1 mg/day to about 750 mg/day, about 1 mg/day to about 500 mg/day, about 1 mg/day to about 250 mg/day or about 100 mg/day to about 1000 mg/day of a solid form of Compound 1 described herein to a subject in need thereof.

In another embodiment, provided herein are unit dosage formulations that comprise between about 1 mg and 1000 mg, about 5 mg and about 1000 mg, about 10 mg and about 1000 mg, about 25 mg and about 1000 mg, about 50 mg and about 1000 mg, about 100 mg and about 1000 mg, or about 250 mg and about 1000 mg of a solid form of Compound 1 described herein.

A solid forms of Compound 1 described herein can be administered once, twice, three, four or more times daily. In a particular embodiment, doses of 600 mg or less are administered as a once daily dose and doses of more than 600 mg are administered twice daily in an amount equal to one half of the total daily dose.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of a solid form of Compound 1 described herein.

In a particular embodiment, provided herein are unit dosage formulations comprising about 100 mg or 400 mg of a solid form of Compound 1 described herein.

In another embodiment, provided herein are unit dosage formulations that comprise 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a solid form of Compound 1 described herein.

The solid forms of Compound 1 described herein can be administered once, twice, three, four or more times daily. In a particular embodiment, doses of 600 mg or less are administered as a once daily dose and doses of more than 600 mg are administered twice daily in an amount equal to one half of the total daily dose.

The solid forms of Compound 1 described herein can be administered orally for reasons of convenience. In one embodiment, when administered orally, a solid form of Compound 1 is administered with a meal and water. In another embodiment, the solid form of Compound 1 is dispersed in water or juice (e.g., apple juice or orange juice) and administered orally as a suspension.

The solid forms of Compound 1 described herein can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in part upon the site of the medical condition.

In one embodiment, provided herein are capsules containing a solid form of Compound 1 described herein without an additional carrier, excipient or vehicle.

In another embodiment, provided herein are compositions comprising an effective amount of a solid form of Compound 1 described herein and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a solid form of Compound 1 described herein with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Compression of the solid forms of Compound 1 described herein may not reduce or modulate the activity of the administered drug to a patient. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a solid form of Compound 1 described herein as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the solid form of Compound 1 described herein can be delayed or prolonged by proper formulation. For example, a slowly soluble pellet of the solid form of Compound 1 described herein can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the solid form of Compound 1 described herein in oily or emulsified vehicles that allow it to disperse slowly in the serum.

In certain embodiments, the pharmaceutical compositions provided herein comprise Form A, including substantially pure Form A.

In certain embodiments, the pharmaceutical compositions provided herein comprise HCl Salt Form 1, including substantially pure starting material HCl Salt Form.

In certain embodiments, the pharmaceutical compositions provided herein comprise HCl Salt Form 1, including substantially pure HCl Salt Form 1.

In certain embodiments, the pharmaceutical compositions provided herein comprise Form B, including substantially pure Form B.

In certain embodiments, the pharmaceutical compositions provided herein comprise HCl Salt Form 2, including substantially pure HCl Salt Form 2.

In certain embodiments, the pharmaceutical compositions provided herein comprise Form C, including substantially pure Form C.

In certain embodiments, the pharmaceutical compositions provided herein comprise HCl Salt Form 3, including substantially pure HCl Salt Form 3.

In certain embodiments, the pharmaceutical compositions provided herein comprise Form D, including substantially pure Form D.

In certain embodiments, the pharmaceutical compositions provided herein comprise HCl Salt Form 4, including substantially pure HCl Salt Form 4.

In certain embodiments, the pharmaceutical compositions provided herein comprise Form E, including substantially pure Form E.

In certain embodiments, the pharmaceutical compositions provided herein comprise HCl Salt Form 5, including substantially pure HCl Salt Form 5.

In certain embodiments, the pharmaceutical compositions provided herein comprise Form F, including substantially pure Form F.

In certain embodiments, the pharmaceutical compositions provided herein comprise HCl Salt Form 6, including substantially pure HCl Salt Form 6.

In certain embodiments, the pharmaceutical compositions provided herein comprise Form G, including substantially pure Form G.

In certain embodiments, the pharmaceutical compositions provided herein comprise HCl Salt Form 7, including substantially pure HCl Salt Form 7.

In certain embodiments, the pharmaceutical compositions provided herein comprise Form H, including substantially pure Form H.

In certain embodiments, the pharmaceutical compositions provided herein comprise HCl Salt Form 8, including substantially pure HCl Salt Form 8.

In certain embodiments, the pharmaceutical compositions provided herein comprise Form I, including substantially pure Form I.

In certain embodiments, the pharmaceutical compositions provided herein comprise Form Y, including substantially pure Form Y.

In certain embodiments, the pharmaceutical compositions provided herein comprise Form Z, including substantially pure Form Z.

In certain embodiments, the pharmaceutical compositions provided herein comprise an amorphous solid, e.g. free base, HCl salt, citrate salt, or other salt described herein, including the substantially pure amorphous solid.

In certain embodiments, the pharmaceutical compositions provided herein comprise a mixture of one or more solid form(s) of Compound 1, including Form A, Form B, Form C, Form D, Form E, Form F, Form G, Form H, Form I, Form Y, Form Z, HCl Salt Form 1, HCl Salt Form 2, HCl Salt Form 3, HCl Salt Form 4, HCl Salt Form 5, HCl Salt Form 6, HCl Salt Form 7, HCl Salt Form 8 or an amorphous solid described herein, wherein every possible combination of the solid forms of Compound 1 is possible.

EXAMPLES

The following Examples are presented by way of illustration, not limitation. The following abbreviations are used in descriptions and examples:
ACN: Acetonitrile
Am: Amorphous
AmPhos: p-Dimethylamino phenylditbutylphosphine API: Active Pharmaceutical Ingredient
Boc: tert-Butoxycarbonyl
n-BuOH: n-Butanol
dba: Dibenzylidene acetone
DBU: 1,8-Diazabicyclo[5.4.0]undec-7-ene
DCM: Dichloromethane
DIPEA: N,N-Diisopropylethylamine
DMAc: N,N-Dimethylacetamide
DMF: N,N-Dimethylformide
DMSO: Dimethylsulfoxide
DSC: Differential Scanning Calorimetry
DVS: Dynamic Vapor Sorption
EDTA: Ethylenediamine tetraacetate
ESI: Electrospray ionization
EtOAc: Ethyl acetate
EtOH: Ethanol
FTIR: Fourier Transform Infrared Spectroscopy
HPLC: High performance liquid chromatography
IPA: 2-Propanol
IPAc: Isopropyl acetate
LCMS: Liquid Chromatography with Mass Spectroscopy
MeCN Acetonitrile
MEK: Methyl ethyl ketone
MeOH: Methanol
2-MeTHF: 2-Methyl tetrahydrofuran
mp: Melting point
MS: Mass spectrometry
MTBE: tert-Butyl methyl ether
NBS: N-Bromosuccinimide
NMP: N-Methyl-2-pyrrolidone
NMR: Nuclear magnetic resonance
RH: Relative Humidity
RT: Room Temperature
Rx Recrystallization
S: Solvent
SDTA: Single Differential Thermal Analysis
SM: Starting material
S-SegPhos (S)-(–)-5,5-Bis(diphenylphosphino)-4,4-bi-1,3-benzodioxole
TA: Thermal Analysis
Tf: Triflate or trifluoromethanesulfonyl
TFA: Trifluoroacetic acid
TFE: 2,2,2-Trifluoroethanol
TGA: Thermogravimetric Analysis
TGA-MS/TG-MS: Thermogravimetric Analysis coupled with Mass Spectroscopy
THF: Tetrahydrofuran
TLC: Thin layer chromatography
XRPD: X-Ray Powder Diffraction

Synthetic Examples

The following non-limiting synthetic examples show methods for the preparation of Compound 1. ACD/NAME (Advanced Chemistry Development, Inc., Ontario, Canada) and/or Chemdraw (Cambridgesoft, Perkin Elmer, Waltham, Mass.) was used to generate names for chemical structures and Chemdraw was used to draw the chemical structures.

In one embodiment, Compound 1 is synthesized in a manner as described in Example 53 of U.S. Pat. No. 9,512,124, which is hereby incorporated by reference in its entirety.

Compound 1 Salt Screening and Selection

Compound 1 salt form screening was conducted using small volume approaches. The pKa of Compound 1 is 5.14. Several counter ions were chosen for salt formation including glycolic, malic, citric, tartaric, phosphoric, maleic, benenesulfonic, methansulonic, toluenesulfonic, sulfuric, hydrochloric acids with various solvents.

Free base Compound 1 is hydrate material (a monohydrate). TGA weight loss amounted to 2.9% weight loss prior to decomposition, and DSC showed two endothermic peaks, broad at low temperature due to dehydration and then melting peak at 182° C. The crystal form remained unchanged after either slurry in water. The free base is stable in solution (pH 1.2 to 7.5) at 40° C. It has chemical and physical stability in solid state under stress conditions up to seven weeks. Under dry conditions, the hydrate form changed to partial or hemihydrates. The salt form likely improves the solid state properties and the pH-dependent solubility. The crystal form of monohydrate remained unchanged unless dried (<5% RH) or maintained at higher temperature (>60° C.). The monohydrate free base is slightly hygroscopicity.

The solid samples were examined using X-ray diffractometer (SmartLab, Rigaku). The detector was equipped with a photomultiplier with preamplifier X-ray detection technology. The samples were scanned from 3 to 40° 2θ, at a step size 0.02° 2θ and a time per step of 20 seconds. The tube voltage and current were 40 KV and 44 mA, respectively. The sample was transferred from sample container onto zero background XRD-holder and gently ground.

TGA analyses were carried out on a TA Instruments TGA Q5000. Approximately 1.50 mg of samples was placed in a tared platinum or aluminum pan, automatically weighed, and inserted into the TGA furnace. The samples were heated at a rate of 10° C./min, to final temperature of 300° C. The purge gas was nitrogen for balance at ca. 10 cc/min and for furnace at ca 90 cc/min, respectively.

DSC analyses were conducted on a TA Instruments Q2000. The calibration standard was indium. A sample 1.50 mg in weight was placed into a tared TA DSC pan, and weight accurately recorded. Crimped pans were used for analysis and the samples were heated under nitrogen (50 cc/min) at a rate of 10° C./min, up to a final temperature of 300° C. The data were processed using a thermal analyzer (Universal Analyzer 2000, TA Instruments).

Proton NMR was used to study the chemical shifts of compound resulted from salt formation. Proton NMR was performed using Bruker Advance 300 Ultrashield™ equipped with automated sample (B-ACS 60). Dimethyl sulfoxide-$d_6$ (DMSO-$d_6$) was used as a solvent for NMR analysis. Acquisition time was about 16 seconds, Dynamic vapor sorption (DVS) was measured using DVS advantage (Surface Measurement Systems Ltd). The samples were tested under isotherm (25° C.) at a targeted RH of 0 to 95% full cycle in step mode. For an isotherm test, the chamber temperature was maintained by a water bath at constant 25.0±1.0° C. The relative humidity in the sample chamber was generated by combining different flows of wet and dry nitrogen with variable flow rates. The analysis was performed in 10% RH increments. Sampling rate was 1 sec save data rate is 20 sec. The dm/dt (%) value was set at 0.001 with a dm/dt window of 5 min., a minimum stability duration time of 10 min, and a maximum stage time of 180 min. The sample's equilibrium weight corresponding to each RH was recorded. A sorption isotherm was obtained by plotting equilibrium moisture content versus RH.

1.00 gram of Compound 1 free base was dissolved in 10 mL of methanol. 100 μL of the stock solution was then added into each well on 96-well plate. Acid solutions were added with molar 1:1 ratio into each well on to plate, one acid to 8 wells in the same row. After drying of the plate, aliquots of 400 μL of 8 different solvents were added into well onto the plate in column fashion. The plates were then covered and allowed to evaporate in an operating laboratory fume hood under ambient conditions of temperature and humidity. Solvents were used for the screening including ethanol, 2-propanol, 3-methyl-butanol, acetonitrile, methyl tert-butyl ether (MTBE), acetone, water, ethyl acetate.

The starting non-salt form of Compound 1 free base was characterized by XRPD, TGA, and DSC. It is crystalline monohydrate and here designed to be Form 1.

Figure 89:
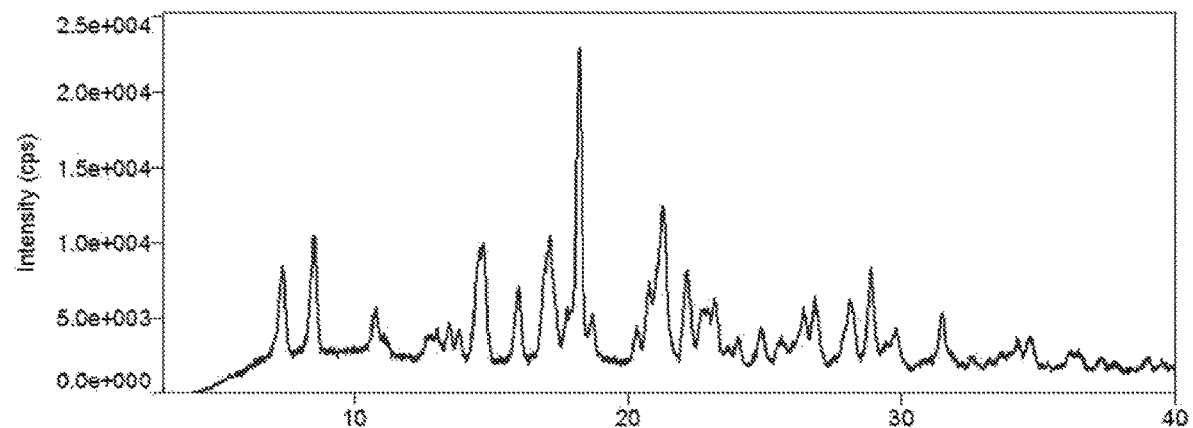
FIG. 89 depicts a XRPD Pattern of Compound 1.

Powder X-ray diffraction was performed on Compound 1, and the profile is shown in FIG. 89.

Figure 90:
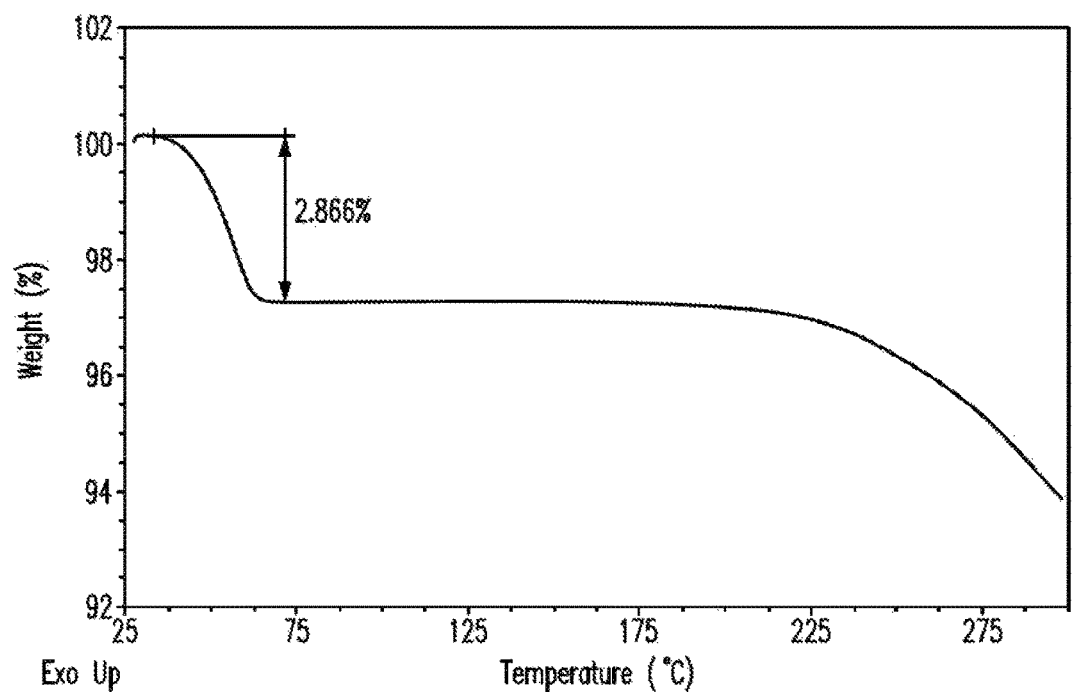
FIG. 90 depicts a TGA Thermogram of Compound 1.

In FIG. 90, the TGA thermogram of Compound 1 shows that about a 2.9% weight loss was observed at relative low temperature (<75° C.) due to dehydration. The final weight loss is from decomposition of the drug compound.

Figure 91:
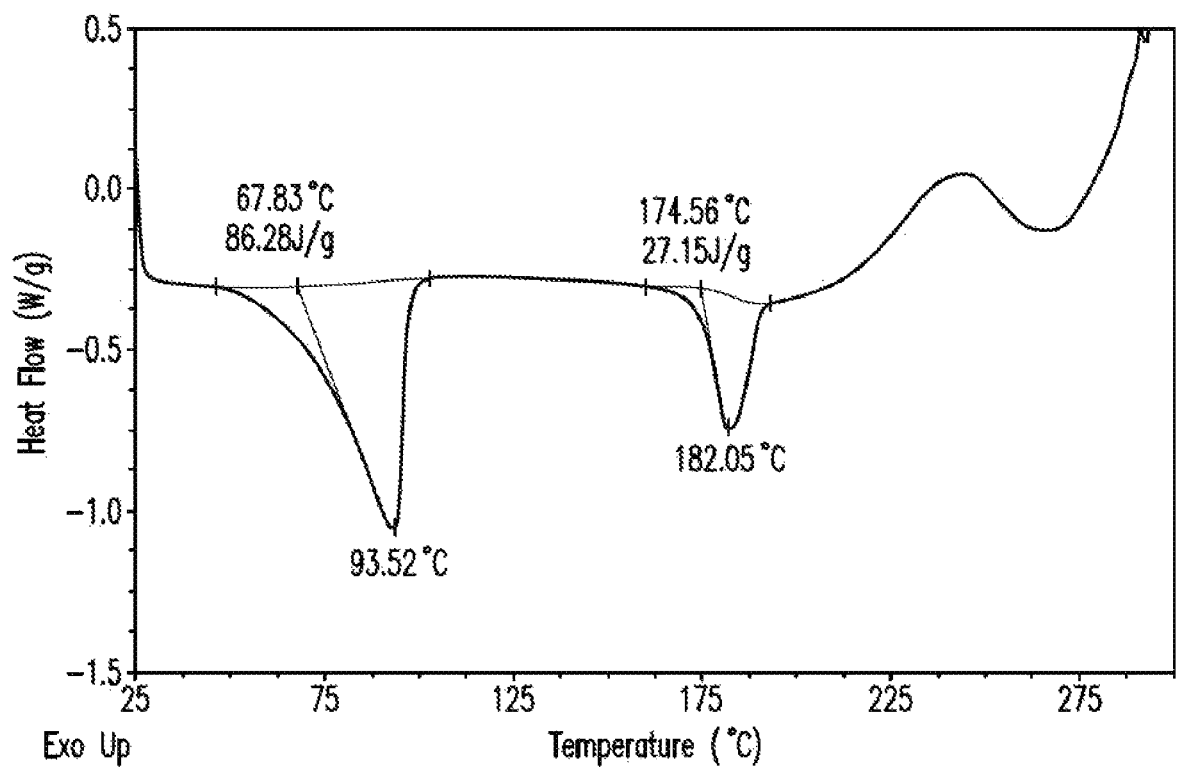
FIG. 91 depicts a DSC Thermogram of Compound 1.

In FIG. 91, the DSC thermogram of Compound 1 showed that the crystalline solid has a broad endothermic event at relative low temperature corresponding to dehydration/desolvation, and the endothermic peak with onset and peak temperature of 174.6 and 182.1° C., respectively, with enthalpy of 52.0 J/g due to the melt of the dehydrated form.

Figure 92:
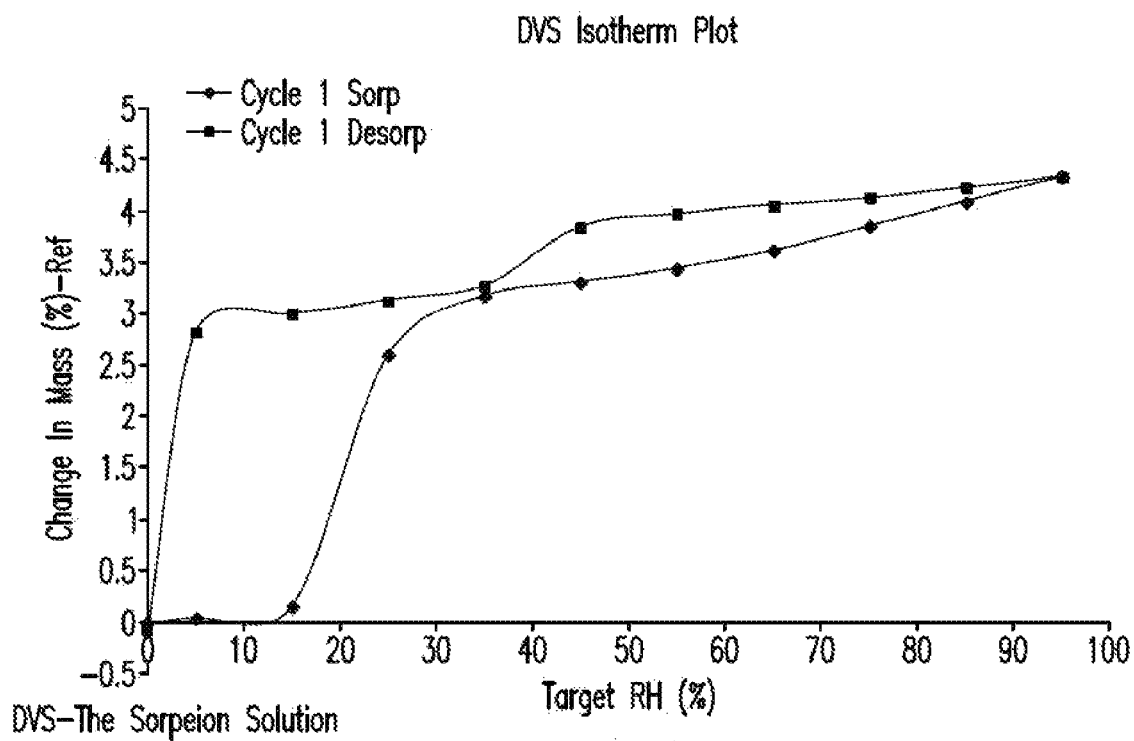
FIG. 92 depicts a DVS Isotherm Plot of Compound 1.
Figure 93:
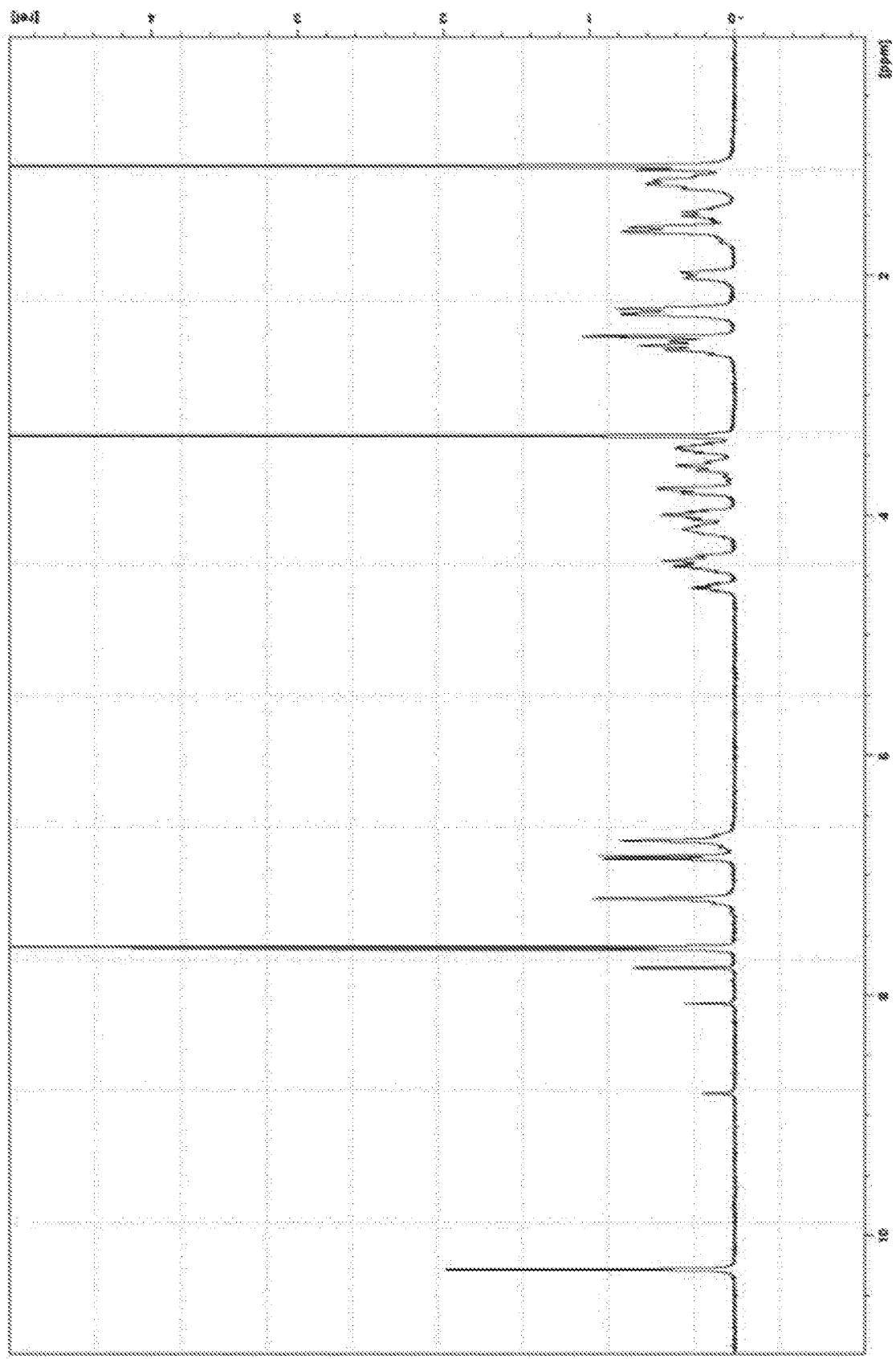
FIG. 93 depicts a $^1$H NMR of Compound 1.

The profiles of DVS showed the sample (Compound 1) is slightly hygroscopic (<4.3%) from 0-95% RH with respect to monohydrate free base as shown in FIG. 92. The monohydrate free base converted to anhydrous when first placed through a drying cycle at zero or very low humidity. Then ~2.6% (wt) of water was gained when the solid particles were exposed to increasing relative humidity up to 25% RH, converted back monohydrate in this range of humidity. Additional ~1.7% moisture sorption is slowly and steadily gained from 25 to 95% RH. During desorption cycle from 95 down to 5% RH, the loss of water content is very slowly ~1.5%, the monohydrate structure maintained. Then, the remaining ~2.8% wt of water was suddenly released from the sample as relative humidity decreased from 5% RH to dry. The level of 3.0% water content is corresponding to monohydrate.

The adsorption/desorption are almost reversible above 30% RH. Below 30% RH, the release of water during desorption is more difficult than up take during sorption.

Proton NMR of Compound 1 was examined in DMSO and shown in FIG. 6. Compound 1 free base (1.00 gram) was dissolved in methanol (10.0 mL). Aliquots of 100 μL of the solution were then distributed into each well onto a 96-well plate (1.0 mL flat bottom clear glass inserts). Eleven acids including glycolic, malic, citric, tartaric, phosphoric, maleic, benenesulfonic, methansulfonic, toluenesulfonic, sulfuric, hydrochloric acids were added with molar ratio of 1:1 into wells, see Table 1. Solvent was evaporated in an operation laboratory fume hood under ambient conditions of temperature and humidity. After dryness, the solvents for crystallization were introduced, see Table 1. Then, the plate was covered with a round-welled-cap mat w/silicone/PTFE liner to allow slow evaporation and crystallization at ambient environment.

TABLE 1

The content salt formers and solvents in 96-well plate.

|   | A | B | C | D |
|---|---|---|---|---|
| 1 | HCl | HCl | HCl | HCl |
| 2 | H2SO4 | H2SO4 | H2SO4 | H2SO4 |
| 3 | TsOH | TsOH | TsOH | TsOH |

TABLE 1-continued

The content salt formers and solvents in 96-well plate.

|   | A | B | C | D |
|---|---|---|---|---|
| 4 | MsOH | MsOH | MsOH | MsOH |
| 5 | BenzeOH | BenzeOH | BenzeOH | BenzeOH |
| 6 | Maleic | Maleic | Maleic | Maleic |
| 7 | H3PO4 | H3PO4 | H3PO4 | H3PO4 |
| 8 | Tartaric | Tartaric | Tartaric | Tartaric |
| 9 | Citric | Citric | Citric | Citric |
| 10 | Malic | Malic | Malic | Malic |
| 11 | Glycolic | Glycolic | Glycolic | Glycolic |
| 12 | Free Base | Free Base | Free Base | Free Base |
| 13 | Ethanol | IPA | 3-methyl-butanol | Acetonitrile |

|   | E | F | G | H |
|---|---|---|---|---|
| 1 | HCl | HCl | HCl | HCl |
| 2 | H2SO4 | H2SO4 | H2SO4 | H2SO4 |
| 3 | TsOH | TsOH | TsOH | TsOH |
| 4 | MsOH | MsOH | MsOH | MsOH |
| 5 | BenzeOH | BenzeOH | BenzeOH | BenzeOH |
| 6 | Maleic | Maleic | Maleic | Maleic |
| 7 | H3PO4 | H3PO4 | H3PO4 | H3PO4 |
| 8 | Tartaric | Tartaric | Tartaric | Tartaric |
| 9 | Citric | Citric | Citric | Citric |
| 10 | Malic | Malic | Malic | Malic |
| 11 | Glycolic | Glycolic | Glycolic | Glycolic |
| 12 | Free Base | Free Base | Free Base | Free Base |
| 13 | MTBE | Acetone | Water | EtoAc |

Figure 94:
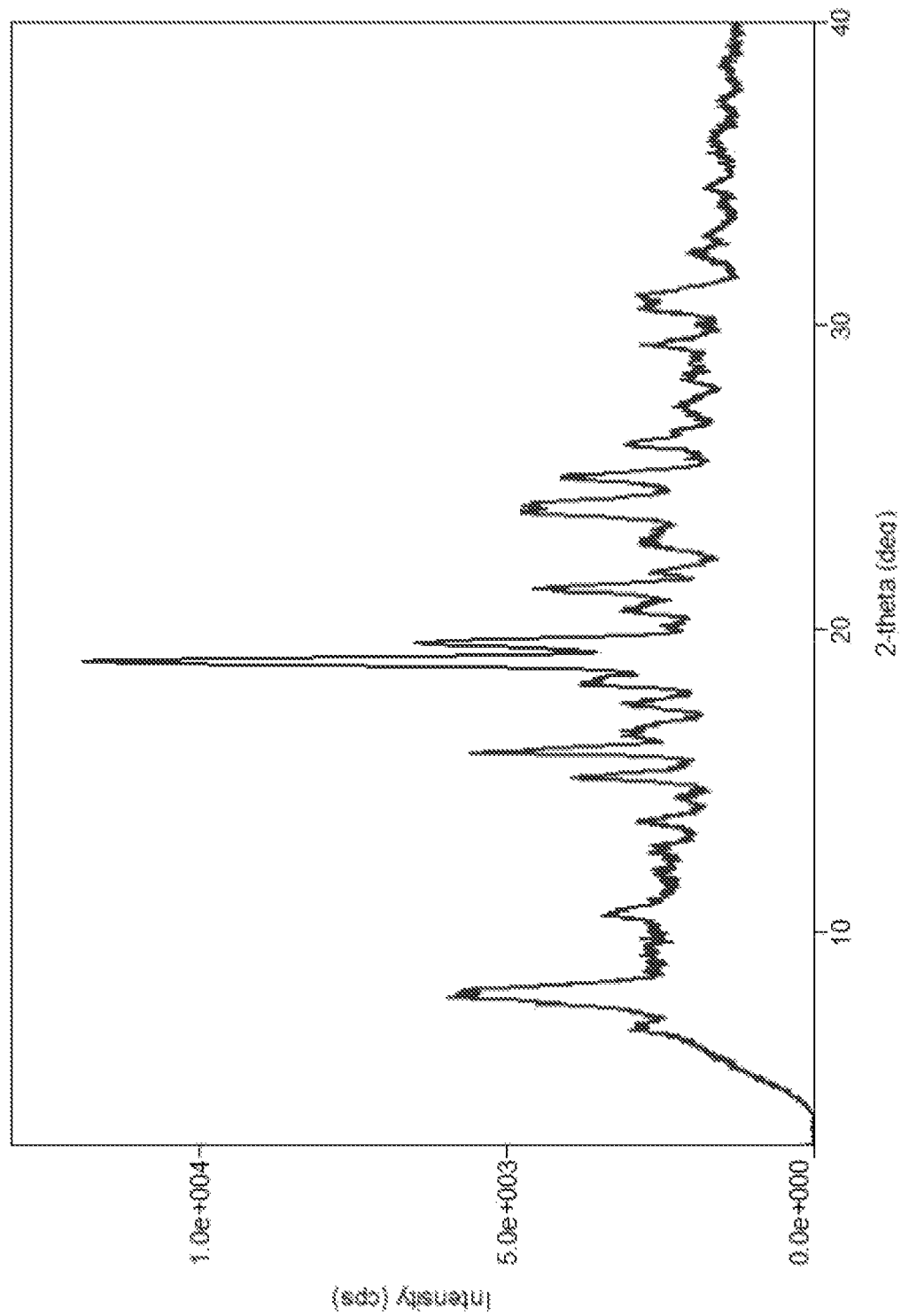
FIG. 94 depicts a XRPD Pattern of Compound 1 HCl salt isolated from solubility study in SGF.
Figure 95:
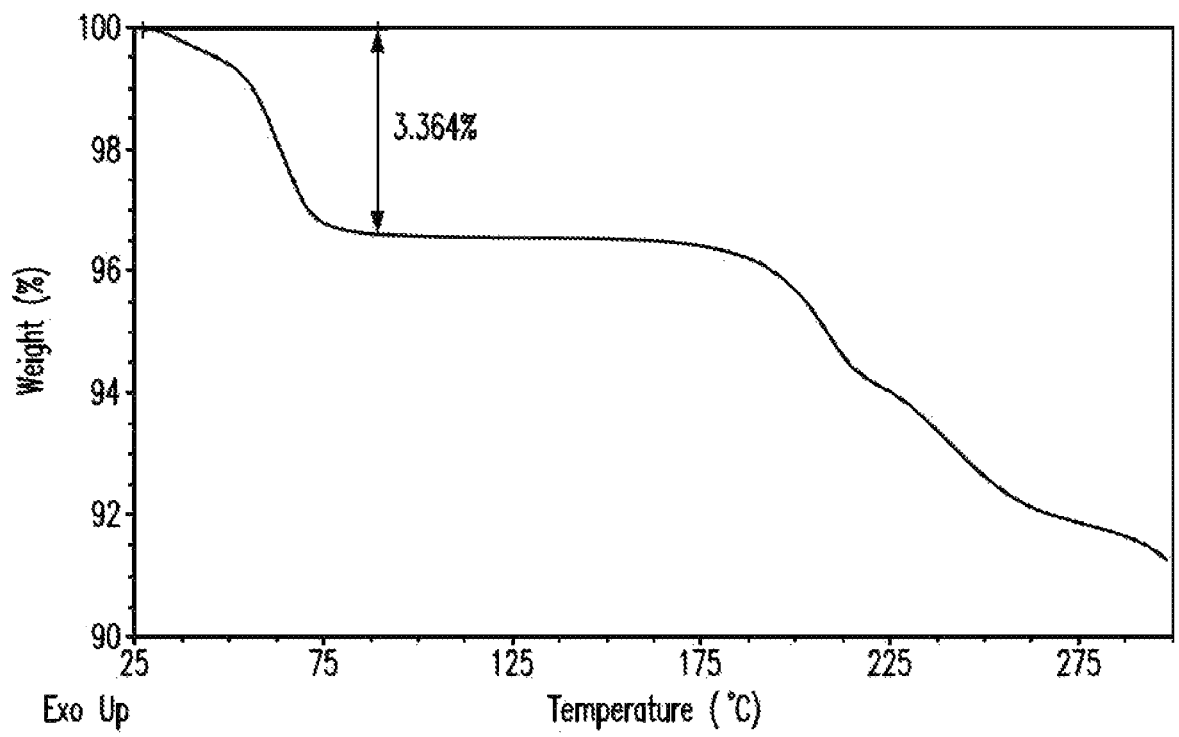
FIG. 95 depicts a TGA Thermogram of Compound 1 HCl salt isolated from solubility study in SGF.
Figure 96:
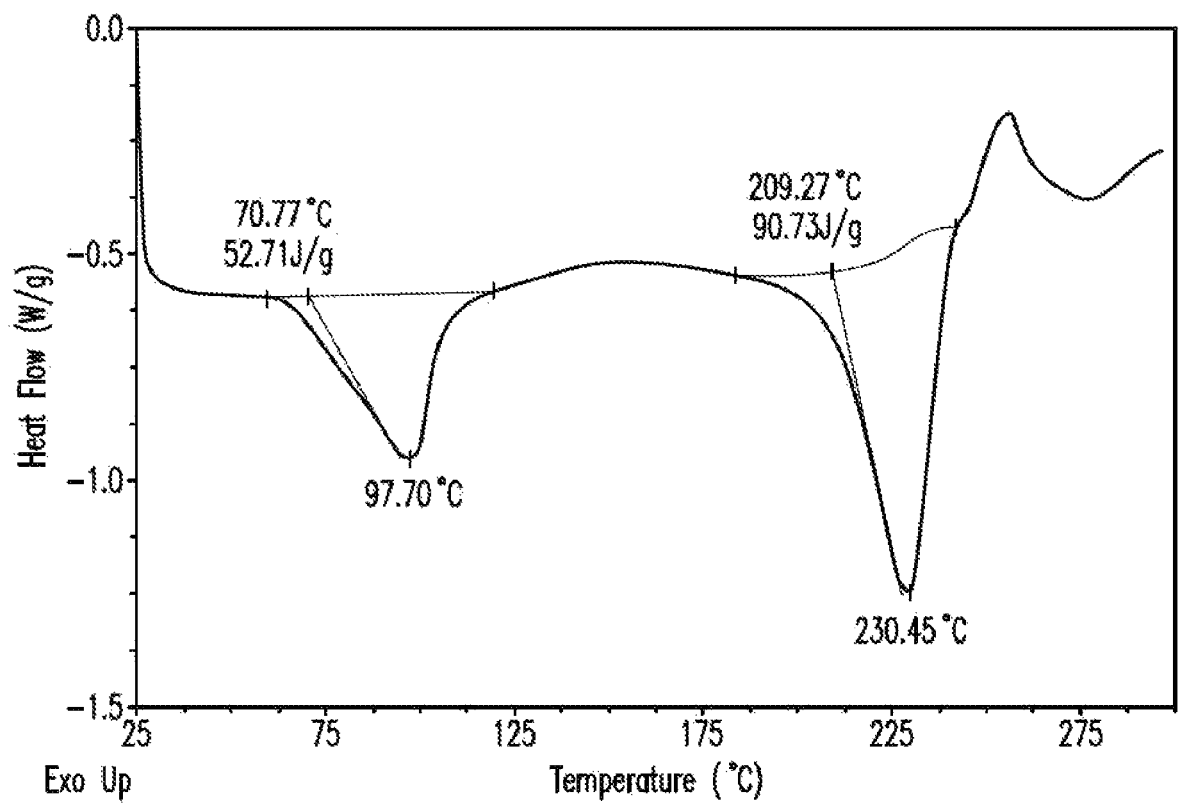
FIG. 96 depicts a DSC Thermogram of Compound 1 HCl salt isolated from solubility study in SGF.
Figure 97:
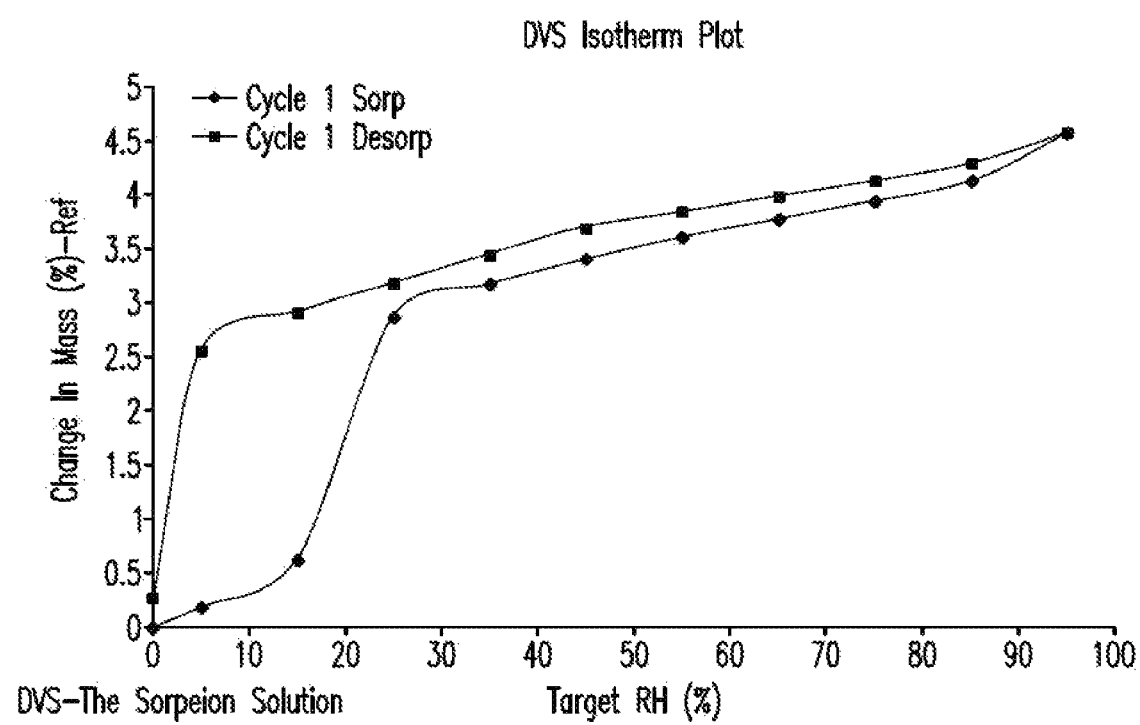
FIG. 97 depicts a DVS Isotherm Plot of Compound 1 HCl salt isolated from solubility study in SGF.
Figure 98:
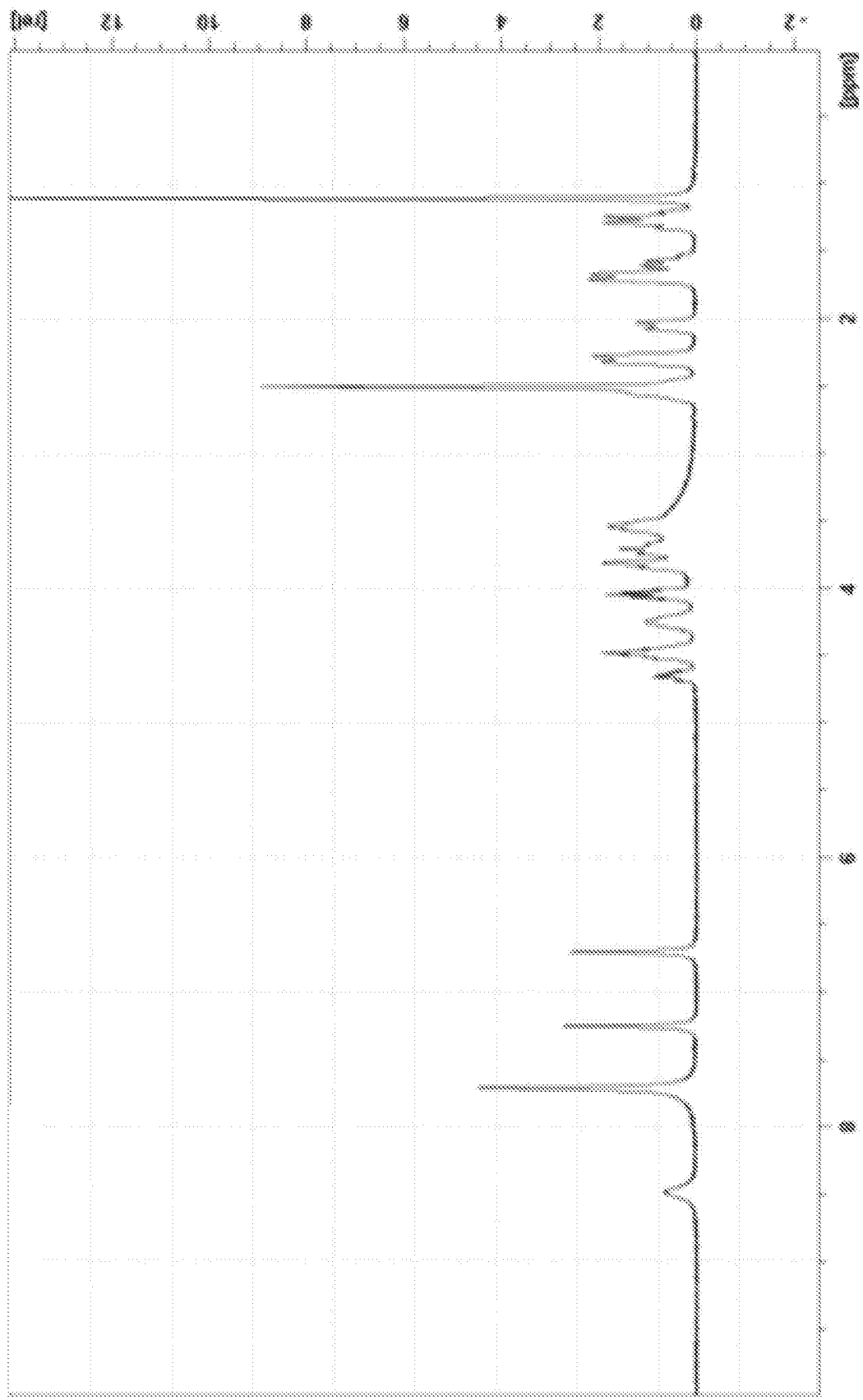
FIG. 98 depicts a $^1$H NMR in D$^6$-DMSO of Compound 1 HCl salt from SGF solubility.

HCl was initially found during the solubility study of Compound 1 freebase in simulated gastric fluid (SGF) solution. About 30 mg of Compound 1 free base was weighed into a glass vial, and 1 mL of SGF was introduced. The mixture soon became clear solution. Overnight, precipitation occurred. The solid particles were collected via filtration and were characterized. The XRPD profile is different from the freebase, as shown in FIG. 94. TGA showed about 3.3% weight loss at relatively low temperature (<70° C.) prior to decomposition (FIG. 95). The DSC profile had two endothermic events 1) at relatively low temperature due to dehydration and melting dehydrated form with onset and peak temperatures of 209.3 and 230.5° C., respectively (FIG. 96). Dynamic vapor sorption was performed on this sample at isotherm and is shown in FIG. 97. $^1$H NMR showed that chemical shifts were observed on hydrogen in purine and benzene ring, suggested the salt formation (FIG. 98).

TABLE 2

Small volume salt screening of Compound 1.

|   | A | B | C | D |
|---|---|---|---|---|
| 1 | HCl | HCl | HCl | HCl |
| 2 | H2SO4 | H2SO4 | H2SO4 | H2SO4 |
| 3 | TsOH | TsOH | TsOH | TsOH |
| 4 | MsOH | MsOH | MsOH | MsOH |
| 5 | BenzeOH | BenzeOH | BenzeOH | BenzeOH |
| 6 | Maleic | Maleic | Maleic | Maleic |
| 7 | H3PO4 | H3PO4 | H3PO4 | H3PO4 |
| 8 | Tartaric | Tartaric | Tartaric | Tartaric |
| 9 | Citric | Citric | Citric | Citric |
| 10 | Malic | Malic | Malic | Malic |
| 11 | Glycolic | Glycolic | Glycolic | Glycolic |
| 12 | Free Base | Free Base | Free Base | Free Base |
| 13 | Ethanol | IPA | 3-methyl-butanol | Acetonitrile |

|   | E | F | G | H |
|---|---|---|---|---|
| 1 | HCl | HCl | HCl | HCl |
| 2 | H2SO4 | H2SO4 | H2SO4 | H2SO4 |

TABLE 2-continued

Small volume salt screening of Compound 1.

| 3 | TsOH | TsOH | TsOH | TsOH |
|---|---|---|---|---|
| 4 | MsOH | MsOH | MsOH | MsOH |
| 5 | BenzeOH | BenzeOH | BenzeOH | BenzeOH |
| 6 | Maleic | Maleic | Maleic | Maleic |
| 7 | H3PO4 | H3PO4 | H3PO4 | H3PO4 |
| 8 | Tartaric | Tartaric | Tartaric | Tartaric |
| 9 | Citric | Citric | Citric | Citric |
| 10 | Malic | Malic | Malic | Malic |
| 11 | Glycolic | Glycolic | Glycolic | Glycolic |
| 12 | Free Base | Free Base | Free Base | Free Base |
| 13 | MTBE | Acetone | Water | EtOAc |

Dynamic vapor sorption (DVS) showed the HCl salt is low hygroscopicity (<1.0%) from 0-95% RH with respect to monohydrate HCl as shown in FIG. 97. The HCl monohydrate converted to anhydrous when first placed through a drying cycle at zero or very low humidity. Then ~2.9% (wt) of water was gained when the solid particles were exposed to increasing relative humidity up to 25% RH, converted back monohydrate in this range of humidity. Additional ~1.7% moisture sorption was slowly and steadily gained from 25 to 95% RH. During desorption cycle from 95 down to 5% RH, the loss of water content was very slowly ~1.5%, the monohydrate structure maintained. Then, the remaining ~2.8% wt of water was rapidly released from the sample as relative humidity decreased from 5% RH to dry. The level of 3.0% water content is corresponding to monohydrate.

The adsorption/desorption were almost reversible above 30% RH. Below 30% RH, the release of water during desorption was more difficult than up take during sorption. Hysteresis was observed between the sorption and desorption curves below 25% RH.

Figure 99:
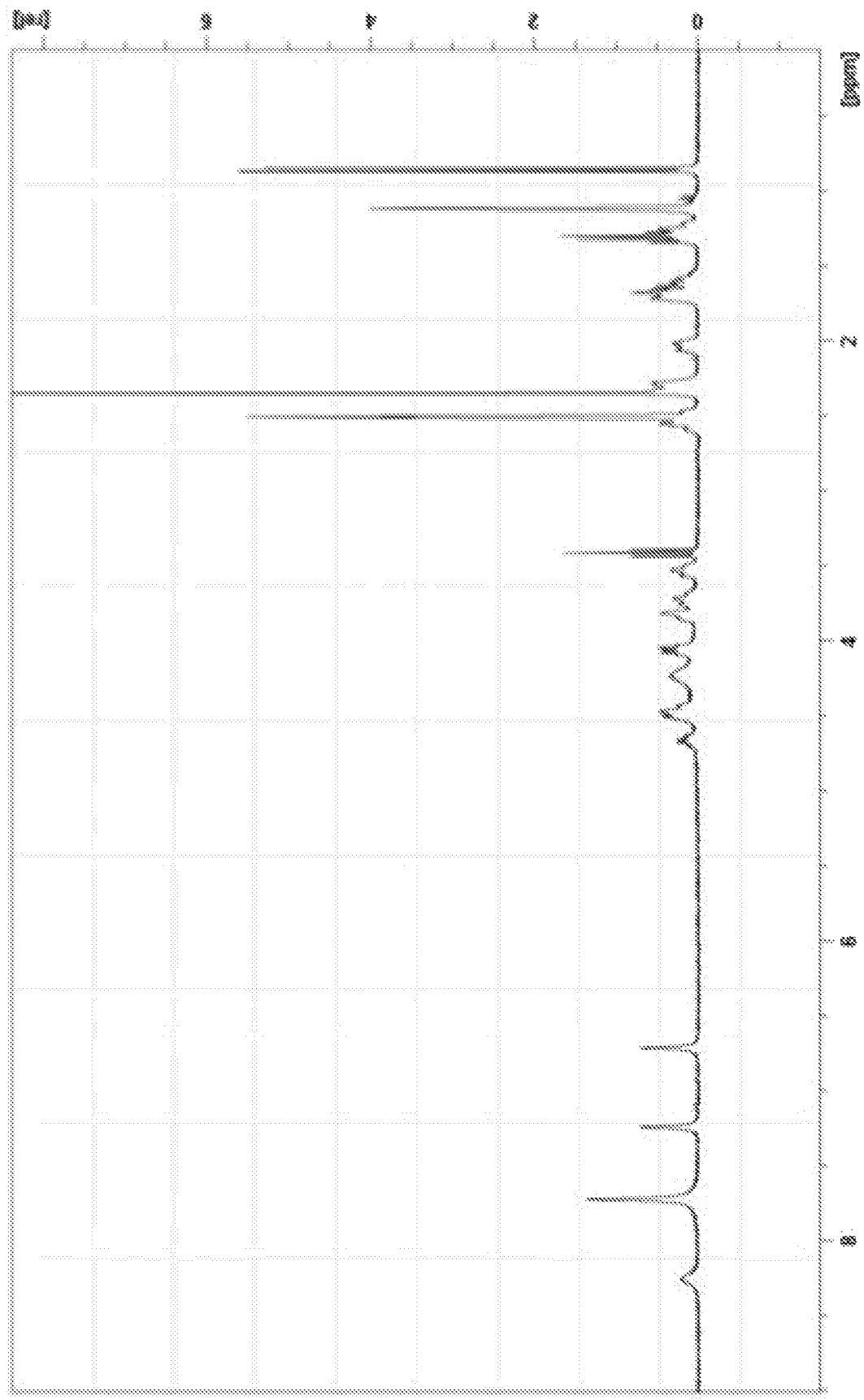
FIG. 99 depicts a $^1$H NMR in D$^6$-DMSO of Compound 1 sulfate salt from SVSS Well# H2.
Figure 100:
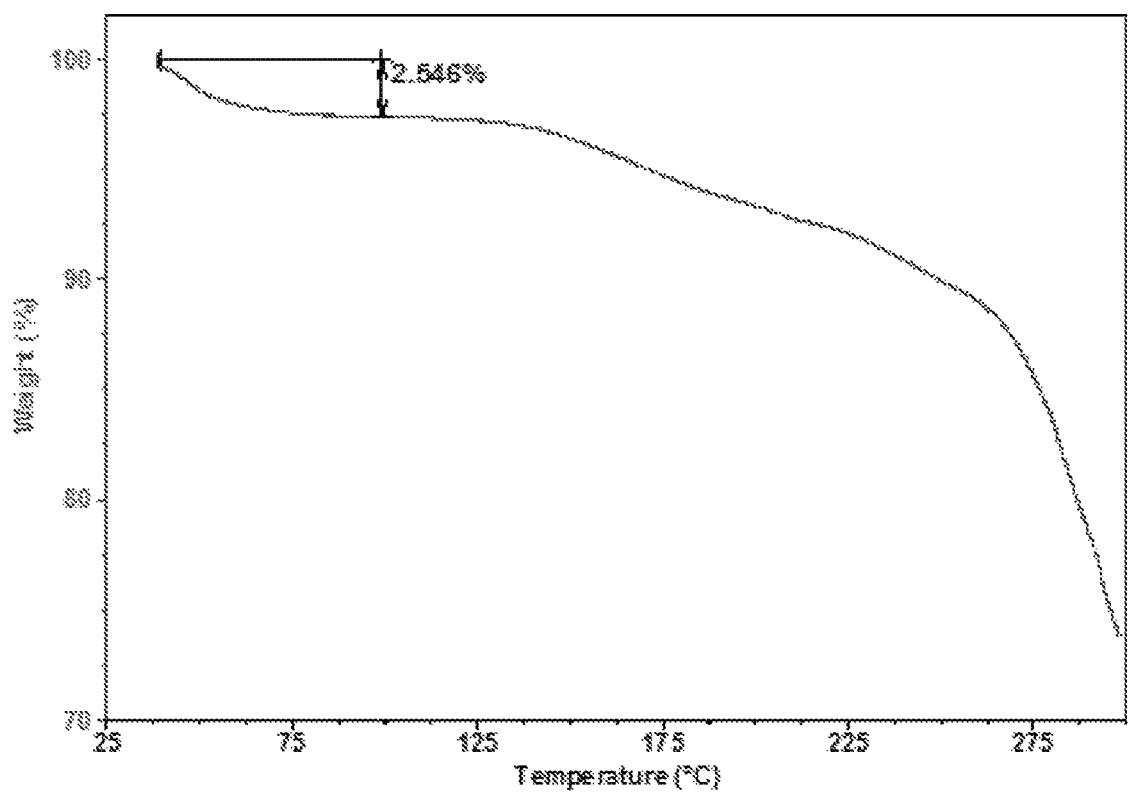
FIG. 100 depicts a TGA Thermogram of sulfate salt SVSS Well# A2.
Figure 101:
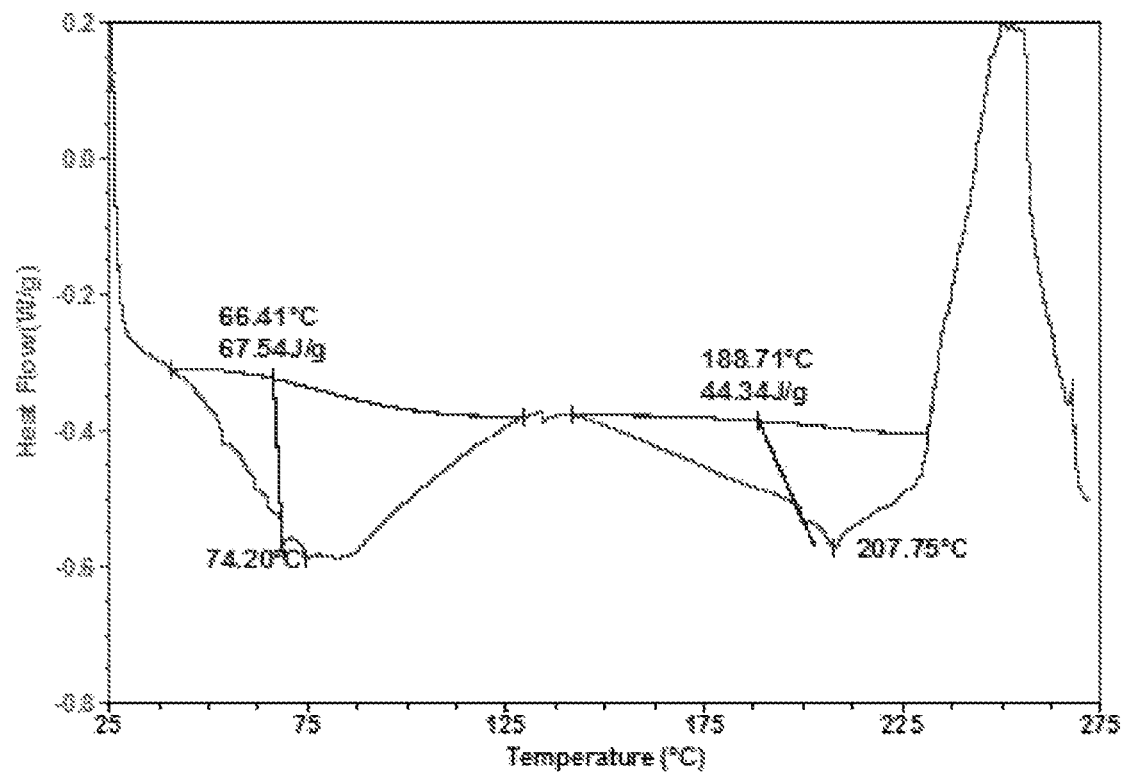
FIG. 101 depicts a DSC Thermogram of sulfate salt SVSS Well# A2.
Figure 102:
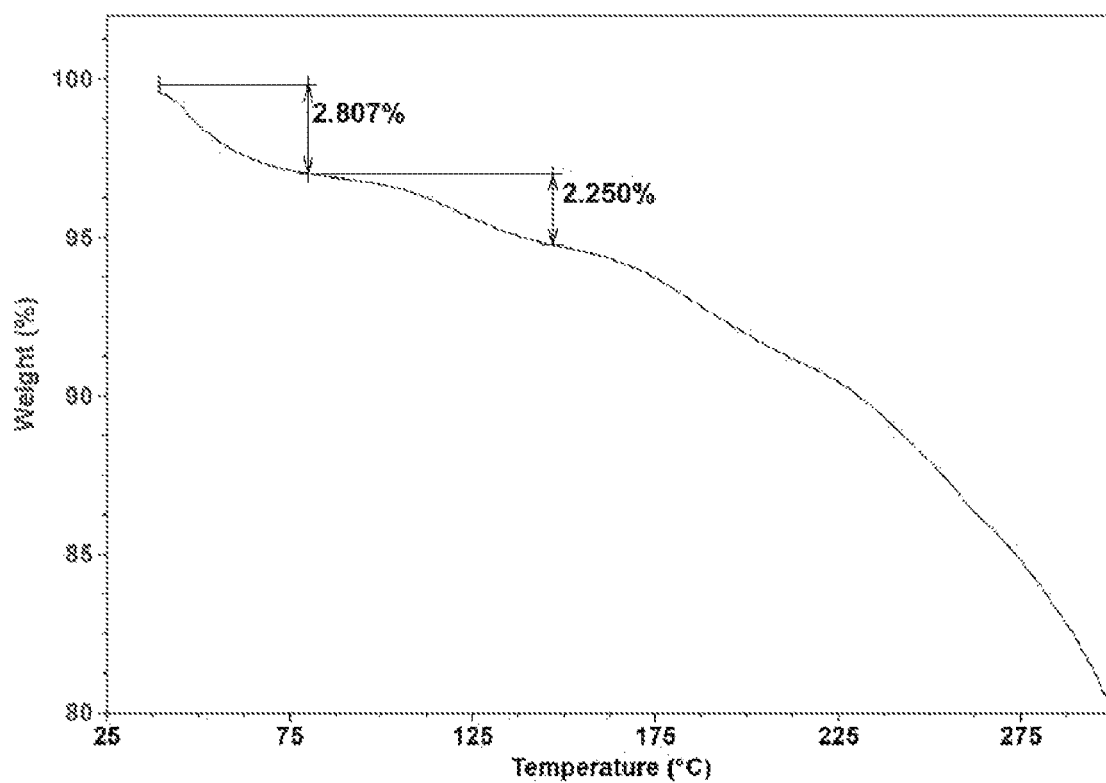
FIG. 102 depicts a TGA Thermogram of sulfate salt SVSS Well# D2.
Figure 103:
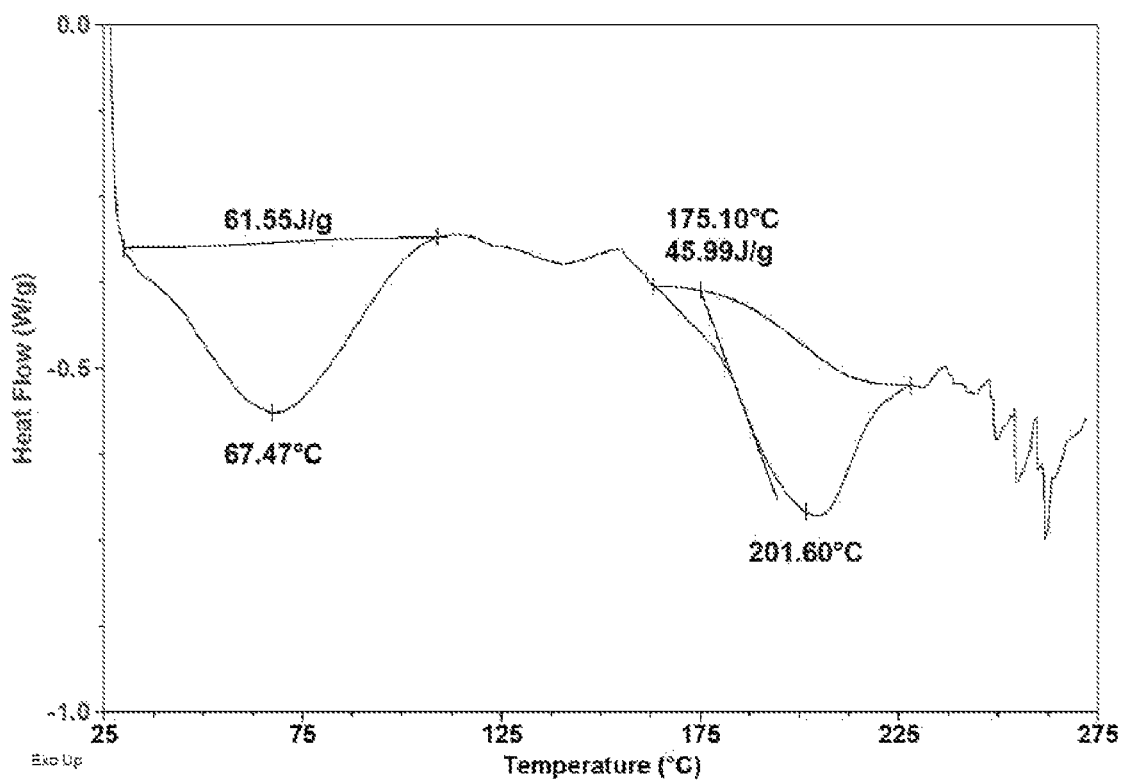
FIG. 103 depicts a DSC Thermogram of sulfate salt SVSS Well# D2.
Figure 104:
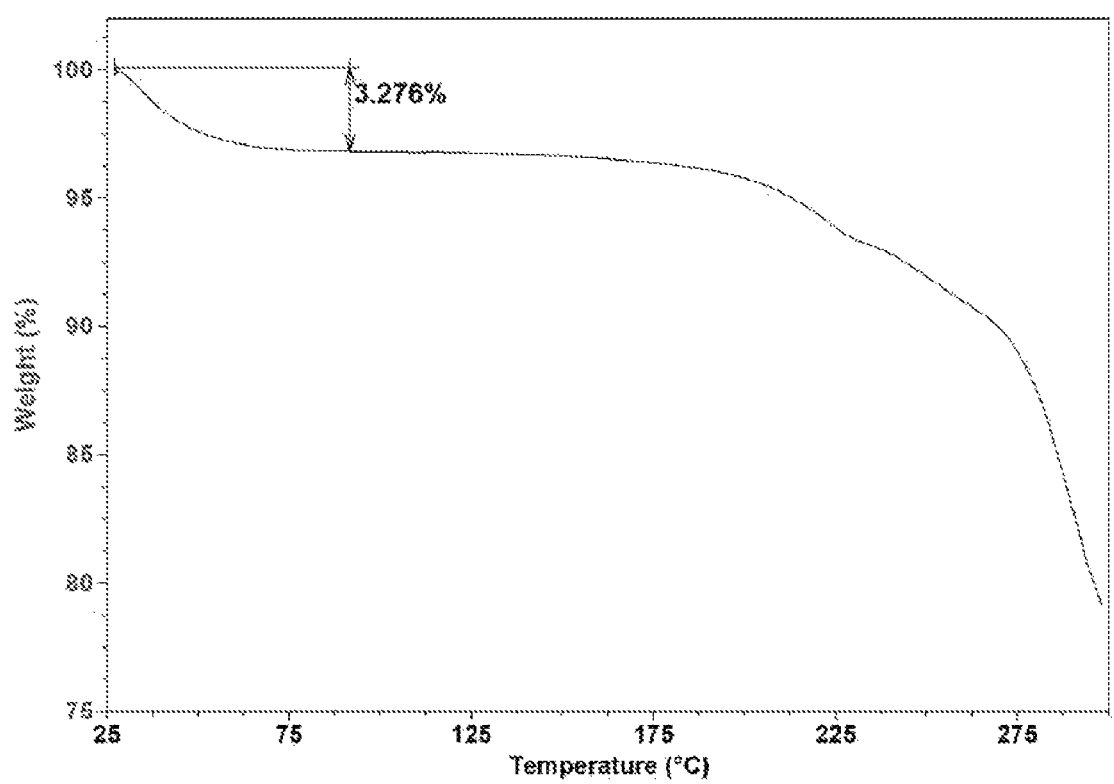
FIG. 104 depicts a TGA Thermogram of sulfate salt SVSS Well# G2.
Figure 105:
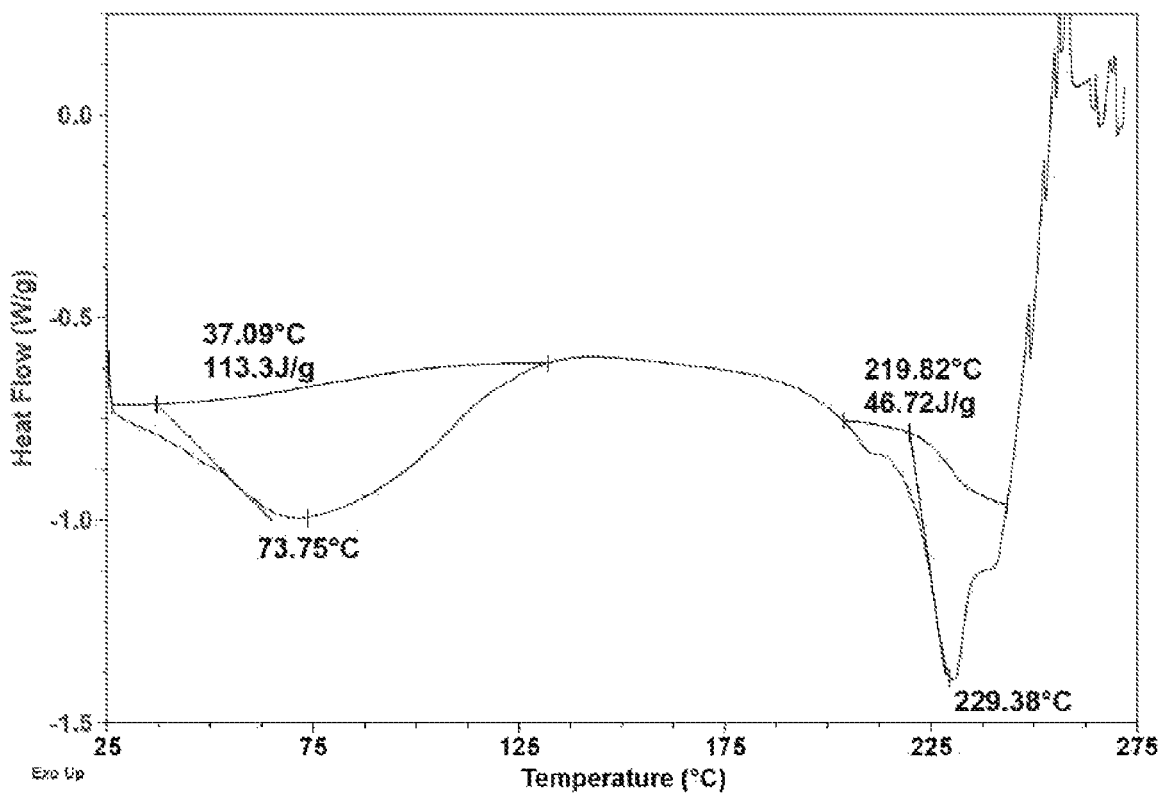
FIG. 105 depicts a DSC Thermogram of sulfate salt SVSS Well# A2.

Sample from well# H2 containing both Compound 1 free base and sulfuric acid was analyzed by $^1$H NMR in DMSO-$d_6$, FIG. 99. $^1$H NMR showed that chemical shifts were observed on hydrogen in purine and benzene ring, suggested the salt formation. Selected samples were analyzed by TGA and DSC, FIG. 100 to FIG. 105. TGA profiles all showed initial weight losses (2.5-3.2%) at relatively low temperature, however, were not same behaviors. DSC profiles from these wells also showed broad endothermic events at relatively low temperatures, but were not same profile. Sulfate salts are solvates, depending on the use of solvent for crystallization.

Figure 106:
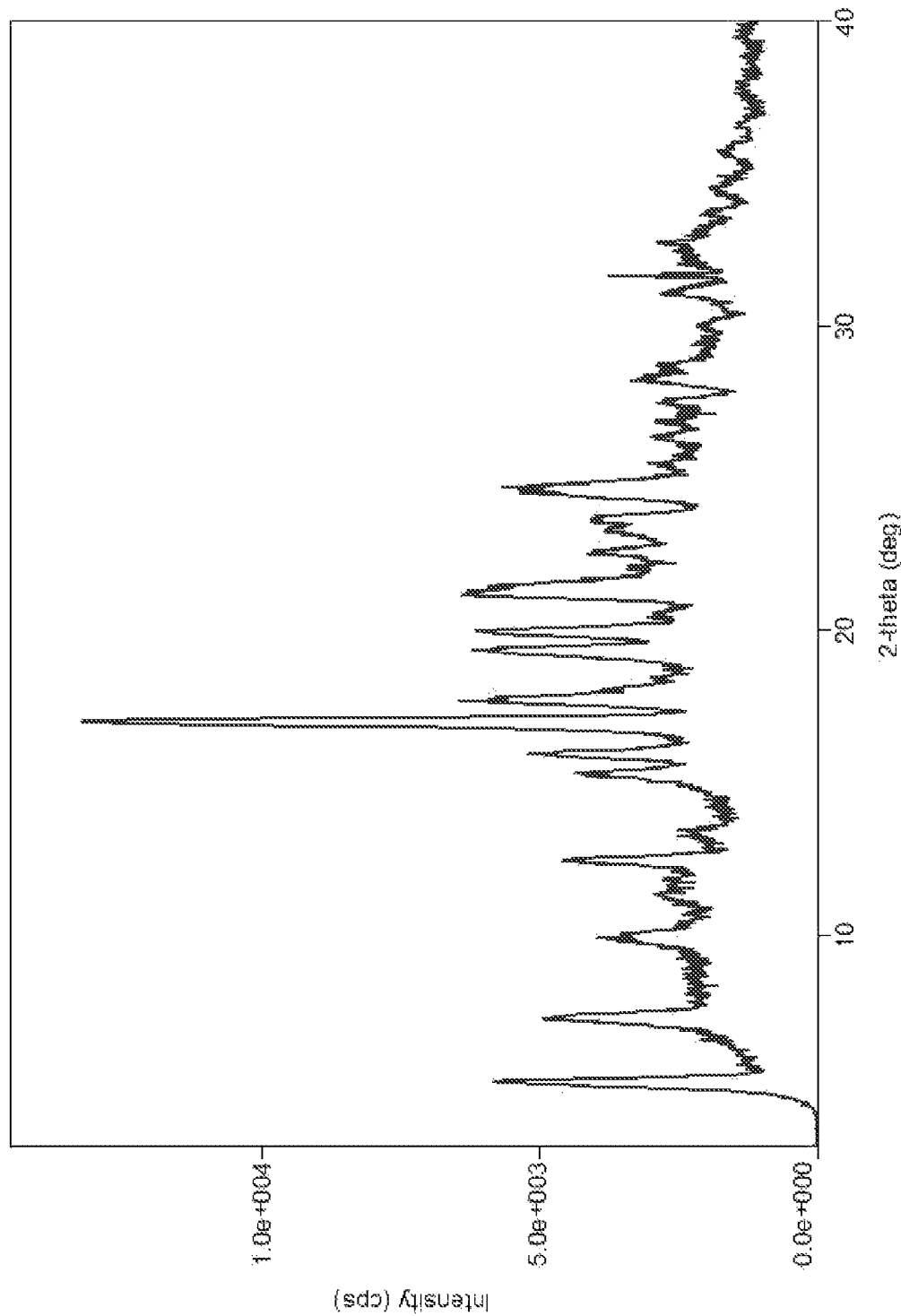
FIG. 106 depicts a XRPD Pattern of mesylate salts from SVSS study in EtOAc.
Figure 107:
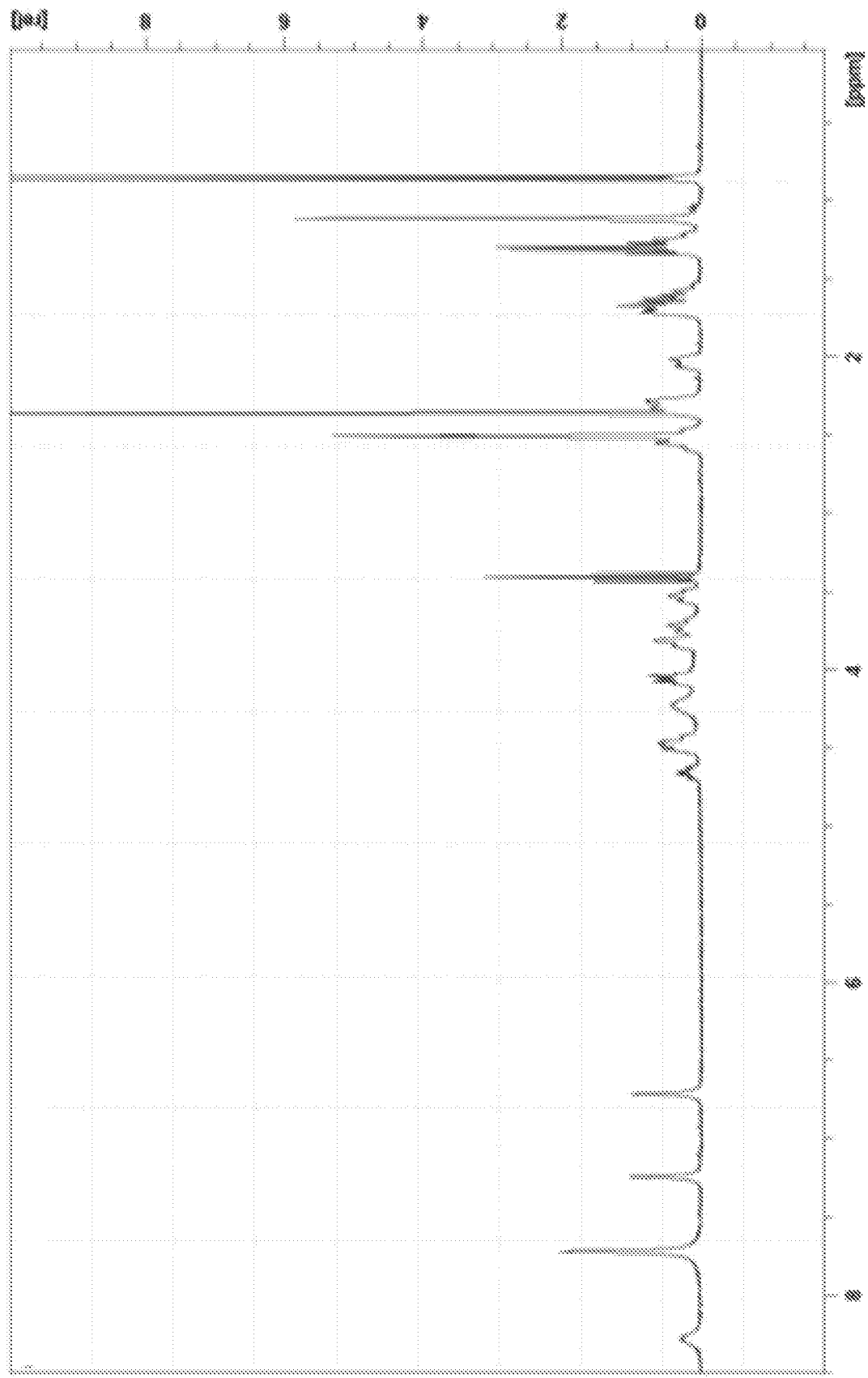
FIG. 107 depicts a $^1$H NMR in D$^6$-DMSO of Compound 1 mesylate salt from SVSS Well# B4.
Figure 108:
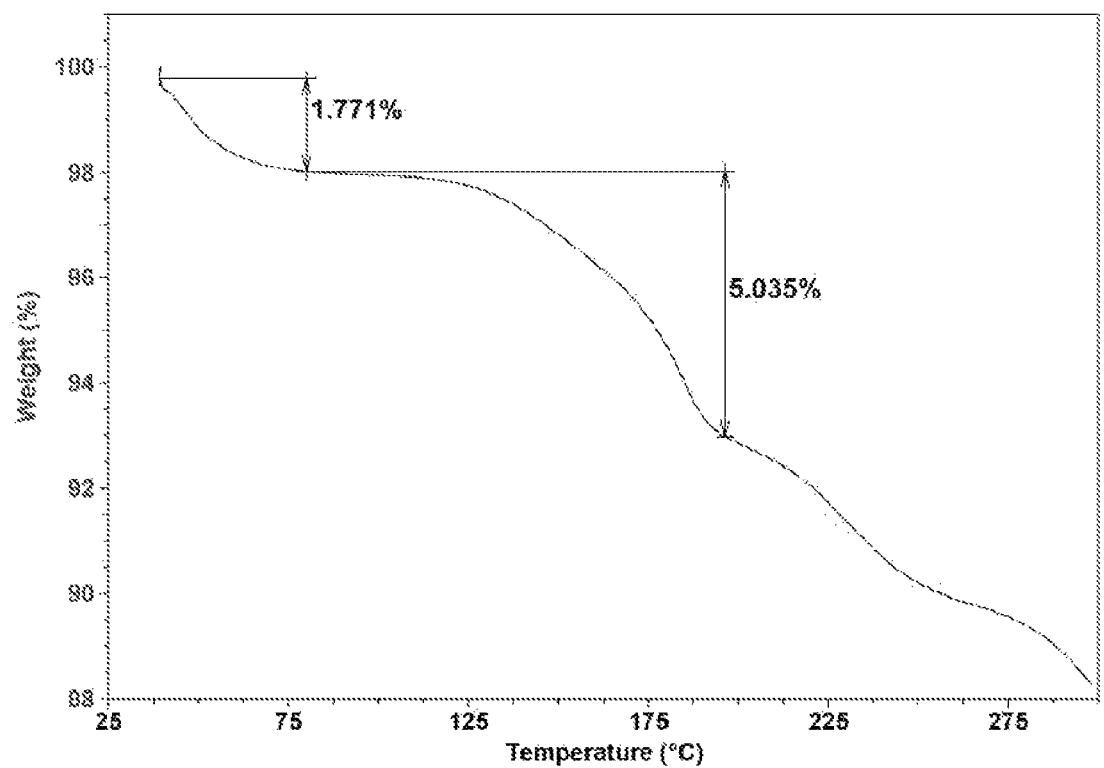
FIG. 108 depicts a TGA Thermogram of mesylate salt SVSS Well# A4.
Figure 109:
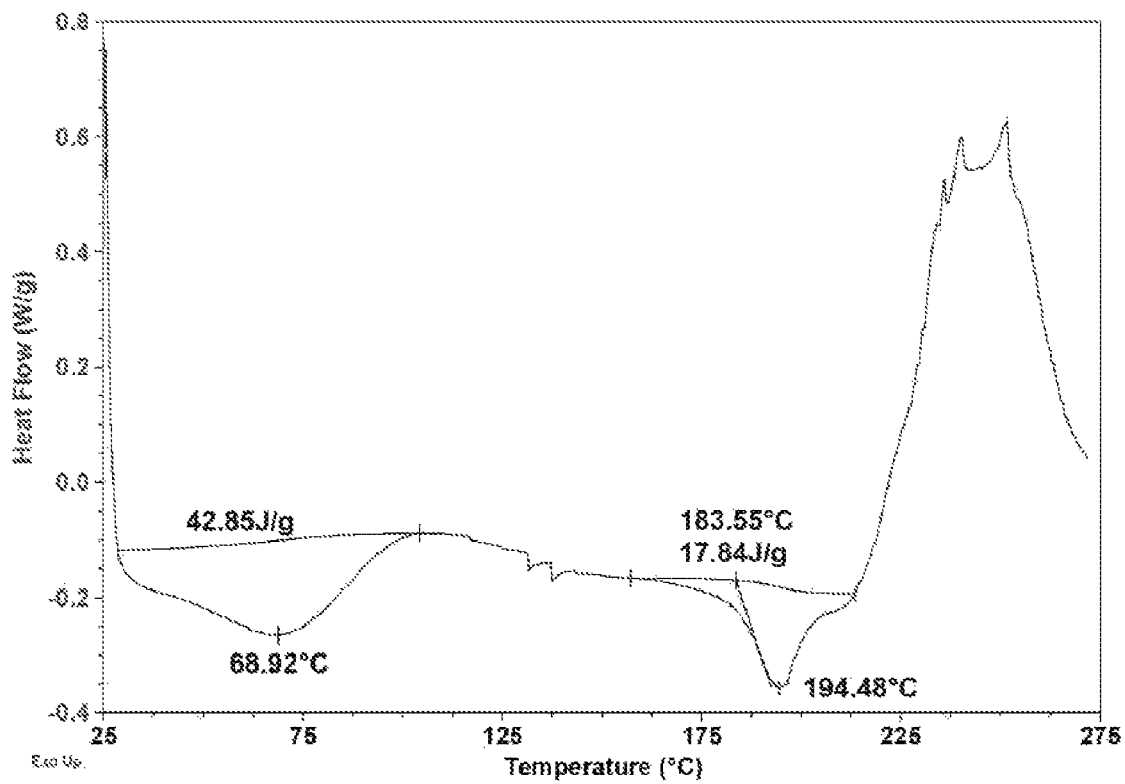
FIG. 109 depicts a DSC Thermogram of mesylate salt SVSS Well# A4.
Figure 110:
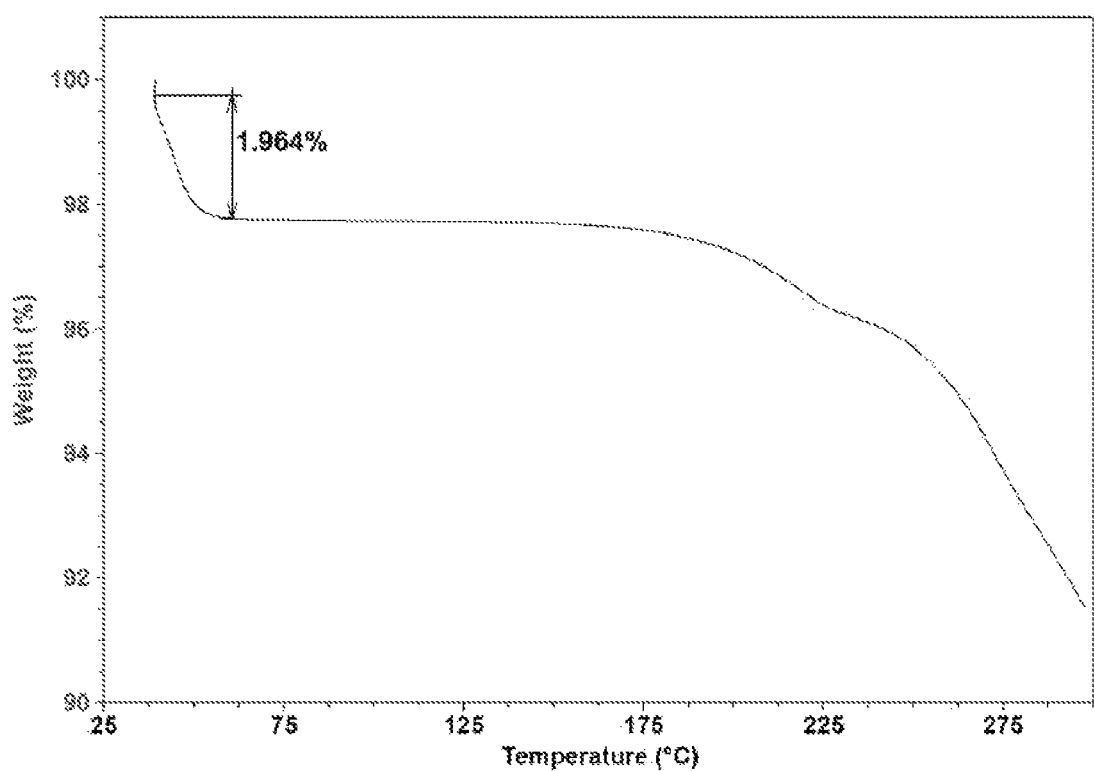
FIG. 110 depicts a TGA Thermogram of mesylate salt SVSS Well# B4.
Figure 111:
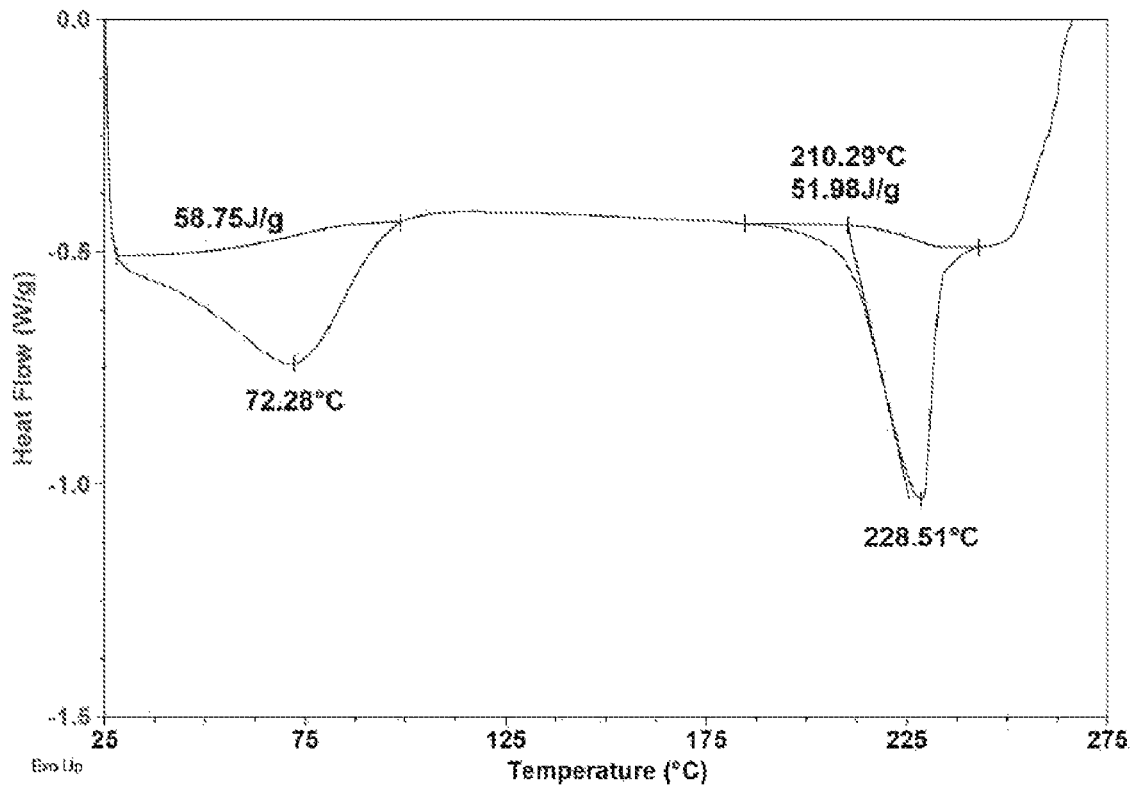
FIG. 111 depicts a DVS Isotherm Plot of mesylate salt SVSS Well# B4.
Figure 112:
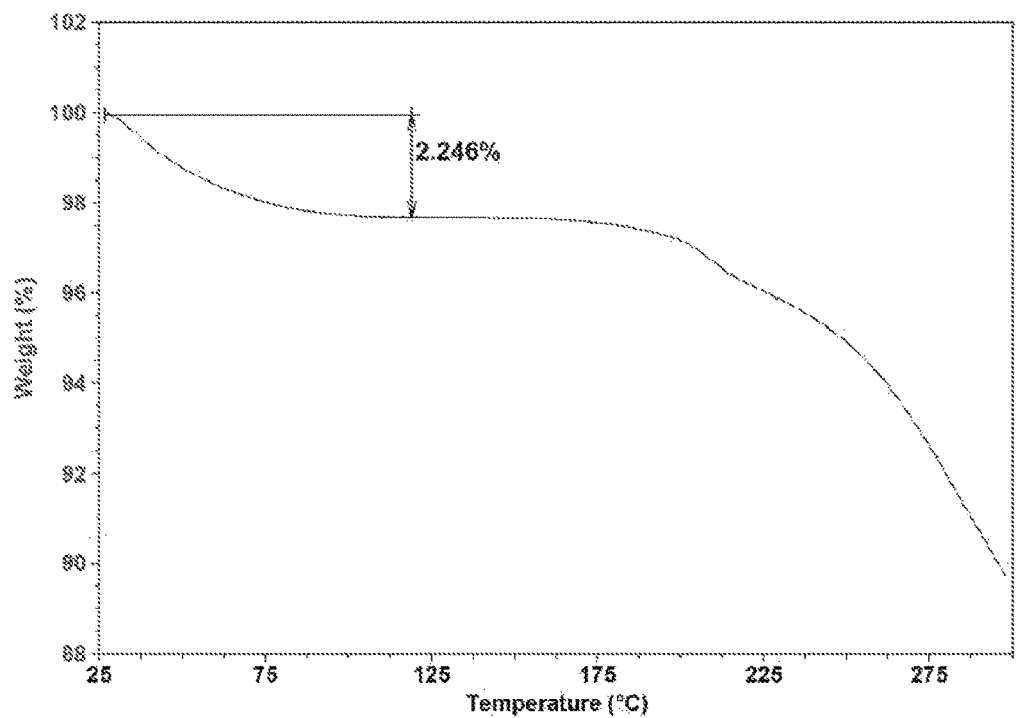
FIG. 112 depicts a TGA Thermogram of mesylate salt SVSS Well# E4.
Figure 113:
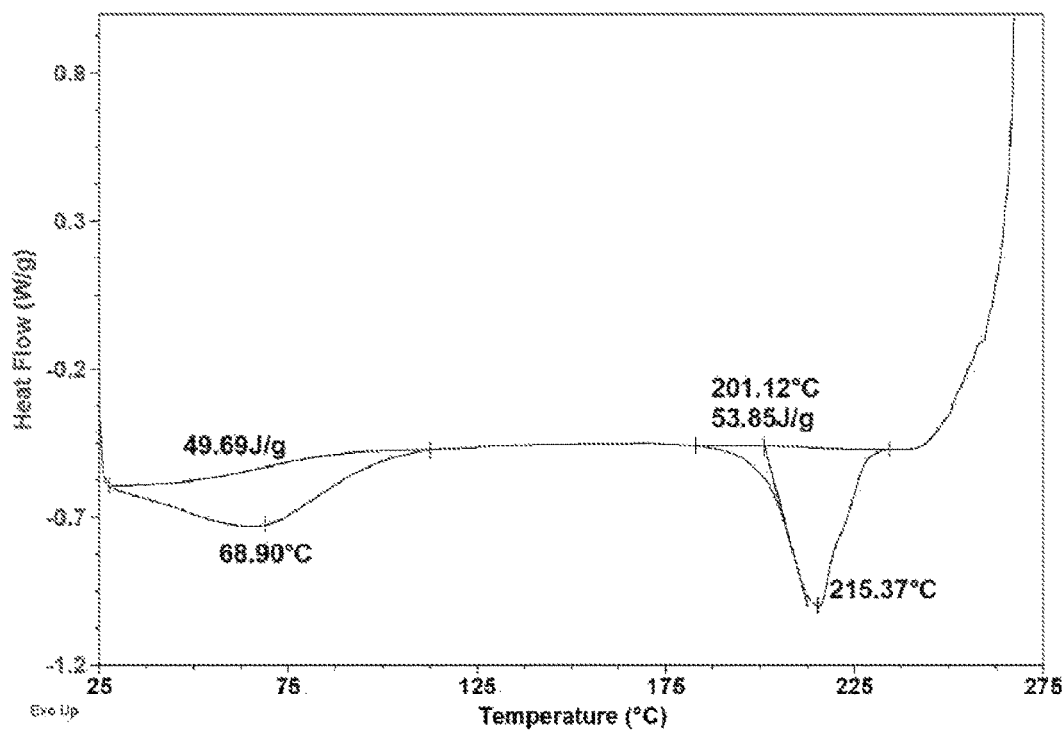
FIG. 113 depicts a DSC Thermogram of mesylate salt SVSS Well# E4.
Figure 114:
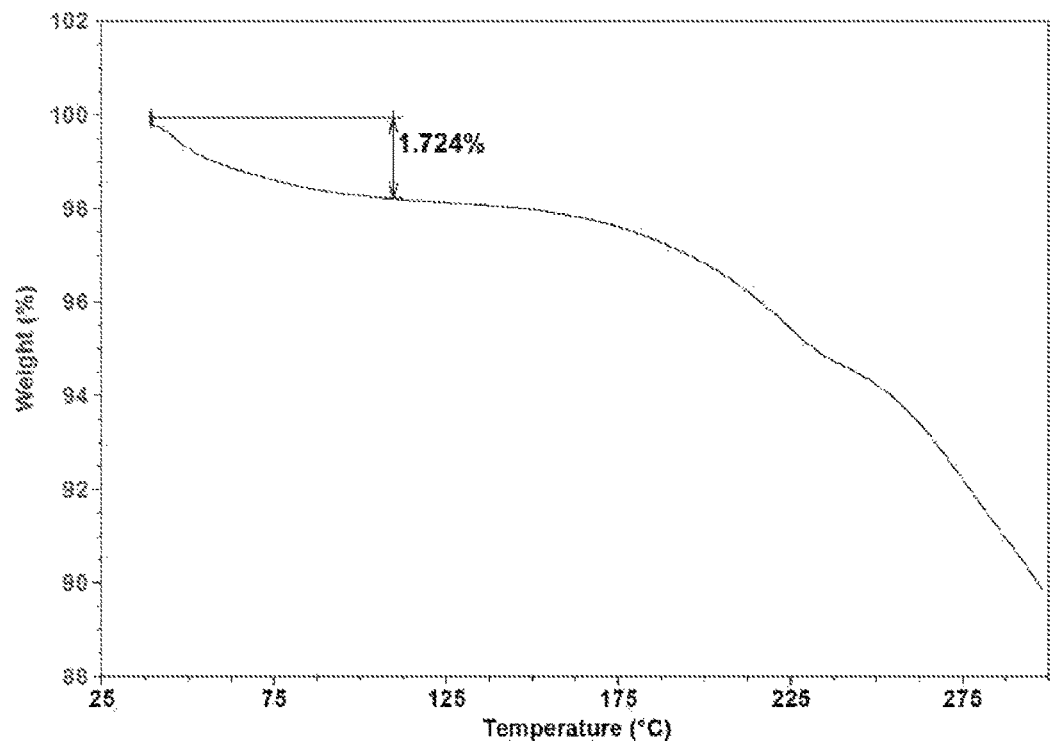
FIG. 114 depicts a TGA Thermogram of mesylate salt SVSS Well# G4.
Figure 115:
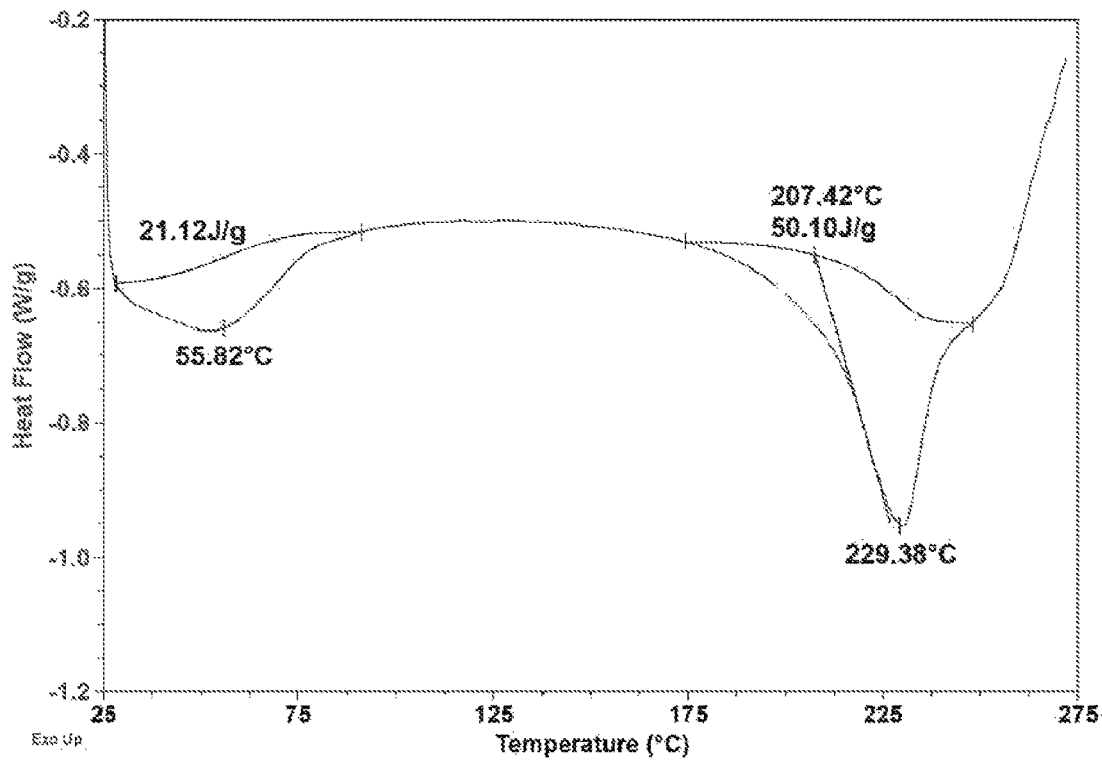
FIG. 115 depicts a DSC Thermogram of mesylate salt SVSS Well# G4.
Figure 116:
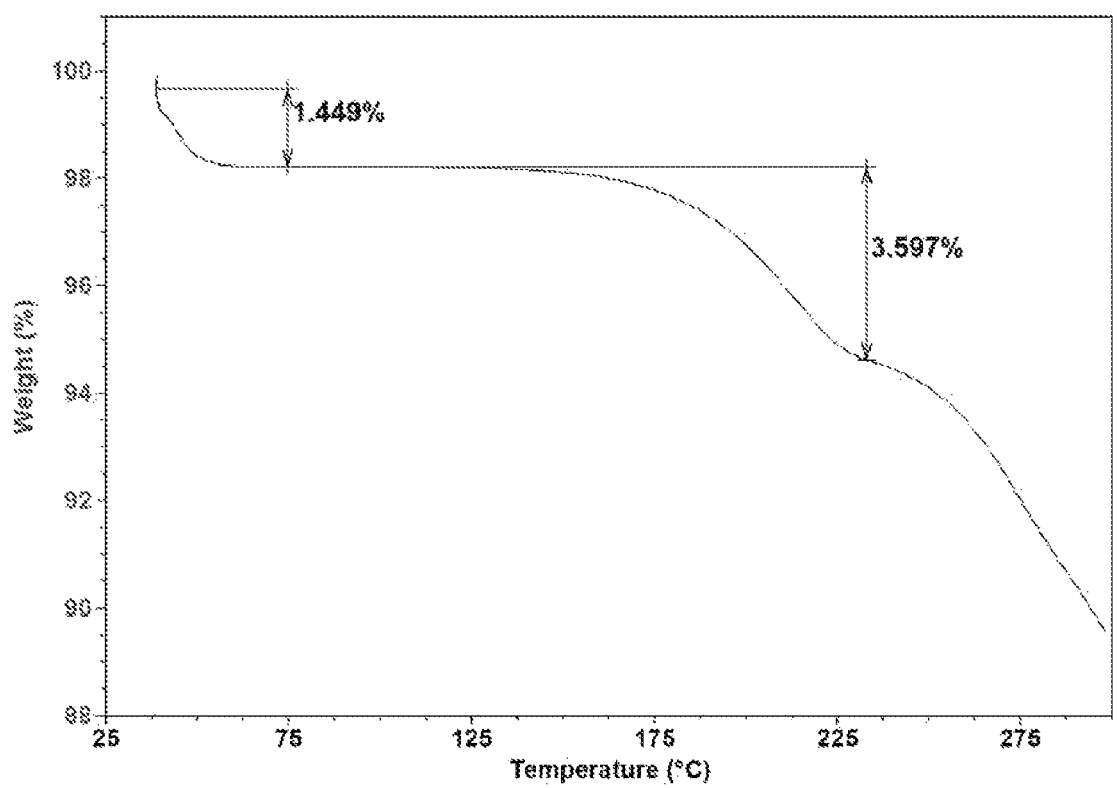
FIG. 116 depicts a TGA Thermogram of mesylate salt SVSS Well# H4.
Figure 117:
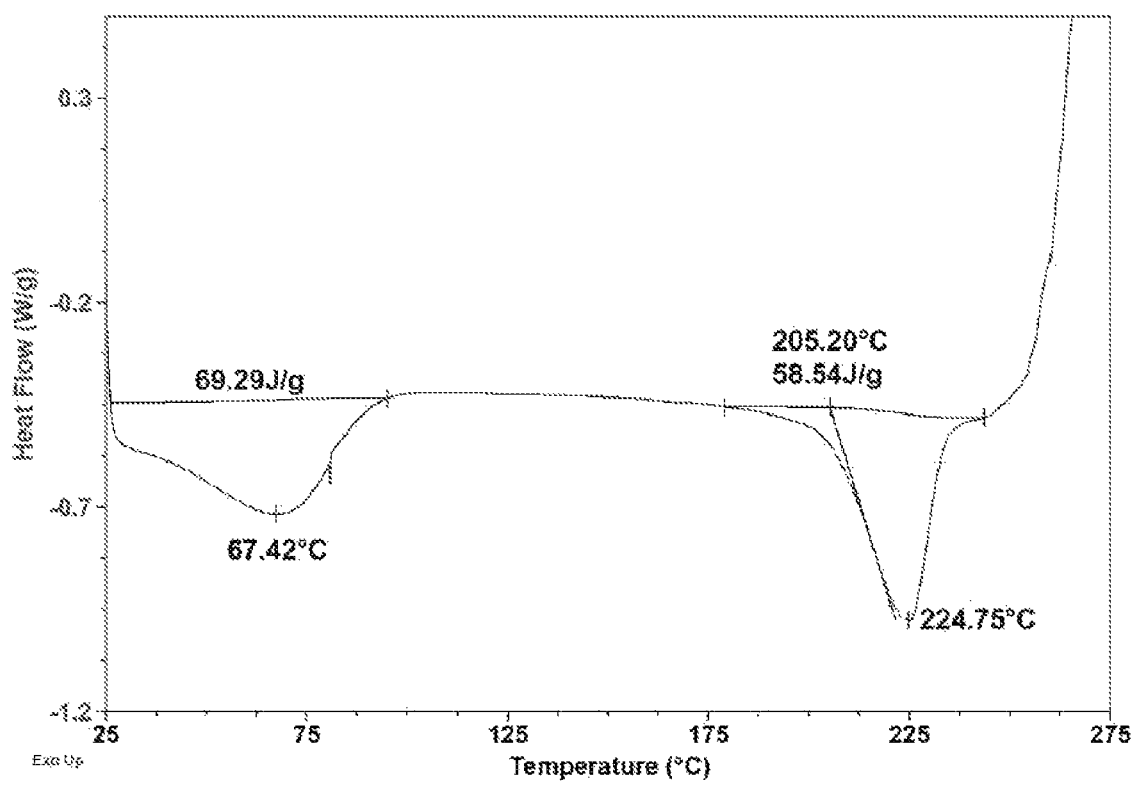
FIG. 117 depicts a DSC Thermogram of mesylate salt SVSS Well# H4.
Figure 118:
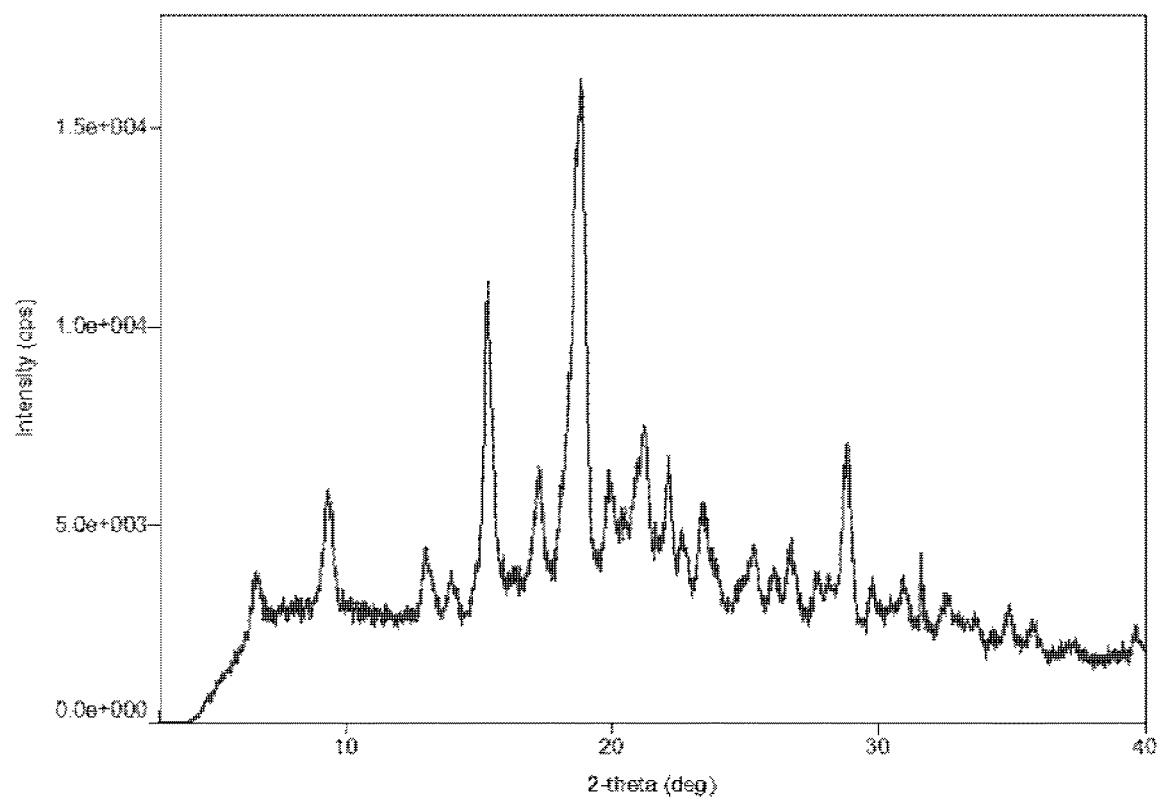
FIG. 118 depicts a XRPD Pattern of Compound 1 citrate salt from SVSS in ethanol.
Figure 119:
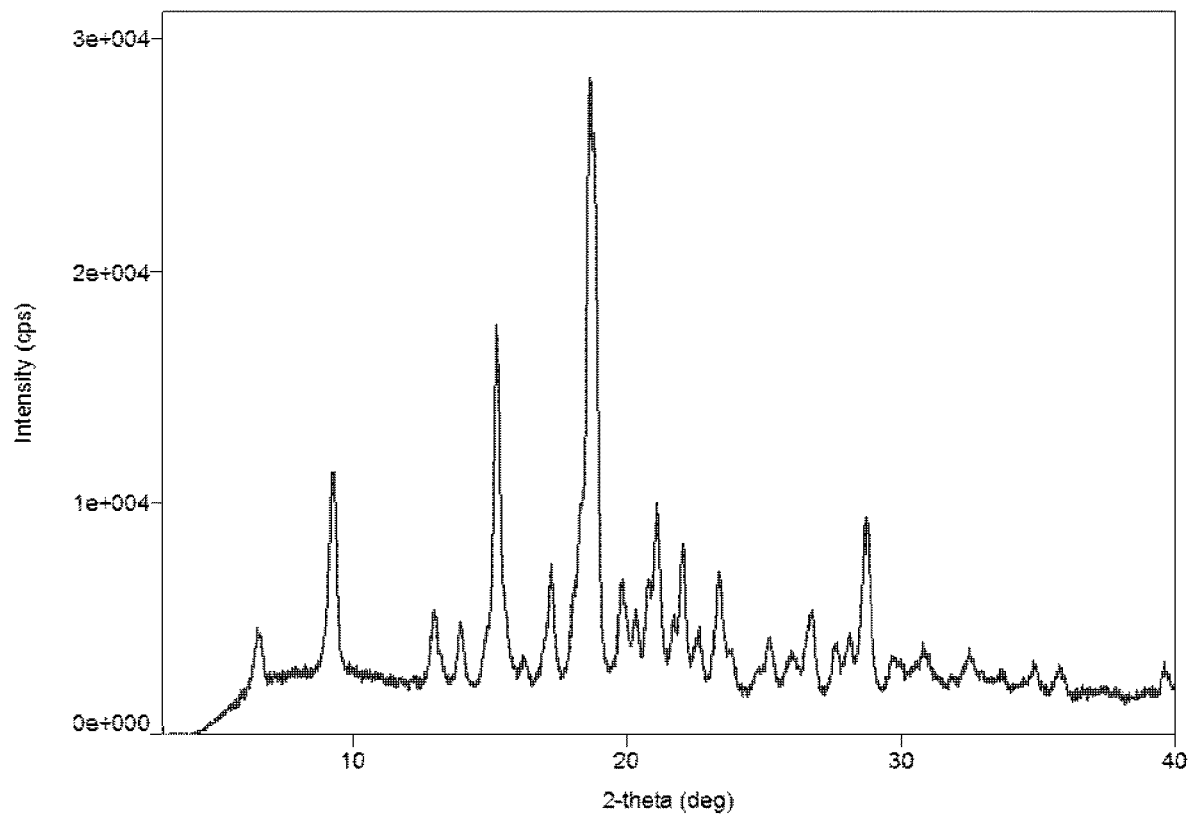
FIG. 119 depicts a XRPD Pattern of Compound 1 citrate salt from SVSS in IPA.
Figure 120:
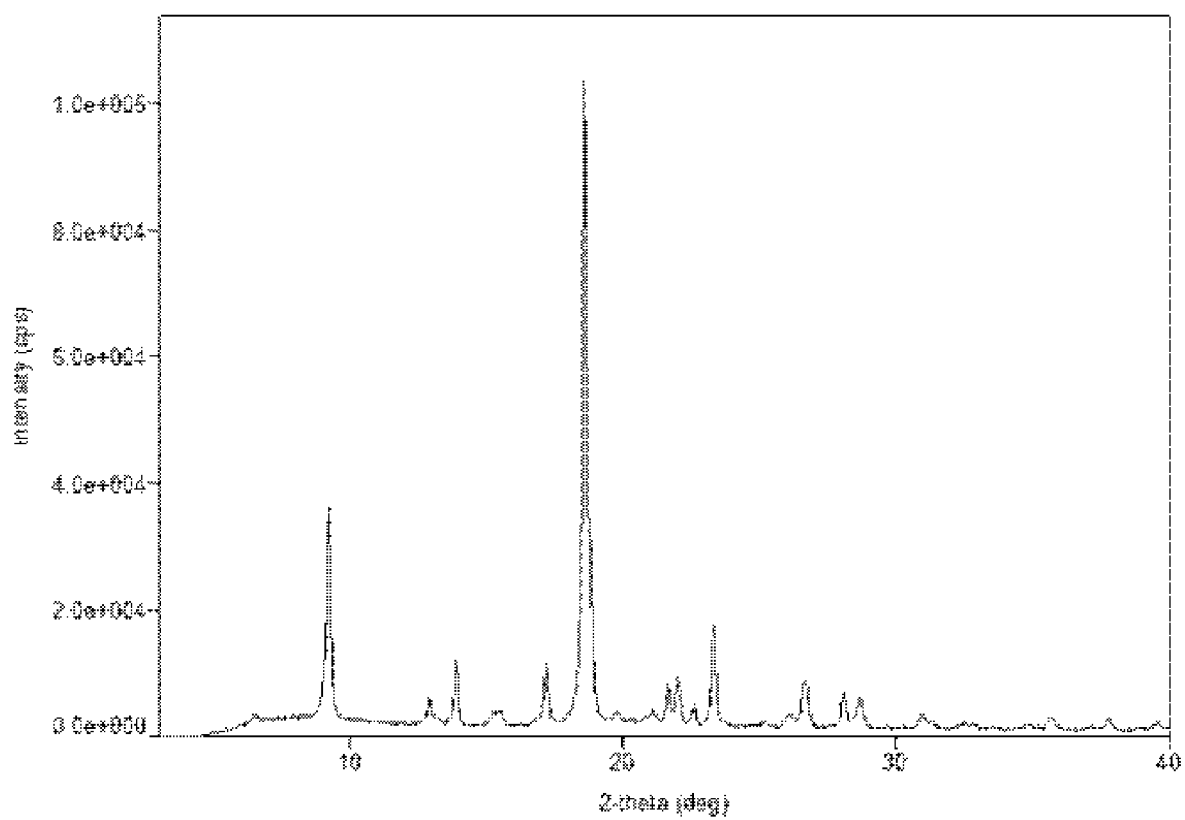
FIG. 120 depicts a XRPD Pattern of Compound 1 citrate salt from SVSS in 3-methyl-2-butanol.
Figure 121:
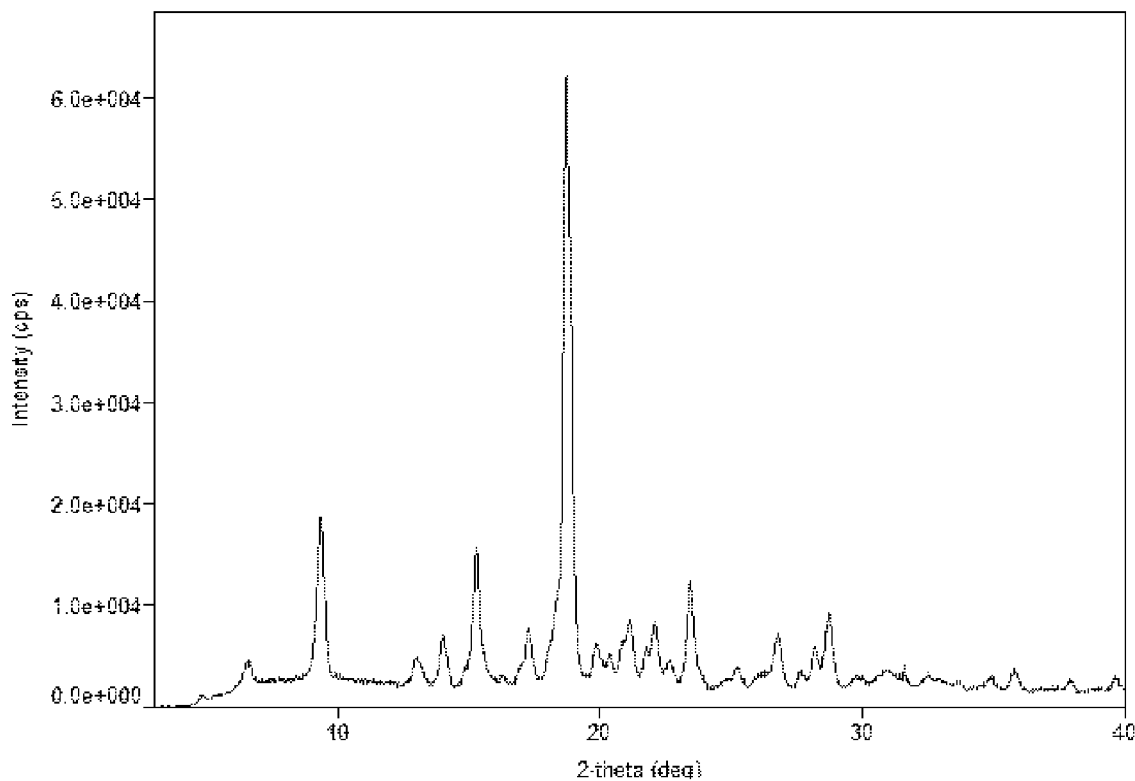
FIG. 121 depicts a XRPD Pattern of Compound 1 citrate salt from SVSS in acetonitrile.
Figure 122:
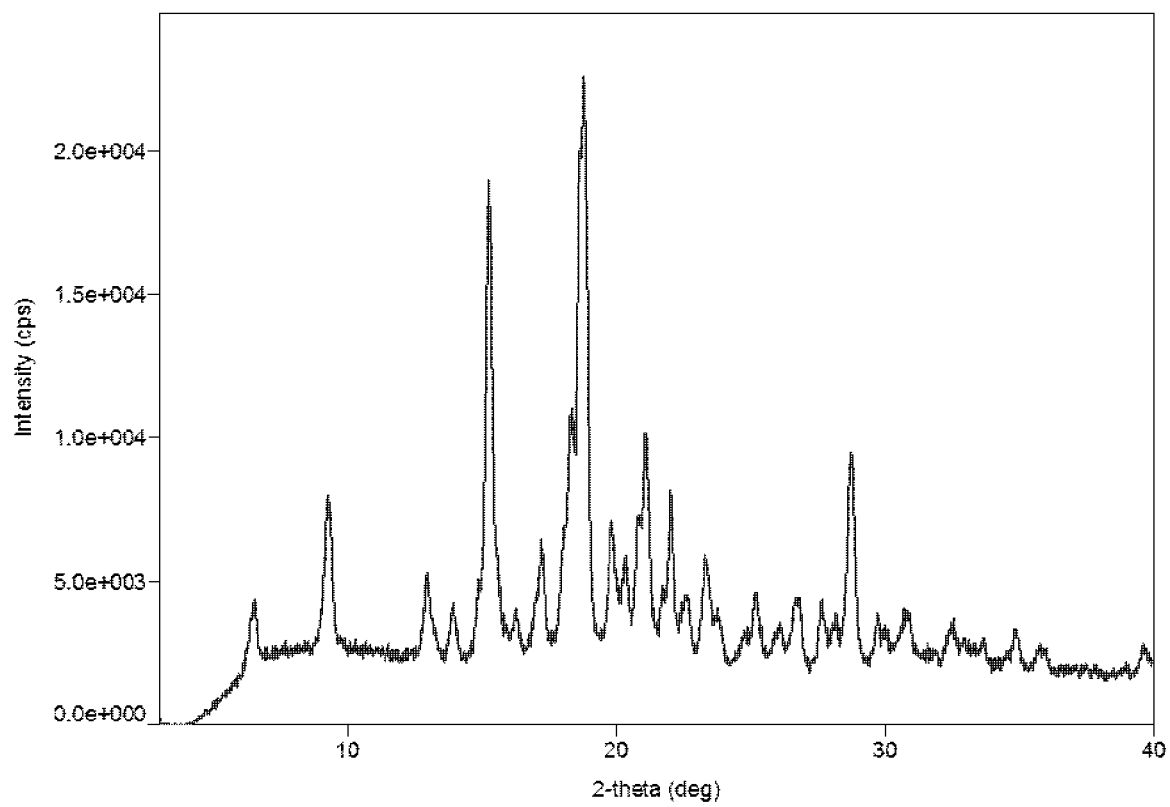
FIG. 122 depicts a XRPD Pattern of Compound 1 citrate salt from SVSS in MTBE.
Figure 123:
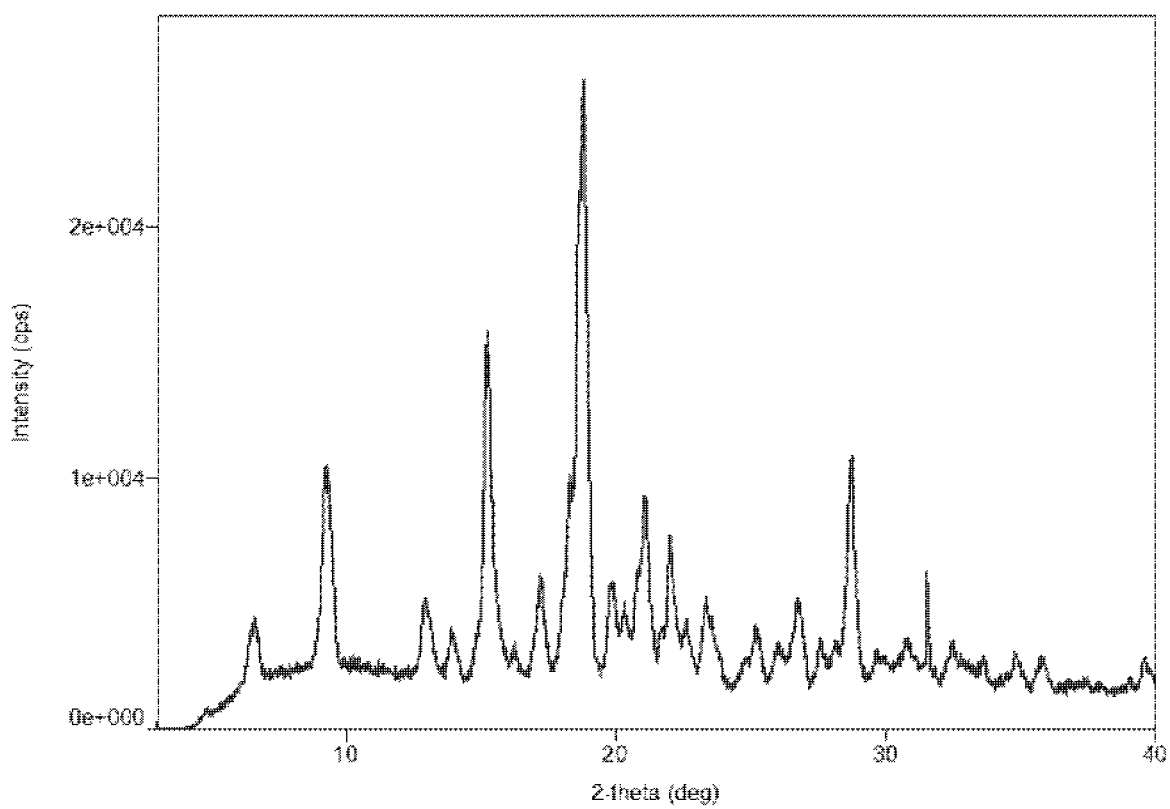
FIG. 123 depicts a XRPD Pattern of Compound 1 citrate salt from SVSS in acetone.
Figure 124:
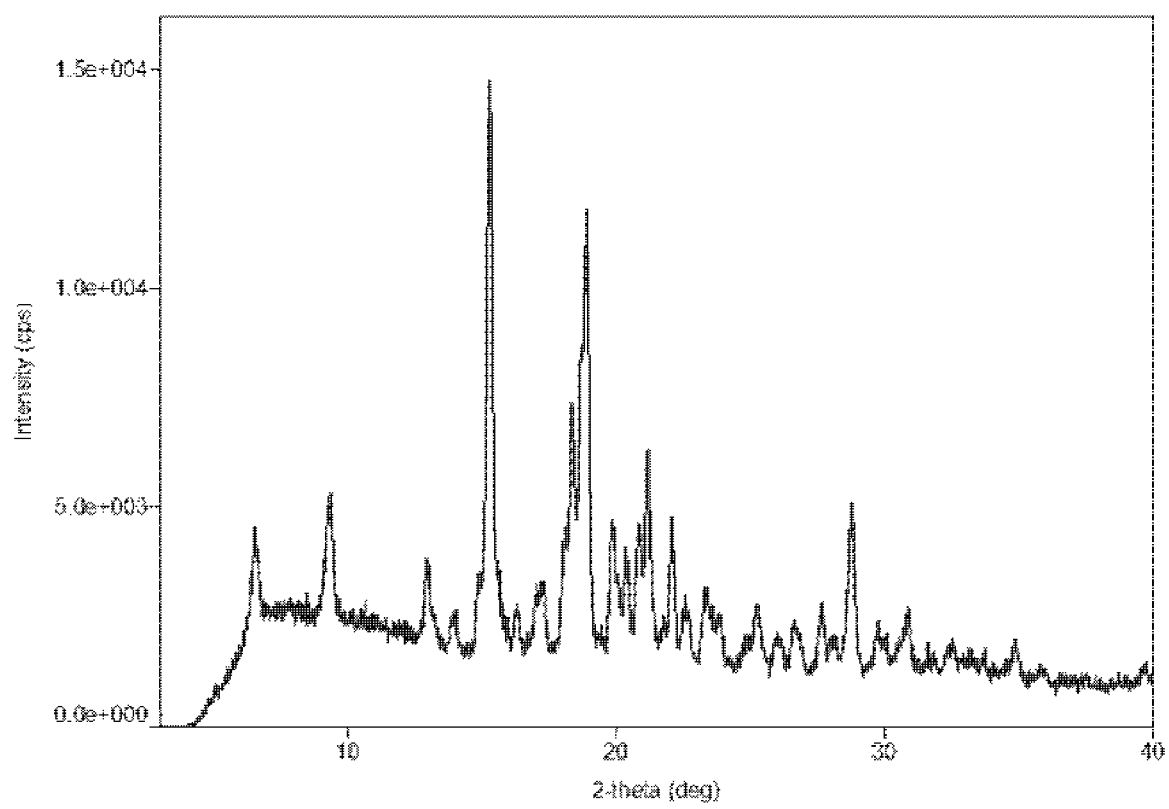
FIG. 124 depicts a XRPD Pattern of Compound 1 citrate salt from SVSS in water.
Figure 125:
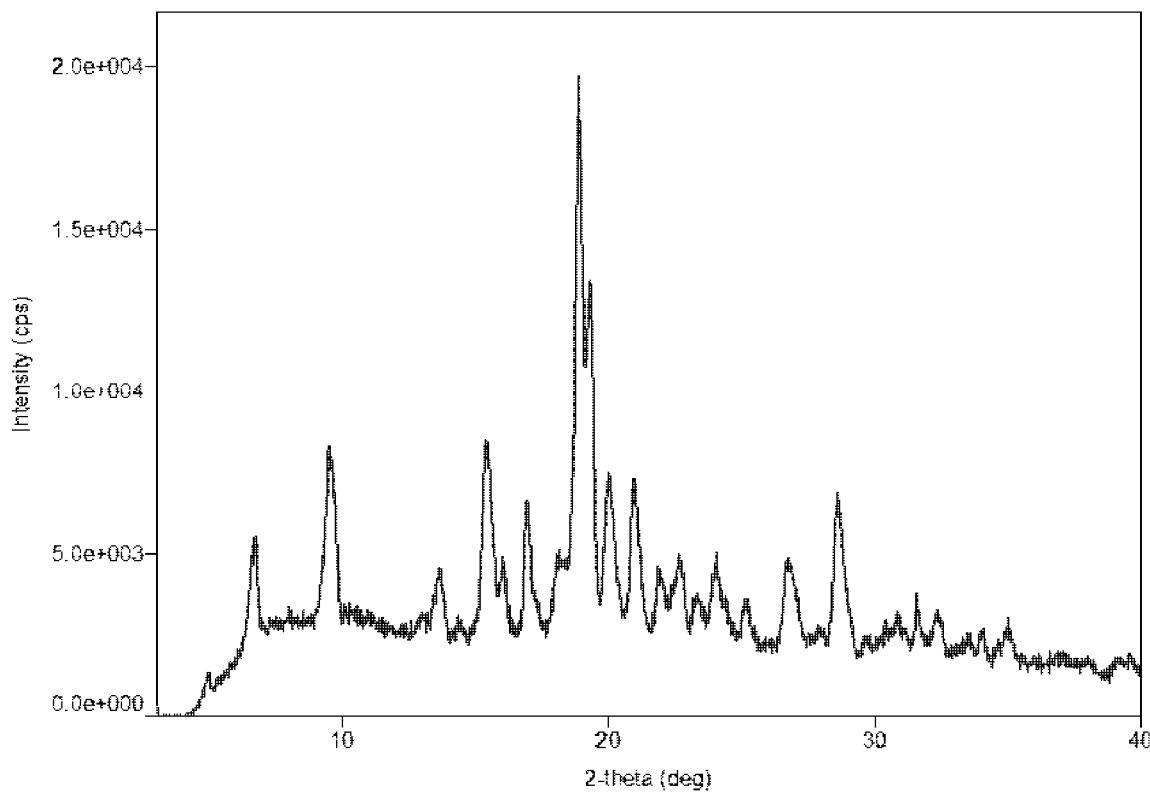
FIG. 125 depicts a XRPD Pattern of Compound 1 citrate salt from SVSS in EtOAc.

Crystalline mesylate salts from SVSS in various solvents were found and XRPD profiles of crystalline citrate salts from various solvents are very similar. A representative XRPD profile of crystalline mesylate salts from SVSS in EtOAC is shown in FIG. 106. Sample containing both Compound 1 free base and methansulfonic acid was analyzed by $^1$H NMR in DMSO-$_{d6}$, FIG. 107. $^1$H NMR showed that chemical shifts were observed on hydrogen in purine and benzene ring, suggested the salt formation. Selected samples were analyzed by TGA and DSC, FIG. 108 to FIG. 117. TGA profiles fall showed initial weight losses (1.4-2.2%) at relatively low temperature, and slightly different behaviors. DSC profiles from these wells also showed broad endothermic events at relatively low temperatures, but different profiles after desolvation.

Figure 126:
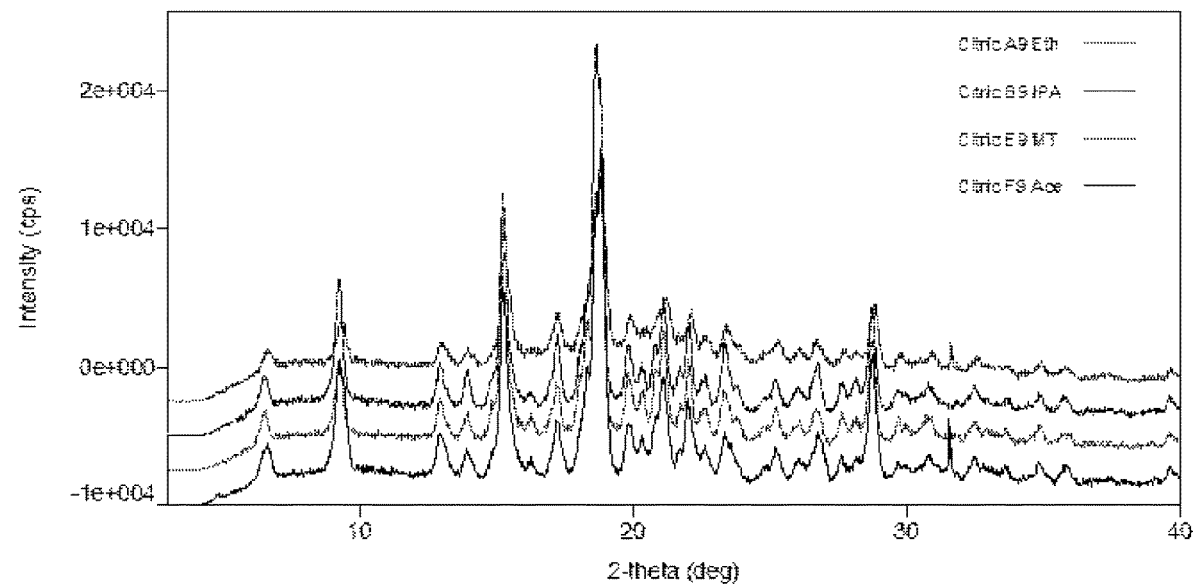
FIG. 126 depicts XRPD comparison profiles of citrate salts from SVSS in ethanol, IPA, MTBA, and acetone.
Figure 127:
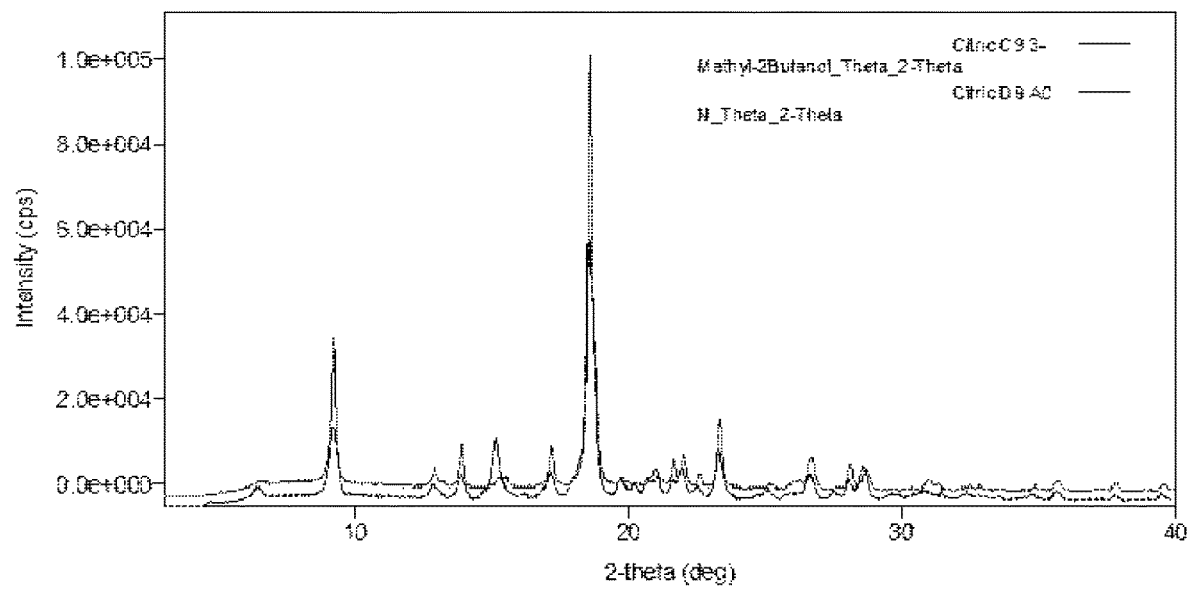
FIG. 127 depicts XRPD comparison profiles of citrate salts from SVSS in 3-methyl-2-butanol and acetonitrile.

Crystalline citrate salts from SVSS in various solvents were found and XRPD profiles of crystalline citrate salts from SVSS are shown in FIG. 118 to FIG. 125. XRPD profiles from ethanol (A9), IPA (B9), 3-methyl-2-butanol (C9), acetonitrile (D9), MTBE (E9), and acetone (F9) appear similar (citrate form 1), as shown in FIG. 126 and FIG. 127.

Figure 128:
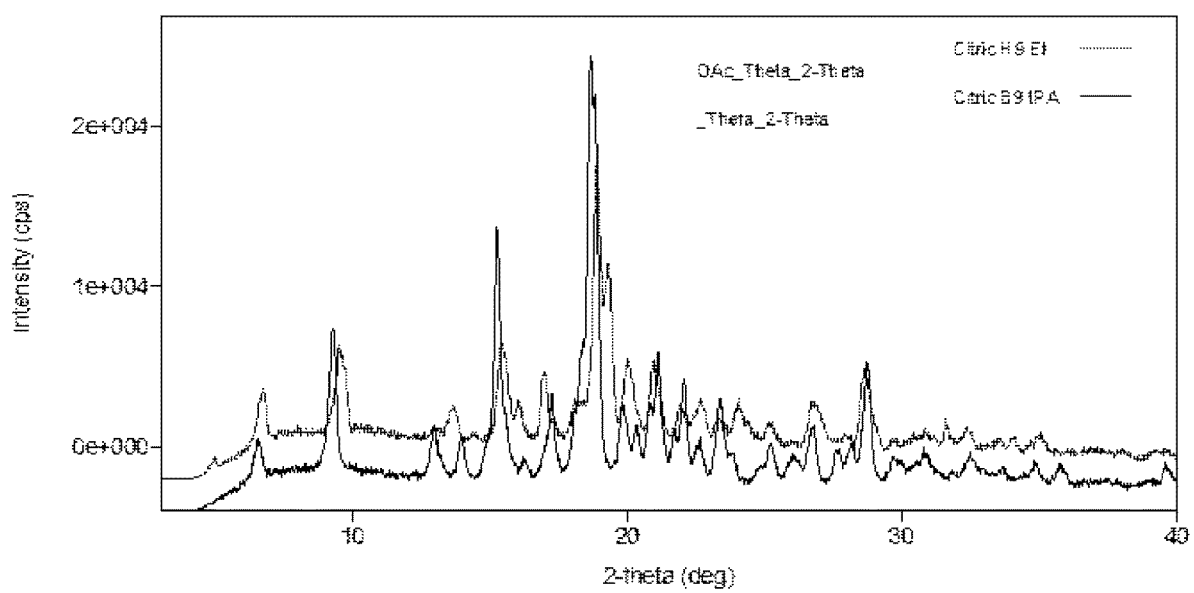
FIG. 128 depicts XRPD comparison profiles of citrate salts from SVSS in EtOAc and IPA.
Figure 129:
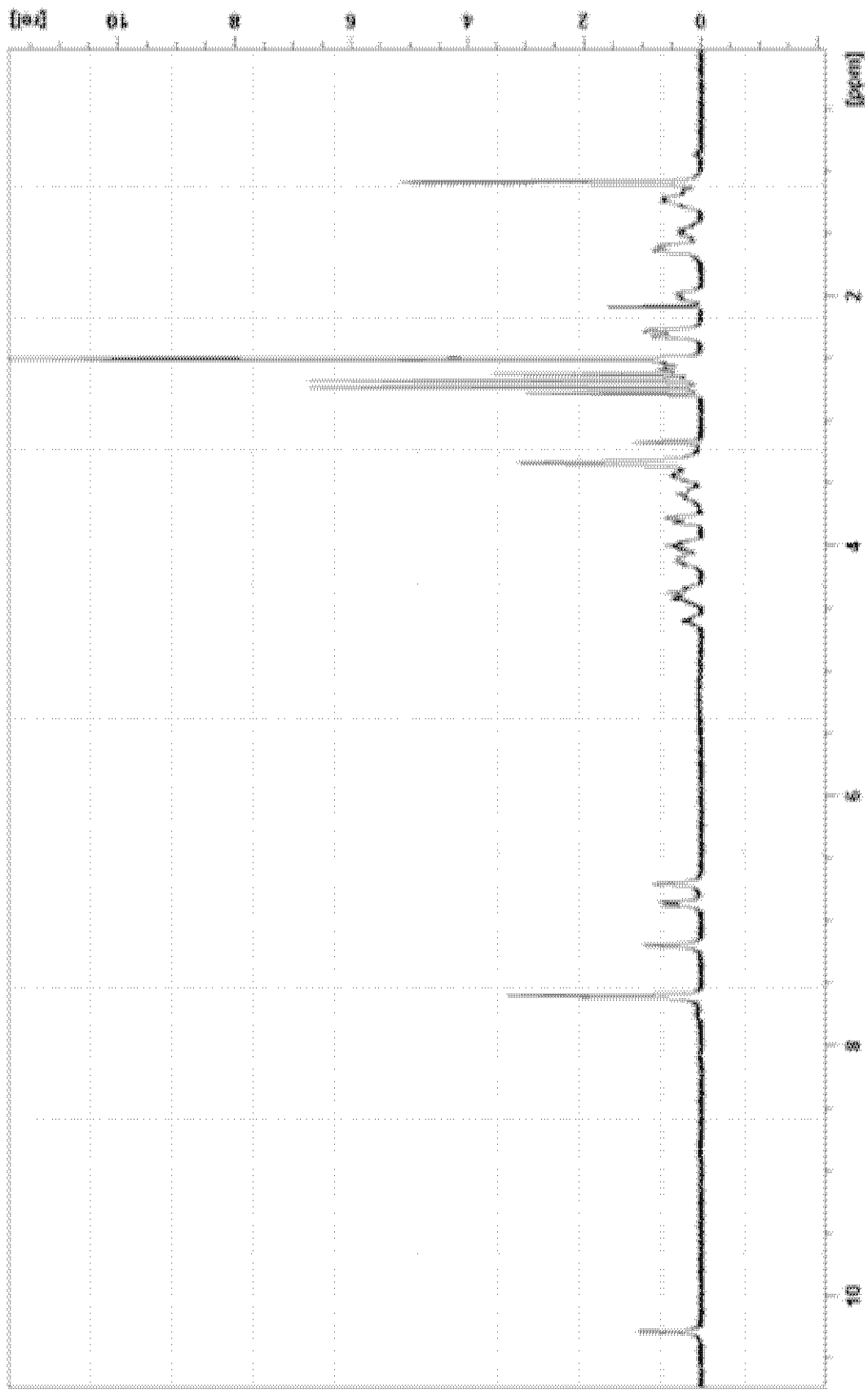
FIG. 129 depicts a $^1$H NMR in D$^6$-DMSO of Compound 1 citrate salt from SVSS Well# D9.
Figure 130:
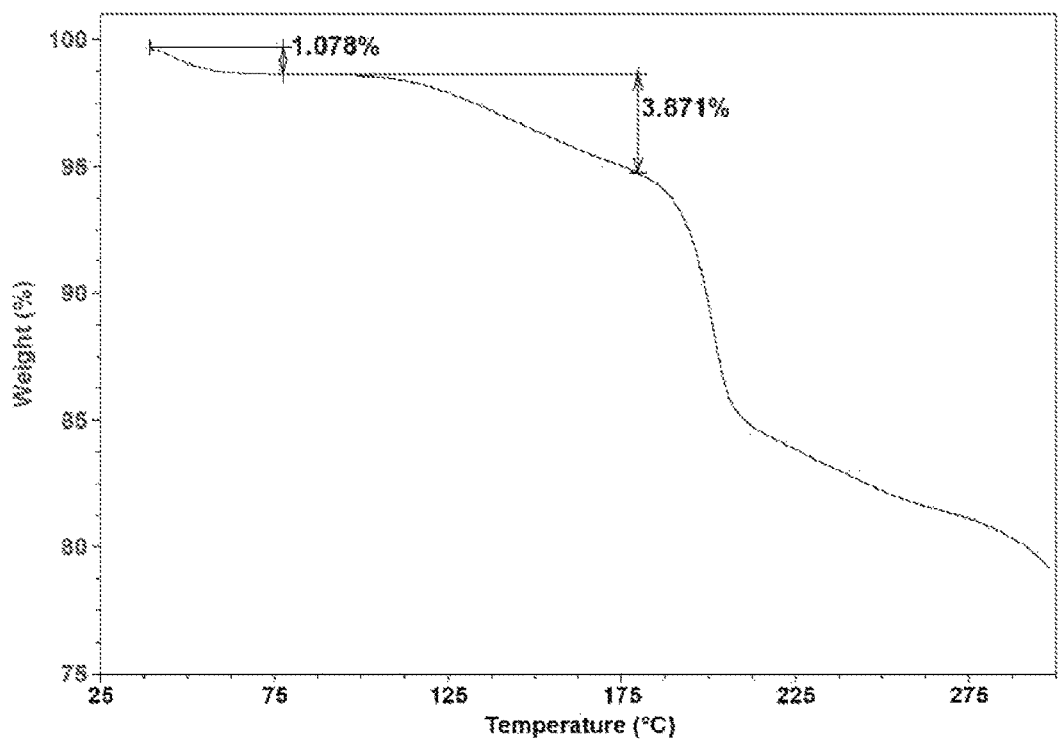
FIG. 130 depicts a TGA Thermogram of citrate salt from SVSS well# A9.
Figure 131:
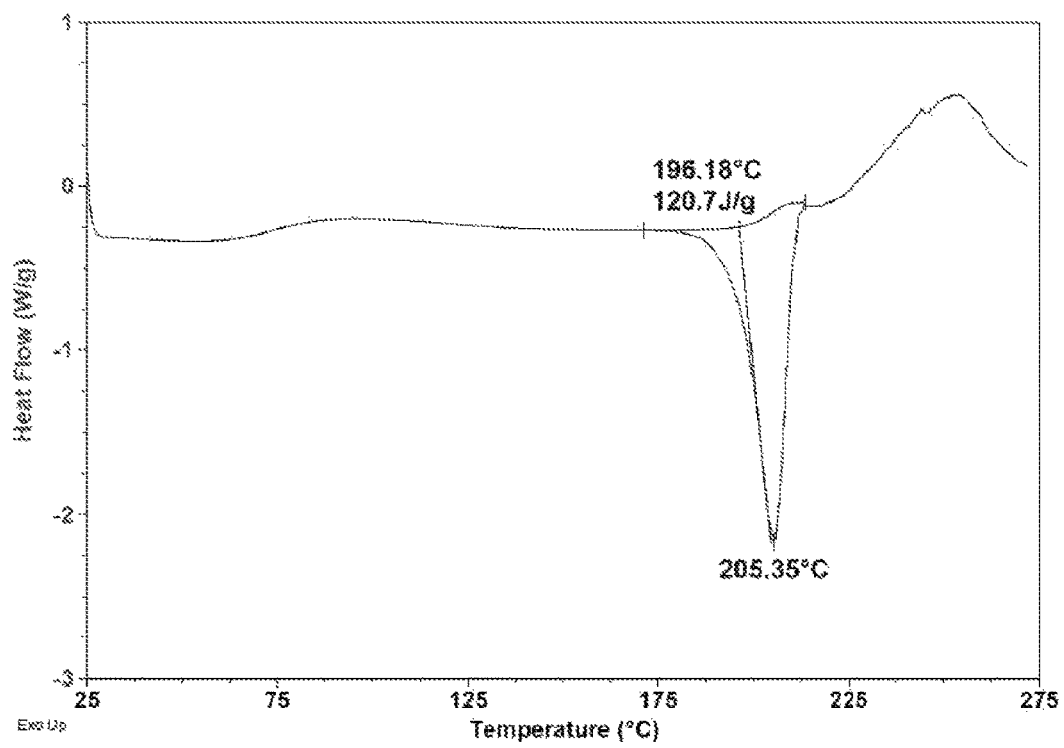
FIG. 131 depicts a DSC Thermogram of citrate salt from SVSS well# A9.
Figure 132:
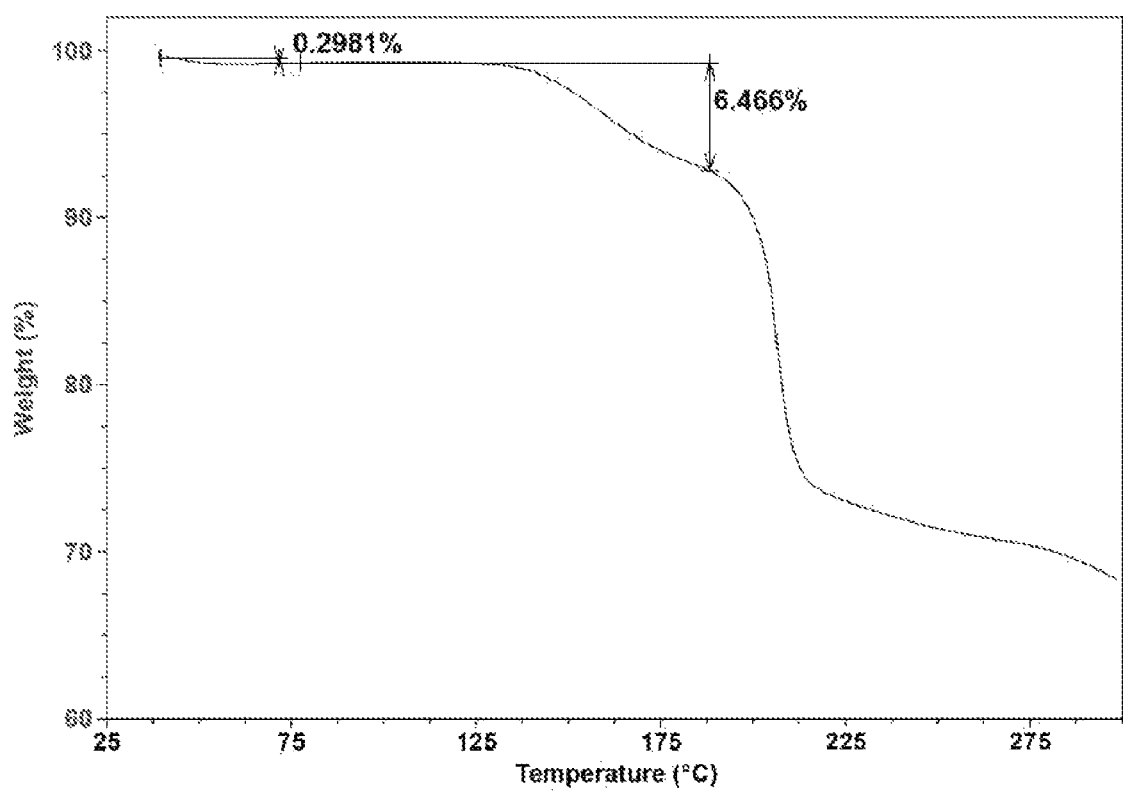
FIG. 132 depicts a TGA Thermogram of citrate salt from SVSS well# B9.
Figure 133:
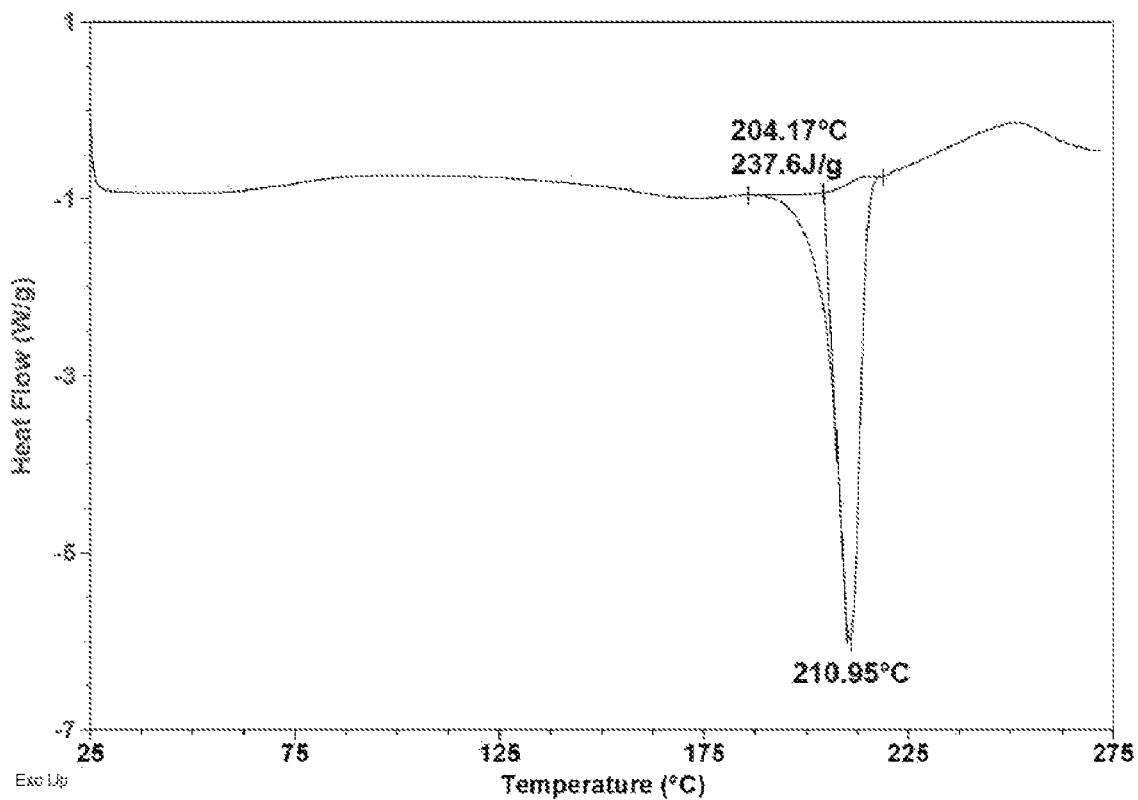
FIG. 133 depicts a TGA Thermogram of citrate salt from SVSS well# B9.
Figure 134:
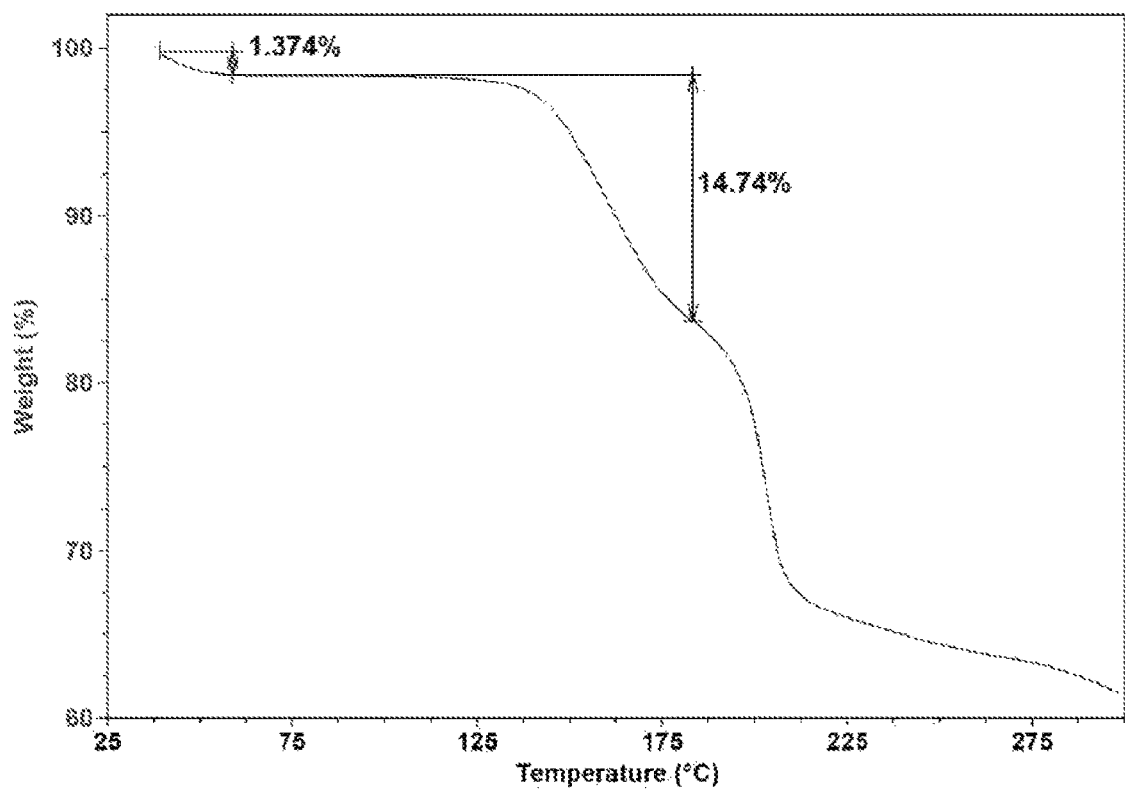
FIG. 134 depicts a TGA Thermogram of citrate salt from SVSS well# E9.
Figure 135:
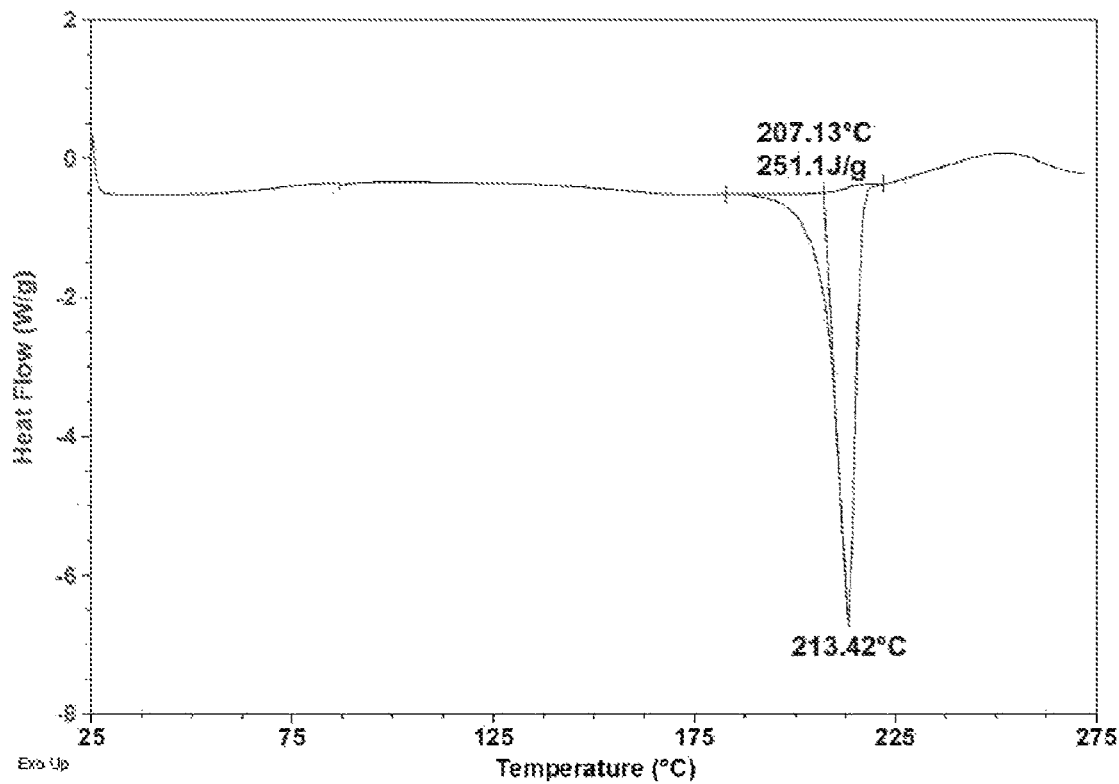
FIG. 135 depicts a DSC Thermogram of citrate salt from SVSS well# D9.
Figure 136:
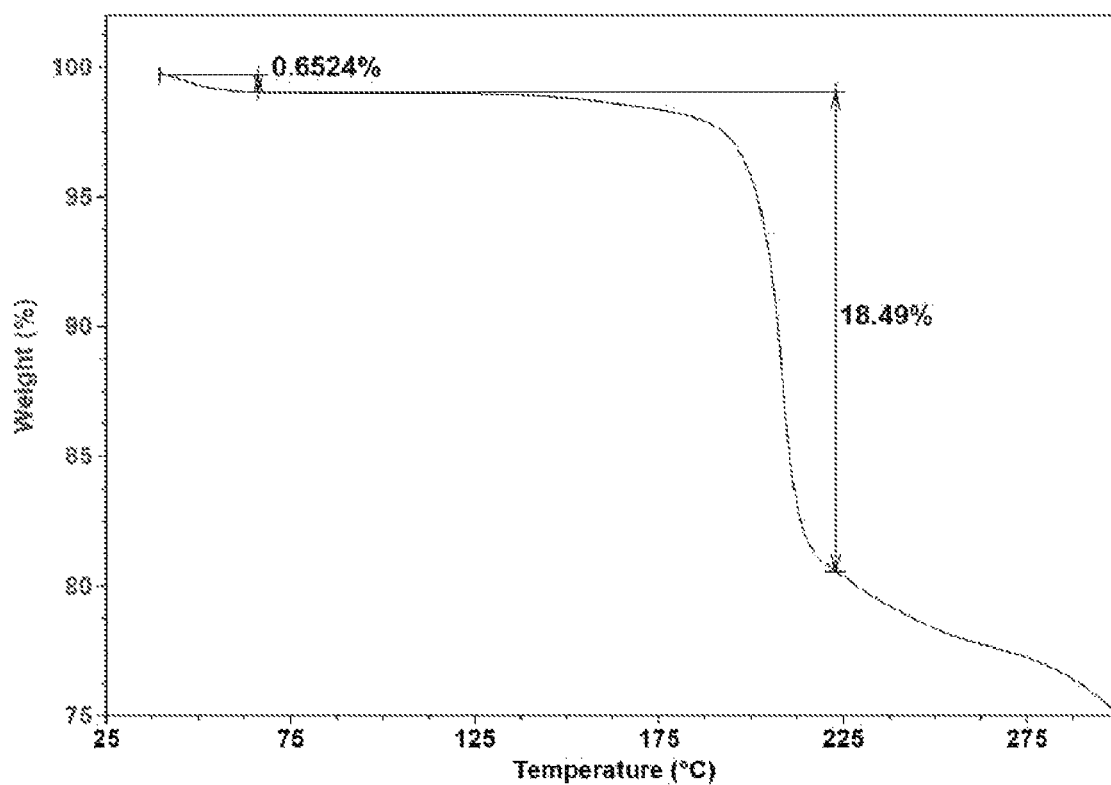
FIG. 136 depicts a TGA Thermogram of citrate salt from SVSS well# G9.
Figure 137:
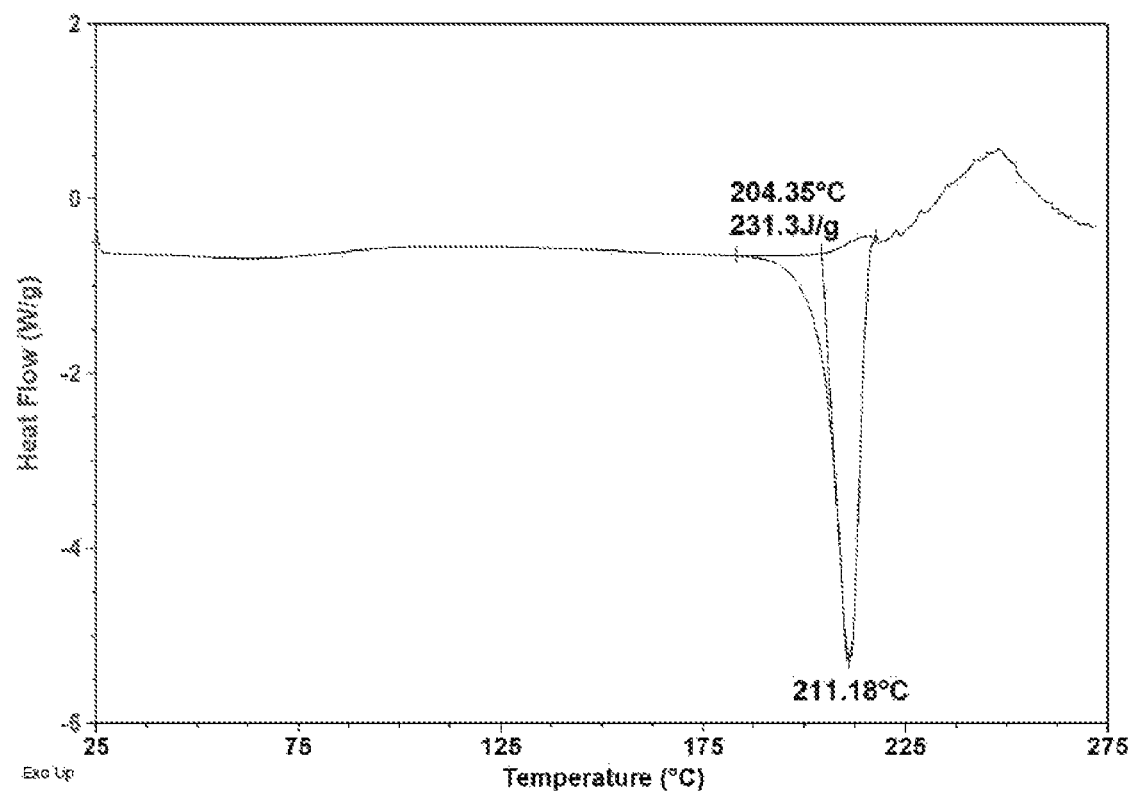
FIG. 137 depicts a DSC Thermogram of citrate salt from SVSS well# G9.
Figure 138:
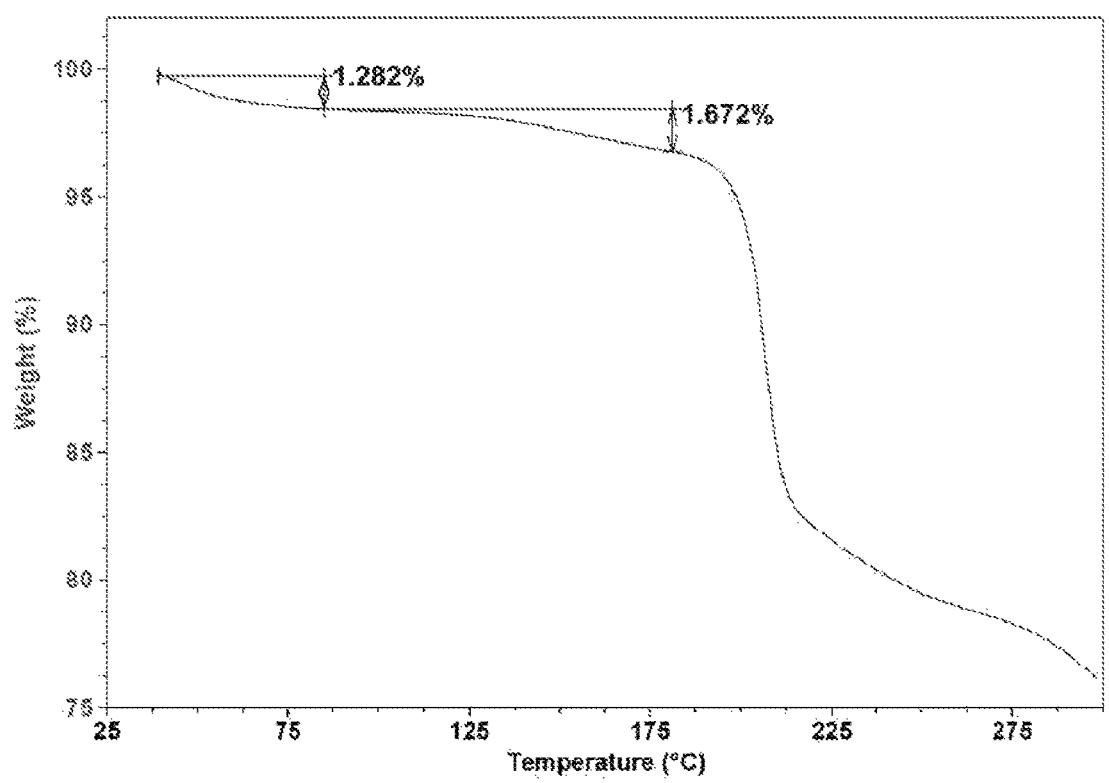
FIG. 138 depicts a TGA Thermogram of citrate salt from SVSS well# H9.
Figure 139:
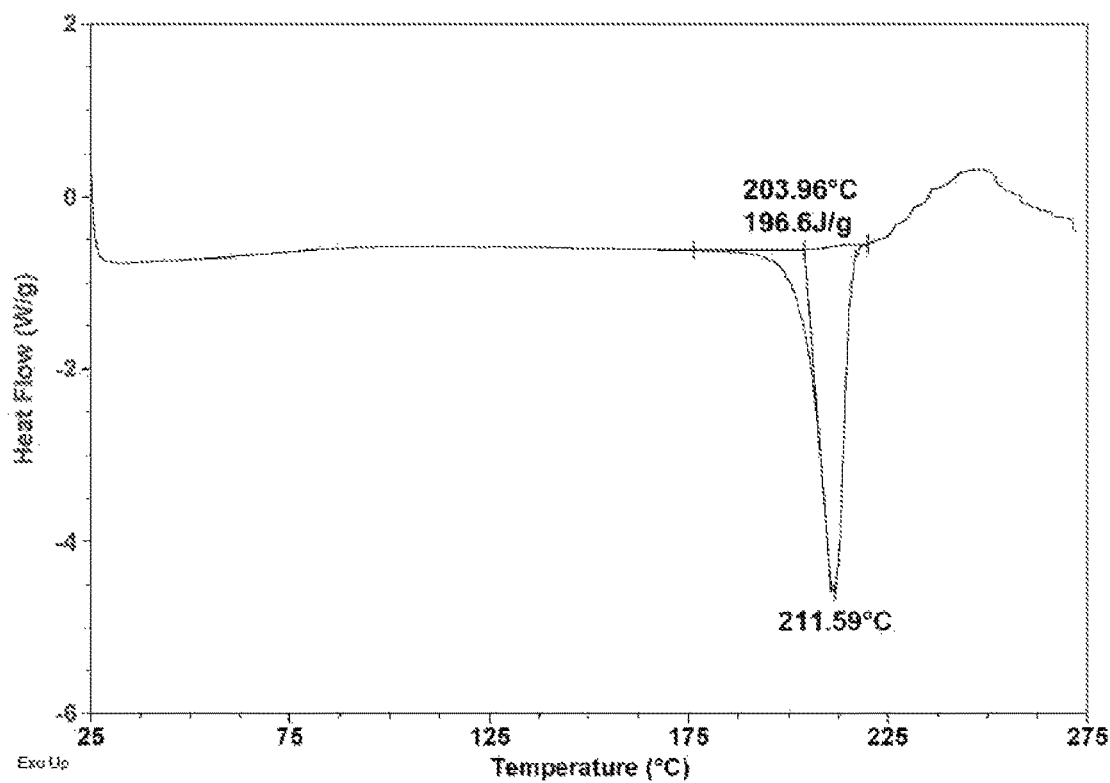
FIG. 139 depicts a DSC Thermogram of citrate salt from SVSS in EtOAc well# H9.

XRPD profile from SVSS in EtOAc (H9) was different (FIG. 128, citrate form 2). XRPD profile from SVSS in water (FIG. 124) was very close to those in FIG. 126. Sample containing both Compound 1 free base and citric acid was analyzed by $^1$H NMR in DMSO-$d_6$, FIG. 129. $^1$H NMR showed that no chemical shifts were observed in hydrogen in purine and benzene ring, suggested that salt formation is weak interaction in solution phase and can be regarded as co-crystal. Selected samples were analyzed by TGA and DSC, FIG. 130 to FIG. 139. TGA profiles all showed minimum initial weight losses (<0.5%) at relatively low temperature prior to decomposition. DSC profiles from these wells also showed a single endothermic due to melt with onset and peak temperatures of ~203 and ~211° C., respectively.

Figure 140:
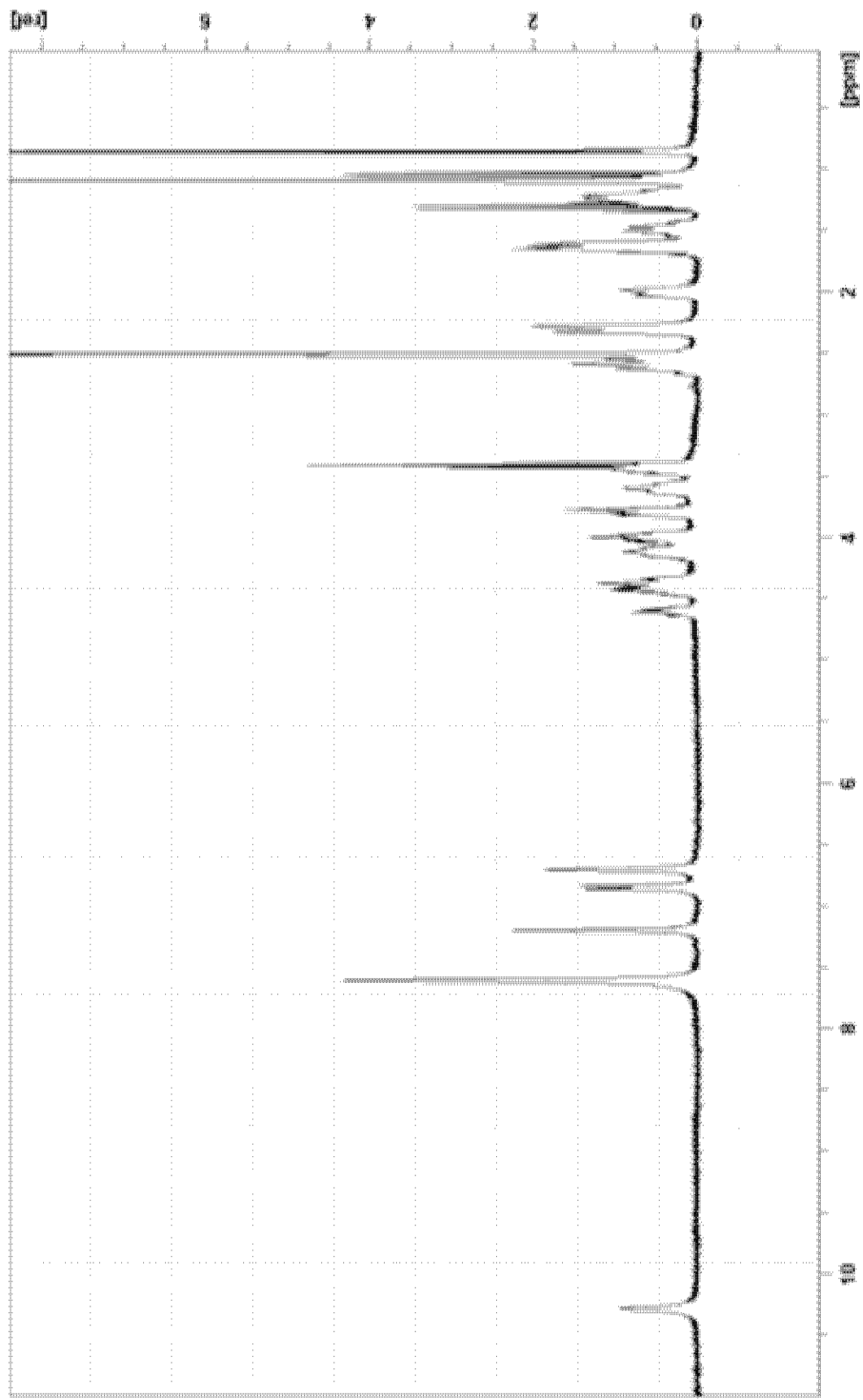
FIG. 140 depicts a $^1$H NMR in D$^6$-DMSO of Compound 1 and phosphoric acid from SVSS Well# E7.

A sample containing both Compound 1 free base and phosphoric acid was analyzed by $^1$H NMR in DMSO-$d_6$, FIG. 140. $^1$H NMR showed that no chemical shifts were observed in hydrogen in purine and benzene ring suggested that salt formation may not likely in solution phase. Different crystal structures were found from SVSS, suggested that co-crystals of phosphate with Compound 1 were formed.

Figure 141:
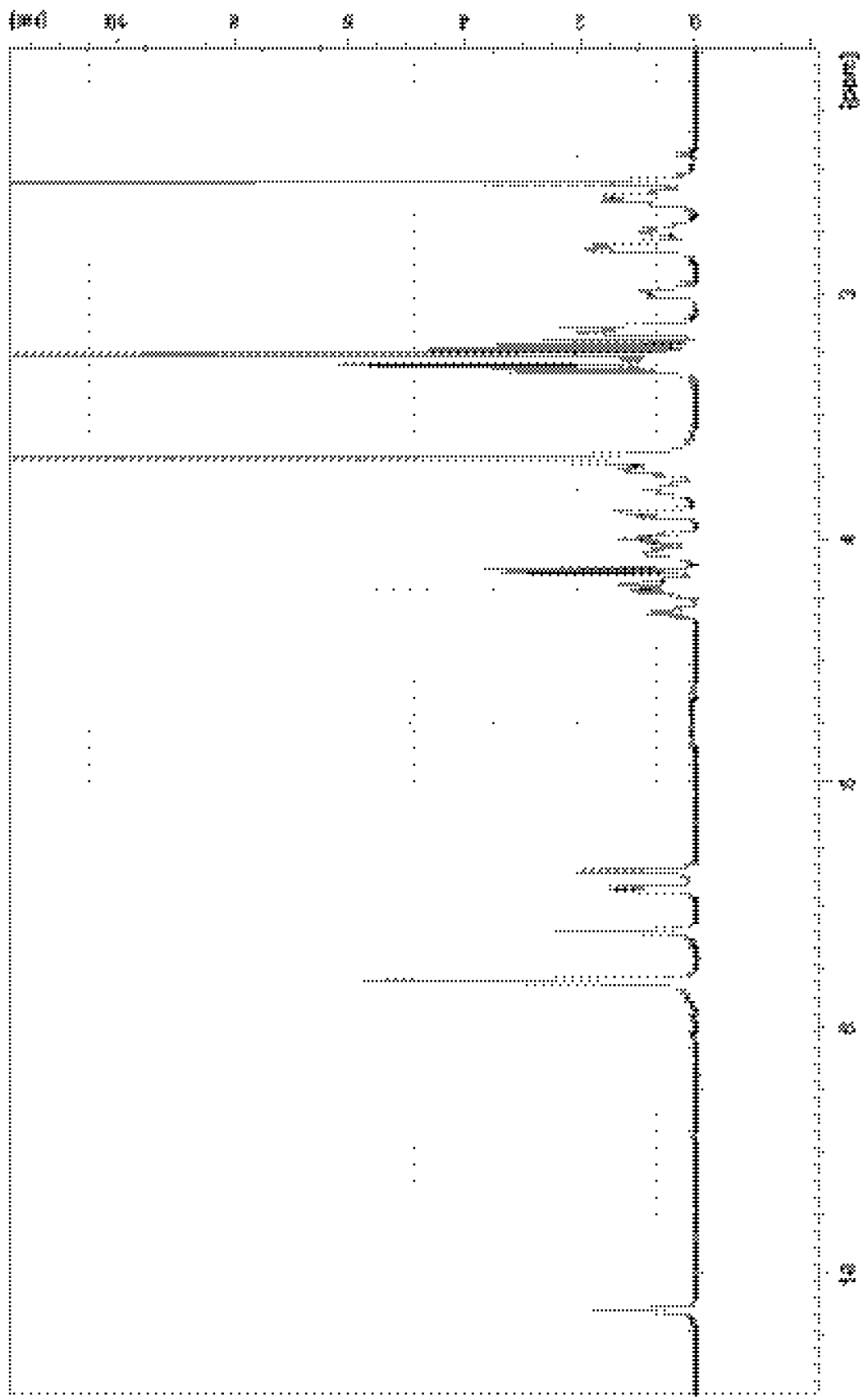
FIG. 141 depicts a $^1$H NMR in D$^6$-DMSO of Compound 1 and malic acid from SVSS Well# G10.

The X-ray powder diffraction patterns of wells B4 and B6 were similar, designated as phosphate Form 1A FIG. 141.

Figure 142:
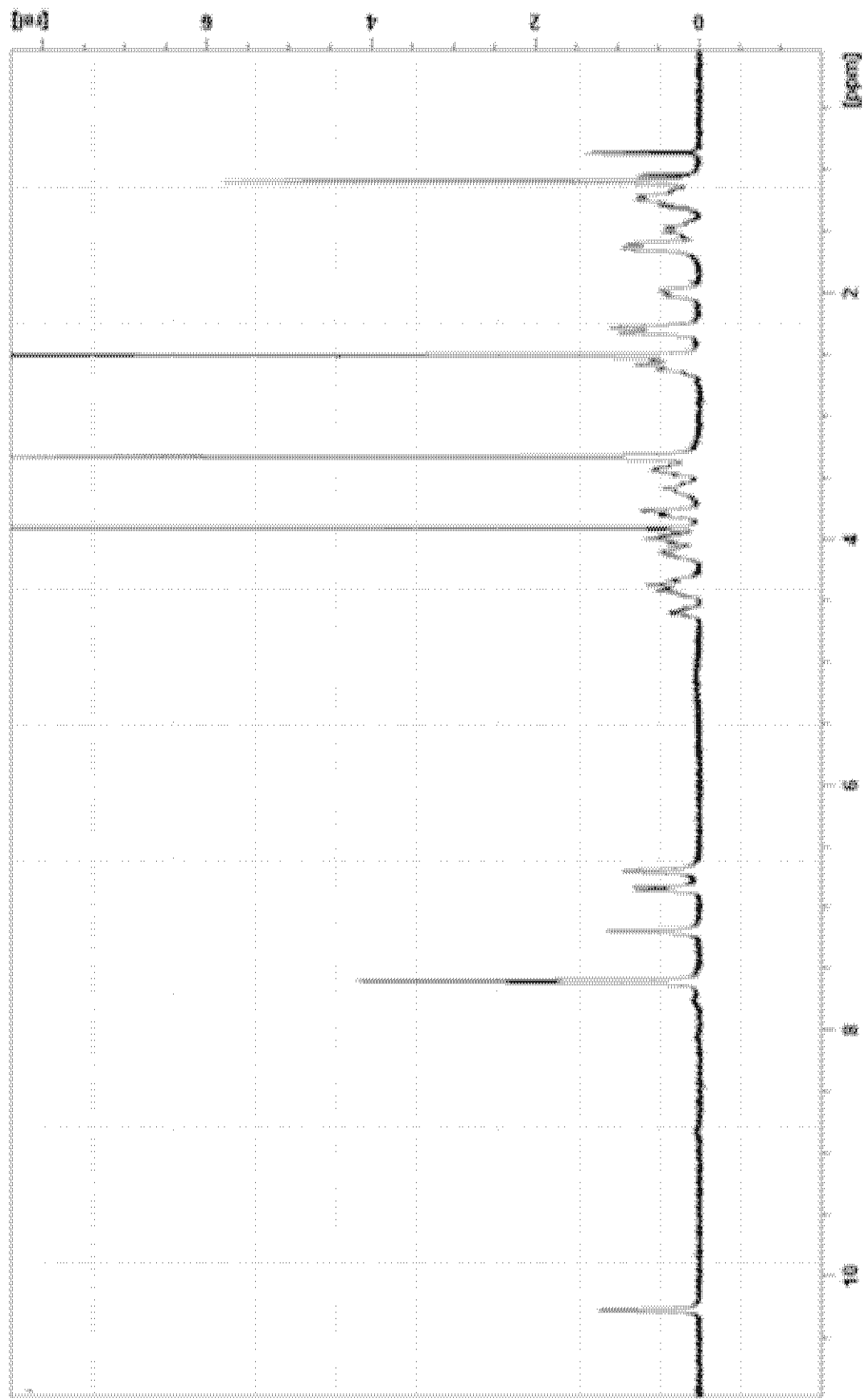
FIG. 142 depicts a $^1$H NMR in D$^6$-DMSO of Compound 1 and glycolic acid from SVSS Well# G11.
Figure 143:
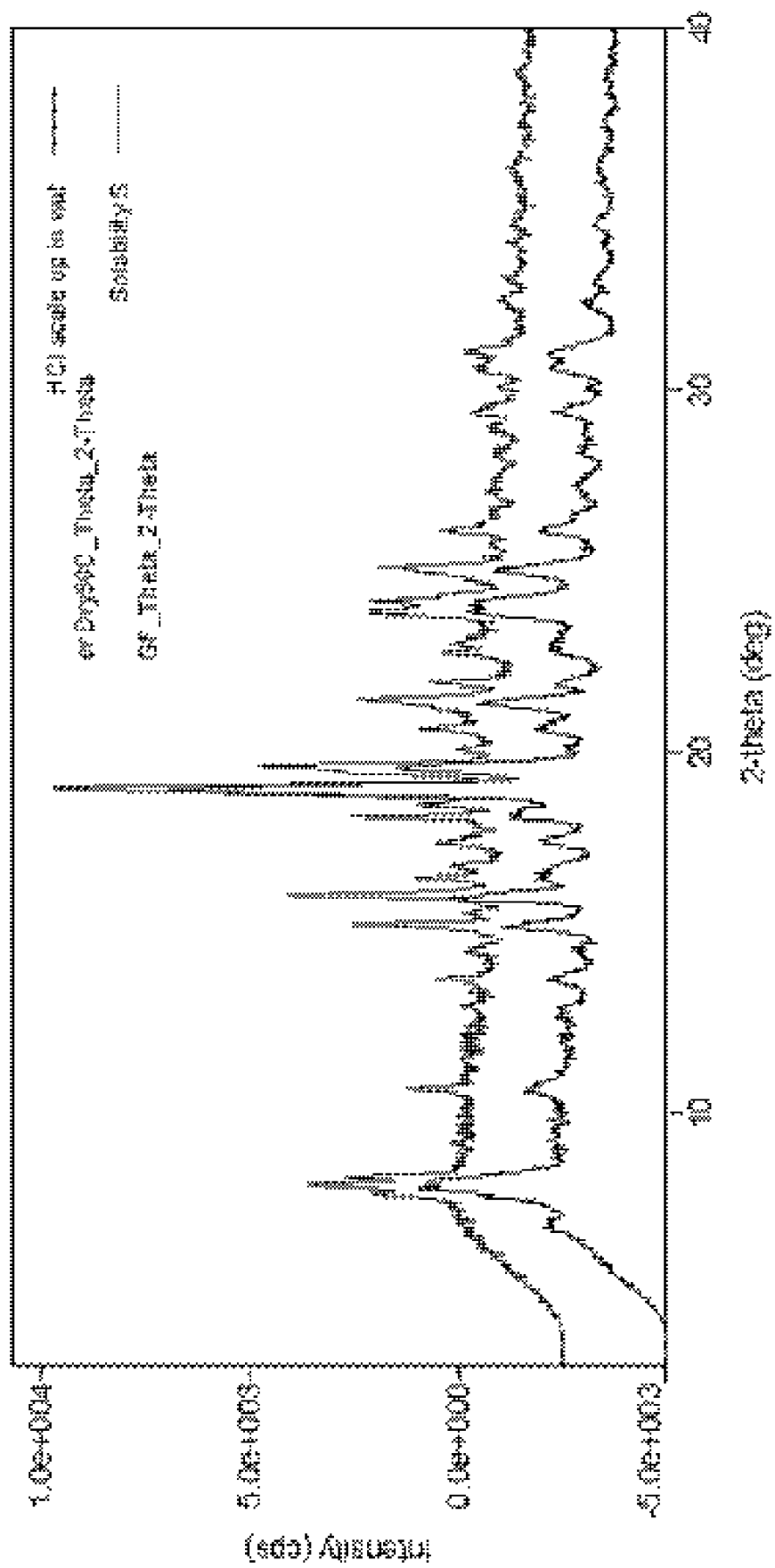
FIG. 143 depicts a XRPD Pattern of HCl salt (top) compared with the one from solubility of free base in SGF (bottom).
Figure 144:
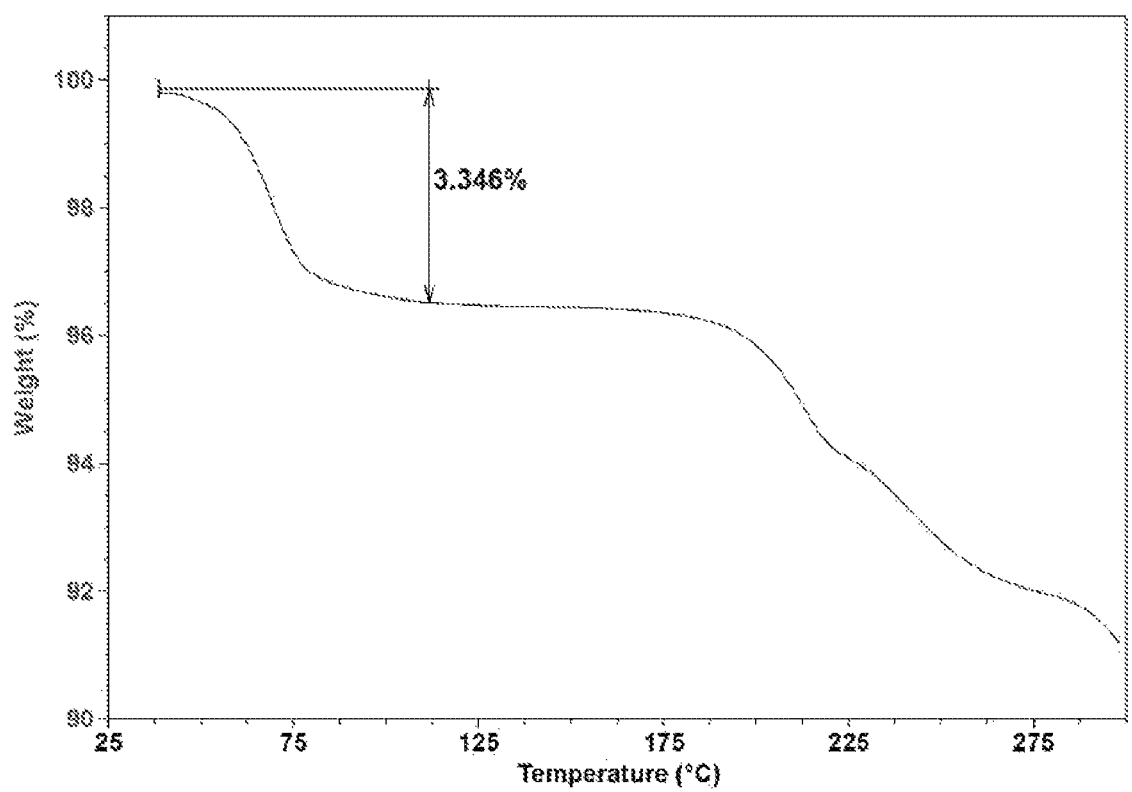
FIG. 144 depicts a TGA Thermogram of HCl salt, monohydrate (1).
Figure 145:
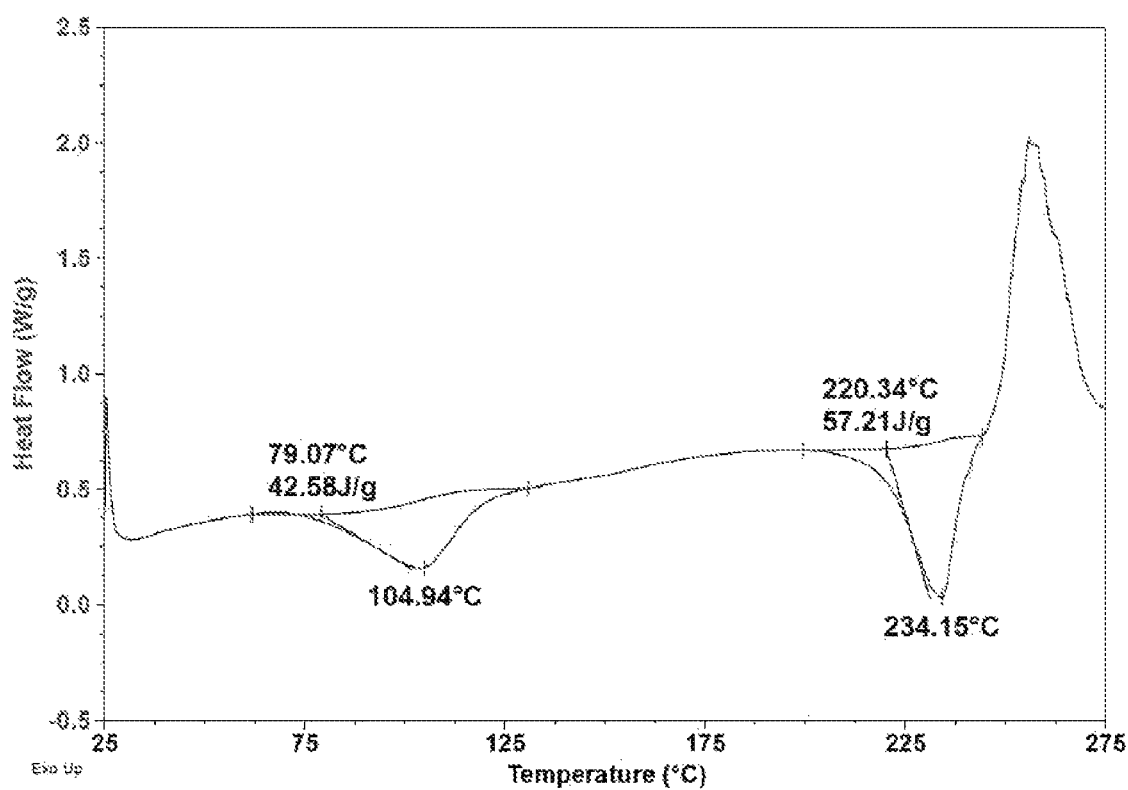
FIG. 145 depicts a DSC Thermogram of HCl salt, monohydrate (1).
Figure 146:
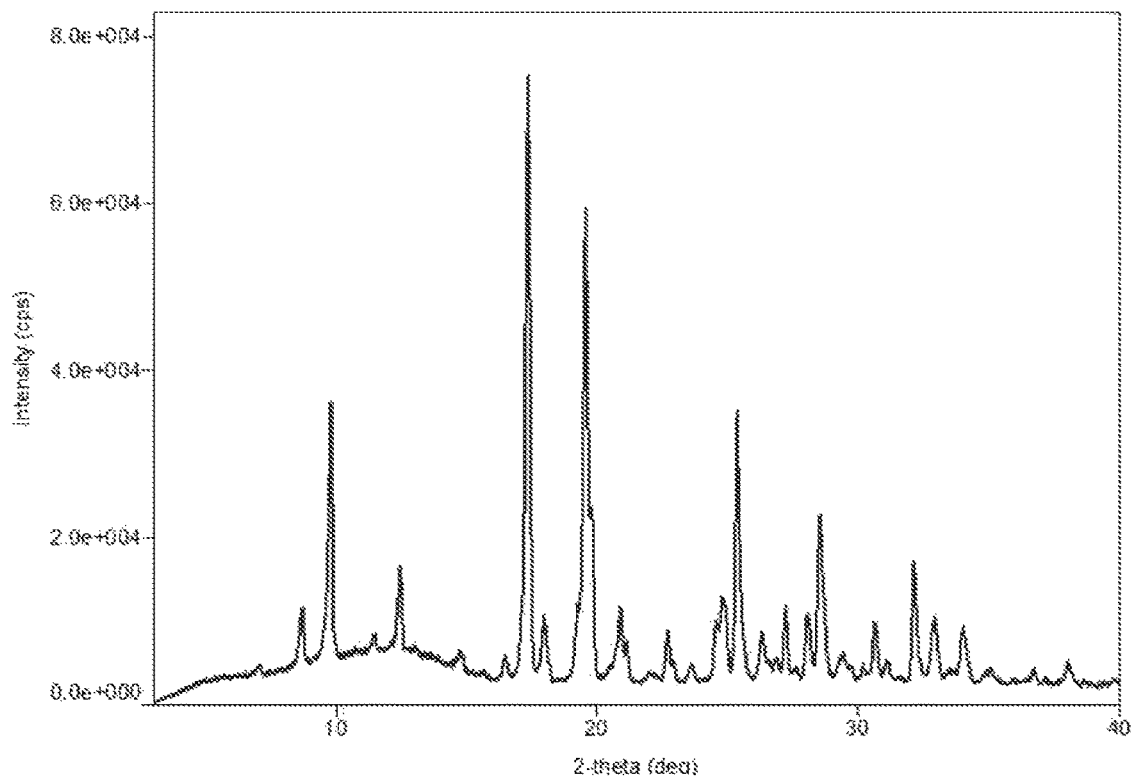
FIG. 146 depicts a XRPD Pattern of HCl salt.
Figure 147:
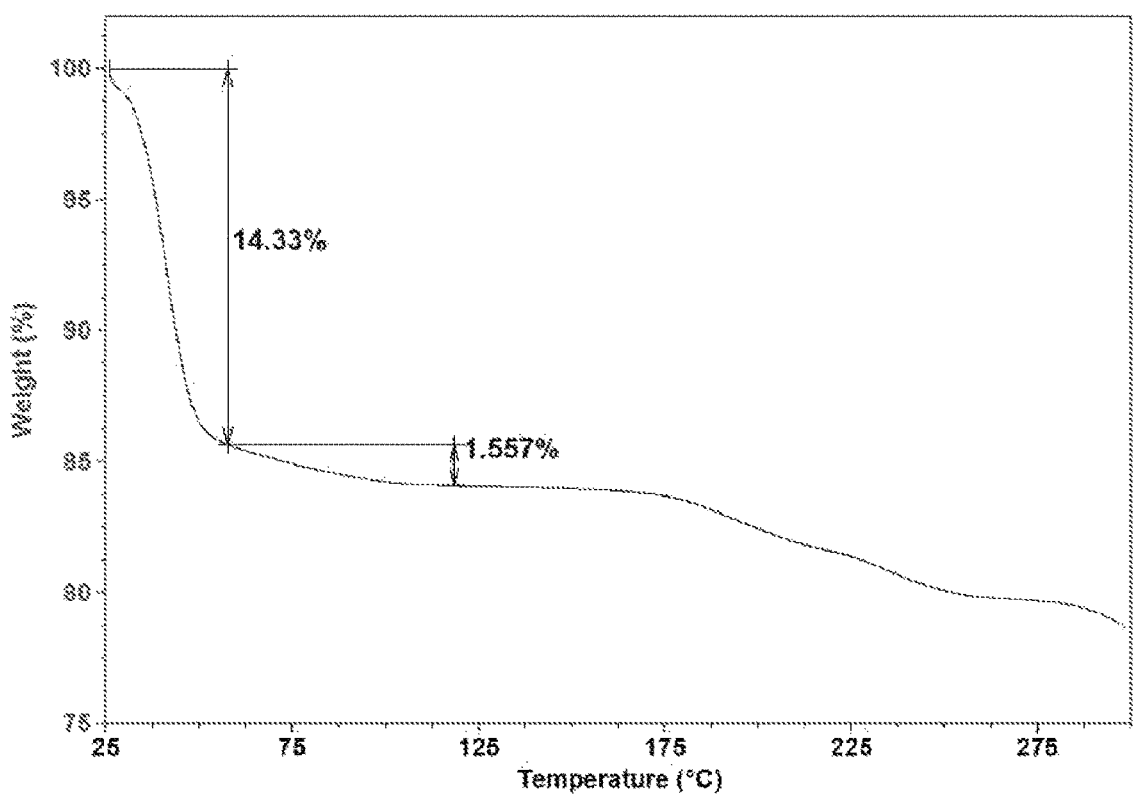
FIG. 147 depicts a TGA Thermogram of HCl salt.
Figure 148:
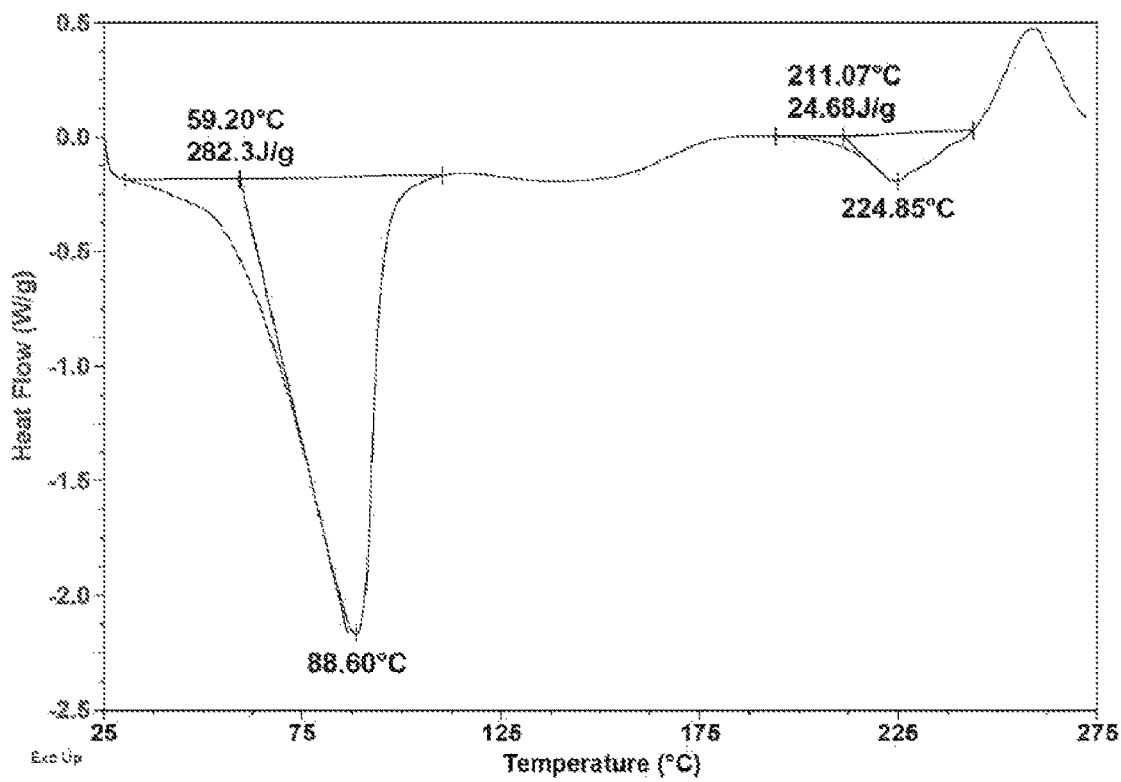
FIG. 148 depicts a DSC Thermogram of HCl salt.
Figure 149:
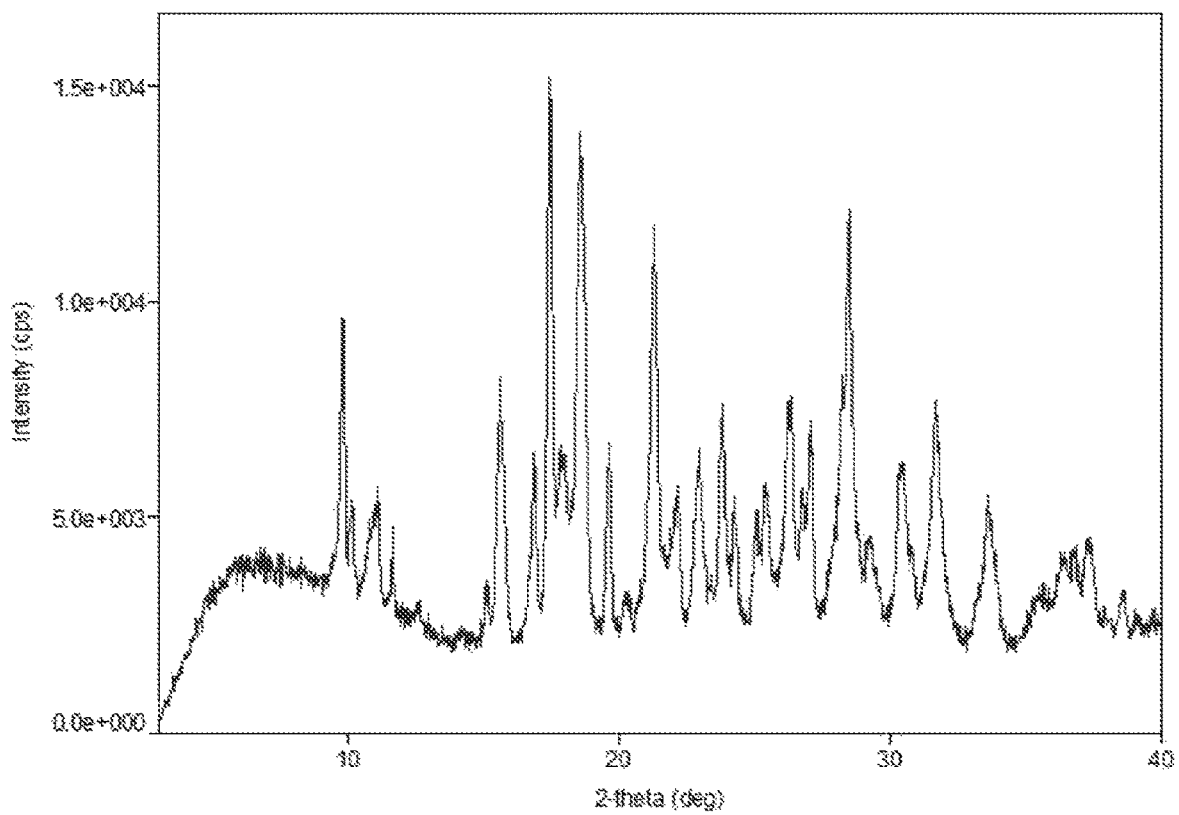
FIG. 149 depicts a XRPD Pattern of Compound 1 dried at 40° C. under vacuum.
Figure 150:
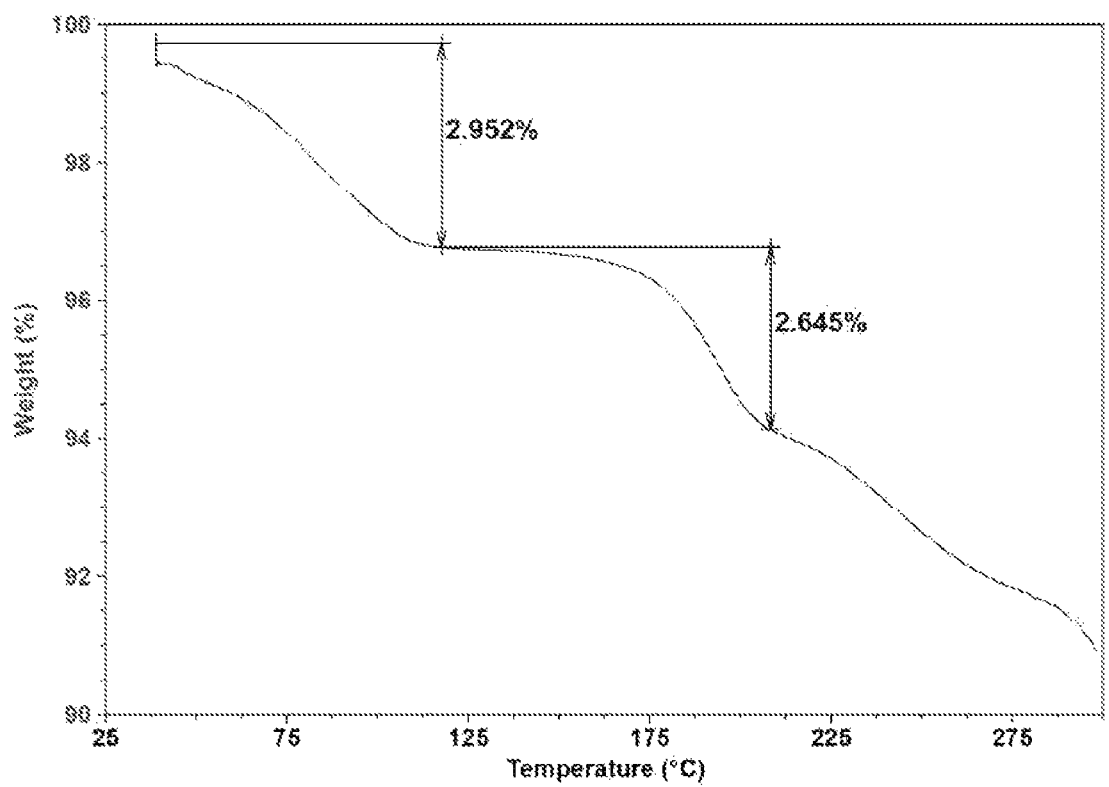
FIG. 150 depicts a TGA Thermogram of Compound 1 dried at 40° C. under vacuum.
Figure 151:
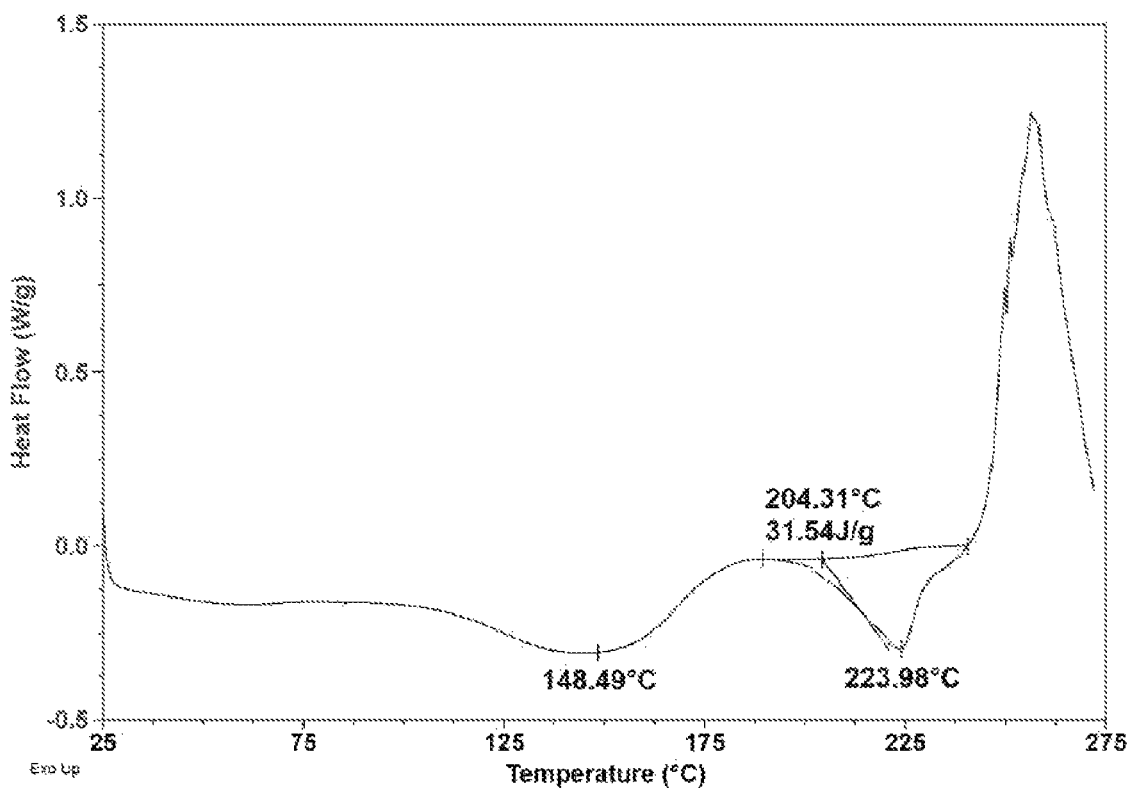
FIG. 151 depicts a DSC Thermogram of Compound 1 dried at 40° C. under vacuum.
Figure 152:
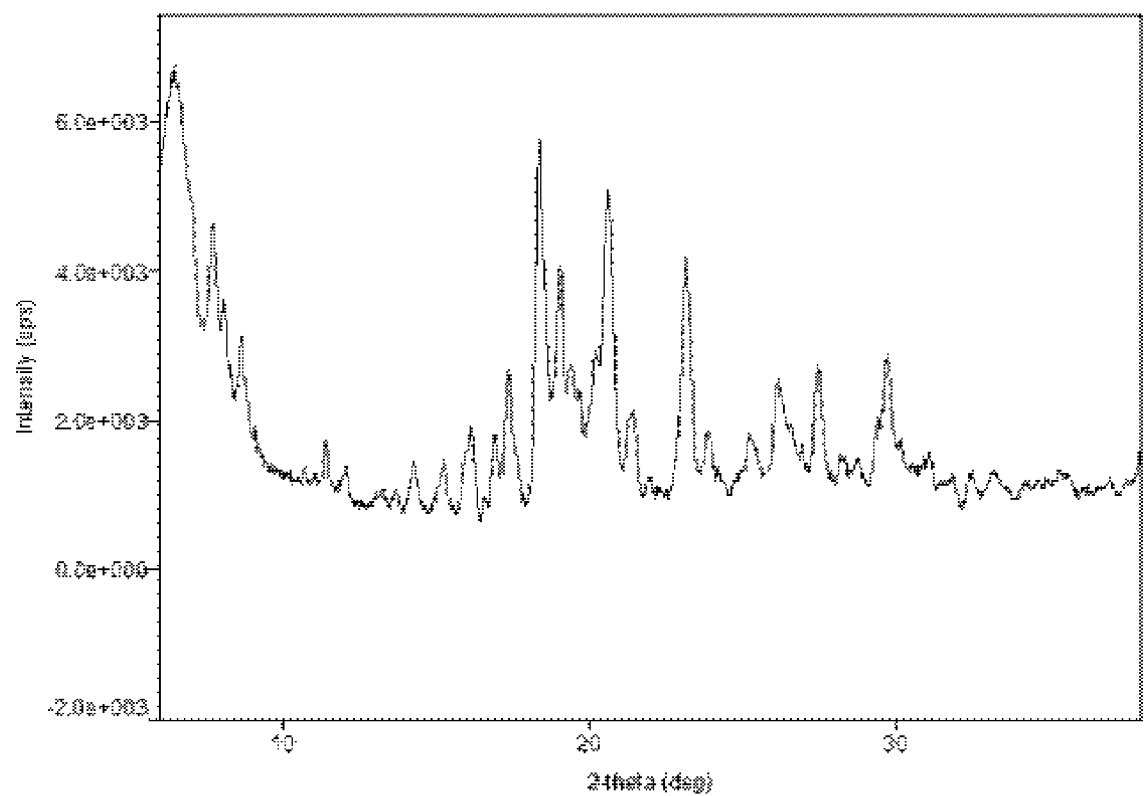
FIG. 152 depicts a XRPD Pattern of Compound 1 HCl salt monohydrate after heated to 140° C. on XRD-DSC stage.

X-ray powder diffraction of wells B7 and B10 were different and also different from the Form 1A, designated as Form 1B and 1C, respectively, as shown in FIG. 142.

The HCl salt monohydrate (1): 240 mg Compound 1 was weighed into a 4-mL glass vial, and then 4.60 mL of 0.1N HCl in water was introduced. The mixture became clear. The solution was filtered via a 0.22 μm filter and the supernatant was placed under hood for crystallization. Soon, precipitation occurred. The solid was collected via filtration.

The solid sample was analyzed to be monohydrate (1), and the XRPD profile is similar with the one from the solubility study of free base in SGF but has better crystallinity, as mL glass vial and then 3.10 mL of 0.5N HCl in water was added. The mixture became clear. Additional 5.0 mL of water was added. The solution was filtered via a 0.22 μm filter. The supernatant was placed under hood for crystallization. Soon, precipitation occurred. The solid was collected via filtration.

303.7 mg Compound 1 was weighed in a 20 mL glass vial and then 10 mL of SGF was added. The mixture became clear. Solid particles of Compound 1 HCl salt were added into the vial, as seeds. The suspension was kept agitation on LabQuake rotation for 24 hours. Solid particles were collected via filtration.

The anhydrous form was not observed in solution precipitation process. The dehydration was performed on XRD-DSC stage.

Figure 153:
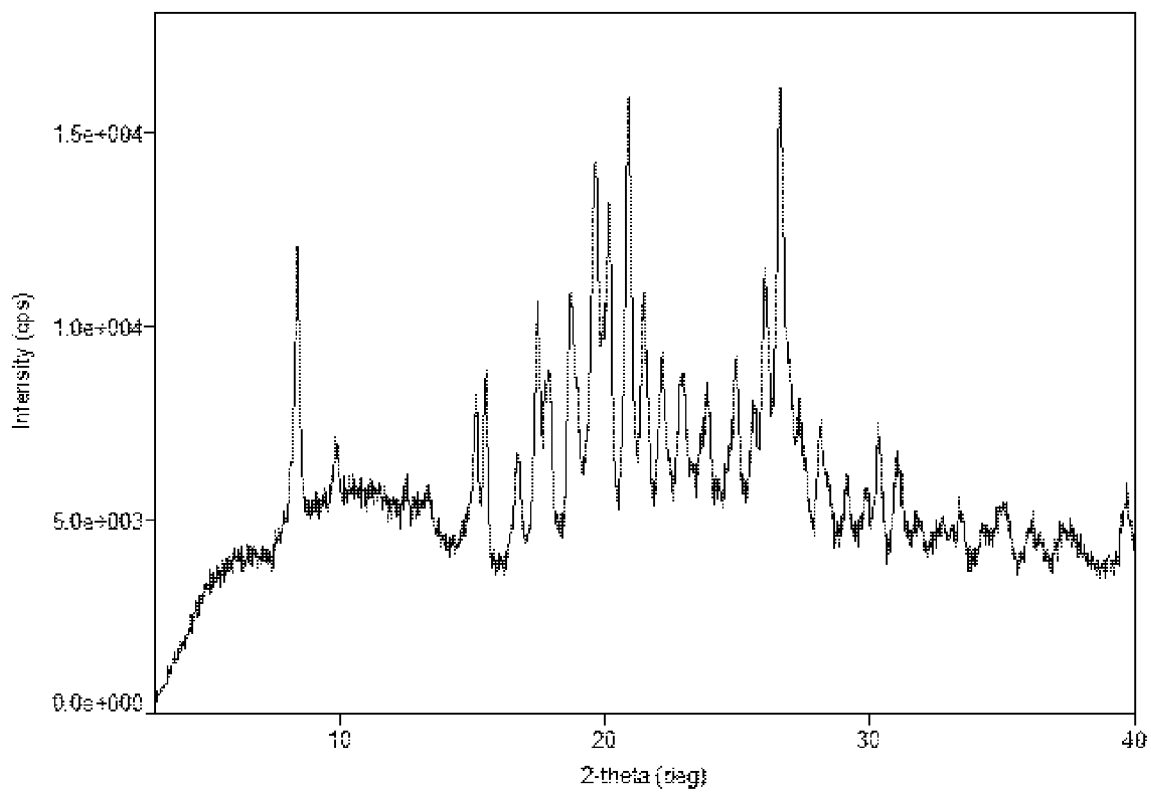
FIG. 153 depicts a XRPD Pattern of Compound 1 sulfate.
Figure 154:
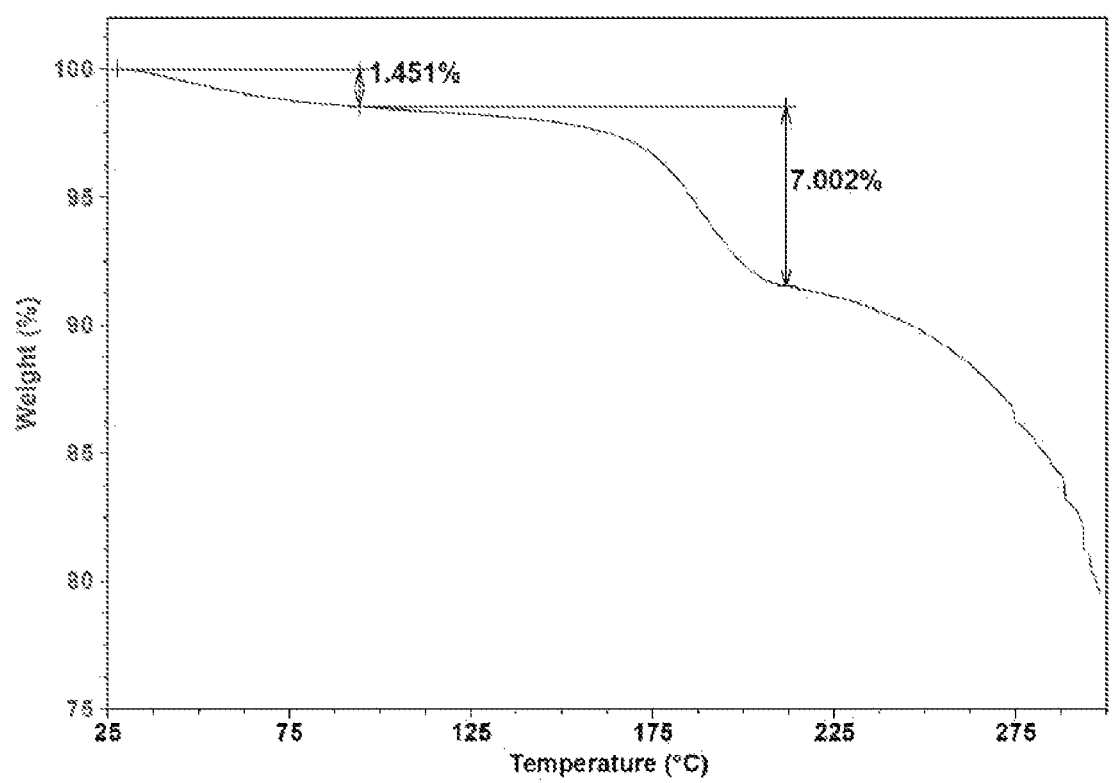
FIG. 154 depicts a TGA Thermogram of Compound 1 sulfate.
Figure 155:
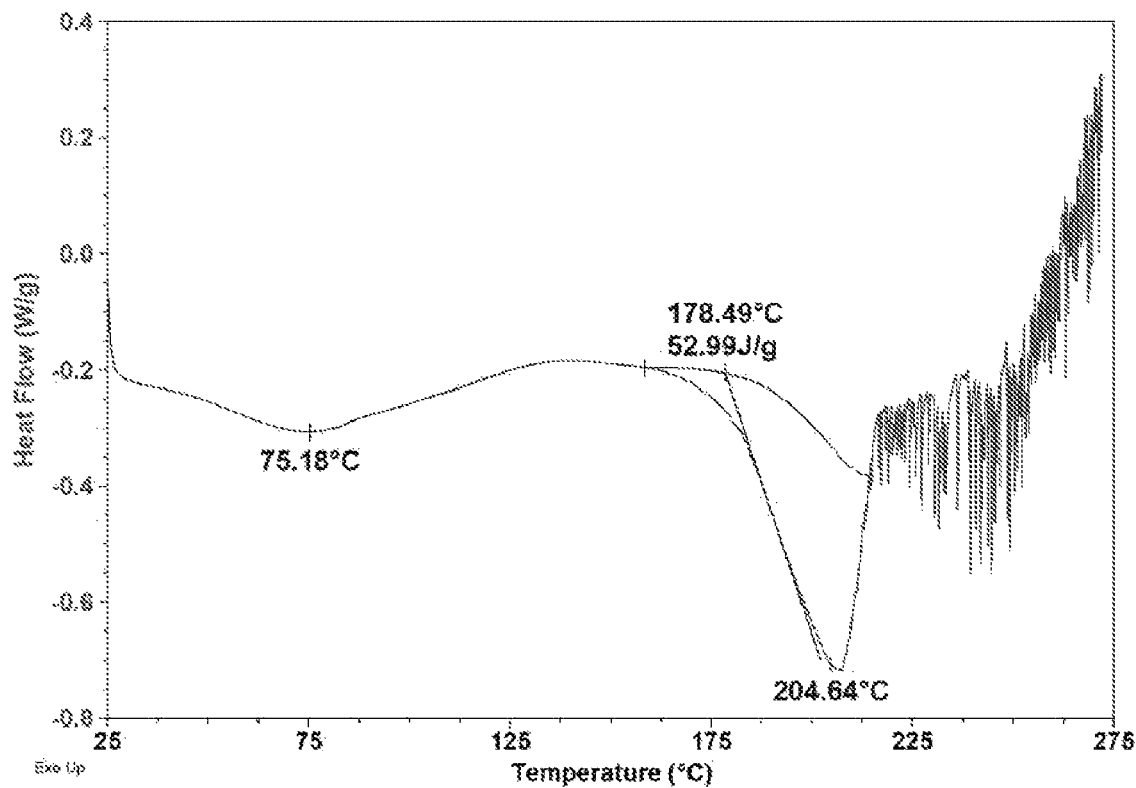
FIG. 155 depicts a DSC Thermogram of Compound 1 sulfate.

170 mg Compound 1 was weighed into a 4 mL glass vial and then 3.3 mL of 0.1M $H_2SO_4$ in EtOAc was introduced. The mixture became gummy/gelling material immediately. After drying, the solid was collected and analyzed by XRPD, TGA and DSC, as shown in FIG. 153 to FIG. 155.

105 mg Compound 1 was weighed into a 4 mL glass vial and 2.0 mL of 0.1M $H_2SO_4$ in water was introduced. The mixture became gel-like material, and addition of 1 mL of water was added. The material was still oil-like sticky.

Figure 156:
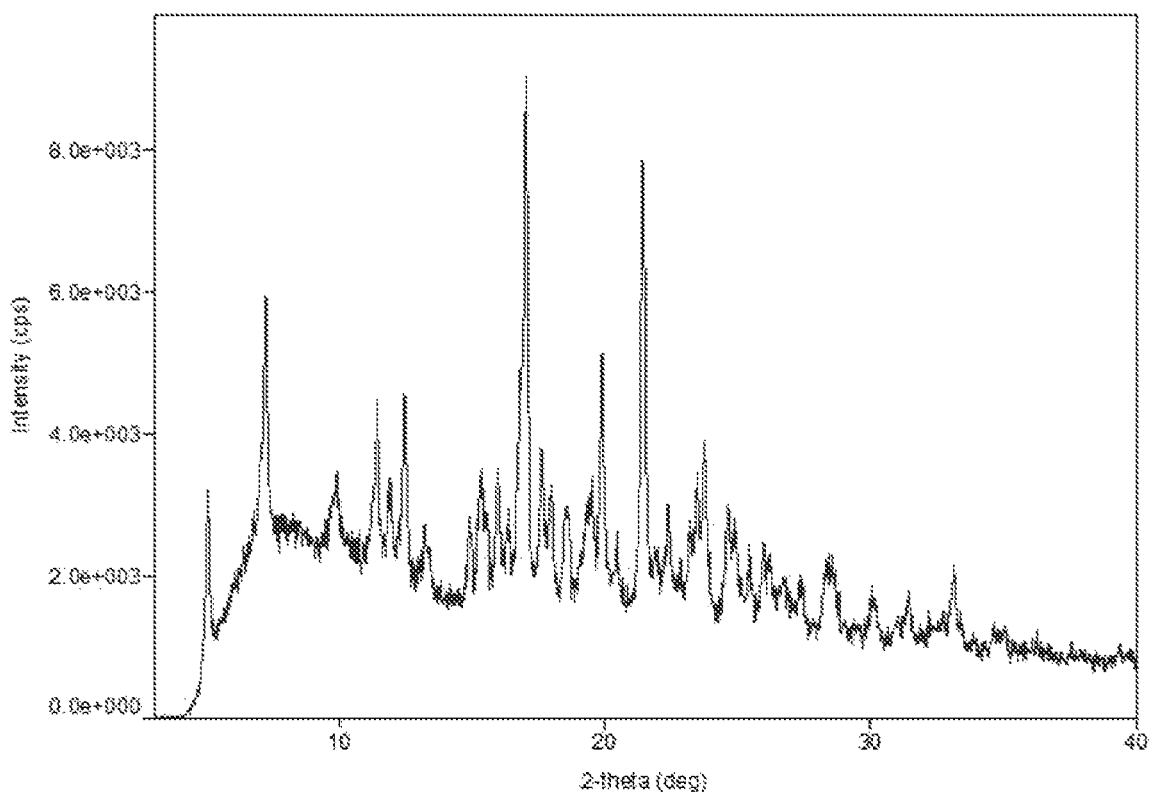
FIG. 156 depicts a XRPD Pattern of Compound 1 mesylate.
Figure 157:
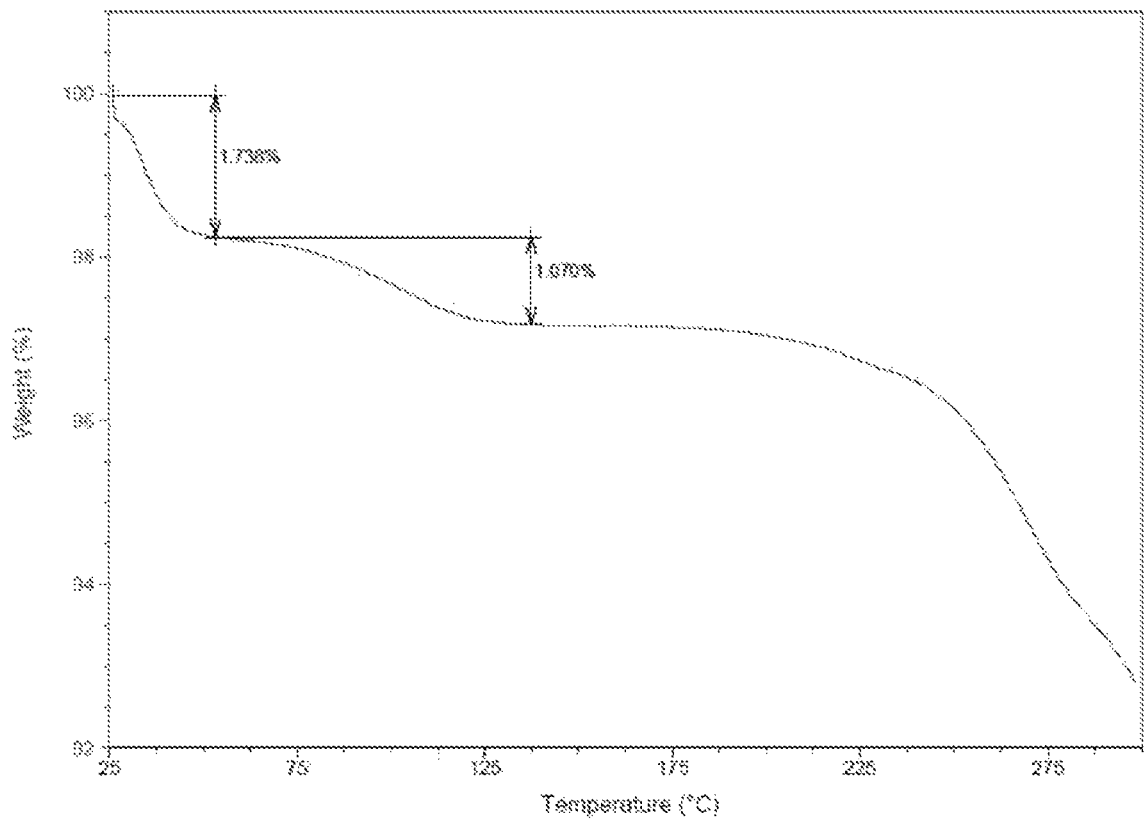
FIG. 157 depicts a TGA Thermogram of Compound 1 mesylate.
Figure 158:
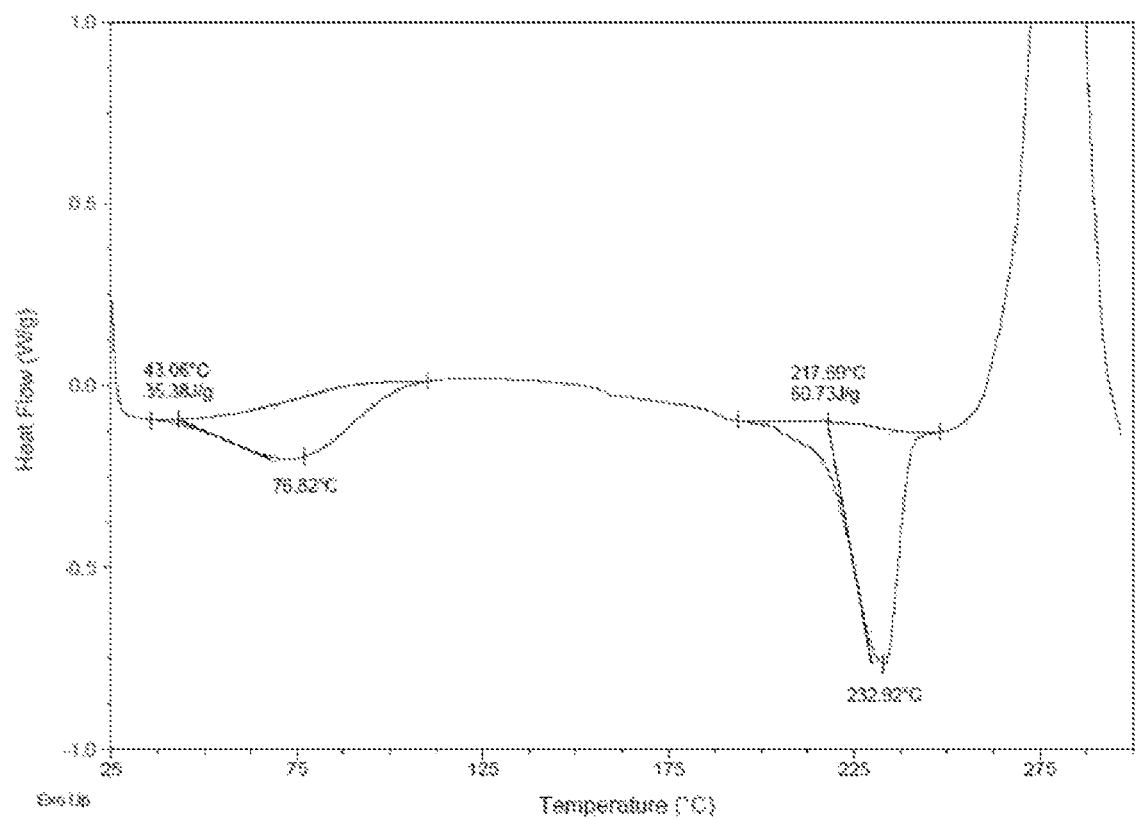
FIG. 158 depicts a DSC Thermogram of Compound 1 mesylate.

138 mg Compound 1 was weighed into a 4 mL glass vial and then 1.0 mL of EtOAc was added to dissolve the material first. Then, 2.60 mL of 0.1M methanesulfonic acid in EtOAc was introduced, and precipitate appeared immediately. The solid was collected via filtration and dried at 40° C. under vacuum overnight, and then analyzed by XRPD, TGA and DSC, as shown in FIG. 156 to FIG. 158.

Figure 159:
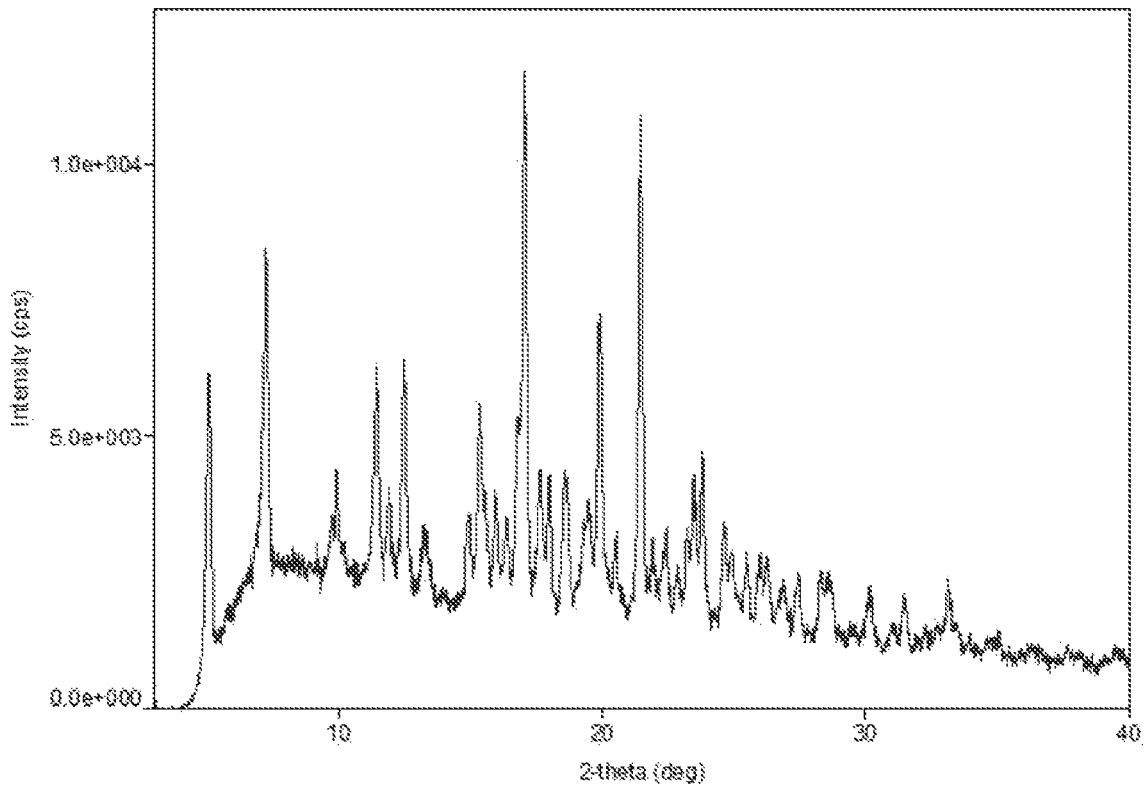
FIG. 159 depicts a XRPD Pattern of Compound 1 mesylate.
Figure 160:
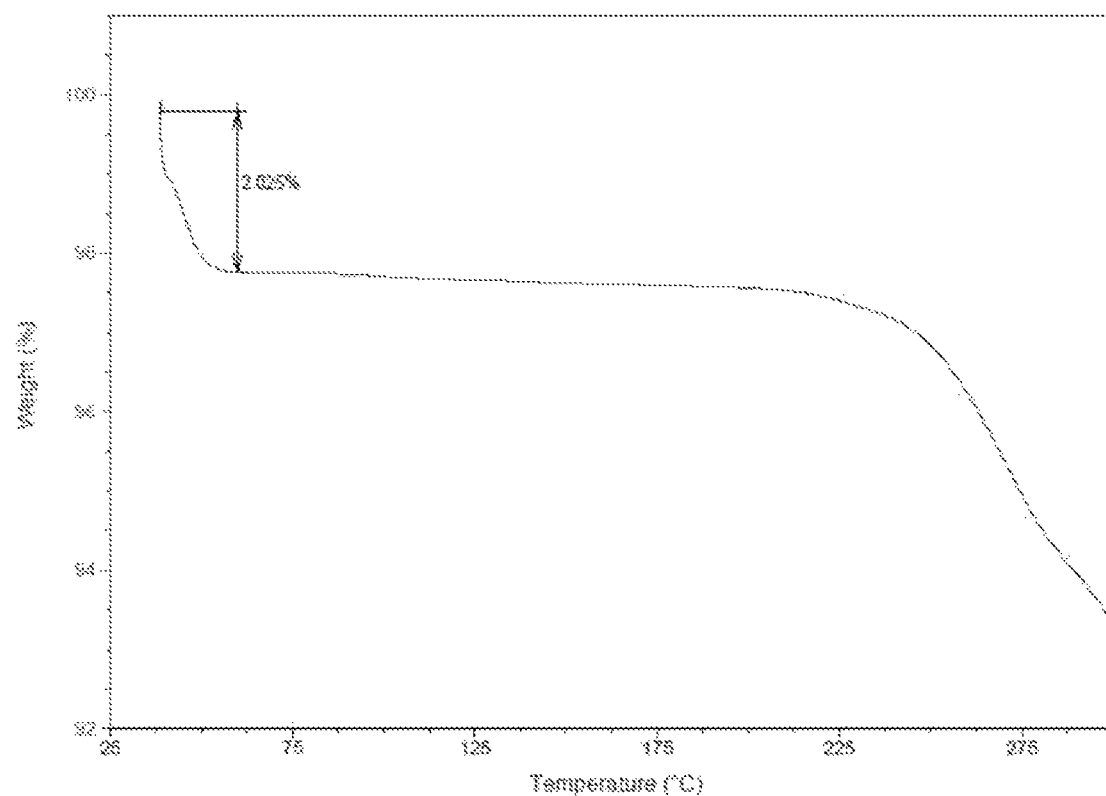
FIG. 160 depicts a TGA Thermogram of Compound 1 mesylate.
Figure 161:
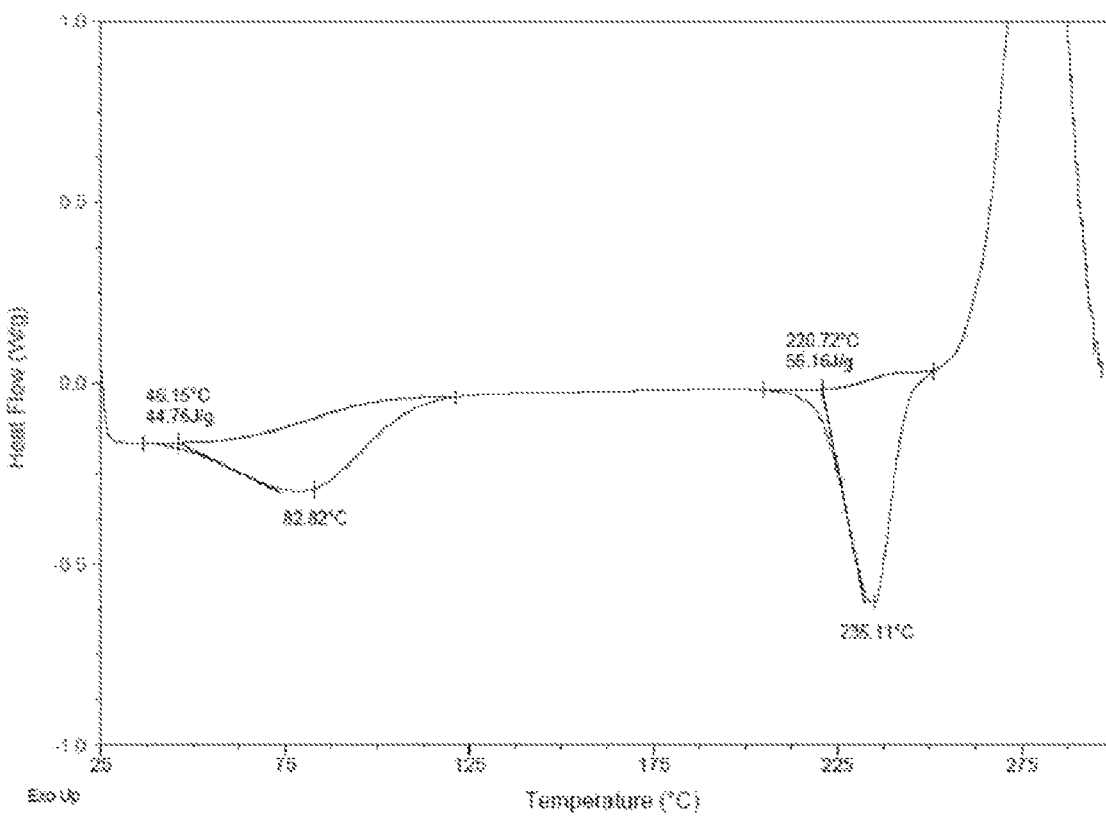
FIG. 161 depicts a DSC Thermogram of Compound 1 mesylate.

34 mg Compound 1 was weighed into a 4-mL glass vial and then 0.65 mL of 0.1M methanesulfonic acid in acetonitrile was added. No clear solution was achieved, however, new solid phase was obviously observed. The solid was collected via filtration and dried at 40° C. under vacuum overnight, and then analyzed by XRPD, TGA and DSC, as shown in FIG. 159 to FIG. 161.

Figure 162:
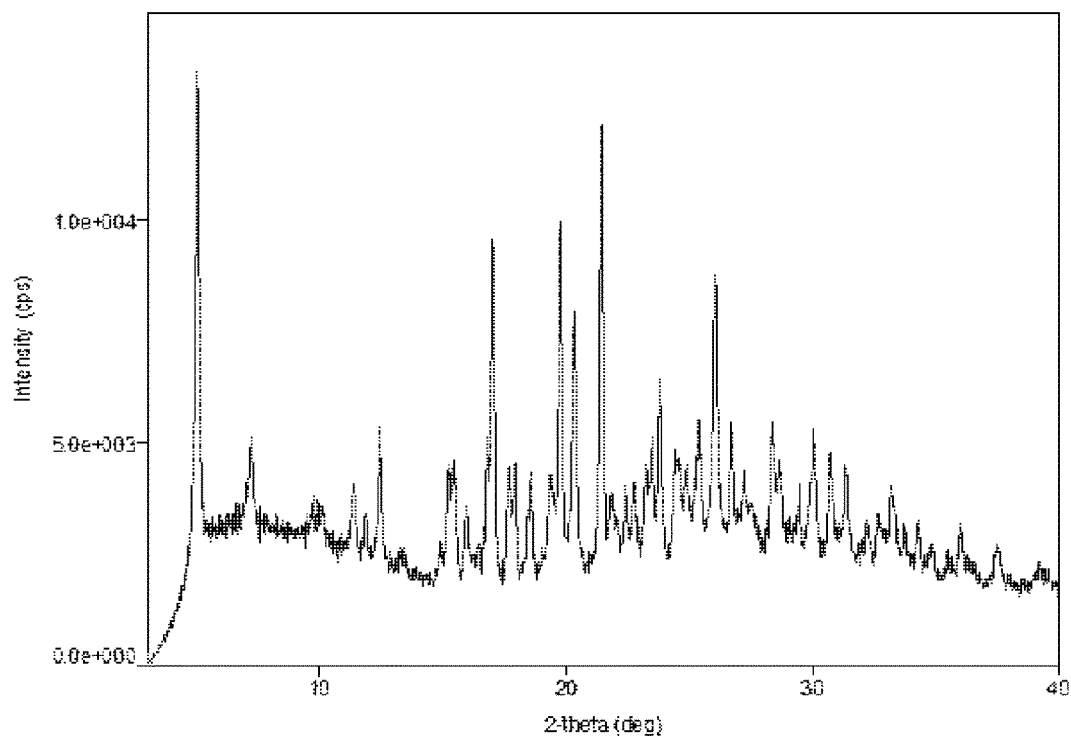
FIG. 162 depicts a XRPD Pattern of Compound 1 mesylate after slurry in water.

Mesylate salt form: After slurry in water, the XRPD profile is slightly different as shown in FIG. 162.

Figure 163:
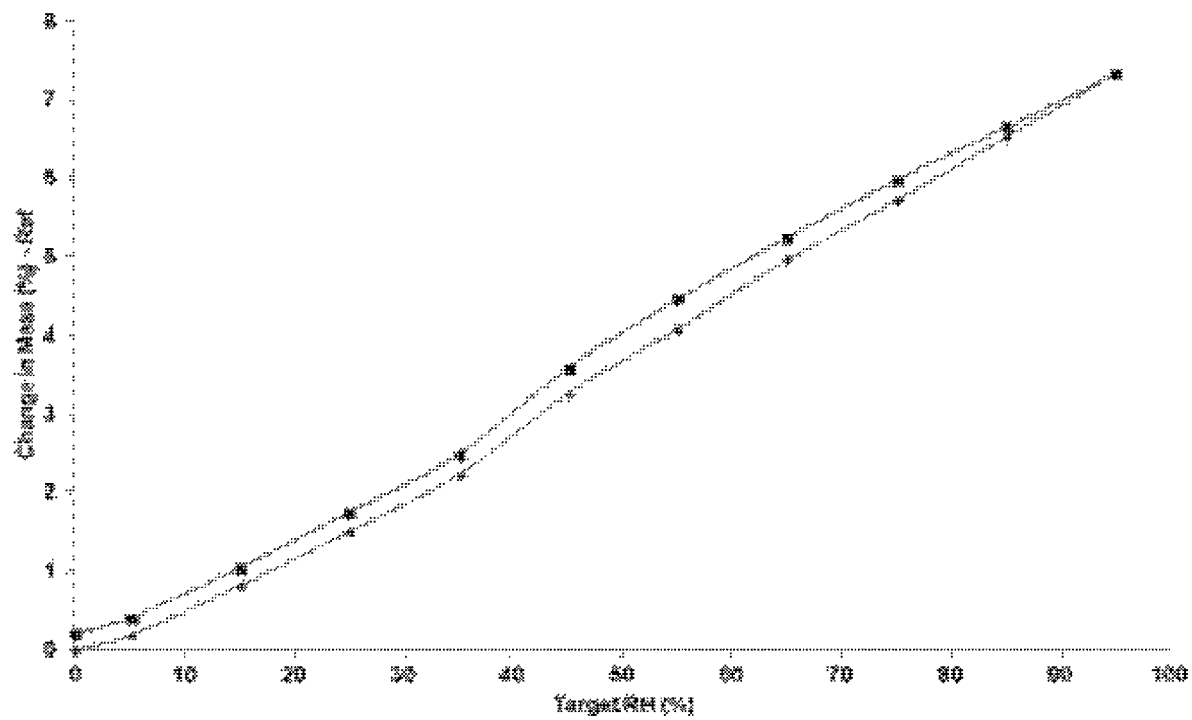
FIG. 163 depicts a DVS Isotherm Plot of Compound 1 mesylate salt.
Figure 164:
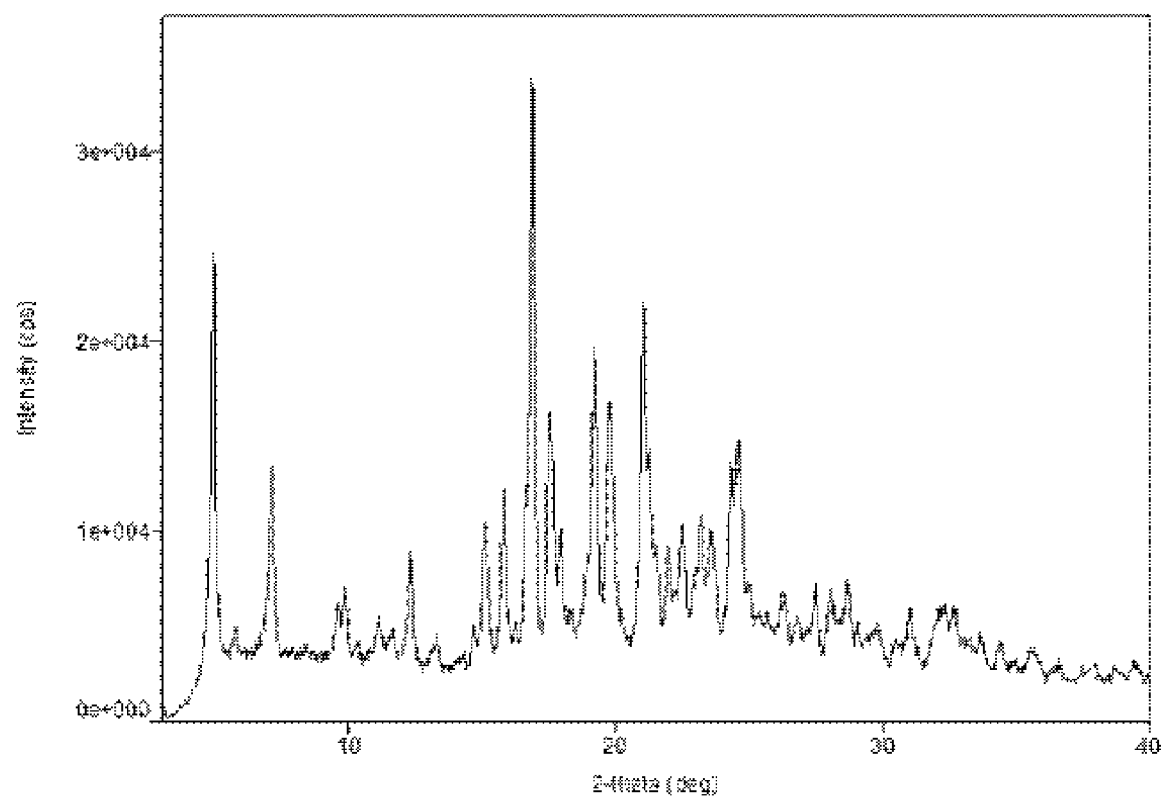
FIG. 164 depicts a XRPD Pattern of Compound 1 mesylate after DVS study.

Meslyate salt was also studied under moisture using dynamic vapour sorption (DVS). After sorption and desorption cycle (FIG. 163), the XRPD pattern is slightly different from the starting material, as shown in FIG. 164.

Figure 165:
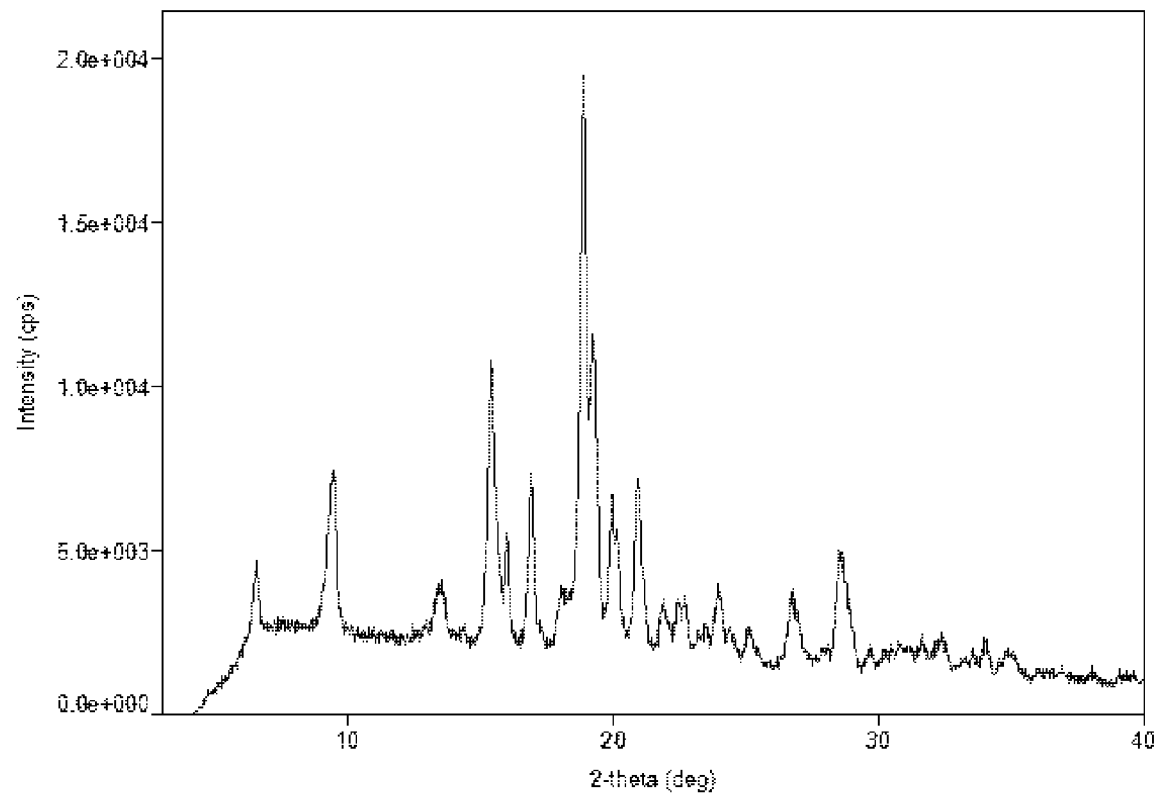
FIG. 165 depicts a XRPD Pattern of Compound 1 citrate in EtOAc-water system.
Figure 166:
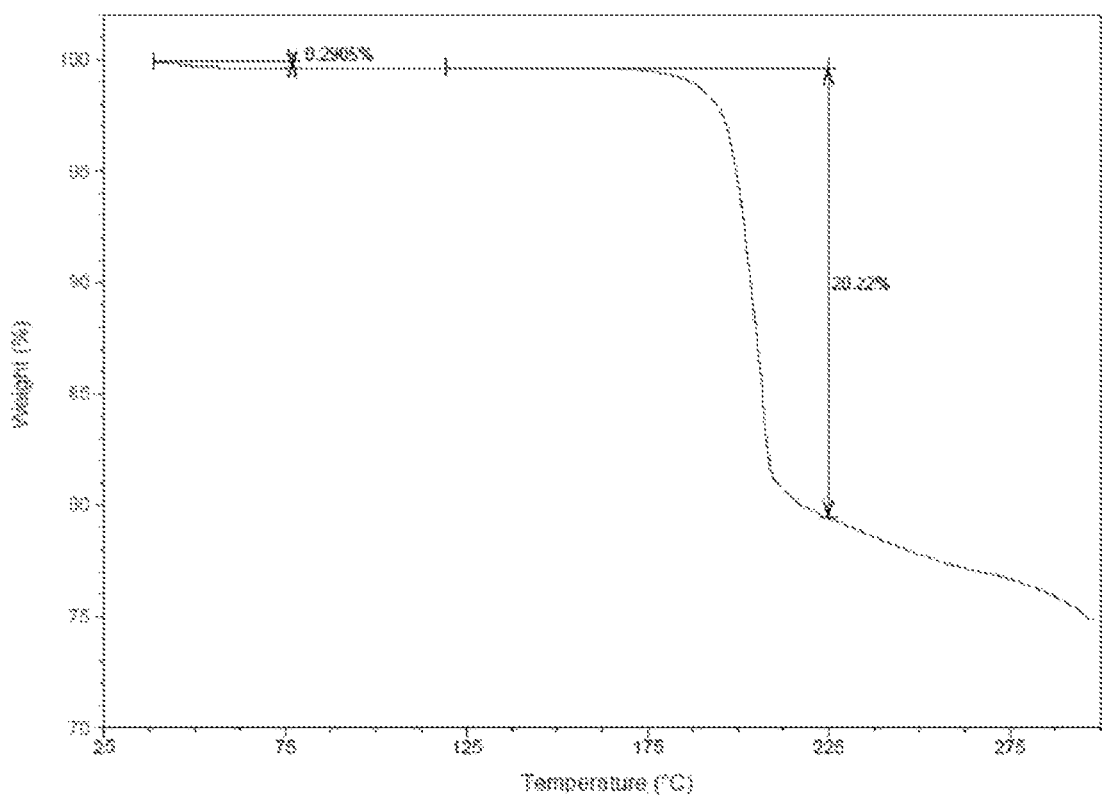
FIG. 166 depicts a TGA Thermogram of Compound 1 citrate in EtOAc-water system.
Figure 167:
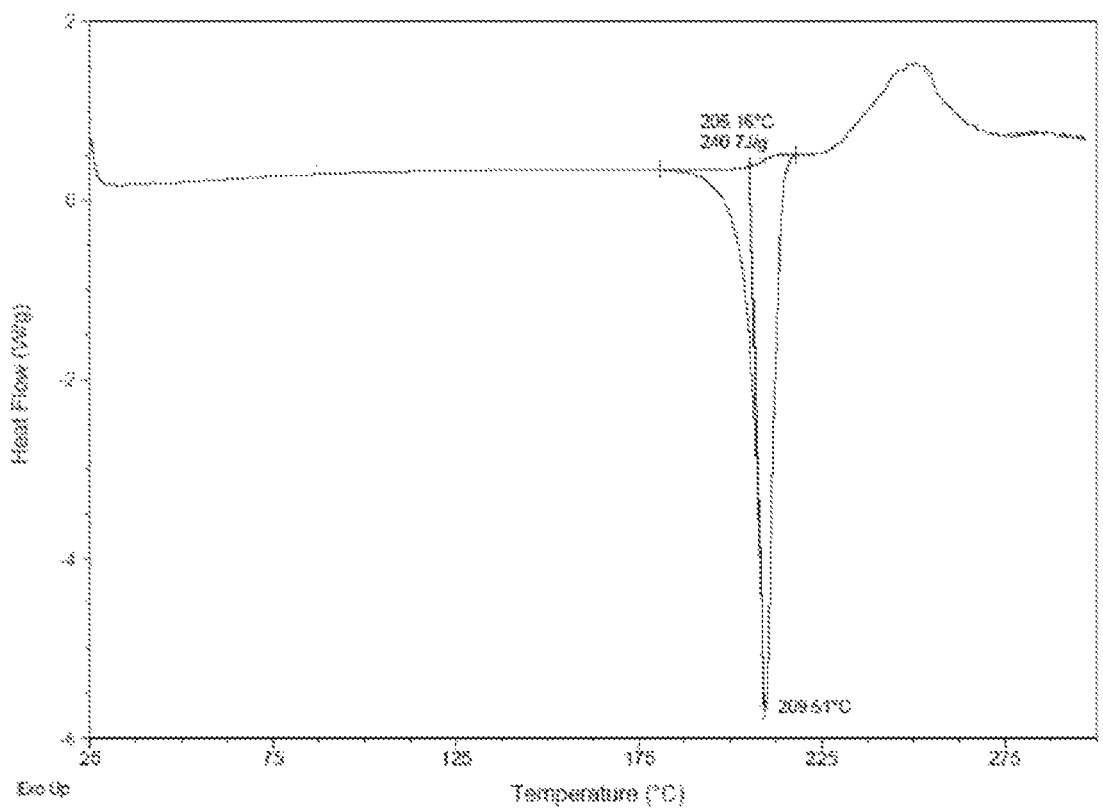
FIG. 167 depicts a DSC Thermogram of Compound 1 citrate in EtOAc-water system.

114 mg Compound 1 was weighed in a glass vial and then 0.6 mL EtOAc solvent was added. The mixture became clear solution after agitation. 2.20 mL of 0.1N citric in water was added into the solution, and cotton-like precipitates appeared immediately. The solid was collected via filtration and characterized, as shown in FIG. 165 to FIG. 167. TGA showed little weight loss (<0.2%) at relatively low temperature prior to decomposition. DSC showed a single endothermic peak due to melting with onset and peak temperatures of 205.2 and 209.5° C., respectively, with enthalpy of 240.7 J/g.

95 mg Compound 1 was weighed in a glass and then 0.5 mL acetone solvent was added to dissolve the material. Then 1.8 mL of 0.1N citric in acetone was added. The clear solution was placed under hood for crystallization. Soon, precipitates appeared.

Figure 168:
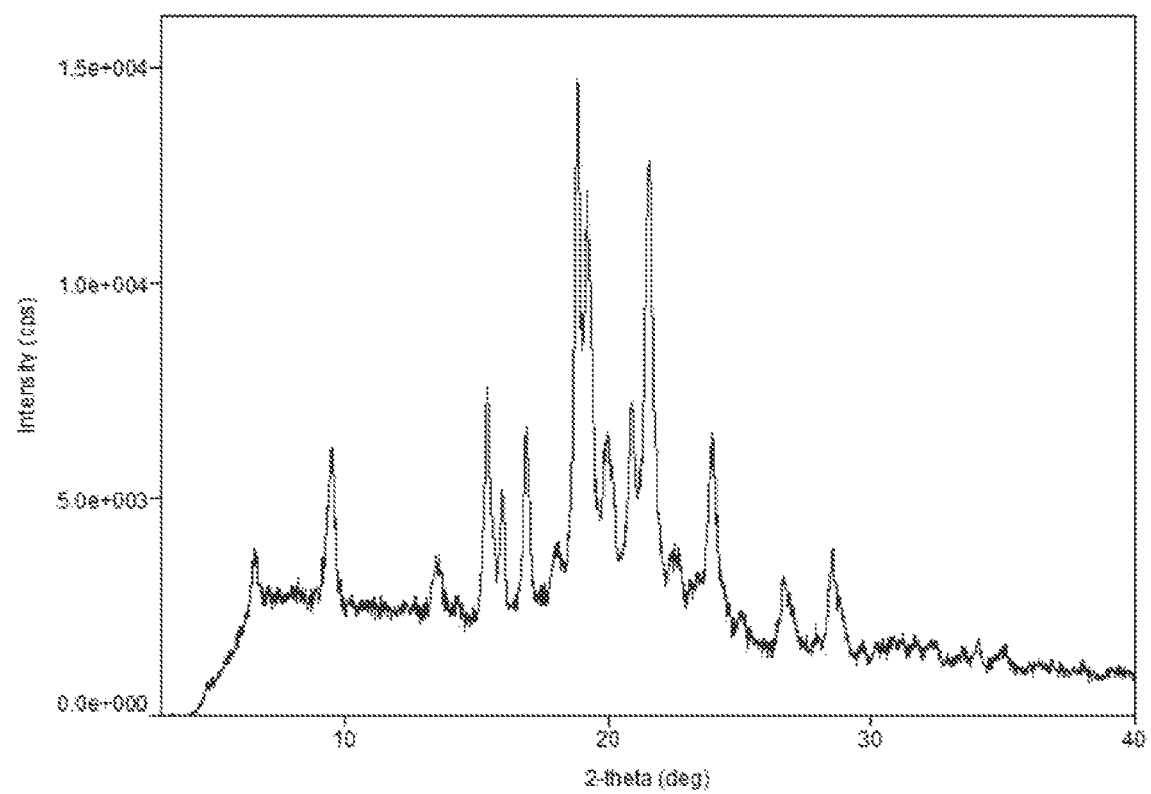
FIG. 168 depicts a XRPD Pattern of Compound 1 citrate in acetone.
Figure 169:
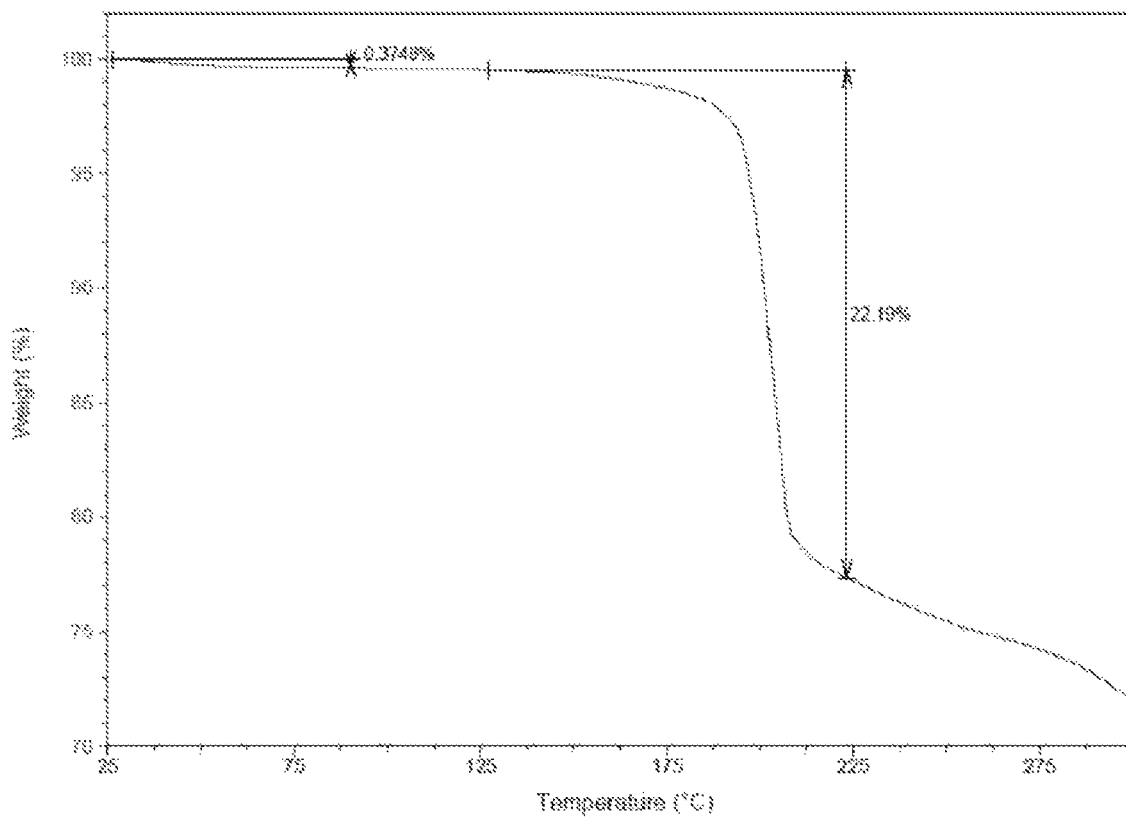
FIG. 169 depicts a TGA Thermogram of Compound 1 citrate in acetone.
Figure 170:
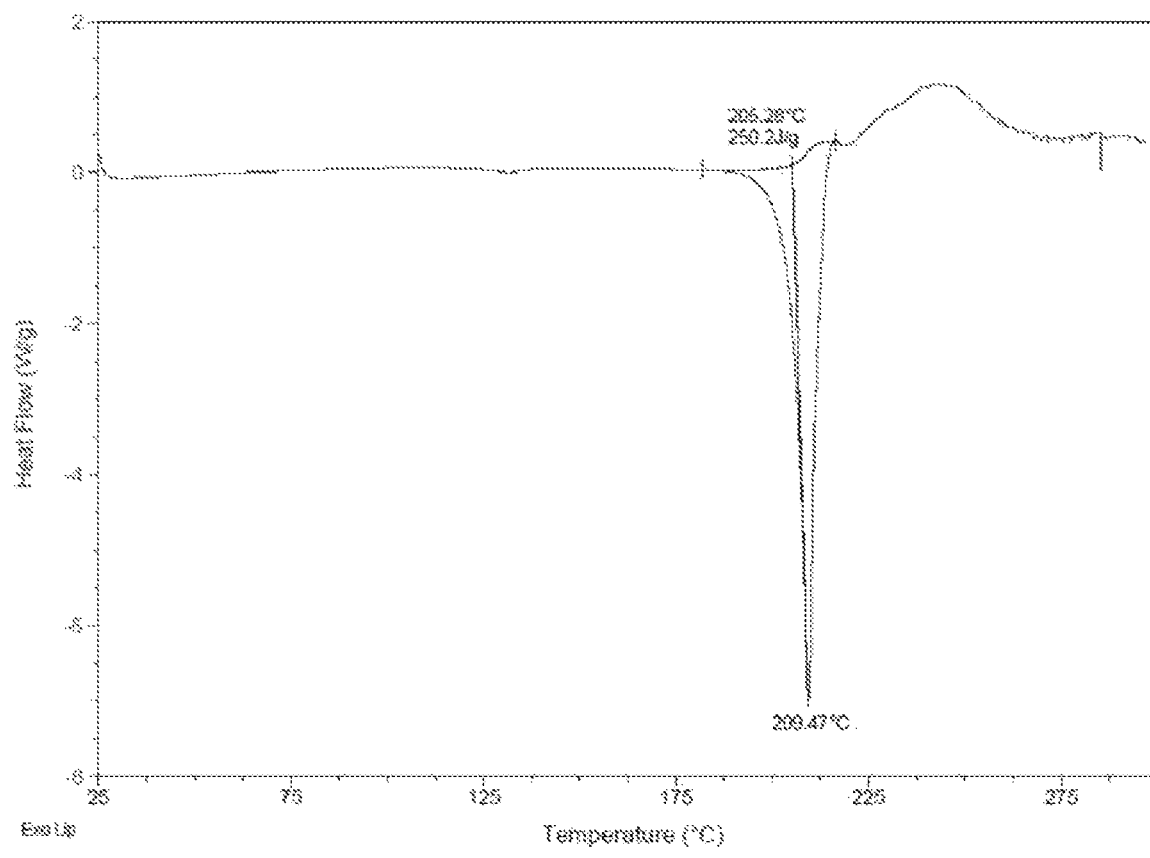
FIG. 170 depicts a DSC Thermogram of Compound 1 citrate in acetone.
Figure 171:
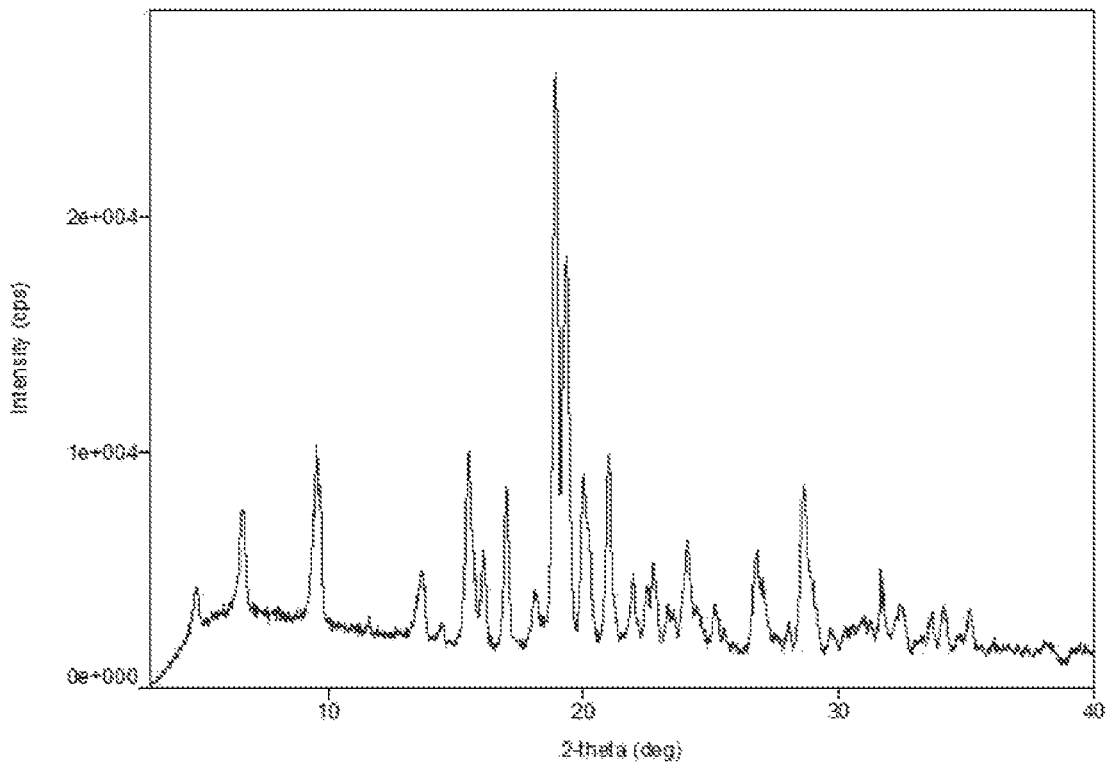
FIG. 171 depicts a XRPD Pattern of Compound 1 citrate.
Figure 172:
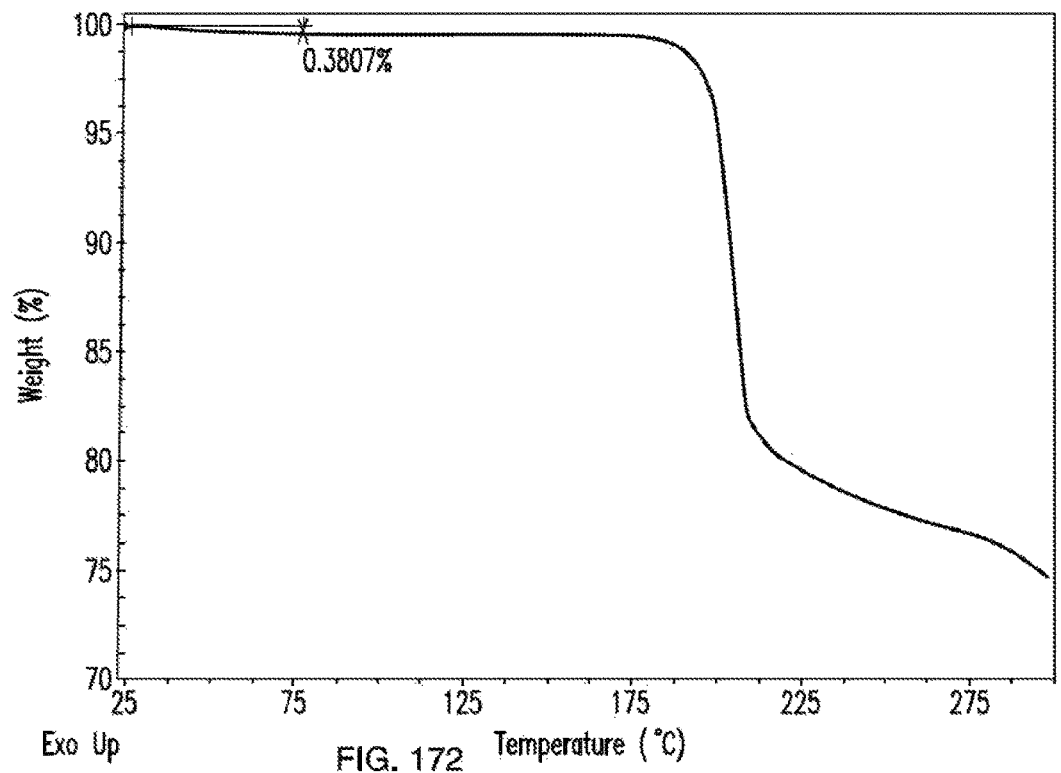
FIG. 172 depicts a TGA Thermogram of Compound 1 citrate.
Figure 173:
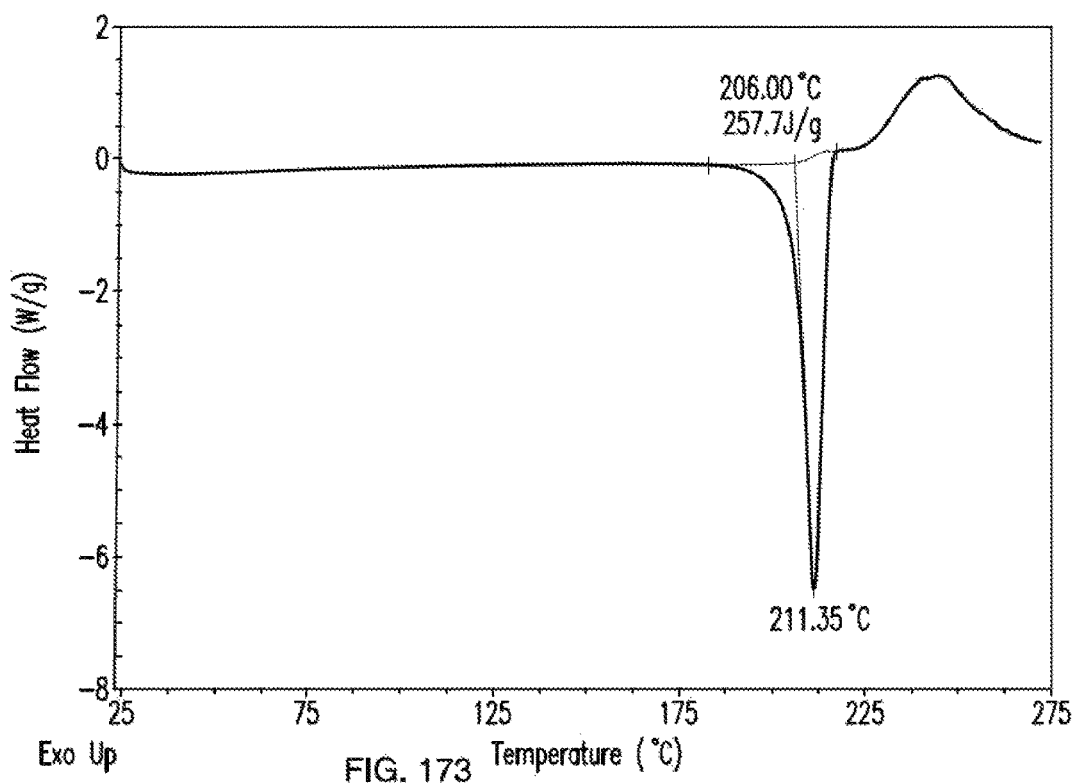
FIG. 173 depicts a DSC Thermogram of Compound 1 citrate.

The solid was collected via filtration and characterized, as shown in FIG. 168 to FIG. 170. XRPD profile was similar to form 1. TGA showed little weight loss (<0.4%) at relatively low temperature prior to decomposition. DSC showed a single endothermic peak due to melting with onset and peak temperatures of 205.3 and 209.5° C., respectively, with enthalpy of 250.2 J/g.

208 mg Compound 1 was weighed in a glass and then 1.0 mL acetone solvent was added to dissolve the material. Then 4.0 mL of 0.1N citric in water was added. The clear solution was placed under hood for crystallization. Soon, precipitates appeared. The solid was collected via filtration and characterized. TGA showed little weight loss (<0.4%) at relatively low temperature prior to decomposition. DSC showed a single endothermic peak due to melting with onset and peak temperatures of 206.0 and 211.4° C., respectively, with enthalpy of 257.7 J/g.

TGA showed nearly no weight losses prior to decomposition, however, both NMR and GC analysis showed the presence of 4000-5000 ppm acetone.

Figure 174:
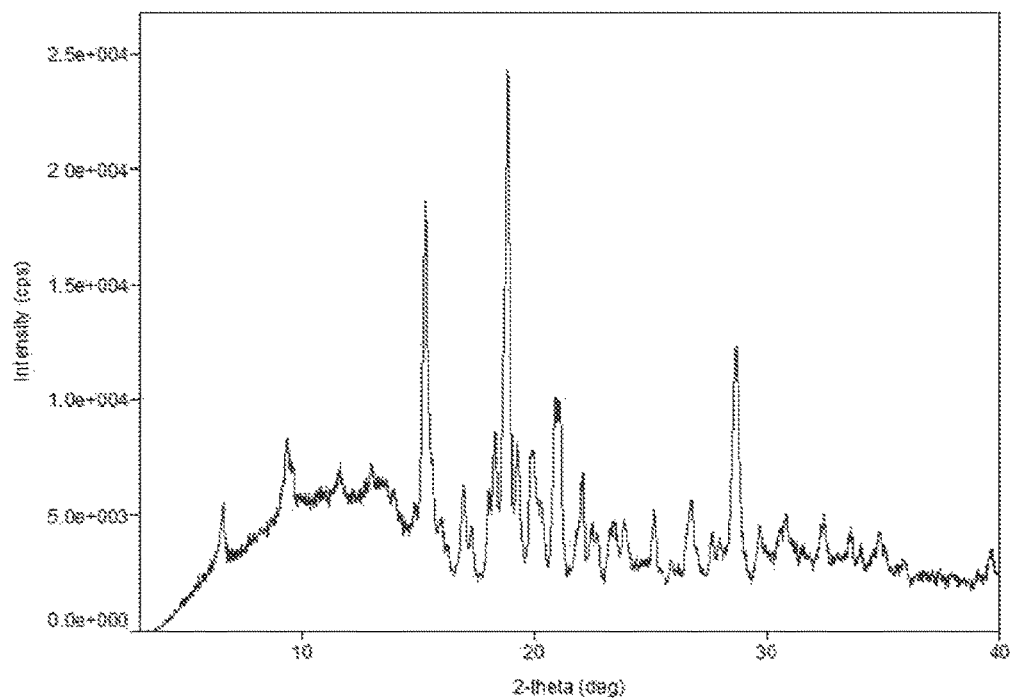
FIG. 174 depicts a XRPD Pattern of Compound 1 citrate.
Figure 175:
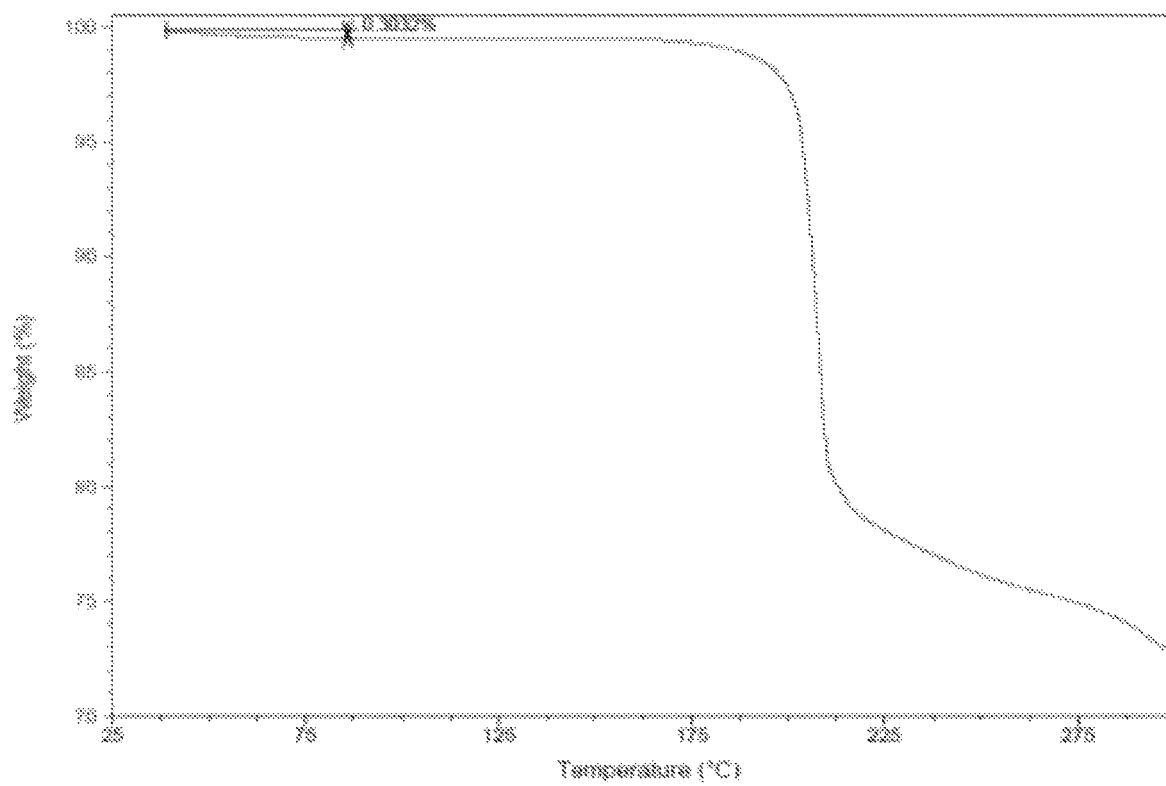
FIG. 175 depicts a TGA Thermogram of Compound 1 citrate.
Figure 176:
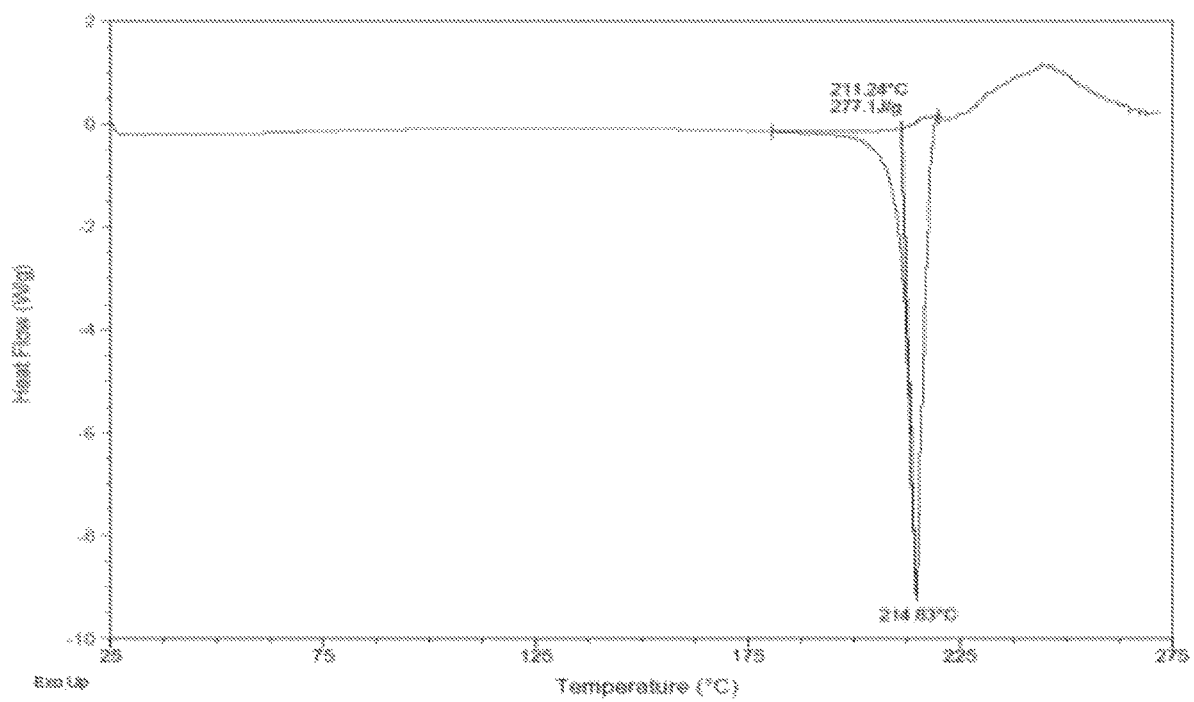
FIG. 176 depicts a DSC Thermogram of Compound 1 citrate.
Figure 177:
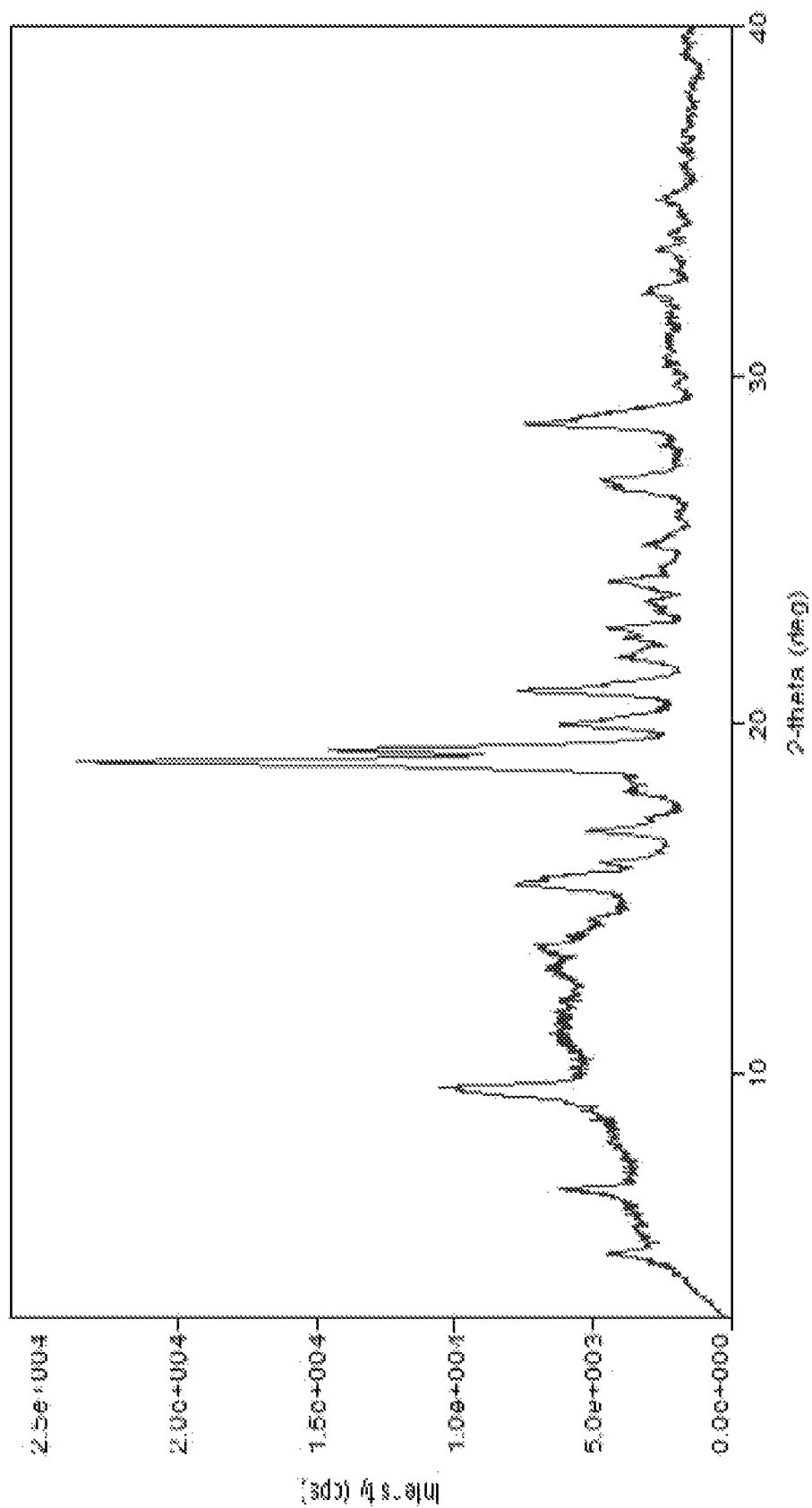
FIG. 177 depicts a XRPD Pattern of Compound 1 citrate.
Figure 178:
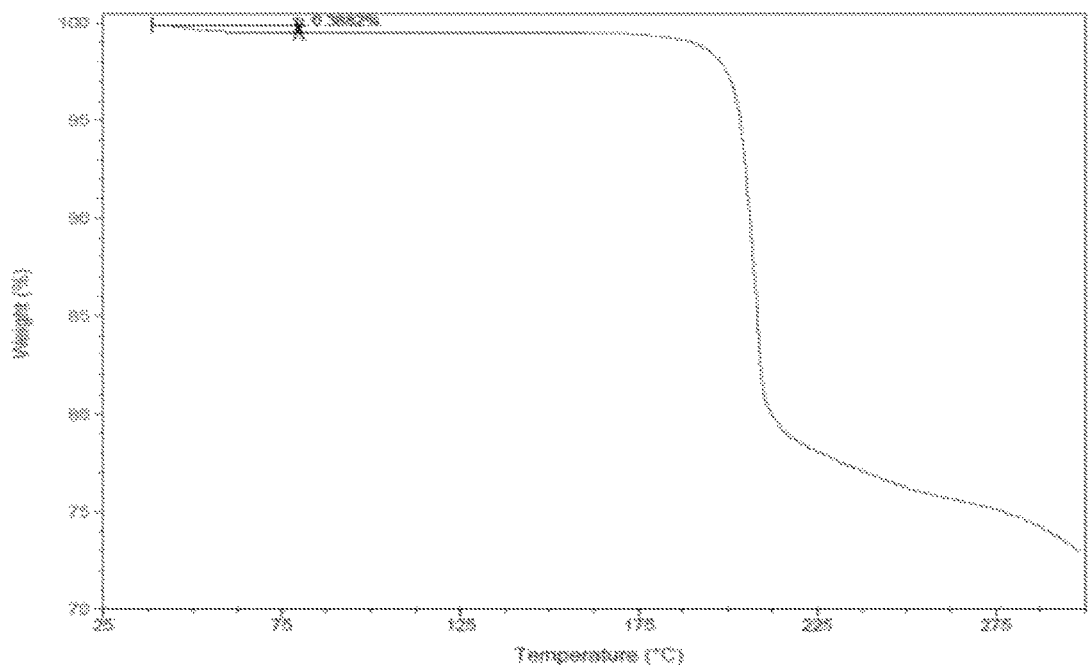
FIG. 178 depicts a TGA Thermogram of Compound 1 citrate.
Figure 179:
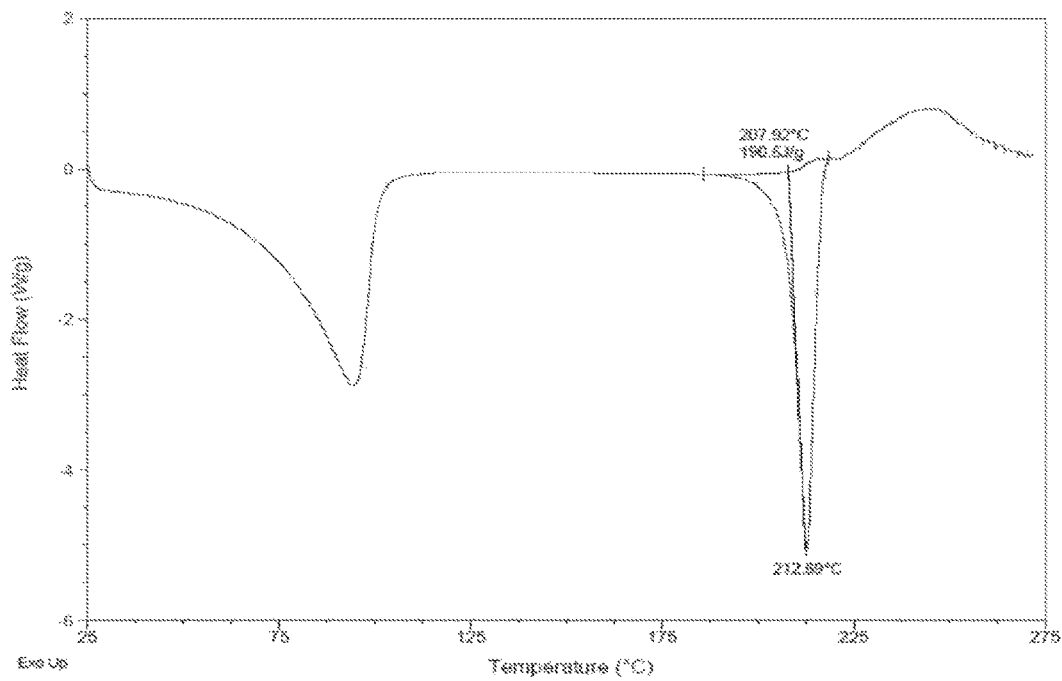
FIG. 179 depicts a DSC Thermogram of Compound 1 citrate.

43.02 mg Compound 1 was weighed in a glass and then 1.0 mL Ethanol solvent was added to dissolve the material (not completely). Then 0.82 mL of 0.1N citric in water was added and the mixture became clear. The clear solution was placed under hood for crystallization. Soon, precipitates appeared. Additional 1.0 mL of water added. The solid was collected via filtration and characterized, as shown in FIG. 174 to FIG. 176.

XRPD profile was different from forms 1, 2, and 3. TGA showed little weight loss (<0.3%) at relatively low temperature prior to decomposition. DSC showed a single endothermic peak due to melting with onset and peak temperatures of 211.2 and 214.8° C., respectively, with enthalpy of 277.1 J/g.

45.74 mg Compound 1 was weighed in a glass and then 1.0 mL IPA solvent was added to dissolve the material (cloudy). Then 0.87 mL of 0.1N citric in water was added, and the mixture became clear. The clear solution was placed under hood for crystallization. Shortly, precipitates appeared.

The solid was collected via filtration and characterized, TGA showed little weight loss (<0.3%) at relatively low temperature prior to decomposition. However, DSC showed a broad endothermic peak at relatively low temperature due possibly to desolvation and melting peak with onset and peak temperatures of 207.9 and 212.7° C., respectively, with enthalpy of 190.7 J/g.

Figure 180:
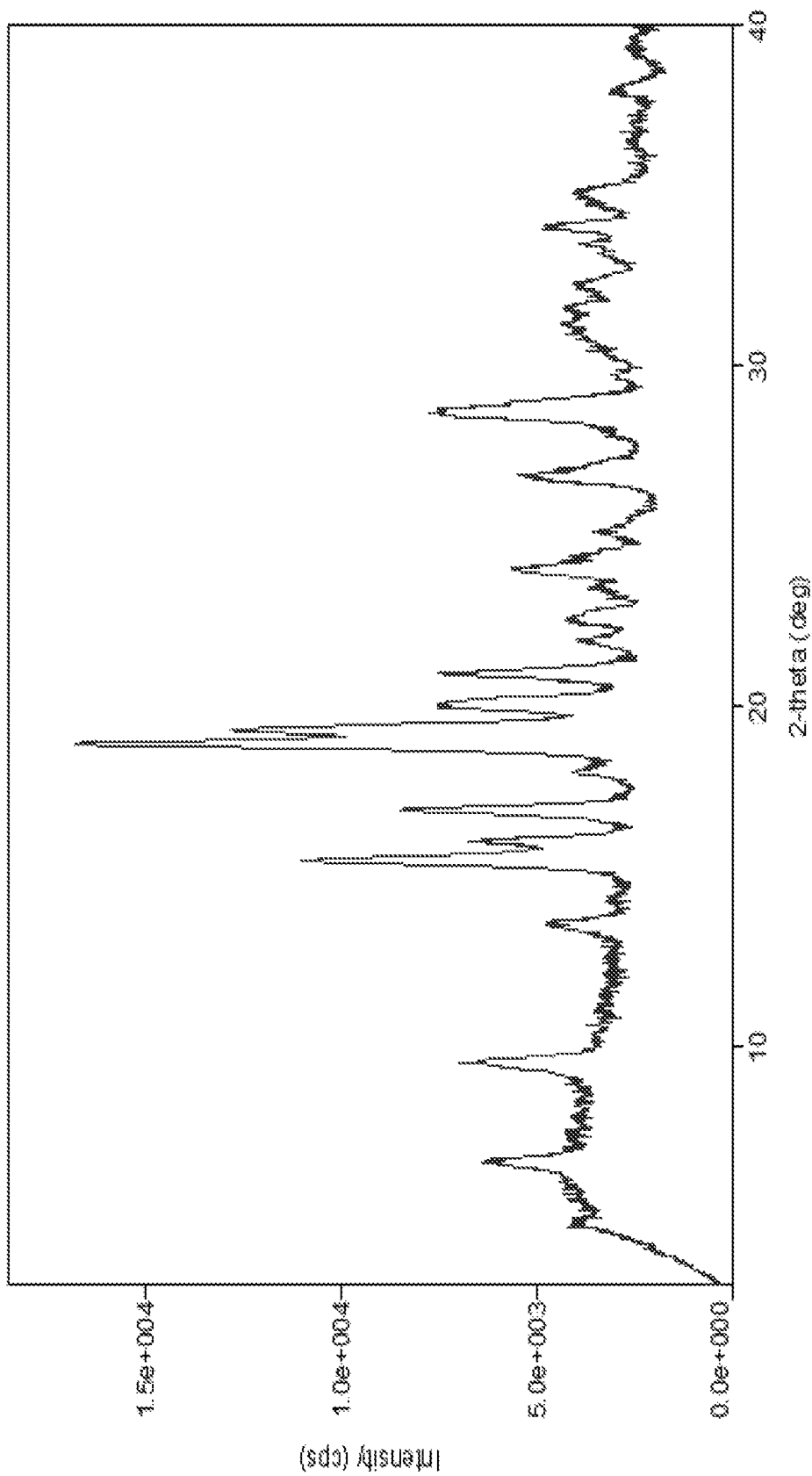
FIG. 180 depicts a XRPD Pattern of Compound 1 citrate.
Figure 181:
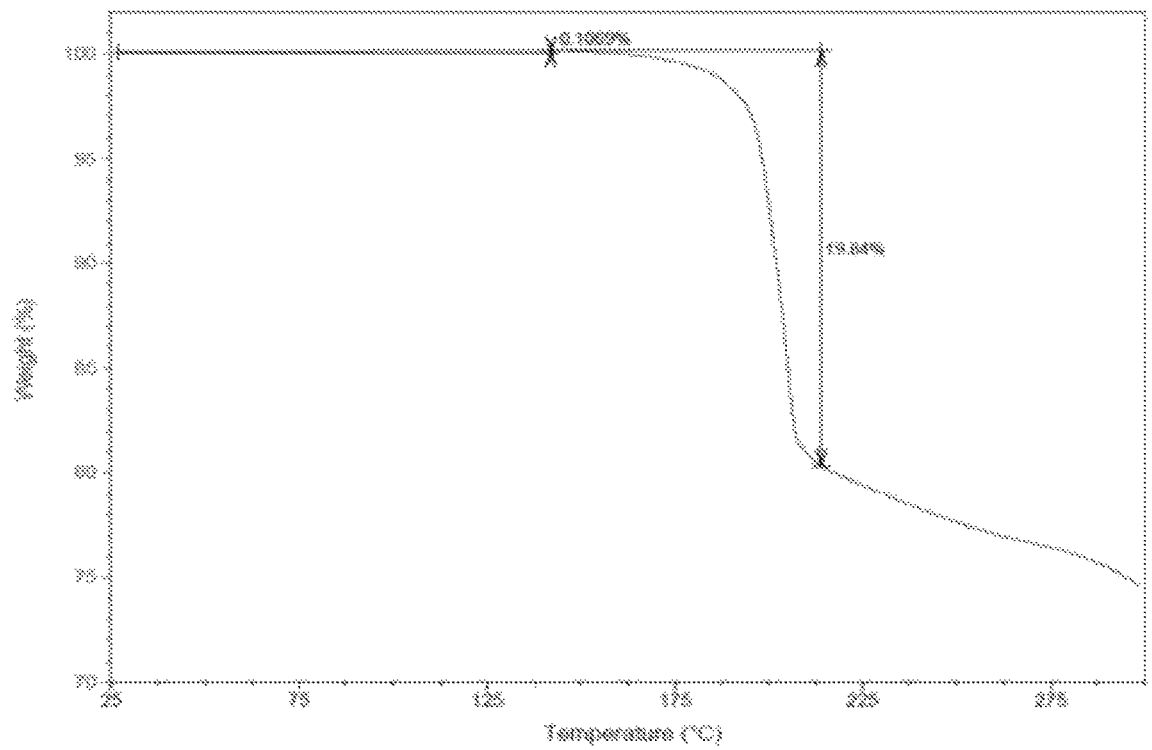
FIG. 181 depicts a TGA Thermogram of Compound 1 citrate.
Figure 182:
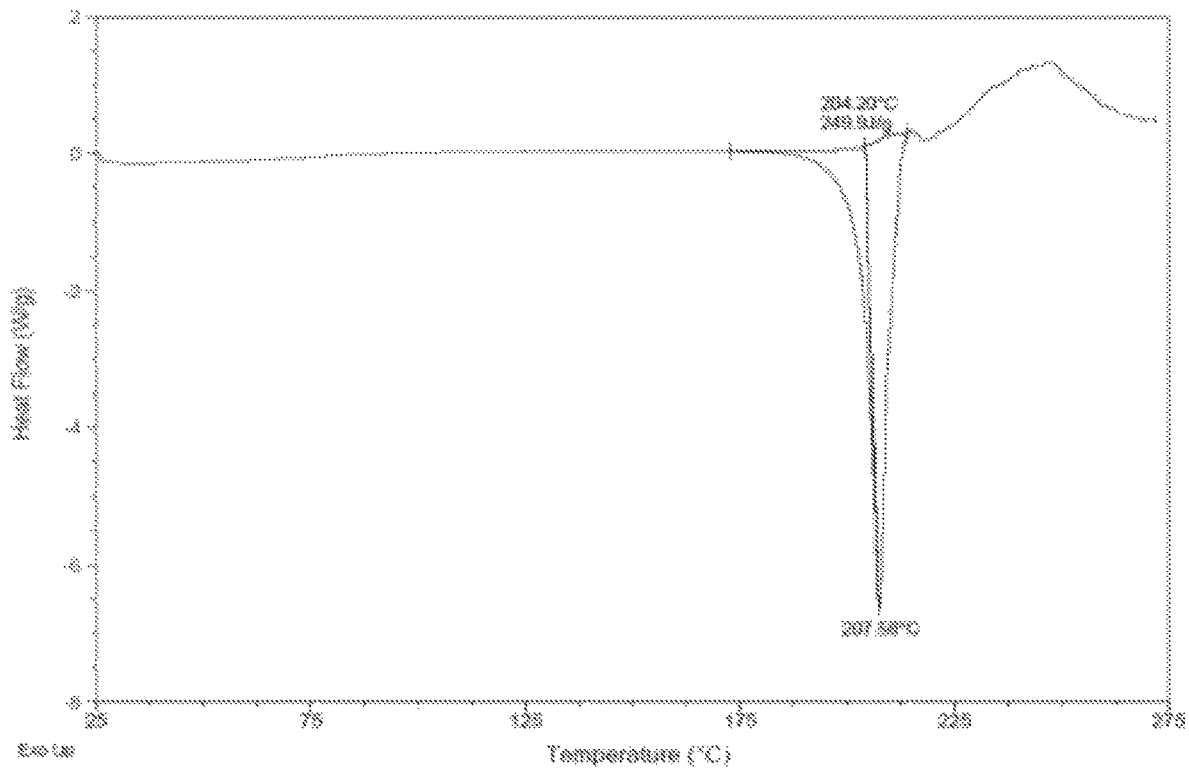
FIG. 182 depicts a DSC Thermogram of Compound 1 citrate.

51.4 mg Compound 1 was weighed in a glass and then 1.0 mL of 0.1N citric acid in water was added. The suspension was kept agitation at ambient for conversion and crystallization. (Addition 1 mL water). The solid was collected via filtration and characterized, as shown in FIG. 180 to FIG. 182. TGA showed little weight loss (<0.1%) at relatively low temperature prior to decomposition. DSC showed a single of melting peak with onset and peak temperatures of 204.2 and 207.6° C., respectively, with enthalpy of 249.9 J/g.

Figure 183:
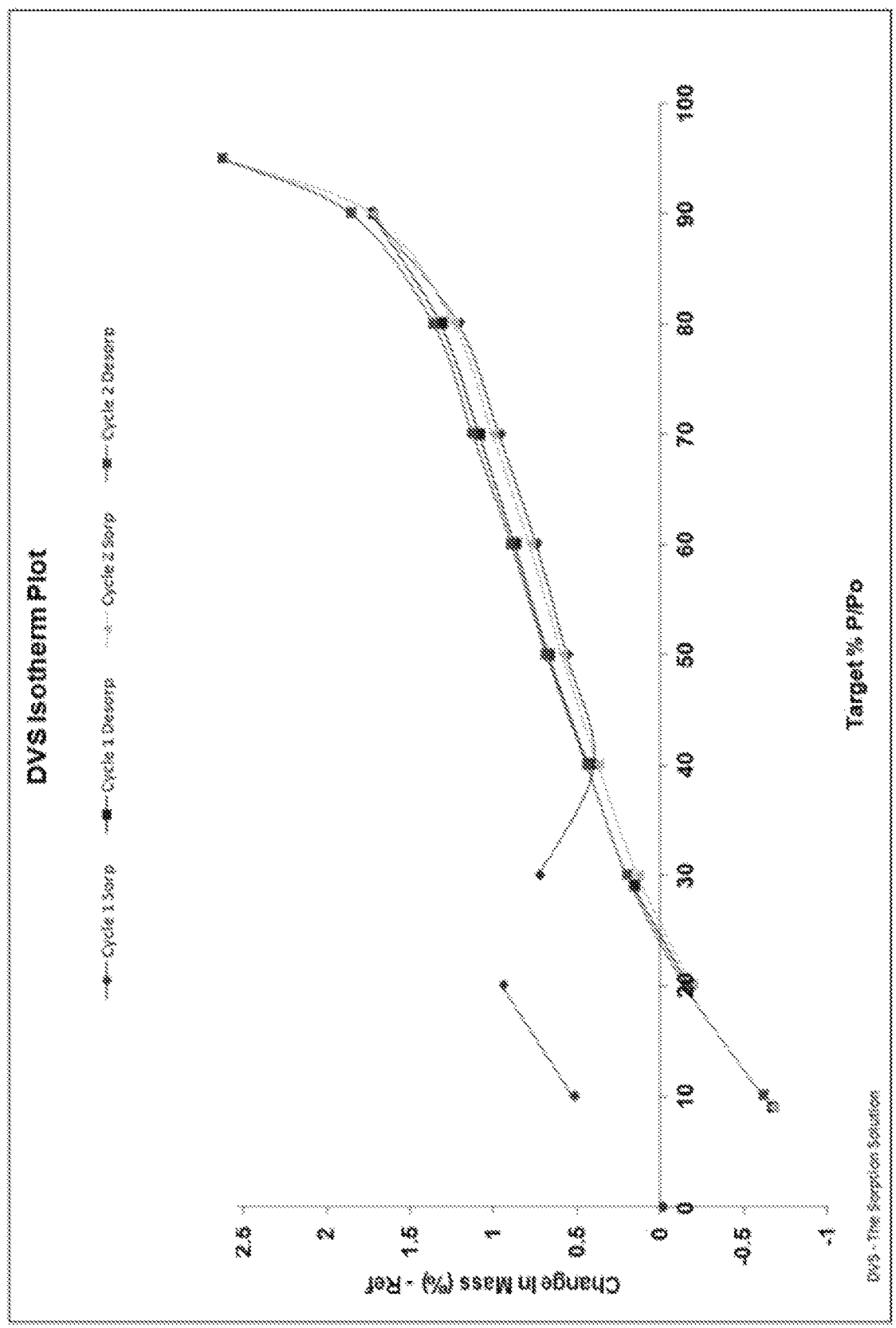
FIG. 183 depicts a DVS Isotherm Plot of Compound 1 citrate salt.
Figure 184:
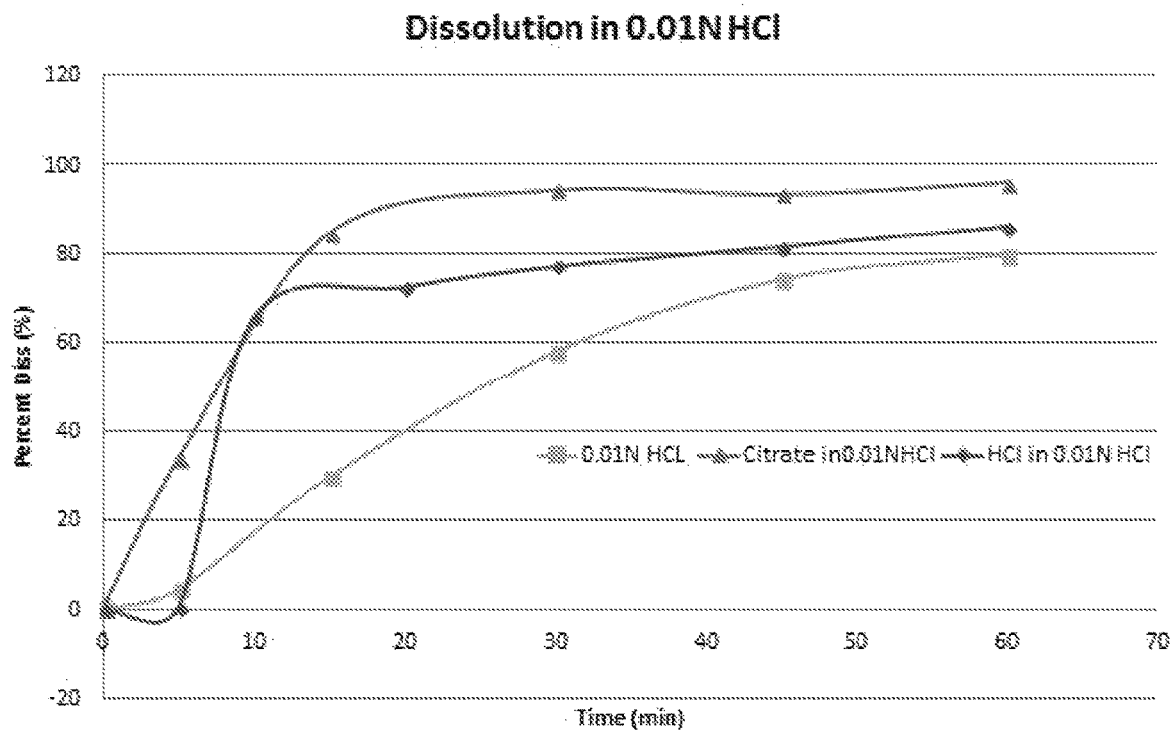
FIG. 184 depicts a Dissolution of free base (FB), citrate and HCl salt in 0.01N HCl solution.
Figure 185:
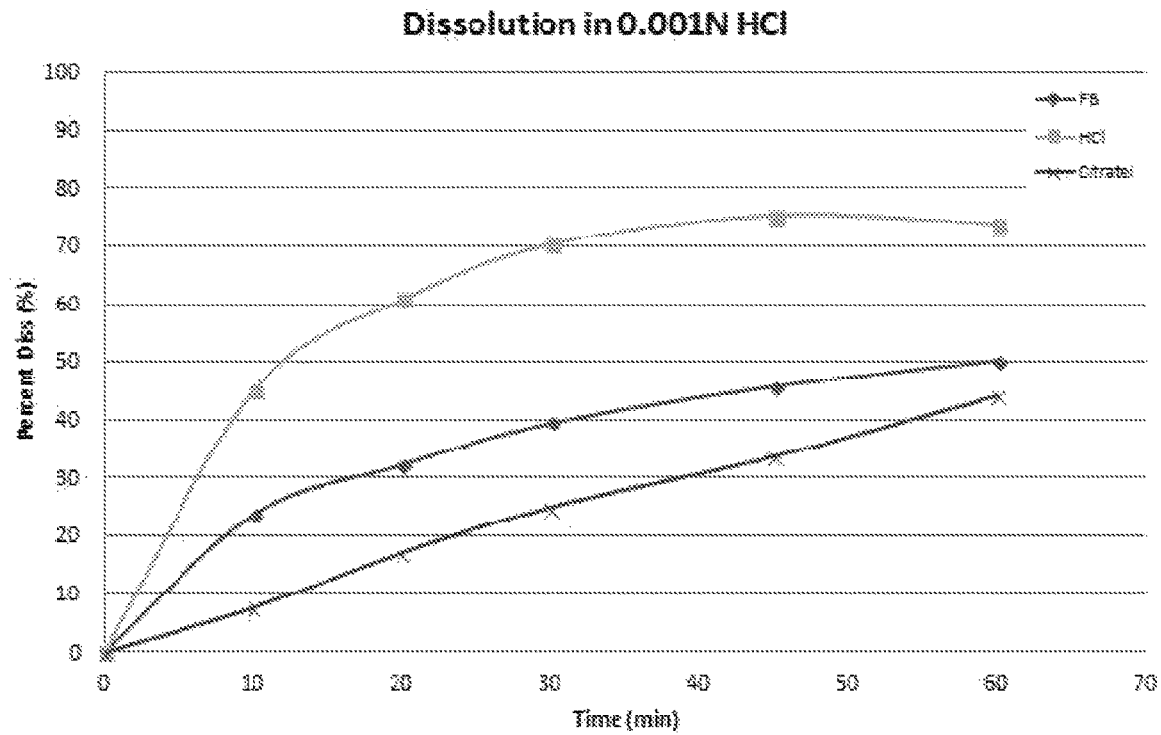
FIG. 185 depicts a Dissolution of Compound 1 free base (FB), citrate, and HCl salt in 0.001N HCl solution.

Citrate salt showed low hygroscopicity as demonstrated from dynamic vapor sorption (DVS) study (FIG. 183). From SVSS screening, the solid forms with citric acid in various solvents resulted in similar XRPD profile, which are likely an isostructural solvates. TGA showed slight weight loss (<0.5%) at relatively low temperature, DSC showed single endothermic peak with onset and peak temperatures of 205.3 and 209.5° C. Citrate salt produced in several solvents including ethanol, IPA, acetone, and EtOAc.

The solubility of HCl hydrate Form (2), citrate salt Form Z (2) and free base was determined in water, simulated gastric fluid (SGF), simulated intestinal fluid (SIF), and 0.5% HPMC in 0.25% Tween 80. The solubility in water varied, depending on pH. It can be seen from Table 3 that HCl salt monohydrate has highest solubility in water (sparingly soluble in water) at pH 3.65. The solubility of citrate salt and free base in water are 0.252 and 0.003 mg/mL, respectively, depending on pH. The pH in water media was determined by both counter-ions and solubility. HCl salts resulted in lowest pH 3.65 in water while citrate resulted in pH relative high pH=4.61. Solubility of HCl salt form in SGF has effect of common ions; however, free base has significant high kinetic solubility in SGF, followed by citrate salt. Solubility of these salts as well as free base in SIF is quite low, practically insoluble in SIF.

TABLE 3

Solubility of various salt forms in water, SGF, SIF and 0.5% HPMC in 0.25 Tween80.

| Forms | Media | Conc. at 2 Hrs (mg/mL) | Conc. at 24 Hrs (mg/mL) | pH at final |
|---|---|---|---|---|
| Free Base | Water | 0.000 | 0.003 | 8.11 |
| | SGF | >31 | 3.480 | 1.93 |
| | SIF | 0.000 | 0.002 | 7.33 |
| | 0.5% HPMC/0.25% Tween80 | 0.208 | 0.178 | 4.23 |
| HCl Salt | Water | 1.664 | 1.726 | 3.65 |
| | SGF | 0.361 | 0.351 | 1.17 |
| | SIF | 0.000 | 0.000 | 7.22 |
| | 0.5% HPMC/0.25% Tween80 | 3.878 | 4.696 | 3.06 |
| Citrate | Water | 0.076 | 0.252 | 4.61 |
| | SGF | 1.954 | 1.691 | 1.44 |
| | SIF | 0.000 | 0.000 | 7.32 |
| | 0.5% HPMC/0.25% Tween80 | 0.186 | 0.325 | 3.81 |

The solubility of HCl and citrate salt was also determined in biorelevant media in comparison with free base. In the presence of surfactants (Sodium taurocholate and Lecithin), the solubility values of HCl salt, citrate and free base are similar in both FeSSIF and FaSSIF (Table 4).

TABLE 4

Solubility of HCl and citrate salts in biorelevant media in comparison with free base.

| | Free Base | | HCl salt | | Citrate | |
|---|---|---|---|---|---|---|
| Media | Conc. mg/mL | pH | Conc. mg/mL | pH | Conc. mg/mL | pH |
| FeSSIF | 1.920 | 4.95 | 1.978 | 4.85 | 1.957 | 4.71 |
| FaSSIF | 0.025 | 6.37 | 0.043 | 6.12 | 0.024 | 4.65 |
| FaSSGF | 3.847 | 2.77 | 0.121 | 1.82 | 0.227 | 1.93 |
| FeSSGF | 0.002 | 6.23 | 0.001 | 5.66 | 0.001 | 5.21 |

Figure 186:
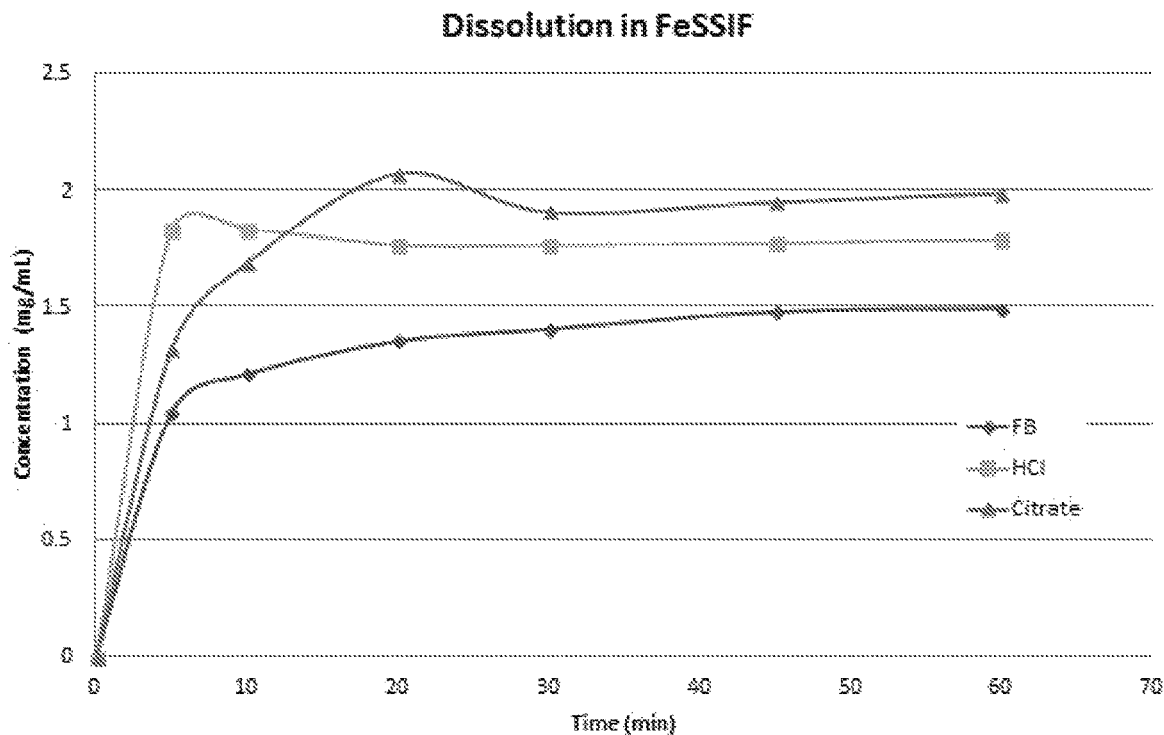
FIG. 186 depicts a Kinetic solubility of free base (FB), citrate, and HCl salt in FeSSIF.
Figure 187:
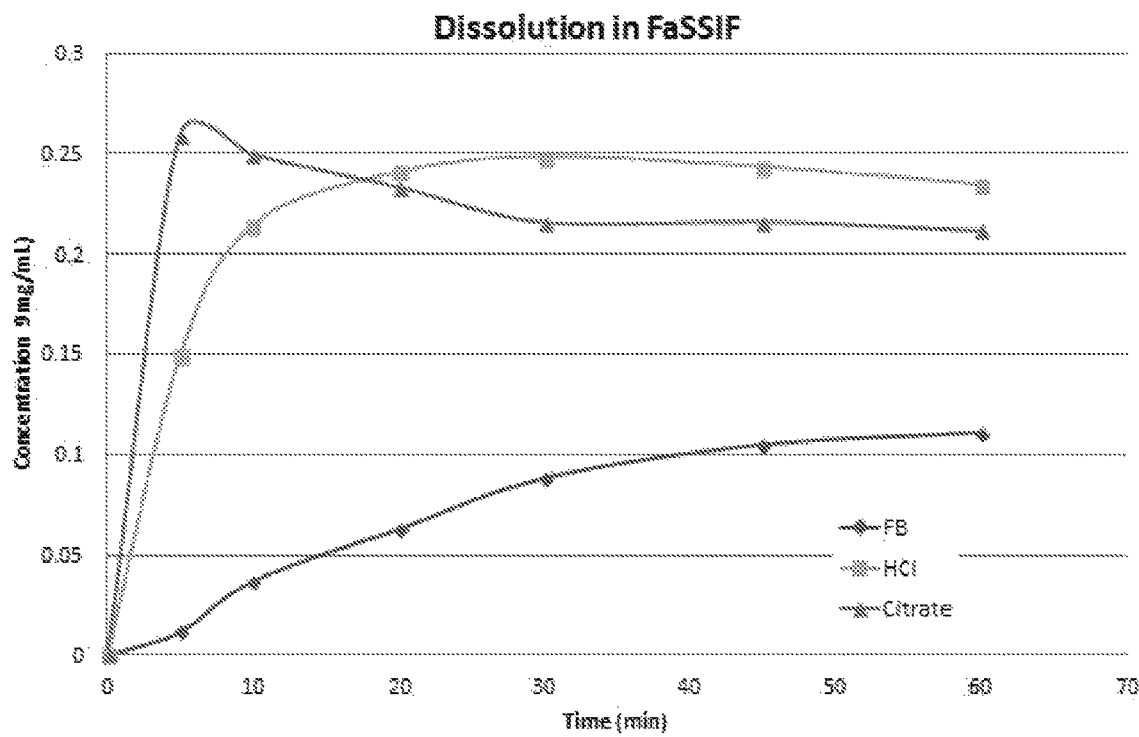
FIG. 187 depicts a Kinetic solubility of free base (FB), citrate, and HCl salt in FaSSIF.

Among the free base, HCl and citrate salt, there did not no significant difference in the solid state properties. They are all chemically and physically stable in solid state. The data herein suggest that the solubility of free base, HCl and citrate salt depends on the pH, the effect of common ions, and the presence of surfactants. No conclusive PK results were obtained from single dog PK comparison study. All of solid forms showed similar dissolution profiles in both FeSSIF and FaSSIF, (FIG. 186 and FIG. 187) and demonstrated similar dissolution profiles of BIC in both 0.01N HCl and 0.001N HCl.

TABLE 5

Solid state stability of salt forms and free base.

| Solid Forms | Chemical (40° C./ 75% RH) RRT = 2.2 | Chemical (60° C.) RRT2.2 | Physical (40° C./ 75% RH) | Physical (60° C.) |
|---|---|---|---|---|
| Free Base, hydrate | — | <0.03% | Stable | Dehydration (−), reversible + RH |
| HCl, hydrate2 | 0.02% | 0.05% | Stable | Stable |
| Citrate | 0.02% | 0.06% | Stable | Stable |

Solid Forms

Analytical Methods—Free Base

A polymorph screen of Compound 1 was performed to investigate whether different solid forms could be generated under various conditions, such as different solvents, temperature and humidity changes.

The solvents used in the polymorph screen were either HPLC or reagent grade, including acetonitrile (MeCN), MeCN/water (1:1), n-butanol (n-BuOH), absolute ethanol (EtOH), ethanol/water (1:1), methanol (MeOH), 2-propanol (IPA), ethyl acetate (EtOAc), methyl acetate (MeOAc), dichloromethane (DCM), methyl ethyl ketone (MEK), methyl t-butyl ether (MTBE), heptane, toluene, methyl acetate (MeOAc), isopropyl acetate (IPAc), methyl isobutyl ketone (MIBK), 2-methyltetrahydrofuran (2-MeTHF), 1,4-dioxane, tetrahydrofuran (THF), THF/water (1:1), and water.

A weighed sample of Compound 1 was treated with a known volume of a test solvent. The resulting mixture was agitated for about 1 day at room temperature. If all of the solids appeared to be dissolved by visual inspection, the estimated solubility was calculated based on the total volume of solvent used to give a complete solution. If solids were present, a known volume of filtrate was evaporated to dryness and the weight of the residue was measured to estimate the solubility.

All of the solid samples generated in the polymorph screen were analyzed by XRPD. XRPD analysis was conducted on a PANalytical Empyrean X-ray powder diffractometer using Cu Kα radiation at 1.54 Å.

The PANalytical Empyrean instrument was equipped with a fine focus X-ray tube. The voltage and amperage of the X-ray generator were set at 45 kV and 40 mA, respectively. The divergence slits were set at $\frac{1}{16}°$ and $\frac{1}{8}°$, and the receiving slit was set at $\frac{1}{16}°$. Diffracted radiation was measured using a Pixel 2D detector. A theta-two theta continuous scan was set at step size 0.013 from 3° to 40° 2θ with sample spinning rate at 4. A sintered alumina standard was used to check the peak positions.

DSC analyses were performed on a TA Discovery Differential Scanning Calorimeter. Indium was used as the calibration standard. Approximately 1-5 mg of sample was placed into a DSC pan. The sample was heated under nitrogen at a rate of 10° C./min, up to a final temperature of 220° C. Melting points were reported as the extrapolated onset temperatures.

TGA analyses were performed on a TA Discovery Thermogravimetric Analyzer. Approximately 2-10 mg of accurately weighed sample was placed on a pan and loaded into the TGA furnace. The sample was heated under nitrogen at a rate of 10° C./min, up to a final temperature of 220° C.

Morphology analysis of the samples was carried out on an Evex Mini-SEM. Small amounts of samples were dispersed on a sample holder, coated with gold using an Evex Mini Au Sputter Coater, and imaged with 300× to 1000× magnification.

Hygroscopicity was determined on a Surface Measurement Systems DVS. A sample size of 5-20 mg was loaded into the DVS instrument sample pan and the sample was analyzed on a DVS automated sorption analyzer at room temperature. The relative humidity was increased from 0% to 90% RH at 10% RH step, then decreased in a similar manner to accomplish a full adsorption/desorption cycle.

$^1$H NMR spectra were obtained on a Bruker 300 MHz NMR spectrometer. Samples were dissolved in DMSO-D$^6$ and analyzed with 8-64 scans.

Karl Fischer (KF) water content was measured using a Metrohm KF coulometric oven titrator equipped with an oven sample processor. The oven temperature was set as 100° C.

Equilibration/Slurry and Evaporation Experiments

Equilibrium and evaporation experiments carried out at room temperature. If solids were present after 1 day, they were filtered using a 0.45 μm PTFE filter and air-dried before analysis. The remaining supernatant was evaporated to dryness and the solids were isolated for analysis.

Equilibration and evaporation experiments at 50° C. were carried out by adding an excess of solid Compound 1 to up to 1 mL of a test solvent. The resulting mixture was agitated for 1 day at room temperature and 1 day at 50° C. separately. Upon reaching equilibrium, the saturated supernatant solution was removed, filtered using 0.45 μm PTFE filters and allowed to evaporate in an open vial under nitrogen at room temperature and 50° C., respectively. The solid resulting from the equilibration was isolated and air-dried before analysis.

TABLE 6

Summary Equilibrium (EQ) and Evaporation (EV) Results

| Solvent | EQ at RT | EV at RT | EQ at 50° C. | EV at 50° C. |
|---|---|---|---|---|
| 1,4-dioxane | — | amorphous | — | amorphous |
| 2-MeTHF | — | amorphous | — | amorphous |
| acetone | — | amorphous | — | amorphous |
| DCM | — | amorphous | — | amorphous |
| MeCN | A + C | — | C + A | — |
| MeCN/water (1:1) | A + C | — | C + A | — |
| EtOAc | — | amorphous | H + A | amorphous |
| EtOH | — | amorphous | H + A | amorphous |
| EtOH/water (1:1) | A + H | — | E | — |
| water | A | — | A | — |
| Heptane | A | — | A | — |
| IPA | D | amorphous | F | F |
| IPAc | — | amorphous | — | amorphous |
| MEK | — | amorphous | — | amorphous |
| MeOAc | — | amorphous | — | amorphous |
| MeOH | — | amorphous | — | amorphous |
| MIBK | — | amorphous | — | amorphous |
| MTBE | — | amorphous | G | — |
| n-BuOH | — | — | — | amorphous |
| THF | — | amorphous | — | amorphous |
| THF/water (1:1) | — | amorphous | — | amorphous |
| Toluene | A | — | * | amorphous+* |

— not analyzable
*not enough crystalline material for accurate characterization

Anti-Solvent Recrystallization and Cooling Recrystallization Experiments

For cooling recrystallization, each of the selected solvents was saturated with solid Compound 1 at 65° C. The solvents included MeCN, MeCN/water (1:1), EtOH, EtOH/water (1:1), IPA, and THF/water (1:1). The solution was stirred for about 10 minutes, filtered using a 0.45 μm PTFE syringe filter, and then cooled to about −15° C. by placing the vials into a freezer. The solid resulting from the recrystallization was isolated and air-dried before analysis. For cooling recrystallization, each of the selected solvents (MeOH, EtOH, and EtOH/water) was saturated with Compound 1 at 60° C. The solution was stirred at 60° C. for 10 minutes, filtered using a 0.45 μm PTFE syringe filter, and then cooled to room temperature naturally and then placed into a refrigerator. The solid resulting from the recrystallization was isolated and air-dried before analysis.

TABLE 7

Cooling Recrystallization Results

| Solvent | Conditions | Form by XRPD |
|---|---|---|
| MeCN | 65° C. to −15° C. | I |
| MeCN/water (1:1) | 65° C. to −15° C. | C |
| EtOH | 65° C. to −15° C. | — |
| EtOH/water (1:1) | 65° C. to −15° C. | — |
| THF/water (1:1) | 65° C. to −15° C. | — |
| IPA | 65° C. to −15° C. | — |

— no precipitation/not enough material for analysis

For anti-solvent recrystallization, the selected solvents MeCN and MeOH were saturated with solid Compound 1 at the room temperature. Once the solid was completely dissolved, a portion of the solution was filtered into a vial containing a selected anti-solvent (water). The mixture was cooled to 4° C. by placing the vials into a refrigerator. The solid resulting from the recrystallization was isolated and air-dried before analysis. For anti-solvent recrystallization, the selected solvents (MeOH, EtOH, IPA, and EtOAc) were saturated with Compound 1 at 60° C. Once the solid was completely dissolved, a portion of the solution was filtered into a pre-heated vial and a selected anti-solvent (water, MTBE, or heptane) was added at 60° C. The mixture was cooling to room temperature naturally and then placed into a refrigerator. The solid resulting from the recrystallization was isolated and air-dried before analysis.

TABLE 8

Experiments to Generate Materials for Characterization

| Solvent | Experimental Conditions | Form by XRPD |
|---|---|---|
| none | starting with Form A, dried in vacuum oven at 40° C. | B |
| MeCN | Slurry starting with Form A at 50° C. | C |
| IPA | Slurry starting with Form A at RT | D |
| EtOH/water (1:1) | Slurry starting with Form A at 50° C. | H |
| IPA | Slurry starting with Form A at 50° C. | F |
| MTBE | Slurry starting with Form A at 50° C. | G |
| EtOH | Slurry starting with Form A at 50° C. | H |
| MeCN | Recrystallization from saturated solution of Form A at 65° C. cooled to −15° C. | I |

MeOH, EtOH, EtOH/water, IPA, and EtOAc were used as single or primary solvents. Water, MTBE, and heptanes were used as anti-solvent. The results are summarized in Table 6. Only crystallizations using water as anti-solvents generated Form A. All other solvents or solvent combinations afforded similar solvate forms as observed during equilibration experiment.

TABLE 9

Anti-solvent Recrystallization Results

| Solvent | Anti-solvent | Ratio | Form by XRPD |
|---|---|---|---|
| MeCN | water | 1:10 | C + A |
| MeOH | water | 1:2 | amorphous |

Summary of Polymorphic Forms

A total of nine crystalline forms and an amorphous form for Compound 1 as a free base were found during this polymorph screen study. The stack plot of XRPD patterns for the nine crystalline forms are shown in FIG. 1, and the physical characteristics are summarized in Table 10. The XRPD pattern of the amorphous form is shown in FIG. 40.

TABLE 10

Summary of Solid Forms and Amorphous Form for Compound 1 Free Base

| Form | Description | Representative Conditions | DSC peaks (° C.) | TGA (% wt loss) | DVS or other notes |
|---|---|---|---|---|---|
| A | monohydrate | Starting material | 117, 182 | 2.8 | 4.7 wt % water uptake up to 90 % RH |

TABLE 10-continued

Summary of Solid Forms and Amorphous Form for Compound 1 Free Base

| Form | Description | Representative Conditions | DSC peaks (° C.) | TGA (% wt loss) | DVS or other notes |
|---|---|---|---|---|---|
| B | anhydrate | Drying Form A at 40° C. or drying Form C at 50-60° C. in vacuum oven | 182 | <1.3 | Converts to Form A at >20% RH |
| C | MeCN solvate | EQ in MeCN | 165, 186 | 6.6 | Converts to Form A at >20% RH |
| D | IPA solvate | EQ at RT in IPA | 154, 185 | 7.4 | — |
| E | solvate or hydrate | EQ at 50° C. in EtOH/water (1:1) | 104, 115, 119, 165 | 13.7 | — |
| F | IPA solvate | EQ or EV at 50° C. in IPA | 153 | 14.3 | — |
| G | MTBE solvate | EQ at 50° C. in MTBE | 148, 161 | 8.7 | — |
| H | solvate or hydrate | EQ at 50° C. in EtOH/water (1:1), EtOH, EtOAc | 163, 187 | 6.5 | Converts to Form A at >20% RH |
| I | MeCN solvate | Cooling crystallization in MeCN | 75, 183 | 2.3 | — |
|  | amorphous | EV from most solvents at RT and 50° C. | — | — | 6.9 wt % water uptake up to 90 % RH |

—: not applicable or not available
EQ: equilibration
EV: evaporation

Form A

Approximate solubility of free base Form A in various solvents at ambient temperature was estimated as described above. The results are summarized in Table 11. Free base Form A was found to be most soluble (>100 mg/mL) in acetone, EtOAc, MeOAc, and THF. Form A was very soluble (>50 mg/mL) in 1,4-dioxane, 2-MeTHF, DCM, MeCN/water (1:1), IPAc, MEK, MeOH, MIBK, and THF/water (1:1). Form A showed some solubility (>20 mg/mL) in EtOH, MTBE, n-BuOH, (>10 mg/mL) in IPA, Toluene, (>3 mg/mL) in MeCN, and EtOH/water (1:1). Form A showed low solubility (<1 mg/mL) in water and heptane.

TABLE 11

Approximately Solubility of Compound 1 Free Base Form A at Room Temperature.

| Solvent | Approximate Solubility (mg/mL) |
|---|---|
| 1,4-dioxane | >50 |
| 2-MeTHF | >50 |
| acetone | >100 |
| DCM | >50 |
| MeCN | 3 |
| MeCN/water (1:1) | >50 |
| EtOAc | >100 |
| EtOH | 25 |
| EtOH/water (1:1) | 5 |
| water | <1 |
| Heptane | <1 |
| IPA | 18 |
| IPAc | >50 |
| MEK | >50 |
| MeOAc | >100 |
| MeOH | >50 |
| MIBK | >50 |
| MTBE | 34 |
| n-BuOH | 25 |
| THF | >100 |
| THF/water (1:1) | >50 |
| Toluene | 17 |

Equilibrium experiments at 50° C. resulted in Form A in water and heptane. A unique form designated Form E was obtained from Form A in EtOH/water (1:1). A unique form designated Form F was obtained from Form A in IPA. A unique form designated Form G was obtained from Form A in MTBE. A mixture of Form A and Form C was obtained in MeCN and MeCN/water (1:1). A mixture of Form A and Form H was obtained in EtOAc and EtOH. Form F was also obtained from Form A from the evaporation at 50° C. from IPA. Evaporation in toluene resulted in a mixture of the amorphous and low crystalline material (unknown form). All other evaporation experiments at 50° C. resulted in the amorphous form of Compound 1.

Cooling recrystallization experiments were performed as described above. The solvents included MeCN, MeCN/water (1:1), EtOH, EtOH/water (1:1), THF/water (1:1), and IPA. The results are summarized in Table 7. The solids obtained from MeCN/water (1:1) were confirmed to be Form C. The solids obtained from MeCN were confirmed to be a unique form designated Form I. The remaining solvents did not precipitate after 14 days at −15° C.

Recrystallizations with anti-solvents were performed as described above. MeCN and MeOH were used as the primary solvent. Water was used as anti-solvents. The results are summarized in Table 10. Using XRPD, the solids obtained from MeCN/water were confirmed to be a mixture of Form C and Form A. The solids obtained from MeOH/water were confirmed to be amorphous.

Form A is a monohydrate. This form was mostly obtained from recrystallization or slurry experiments in aqueous or "water-rich" solvent systems.

Form A can also be obtained by conversion from Form B, Form C, and Form H by exposure to ambient conditions having greater than about 20% relative humidity (RH).

Form A converts to the anhydrous Form B upon drying at below 10% RH or at elevated temperature.

Form A has a crystalline XRPD pattern as shown in FIG. 2. TGA and DSC thermograms of Form A are shown in FIG. 4 and FIG. 5, respectively. The DSC thermogram showed two events with a first having an onset temperature of about 94° C. and a maximum of about 117° C., attributed to dehydration and a second having an onset temperature of about 174° C. and maximum of about 182° C., corresponding to melt/decomposition. TGA weight loss of 2.8% was observed up to melt. The $^1$H NMR spectrum of Form A was consistent with Compound 1 structure with no significant degradation or residual solvent (see FIG. 7).

The moisture sorption/desorption behavior of Form A was determined by DVS. The results are summarized in FIG. 6A-FIG. 6B. A steep weight change over 3% was observed between 10 and 30% RH. A similar weight change was observed between 10 to 0% RH upon desorption, which is consistent with a hydrate. Additional water uptake of approximately 1.4 wt % was observed between 30-90% RH, suggesting the hydrate is slightly hygroscopic.

FIG. 1 provides an XRPD pattern of Form A. A list of X-Ray Diffraction Peaks for Form A is provided below in Table 12.

TABLE 12

X-Ray Diffraction Peaks for Form A

| Two-theta angle (°) | d Space (Å) | Relative Intensity (%) |
|---|---|---|
| 3.20123 | 27.60013 | 7.39 |
| 7.332486 | 12.05637 | 64.82 |
| 8.513228 | 10.38668 | 72.85 |
| 10.74741 | 8.23198 | 22.68 |
| 11.05949 | 8.00038 | 5.13 |
| 12.67103 | 6.98627 | 8.99 |
| 12.97577 | 6.82287 | 9.21 |
| 13.43725 | 6.58957 | 13.47 |
| 13.77375 | 6.42933 | 11.89 |
| 14.45398 | 6.12825 | 30.43 |
| 14.69756 | 6.02723 | 36.72 |
| 15.94064 | 5.55991 | 25.02 |
| 16.88512 | 5.25098 | 22.32 |
| 17.07588 | 5.19274 | 31.16 |
| 17.32333 | 5.11912 | 12.45 |
| 17.72045 | 5.00529 | 10.31 |
| 18.18509 | 4.87844 | 100 |
| 18.65178 | 4.75741 | 11.04 |
| 20.29581 | 4.37561 | 8.64 |
| 20.73897 | 4.2831 | 19.82 |
| 21.0281 | 4.22485 | 21.03 |
| 21.26496 | 4.17833 | 38.12 |
| 22.11363 | 4.01985 | 19.34 |
| 22.66107 | 3.92397 | 12.51 |
| 22.87923 | 3.88704 | 10.28 |
| 23.1537 | 3.84158 | 13.19 |
| 23.61127 | 3.76816 | 3.67 |
| 24.00033 | 3.70795 | 6.78 |
| 24.83366 | 3.58538 | 7.14 |
| 25.53212 | 3.48886 | 4.65 |
| 26.1405 | 3.40903 | 5.74 |
| 26.40372 | 3.37564 | 12.7 |
| 26.79629 | 3.32707 | 14.69 |
| 27.86908 | 3.20139 | 6.64 |
| 28.08561 | 3.1772 | 13.75 |
| 28.84895 | 3.09484 | 21.58 |
| 29.42683 | 3.03286 | 4.2 |
| 29.77657 | 3.00051 | 7.18 |
| 31.444 | 2.8451 | 10.84 |
| 31.80169 | 2.81158 | 2.81 |
| 32.56458 | 2.74971 | 2.03 |

TABLE 12-continued

X-Ray Diffraction Peaks for Form A

| Two-theta angle (°) | d Space (Å) | Relative Intensity (%) |
|---|---|---|
| 33.14553 | 2.70283 | 1.97 |
| 33.60055 | 2.66727 | 2.6 |
| 33.93018 | 2.63992 | 2.51 |
| 34.21827 | 2.62052 | 5.43 |
| 34.66795 | 2.58755 | 6.41 |
| 36.13494 | 2.4858 | 2.98 |
| 36.4681 | 2.46385 | 3 |
| 37.24883 | 2.41398 | 2.35 |
| 37.73477 | 2.38401 | 1.03 |
| 38.93764 | 2.31308 | 3.18 |
| 39.50587 | 2.28112 | 1.35 |

FIG. 3 is an SEM image of Form A.

Form B

Form B was obtained from drying Form A at about 40° C. under vacuum. Form B can also be obtained from drying Form C at 50-60° C. under vacuum. Form B converts to Form A at ambient conditions that include greater than about 20% RH. Form B had a crystalline XRPD pattern as shown in FIG. 8. TGA and DSC thermograms of Form B obtained from acetone are shown in FIG. 9 and FIG. 10, respectively. The TGA weight loss of 0.1 wt % corresponded to one DSC peak around with an onset of about 174° C. and maximum of about 182° C. and corresponded to the melt/decomposition. These observations suggested that Form B is an anhydrate of Compound 1.

A list of X-Ray Diffraction Peaks for Form B is provided below in Table 13.

TABLE 13

X-Ray Diffraction Peaks for Form B.

| Two-theta angle (°) | d Space (Å) | Relative Intensity (%) |
|---|---|---|
| 6.890295 | 12.82908 | 19.62 |
| 8.730049 | 10.1292 | 21.5 |
| 10.47572 | 8.44486 | 10.12 |
| 11.62559 | 7.61205 | 23.62 |
| 12.00448 | 7.37264 | 21.85 |
| 13.5532 | 6.53345 | 14.74 |
| 13.79915 | 6.41755 | 42.51 |
| 14.0533 | 6.30206 | 23.35 |
| 14.22065 | 6.22827 | 12.68 |
| 16.2888 | 5.44184 | 5.17 |
| 16.91908 | 5.24051 | 5 |
| 17.52557 | 5.0605 | 20.97 |
| 18.04876 | 4.91497 | 24.18 |
| 18.44801 | 4.8095 | 8.46 |
| 19.14447 | 4.63607 | 15.55 |
| 19.4722 | 4.55878 | 100 |
| 19.98866 | 4.44214 | 68.99 |
| 20.76219 | 4.27836 | 30.81 |
| 21.07678 | 4.21521 | 11.17 |
| 22.10397 | 4.02159 | 4.97 |
| 22.68052 | 3.92065 | 10.77 |
| 23.33598 | 3.81199 | 6.7 |
| 25.15811 | 3.53695 | 2.82 |
| 26.02645 | 3.42371 | 18.19 |
| 26.71736 | 3.33672 | 5.74 |
| 27.3612 | 3.25965 | 6.19 |
| 28.39436 | 3.14335 | 6.28 |
| 28.82505 | 3.09479 | 3.02 |
| 29.19153 | 3.0593 | 4.72 |
| 30.11261 | 2.96779 | 8.81 |
| 30.95864 | 2.88859 | 7.7 |

TABLE 13-continued

X-Ray Diffraction Peaks for Form B.

| Two-theta angle (°) | d Space (Å) | Relative Intensity (%) |
|---|---|---|
| 31.51091 | 2.83921 | 7.06 |
| 31.8305 | 2.81143 | 6.03 |

Form C

Form C was obtained from equilibration of Form A in MeCN or MeCN/water at room temperature or 50° C. Form C is also obtainable from process a solution of Compound 1 in MeTHF. MeTHF (10 vol) was distilled under vacuum at constant volume with addition of MeCN (~20 vol) to remove MeTHF (230 torr/46° C.). At the end no more than 5 vol % MeTHF was in the batch. The solids crystallized during the distillation. The batch was cooled, aged, filtered, and dried under vacuum at no higher than 30° C. Form C had a crystalline XRPD pattern as shown in FIG. 11. TGA and DSC thermograms of Form C obtained from MeCN/water are shown in FIG. 12 and FIG. 13, respectively. The TGA weight loss of 6.6 wt % corresponded to broad DSC peak around 165° C. and can be attributed to desolvation in Form C. The DSC peak with onset temperature of 180° C. and a maximum of about 186° C. corresponded to the melt/decomposition. The $^1$H-NMR spectrum was obtained for the Form C sample and was consistent with structure though with high amount of MeCN present (FIG. 14). The theoretical MeCN content of a mono-solvate of Compound 1 is 6.7 wt %, matching the TGA weight loss observed. These observations suggested that Form C is an acetonitrile mono-solvate of Compound 1. Form C in ambient temperatures of greater than about 20% RH resulted conversion to Form A.

A list of X-Ray Diffraction Peaks for Form C is provided below in Table 14.

TABLE 14

X-Ray Diffraction Peaks for Form C.

| Two-theta angle (°) | d Space (Å) | Relative Intensity (%) |
|---|---|---|
| 3.146478 | 28.08028 | 4.17 |
| 7.733216 | 11.4325 | 76.48 |
| 8.895852 | 9.94078 | 39.19 |
| 10.33009 | 8.56359 | 100 |
| 13.28054 | 6.66697 | 3.82 |
| 13.65962 | 6.48279 | 15.14 |
| 14.15782 | 6.25577 | 2.18 |
| 14.55961 | 6.08403 | 7.73 |
| 14.80553 | 5.98352 | 3.64 |
| 15.01642 | 5.89995 | 5.47 |
| 15.30885 | 5.78791 | 20.22 |
| 15.50492 | 5.71515 | 23.7 |
| 15.66686 | 5.65644 | 26.8 |
| 16.94314 | 5.23313 | 17.53 |
| 17.35927 | 5.10861 | 32.43 |
| 17.79869 | 4.98346 | 16.72 |
| 18.28813 | 4.85118 | 77.42 |
| 18.73191 | 4.73724 | 5.29 |
| 19.48359 | 4.55614 | 4.1 |
| 19.94116 | 4.45262 | 27.34 |
| 20.72705 | 4.28553 | 4.27 |
| 21.1145 | 4.20776 | 6.33 |
| 21.40394 | 4.15151 | 22.87 |
| 22.09642 | 4.02295 | 1.75 |
| 22.43447 | 3.96309 | 5.19 |
| 22.65575 | 3.92488 | 5.57 |
| 23.14226 | 3.84346 | 8.41 |

TABLE 14-continued

X-Ray Diffraction Peaks for Form C.

| Two-theta angle (°) | d Space (Å) | Relative Intensity (%) |
|---|---|---|
| 23.91671 | 3.72073 | 4.29 |
| 24.59886 | 3.61907 | 3.02 |
| 25.02821 | 3.55795 | 33.9 |
| 25.51834 | 3.49072 | 5.57 |
| 25.81841 | 3.45082 | 7.75 |
| 26.14386 | 3.4086 | 34 |
| 26.72919 | 3.33527 | 15.86 |
| 26.94224 | 3.30664 | 2.91 |
| 27.17908 | 3.27836 | 2.5 |
| 27.6642 | 3.22463 | 14 |
| 28.47546 | 3.13199 | 21.49 |
| 29.3905 | 3.03653 | 3.38 |
| 29.79318 | 2.99639 | 1.72 |
| 30.33114 | 2.94446 | 5.58 |
| 30.90051 | 2.8915 | 5.26 |
| 31.31067 | 2.85455 | 6.86 |
| 32.44982 | 2.75689 | 16.95 |
| 32.96986 | 2.71458 | 5.56 |
| 33.58429 | 2.66631 | 4.06 |
| 34.27597 | 2.61407 | 1.27 |
| 35.41687 | 2.53243 | 1.42 |
| 35.94476 | 2.49644 | 2.65 |
| 36.24054 | 2.47674 | 3.82 |
| 37.12225 | 2.41992 | 1.09 |
| 37.89885 | 2.3721 | 1.29 |
| 38.90024 | 2.31331 | 2.87 |

Form D

Form D was obtained from recrystallization equilibration of Form A in IPA at room temperature. Form D had a crystalline XRPD pattern as shown in FIG. 15. TGA and DSC thermograms of Form D are shown in FIG. 17 and FIG. 18, respectively. The TGA weight loss of approximately 7.4 wt % corresponded to a broad DSC peak around 154° C. and can be attributed to loss of solvent in Form D. The smaller DSC peak with onset temperature of 175° C. and maximum of about 185° C. corresponded to the melt/decomposition. The $^1$H-NMR spectrum was obtained for the Form D sample and was consistent with structure and contained IPA (see FIG. 19). These observations suggested that Form D is most likely an IPA solvate of Compound 1.

A list of X-Ray Diffraction Peaks for Form D is provided below in Table 15.

TABLE 15

X-Ray Diffraction Peaks for Form D.

| Two-theta angle (°) | d Space (Å) | Relative Intensity (%) |
|---|---|---|
| 3.143947 | 28.10288 | 5.24 |
| 5.896986 | 14.98764 | 18.38 |
| 7.358024 | 12.01459 | 45.8 |
| 8.731096 | 10.12798 | 41.92 |
| 10.13588 | 8.72723 | 96.48 |
| 11.11409 | 7.96121 | 16.27 |
| 13.65702 | 6.48402 | 8.38 |
| 14.78355 | 5.99237 | 25.56 |
| 15.11394 | 5.86211 | 31.94 |
| 16.34076 | 5.42466 | 6.65 |
| 16.61001 | 5.33732 | 11.13 |
| 17.56252 | 5.04994 | 29.87 |
| 18.06277 | 4.9112 | 100 |
| 19.22765 | 4.61621 | 12.81 |
| 19.77163 | 4.49041 | 11.36 |
| 20.38698 | 4.35624 | 34.4 |
| 21.48209 | 4.13658 | 28.88 |
| 22.14167 | 4.01483 | 13.22 |

TABLE 15-continued

X-Ray Diffraction Peaks for Form D.

| Two-theta angle (°) | d Space (Å) | Relative Intensity (%) |
|---|---|---|
| 22.34634 | 3.97852 | 12.64 |
| 23.95561 | 3.71477 | 12.96 |
| 24.27345 | 3.66381 | 7.94 |
| 24.97168 | 3.56588 | 10.23 |
| 26.20157 | 3.40122 | 16.1 |
| 26.87895 | 3.31703 | 6.79 |
| 27.3269 | 3.26366 | 9.21 |
| 27.60494 | 3.22875 | 8.83 |
| 28.19356 | 3.16528 | 7.43 |
| 28.6337 | 3.11762 | 8.48 |
| 30.89808 | 2.89411 | 8 |
| 31.44552 | 2.84497 | 5.69 |
| 32.89163 | 2.72312 | 1.93 |
| 33.58744 | 2.66828 | 3.68 |
| 34.6305 | 2.59026 | 2.32 |
| 37.15969 | 2.41957 | 2.88 |
| 34.25 | 2.6183 | 1.6 |
| 35.39 | 2.5363 | 0.6 |
| 35.87 | 2.5034 | 2.8 |
| 36.55 | 2.4588 | 1.5 |
| 36.81 | 2.4415 | 2.7 |
| 37.06 | 2.4261 | 2.1 |
| 37.77 | 2.3820 | 2.8 |
| 38.60 | 2.3323 | 1.8 |

Form E

Form E was obtained from equilibration of Form A in EtOH/water (1:1) at 50° C. Form E had a crystalline XRPD pattern as shown in FIG. 20. TGA and DSC thermograms of Form E are shown in FIG. 21 and FIG. 22, respectively. The TGA weight loss of 13.7 wt % corresponded to small broad DSC peak around 104° C. and can be attributed to loss of solvent in Form E. These observations suggested that Form E is a solvate or hydrate containing ethanol.

A list of X-Ray Diffraction Peaks for Form E is provided below in Table 16.

TABLE 16

X-Ray Diffraction Peaks for Form E.

| Two-theta angle (°) | d Space (Å) | Relative Intensity (%) |
|---|---|---|
| 3.119693 | 28.32131 | 3.07 |
| 5.501205 | 16.06499 | 4.73 |
| 7.784643 | 11.35709 | 100 |
| 11.02865 | 8.02269 | 17.75 |
| 13.51128 | 6.55363 | 7.77 |
| 14.60025 | 6.06718 | 60.61 |
| 15.63387 | 5.6683 | 23.37 |
| 16.60508 | 5.3389 | 2.19 |
| 17.49836 | 5.06831 | 47.81 |
| 18.35094 | 4.83472 | 8.95 |
| 19.99003 | 4.44184 | 7.7 |
| 20.7282 | 4.2853 | 18.3 |
| 22.17633 | 4.00531 | 47.51 |
| 22.91616 | 3.87765 | 8.07 |
| 23.53123 | 3.77767 | 20.87 |
| 24.20048 | 3.67469 | 1.84 |
| 24.83745 | 3.58188 | 19.17 |
| 26.06663 | 3.41569 | 20.46 |
| 26.68317 | 3.33815 | 4.14 |
| 27.26868 | 3.26779 | 3.24 |
| 27.81331 | 3.20503 | 16.02 |
| 28.38011 | 3.14229 | 18.04 |
| 29.48873 | 3.02663 | 2.03 |
| 30.00215 | 2.976 | 1.96 |
| 31.08283 | 2.87495 | 2.63 |
| 31.60576 | 2.82856 | 4.57 |

TABLE 16-continued

X-Ray Diffraction Peaks for Form E.

| Two-theta angle (°) | d Space (Å) | Relative Intensity (%) |
|---|---|---|
| 32.05568 | 2.78988 | 3.52 |
| 32.57093 | 2.74692 | 6.43 |
| 33.55435 | 2.66862 | 1.21 |
| 34.00313 | 2.63442 | 1.26 |
| 34.50783 | 2.59704 | 1.26 |
| 35.38724 | 2.53449 | 3.74 |
| 36.34073 | 2.47015 | 1.03 |
| 37.21299 | 2.41423 | 4.79 |
| 38.06575 | 2.36208 | 2.16 |
| 39.36166 | 2.28725 | 1.35 |
| 39.76171 | 2.26515 | 1.83 |

Form F

Form F was obtained from equilibration of Form A in IPA at 50° C. Form F had a crystalline XRPD pattern as shown in FIG. 23. A SEM picture of Form F is provided as FIG. 24. TGA and DSC thermograms of Form F are shown in FIG. 25 and FIG. 26, respectively. The TGA weight loss of 14.3 wt % corresponded to a broad DSC peak with an onset at around 137° C. and can be attributed to loss of solvent in Form F. The DSC peak with a maximum temperature of 153° C. corresponded to the melt/decomposition. The $^1$H-NMR spectrum obtained for the Form F sample was consistent with structure but contained IPA. See FIG. 27. These observations suggested that Form F is an IPA solvate of Compound 1.

A list of X-Ray Diffraction Peaks for Form F is provided below in Table 17.

TABLE 17

X-Ray Diffraction Peaks for Form F.

| Two-theta angle (°) | d Space (Å) | Relative Intensity (%) |
|---|---|---|
| 4.949402 | 17.85475 | 3.12 |
| 7.016064 | 12.59939 | 22.77 |
| 9.436884 | 9.37204 | 100 |
| 11.121 | 7.95627 | 5.93 |
| 11.78187 | 7.51143 | 96.32 |
| 15.45245 | 5.73444 | 24.74 |
| 15.77157 | 5.61912 | 14.12 |
| 16.99932 | 5.21596 | 7.49 |
| 17.5922 | 5.04149 | 10.1 |
| 18.00623 | 4.92649 | 80.55 |
| 18.29209 | 4.85014 | 53.82 |
| 18.972 | 4.67783 | 13.76 |
| 19.74617 | 4.49614 | 33.34 |
| 19.98908 | 4.44205 | 33.31 |
| 20.2534 | 4.38467 | 6.37 |
| 20.87538 | 4.25542 | 48.06 |
| 22.38658 | 3.97146 | 8.46 |
| 22.6346 | 3.9285 | 6.09 |
| 23.18467 | 3.83652 | 15.28 |
| 23.72334 | 3.75061 | 15.45 |
| 24.35122 | 3.65531 | 6.72 |
| 25.08596 | 3.54989 | 6.8 |
| 25.36348 | 3.51168 | 6.38 |
| 25.58845 | 3.48131 | 7.73 |
| 26.40269 | 3.37577 | 4.91 |
| 26.78918 | 3.32794 | 9.12 |
| 27.25453 | 3.27216 | 5.65 |
| 27.73582 | 3.21647 | 13.8 |
| 28.63785 | 3.11718 | 6.16 |
| 29.18351 | 3.06012 | 7.47 |
| 30.04752 | 2.97407 | 8.89 |
| 30.39711 | 2.94066 | 4.57 |
| 30.65469 | 2.91412 | 4.01 |

TABLE 17-continued

X-Ray Diffraction Peaks for Form F.

| Two-theta angle (°) | d Space (Å) | Relative Intensity (%) |
|---|---|---|
| 31.24242 | 2.863 | 2.33 |
| 32.07575 | 2.79049 | 9.62 |
| 34.12926 | 2.62715 | 2.68 |
| 34.43238 | 2.60256 | 1.58 |
| 35.20737 | 2.54913 | 1.97 |
| 35.8216 | 2.50682 | 2.08 |
| 36.53788 | 2.45727 | 4.53 |
| 38.49454 | 2.33868 | 1.47 |
| 38.83843 | 2.31877 | 2.01 |
| 39.24398 | 2.29573 | 1.46 |

Form G

Form G was obtained from equilibration of Form A in MTBE at 50° C. Form G had a crystalline XRPD pattern as shown in FIG. 28. A SEM picture of Form G is provided as FIG. 29. TGA and DSC thermograms of Form G are shown in FIG. 30 and FIG. 31, respectively. The TGA weight loss of 8.7 wt % corresponded to a broad DSC peak around 147° C. and can be attributed to loss of solvent in Form G. The DSC peak with maximum of about 161° C. corresponded to the melt/decomposition. The $^1$H-NMR spectrum obtained for the Form G sample consistent with structure but contained MTBE (see FIG. 32). These observations suggested that Form G is an MTBE solvate of Compound 1.

A list of X-Ray Diffraction Peaks for Form G is provided below in Table 18.

TABLE 18

X-Ray Diffraction Peaks for Form G.

| Two-theta angle (°) | d Space (Å) | Relative Intensity (%) |
|---|---|---|
| 4.47243 | 19.75778 | 2.2 |
| 7.954996 | 11.11426 | 17.71 |
| 8.975498 | 9.85274 | 21.83 |
| 9.866793 | 8.96463 | 100 |
| 9.994242 | 8.85059 | 26.55 |
| 10.16899 | 8.69889 | 7.78 |
| 11.63523 | 7.59947 | 3.23 |
| 11.92189 | 7.42353 | 11.84 |
| 13.47007 | 6.57358 | 1.61 |
| 14.3726 | 6.16276 | 7.5 |
| 14.62417 | 6.05731 | 9.1 |
| 15.2795 | 5.79896 | 53.13 |
| 15.86499 | 5.58625 | 10.48 |
| 16.40464 | 5.40368 | 16.53 |
| 16.93894 | 5.23441 | 18.87 |
| 17.48632 | 5.07177 | 25.51 |
| 17.748 | 4.99758 | 7.4 |
| 17.98435 | 4.93243 | 19.01 |
| 18.36435 | 4.83122 | 33.34 |
| 18.69249 | 4.74714 | 22.02 |
| 18.81186 | 4.71338 | 5.12 |
| 19.3983 | 4.57598 | 21.65 |
| 19.62571 | 4.52347 | 26.03 |
| 20.30466 | 4.37372 | 4.03 |
| 20.78484 | 4.27375 | 2.19 |
| 21.17322 | 4.19622 | 29.62 |
| 21.57257 | 4.11944 | 3.67 |
| 22.034 | 4.0342 | 1.86 |
| 22.23484 | 3.99822 | 3.05 |
| 22.52995 | 3.94651 | 6.98 |
| 22.85136 | 3.89172 | 33.76 |
| 23.3702 | 3.80648 | 5.76 |
| 23.98599 | 3.71014 | 10.82 |
| 24.45111 | 3.6406 | 9.87 |
| 24.6287 | 3.61176 | 5.11 |

TABLE 18-continued

X-Ray Diffraction Peaks for Form G.

| Two-theta angle (°) | d Space (Å) | Relative Intensity (%) |
|---|---|---|
| 24.98931 | 3.5634 | 4.79 |
| 25.18471 | 3.5362 | 4.77 |
| 25.5561 | 3.48564 | 7.07 |
| 25.88694 | 3.43899 | 8.4 |
| 25.99959 | 3.42719 | 9.96 |
| 26.43365 | 3.37189 | 3.76 |
| 26.90873 | 3.31342 | 5.69 |
| 27.32137 | 3.26431 | 1.18 |
| 27.61015 | 3.23082 | 3.29 |
| 27.98048 | 3.1889 | 4.2 |
| 28.16615 | 3.1683 | 2.67 |
| 28.75034 | 3.10524 | 2.95 |
| 29.37178 | 3.04093 | 5.27 |
| 29.87498 | 2.99085 | 1.05 |
| 30.22385 | 2.95712 | 0.8 |
| 30.78081 | 2.90487 | 4.66 |
| 31.43885 | 2.84555 | 9.53 |
| 31.75021 | 2.81836 | 4.58 |
| 32.79725 | 2.73074 | 1.58 |
| 33.21187 | 2.69759 | 2.01 |
| 34.41132 | 2.60626 | 2.37 |
| 34.90557 | 2.57048 | 0.63 |
| 35.666 | 2.5174 | 2.35 |
| 36.10336 | 2.4879 | 2.17 |
| 38.18529 | 2.35691 | 2.36 |
| 38.91115 | 2.3146 | 1.7 |

Form H

Form H was obtained from of Form A in EtOH/water (1:1), EtOH, or EtOAc at 50° C. Form H had a crystalline XRPD pattern as shown in FIG. 33. TGA and DSC thermograms of Form H are shown in FIG. 34 and FIG. 35, respectively. The TGA thermogram weight loss of 6.5 wt % corresponded to broad DSC peak around 163° C. and can be attributed to loss of solvent in Form H. The DSC peak with onset temperature of about 179° C. and maximum of about 187° C. corresponded to the melt/decomposition. The theoretical EtOH content of a mono-solvate of Compound 1 is 7.5%, corresponding to the TGA weight loss observed. These observations suggested that Form H is a solvate or hydrate of Compound 1. Form transfer experiment showed that exposing Form H above 20% RH resulted in Form A.

A list of X-Ray Diffraction Peaks for Form H is provided below in Table 19.

TABLE 19

X-Ray Diffraction Peaks for Form H.

| Two-theta angle (°) | d Space (Å) | Relative Intensity (%) |
|---|---|---|
| 6.13687 | 14.40231 | 13.53 |
| 7.685174 | 11.50386 | 84.29 |
| 8.896353 | 9.94022 | 56.97 |
| 10.2724 | 8.61156 | 100 |
| 10.85454 | 8.15098 | 4.94 |
| 11.31227 | 7.82217 | 7.69 |
| 11.58221 | 7.64046 | 7.47 |
| 13.71878 | 6.45497 | 5.32 |
| 14.39424 | 6.15355 | 8.65 |
| 14.97271 | 5.91708 | 7.68 |
| 15.23389 | 5.81622 | 26.06 |
| 15.36865 | 5.76552 | 20.38 |
| 15.59046 | 5.68399 | 26.21 |
| 15.86336 | 5.58681 | 4.96 |
| 16.90296 | 5.24548 | 16.49 |
| 17.21535 | 5.15099 | 21.58 |
| 17.74632 | 4.99391 | 18.48 |

TABLE 19-continued

X-Ray Diffraction Peaks for Form H.

| Two-theta angle (°) | d Space (Å) | Relative Intensity (%) |
|---|---|---|
| 18.23822 | 4.86434 | 76.87 |
| 18.6664 | 4.75372 | 3.76 |
| 19.42537 | 4.56966 | 10.45 |
| 19.62624 | 4.52335 | 22.96 |
| 20.59336 | 4.31305 | 5.08 |
| 20.90294 | 4.24987 | 11.55 |
| 21.4434 | 4.14396 | 42.91 |
| 22.48423 | 3.95443 | 8.36 |
| 23.20369 | 3.83342 | 8.12 |
| 23.69494 | 3.75505 | 2.99 |
| 24.58745 | 3.62072 | 7.34 |
| 24.91904 | 3.57329 | 22.58 |
| 25.58037 | 3.48239 | 10.14 |
| 25.90445 | 3.43671 | 4.73 |
| 26.15241 | 3.4075 | 4.05 |
| 26.90531 | 3.31384 | 5.27 |
| 27.42283 | 3.25246 | 7.59 |
| 28.13099 | 3.17218 | 10.87 |
| 28.3945 | 3.14334 | 19.67 |
| 28.96609 | 3.0826 | 6.69 |
| 29.38076 | 3.04003 | 1.73 |
| 31.09366 | 2.87635 | 7.22 |
| 32.20206 | 2.77984 | 7.9 |
| 33.11108 | 2.70557 | 3.11 |
| 34.0949 | 2.62972 | 1.71 |
| 34.72511 | 2.58342 | 1.58 |
| 35.26616 | 2.54502 | 1.97 |
| 37.33136 | 2.40884 | 2.19 |
| 38.63271 | 2.33064 | 3.31 |

Form I

Form I was obtained from cooling recrystallization of Form A in MeCN. Form I had a crystalline XRPD pattern as shown in FIG. 36. TGA and DSC thermograms of Form I are shown in FIG. 38 and FIG. 39, respectively. The TGA weight loss of 2.3 wt % corresponded to a broad DSC peak around 75° C. and can be attributed to loss of solvent in Form I. The DSC peak with onset temperature of about 173° C. and maximum of about 183° C. corresponded to the melt/decomposition. Form transfer experiment showed that slurry with MeCN at RT resulted in Form C. These observations suggested that Form I is a solvate or a hydrate of Compound 1.

A list of X-Ray Diffraction Peaks for Form I is provided below in Table 20.

TABLE 20

X-Ray Diffraction Peaks for Form I.

| Two-theta angle (°) | d Space (Å) | Relative Intensity (%) |
|---|---|---|
| 5.228867 | 16.90109 | 7.86 |
| 5.454234 | 16.20324 | 15.45 |
| 6.316221 | 13.99375 | 100 |
| 8.610236 | 10.26988 | 13.9 |
| 9.260653 | 9.54999 | 5.09 |
| 10.44823 | 8.46702 | 7.58 |
| 10.92414 | 8.09921 | 4.42 |
| 11.48793 | 7.70296 | 8.22 |
| 11.94335 | 7.41024 | 4.88 |
| 12.63676 | 7.00513 | 1.81 |
| 15.67971 | 5.65184 | 24.76 |
| 16.61849 | 5.33462 | 20.31 |
| 17.29023 | 5.12885 | 11.91 |
| 18.14668 | 4.88867 | 24.58 |
| 18.69751 | 4.74588 | 11.16 |
| 19.02843 | 4.66408 | 7.63 |
| 20.04536 | 4.4297 | 21.39 |
| 20.88708 | 4.25306 | 5.97 |
| 21.96666 | 4.04642 | 19.84 |
| 22.48101 | 3.95499 | 4.47 |
| 23.28344 | 3.82047 | 1.5 |
| 24.09921 | 3.69296 | 7.58 |
| 24.61163 | 3.61722 | 1.69 |
| 25.41945 | 3.50407 | 4.04 |
| 26.40632 | 3.37531 | 8.22 |
| 27.56053 | 3.23653 | 9.46 |
| 28.37724 | 3.14521 | 1.21 |
| 29.60591 | 3.01742 | 1.4 |
| 30.97981 | 2.88666 | 1.69 |
| 31.64884 | 2.82715 | 1.68 |
| 32.10926 | 2.78535 | 2.02 |
| 33.24588 | 2.69491 | 1.96 |
| 33.93032 | 2.64209 | 0.94 |
| 35.26857 | 2.54485 | 1.03 |
| 35.87462 | 2.50324 | 1.29 |
| 38.49128 | 2.33887 | 0.67 |
| 35.42 | 2.5341 | 0.6 |
| 36.56 | 2.4577 | 0.5 |
| 37.67 | 2.3880 | 1.1 |

Amorphous Solid Free Base

An amorphous solid of Compound 1 was obtained from most evaporation experiments at room temperature or 50° C., as shown in Table 6.

The amorphous solid had an XRPD spectrum as shown in FIG. 40. DSC thermogram of the amorphous solid sample is shown in FIG. 41. The amorphous solid has a glass transition temperature of approximately 84° C. The DVS Isotherm plot of the amorphous solid is shown in FIG. 43A. A reversible weight change of about 3.5% was observed between 10 and 50% RH.

TABLE 21

Summary of Form Conversion Experiments

| Starting Form | Solvent | Conditions | Resulting Form |
|---|---|---|---|
| A | none | RT and ambient RH (~20-30%) for 24 hrs | A |
| A | none | RT and 0% RH 6 days | B + A |
| A | none | 40° C. and vacuum oven for 48 hrs | B |
| B | none | RT and ambient RH (~20-30%) for 5 days | A |
| C | none | RT and ambient RH (~20-30%) for 5 days | A |
| D | none | RT and ambient RH (~20-30%) 5 days | D |
| F | none | RT and ambient RH (~20-30%) 5 days | F |
| G | none | RT and ambient RH (~20-30%) 5 days | G |
| H | none | RT and ambient RH (~20-30%) 5 days | A |
| I | none | RT and ambient RH (~20-30%) 5 days | I |

Solid Forms

Analytical Methods—Citrate Salt Forms

A polymorph screen of the citrate salt Compound 1 was performed to investigate whether different solid forms could be generated under various conditions, such as different solvents, temperature and humidity changes.

The solvents used in the polymorph screen were either HPLC or reagent grade, including acetonitrile (MeCN), MeCN/water (1:1), n-butanol (n-BuOH), absolute ethanol (EtOH), ethanol/water (1:1), methanol (MeOH), 2-propanol (IPA), ethyl acetate (EtOAc), methyl acetate (MeOAc), dichloromethane (DCM), methyl ethyl ketone (MEK), methyl t-butyl ether (MTBE), heptane, toluene, methyl acetate (MeOAc), isopropyl acetate (IPAc), methyl isobutyl ketone (MIBK), 2-methyltetrahydrofuran (2-MeTHF), 1,4-dioxane, tetrahydrofuran (THF), THF/water (1:1), water, dimethyl sulfoxide (DMSO), dimethylacetamide (DMA, DMAc), and N-methylpyrrolidone (NMP).

A weighed sample of Compound 1 citrate was treated with a known volume of a test solvent. The resulting mixture was agitated for 1 day at room temperature. If all of the solids appeared to be dissolved by visual inspection, the estimated solubility was calculated based on the total volume of solvent used to give a complete solution. If solids were present, a known volume of filtrate was evaporated to dryness and the weight of the residue was measured to estimate the solubility.

All of the solid samples generated in the polymorph screen were analyzed by XRPD. XRPD analysis was conducted on a PANalytical Empyrean X-ray powder diffractometer using Cu Kα radiation at 1.54 Å.

The PANalytical Empyrean instrument was equipped with a fine focus X-ray tube. The voltage and amperage of the X-ray generator were set at 45 kV and 40 mA, respectively. The divergence slits were set at ¹⁄₁₆° and ⅛°, and the receiving slit was set at ¹⁄₁₆°. Diffracted radiation was measured using a Pixel 2D detector. A theta-two theta continuous scan was set at step size 0.013 or 0.026 from 3° to 40° 2θ with sample spinning rate at 4. A sintered alumina standard was used to check the peak positions.

DSC analyses were performed on a TA Discovery Differential Scanning Calorimeter. Indium was used as the calibration standard. Approximately 1-5 mg of sample was placed into a DSC pan. The sample was heated under nitrogen at a rate of 10° C./min, up to a final temperature of 260° C. Melting points were reported as the extrapolated onset temperatures.

TGA analyses were performed on a TA Discovery Thermogravimetric Analyzer. Approximately 2-10 mg of accurately weighed sample was placed on a pan and loaded into the TGA furnace. The sample was heated under nitrogen at a rate of 10° C./min, up to a final temperature of 300° C.

Morphology analysis of the samples was carried out on an Evex Mini-SEM. Small amounts of samples were dispersed on a sample holder, coated with gold using an Evex Mini Au Sputter Coater, and imaged with 500× to 1000× magnification.

Hygroscopicity was determined on a Surface Measurement Systems DVS. A sample size of 5-20 mg was loaded into the DVS instrument sample pan and the sample was analyzed on a DVS automated sorption analyzer at room temperature. The relative humidity was increased from 0% to 90% RH at 10% RH step, then decreased in a similar manner to accomplish a full adsorption/desorption cycle.

$^1$H NMR spectra were obtained on a Bruker 300 MHz NMR spectrometer. Samples were dissolved in DMSO-$D^6$ and analyzed with 128 scans.

Solubility of Form A and Form B in selected organic solvents was determined by mixing the individual solid forms with selected solvents at room temperature. Aliquots were obtained at multiple time points (18 hrs, 4 days, 8 days or 12 days), filtered, and quantified by an HPLC method. The recovered solids were analyzed by XRPD to confirm the solid forms.

Equilibration/Slurry and Evaporation Experiments

Equilibration and evaporation experiments at room temperature and 50° C. were carried out by adding an excess of Compound 1 citrate solid to up to 1 mL of a test solvent. The resulting mixture was agitated for 1 day at room temperature and 1 day at 50° C. separately. Upon reaching equilibrium, the saturated supernatant solution was removed, filtered using 0.45 μm PTFE filters and allowed to evaporate in an open vial under nitrogen at room temperature and 50° C., respectively. The solid resulting from the equilibration was isolated and air-dried before analysis.

Anti-Solvent Recrystallization and Cooling Recrystallization Experiments

For cooling recrystallization, each of the selected solvents was saturated with Compound 1 citrate at 65° C. The solvents included MeCN/water (1:1), EtOH, EtOH/water (1:1), MeOH, THF/water (1:1) and THF. The solution was stirred for 10 minutes, filtered using a 0.45 μm PTFE syringe filter, and then cooled to −15° C. by placing the vials into a freezer. The solid resulting from the recrystallization was isolated and air-dried before analysis.

For anti-solvent recrystallization, the selected solvent DMA was saturated with Compound 1 citrate material at the room temperature. Once the solid was completely dissolved, a portion of the solution was filtered into a vial containing a selected anti-solvent (MeCN, MeOH, heptane, EtOAc, toluene and water). The mixture was cooled to −15° C. and 4° C. by placing the vials into a freezer or a refrigerator. The solid resulting from the recrystallization was isolated and air-dried before analysis.

Summary of Polymorphic Forms

Figure 44:
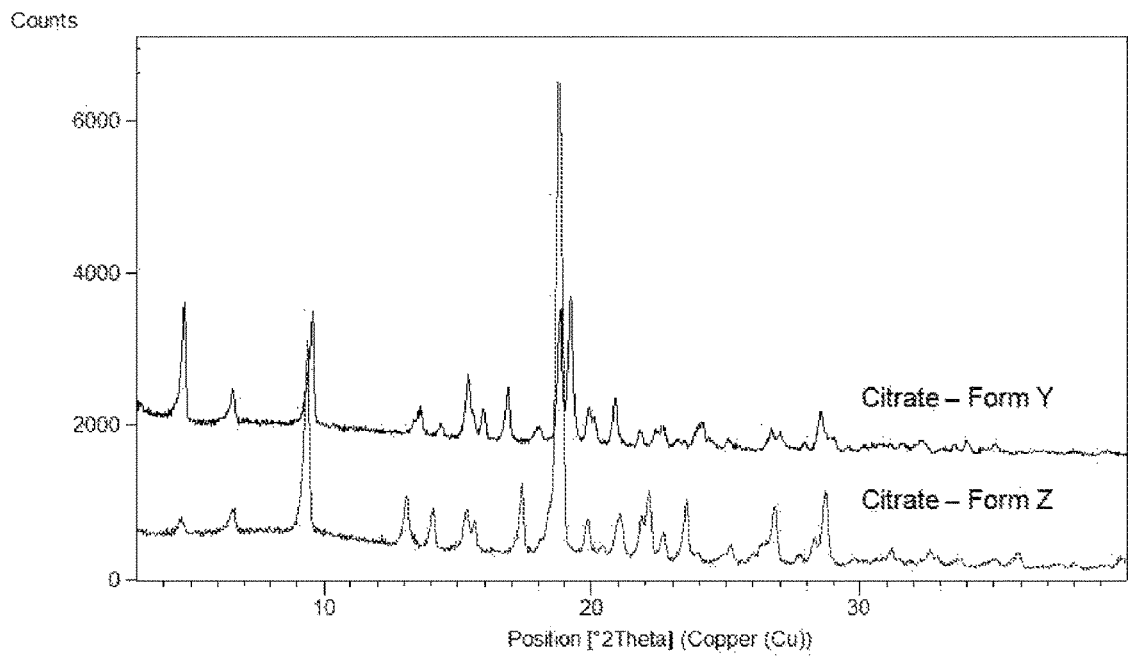
FIG. 44 depicts a XRPD Stack Plot of Citrate Forms Y and Z.

Two crystalline forms for Compound 1 citrate salt were found during this polymorph screen study. The stack plot of XRPD patterns for these forms are shown in FIG. 44, and the physical characteristics are summarized in Table 29.

Form Y

Form Y was obtained from dissolving Compound 1 starting material in 5 Vol Acetone @ 25 C. About 1.15 eq citric acid in water (~0.2 M) was charged into the batch to form the Compound 1 citrate salt. The Compound 1 citrate salt was aged at 25° C. until the mother liquor concentration was below 1 mg/ml. The slurry was filtered off and washed using ~4 vol (1:1) Acetone/H$_2$O to wash the cake. The cake was dried in a vacuum oven at 50° C. until no acetone was detected by NMR.

Approximate solubility of Compound 1 citrate Form Y in various solvents at ambient temperature was estimated as described above. The results are summarized in Table 22. Compound 1 citrate Form Y was found to be most soluble (>50 mg/mL) in DMSO, DMA and NMP. Compound 1 citrate Form Y showed some solubility (>20 mg/mL) in THF/water, (>5 mg/mL) in THF, (>3 mg/mL) in MeCN/water (1:1) and MeOH, (>2 mg/mL) in 1,4 dioxane. Compound 1 citrate Form Y showed low solubility (<1-2 mg/mL) in all other solvents tested, including Acetone, n-BuOH, MeCN, EtOH, EtOH/water (1:1), IPA, EtOAc, MeOAc, DCM, MTBE, MEK, heptane, toluene, 2-MeTHF and water.

TABLE 22

Approximate Solubility of Compound 1 citrate Form Y at Room Temperature.

| Solvent | Approximate Solubility (mg/mL) |
|---|---|
| Acetone | <1 |
| MeCN | <1 |
| MeCN/water (1:1) | <4 |
| n-BuOH | <1 |
| EtOH | <2 |
| EtOH/water (1:1) | <3 |
| EtOAc | <1 |
| Heptane | <1 |
| IPA | <1 |
| DCM | <1 |
| MeOAc | <1 |
| MeOH | <4 |
| MTBE | <1 |
| MEK | <1 |
| Toluene | <1 |
| THF | <6 |
| THF/water (1:1) | <23 |
| water | <1 |
| 1,4-dioxane | <3 |
| MIBK | <1 |
| IPAc | <1 |
| 2-MeTHF | <2 |
| DMA | >50 |
| NMP | >50 |
| DMSO | >50 |

Equilibration and evaporation experiments were performed at room temperature and 50° C. using Compound 1 citrate Form Y as starting material, as described above. The results are summarized in Table 23. Equilibration in MeOH and MeCN/water at 50° C. afforded a unique form, designated as Citrate Salt Form Z. All other equilibration experiments afforded Compound 1 citrate Form Y or Compound 1 citrate Form Y mixed with Compound 1 citrate Form Z. Due to relatively low solubility, most evaporation experiments didn't afford analyzable solid. Evaporation from EtOH and EtOH/water afforded mixture of Compound 1 citrate Forms Y and Z. Solids from MeOH evaporation afforded Compound 1 citrate Form Z.

TABLE 23

Summary of Equilibration and Evaporation Results.

| | Form by XRPD | | | |
|---|---|---|---|---|
| Solvent | EQ at RT | EV at RT | EQ at 50° C. | EV at 50° C. |
| Acetone | Y | — | Y | — |
| MeCN | Y | — | Y | — |
| MeCN/water | Z + Y | — | Z | — |
| n-BuOH | Y | — | Y | — |
| EtOH | Y | — | Z + Y | Z + Y |
| EtOH/water | Z + Y | Y + Z | Z + Y | Y + Z |
| EtOAc | Y | — | Y | — |
| Heptane | Y | — | Y | — |
| IPA | Y | — | Y | — |
| DCM | Y | — | Y | — |
| MeOAc | Y | — | Y | — |
| MeOH | Z | Z | Z | Z |
| MTBE | Y | — | Y | — |
| MEK | Y | — | Y | — |
| Toluene | Y | — | Y | — |
| THF | Y | Y | Y | Y |
| THF/water | Y | Y | Y | Z + Y |
| water | Y | — | Y | — |

TABLE 23-continued

Summary of Equilibration and Evaporation Results.

| | Form by XRPD | | | |
|---|---|---|---|---|
| Solvent | EQ at RT | EV at RT | EQ at 50° C. | EV at 50° C. |
| 1,4-dioxane | Y | — | Y | — |
| MIBK | Y | — | Y | — |
| IPAc | Y | — | Y | — |
| 2-MeTHF | Y | — | Y | — | n/a: no experiment
—: not analyzable.
* significant degradation occurred.

Cooling recrystallization experiments were performed as described above. The solvents included MeCN/water (1:1), EtOH/water (1:1), THF/water (1:1), EtOH, MeOH and THF. The results are summarized in Table 24. The solids obtained from THF and THF/water were confirmed to be Compound 1 citrate Form Y. The solids obtained from MeOH and MeCN/water were confirmed to be Compound 1 citrate Form Z. The solids obtained from EtOH and EtOH/water were confirmed to be mixture of Compound 1 citrate Forms Y and Z.

TABLE 24

Results from Cooling Recrystallization

| Solvent | Cooling Profile | Form by XRPD |
|---|---|---|
| MeCN/water (1:1) | 65 to −15° C. | Z |
| EtOH | 65 to −15° C. | Z + Y |
| EtOH/water (1:1) | 65 to −15° C. | Z + Y |
| MeOH | 65 to −15° C. | Z |
| THF | 65 to −15° C. | Y |
| THF/water (1:1) | 65 to −15° C. | Y |

Recrystallizations with anti-solvents were performed as described above. DMA was used as the primary solvent. MeCN, MeOH, heptane, EtOAc, toluene and water were used as anti-solvents. The results are summarized in Table 25. Using XRPD, the solids obtained from DMA/MeCN, DMA/MeOH and DMA/water were confirmed to be Compound 1 citrate Form Z. The solids obtained from DMA/EtOAc were confirmed to be Compound 1 citrate Form Y and the solids obtained from DMA/toluene were confirmed to be a mixture of Compound 1 citrate Forms Y and Z. Precipitation was not observed from the DMA/heptane recrystallization experiment.

TABLE 25

Results from Anti-Solvent Recrystallization

| Primary solvent | Anti-Solvent | Solvent Ratio | Cooling profile | Form by XRPD |
|---|---|---|---|---|
| DMA | MeCN | 1:15 | RT to −15° C. | Z |
| DMA | MeOH | 1:15 | RT to −15° C. | Z |
| DMA | heptane | 1:15 | RT to −15° C. | — |
| DMA | EtOAc | 1:15 | RT to −15° C. | Y |
| DMA | toluene | 1:15 | RT to −15° C. | Y + Z |
| DMA | water | 1:15 | RT to 4° C. | Z |

RT: room temperature
—: no precipitation

Form Y was designated as the crystalline form of the DSD sample used as the starting material for this screen. Form Y has a crystalline XRPD pattern as shown in FIG. 45. The SEM picture is shown in FIG. 46. TGA and DSC thermograms of Form Y are shown in FIG. 47 and FIG. 48, respectively. No TGA weight loss was observed up to 150° C. for Form Y. Small additional weight loss was observed up to the melting temperature of Form Y. The DSC thermogram showed a melting event with an onset temperature of 213° C. and a maximum of 217° C. Form Y is a slightly hygroscopic, with about 2.1% w/w water uptake between 0 and 90% RH. The $^1$H NMR spectrum is consistent with the structure of a citrate salt, with about 0.2% w/w of residual acetone (FIG. 50). The citric acid content was 25.1 wt % as determined by HPLC, consistent with a 1:1 salt (with theoretically 25.2 wt % of citric acid). These observations suggest Form Y is most likely an anhydrate of Compound 1 citrate.

Figure 51:
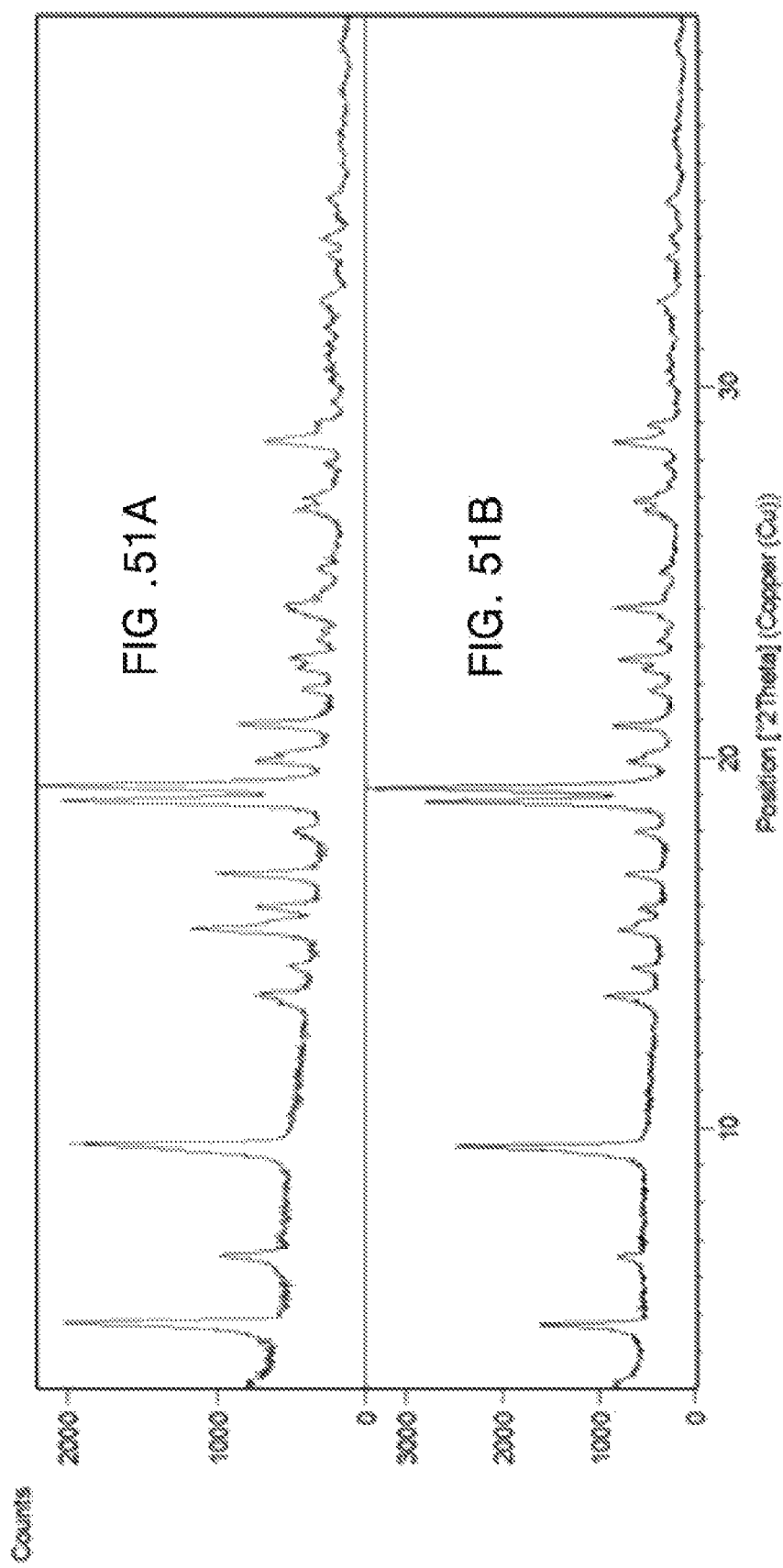
FIG. 51A depicts a Comparison of XRPD Patterns of Citrate Form Y before Compression.
FIG. 51B depicts a Comparison of XRPD Patterns of Citrate Form Y after Compression.

The stability of Form Y was further characterized by compression test and form transfer experiments. Upon application of 2000-psi pressure for about 1 minute, the material was still Form Y (FIG. 51A and FIG. 51B).

TABLE 26

HPLC Solubility of Compound 1 citrate Form Y and Form Z in Selected Solvents at Room Temperature.

| Form | Solvent | Solubility (mg/mL) | | | |
|---|---|---|---|---|---|
| | | 18 hours | 4 days | 8 days | 12 days |
| Y | Acetone | 0.91 | — | — | — |
| Z | Acetone | 1.30 | — | — | — |
| Y | EtOH | 2.27 | — | — | — |
| Z | EtOH | 1.35 | — | — | — |
| Y | MeOAc | 0.15 | 0.20 | — | 0.20 |
| Z | MeOAc | 0.28 | 0.27 | — | 0.32 |
| Y | 2-MeTHF | 1.48 | — | 1.25 | — |
| Z | 2-MeTHF | 1.89 | — | 1.91 | — |

—: not tested
Note:
all solids recovered from the solubility tests remained as the starting form by XRPD.

A list of X-Ray Diffraction Peaks for Form Y is provided below in Table 27.

TABLE 27

X-Ray Diffraction Peaks for Form Y

| Two-theta angle (°) | d Space (Å) | Relative Intensity (%) |
|---|---|---|
| 4.783092 | 18.47519 | 77.84 |
| 6.5819 | 13.42948 | 22.24 |
| 9.59256 | 9.22029 | 77.51 |
| 13.60691 | 6.50778 | 15.93 |
| 14.38278 | 6.15842 | 8.39 |
| 15.38972 | 5.75768 | 42.05 |
| 15.96684 | 5.55084 | 21.08 |
| 16.88841 | 5.24996 | 35.58 |
| 18.02213 | 4.92218 | 8.66 |
| 18.85463 | 4.70668 | 90.57 |
| 19.24503 | 4.61208 | 100 |
| 19.93024 | 4.45503 | 24.22 |
| 20.10453 | 4.4168 | 17.8 |
| 20.90504 | 4.24944 | 31.37 |
| 21.84462 | 4.06875 | 9.14 |
| 22.41502 | 3.96648 | 11.55 |
| 22.68635 | 3.91965 | 13.81 |
| 23.18753 | 3.83605 | 4.81 |
| 23.41127 | 3.79675 | 3.74 |
| 23.96094 | 3.71088 | 13.54 |
| 24.11531 | 3.68748 | 15.13 |
| 24.34514 | 3.65318 | 6.5 |
| 25.08466 | 3.55007 | 5.52 |
| 26.69176 | 3.33986 | 14.16 |
| 27.00945 | 3.3013 | 11.93 |

TABLE 27-continued

X-Ray Diffraction Peaks for Form Y

| Two-theta angle (°) | d Space (Å) | Relative Intensity (%) |
|---|---|---|
| 27.91142 | 3.19663 | 4.49 |
| 28.54004 | 3.12764 | 26.41 |
| 29.0111 | 3.07791 | 8.77 |
| 29.56958 | 3.02104 | 2.96 |
| 30.15901 | 2.96333 | 3.37 |
| 30.44673 | 2.93355 | 6.11 |
| 30.78504 | 2.90208 | 4.71 |
| 31.14674 | 2.87157 | 5.23 |
| 31.59191 | 2.83212 | 5.94 |
| 32.30739 | 2.77101 | 7.96 |
| 33.13792 | 2.7012 | 2.5 |
| 33.53919 | 2.67201 | 5.44 |
| 33.98455 | 2.638 | 8.13 |
| 34.59426 | 2.59075 | 2.82 |
| 35.05464 | 2.55989 | 5.67 |

Form Z

Compound 1 citrate Form Z was generated by equilibration experiment in MeOH and MeCN/water (1:1) at 50° C. and various recrystallization experiments, including cooling recrystallization from MeCN/water, and anti-solvent recrystallization from DMA/MeCN, DMA/MeOH and DMA/water. Form Z has a crystalline XRPD pattern as shown in FIG. 52. The SEM picture is shown in FIG. 53. TGA and DSC thermograms of Form Z are shown in FIG. 54 and FIG. 55, respectively. No significant TGA weight loss was observed for Form Z up to 150° C. Additional weight loss (up to a few percent) was observed up to the melting temperature of Form Z. The DSC thermogram showed a melting event with an onset temperature of 217° C. and a maximum of 221° C. Form Z is slightly hygroscopic, with about 1.6% w/w water uptake between 0 and 90% RH. The $^1$H NMR spectrum for the Form Z sample out equilibration in MeCN/water at 50° C. is consistent with the structure of Compound 1 citrate salt, with about 1.0% w/w of residual MeCN (FIG. 57). The citric acid content was 24.6 wt % as determined by HPLC, consistent with a 1:1 salt (with theoretically 25.2 wt % of citric acid). These observations suggest Form Z is most likely an anhydrate of Compound 1 citrate.

TABLE 28

Experiments to Generate Materials for Characterization

| Solvent | Experimental Conditions | Form by XRPD |
|---|---|---|
| MeOH | Slurry starting with Form Y, shaking at 50° C. for 1 day | Z |
| MeCN/Water(1:1) | Slurry starting with Form Y, shaking at 50° C. for 1 day | Z |

Further drying study was performed to understand the weight loss observed above 150° C. Aliquots of Form Z sample was dried in KF oven (with N2 sweep) at 150 and 180° C., respectively. Citric acid content of the recovered solids was 24.2 and 17.8 wt %, respectively, suggesting loss of citric acid. Residual solvent in the dried samples were also significantly lower than the "as-is" Form Z sample.

Figure 62:
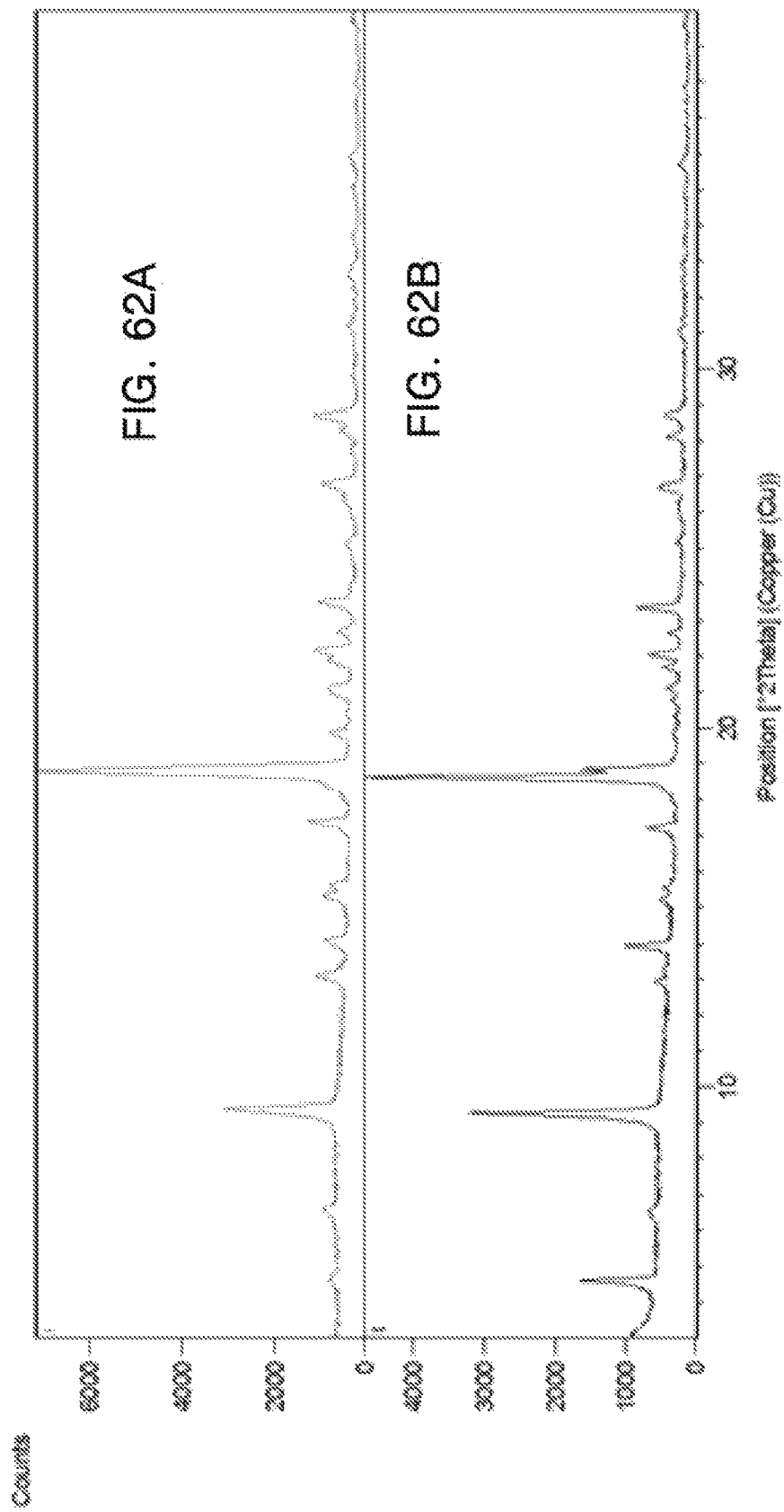
FIGS. 62A-62B depict a Comparison of XRPD Patterns of Citrate Form Z.

The stability of Form Z was further characterized by compression test and form transfer experiments. Upon application of 2000-psi pressure for about 1 minute, the material was still Form Z (FIGS. 62A-62B).

TABLE 29

Summary of Characterization Data for Compound 1 Citrate Salt Polymorphs

| Form | Description | Representative conditions | DSC peak (° C.) | TGA loss (wt %) | DVS or other comments |
|---|---|---|---|---|---|
| Y | anhydrate | starting material lot 8153-002; recrystallization in THF and THF/water; anti-solvent recrystallization in DMA/EtOAc | 213 (onset) | 0.0 (up to 150° C.) | ~2.1 wt % water uptake up to 90% RH; |
| Z | anhydrate | recrystallization or equilibration in MeOH and MeCN/water; anti-solvent recrystallization in DMA/MeCN, DMA/MeOH, DMA/water | 217 (onset) | 0.1 (up to 150° C.) | ~1.6 wt % water uptake up to 90% RH; |

A list of X-Ray Diffraction Peaks for Form Z is provided below in Table 30.

TABLE 30

X-Ray Diffraction Peaks for Form Z.

| Two-theta angle (°) | d Space (Å) | Relative Intensity (%) |
|---|---|---|
| 4.648808 | 19.00855 | 146.09 |
| 6.594748 | 13.40334 | 240.86 |
| 9.398551 | 9.41017 | 2485.09 |
| 13.10081 | 6.75803 | 615.48 |
| 14.08974 | 6.28584 | 474.71 |
| 15.33978 | 5.77631 | 478.60 |
| 15.62982 | 5.66976 | 353.57 |
| 17.40622 | 5.09493 | 817.10 |
| 18.80665 | 4.71858 | 6793.99 |
| 18.95349 | 4.68235 | 3368.79 |
| 19.8844 | 4.4652 | 486.73 |
| 20.41888 | 4.34951 | 138.16 |
| 21.09284 | 4.21203 | 552.13 |
| 21.89109 | 4.06021 | 539.72 |
| 22.16856 | 4.01002 | 861.32 |
| 22.70611 | 3.91629 | 337.89 |
| 23.51471 | 3.78342 | 774.70 |
| 23.9067 | 3.72226 | 103.10 |
| 25.16965 | 3.53828 | 208.07 |
| 26.30357 | 3.38827 | 243.12 |
| 26.80383 | 3.32615 | 737.22 |
| 27.7519 | 3.21464 | 133.59 |
| 28.29834 | 3.1538 | 359.75 |
| 28.72703 | 3.1077 | 950.99 |
| 29.79863 | 2.99834 | 103.84 |
| 31.19139 | 2.86756 | 240.17 |
| 31.88523 | 2.80673 | 82.73 |
| 32.60755 | 2.74619 | 220.23 |
| 33.73557 | 2.6569 | 113.82 |
| 35.08647 | 2.55764 | 120.37 |
| 35.93019 | 2.49949 | 177.27 |
| 37.39344 | 2.40498 | 35.78 |
| 37.99067 | 2.36853 | 47.79 |

The thermodynamic relationship between the two forms was explored through form conversion experiments (Table 31). Competitive slurries starting with mixtures of Forms Y and Z resulted in solvent specific results. Form Y resulted from slurries in THF at room temperature and from slurries in THF and EtOAc at 50° C. Form Z resulted from slurries in EtOH, water, MEK, and MeCN at both room temperature and 50° C.

The thermodynamic relationship between the two forms was further explored through solubility experiments (Table 26). These experiments were designed to determine whether results from competitive slurries were due to the different dissolution/growth kinetics of each form in a specific solvent or the overall thermodynamics. As shown in Table 26, the solubility of Form Z was lower than that of Form Y in EtOH, while the solubility of Form Y was lower in acetone, MeOAc, and 2-MeTHF. These results appear consistent with observations from competitive slurries, suggesting that the dissolution/growth kinetics was not the cause for the solvent specific form conversion.

TABLE 31

Summary of Form Transfer Experiments

| Starting Form(s) | Solvent | Temperature/ Condition | Resulting Form(s) |
|---|---|---|---|
| Y + Z | Slurry in MeCN | RT, 5 days | Y |
| Y + Z | Slurry in EtOH | RT, 5 days | Z |
| Y + Z | Slurry in EtOAc | RT, 5 days | Y + Z |
| Y + Z | Slurry in Toluene | RT, 5 days | Z + Y |
| Y + Z | Slurry in THF | RT, 5 days | Y |
| Y + Z | Slurry in Water | RT, 5 days | Z |
| Y + Z | Slurry in MEK | RT, 5 days | Z |
| Y + Z | Slurry in MeCN | RT, 10 days | Z |
| Y + Z | Slurry in EtOH | RT, 10 days | Z |
| Y + Z | Slurry in EtOAc | RT, 10 days | Y + Z |
| Y + Z | Slurry in Toluene | RT, 10 days | Z + Y |
| Y + Z | Slurry in THF | RT, 10 days | Y |
| Y + Z | Slurry in MEK | RT, 10 days | Z |
| Y + Z | Slurry in MeCN | 50° C., 4 days | Z |
| Y + Z | Slurry in EtOH | 50° C., 4 days | Z |
| Y + Z | Slurry in EtOAc | 50° C., 4 days | Y |
| Y + Z | Slurry in Toluene | 50° C., 4 days | Z + Y |
| Y + Z | Slurry in THF | 50° C., 4 days | Y |
| Y + Z | Slurry in MEK | 50° C., 4 days | Z |

Solid Forms

Analytical Methods—HCL Salt Forms

A polymorph screen of Compound 1 was performed to investigate whether different solid forms could be generated under various conditions, such as different solvents, temperature and humidity changes.

The starting material was generated by dissolving Compound 1 in 10 vol MeOH at 25-30° C. Then 1.10 equiv HCl in MeOH (~1.25 M) was charged into the batch to form Compound 1 HCl Salt. Constant vacuum distillation to solvent switch from MeOH to EtOAc (~30-35 vol) was performed and the batch temperature was maintained at 25-35° C. The slurry was filtered off, and ~5 vol (1:1) EtOAc was used to wash the cake, which was dried in a vacuum oven at 50° C.

Starting material is in relatively low crystallinity with a weight loss of 1.1% wt % up to 100° C. in TGA and one melting peak at 238.5° C. (onset temperature) in DSC.

A mass change of 3.6 wt % was observed for starting material from 0% RH to 95% RH at 25° C. The sample is moderately hygroscopic The theoretical Cl content for a 1:1 HCl salt is 5.84 wt %. The Cl content of the HCl salt of Compound 1 was 5.70 wt %.

Solubility of the starting mater in selected organic solvents was determined by mixing with selected solvents at room temperature.

TABLE 32

Approximate solubility of anhydrate/amorphous starting material

| Solvent | Approximate Solubility (mg/mL) | Solvent | Approximate Solubility (mg/mL) |
|---|---|---|---|
| MeOH | S > 31 | DCM | S < 1.6 |
| EtOH | S > 28 | CHCl3 | 1.3 < S < 2.0 |
| IPA | 5.5 > S > 7.3 | Toluene | S < 1.4 |
| Acetone | 2.4 < S < 2.7 | Heptane | S < 1.7 |
| MIBK | S < 1.5 | DMAc | S > 18 |
| EtOAc | S < 1.5 | DMSO | S > 22 |
| IPAc | S < 1.3 | NMP | S > 24 |
| THF | 2.3 < S < 3.4 | H2O | S < 1.0 |
| 2-MeTHF | S < 0.9 | n-BuOH | 4.8 < S < 6.3 |
| 1,4-dioxane | 1.5 < S < 1.9 | MeOAc | S < 0.9 |

TABLE 32-continued

Approximate solubility of anhydrate/amorphous starting material

| Solvent | Approximate Solubility (mg/mL) | Solvent | Approximate Solubility (mg/mL) |
|---|---|---|---|
| MTBE | S < 1.0 | MEK | 1.8 < S < 2.3 |
| MeCN | 1.1 < S < 1.5 | | |

Eight crystalline forms were found during the polymorph screen, and termed HCl Salt Form 1 through HCl Salt Form 8 herein. General characteristics of the crystalline forms are provided in Table 33.

TABLE 33

Polymorph Characterization

| Form | Description | Representative Conditions | DSC endo peaks (onset ° C.) | TGA (% wt loss up to ° C.) | DVS |
|---|---|---|---|---|---|
| | Anhydrate (mixed with amorphous) | Starting material | 238 | 1.1 (100° C.) | ~3.6% wt gain @ 95% RH; |
| 1 | solvate (IPA) | EV @ RT in IPA | 102, 146, . . . | 6.6 (140° C.) 16.8 (205° C.) | |
| 2 | unknown | LVD in IPA/toluene | 151, . . . | 2.6 (140° C.) 16.8 (200° C.) | |
| 3 | unknown | LVD in n-BuOH/heptane | 153, . . . | 2.3 (140° C.) 13.2 (210° C.) | |
| 4 | solvate | LVD in MeOH/IPAc | 94, 161^, 219 | 4.5 (140° C.) | |
| 5 | solvate or hydrate | SVD in DMF | 104 . . . 162, 192 | 4.2 (140° C.) | |
| 6 | Pentahydrate | Slurry anhydrate in 0.1N HCl at RT | 53, 201 | 11.6 (100° C.) | |
| 7 | monohydrate 1 | Slurry anhydrate in water at RT | 80, 215 | 3.8 (100° C.) | ~4.5% wt gain @ 95% RH, w/hysterisis |
| 8 | monohydrate 2 | Slurry anhydrate in water at 50° C. | 117, 208 | 3.2 (100° C.) | ~2% wt gain @ 95% RH |

EV = evaporation
RH = Relative Humidity
RT = Room Temperature
LVD = Liquid Vapor Diffusion
SVD = Solid Vapor Diffusion HCL Salt Form 1

HCl Salt Form 1 has a crystalline XRPD pattern as shown in FIG. 66. TGA and DSC thermograms of HCl Salt Form 1 are shown in FIG. 67. The DSC thermogram showed multiple thermal events one event having an onset temperature of about 102° C. and maximum of about 114° C., attributed to dehydration and a second having an onset temperature of about 146° C. and maximum of about 181° C., corresponding to melt/decomposition. TGA weight loss was 6.6% weight loss before 140° C. and another 10% weight loss before 205° C. HCl Salt Form 1 was obtained from slow evaporation with IPA. HCl Salt Form 1 is an IPA solvate of the HCl salt of Compound 1.

A list of X-Ray Diffraction Peaks for HCl Salt Form 1 is provided below in Table 34.

TABLE 34

X-Ray Diffraction Peaks for HCl Salt Form 1.

| Two-theta angle (°) | d Space (Å) | Relative Intensity (%) |
|---|---|---|
| 7.043121 | 12.55104 | 17.58 |
| 8.750653 | 10.10539 | 15.35 |
| 9.852726 | 8.9774 | 100 |
| 11.47008 | 7.7149 | 17.12 |
| 12.15803 | 7.27987 | 11.47 |
| 12.43821 | 7.1165 | 66.17 |
| 14.72797 | 6.01485 | 19.95 |
| 16.34789 | 5.42231 | 25.48 |
| 16.7059 | 5.30251 | 3.34 |
| 17.47299 | 5.07561 | 64.11 |
| 17.91231 | 4.95211 | 76.6 |
| 18.2135 | 4.87089 | 8.18 |
| 18.60715 | 4.76872 | 4.99 |
| 19.16845 | 4.63033 | 42.87 |
| 19.35014 | 4.58726 | 15.37 |
| 19.71049 | 4.5042 | 86.74 |
| 19.89059 | 4.46382 | 56.77 |
| 20.26675 | 4.38181 | 3.67 |
| 20.99857 | 4.23073 | 21.73 |
| 21.24423 | 4.18236 | 6.59 |
| 21.89672 | 4.05918 | 9.98 |
| 22.69272 | 3.91857 | 11.28 |
| 22.87039 | 3.88853 | 12.81 |
| 23.71329 | 3.75218 | 11.12 |
| 24.62266 | 3.61563 | 16.07 |
| 24.95768 | 3.56785 | 21.97 |
| 25.58616 | 3.48162 | 20.79 |
| 26.26022 | 3.39376 | 11.72 |
| 26.54722 | 3.35772 | 6.89 |
| 26.79783 | 3.32688 | 12.32 |
| 27.24697 | 3.27306 | 20.4 |
| 27.60085 | 3.22921 | 3.05 |
| 28.22986 | 3.16129 | 10.88 |
| 28.68693 | 3.11195 | 16.16 |
| 29.10407 | 3.06576 | 4.81 |
| 29.63481 | 3.01454 | 12.04 |
| 30.27581 | 2.95216 | 2.91 |
| 30.83935 | 2.89949 | 6 |
| 31.23123 | 2.864 | 4.49 |
| 31.67746 | 2.82466 | 2.46 |
| 32.26273 | 2.77475 | 23.06 |
| 32.84882 | 2.72657 | 0.93 |
| 33.26344 | 2.69352 | 3 |
| 33.97406 | 2.63661 | 2.64 |
| 34.30005 | 2.61446 | 4 |
| 35.31073 | 2.54191 | 1.4 |
| 36.2495 | 2.4782 | 2.54 |
| 36.95941 | 2.43222 | 1.43 |

HCL Salt Form 2

HCl Salt Form 2 has a crystalline XRPD pattern as shown in FIG. 68. TGA and DSC thermograms of HCl Salt Form 2 are shown in FIG. 69. The DSC thermogram showed a broad thermal event with an onset of about 151° C., attributed to melting, decomposition, and disproportionation. TGA weight loss was 2.6% weight loss before 140° C. and another 14% weight loss before 200° C. HCl Salt Form 2 was obtained from liquid vapor diffusion with IPA/Toluene.

A list of X-Ray Diffraction Peaks for HCl Salt Form 2 is provided below in Table 35.

TABLE 35

X-Ray Diffraction Peaks for HCl Salt Form 2.

| Two-theta angle (°) | d Space (Å) | Relative Intensity (%) |
|---|---|---|
| 5.513929 | 16.02795 | 39.15 |
| 5.818358 | 15.19 | 8.38 |
| 8.983458 | 9.84403 | 56.91 |
| 9.766082 | 9.05685 | 50.75 |
| 9.902449 | 8.93243 | 56.24 |
| 10.72871 | 8.24629 | 18.43 |
| 10.99295 | 8.04866 | 10.95 |
| 12.26058 | 7.21921 | 27.19 |
| 12.57368 | 7.04013 | 31.94 |
| 13.97997 | 6.33495 | 7.85 |
| 16.73809 | 5.29677 | 95.21 |
| 18.12082 | 4.89559 | 22.15 |
| 19.03805 | 4.66175 | 100 |
| 19.52223 | 4.54721 | 7.52 |
| 19.94127 | 4.44891 | 7.08 |
| 20.14258 | 4.40854 | 10.91 |
| 20.76643 | 4.27749 | 13.97 |
| 21.45635 | 4.14149 | 23.47 |
| 21.7551 | 4.08529 | 6.27 |
| 22.04131 | 4.03288 | 18.86 |
| 22.8351 | 3.89446 | 39.99 |
| 23.29623 | 3.8184 | 9.22 |
| 23.98663 | 3.71004 | 5.4 |
| 24.28375 | 3.66531 | 11.47 |
| 24.61877 | 3.61619 | 7.17 |
| 24.93034 | 3.5717 | 13.85 |
| 25.31155 | 3.51876 | 6.55 |
| 25.98875 | 3.42859 | 4.92 |
| 26.50429 | 3.36028 | 3.72 |
| 26.80338 | 3.32621 | 16.19 |
| 27.02674 | 3.29922 | 8.76 |
| 27.60649 | 3.22857 | 2.25 |
| 28.3911 | 3.1437 | 2.89 |
| 29.16521 | 3.062 | 11.63 |
| 29.73827 | 3.00429 | 15.98 |
| 30.73751 | 2.90886 | 3.83 |
| 32.9862 | 2.71552 | 7.23 |
| 35.1076 | 2.55615 | 3.37 |

HCL Salt Form 3

HCl Salt Form 3 has a crystalline XRPD pattern as shown in FIG. 70. TGA and DSC thermograms of HCl Salt Form 3 are shown in FIG. 71. The DSC thermogram showed a broad thermal event at 153° C. (onset), attributed likely to melting, decomposition, and disproportionation. TGA weight loss was 2.3% weight loss before 140° C. and another 11% weight loss before 210° C. HCl Salt Form 3 was obtained from multiple conditions related to n-BuOH.

A list of X-Ray Diffraction Peaks for HCl Salt Form 3 is provided below in Table 36.

TABLE 36

X-Ray Diffraction Peaks for HCl Salt Form 3.

| Two-theta angle (°) | d Space (Å) | Relative Intensity (%) |
|---|---|---|
| 5.479806 | 16.12768 | 100 |
| 6.487877 | 13.62388 | 23.65 |
| 7.727824 | 11.44046 | 2.98 |
| 10.02748 | 8.82133 | 5.09 |
| 10.45605 | 8.45371 | 4.84 |
| 10.87943 | 8.13239 | 20.4 |
| 12.93306 | 6.8453 | 18.49 |
| 14.84169 | 5.96902 | 7.58 |
| 15.91137 | 5.56546 | 10.26 |
| 16.23176 | 5.46084 | 80.27 |
| 18.30041 | 4.84795 | 5.46 |
| 18.92492 | 4.68936 | 9.72 |
| 19.44416 | 4.56529 | 52.36 |
| 20.41197 | 4.35097 | 28.32 |

TABLE 36-continued

X-Ray Diffraction Peaks for HCl Salt Form 3.

| Two-theta angle (°) | d Space (Å) | Relative Intensity (%) |
|---|---|---|
| 20.95774 | 4.23888 | 5.68 |
| 21.77105 | 4.08233 | 18.78 |
| 22.20912 | 4.00279 | 22.42 |
| 22.48069 | 3.95504 | 23.87 |
| 24.06092 | 3.69875 | 5.4 |
| 25.99089 | 3.42831 | 8.79 |
| 28.79054 | 3.10099 | 1.8 |
| 29.8991 | 2.98849 | 3.51 |
| 32.70738 | 2.73803 | 2.18 |
| 39.41492 | 2.28617 | 4.53 |

HCL Salt Form 4

HCl Salt Form 4 has a crystalline XRPD pattern as shown in FIG. 72. TGA and DSC thermograms of HCl Salt Form 4 are shown in FIG. 73. The DSC thermogram showed a desolvation endotherm at 94° C. and a following exotherm and another endotherm at 219° C. TGA weight loss 4.5% weight loss before 140° C. HCl Salt Form 4 was obtained from liquid vapor diffusion with MeOH/IPAc. HCl Salt Form 4 may be a solvate of the HCl salt of Compound 1.

A list of X-Ray Diffraction Peaks for HCl Salt Form 4 is provided below in Table 37.

TABLE 37

X-Ray Diffraction Peaks for HCl Salt Form 4.

| Two-theta angle (°) | d Space (Å) | Relative Intensity (%) |
|---|---|---|
| 7.938752 | 11.13696 | 84.85 |
| 8.058138 | 10.97223 | 51.11 |
| 8.219399 | 10.74841 | 15.24 |
| 8.403137 | 10.52251 | 48.95 |
| 10.82405 | 8.17387 | 4.19 |
| 14.02049 | 6.31673 | 2.92 |
| 15.33837 | 5.77683 | 10.12 |
| 15.88631 | 5.5788 | 61.42 |
| 16.43516 | 5.38925 | 2.52 |
| 16.80188 | 5.2768 | 25.48 |
| 17.76391 | 4.99314 | 2.94 |
| 18.28634 | 4.85165 | 12.92 |
| 18.89575 | 4.69653 | 35.91 |
| 19.14411 | 4.63616 | 100 |
| 19.66527 | 4.51446 | 24.64 |
| 20.25129 | 4.38512 | 2.59 |
| 21.01279 | 4.2279 | 14.75 |
| 21.59817 | 4.11121 | 3.83 |
| 22.12687 | 4.01748 | 1.47 |
| 23.30987 | 3.8162 | 7.57 |
| 23.64596 | 3.76271 | 13.56 |
| 24.92983 | 3.57177 | 5.47 |
| 25.29449 | 3.5211 | 14.93 |
| 26.25757 | 3.3941 | 6.32 |
| 27.63529 | 3.22794 | 2.52 |
| 28.46236 | 3.136 | 4.08 |
| 29.07177 | 3.07163 | 2.25 |
| 29.89888 | 2.98852 | 5.3 |
| 30.55282 | 2.92603 | 5.48 |
| 30.85491 | 2.89806 | 4.83 |
| 31.85292 | 2.8095 | 2.13 |
| 32.84365 | 2.72698 | 4.22 |
| 34.62294 | 2.59081 | 1.65 |
| 36.19538 | 2.48179 | 1.87 |

HCL Salt Form 5

HCl Salt Form 5 has a crystalline XRPD pattern as shown in FIG. 74. TGA and DSC thermograms of HCl Salt Form 5 are shown in FIG. 75. The DSC thermogram showed a desolvation endotherm at about 104° C. and about 162° C. followed by a possible melting endotherm with an onset at 192° C. and maximum at 209° C. TGA weight loss was 4.2% weight loss before 140° C. HCl Salt Form 5 was obtained from solid vapor diffusion with DMF. HCl Salt Form 5 may be a solvate of the HCl salt of Compound 1. HCl Salt Form 5 may be a hydrate of the HCl salt of Compound 1.

A list of X-Ray Diffraction Peaks for HCl Salt Form 5 is provided below in Table 38.

TABLE 38

X-Ray Diffraction Peaks for HCl Salt Form 5.

| Two-theta angle (°) | d Space (Å) | Relative Intensity (%) |
|---|---|---|
| 7.937265 | 11.13905 | 82.3 |
| 8.689078 | 10.17687 | 44.75 |
| 9.993996 | 8.85081 | 31.28 |
| 11.70052 | 7.56347 | 22.93 |
| 13.31624 | 6.64917 | 17.53 |
| 13.5735 | 6.51833 | 6.97 |
| 15.06167 | 5.88233 | 35.16 |
| 15.69989 | 5.64462 | 44.81 |
| 17.1975 | 5.15629 | 40.42 |
| 17.88152 | 4.95646 | 9.74 |
| 19.86425 | 4.46968 | 100 |
| 20.55088 | 4.32187 | 46.64 |
| 21.33943 | 4.16391 | 21.55 |
| 23.28608 | 3.82004 | 15.52 |
| 24.21503 | 3.67556 | 21.33 |
| 25.5195 | 3.49056 | 11.25 |
| 26.96277 | 3.30691 | 55.77 |
| 28.52699 | 3.12904 | 17.37 |
| 29.26391 | 3.0519 | 6.89 |
| 30.12972 | 2.96614 | 6.25 |
| 31.71499 | 2.81907 | 13.29 |
| 32.19053 | 2.7808 | 11.4 |
| 34.09124 | 2.62999 | 4.68 |
| 35.35318 | 2.53895 | 2.83 |
| 36.98646 | 2.4305 | 2.08 |
| 38.75596 | 2.32351 | 2.17 |

HCL Salt Form 6

HCl Salt Form 6 has a crystalline XRPD pattern as shown in FIG. 76. TGA and DSC thermograms of HCl Salt Form 6 are shown in FIG. 77. The DSC thermogram showed a dehydration endotherm at 88° C. and another endotherm with an onset at 201° C. and maximum at 228° C. TGA weight loss was 11.6% weight loss before 100° C. A second run DSC thermogram showed an endotherm at 89° C. and another endotherm with an onset at 211° C. and maximum at 225° C. (FIG. 79). The TGA weight loss corresponded to 15.9% weight loss before 120° C. (FIG. 78). The sample appeared to contain both surface and crystal water. The theoretical water content for a pentahydrate and hexahydrate is 12.9% and 15.1%, respectively. HCl Salt Form 6 was obtained from slurry in 0.1N HCl in water. HCl Salt Form 6 is a pentahydrate or a hexahydrate of the HCl salt of Compound 1.

A list of X-Ray Diffraction Peaks for HCl Salt Form 6 is provided below in Table 39.

TABLE 39

X-Ray Diffraction Peaks for HCl Salt Form 6.

| Two-theta angle (°) | d Space (Å) | Relative Intensity (%) |
|---|---|---|
| 7.043121 | 12.55104 | 17.58 |
| 8.750653 | 10.10539 | 15.35 |
| 9.852726 | 8.9774 | 100 |
| 11.47008 | 7.7149 | 17.12 |
| 12.15803 | 7.27987 | 11.47 |
| 12.43821 | 7.1165 | 66.17 |
| 14.72797 | 6.01485 | 19.95 |
| 16.34789 | 5.42231 | 25.48 |
| 16.7059 | 5.30251 | 3.34 |
| 17.47299 | 5.07561 | 64.11 |
| 17.91231 | 4.95211 | 76.6 |
| 18.2135 | 4.87089 | 8.18 |
| 18.60715 | 4.76872 | 4.99 |
| 19.16845 | 4.63033 | 42.87 |
| 19.35014 | 4.58726 | 15.37 |
| 19.71049 | 4.5042 | 86.74 |
| 19.89059 | 4.46382 | 56.77 |
| 20.26675 | 4.38181 | 3.67 |
| 20.99857 | 4.23073 | 21.73 |
| 21.24423 | 4.18236 | 6.59 |
| 21.89672 | 4.05918 | 9.98 |
| 22.69272 | 3.91857 | 11.28 |
| 22.87039 | 3.88853 | 12.81 |
| 23.71329 | 3.75218 | 11.12 |
| 24.62266 | 3.61563 | 16.07 |
| 24.95768 | 3.56785 | 21.97 |
| 25.58616 | 3.48162 | 20.79 |
| 26.26022 | 3.39376 | 11.72 |
| 26.54722 | 3.35772 | 6.89 |
| 26.79783 | 3.32688 | 12.32 |
| 27.24697 | 3.27306 | 20.4 |
| 27.60085 | 3.22921 | 3.05 |
| 28.22986 | 3.16129 | 10.88 |
| 28.68693 | 3.11195 | 16.16 |
| 29.10407 | 3.06576 | 4.81 |
| 29.63481 | 3.01454 | 12.04 |
| 30.27581 | 2.95216 | 2.91 |
| 30.83935 | 2.89949 | 6 |
| 31.23123 | 2.864 | 4.49 |
| 31.67746 | 2.82466 | 2.46 |
| 32.26273 | 2.77475 | 23.06 |
| 32.84882 | 2.72657 | 0.93 |
| 33.26344 | 2.69352 | 3 |
| 33.97406 | 2.63661 | 2.64 |
| 34.30005 | 2.61446 | 4 |
| 35.31073 | 2.54191 | 1.4 |
| 36.2495 | 2.4782 | 2.54 |
| 36.95941 | 2.43222 | 1.43 |

HCL Salt Form 7

HCl Salt Form 7 has a crystalline XRPD pattern as shown in FIG. 80. TGA and DSC thermograms of HCl Salt Form 7 are shown in FIG. 81. The DSC thermogram showed a dehydration endotherm with an onset at 80° C. and maximum at 110° C. and another endotherm with an onset at 215° C. and maximum at 233° C. TGA weight loss was 3.8% weight loss before 100° C. A second run DSC thermogram showed an endotherm with an onset at 71° C. and maximum at 98° C. and another endotherm with an onset at 209° C. and maximum at 230° C. (FIG. 83). The TGA weight loss corresponded to 3.4% weight loss before about 90° C. (FIG. 82). The theoretical water content for a monohydrate is 2.9%. HCl Salt Form 7 was obtained from water slurry at RT and air dried for 2 weeks. HCl Salt Form 7 is a monohydrate of the HCl salt of Compound 1.

A list of X-Ray Diffraction Peaks for HCl Salt Form 7 is provided below in Table 40.

TABLE 40

X-Ray Diffraction Peaks for HCl Salt Form 7.

| Two-theta angle (°) | d Space (Å) | Relative Intensity (%) |
|---|---|---|
| 7.850335 | 11.2622 | 40.81 |
| 8.092129 | 10.92622 | 63.33 |
| 8.328633 | 10.61647 | 44.79 |
| 10.76644 | 8.21748 | 20.86 |
| 13.81036 | 6.41237 | 13.87 |
| 14.50773 | 6.10566 | 3.83 |
| 15.29982 | 5.7913 | 36.58 |
| 15.60044 | 5.67568 | 5.43 |
| 16.15992 | 5.48495 | 43.64 |
| 16.64025 | 5.32769 | 18.84 |
| 16.97677 | 5.22283 | 11.15 |
| 17.63451 | 5.02949 | 11.9 |
| 18.33576 | 4.83869 | 29.55 |
| 18.64924 | 4.75805 | 17.26 |
| 19.11633 | 4.64284 | 100 |
| 19.57 | 4.53246 | 32.57 |
| 19.73225 | 4.49928 | 51.13 |
| 20.1927 | 4.39408 | 5.64 |
| 20.74966 | 4.28091 | 14.35 |
| 21.5192 | 4.12953 | 21.4 |
| 22.03008 | 4.03491 | 12.02 |
| 22.87123 | 3.88838 | 10.43 |
| 24.00267 | 3.7076 | 25.58 |
| 24.25357 | 3.66981 | 24.51 |
| 25.1557 | 3.54021 | 21.68 |
| 26.22969 | 3.39764 | 14.85 |
| 28.35525 | 3.1476 | 5.24 |
| 29.02731 | 3.07369 | 7.17 |
| 29.51012 | 3.02699 | 9.94 |
| 30.17205 | 2.95963 | 5.92 |
| 30.75171 | 2.90515 | 13.78 |
| 31.15329 | 2.87098 | 13.8 |
| 32.53576 | 2.75208 | 5.9 |
| 33.12518 | 2.70221 | 7.24 |
| 34.66455 | 2.5878 | 6.58 |
| 36.3054 | 2.47452 | 5.15 |

HCL Salt Form 8

HCl Salt Form 8 has a crystalline XRPD pattern as shown in FIG. 85. TGA and DSC thermograms of HCl Salt Form 8 are shown in FIG. 86. The DSC thermogram showed a dehydration endotherm with an onset at 117° C. and maximum at 146° C. and another endotherm with an onset at 208° C. and maximum at 221° C. TGA weight loss was 3.2% weight loss before 100° C. A second run DSC thermogram showed an endotherm at 148° C. (maximum) and another endotherm with an onset at 204° C. and maximum at 224° C. (FIG. 88). The TGA weight loss corresponded to 3.0% weight loss before 120° C. (FIG. 87). The theoretical water content for a monohydrate is 2.9%. HCl Salt Form 8 was obtained from water slurry at 50° C. and air dried for 2 weeks. HCl Salt Form 8 is a monohydrate of the HCl salt of Compound 1.

A list of X-Ray Diffraction Peaks for HCl Salt Form 8 is provided below in Table 41.

TABLE 41

X-Ray Diffraction Peaks for HCl Salt Form 8.

| Two-theta angle (°) | d Space (Å) | Relative Intensity (%) |
|---|---|---|
| 8.103976 | 10.91027 | 8.9 |
| 9.75706 | 9.0652 | 76.5 |
| 10.11246 | 8.7474 | 14.63 |
| 10.81305 | 8.17539 | 6.87 |
| 11.07871 | 7.98655 | 11.12 |
| 11.61823 | 7.61686 | 3.64 |

TABLE 41-continued

X-Ray Diffraction Peaks for HCl Salt Form 8.

| Two-theta angle (°) | d Space (Å) | Relative Intensity (%) |
|---|---|---|
| 15.67207 | 5.65457 | 10.72 |
| 16.16669 | 5.48267 | 7.71 |
| 16.85717 | 5.25962 | 6.54 |
| 17.39887 | 5.09707 | 100 |
| 17.96866 | 4.9367 | 48.71 |
| 18.67773 | 4.75086 | 86.44 |
| 19.16066 | 4.63219 | 8.88 |
| 19.60107 | 4.5291 | 14.54 |
| 21.35427 | 4.16105 | 18 |
| 22.05148 | 4.03104 | 3.73 |
| 22.94882 | 3.87541 | 14.4 |
| 23.84358 | 3.73197 | 13.2 |
| 24.24392 | 3.67125 | 13.61 |
| 25.06726 | 3.5525 | 4.2 |
| 25.45586 | 3.49914 | 5.79 |
| 26.24939 | 3.39514 | 71.25 |
| 26.70115 | 3.33871 | 10.55 |
| 28.15429 | 3.16961 | 11.3 |
| 28.43738 | 3.13869 | 12.07 |
| 29.57393 | 3.02061 | 3.56 |
| 30.49194 | 2.93173 | 10.08 |
| 31.73701 | 2.8195 | 10.32 |
| 31.99273 | 2.79754 | 8.69 |
| 33.69307 | 2.66015 | 4.23 |
| 35.57793 | 2.52343 | 4.42 |
| 36.36242 | 2.47077 | 3.1 |
| 37.37213 | 2.4063 | 4.35 |

Starting Material HCL Salt Form

The starting material HCl Salt Form has a crystalline XRPD pattern as shown in FIG. 63. TGA and DSC thermograms of starting material HCl Salt Form are shown in FIG. 64. The DSC thermogram showed one endotherm with an onset at about 238° C. and maximum at about 248° C. The TGA weight loss corresponded to about 1.0% weight loss before 100° C. A mass change of 3.6 wt % was observed for starting material from 0% RH to 95% RH at 25° C. The Cl content was 5.70 wt % and is in agreement with the theoretical Cl content for a 1:1 HCl salt of 5.84 wt %. The sample is moderately hygroscopic. The starting material HCl Salt Form may be an anhydrate form of the HCl salt of Compound 1.

A list of X-Ray Diffraction Peaks for starting material HCl Salt Form is provided below in Table 42.

TABLE 42

X-Ray Diffraction Peaks for starting material HCl Salt Form.

| Two-theta angle (°) | d Space (Å) | Relative Intensity (%) |
|---|---|---|
| 5.828535 | 15.1635 | 15.88 |
| 7.062807 | 12.5161 | 15.18 |
| 8.277888 | 10.68144 | 26.8 |
| 10.14078 | 8.72303 | 46.8 |
| 11.34123 | 7.80226 | 54.67 |
| 11.60621 | 7.62472 | 56.11 |
| 12.71036 | 6.96473 | 34.71 |
| 15.51306 | 5.71217 | 40.65 |
| 16.13662 | 5.49282 | 53.48 |
| 17.82084 | 4.97732 | 56.68 |
| 19.19574 | 4.62381 | 75.92 |
| 19.67368 | 4.51255 | 50.35 |
| 20.53309 | 4.32557 | 62.22 |
| 21.13495 | 4.20374 | 100 |
| 22.97894 | 3.8704 | 30.97 |
| 23.97222 | 3.71224 | 27.38 |
| 25.54515 | 3.48711 | 19.36 |
| 26.33352 | 3.38448 | 22.8 |
| 27.20446 | 3.27807 | 29.09 |
| 28.42589 | 3.13994 | 21.17 |
| 31.04672 | 2.88059 | 6.68 |

Cell Assays

Multiplexed cytotoxicity Assay.

Cells are grown in RPMI1640, 10% FBS, 2 mM L-alanyl-L-Glutamine, 1 mM Na pyruvate or a special medium in a humidified atmosphere of 5% $CO_2$ at 37° C. Cells are seeded into 384-well plates and incubated in a humidified atmosphere of 5% $CO_2$ at 37° C. Compounds are added 24 h post cell seeding. At the same time, a time zero untreated cell plate is generated. After a 72 hour incubation period, cells are fixed and stained with fluorescently labeled antibodies and nuclear dye to allow visualization of nuclei, apoptotic cells and mitotic cells. Apoptotic cells are detected using an anti-active caspase-3 antibody. Mitotic cells are detected using an anti phospho-histone-3 antibody. Compounds are serially diluted 3.16-fold and assayed over 10 concentrations in a final assay concentration of 0.1% DMSO from the highest test concentration of 10 µM. Automated fluorescence microscopy was carried out using a Molecular Devices ImageXpress Micro XL high-content imager, and images are collected with a 4x objective.

Data Analysis.

Sixteen-bit TIFF images are acquired and analyzed with MetaXpress 5.1.0.41 software. Cell proliferation is measured by the signal intensity of the incorporated nuclear dye. The cell proliferation assay output is referred to as the relative cell count. To determine the cell proliferation end point, the cell proliferation data output is transformed to percentage of control (POC) using the following formula:

POC=relative cell count(compound wells)/relative cell count(vehicle wells)×100

Relative cell count $IC_{50}$ is the test compound concentration at 50% of maximal possible response relative to the DMSO control. $GI_{50}$ is the concentration needed to reduce the observed growth by half. This is the concentration that inhibits the growth to the level midway between growth in untreated cells and the number of cells seeded in the well (Time zero value). The $IC_{50}$ values are calculated using nonlinear regression to fit data to a sigmoidal 4 point, 4 parameter One-Site dose response model, where:

$$y(\text{fit})=A+[(B-A)/(1+((C/x)\hat{}D))].$$

The activated caspase-3 marker labels cells from early to late stage apoptosis. Concentrations of test compound that cause a 5-fold induction in the caspase-3 signal (Cal_X5) indicate significant apoptosis induction. The maximal induction of caspase 3 by compound in comparison with DMSO control is reported as Max_Fold_Change.

TABLE 43

Cell lines used in multiplexed cytotoxicity assays

| Cell Line | Type | Subtype |
|---|---|---|
| SW-13 | Endocrine | Adrenal gland |
| NCI-H295R | Endocrine | Adrenal gland |
| 639-V | Bladder | Bladder |
| BFTC-905 | Bladder | Bladder |
| HT1376 | Bladder | Bladder |
| SCaBER | Bladder | Bladder |
| T24 | Bladder | Bladder |
| 5637 | Bladder | Bladder |
| 647-V | Bladder | Bladder |
| HT-1197 | Bladder | Bladder |
| TCCSUP | Bladder | Bladder |
| J82 | Bladder | Bladder |
| UM-UC-3 | Bladder | Bladder |
| MDA-MB-436 | Breast | Breast |
| Hs 578T | Breast | Breast |
| AU565 | Breast | Breast |
| BT20 | Breast | Breast |
| SK-BR-3 | Breast | Breast |
| BT474 | Breast | Breast |
| CAMA-1 | Breast | Breast |
| EFM-19 | Breast | Breast |
| KPL-1 | Breast | Breast |
| MDA MB 231 | Breast | Breast |
| MDA MB 453 | Breast | Breast |
| MCF7 | Breast | Breast |
| T47D | Breast | Breast |
| MDA-MB-415 | Breast | Breast |
| ZR-75-1 | Breast | Breast |
| BT-549 | Breast | Breast |
| MDA MB 468 | Breast | Breast |
| C-33A | Female GU | Cervix |
| C-4 I | Female GU | Cervix |
| C-4 II | Female GU | Cervix |
| HeLa | Female GU | Cervix |
| SiHa | Female GU | Cervix |
| DoTc2 4510 | Female GU | Cervix |
| HT-3 | Female GU | Cervix |
| LS513 | Colon | Colon |
| LS411N | Colon | Colon |
| SNU-C2B | Colon | Colon |
| LS123 | Colon | Colon |
| MT-3 | Colon | Colon |
| SW403 | Colon | Colon |
| RKO-AS45-1 | Colon | Colon |
| SW480 | Colon | Colon |
| SW948 | Colon | Colon |
| Colo 320 HSR | Colon | Colon |
| HCT-15 | Colon | Colon |
| HCT-116 | Colon | Colon |
| RKOE6 | Colon | Colon |
| SW48 | Colon | Colon |
| SW837 | Colon | Colon |
| SW1463 | Colon | Colon |
| Colo 320DM | Colon | Colon |
| HT-29 | Colon | Colon |
| LS1034 | Colon | Colon |
| Colo 201 | Colon | Colon |
| Colo 205 | Colon | Colon |
| NCI-H747 | Colon | Colon |
| RKO | Colon | Colon |
| SW1417 | Colon | Colon |
| DLD-1 | Colon | Colon |
| NCI-H508 | Colon | Colon |
| SW620 | Colon | Colon |
| WiDr | Colon | Colon |
| HRT-18 | Colon | Colon |
| LS-174T | Colon | Colon |
| HuTu 80 | Duodenum | Duodenum |
| Y79 | Eye | Eye |
| Hs 683 | Central Nervous System | Glioma |
| U-118 MG | Central Nervous System | Glioma |
| M059J | Central Nervous System | Glioma |
| PFSK-1 | Central Nervous System | Glioma |
| SW1783 | Central Nervous System | Glioma |
| SW1088 | Central Nervous System | Glioma |
| T98G | Central Nervous System | Glioma |

TABLE 43-continued

Cell lines used in multiplexed cytotoxicity assays

| Cell Line | Type | Subtype |
|---|---|---|
| CCF-STTG1 | Central Nervous System | Glioma |
| A172 | Central Nervous System | Glioma |
| DBTRG-05MG | Central Nervous System | Glioma |
| H4 | Central Nervous System | Glioma |
| SNB-19 | Central Nervous System | Glioma |
| U-138MG | Central Nervous System | Glioma |
| U-87 MG | Central Nervous System | Glioma |
| DK-MG | Central Nervous System | Glioma |
| A-253 | Head and Neck | Head and Neck |
| A388 | Head and Neck | Head and Neck |
| Detroit 562 | Head and Neck | Head and Neck |
| A431 | Head and Neck | Head and Neck |
| Cal 27 | Head and Neck | Head and Neck |
| OE19 | Head and Neck | Head and Neck |
| OE33 | Head and Neck | Head and Neck |
| SCC-4 | Head and Neck | Head and Neck |
| FaDu | Head and Neck | Head and Neck |
| OE21 | Head and Neck | Head and Neck |
| SCC-25 | Head and Neck | Head and Neck |
| SCC-9 | Head and Neck | Head and Neck |
| A-704 | Kidney | Kidney |
| 769-P | Kidney | Kidney |
| 786-O | Kidney | Kidney |
| G-402 | Kidney | Kidney |
| ACHN | Kidney | Kidney |
| Caki-1 | Kidney | Kidney |
| Caki-2 | Kidney | Kidney |
| SK-NEP-1 | Kidney | Kidney |
| G-401 | Kidney | Kidney |
| A498 | Kidney | Kidney |
| KG-1 | Hematopoietic | Leukemia |
| RS4; 11 | Hematopoietic | Leukemia |
| KU812 | Hematopoietic | Leukemia |
| TF-1 | Hematopoietic | Leukemia |
| MX1 | Hematopoietic | Leukemia |
| NALM-6 | Hematopoietic | Leukemia |
| MOLT-3 | Hematopoietic | Leukemia |
| MOLT-16 | Hematopoietic | Leukemia |
| MEG01 | Hematopoietic | Leukemia |
| MHH-PREB-1 | Hematopoietic | Leukemia |
| MV-4-11 | Hematopoietic | Leukemia |
| Thp1 | Hematopoietic | Leukemia |
| BV-173 | Hematopoietic | Leukemia |
| CCRFCEM | Hematopoietic | Leukemia |
| CML-T1 | Hematopoietic | Leukemia |
| HEL-92-1-7 | Hematopoietic | Leukemia |
| J-RT3-T3-5 | Hematopoietic | Leukemia |
| Jurkat | Hematopoietic | Leukemia |
| CEM-C1 | Hematopoietic | Leukemia |
| EM-2 | Hematopoietic | Leukemia |
| K562 | Hematopoietic | Leukemia |
| HuCCT1 | Liver | Liver |
| HLE | Liver | Liver |
| HUH-6 Clone 5 | Liver | Liver |
| HepG2 | Liver | Liver |
| HLF | Liver | Liver |
| OCUG-1 | Liver | Liver |
| SNU-423 | Liver | Liver |
| Hs 611.T | Hematopoietic | Lymphoma |
| EB2 | Hematopoietic | Lymphoma |
| GA-10 | Hematopoietic | Lymphoma |
| H9 | Hematopoietic | Lymphoma |
| JeKo-1 | Hematopoietic | Lymphoma |
| SU-DHL-8 | Hematopoietic | Lymphoma |
| SUP-TI | Hematopoietic | Lymphoma |
| TUR | Hematopoietic | Lymphoma |
| Hs 445 | Hematopoietic | Lymphoma |
| BCP-1 | Hematopoietic | Lymphoma |
| CA46 | Hematopoietic | Lymphoma |
| Jiyoye | Hematopoietic | Lymphoma |
| MC116 | Hematopoietic | Lymphoma |
| NAMALWA | Hematopoietic | Lymphoma |
| REC-1 | Hematopoietic | Lymphoma |
| SU-DHL-4 | Hematopoietic | Lymphoma |
| SU-DHL-5 | Hematopoietic | Lymphoma |
| SU-DHL-10 | Hematopoietic | Lymphoma |

TABLE 43-continued

Cell lines used in multiplexed cytotoxicity assays

| Cell Line | Type | Subtype |
|---|---|---|
| DB | Hematopoietic | Lymphoma |
| DOHH-2 | Hematopoietic | Lymphoma |
| HT | Hematopoietic | Lymphoma |
| RPMI 6666 | Hematopoietic | Lymphoma |
| Raji | Hematopoietic | Lymphoma |
| SR | Hematopoietic | Lymphoma |
| ST486 | Hematopoietic | Lymphoma |
| BC-1 | Hematopoietic | Lymphoma |
| Daudi | Hematopoietic | Lymphoma |
| L-428 | Hematopoietic | Lymphoma |
| EB-3 | Hematopoietic | Lymphoma |
| Ramos (RA 1) | Hematopoietic | Lymphoma |
| CRO-AP2 | Hematopoietic | Lymphoma |
| D341 Med | Central Nervous System | Medulloblastoma |
| D283 Med | Central Nervous System | Medulloblastoma |
| Daoy | Central Nervous System | Medulloblastoma |
| Hs 852.T | Skin (Melanoma) | Melanoma |
| WM-266-4 | Skin (Melanoma) | Melanoma |
| Hs 934.T | Skin (Melanoma) | Melanoma |
| A2058 | Skin (Melanoma) | Melanoma |
| G-361 | Skin (Melanoma) | Melanoma |
| Hs 688(A).T | Skin (Melanoma) | Melanoma |
| Hs 936.T(C1) | Skin (Melanoma) | Melanoma |
| Hs 895.T | Skin (Melanoma) | Melanoma |
| A7 | Skin (Melanoma) | Melanoma |
| C32 | Skin (Melanoma) | Melanoma |
| CHL-1 | Skin (Melanoma) | Melanoma |
| SK-MEL-28 | Skin (Melanoma) | Melanoma |
| SH-4 | Skin (Melanoma) | Melanoma |
| RPMI-7951 | Skin (Melanoma) | Melanoma |
| MALME3M | Skin (Melanoma) | Melanoma |
| MeWo | Skin (Melanoma) | Melanoma |
| SK-MEL-1 | Skin (Melanoma) | Melanoma |
| SK-MEL-3 | Skin (Melanoma) | Melanoma |
| C32TG | Skin (Melanoma) | Melanoma |
| Hs 294T | Skin (Melanoma) | Melanoma |
| Hs 695T | Skin (Melanoma) | Melanoma |
| A101D | Skin (Melanoma) | Melanoma |
| A375 | Skin (Melanoma) | Melanoma |
| COLO 829 | Skin (Melanoma) | Melanoma |
| HMCB | Skin (Melanoma) | Melanoma |
| IM-9 | Hematopoietic | Myeloma |
| SKO-007 | Hematopoietic | Myeloma |
| U266B1 | Hematopoietic | Myeloma |
| RPMI 8226 | Hematopoietic | Myeloma |
| ARH-77 | Hematopoietic | Myeloma |
| BE(2)C | Central Nervous System | Neuroblastoma |
| SK-N-FI | Central Nervous System | Neuroblastoma |
| CHP-212 | Central Nervous System | Neuroblastoma |
| SK-N-AS | Central Nervous System | Neuroblastoma |
| MC-IXC | Central Nervous System | Neuroblastoma |
| SK-N-DZ | Central Nervous System | Neuroblastoma |
| Hs 229.T | Lung | NSCLC |
| NCI-H661 | Lung | NSCLC |
| A427 | Lung | NSCLC |
| Calu6 | Lung | NSCLC |
| NCI-H460 | Lung | NSCLC |
| NCI-H520 | Lung | NSCLC |
| NCI-H596 | Lung | NSCLC |
| NCIH441 | Lung | NSCLC |
| A549 | Lung | NSCLC |
| ChaGoK1 | Lung | NSCLC |
| Calu1 | Lung | NSCLC |
| COR-L23 | Lung | NSCLC |
| SKMES1 | Lung | NSCLC |
| NCI-H292 | Lung | NSCLC |
| COR-L105 | Lung | NSCLC |
| G-292, clone A141B1 | Soft Tissue | Osteosarcoma |
| Hs 888.Sk | Soft Tissue | Osteosarcoma |
| HOS | Soft Tissue | Osteosarcoma |
| MG-63 | Soft Tissue | Osteosarcoma |
| SJSA1 | Soft Tissue | Osteosarcoma |
| SW1353 | Soft Tissue | Osteosarcoma |
| SaOS2 | Soft Tissue | Osteosarcoma |
| U2OS | Soft Tissue | Osteosarcoma |
| KHOS-240S | Soft Tissue | Osteosarcoma |
| ME-180 | Female GU | Ovary |
| PA-1 | Female GU | Ovary |
| Ca Ski | Female GU | Ovary |
| MS751 | Female GU | Ovary |
| CaOV3 | Female GU | Ovary |
| OVCAR3 | Female GU | Ovary |
| SKOV3 | Female GU | Ovary |
| PSN-1 | Pancreas | Pancreas |
| AsPC-1 | Pancreas | Pancreas |
| PANC-1 | Pancreas | Pancreas |
| Hs 766T | Pancreas | Pancreas |
| Mia PaCa-2 | Pancreas | Pancreas |
| SU.86.86 | Pancreas | Pancreas |
| YAPC | Pancreas | Pancreas |
| BxPC-3 | Pancreas | Pancreas |
| CFPAC-1 | Pancreas | Pancreas |
| Capan-1 | Pancreas | Pancreas |
| Capan-2 | Pancreas | Pancreas |
| HPAF-II | Pancreas | Pancreas |
| HuP-T4 | Pancreas | Pancreas |
| BeWo | Placenta | Placenta |
| JAR | Placenta | Placenta |
| JEG-3 | Placenta | Placenta |
| 22Rv1 | Prostate | Prostate |
| DU145 | Prostate | Prostate |
| PC-3 | Prostate | Prostate |
| LNCaP | Prostate | Prostate |
| BM-1604 | Prostate | Prostate |
| BPH1 | Prostate | Prostate |
| Hs 729 | Soft Tissue | Sarcoma |
| VA-ES-BJ | Soft Tissue | Sarcoma |
| Hs 821.T | Soft Tissue | Sarcoma |
| TE 125.T | Soft Tissue | Sarcoma |
| RD | Soft Tissue | Sarcoma |
| SK-UT-1 | Soft Tissue | Sarcoma |
| A-673 | Soft Tissue | Sarcoma |
| SW684 | Soft Tissue | Sarcoma |
| A204 | Soft Tissue | Sarcoma |
| SW872 | Soft Tissue | Sarcoma |
| SW982 | Soft Tissue | Sarcoma |
| HT-1080 | Soft Tissue | Sarcoma |
| MES-SA | Soft Tissue | Sarcoma |
| SJRH30 | Soft Tissue | Sarcoma |
| SK-LMS-1 | Soft Tissue | Sarcoma |
| TE 381.T | Soft Tissue | Sarcoma |
| NCI-H510A | Lung | SCLC |
| NCIH446 | Lung | SCLC |
| SHP-77 | Lung | SCLC |
| DMS114 | Lung | SCLC |
| SW900 | Lung | SCLC |
| DMS53 | Lung | SCLC |
| NCI-H69 | Lung | SCLC |
| DMS273 | Lung | SCLC |
| SK-PN-DW | Stomach | Stomach |
| AGS | Stomach | Stomach |
| HS 746T | Stomach | Stomach |
| SNU-1 | Stomach | Stomach |
| KATO III | Stomach | Stomach |
| SNU-16 | Stomach | Stomach |
| SNU-5 | Stomach | Stomach |
| NTERA-2 cl.D1 | Testis | Testis |
| TT | Endocrine | Thyroid |
| BHT-101 | Endocrine | Thyroid |
| CAL-62 | Endocrine | Thyroid |
| CGTH-W-1 | Endocrine | Thyroid |
| SW579 | Endocrine | Thyroid |
| HEC-1-A | Female GU | Uterus |
| RL95-2 | Female GU | Uterus |
| KLE | Female GU | Uterus |
| AN3 CA | Female GU | Uterus |
| SW962 | Female GU | Vulva |
| SW954 | Female GU | Vulva |

The solid forms of Compound 1 described herein show or will be shown to have anti-proliferative activity in a variety of cancer cell lines. Anti-proliferative activity in these cancer cell lines indicates that the Aminopurine compounds may be useful in the treatment of cancers, including solid tumors, as exemplified by melanoma, colorectal cancer, stomach cancer, head and neck cancer, thyroid cancer, bladder cancer, CNS cancer, lung cancer, pancreatic cancer, and soft tissue cancer.

In another embodiment, solid forms of Compound 1 described herein show or will be shown to induce apoptosis in a variety of cancer cell lines. Induction of apoptosis indicates that the solid forms of Compound 1 described herein may be useful in the treatment of cancers, including solid tumors, as exemplified by bladder cancer, breast cancer, CNS cancer (including neuroblastoma and glioma), colon cancer, gastrointestinal cancer (for example, stomach cancer or colon cancer), endocrine cancer (for example, thyroid cancer or adrenal gland cancer), female genitoureal cancer (for example, cervix cancer or ovary clear cell cancer, vulva cancer, uterus cancer, or ovary cancer), head and neck cancer, hematopoietic cancer (for example, leukemia or myeloma), kidney cancer, liver cancer, lung (for example, NSCLC or SCLC), melanoma, pancreas cancer, prostate cancer, or soft tissue cancer (for example, sarcoma or osteosarcoma).

In another embodiment, solid forms of Compound 1 described herein show or will be shown to cause G1/S arrest in a variety of cancer cell lines. Causing G1/S arrest in these cancer cell lines indicates that the compounds may be useful in the treatment of cancers, including solid tumors, as exemplified by bladder cancer, breast cancer, CNS cancer (for example, glioma or neuroblastoma), colon cancer, gastrointestinal cancer (for example, stomach cancer), endocrine cancer (for example, thyroid cancer or adrenal gland cancer), female genitoureal cancer (for example, uterus cancer, cervix cancer, ovary clear cell cancer, or vulva cancer), head and neck cancer, hematopoietic cancer (for example, leukemia or myeloma), kidney cancer, liver cancer, lung cancer (for example, NSCLC or SCLC), melanoma, pancreas cancer, prostate cancer, or soft tissue cancer (sarcoma or osteosarcoma).

Multiplexed Cytotoxicity Assay.

In another experiment, cells were grown in RPMI1640, 10% FBS, 2 mM L-alanyl-L-Glutamine, 1 mM Na pyruvate or a special medium in a humidified atmosphere of 5% $CO_2$ at 37° C. Cells were seeded into 384-well plates and incubated in a humidified atmosphere of 5% $CO_2$ at 37° C. Compounds were added 24 h post cell seeding. At the same time, a time zero untreated cell plate was generated. After a 72 hour incubation period, cells were fixed and stained with fluorescently labeled antibodies and nuclear dye to allow visualization of nuclei, apoptotic cells and mitotic cells. Apoptotic cells were detected using an anti-active caspase-3 antibody. Mitotic cells were detected using an anti phospho-histone-3 antibody. Compounds were serially diluted 3.16-fold and assayed over 10 concentrations in a final assay concentration of 0.1% DMSO from the highest test concentration of 10 μM. Automated fluorescence microscopy was carried out using a Molecular Devices ImageXpress Micro XL high-content imager, and images were collected with a 4× objective.

Data Analysis.

Sixteen-bit TIFF images were acquired and analyzed with MetaXpress 5.1.0.41 software. Cell proliferation was measured by the signal intensity of the incorporated nuclear dye. The cell proliferation assay output was referred to as the relative cell count. To determine the cell proliferation end point, the cell proliferation data output was transformed to percentage of control (POC) using the following formula:

POC=relative cell count(compound wells)/relative cell count(vehicle wells)×100

Relative cell count $IC_{50}$ was the test compound concentration at 50% of maximal possible response relative to the DMSO control. $GI_{50}$ refers to the concentration needed to reduce the observed growth by half. This corresponds to the concentration that inhibits the growth to the level midway between growth in untreated cells and the number of cells seeded in the well (Time zero value). The $IC_{50}$ values were calculated using nonlinear regression to fit data to a sigmoidal 4 point, 4 parameter One-Site dose response model, where:

$y(\text{fit})=A+[(B-A)/(1+((C/x)^D))]$.

The activated caspase-3 marker labels cells from early to late stage apoptosis. Concentrations of test compound that cause a 2-fold (Cal-X2) or 5-fold induction in the caspase-3 signal (Cal_X5) indicated significant apoptosis induction. The maximal induction of caspase 3 by compound in comparison with DMSO control was reported as Max_Fold_Change.

TABLE 44

Results of Cytotoxicity Assays

| Cell line | Tumor Type | Subtype | GI50 (μM) | IC50 (μM) | CalX2 (μM) | CalX5 (μM) | Max fold change |
|---|---|---|---|---|---|---|---|
| NCIH295R | Endocrine | Adrenal gland | 10 | 10 | 10 | 10 | 1.74 |
| SW13 | Endocrine | Adrenal gland | 0.0711 | 0.135 | 0.04 | 0.535 | 8.74 |
| 5637 | Bladder | Bladder | 6.85 | 9.77 | 10 | 10 | 2.12 |
| 639V | Bladder | Bladder | 0.184 | 0.206 | 0.0841 | 0.465 | 6.33 |
| 647V | Bladder | Bladder | 6.93 | 7.82 | 2.7413 | 4.45 | 19.29 |
| BFTC905 | Bladder | Bladder | 0.0515 | 0.0546 | 0.0179 | 0.0414 | 45.3 |
| HT1197 | Bladder | Bladder | 0.444 | 10 | 0.1601 | 10 | 4.16 |
| HT1376 | Bladder | Bladder | 0.792 | 3.48 | 0.0524 | 0.167 | 10.87 |
| J82 | Bladder | Bladder | 10 | 10 | 2.4365 | 10 | 3.17 |
| SCABER | Bladder | Bladder | 0.0665 | 0.0772 | 0.0086 | 0.0506 | 29.47 |
| T24 | Bladder | Bladder | 0.233 | 0.274 | 4.5443 | 10 | 2.61 |
| TCCSUP | Bladder | Bladder | 2.21 | 6.59 | 5.6435 | 10 | 3.67 |
| UMUC3 | Bladder | Bladder | 0.149 | 0.201 | 2.7934 | 5.76 | 6.56 |
| AU565 | Breast | Breast | 8.15 | 8.77 | 3.8749 | 7.14 | 14.18 |
| BT20 | Breast | Breast | 8.36 | 10 | 10 | 10 | 1.81 |

TABLE 44-continued

Results of Cytotoxicity Assays

| Cell line | Tumor Type | Subtype | GI50 (µM) | IC50 (µM) | CalX2 (µM) | CalX5 (µM) | Max fold change |
|---|---|---|---|---|---|---|---|
| BT474 | Breast | Breast | 10 | 10 | 10 | 10 | 0.94 |
| BT549 | Breast | Breast | 10 | 10 | 5.4537 | 10 | 3.14 |
| CAMA1 | Breast | Breast | 0.298 | 2.24 | 6.4981 | 10 | 2.85 |
| EFM19 | Breast | Breast | 4.2 | 10 | 10 | 10 | 2.1 |
| HS578T | Breast | Breast | 0.153 | 0.837 | 2.6723 | 6.58 | 5.94 |
| KPL1 | Breast | Breast | 10 | 10 | 0.0481 | 10 | 2.63 |
| MCF7 | Breast | Breast | 0.636 | 3.47 | 6.5592 | 9.74 | 5.78 |
| MDAMB231 | Breast | Breast | 0.0339 | 0.0624 | 0.0242 | 0.257 | 5.94 |
| MDAMB415 | Breast | Breast | 0.729 | 10 | 10 | 10 | 1.85 |
| MDAMB436 | Breast | Breast | 0.262 | 10 | 5.118 | 10 | 4.25 |
| MDAMB453 | Breast | Breast | 0.656 | 2.82 | 10 | 10 | 1.07 |
| MDAMB468 | Breast | Breast | 0.0363 | 0.0721 | 0.0969 | 10 | 3.81 |
| MT3 | Breast | Breast | 0.674 | 1.08 | 7.6544 | 10 | 2.81 |
| SKBR3 | Breast | Breast | 6.81 | 8.45 | 3.2211 | 6.2 | 12.79 |
| T47D | Breast | Breast | 10 | 10 | 10 | 10 | 2 |
| ZR751 | Breast | Breast | 0.0943 | 7.7 | 5.9055 | 6.44 | 7.36 |
| A431 | Skin | Carcinoma | 0.228 | 0.311 | 0.0801 | 1.76 | 5.11 |
| C33A | Female GU | Cervix | 0.191 | 0.407 | 3.6798 | 5.39 | 9.45 |
| C4I | Female GU | Cervix | 10 | 10 | 5.7177 | 7.94 | 7.38 |
| C4II | Female GU | Cervix | 10 | 10 | 0.044 | 10 | 3.7 |
| DOTC24510 | Female GU | Cervix | 0.04 | 0.132 | 0.0268 | 10 | 5.03 |
| HELA | Female GU | Cervix | 6.75 | 8.71 | 7.0794 | 10 | 3.65 |
| HT3 | Female GU | Cervix | 0.856 | 3.21 | 0.2906 | 3.74 | 7.49 |
| SIHA | Female GU | Cervix | 10 | 10 | 7.6882 | 8.82 | 5.49 |
| COLO201 | Colon | Colon | 0.0128 | 0.0172 | 0.0225 | 0.267 | 6.09 |
| COLO205 | Colon | Colon | 0.0095 | 0.0117 | 0.0102 | 0.0248 | 9.86 |
| COLO320DM | Colon | Colon | 9.11 | 10 | 6.1862 | 9.53 | 5.28 |
| COLO320HSR | Colon | Colon | 4.19 | 4.44 | 2.0186 | 3.53 | 49.73 |
| DLD1 | Colon | Colon | 0.162 | 0.197 | 0.0474 | 0.104 | 21.95 |
| HCT116 | Colon | Colon | 0.0194 | 0.0204 | 0.0196 | 0.0448 | 45.43 |
| HCT15 | Colon | Colon | 1.97 | 2.23 | 5.1211 | 7.03 | 7.97 |
| HRT18 | Colon | Colon | 0.0775 | 0.0819 | 0.0657 | 0.147 | 11.1 |
| HT29 | Colon | Colon | 0.0129 | 0.0167 | 0.0092 | 0.0318 | 61.59 |
| LS1034 | Colon | Colon | 0.224 | 0.676 | 1.4781 | 10 | 2.52 |
| LS123 | Colon | Colon | 0.061 | 0.188 | 0.0766 | 10 | 4.74 |
| LS174T | Colon | Colon | 0.194 | 0.259 | 0.2846 | 0.412 | 5.63 |
| LS411N | Colon | Colon | 0.0358 | 0.053 | 0.0575 | 10 | 5.58 |
| LS513 | Colon | Colon | 0.0353 | 0.0386 | 0.0233 | 0.0356 | 64.31 |
| NCIH508 | Colon | Colon | 0.0288 | 0.0481 | 0.0778 | 1.25 | 5.37 |
| NCIH747 | Colon | Colon | 0.012 | 0.0445 | 0.0226 | 0.0756 | 8.21 |
| RKO | Colon | Colon | 0.0353 | 0.0405 | 0.0407 | 0.378 | 11.14 |
| RKOAS451 | Colon | Colon | 0.0405 | 0.0449 | 0.1873 | 1.16 | 10.06 |
| RKOE6 | Colon | Colon | 0.0753 | 0.107 | 1.6988 | 3.6 | 29.26 |
| SNUC2B | Colon | Colon | 0.0544 | 0.722 | 10 | 10 | 1.67 |
| SW1417 | Colon | Colon | 0.0088 | 0.0351 | 0.0221 | 0.0693 | 6.76 |
| SW1463 | Colon | Colon | 0.135 | 0.181 | 2.4138 | 10 | 2.82 |
| SW403 | Colon | Colon | 0.0476 | 0.173 | 0.1084 | 10 | 4.02 |
| SW48 | Colon | Colon | 0.0018 | 0.0031 | 0.0047 | 0.0266 | 13.66 |
| SW480 | Colon | Colon | 0.0184 | 0.0311 | 0.0638 | 0.248 | 6.26 |
| SW620 | Colon | Colon | 0.0492 | 0.0798 | 1.4774 | 3.88 | 14.66 |
| SW837 | Colon | Colon | 0.172 | 0.348 | 0.325 | 10 | 4.34 |
| SW948 | Colon | Colon | 0.195 | 0.327 | 10 | 10 | 1.57 |
| WIDR | Colon | Colon | 0.0104 | 0.0133 | 0.0085 | 0.021 | 79.03 |
| HUTU80 | Duodenum | Duodenum | 0.057 | 0.0695 | 0.0161 | 0.354 | 9.27 |
| Y79 | Eye-retinoblastoma | Eye | 10 | 10 | 7.8739 | 10 | 2.58 |
| A172 | CNS | Glioma | 0.0649 | 0.139 | 0.1174 | 2.36 | 5.95 |
| CCFSTTG1 | CNS | Glioma | 10 | 10 | 10 | 10 | 1.03 |
| DBTRG05MG | CNS | Glioma | 0.0432 | 0.0984 | 0.1963 | 10 | 3.94 |
| DKMG | CNS | Glioma | 0.0207 | 0.126 | 0.0463 | 0.16 | 10.86 |
| H4 | CNS | Glioma | 0.758 | 0.943 | 1.7285 | 3.78 | 14.47 |
| HS683 | CNS | Glioma | 0.148 | 0.305 | 10 | 10 | 2.54 |
| M059J | CNS | Glioma | 0.612 | 3.31 | 4.9633 | 10 | 2.8 |
| PFSK1 | CNS | Glioma | 0.0234 | 10 | 10 | 10 | 1.06 |
| SNB19 | CNS | Glioma | 0.163 | 0.244 | 0.4478 | 10 | 3.29 |
| SW1088 | CNS | Glioma | 3.35 | 5.98 | 5.2615 | 7.5 | 9.59 |
| SW1783 | CNS | Glioma | 5.92 | 9.85 | 9.0994 | 10 | 2.49 |
| T98G | CNS | Glioma | 10 | 10 | 5.4225 | 10 | 3.16 |
| U118MG | CNS | Glioma | 0.175 | 10 | 10 | 10 | 1.92 |
| U138MG | CNS | Glioma | 0.053 | 10 | 0.1598 | 0.417 | 8.01 |
| U87MG | CNS | Glioma | 0.0692 | 0.101 | 9.3615 | 10 | 2.14 |
| A253 | Head and Neck | Head and Neck | 0.171 | 10 | 8.7811 | 10 | 2.85 |

TABLE 44-continued

Results of Cytotoxicity Assays

| Cell line | Tumor Type | Subtype | GI50 (μM) | IC50 (μM) | CalX2 (μM) | CalX5 (μM) | Max fold change |
|---|---|---|---|---|---|---|---|
| A388 | Head and Neck | Head and Neck | 0.422 | 1.12 | 0.0902 | 3.52 | 6.48 |
| CAL27 | Head and Neck | Head and Neck | 0.0592 | 0.0661 | 0.0877 | 0.46 | 7.98 |
| DETROIT562 | Head and Neck | Head and Neck | 0.347 | 10 | 4.9484 | 7.16 | 6.02 |
| FADU | Head and Neck | Head and Neck | 0.435 | 0.787 | 4.0608 | 5.64 | 8.64 |
| SCC25 | Head and Neck | Head and Neck | 0.0439 | 0.051 | 0.1187 | 0.304 | 6.72 |
| SCC4 | Head and Neck | Head and Neck | 0.0512 | 0.108 | 0.0317 | 0.065 | 7.38 |
| SCC9 | Head and Neck | Head and Neck | 0.117 | 0.28 | 0.6679 | 3.86 | 9.58 |
| 769P | Kidney | Kidney | 0.194 | 0.255 | 0.2023 | 5.11 | 5.67 |
| 786O | Kidney | Kidney | 2.04 | 6.92 | 10 | 10 | 0.83 |
| A498 | Kidney | Kidney | 0.522 | 0.808 | 0.5562 | 10 | 4.72 |
| A704 | Kidney | Kidney | 10 | 10 | 10 | 10 | 0.96 |
| ACHN | Kidney | Kidney | 0.306 | 0.55 | 0.78 | 10 | 2.97 |
| CAKI1 | Kidney | Kidney | 0.0914 | 0.151 | 0.2015 | 10 | 4.12 |
| CAKI2 | Kidney | Kidney | 0.139 | 0.193 | 0.1631 | 0.449 | 6.26 |
| G401 | Kidney | Kidney | 0.0774 | 0.086 | 0.0717 | 0.179 | 30.87 |
| G402 | Kidney | Kidney | 0.0504 | 0.0925 | 0.0162 | 0.637 | 7.34 |
| SKNEP1 | Kidney | Kidney | 10 | 10 | 10 | 10 | 1.15 |
| BV173 | Hematopoietic and lymphoid | Leukemia | 1.1 | 10 | 0.4959 | 10 | 2.91 |
| CCRFCEM | Hematopoietic and lymphoid | Leukemia | 5.03 | 6.05 | 3.4279 | 6.95 | 12.74 |
| CEMC1 | Hematopoietic and lymphoid | Leukemia | 10 | 10 | 4.1828 | 5.22 | 11.27 |
| CMLT1 | Hematopoietic and lymphoid | Leukemia | 0.149 | 10 | 0.0948 | 10 | 4.85 |
| EM2 | Hematopoietic and lymphoid | Leukemia | 0.0481 | 0.0936 | 10 | 10 | 1.55 |
| HEL9217 | Hematopoietic and lymphoid | Leukemia | 4.62 | 8.23 | 3.2991 | 6.57 | 6.23 |
| JRT3T35 | Hematopoietic and lymphoid | Leukemia | 3.58 | 4.78 | 2.6364 | 3.8 | 14.26 |
| JURKAT | Hematopoietic and lymphoid | Leukemia | 3.34 | 3.73 | 1.6173 | 3.28 | 14.48 |
| K562 | Hematopoietic and lymphoid | Leukemia | 10 | 10 | 2.9298 | 4.86 | 51.89 |
| KG1 | Hematopoietic and lymphoid | Leukemia | 0.0017 | 0.0325 | 2.5811 | 10 | 2.5 |
| KU812 | Hematopoietic and lymphoid | Leukemia | 0.003 | 0.0159 | 0.03 | 8.02 | 5.63 |
| MEG01 | Hematopoietic and lymphoid | Leukemia | 0.0818 | 0.221 | 0.5718 | 10 | 2.77 |
| MHHPREB1 | Hematopoietic and lymphoid | Leukemia | 6.69 | 6.97 | 5.1142 | 7.66 | 11.43 |
| MOLT16 | Hematopoietic and lymphoid | Leukemia | 2.88 | 3.35 | 2.4102 | 4.97 | 8.06 |
| MOLT3 | Hematopoietic and lymphoid | Leukemia | 0.946 | 3.03 | 5.88 | 10 | 3.63 |
| MV411 | Hematopoietic and lymphoid | Leukemia | 0.107 | 0.184 | 0.0933 | 1.15 | 8.12 |
| MX1 | Hematopoietic and lymphoid | Leukemia | 0.0401 | 0.0619 | 1.1016 | 10 | 3.78 |
| NALM6 | Hematopoietic and lymphoid | Leukemia | 10 | 10 | 0.1241 | 10 | 5 |
| RS411 | Hematopoietic and lymphoid | Leukemia | 0.359 | 2.96 | 3.8025 | 8.4 | 5.83 |
| TF1 | Hematopoietic and lymphoid | Leukemia | 0.0015 | 0.0095 | 0.006 | 0.0296 | 16.1 |
| THP1 | Hematopoietic and lymphoid | Leukemia | 0.0251 | 0.0495 | 0.132 | 3.9 | 6.3 |
| HEPG2 | Liver | Liver | 0.0224 | 0.0643 | 0.0041 | 0.0108 | 62.47 |
| HLE | Liver | Liver | 0.683 | 1.04 | 0.8174 | 10 | 2.5 |
| HLF | Liver | Liver | 4.76 | 6.47 | 10 | 10 | 1.95 |
| HUCCT1 | Liver | Liver | 0.0537 | 0.0633 | 0.0222 | 0.0406 | 11.54 |
| HUH6CLONE5 | Liver | Liver | 0.145 | 0.354 | 0.0631 | 0.302 | 8.25 |
| OCUG1 | Liver | Liver | 0.464 | 1.29 | 0.0848 | 0.49 | 5.49 |
| SNU423 | Liver | Liver | 0.192 | 0.276 | 0.0909 | 1.65 | 7.32 |

TABLE 44-continued

Results of Cytotoxicity Assays

| Cell line | Tumor Type | Subtype | GI50 (μM) | IC50 (μM) | CalX2 (μM) | CalX5 (μM) | Max fold change |
|---|---|---|---|---|---|---|---|
| BC1 | Hematopoietic and lymphoid | Lymphoma | 10 | 10 | 5.1005 | 6.54 | 8.72 |
| BCP1 | Hematopoietic and lymphoid | Lymphoma | 0.0205 | 0.0797 | 4.8663 | 7.36 | 6.56 |
| CA46 | Hematopoietic and lymphoid | Lymphoma | 0.0146 | 0.0213 | 3.2395 | 8.08 | 9.46 |
| CROAP2 | Hematopoietic and lymphoid | Lymphoma | 0.996 | 2.58 | 2.9603 | 4.2 | 50.79 |
| DAUDI | Hematopoietic and lymphoid | Lymphoma | 0.0177 | 10 | 3.9392 | 5.33 | 10.08 |
| DB | Hematopoietic and lymphoid | Lymphoma | 0.0131 | 10 | 6.1153 | 6.5 | 7.11 |
| DOHH2 | Hematopoietic and lymphoid | Lymphoma | 5.54 | 5.79 | 2.4833 | 3.99 | 20.41 |
| EB2 | Hematopoietic and lymphoid | Lymphoma | 0.389 | 0.55 | 5.7381 | 10 | 4.16 |
| EB3 | Hematopoietic and lymphoid | Lymphoma | 1.63 | 2.15 | 6.1469 | 7.66 | 5.5 |
| GA10 | Hematopoietic and lymphoid | Lymphoma | 0.0468 | 0.0567 | 0.6477 | 1.94 | 6.49 |
| H9 | Hematopoietic and lymphoid | Lymphoma | 0.0232 | 0.039 | 0.0222 | 0.4 | 7.33 |
| HS445 | Hematopoietic and lymphoid | Lymphoma | 0.0143 | 0.0377 | 4.9128 | 7.7 | 5.65 |
| HS611T | Hematopoietic and lymphoid | Lymphoma | 0.0106 | 0.0123 | 2.8507 | 10 | 3.84 |
| HT | Hematopoietic and lymphoid | Lymphoma | 8.3 | 10 | 8.6354 | 10 | 2.44 |
| JEKO1 | Hematopoietic and lymphoid | Lymphoma | 0.461 | 0.83 | 4.3369 | 10 | 3.11 |
| JIYOYE | Hematopoietic and lymphoid | Lymphoma | 0.0814 | 0.21 | 4.4004 | 5.35 | 11.1 |
| L428 | Hematopoietic and lymphoid | Lymphoma | 1.63 | 3.46 | 4.2384 | 5.88 | 7.51 |
| MC116 | Hematopoietic and lymphoid | Lymphoma | 6.02 | 6.49 | 2.8763 | 5.18 | 9.46 |
| NAMALWA | Hematopoietic and lymphoid | Lymphoma | 0.0181 | 0.0239 | 5.9431 | 10 | 2.68 |
| RAJI | Hematopoietic and lymphoid | Lymphoma | 0.179 | 10 | 2.5564 | 4.07 | 24.81 |
| RAMOSRA1 | Hematopoietic and lymphoid | Lymphoma | 3.66 | 3.84 | 4.5496 | 7.39 | 25.1 |
| REC1 | Hematopoietic and lymphoid | Lymphoma | 0.0053 | 0.193 | 10 | 10 | 1.86 |
| RPMI6666 | Hematopoietic and lymphoid | Lymphoma | 0.0801 | 0.37 | 3.0419 | 4.37 | 26.35 |
| SR | Hematopoietic and lymphoid | Lymphoma | 1.42 | 1.84 | 1.2842 | 3.07 | 33.52 |
| ST486 | Hematopoietic and lymphoid | Lymphoma | 5.02 | 6.14 | 4.2422 | 6.11 | 10.85 |
| SUDHL10 | Hematopoietic and lymphoid | Lymphoma | 1.23 | 1.4 | 3.611 | 4.87 | 11.63 |
| SUDHL4 | Hematopoietic and lymphoid | Lymphoma | 0.168 | 0.332 | 2.5668 | 4.83 | 10.75 |
| SUDHL5 | Hematopoietic and lymphoid | Lymphoma | 0.0011 | 0.0013 | 1.6359 | 4.54 | 10.37 |
| SUDHL8 | Hematopoietic and lymphoid | Lymphoma | 0.0193 | 0.0406 | 1.2344 | 4.19 | 10.79 |
| SUPT1 | Hematopoietic and lymphoid | Lymphoma | 0.0196 | 0.0466 | 4.5476 | 9.21 | 5.76 |
| TUR | Hematopoietic and lymphoid | Lymphoma | 0.0415 | 0.0539 | 0.6984 | 3.45 | 17.35 |
| D283MED | CNS | Medulloblastoma | 2.56 | 7.55 | 8.3456 | 10 | 2.23 |
| D341MED | CNS | Medulloblastoma | 10 | 0.0219 | 7.7855 | 10 | 2.14 |
| DAOY | CNS | Medulloblastoma | 0.749 | 1.09 | 3.2773 | 5.22 | 16.68 |
| A101D | Skin | Melanoma | 0.0424 | 0.0815 | 0.4207 | 3.71 | 7.93 |
| A2058 | Skin | Melanoma | 0.212 | 0.288 | 0.065 | 0.204 | 11.68 |
| A375 | Skin | Melanoma | 0.0065 | 0.0072 | 0.0673 | 0.0827 | 103.79 |
| A7 | Skin | Melanoma | 1.72 | 7.27 | 5.0814 | 9.4 | 5.51 |
| C32 | Skin | Melanoma | 0.0289 | 0.111 | 0.0451 | 0.0778 | 110.9 |
| C32TG | Skin | Melanoma | 0.0408 | 0.109 | 0.0608 | 0.117 | 42.82 |
| CHL1 | Skin | Melanoma | 0.103 | 0.117 | 1.2376 | 10 | 3.46 |
| COLO829 | Skin | Melanoma | 0.0121 | 0.0343 | 0.0421 | 0.125 | 24.28 |
| G361 | Skin | Melanoma | 0.102 | 0.15 | 0.0428 | 0.12 | 24.48 |

TABLE 44-continued

Results of Cytotoxicity Assays

| Cell line | Tumor Type | Subtype | GI50 (µM) | IC50 (µM) | CalX2 (µM) | CalX5 (µM) | Max fold change |
|---|---|---|---|---|---|---|---|
| HMCB | Skin | Melanoma | 0.0724 | 0.113 | 10 | 10 | 1.8 |
| HS294T | Skin | Melanoma | 0.0507 | 0.0706 | 0.154 | 2.15 | 5.74 |
| HS688AT | Skin | Melanoma | 0.0822 | 10 | 10 | 10 | 1.61 |
| HS695T | Skin | Melanoma | 0.0363 | 0.16 | 0.0253 | 0.0727 | 22.05 |
| HS852T | Skin | Melanoma | 0.0564 | 0.715 | 0.05 | 0.234 | 6.51 |
| HS895T | Skin | Melanoma | 10 | 10 | 10 | 10 | 1.52 |
| HS934T | Skin | Melanoma | 0.0052 | 10 | 0.3638 | 1.4 | 5.1 |
| HS936TC1 | Skin | Melanoma | 0.0184 | 0.0258 | 0.0084 | 0.0224 | 134.98 |
| MALME3M | Skin | Melanoma | 0.0034 | 0.012 | 0.0025 | 0.0045 | 102.73 |
| MEWO | Skin | Melanoma | 0.102 | 0.159 | 0.167 | 0.373 | 14.34 |
| RPMI7951 | Skin | Melanoma | 0.0716 | 0.0945 | 0.1237 | 1.29 | 28.15 |
| SH4 | Skin | Melanoma | 0.0208 | 0.029 | 0.0157 | 0.0382 | 66.44 |
| SKMEL1 | Skin | Melanoma | 0.001 | 0.0291 | 0.1019 | 0.194 | 7.63 |
| SKMEL28 | Skin | Melanoma | 0.0279 | 0.0571 | 0.2907 | 0.344 | 16.64 |
| SKMEL3 | Skin | Melanoma | 0.0284 | 0.0625 | 10 | 10 | 1.74 |
| WM2664 | Skin | Melanoma | 0.012 | 0.0354 | 0.0023 | 0.0151 | 83.29 |
| ARH77 | Hematopoietic and lymphoid | Myeloma | 10 | 10 | 10 | 10 | 1.86 |
| IM9 | Hematopoietic and lymphoid | Myeloma | 0.0911 | 0.143 | 0.043 | 10 | 4.85 |
| RPMI8226 | Hematopoietic and lymphoid | Myeloma | 1.09 | 2.48 | 3.3103 | 5.34 | 8.35 |
| SKO007 | Hematopoietic and lymphoid | Myeloma | 0.0274 | 0.482 | 0.1758 | 2.79 | 7.24 |
| U266B1 | Hematopoietic and lymphoid | Myeloma | 0.0133 | 0.109 | 0.0493 | 10 | 4.36 |
| BE2C | CNS | Neuroblastoma | 0.146 | 0.21 | 0.1223 | 10 | 5.47 |
| CHP212 | CNS | Neuroblastoma | 0.0066 | 0.0165 | 0.019 | 0.341 | 5.97 |
| MCIXC | CNS | Neuroblastoma | 2.04 | 2.33 | 1.9309 | 4.62 | 5.15 |
| SKNAS | CNS | Neuroblastoma | 0.0489 | 0.132 | 0.0675 | 0.227 | 8.86 |
| SKNDZ | CNS | Neuroblastoma | 7.4 | 10 | 10 | 10 | 1.23 |
| SKNFI | CNS | Neuroblastoma | 0.0151 | 0.135 | 0.0897 | 10 | 3.51 |
| A427 | Lung | NSCLC | 0.0475 | 0.0763 | 0.0018 | 10 | 3.34 |
| A549 | Lung | NSCLC | 0.102 | 0.128 | 0.0297 | 0.0946 | 13.03 |
| CALU1 | Lung | NSCLC | 0.0967 | 0.149 | 0.2575 | 10 | 3.73 |
| CALU6 | Lung | NSCLC | 0.0463 | 0.083 | 0.11 | 10 | 4.86 |
| CHAGOK1 | Lung | NSCLC | 10 | 10 | 10 | 10 | 1.23 |
| CORL105 | Lung | NSCLC | 0.0165 | 0.0414 | 0.0583 | 0.571 | 6.55 |
| CORL23 | Lung | NSCLC | 0.0238 | 0.0283 | 0.0176 | 0.0569 | 12.96 |
| HS229T | Lung | NSCLC | 0.415 | 10 | 0.8448 | 7.22 | 5.29 |
| NCIH292 | Lung | NSCLC | 0.278 | 0.686 | 2.4602 | 4.85 | 10.26 |
| NCIH441 | Lung | NSCLC | 0.271 | 1.25 | 7.7406 | 10 | 4.32 |
| NCIH460 | Lung | NSCLC | 10 | 10 | 10 | 10 | 0.98 |
| NCIH520 | Lung | NSCLC | 0.991 | 2.13 | 3.637 | 5.03 | 13.95 |
| NCIH596 | Lung | NSCLC | 2.75 | 10 | 10 | 10 | 1.11 |
| NCIH661 | Lung | NSCLC | 1.44 | 2.64 | 0.0833 | 10 | 4.58 |
| SKMES1 | Lung | NSCLC | 0.103 | 0.122 | 0.0384 | 0.212 | 27.03 |
| OE19 | Head and Neck | Esophageal | 0.34 | 10 | 10 | 10 | 1.79 |
| OE21 | Head and Neck | Esophageal | 0.0939 | 0.124 | 0.0221 | 0.948 | 5.91 |
| OE33 | Head and Neck | Esophageal | 0.063 | 0.0969 | 0.0317 | 0.495 | 5.9 |
| G292CLONEA141B1 | Soft Tissue | Osteosarcoma | 0.0272 | 0.0493 | 0.0401 | 0.211 | 7.61 |
| HOS | Soft Tissue | Osteosarcoma | 2.57 | 3.69 | 6.2324 | 8.81 | 7.12 |
| HS888SK | Soft Tissue | Osteosarcoma | 0.111 | 10 | 0.1023 | 0.175 | 15.7 |
| KHOS240S | Soft Tissue | Osteosarcoma | 10 | 10 | 4.3797 | 4.93 | 18.16 |
| MG63 | Soft Tissue | Osteosarcoma | 0.108 | 0.115 | 4.1626 | 5.71 | 17.21 |
| SAOS2 | Soft Tissue | Osteosarcoma | 3.57 | 6.88 | 3.2386 | 5.98 | 6.35 |
| SJSA1 | Soft Tissue | Osteosarcoma | 1.16 | 2.46 | 2.9744 | 6.21 | 62.65 |
| SW1353 | Soft Tissue | Osteosarcoma | 0.184 | 0.292 | 0.404 | 10 | 4.79 |
| U2OS | Soft Tissue | Osteosarcoma | 0.23 | 0.373 | 0.0332 | 0.0801 | 20.57 |
| CAOV3 | Female GU | Ovary | 0.429 | 10 | 2.0076 | 10 | 2.95 |
| CASKI | Female GU | Ovary | 6.76 | 10 | 0.9719 | 10 | 2.61 |
| ME180 | Female GU | Ovary | 10 | 10 | 5.1674 | 6.32 | 12.19 |
| MS751 | Female GU | Ovary | 6.91 | 9.51 | 5.4363 | 10 | 3.62 |
| OVCAR3 | Female GU | Ovary | 10 | 10 | 10 | 10 | 1.19 |
| PA1 | Female GU | Ovary | 0.471 | 2.62 | 3.6547 | 5.1 | 11.55 |
| SKOV3 | Female GU | Ovary | 0.547 | 10 | 0.2939 | 10 | 2.65 |
| ASPC1 | Pancreas | Pancreas | 0.0308 | 10 | 0.0471 | 10 | 4.08 |
| BXPC3 | Pancreas | Pancreas | 0.0369 | 0.0455 | 0.025 | 10 | 4.98 |
| CAPAN1 | Pancreas | Pancreas | 0.105 | 10 | 10 | 10 | 1.97 |
| CAPAN2 | Pancreas | Pancreas | 0.136 | 0.291 | 10 | 0.209 | 6.62 |
| CFPAC1 | Pancreas | Pancreas | 10 | 10 | 10 | 10 | 1.46 |

TABLE 44-continued

Results of Cytotoxicity Assays

| Cell line | Tumor Type | Subtype | GI50 (µM) | IC50 (µM) | CalX2 (µM) | CalX5 (µM) | Max fold change |
|---|---|---|---|---|---|---|---|
| HPAFII | Pancreas | Pancreas | 0.013 | 0.0175 | 0.0034 | 0.0093 | 52.77 |
| HS766T | Pancreas | Pancreas | 0.0343 | 0.0793 | 0.0646 | 0.632 | 6.36 |
| HUPT4 | Pancreas | Pancreas | 0.0434 | 0.0505 | 0.0998 | 10 | 5.3 |
| MIAPACA2 | Pancreas | Pancreas | 0.0357 | 0.0396 | 0.0387 | 0.578 | 15.16 |
| PANC1 | Pancreas | Pancreas | 0.0416 | 0.08 | 0.0227 | 0.173 | 10.76 |
| PSN1 | Pancreas | Pancreas | 0.0083 | 0.0092 | 0.036 | 0.0701 | 8.75 |
| SU8686 | Pancreas | Pancreas | 0.0635 | 0.132 | 10 | 10 | 2.09 |
| YAPC | Pancreas | Pancreas | 0.183 | 0.67 | 10 | 10 | 1.59 |
| BEWO | Female GU | Placenta | 5.16 | 5.69 | 3.9778 | 6.42 | 10.1 |
| JAR | Female GU | Placenta | 3.17 | 3.21 | 1.0062 | 2.99 | 102.66 |
| JEG3 | Female GU | Placenta | 6.34 | 7.75 | 5.8823 | 7.95 | 6.39 |
| 22RV1 | Prostate | Prostate | 2.66 | 5.58 | 3.0283 | 4.45 | 18.69 |
| BM1604 | Prostate | Prostate | 0.141 | 0.401 | 10 | 10 | 1.8 |
| BPH1 | Prostate | Prostate | 0.0578 | 0.0675 | 0.0577 | 0.116 | 35.09 |
| DU145 | Prostate | Prostate | 0.0738 | 0.0965 | 5.1233 | 8.37 | 6.15 |
| LNCAP | Prostate | Prostate | 2.43 | 5.07 | 4.1807 | 10 | 3.85 |
| PC3 | Prostate | Prostate | 7.82 | 8.54 | 10 | 10 | 3.64 |
| A204 | Soft Tissue | Sarcoma | 10 | 10 | 0.2906 | 10 | 3.48 |
| A673 | Soft Tissue | Sarcoma | 3.75 | 3.87 | 3.411 | 4.59 | 27.78 |
| HS729 | Soft Tissue | Sarcoma | 0.54 | 10 | 10 | 10 | 1.87 |
| HS821T | Soft Tissue | Sarcoma | 0.169 | 10 | 10 | 10 | 1.53 |
| HT1080 | Soft Tissue | Sarcoma | 0.0648 | 0.0727 | 0.0509 | 0.107 | 63.63 |
| MESSA | Soft Tissue | Sarcoma | 0.81 | 1.1 | 4.196 | 5.47 | 8.03 |
| RD | Soft Tissue | Sarcoma | 0.0367 | 0.0443 | 0.0297 | 0.0581 | 14.86 |
| SJRH30 | Soft Tissue | Sarcoma | 0.219 | 1.47 | 0.039 | 10 | 5.61 |
| SKLMS1 | Soft Tissue | Sarcoma | 0.146 | 0.166 | 0.1405 | 0.876 | 12.5 |
| SKUT1 | Soft Tissue | Sarcoma | 10 | 10 | 6.5345 | 10 | 4.63 |
| SW684 | Soft Tissue | Sarcoma | 0.0869 | 0.37 | 0.256 | 0.308 | 16.88 |
| SW872 | Soft Tissue | Sarcoma | 0.105 | 0.136 | 0.0538 | 0.434 | 9.48 |
| SW982 | Soft Tissue | Sarcoma | 0.0156 | 0.0614 | 10 | 10 | 1.94 |
| TE125T | Soft Tissue | Sarcoma | 1.09 | 10 | 3.9673 | 10 | 2.5 |
| TE381T | Soft Tissue | Sarcoma | 0.0076 | 0.0128 | 0.0048 | 0.0143 | 15.88 |
| VAESBJ | Soft Tissue | Sarcoma | 0.336 | 0.58 | 3.1752 | 10 | 3.26 |
| DMS114 | Lung | SCLC | 0.0688 | 0.6 | 0.9142 | 10 | 3.38 |
| DMS273 | Lung | SCLC | 5.96 | 6.79 | 6.5676 | 8.53 | 6.76 |
| DMS53 | Lung | SCLC | 0.998 | 10 | 0.0661 | 1.4 | 7.01 |
| NCIH446 | Lung | SCLC | 0.327 | 10 | 10 | 10 | 1.63 |
| NCIH510A | Lung | SCLC | 3.7 | 6.61 | 3.8517 | 8.62 | 6.44 |
| NCIH69 | Lung | SCLC | 5 | 10 | 10 | 10 | 1.7 |
| SHP77 | Lung | SCLC | 4.79 | 5.82 | 6.8591 | 10 | 3.64 |
| SW900 | Lung | SCLC | 0.0216 | 0.0399 | 0.0162 | 0.0849 | 10.26 |
| AGS | Stomach | Stomach | 0.0086 | 0.0098 | 0.0075 | 0.0131 | 31.12 |
| HS746T | Stomach | Stomach | 0.0396 | 0.122 | 0.0471 | 10 | 4.41 |
| KATOIII | Stomach | Stomach | 0.0612 | 0.0787 | 0.0137 | 0.123 | 29.59 |
| SKPNDW | Stomach | Stomach | 3.6 | 10 | 7.8388 | 10 | 2.58 |
| SNU1 | Stomach | Stomach | 0.0355 | 0.0631 | 0.041 | 2.57 | 5.5 |
| SNU16 | Stomach | Stomach | 10 | 10 | 3.2968 | 5.11 | 10.66 |
| SNU5 | Stomach | Stomach | 0.0368 | 0.0943 | 0.1664 | 10 | 3.21 |
| NTERA2CLD1 | Testis | Testis | 0.044 | 0.0507 | 0.0707 | 0.0957 | 9.95 |
| BHT101 | Endocrine | Thyroid | 0.0376 | 0.0412 | 0.0438 | 0.0864 | 22.52 |
| CAL62 | Endocrine | Thyroid | 0.0836 | 0.0936 | 0.0795 | 0.129 | 6.49 |
| CGTHW1 | Endocrine | Thyroid | 0.0547 | 0.0605 | 0.065 | 0.103 | 91.55 |
| SW579 | Endocrine | Thyroid | 0.0477 | 0.0708 | 0.1374 | 0.256 | 51.22 |
| TT | Endocrine | Thyroid | 0.0863 | 10 | 0.5946 | 10 | 2.79 |
| AN3CA | Female GU | Uterus | 0.713 | 7.03 | 8.777 | 10 | 2.75 |
| HEC1A | Female GU | Uterus | 1.8 | 2.81 | 1.6552 | 3.7 | 30.12 |
| KLE | Female GU | Uterus | 10 | 10 | 10 | 10 | 1.37 |
| RL952 | Female GU | Uterus | 0.009 | 0.0599 | 0.1762 | 10 | 4.12 |
| SW954 | Female GU | Vulva | 0.114 | 0.142 | 0.1749 | 0.521 | 9.14 |
| SW962 | Female GU | Vulva | 0.0828 | 0.232 | 0.0686 | 10 | 3.39 |

Effect on HCC Proliferation.

HCC cell lines were treated with DMSO or increasing concentrations of Compound 1 for 72 h. Specifically, Compound 1 at various concentrations in dimethyl sulfoxide (DMSO) was spotted via an acoustic dispenser (EDC ATS-100) into an empty 384-well plate. Compound 1 was spotted in a 10-point serial dilution fashion (3-fold dilution) in duplicate within the plate. Replicates of plates spotted with Compound 1 were made for use with different cell lines. After compound plate replication, all plates were sealed (Agilent ThermoLoc) and stored at −20° C. for up to 1 month. When ready for testing, plates were removed from the freezer, thawed, and unsealed just prior to the addition of the test cells.

Prior to testing, cells were grown and expanded in culture flasks to provide sufficient amounts of starting material. Cells were then diluted to the appropriate densities and added directly to the compound-spotted 384-well plates. Cells were allowed to grow for 72 h at 37° C./5% $CO_2$. At the time when compound was added (t0), initial cell number was assessed via a viability assay (Cell Titer-Glo) by quantifying the level of luminescence generated by ATP present in viable cells. After 72 h, cell viability of compound-treated cells was assessed via Cell Titer-Glo and luminescence measurement. The apoptotic response to Compound 1 was assessed by quantifying the activities of caspase 3 and caspase 7 (Caspase 3/7-Glo) in treated cells and DMSO control cells.

Determination of $GI_{50}$ and $IC_{50}$ Values.

A Four Parameter Logistic Model (Sigmoidal Dose-Response Model) was used to determine the compound's $GI_{50}$ value.

$$y = (A + ((B-A)/(1+((C/x)^\wedge D))))$$

$A = Y_{Min}$
$B = Y_{Max}$
$C = EC_{50}$
$D = $ Hill Slope
$GI_{50}$ is the concentration of the compound when $Y = (Y_{Max} + Y_{t0})/2$
$IC_{50}$ is the concentration of the compound when Y=50% of DMSO control
Y=Cell viability measured as luminescence unit
$t_0$=time when compound was added Proliferation and apoptosis were measured using CellTiter-Glo and Caspase 3/7-Glo. CalX2 values are the lowest concentration at which Compound 1 induces a 2-fold increase of cleaved caspase 3/7 compared to DMSO control. Proliferation and apoptosis data is the average of 3 experiments.

TABLE 45

Effect of Compound 1 on HCC cell line proliferation.

| Cell Line | $GI_{50}$ | $IC_{50}$ | Cal_X2 |
|---|---|---|---|
| JHH-1 | 0.0016 | 0.0946 | 0.0427 |
| JHH-5 | 0.0045 | 0.0072 | 0.0139 |
| Hep3B | 0.0053 | 0.0147 | 0.0028 |
| HuH-7 | 0.0212 | 0.4894 | 0.0118 |
| HuCCT1 | 0.0253 | 1.3033 | 0.0213 |
| HuH-6-Clone5 | 0.0291 | 1.2236 | 1.5813 |
| SNU-387 | 0.0332 | 0.1041 | 0.0046 |
| HepG2 | 0.0346 | 1.2420 | 0.0129 |
| SNU-182 | 0.0764 | 4.9775 | 5.2385 |
| JHH-7 | 0.0834 | 0.5476 | 4.7601 |
| JHH-2 | 0.1289 | 4.4850 | 0.2806 |
| HuH-1 | 0.2351 | 7.2643 | 6.5641 |
| SNU-398 | 0.2652 | 1.9653 | 0.0378 |
| JHH-4 | 0.3627 | 2.3178 | 0.0588 |
| PLC-PRF-5 | 0.8884 | 4.0089 | 3.8310 |
| FOCUS | 1.4994 | 4.2962 | 3.8562 |
| HepG2/C3A | 4.6211 | 10.0000 | 0.8273 |
| HLE | 4.8451 | 9.6157 | 10.0000 |
| SNU-423 | 6.2355 | 10.0000 | 10.0000 |
| HLF | 6.6814 | 7.3878 | 7.2156 |
| SK-HEP-1 | 7.0390 | 10.0000 | 10.0000 |
| SNU-475 | 9.9879 | 10.0000 | 10.0000 |
| JHH-6 | 10.0000 | 10.0000 | 10.0000 |
| SNU-449 | 10.0000 | 10.0000 | 10.0000 |

Conclusion:

Compound 1 inhibits proliferation and induces apoptosis in multiple HCC lines.

Anti-Proliferative Activity Across a Panel of 64 Cancer Cell Lines.

Cells were treated with DMSO or increasing concentrations of Compound 1 for 72 h. Proliferation was measured using CellTiter-Glo as described. Results are shown in Table 46.

TABLE 46

Anti-proliferative activity of Compound 1 across a panel of 64 cancer cell lines.

| Cell line | Tumor Type | $GI_{50}$ (µM) | $IC_{50}$ (µM) |
|---|---|---|---|
| SW48 | Colon | 0.0057 | 0.088 |
| MALME-3M | Melanoma | 0.0011 | 0.0038 |
| HT29/219 | Colon | 0.0017 | 0.0045 |
| HCT-116 | Colon | 0.017 | 0.022 |
| LOX-IMVI | Melanoma | 0.022 | 0.025 |
| HT29 | Colon | 0.016 | 0.025 |
| A375 | Melanoma | 0.021 | 0.024 |
| Colo 205 | Colon | 0.025 | 0.040 |
| AGS | Stomach | 0.023 | 0.028 |
| JHH-5 | Liver | 0.0045 | 0.007 |
| SW620 | Colon | 0.047 | 0.092 |
| MiaPaCa-2 | Pancreas | 0.047 | 0.80 |
| JHH-5 | Liver | 0.0045 | 0.0072 |
| SW620 | Colon | 0.0474 | 0.0918 |
| MiaPaCa-2 | Pancreas | 0.0471 | 0.0798 |
| JHH-1 | Liver | 0.0016 | 0.0946 |
| NCI-H2122 | Lung | 0.0318 | 0.0427 |
| Hep3B | Liver | 0.0053 | 0.0147 |
| NCI-H1755 | Lung | 0.0404 | 0.0584 |
| 92-1 | Melanoma | 0.0102 | 0.0316 |
| BxPC-3 | Pancreas | 0.0368 | 0.0708 |
| SW1417 | Colon | 0.0005 | 0.0169 |
| HOP92 | Lung | 0.1077 | 0.1173 |
| NCI-H23 | Lung | 0.0364 | 0.1821 |
| PC-9 | Lung | 0.2167 | 0.3791 |
| HuH-7 | Liver | 0.0212 | 0.4894 |
| MEL-202 | Melanoma | 0.0385 | 0.0968 |
| SW900 | Lung | 0.0048 | 0.0217 |
| NCI-H1299 | Lung | 0.2336 | 0.4982 |
| A549 | Lung | 0.0402 | 0.0822 |
| LOVO | Colon | 0.0630 | 0.1256 |
| NCI-H460 | Lung | 0.2441 | 0.6445 |
| SNU-387 | Liver | 0.0332 | 0.1041 |
| HuCCT1 | Liver | 0.0253 | 1.3033 |
| HOP62 | Lung | 0.3390 | 3.4861 |
| HuH-6-Clone5 | Liver | 0.0291 | 1.2236 |
| JHH-7 | Liver | 0.0834 | 0.5476 |
| NCI-H838 | Lung | 0.5670 | 9.1808 |
| NCI-H226 | Lung | 1.6266 | 6.1499 |
| NCI-H28 | Lung | 1.2797 | 2.3574 |
| MDA-MB-231 | Breast | 0.0353 | 3.3333 |
| JHH-2 | Liver | 0.1289 | 4.4850 |
| HepG2 | Liver | 0.0346 | 1.2420 |
| RPMI-8226 | Multiple myeloma | 3.2365 | 9.7392 |
| K-562 | Leukemia | 5.4223 | 6.0279 |
| SNU-182 | Liver | 0.0764 | 4.9775 |
| HuH-1 | Liver | 0.2351 | 7.2643 |
| SNU-398 | Liver | 0.2652 | 1.9653 |
| JHH-4 | Liver | 0.3627 | 2.3178 |
| PLC-PRF-5 | Liver | 0.8884 | 4.0089 |
| FOCUS | Liver | 1.4994 | 4.2962 |
| HepG2/C3A | Liver | 4.6211 | 10.0000 |
| HLE | Liver | 4.8451 | 9.6157 |
| SNU-423 | Liver | 6.2355 | 10.0000 |
| HLF | Liver | 6.6814 | 7.3878 |
| SK-HEP-1 | Liver | 7.0390 | 10.0000 |
| SNU-475 | Liver | 9.9879 | 10.0000 |
| JHH-6 | Liver | 10.0000 | 10.0000 |
| SNU-449 | Liver | 10.0000 | 10.0000 |
| NCI-H441 | Lung | 0.1838 | 6.3503 |
| NCI-H1703 | Lung | 1.3513 | 1.6795 |
| NCI-H1975 | Lung | 2.0476 | 3.1940 |
| NCI-H520 | Lung | 5.2445 | 8.3699 |
| CFPAC-1 | Pancreas | 1.9512 | 7.3967 |
| PANC-1 | Pancreas | 5.4360 | 10.0000 |
| KATOIII | Stomach | 7.0455 | 8.0240 |

Compound 1 was shown to inhibit the proliferation of multiple cancer cell lines derived from CRC, melanoma, gastric cancer, HCC, lung cancer, pancreatic cancer, leukemia, and multiple myeloma.

Anti-proliferative and apoptotic activity in BRAF mutant and beta-catenin mutant or active cancer cell lines. The mutation status of BRAF, CTNNB1, KRAS, and EGFR in five cell lines evaluated was based on public data (COSMIC and CCLE) and confirmed internally. β-catenin status was evaluated using TOP Flash reporter system by transient transfection. A cell line was defined as β-catenin active if a ratio of Top Flash reporter over Fop Flash reporter is greater than 2. N/A: Not available. Transfection efficiency in Colo 205 (BRAF V600E) was too low to access its β-catenin activity using this approach. Antiproliferative and apoptotic activity of Compound 1 in the five cell lines were measured as described above.

TABLE 47

Antiproliferative and apoptosis activity of Compound 1 in BRAF mutant and beta-catenin mutant and active cell lines.

| Cell lines | Tumor type | Mutation status of key genes | β-catenin status | Proliferation IC$_{50}$ (μM) | Apoptosis induction CalX2 (μM) |
| --- | --- | --- | --- | --- | --- |
| Colo 205 | CRC | BRAF (V600E) | N/A | 0.036 +/− 0.023 | 0.053 +/− 0.039 |
| LOX-IMVI | Melanoma | BRAF (V600E) | Inactive | 0.025 +/− 0.008 | 0.034 +/− 0.028 |
| SW48 | CRC | CTNNB1 (S33Y); EGFR (G179S) | Active | 0.009 +/− 0.007 | 0.005 +/− 0.001 |
| AGS | Gastric | CTNNB1 (G43E); KRAS (G12D) | Active | 0.028 +/− 0.021 | 0.004 +/− 0.002 |
| Hep3B | HCC | — | Active | 0.014 +/− 0.006 | 0.002 +/− 0.002 |

Compound 1 potently inhibits proliferation and induces apoptosis in both BRAF mutant and beta-catenin mutant or active cancer cell lines, including BRAF mutant CRC, BRAF mutant melanoma, beta-catenin mutant/EGFR mutant CRC (i.e. beta-catenin active/EGFR mutant CRC), beta-catenin mutant/KRAS mutant gastric cancer (i.e. beta-catenin active/KRAS mutant gastric cancer), and HCC.

Oncogenic Pathway Inhibition. Effect on MAPK Signaling.

Cancer cells were seeded at a density of 25,000 cells per well in 96-well tissue culture plates and incubated at 37° C. in a CO$_2$ incubator overnight. After treatment with Compound 1 at 37° C. for 2 h, the cells were lysed with Mesoscale lysis buffer and pRSK S380 levels in each lysate were measured via Mesoscale ELISA technology.

Conclusion.

Compound 1 potently inhibited pRSK1 in multiple cancer cell lines (Table 48).

TABLE 48

Compound 1 pRSK1 S380 IC$_{50}$ Values in BRAF Mutant LOX-IMVI and Colo 205 Cancer Cell Lines.

| Cell line (n = 3) | pRSK1 S380 IC$_{50}$ (μM) |
| --- | --- |
| LOX-IMVI | 0.038 +/− 0.009 |
| Colo 205 | 0.047 +/− 0.01 |
| SW48 | 0.021 +/− 0.001 |
| AGS | 0.020 +/− 0.001 |

Figure 188:
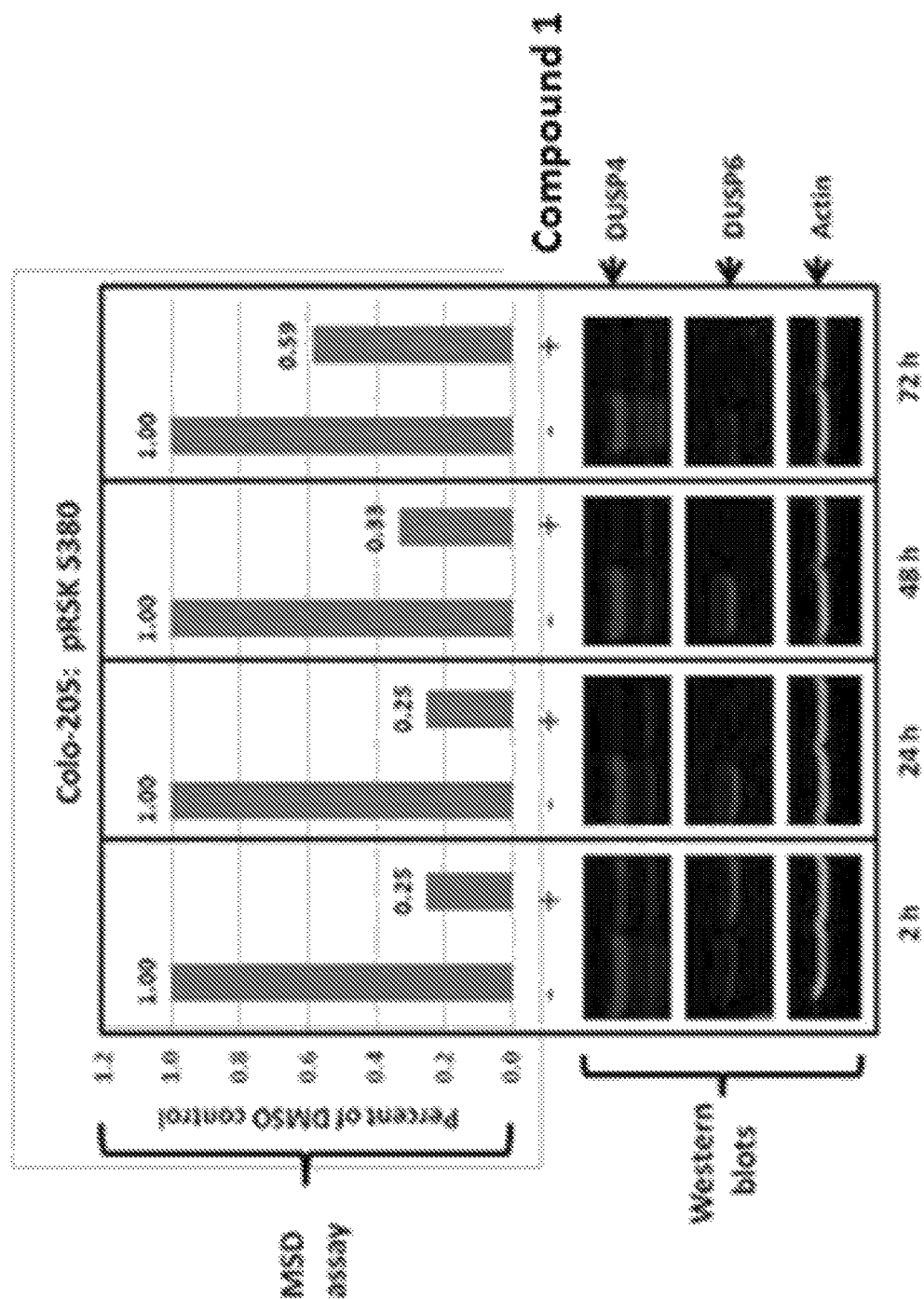
FIG. 188 illustrates Compound 1 Treatment Causes Sustained Inhibition of the ERK Substrate pRSK1 S380 in Colo 205 (mut BRAFV600E) Cells. Colo 205 cells were treated with DMSO or 0.5 µM Compound 1 for indicated time. pRSK1 S380 was measured by MSD assay (Top). DUSP4 and DUSP6 were detected by Western blotting (Bottom).

In a time course experiment, Colo-205 cancer cells were treated with 0.5 μM Compound 1 for various time periods. The effect of Compound 1 on pRSK S380 was measured as described. The effect of Compound 1 on other MAPK pathway markers (DUSP4 and DUSP6) was measured via Western blotting with specific antibodies. The time course data in FIG. 188 indicates Compound 1 causes sustained inhibition (up to 72 hr) of the following ERK targets: pRSK1, DUSP4 and DUSP6. BRAF inhibitors (BRAFi) do not cause sustained ERK inhibition in BRAF mutant CRC lines (Corcoran et al., *Cancer Discov.* 2012, 2:227-35). Sufficient and sustained inhibition of ERK seems to be critical for clinical efficacy of BRAFi and MEK inhibitors (MEKi) in BRAF mutant melanoma (Bollag et al., *Nat Rev Drug Disc.* 2012; 11, 873-886) and CRC patients (Corcoran et al., *Cancer Discov.* 2012, 2:227-35). Lack of sustained inhibition of ERK by BRAFi may contribute to the lack of clinical activity of BRAFi in BRAF mutant CRC patients. The sustained inhibition of ERK by Compound 1 may provide an advantage over BRAFi in BRAF mutant CRC patients.

The ability of Compound 1 to inhibit MAPK signaling was assessed by determining the DUSP4 and DUSP6 protein expression. Colon cancer cell line Colo 205 (BRAF V600E) cultures were treated with DMSO or increasing concentrations of Compound 1 for 2, 8 or 24 h. Proteins were extracted from treated cells and analyzed by Western blot using antibodies against DUSP4, DUSP6, cyclin D1, c-Myc, YAP or β-actin. RNAs were extracted using Cell-To-CT kit and quantitative PCR was performed with probes specific for DUSP4, DUSP6, SPRY2, c-Myc and cyclin D1. Specific probes for β-actin were used for normalization.

Figure 189A:
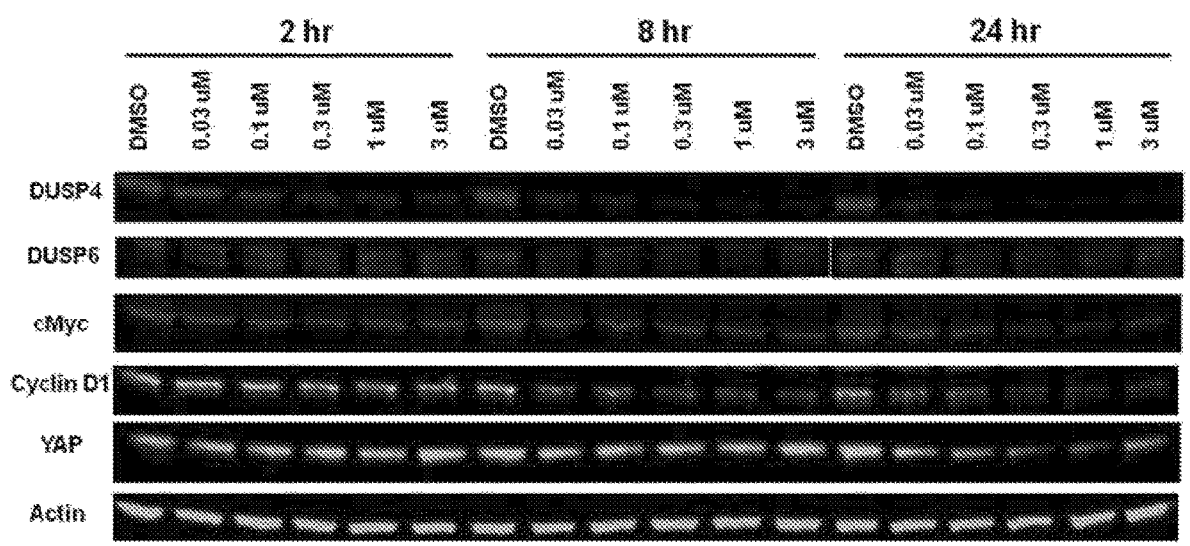
FIGS. 189A-189I illustrates Compound 1 potently inhibits MAP kinase signaling and downstream target genes in Colo 205. Colon cancer cell line Colo 205 (BRAF V600E) cultures were treated with DMSO or increasing concentrations of Compound 1 for 2, 8 or 24 h.
Figure 189B:
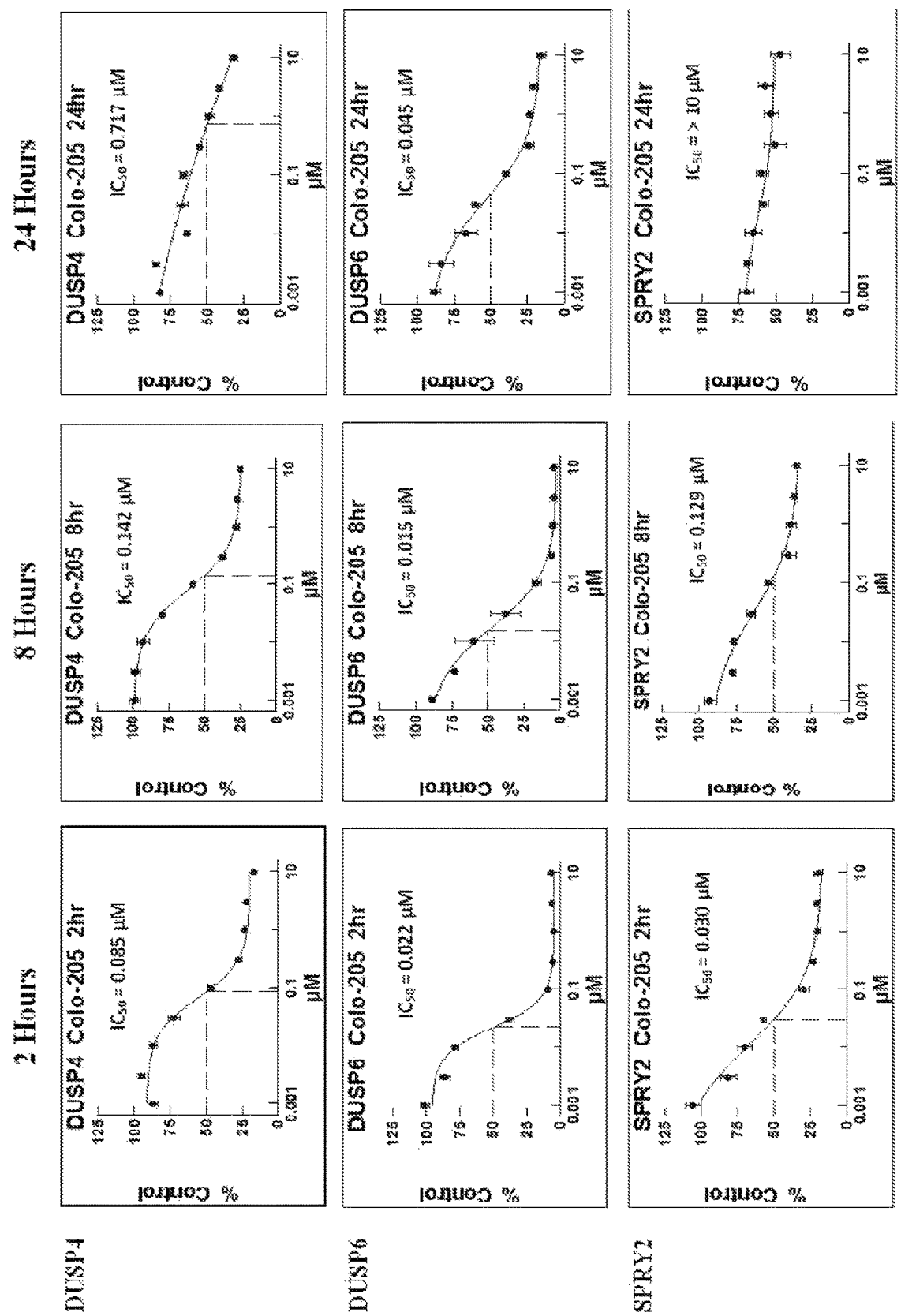
Figure 189C:
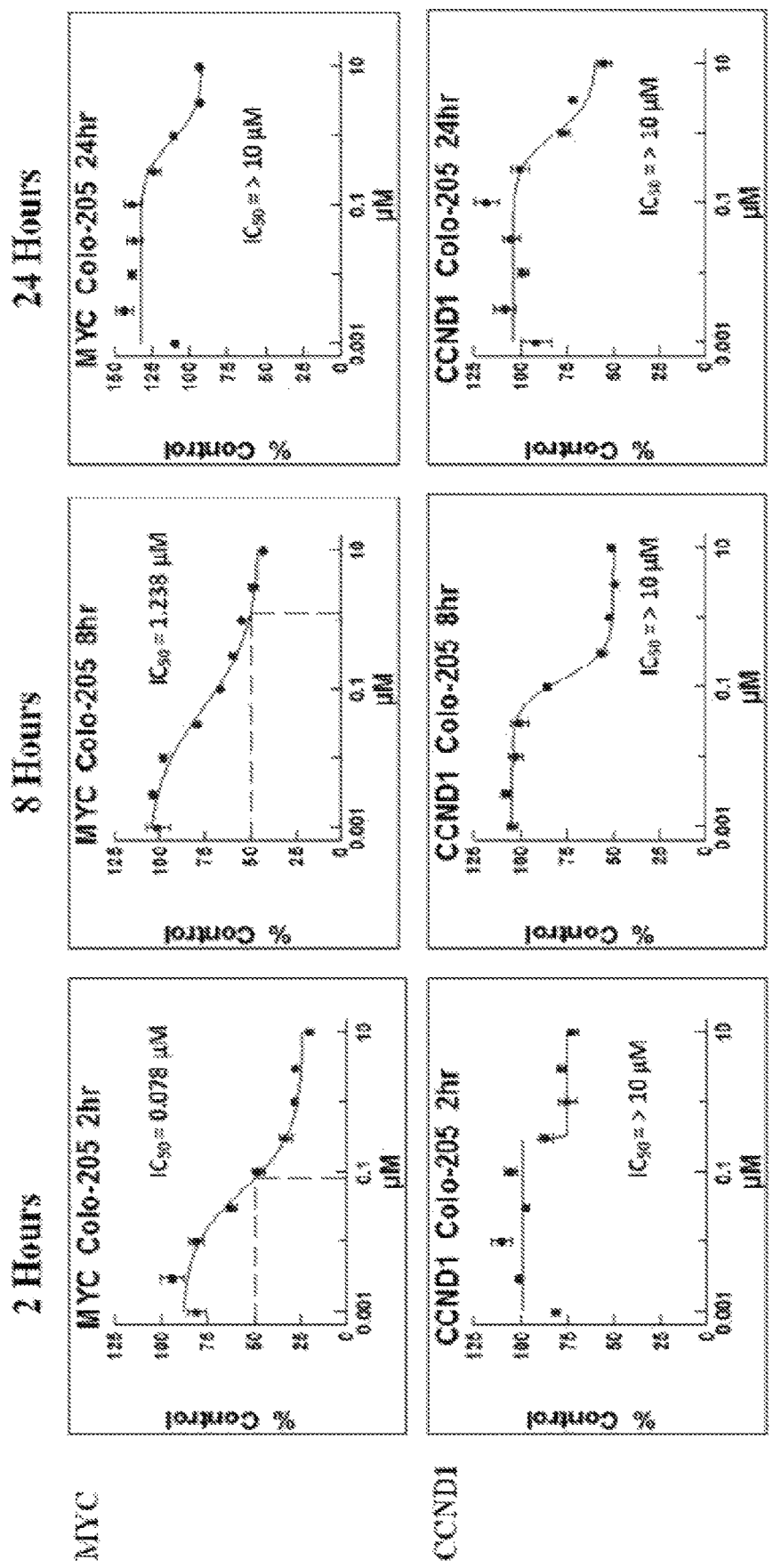
Figure 189D:
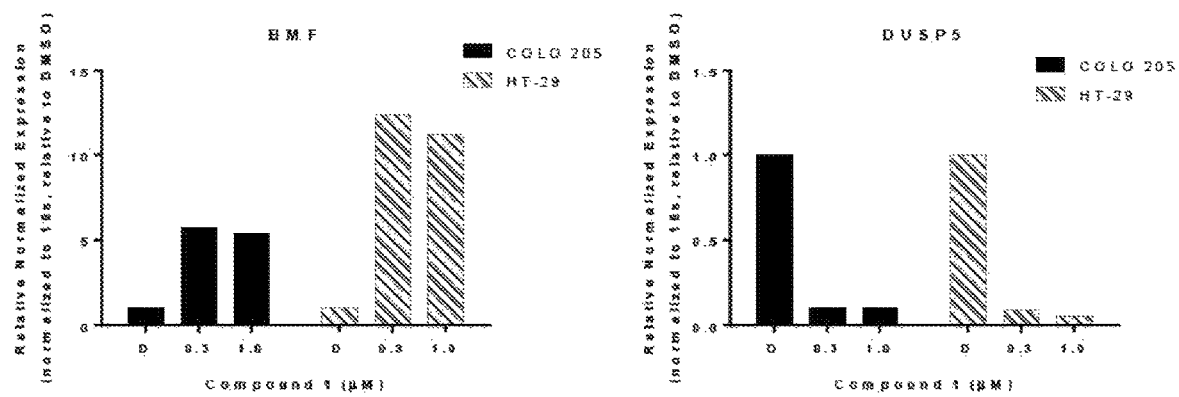
Figure 189E:
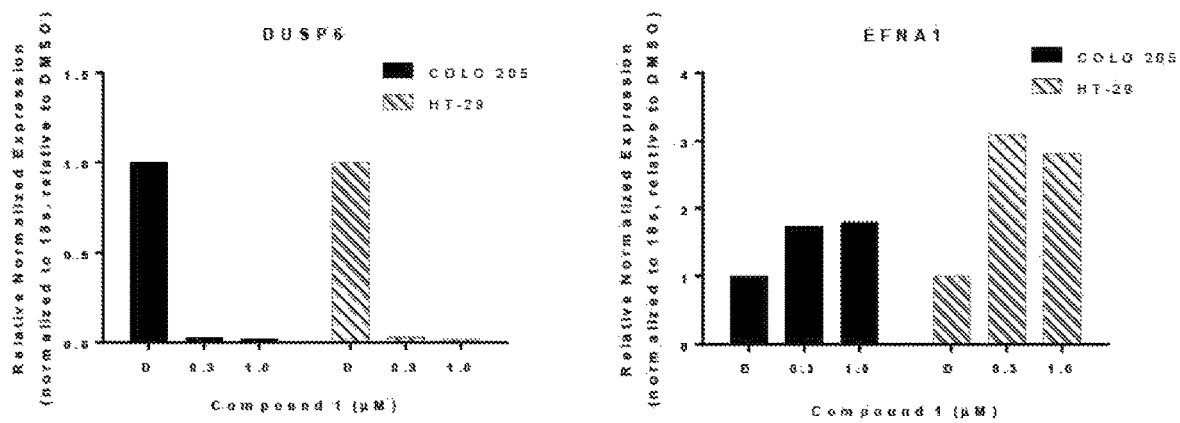
Figure 189F:
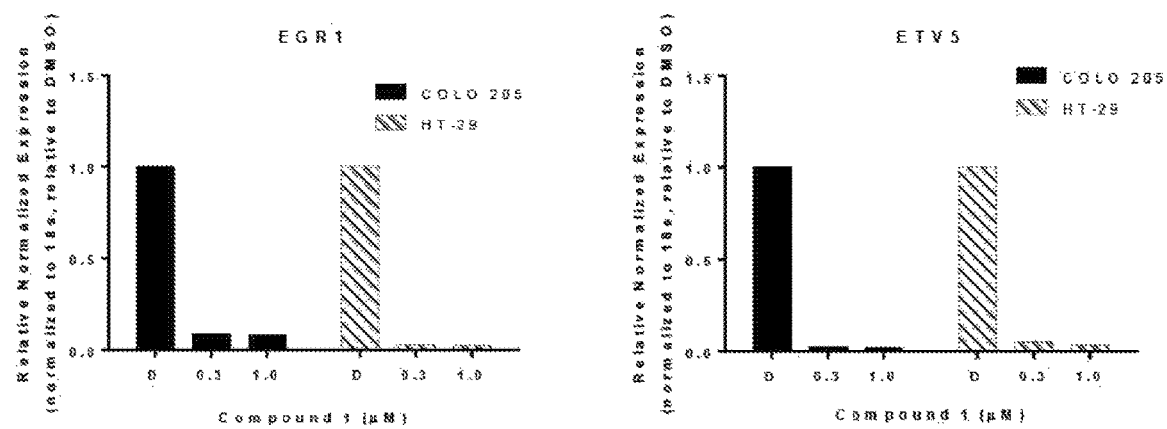
Figure 189G:
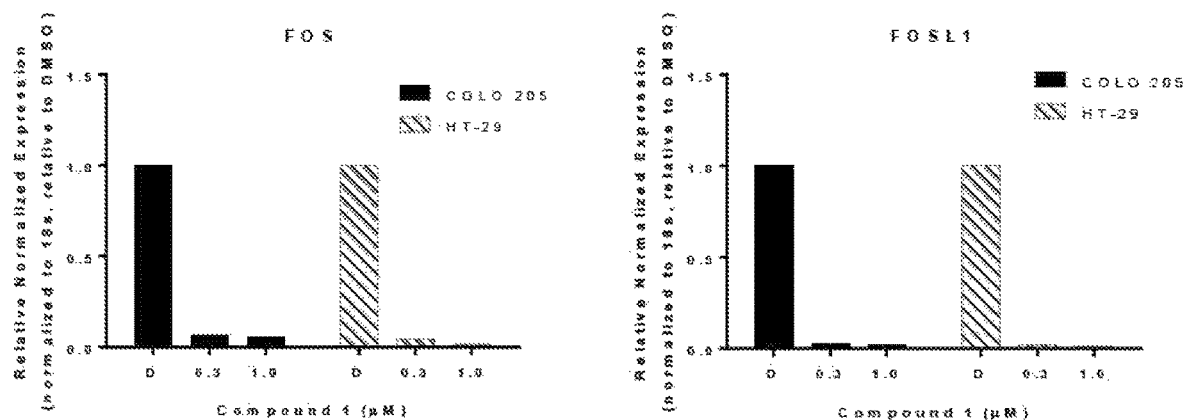
Figure 189H:
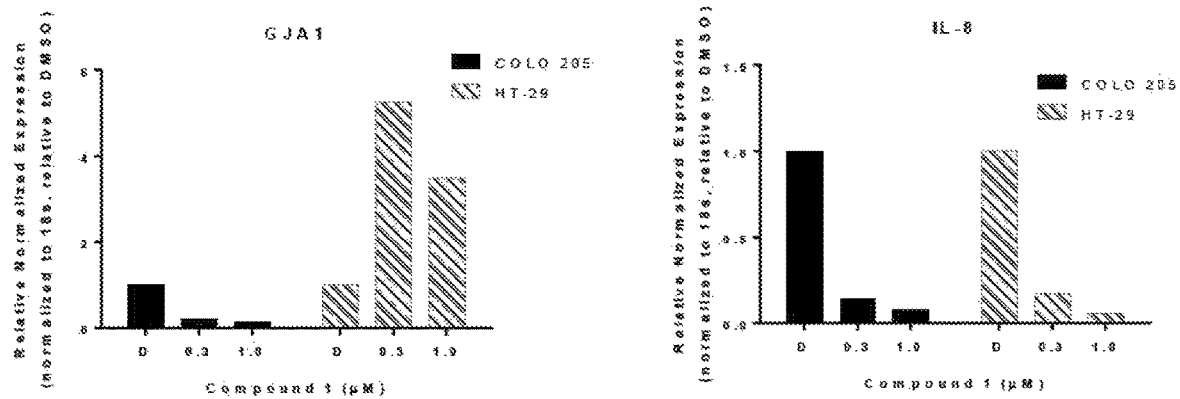
Figure 189I:
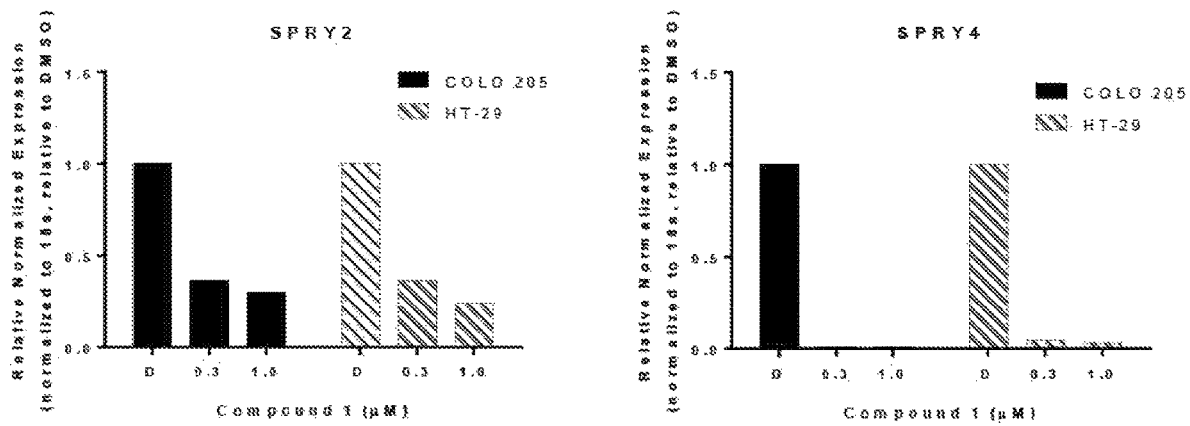

In Colo 205 (BRAF V600E), DUSP4 and DUSP6 were significantly reduced by Compound 1 as early as 2 h and the reduction was sustained through 24 h (FIG. 189A). Compound 1 treatment led to the reduction of SPRY2 transcription in a concentration-dependent manner in Colo 205 (FIG. 189B), consistent with potent ERK inhibition. Levels of cyclin D1 and c-Myc, which are downstream of both canonical Wnt and MAPK signaling, were assessed. Compound 1 significantly decreased cyclin D1 and c-Myc RNA and protein levels in Colo 205 cells (FIGS. 189A-189C). Compound 1 treatment resulted in decreased YAP protein at 24 h in Colo 205 (FIG. 189A). Taken together, our cellular data is consistent with strong, sustained MAPK pathway inhibition.

To further evaluate the ability of Compound 1 to inhibit MAPK signaling, RNA expression was assessed of additional MAPK targets (BMF, DUSP5, DUSP6, EFNA1, EGR1, ETV5, FOS, FOSL1, GJA1, IL-8, SPRY2, and SPRY4). Cultures of the colon cancer cell lines Colo 205 (characterized by a BRAF V600E mutation) and HT-29 (characterized by a BRAF V600E mutation) were treated with DMSO or Compound 1 at 0.3 or 1 μM for 6 h. RNAs were extracted using MagMAX Total RNA Isolation kit and quantitative PCR was performed with probes specific for BMF, DUSP5, DUSP6, EFNA1, EGR1, ETV5, FOS, FOSL1, GJA1, IL-8, SPRY2, SPRY4. Specific probes for 18S rRNA were used for normalization.

In both cell lines, mRNA levels of DUSP5, DUSP6, EGR1, ETV5, FOS, FOSL1, IL-8, SPRY2, SPRY4 were reduced by Compound 1 (FIGS. 189D-189I), consistent with ERK inhibition. The finding that mRNA levels of GJA1 are reduced in Colo205 cells and increased in HT29 may be related to our finding that Compound 1 is cytotoxic in Colo205 and cytostatic in HT29. Compound 1 treatment resulted in increased mRNA levels of BMF and EFNA1 at 6 h in Colo 205 and HT-29. Taken together, our cellular data is consistent with MAPK pathway inhibition.

Effect on Beta-Catenin and YAP Signaling.

Cellular activity against beta-catenin and YAP target genes by Compound 1 was evaluated. Colon cancer cell line Colo 205 (BRAF V600E) cultures were treated with DMSO or increasing concentrations of Compound 1 for 2, 8 or 24 h. RNAs were extracted using Cell-To-CT kit and quantitative PCR was performed with probes specific for Axin2, CTGF, and AREG. Specific probes for β-actin were used for normalization.

Figure 190A:
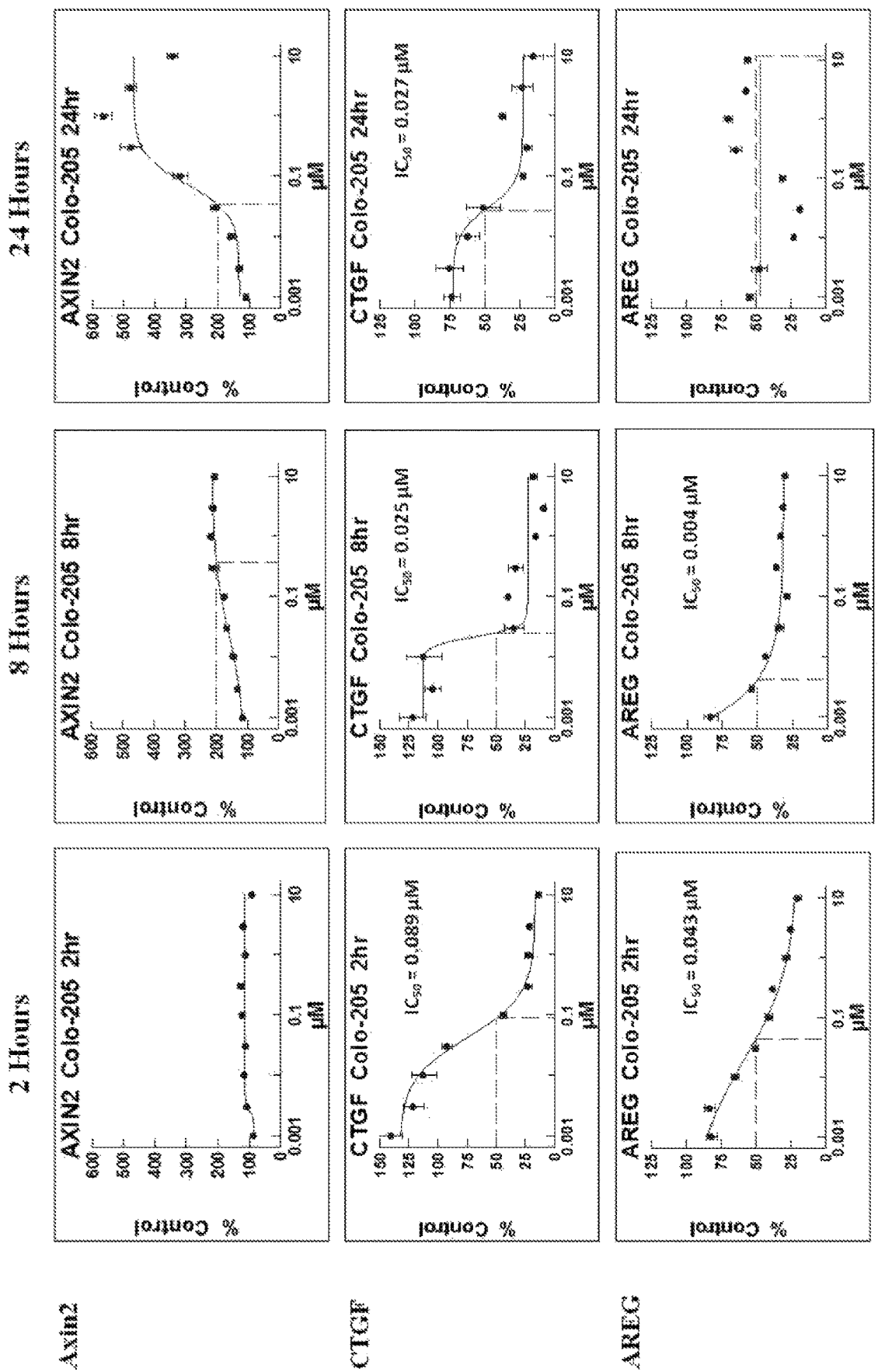
FIG. 190A illustrates Compound 1 effects on WNT/beta-catenin and HIPPO/YAP signaling pathway target genes in Colo 205. Colon cancer cell line Colo 205 (BRAF V600E) cultures were treated with DMSO or increasing concentrations of Compound 1 for 2, 8 or 24 h. RNAs were extracted using Cell-To-CT kit and quantitative PCR was performed with probes specific for Axin2, CTGF, and AREG. Specific probes for β-actin were used for normalization.
Figure 190B:
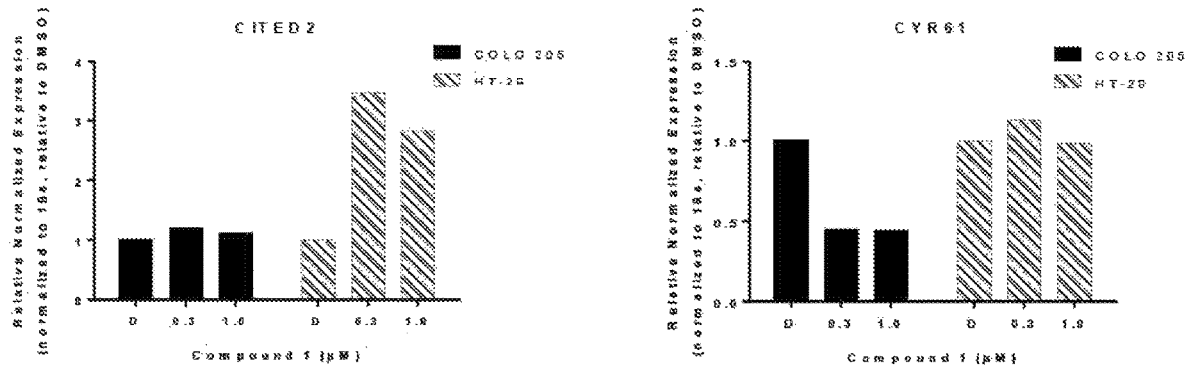
FIGS. 190B-190E illustrate Compound 1 treatment regulates YAP-driven mRNA levels in Colo 205 (mut BRAFV600E) and HT-29 (mut BRAFV600E) Cells. Colo 205 or HT-29 cells were treated with DMSO or 0.3 or 1 µM Compound 1 for 6 h. RNAs were extracted using MagMAX Total RNA Isolation kit and quantitative PCR was performed.
Figure 190C:
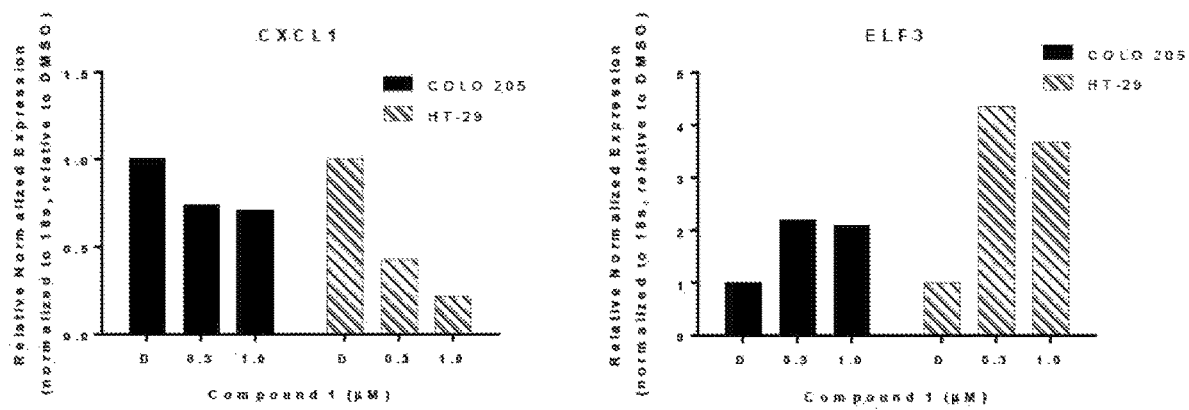
Figure 190D:
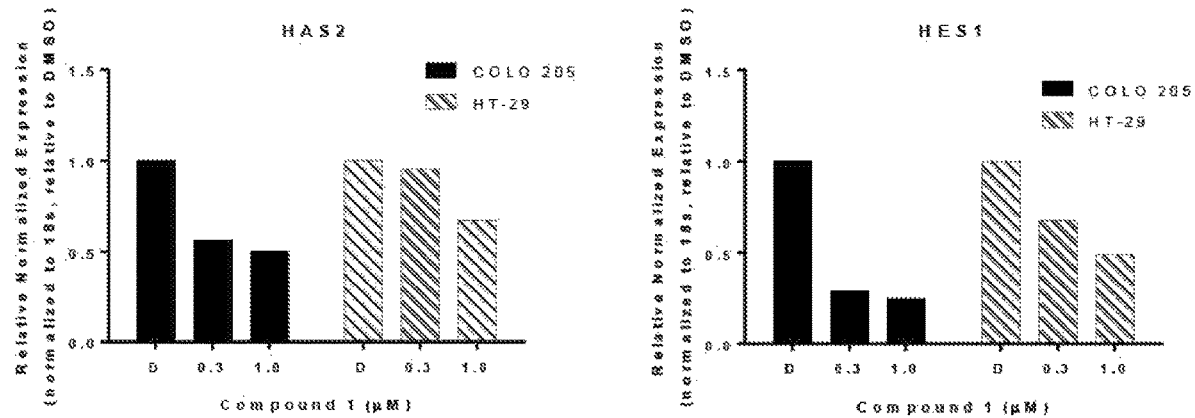
Figure 190E:
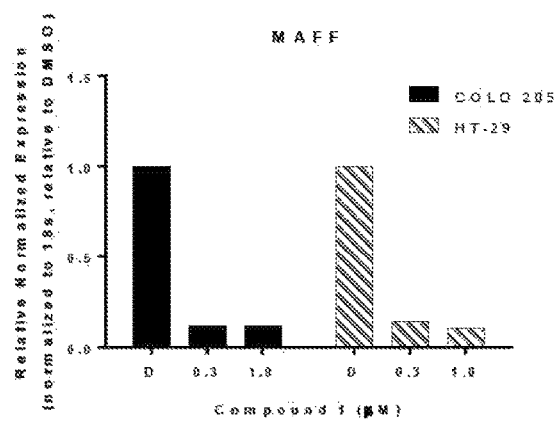

Compound 1 treatment led to increased Axin2 RNA (FIG. 190A). Compound 1 significantly reduced the expression of Hippo/YAP target genes (CTGF, AREG) in Colo 205 (BRAF V600E) at 2, 8 and 24 hr (FIG. 190A). Taken together, these data suggest that Compound 1 impacts Wnt signaling and blocks Hippo signaling in Colo 205 cancer cells.

Cellular activity against additional YAP target genes by Compound 1 was evaluated (FIGS. 190B-190E). Cultures of the colon cancer cell lines Colo 205 and HT-29 were treated with DMSO or Compound 1 at 0.3 or 1 µM for 6 h. RNAs were extracted using MagMAX Total RNA Isolation kit and quantitative PCR was performed with probes specific for CYR61, CITED2, CXCL1, ELF3, HAS2, HES1, and MAFF. Specific probes for 18S rRNA were used for normalization.

In both cell lines, mRNA levels of CYR61, CXCL1, HAS2, HES1 and MAFF were reduced by Compound 1. The finding that CYR61 mRNA levels are reduced in Colo205 cells but not in HT29 and that mRNA levels of CITED2 are increased in HT29, but not in Colo205, may be related to our finding that Compound 1 is cytotoxic in Colo205 and cytostatic in HT29. Compound 1 treatment resulted in increased mRNA levels for CITED2 and ELF3 mRNA at 6 h in Colo 205 and HT-29. (FIG. 190B) Taken together, our cellular data is consistent with YAP pathway inhibition.

Figure 205:
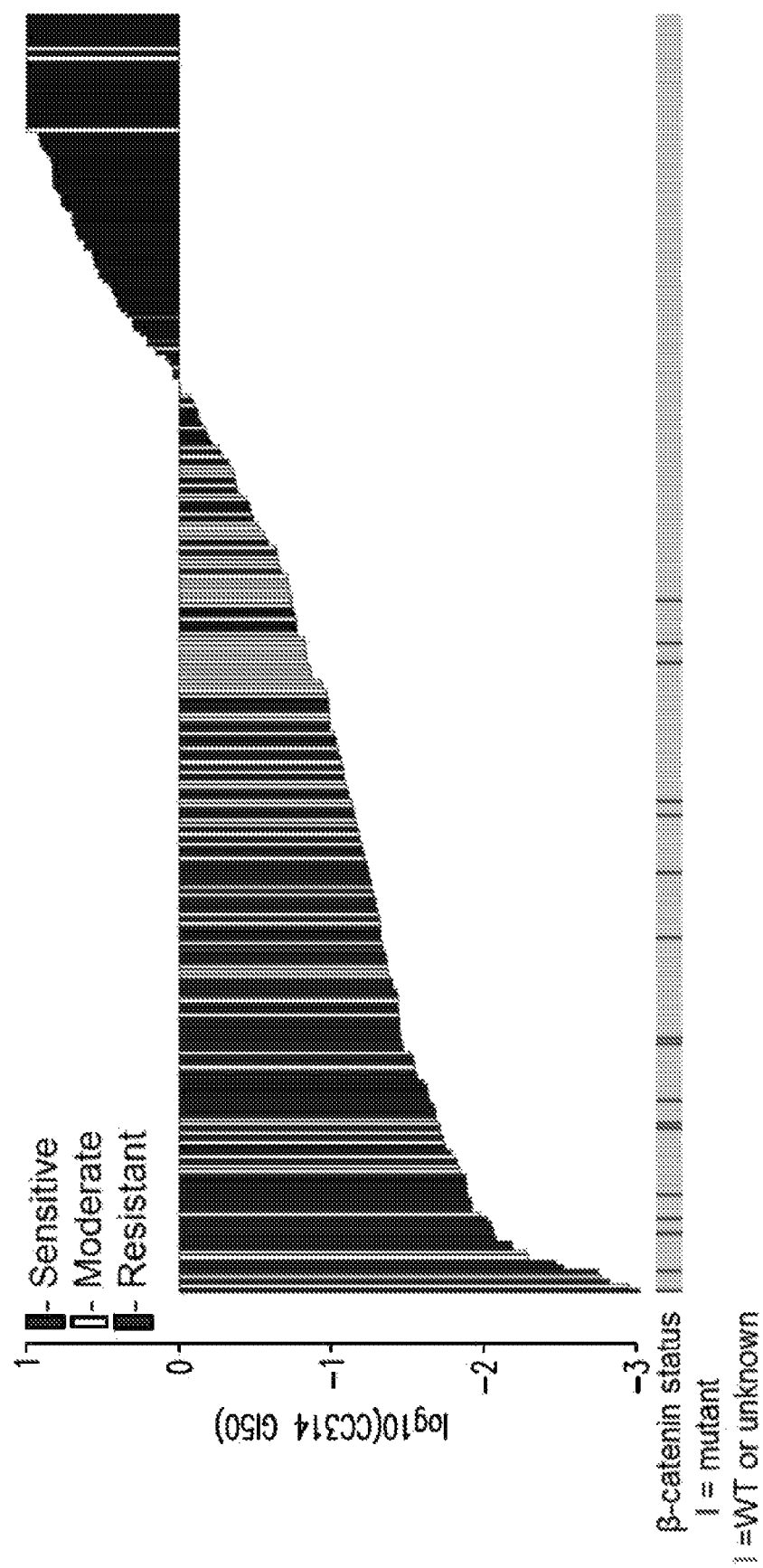
FIG. 205 illustrates sensitivity of cell lines having β-catenin mutations to Compound 1 treatment and shows that cell lines with mutated β-catenin are generally more sensitive to Compound 1 treatment.
Figure 206A:
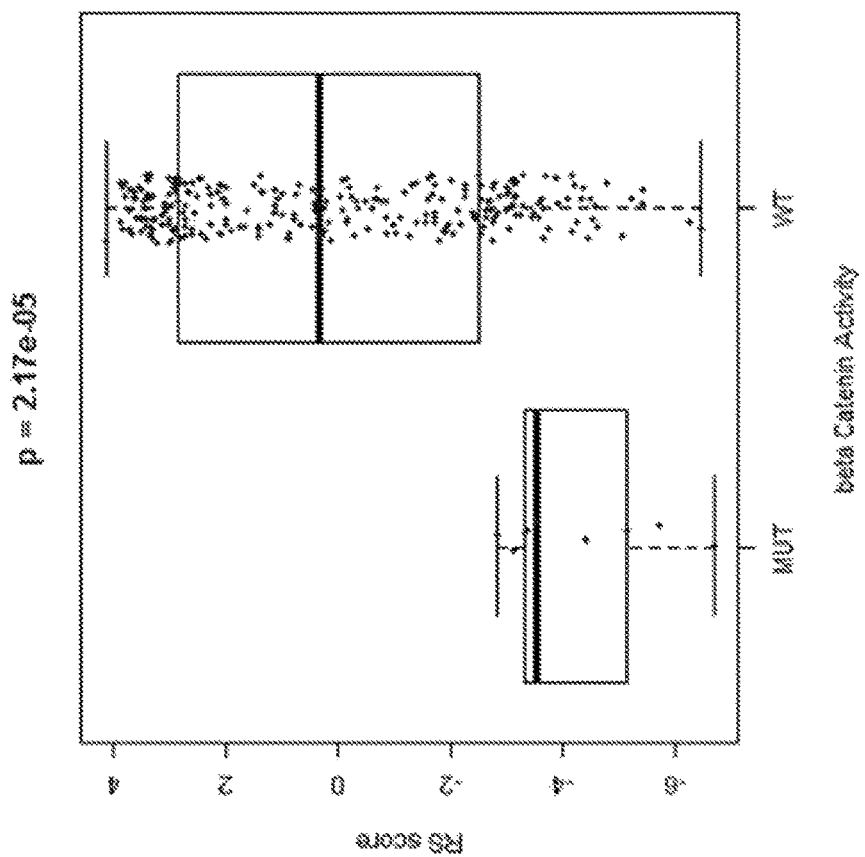
FIGS. 206A-206E illustrate cell line sensitivity and resistance to treatment with Compound 1.
Figure 206B:
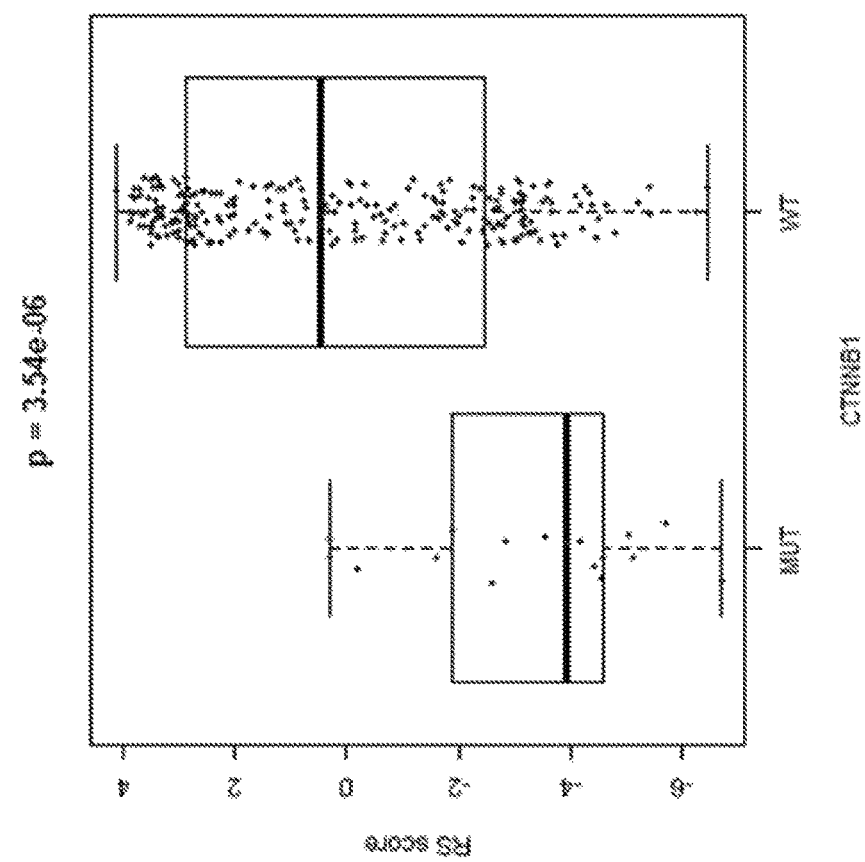
Figure 206D:
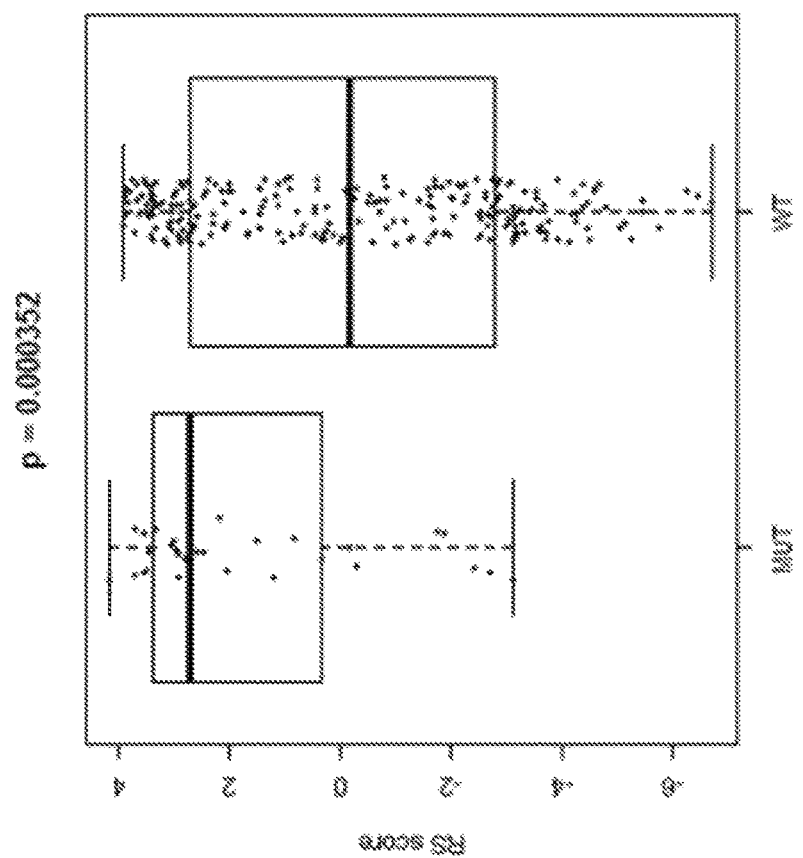
Figure 206C:
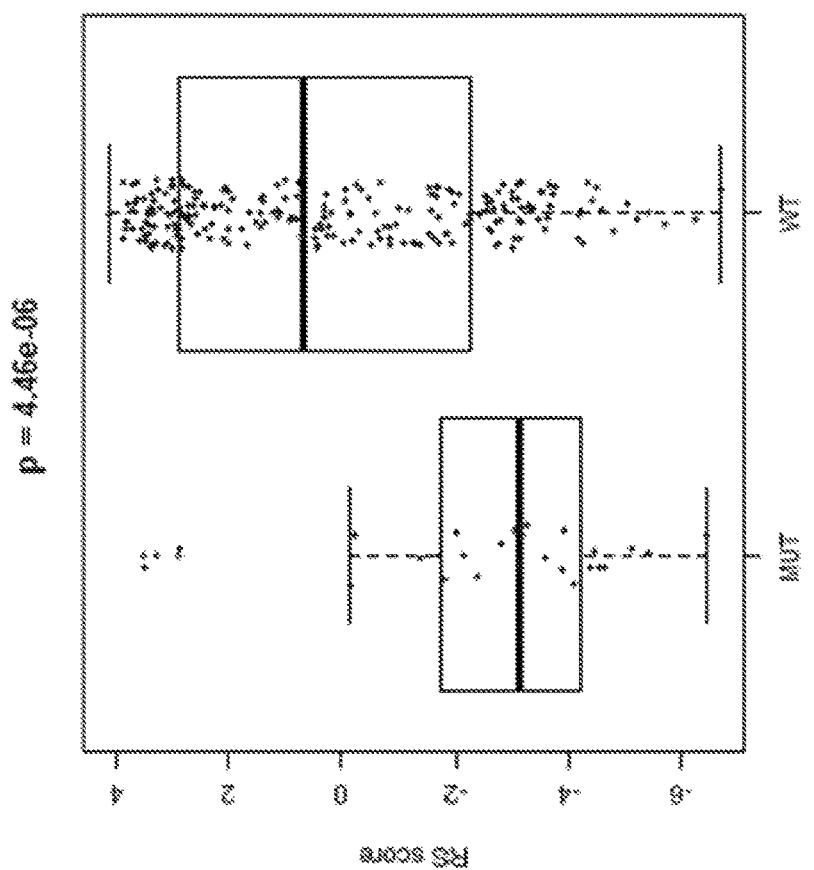
Figure 206E:
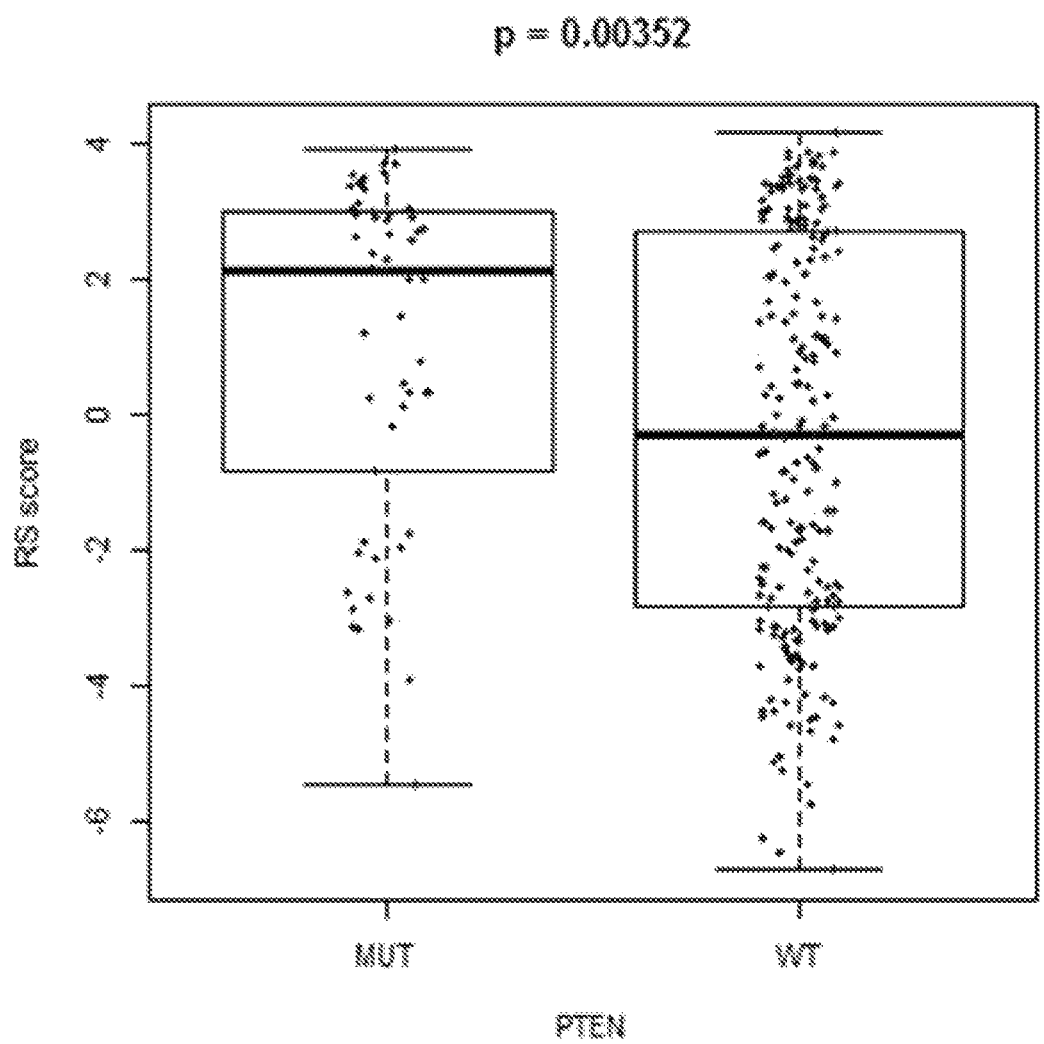
Figure 207:
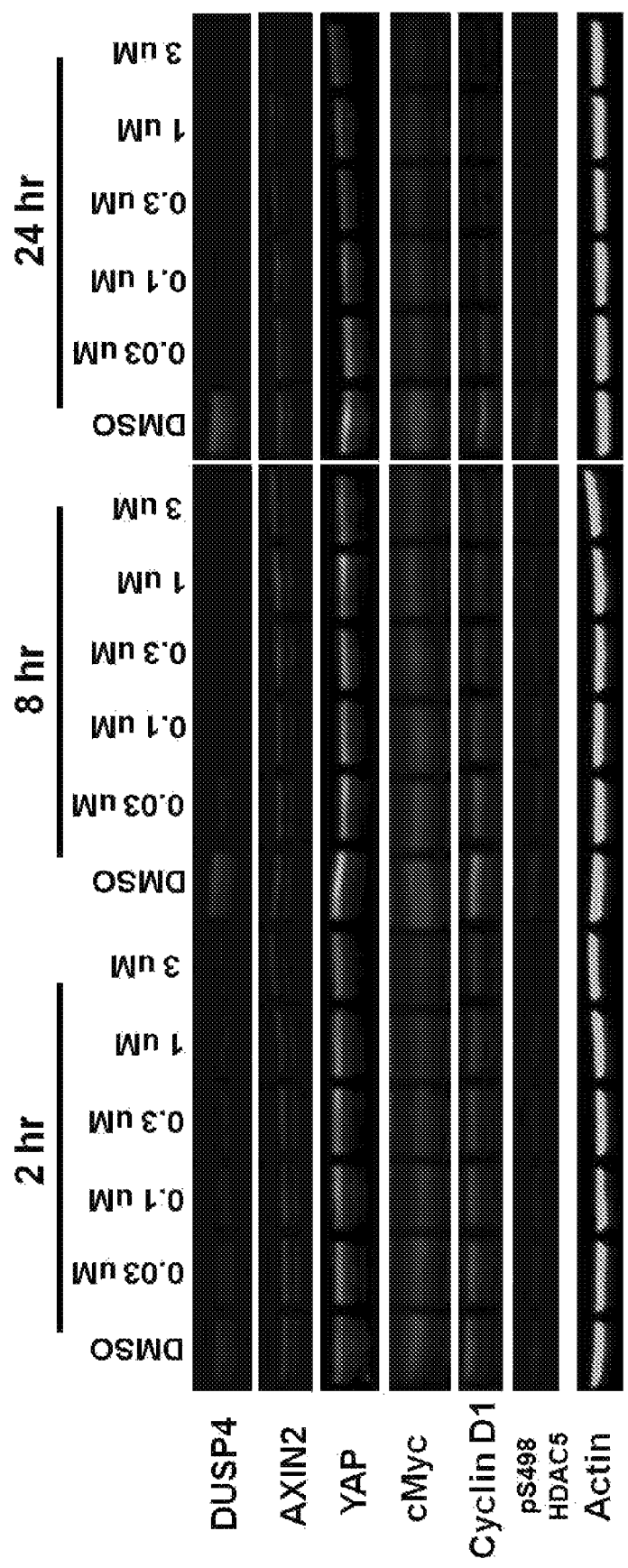
FIG. 207 illustrates Compound 1 modulates MAPK, β-catenin, and YAP in the BRAF and CTNNB1 mutant cell line SW48.
Figure 208A:
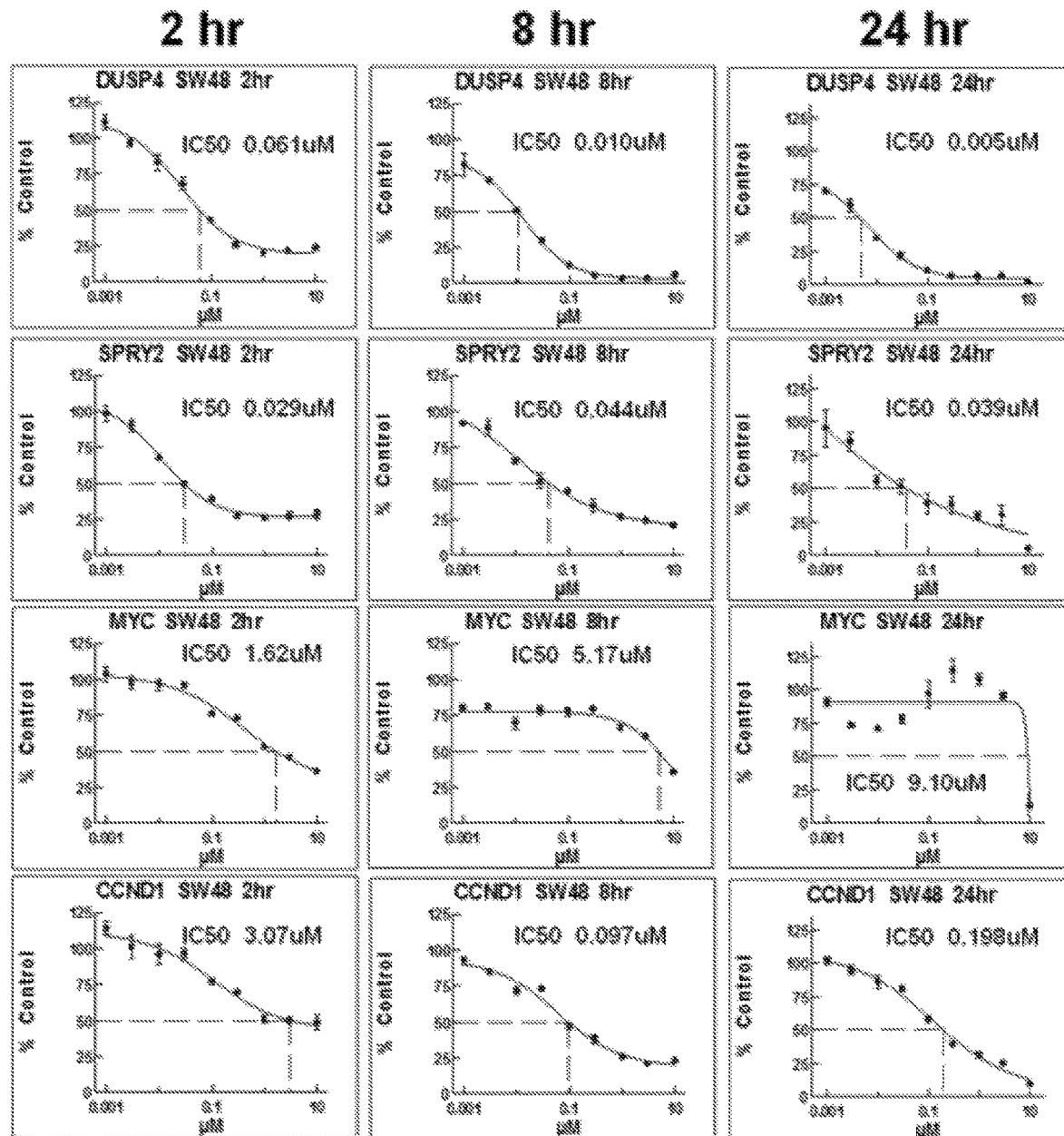
FIGS. 208A-208B illustrate Compound 1 modulates target gene expression controlled by MAPK, β-catenin, and YAP in the BRAF and CTNNB1 mutant cell line SW48.
Figure 208B:
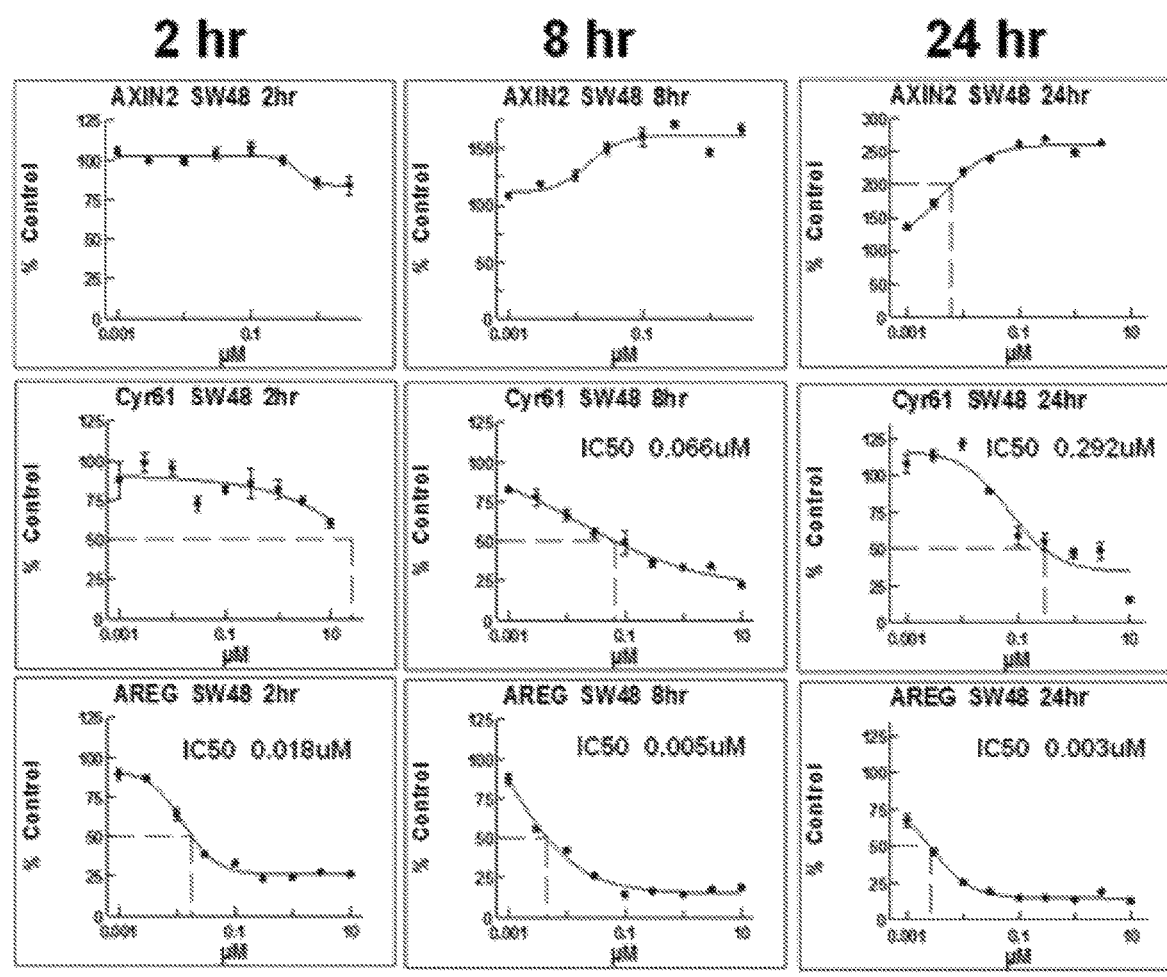

Evaluation of sensitivity in cell lines having beta-catenin mutations. The effect of Compound 1 on cell lines having β-catenin mutations was evaluated. (FIG. 205 and FIGS. 206A-206B). Compound 1 showed efficacy against cell lines with mutated β-catenin. Such cell lines demonstrate that cancers characterized by mutated β-catenin are more sensitive to treatment with Compound 1. Compound 1 was further shown to modulate β-catenin, and YAP in BRAF and CTNNB1 mutant cell lines as shown in FIG. 207. Compound 1 also modulates target gene expression controlled by MAPK, β-catenin, and YAP in BRAF and CTNNB1 mutant cell lines as provided in FIGS. 208A-208B.

Western Blot.

Compound 1 modulation of MAPK, WNT/β-catenin, and Hippo/YAP pathway markers was evaluated by standard Western blotting. LOX-IMVI, SW48, and Colo-205 cells were plated in 6-well plates at a density of 250,000 cells per well and were allowed to attach overnight. Compound 1 was added to cells at concentrations of 0.03, 0.1, 0.3, 1, and 3 µM for durations of 2, 8, and 24 hours. Cells were harvested and lysed in RIPA buffer (50 mM Tris-HCl, pH 7.4, 150 mM sodium chloride [NaCl], 0.25% deoxycholic acid, 1% Nonidet P-40, 1 mM ethylenediaminetetraacetic acid [EDTA], protease and phosphatase inhibitors). The cell lysates were heated in sodium dodecyl sulfate (SDS)-sample buffer and 40 µg of cell lysate per condition were loaded onto gels and separated using SDS polyacrylamide gel electrophoresis (PAGE). Protein was transferred to nitrocellulose membrane, and immunoblotted with anti DUSP4, DUSP6, cMyc, Cyclin D1, YAP, AXIN2, HDAC5 (phospho S498), and β-actin antibodies. Membranes were scanned on the Licor Odyssey system.

Quantitative Polymerase Chain Reaction.

Compound 1 modulation of MAPK, WNT/β-catenin, and Hippo/YAP pathway genes was evaluated by real-time (RT)-qPCR. Lysyl oxidase IMVI, SW48, and Colo-205 cells were plated in 96-well plates at a density of 20,000 cells per well and were allowed to attach overnight. Compound 1 was added to cells at half log concentrations from 1 nM to 10 µM for durations of 2, 8, and 24 hours. Cells were harvested using the TaqMan Gene Expression Cells-to-CT Kit according to the product manual. Next, RT-PCR was performed and the resulting cDNA was used in qPCR reactions on the ViiA7 Real-Time PCR System (Thermo Fisher Scientific). TaqMan probes were used to monitor changes in DUSP4, DUSP6, SPRY2, MYC, CCND1, AXIN2, CTGF, Cyr61, AREG, and ACTB genes. All genes were normalized to ACTB expression and reported as percentage of DMSO-only control.

Figure 209:
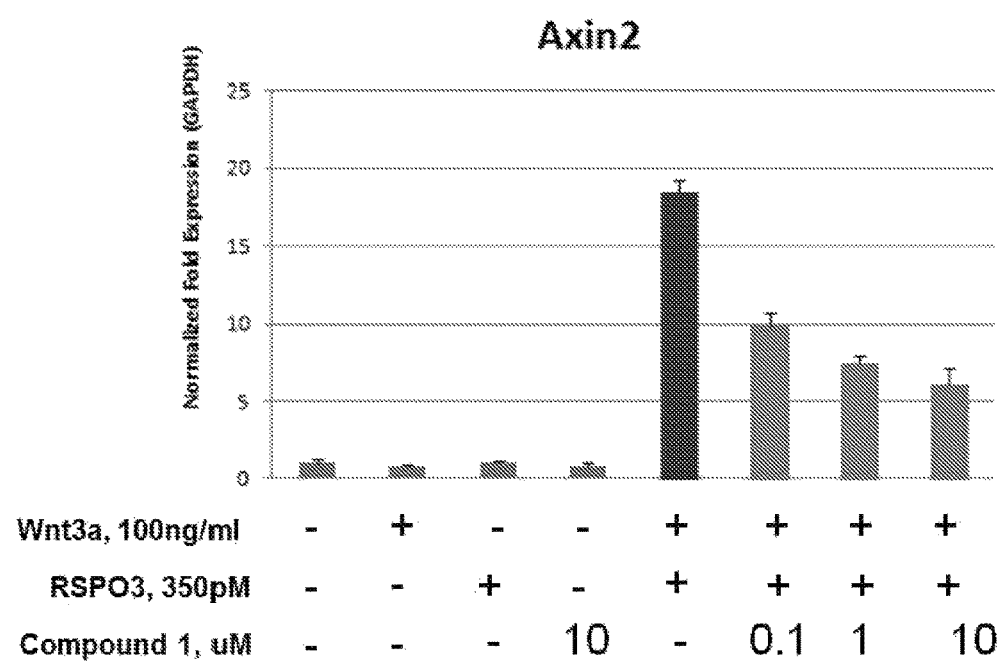
FIG. 209 illustrates that Compound 1 inhibits Axin2 expression in human bronchial epithelial cells. Gene expression was measured at 24 hours.
Figure 210A:
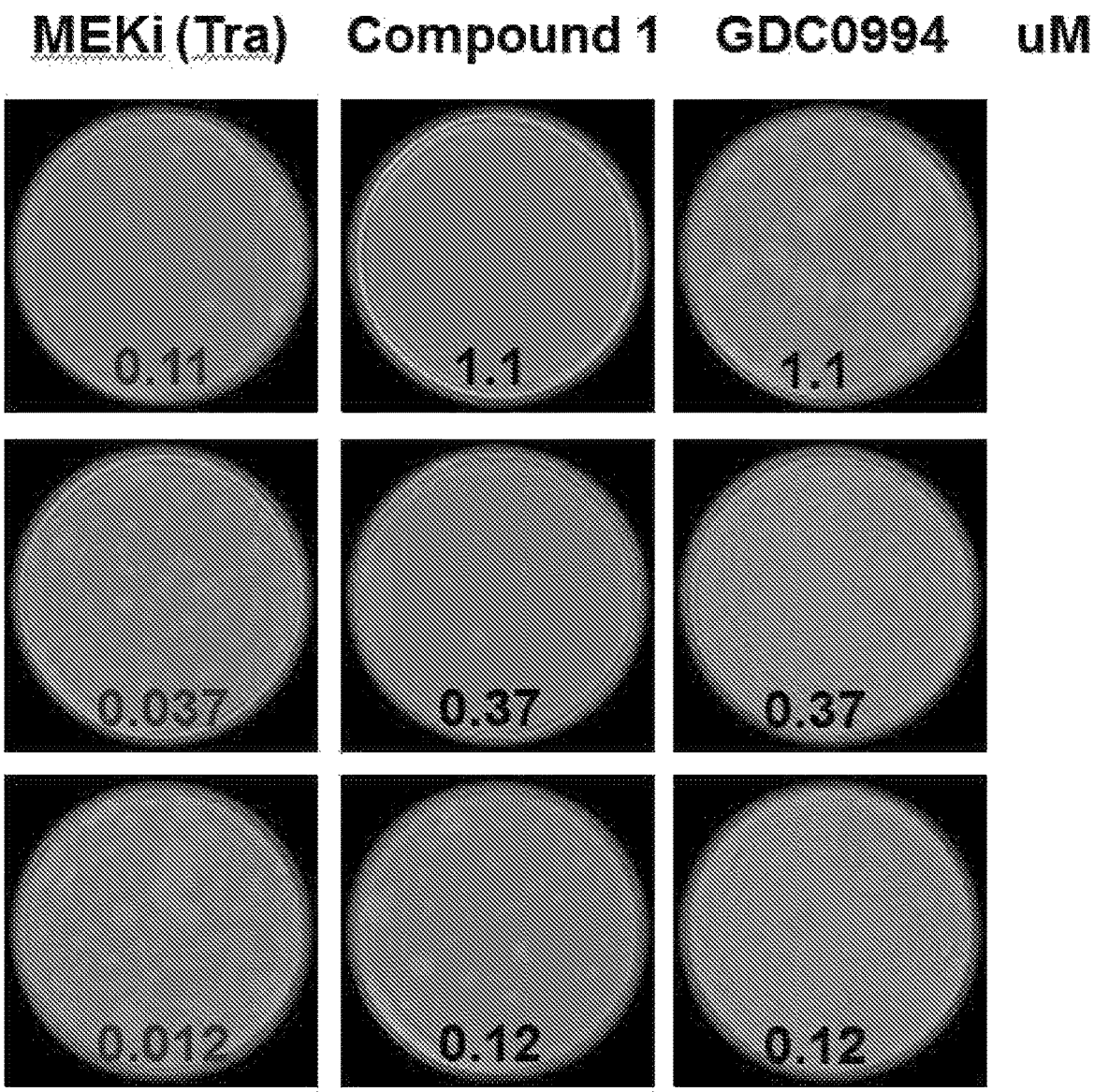
FIGS. 210A-210D illustrate that Compound 1 inhibits colony formation of β-catenin mutant cells at a level greater than MEK inhibitors (trametinib) and ERK inhibitors (GDC0994).
Figure 210B:
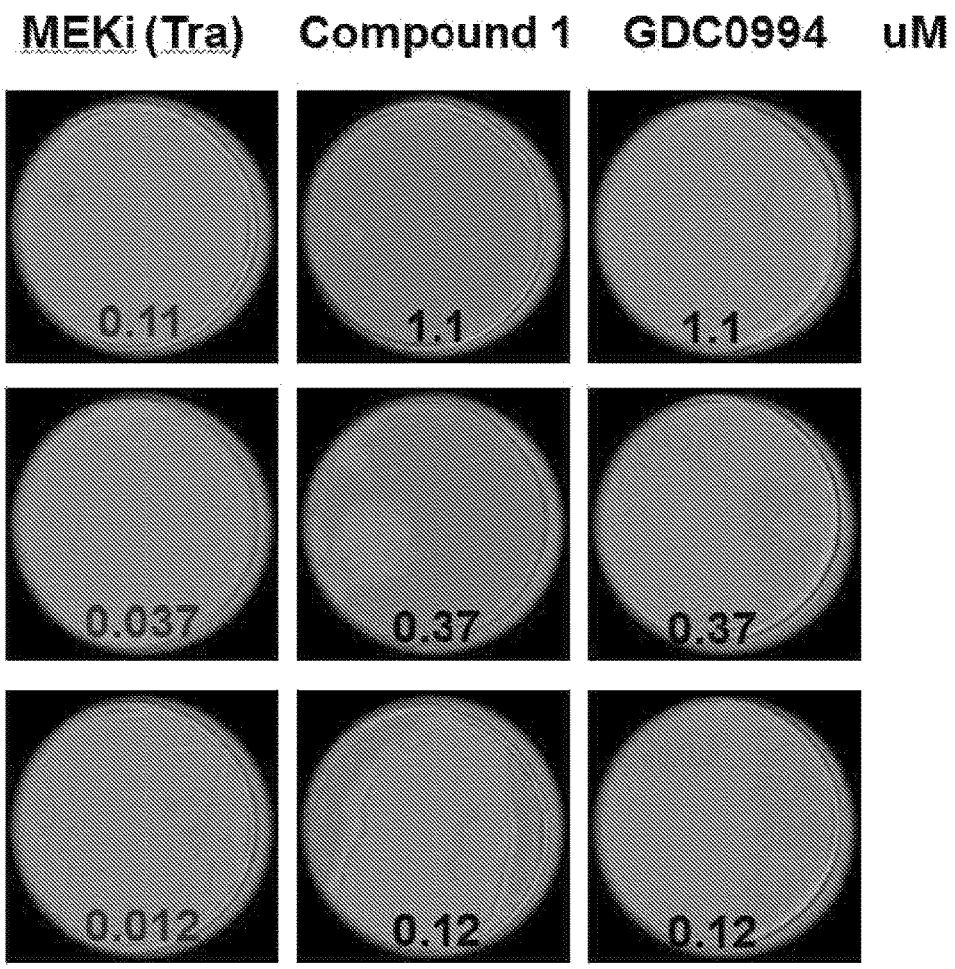
Figure 210C:
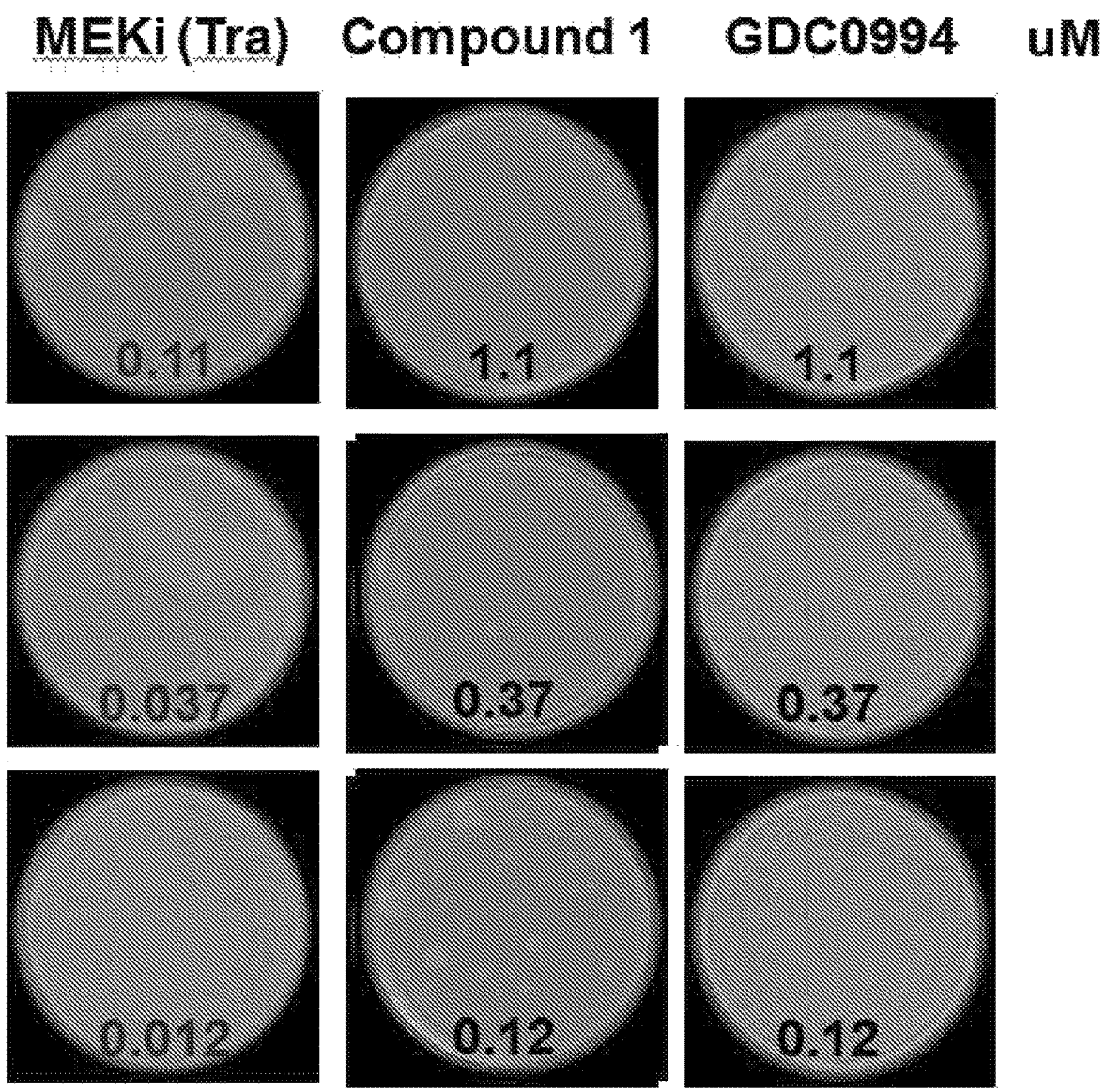
Figure 210D:
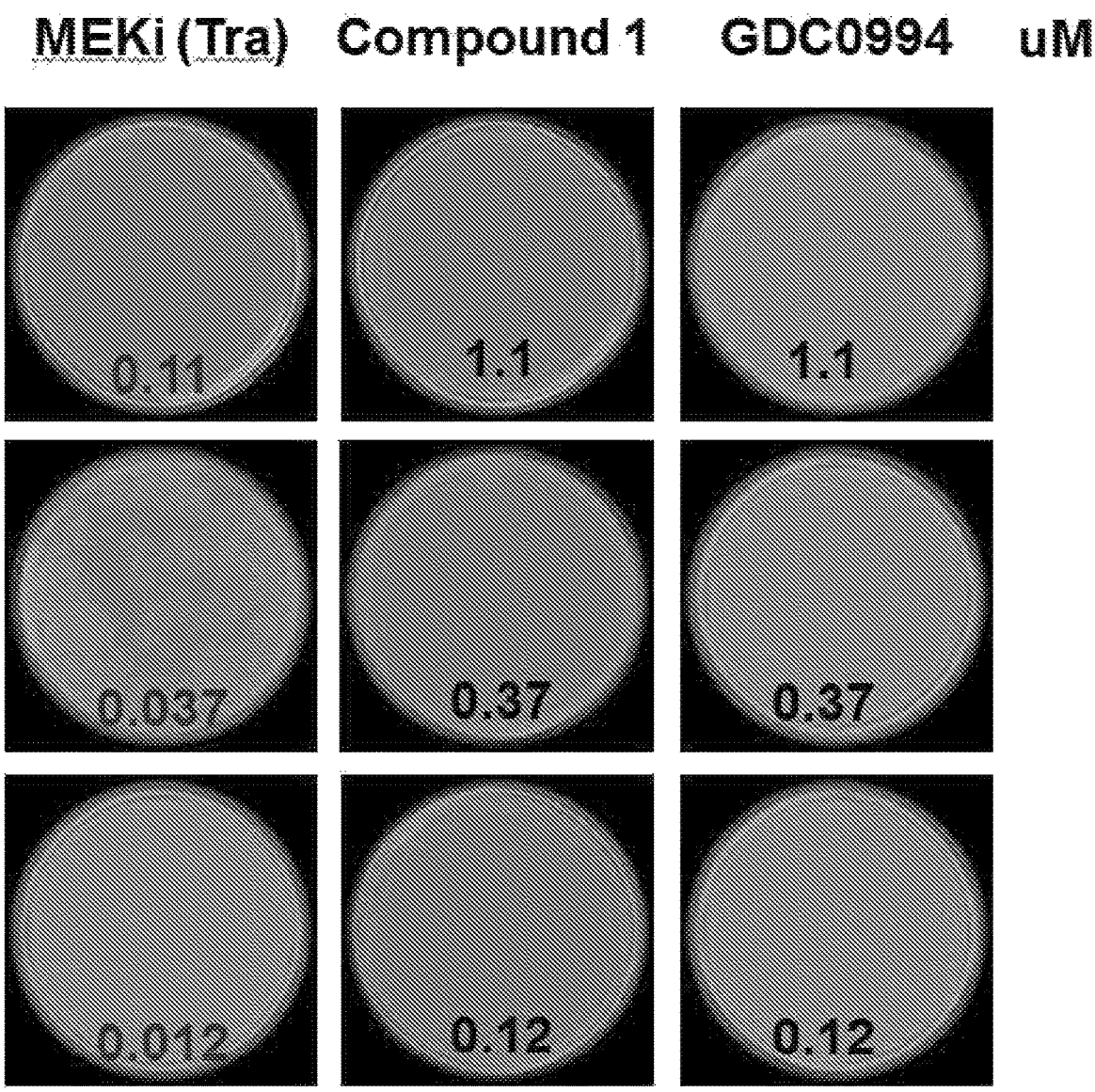
Figure 211:
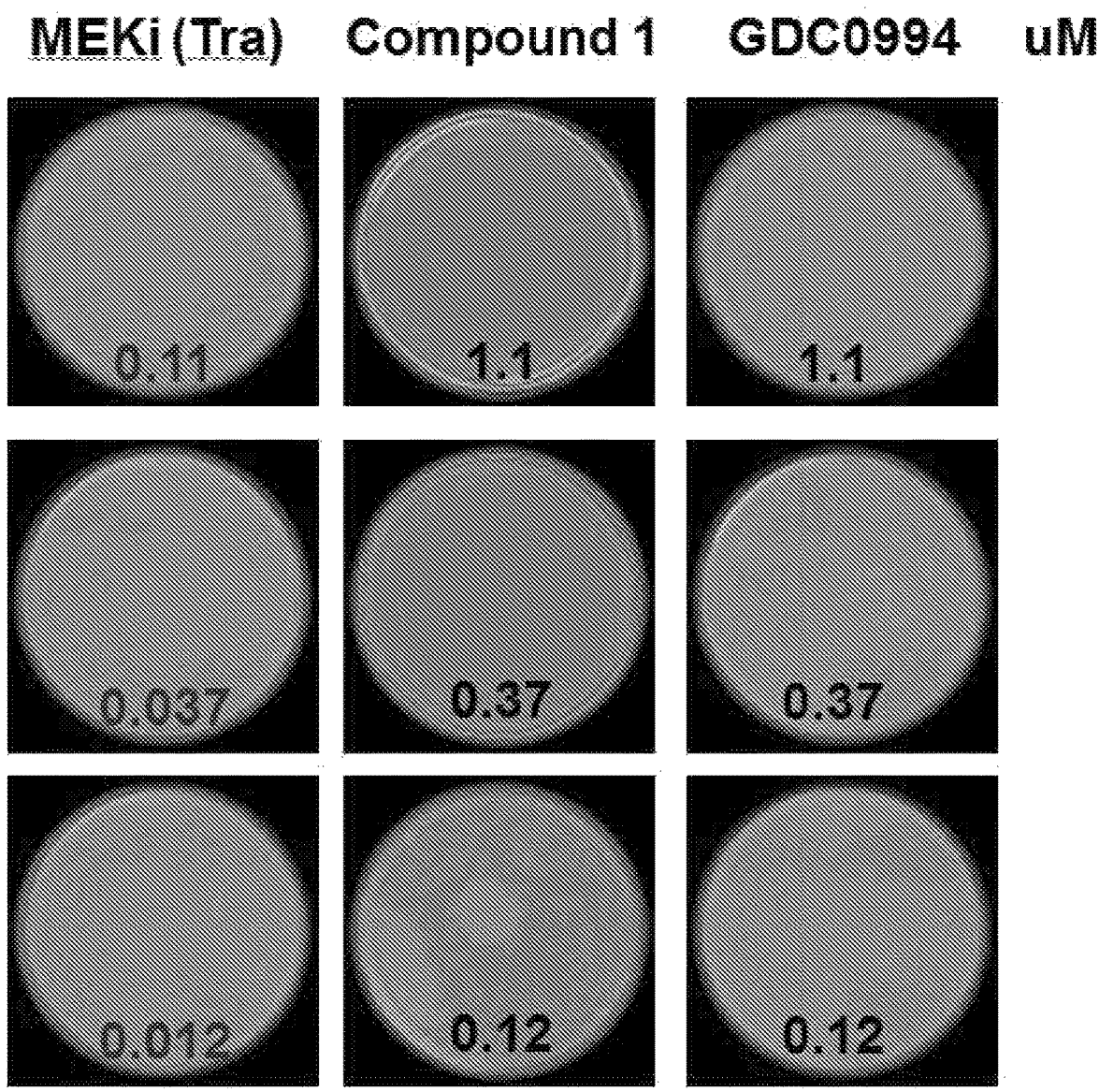
FIG. 211 illustrates that AGS cells resistant to the MEK inhibitor trametinib are sensitive to Compound 1 in a colony formation assay.

Gene Expression Analysis:

Human bronchial epithelial cells were cultured in T-150 flasks in BEpiCM growth medium and allowed to reach 80% confluency. Cells were plated in 12-well plastic culture plates at 150,000 cells per well in BEpiCM medium for 24 hours. After a 24-hour incubation, cells were treated with dimethyl sulfoxide (DMSO) as a control, Compound 1 at 0.1, 1, 10 µM, for 30 minutes. Cells were then stimulated with 100 ng/ml recombinant Wnt3a (formulated in phosphate buffered saline [PBS]), 350 pM RSPO3 (formulated in PBS) or a combination of Wnt3 and RSPO3 for 24 hours. Ribonucleic acid (RNA) was isolated using a Qiagen Rneasy Mini Kit according to manufacturer's instruction. Axin2 and gene expression was determined using reverse transcription polymerase chain reaction (RT-PCR) Taq-Man assays. Quantitative PCR (qPCR) was performed using SuperScript® III One-Step RT-PCR System and ran on a Viia 7 Real-Time PCR System. Data was normalized to glyceraldehyde 3-phosphate dehydrogenase. Compound 1 inhibits Axin2 expression in human bronchial epithelial cells. Gene expression was measured at 24 hours. From these results it was shown that Compound 1 inhibits Axin2 expression in human bronchial epithelial cells. (FIG. 209).

Long Term Colony Assay.

Compound 1 was assessed for its ability to inhibit the colony formation of cancer cells via a long-term colony forming assay. Cells and compounds were added to 96-well plates and were monitored for up to 8 weeks for the formation of colonies. Compound and media were replenished every 1 week throughout the course of the assay. Colony formation was detected via imaging at 4× on the IncuCyte ZOOM System. Compound 1 demonstrated inhibition of colony formation of β-catenin mutant cells at a level greater than MEK inhibitors (trametinib) and ERK inhibitors (GDC0994). SW48 (colo) cells, HCT-116 (colo) cells, AGS (gastric) cells, and Hep3B (HCC) cells were treated with Compound 1 and showed greater levels of inhibition than seen with treatment with MEK inhibitors or ERK inhibitors. (FIGS. 210A-210D). Compound 1 was further shown to surprisingly inhibit colony formation of AGS cells that are resistant to MEK inhibitor treatment with trametinib. Such results suggest Compound 1 can be useful in treating cancers resistant to other treatments.

Evaluation of Immunomodulatory Effects.

The effect of Compound 1 was evaluated on PD-L1 expression levels. Cells were cultured in presence or absence of Compound 1 for indicated time before expression levels of PD-L1, DUSP4 and α-tubulin or α-actin were measured by Western blot. To detect surface levels of PD-L1, cells were treated with DMSO or Compound 1 at indicated concentrations for 48 h and cell surface expression of PD-L1 was detected using flow cytometry analysis (FACS) with an APC-labeled antibody to PD-L1 (clone 29E.1A3.; BioLegend, San Diego, Calif.). Geometric mean of PD-L1 positive cells was determined by FlowJo 10 (Treestar, Ashland, Oreg.).

Conclusion.

Compound 1 directly inhibits PD-L1 expression in multiple cancer cells including HOP62, KARPAS-299, and LOX-IMVI (BRAF V600E) (FIG. 191A). FACS analysis indicates that surface PD-L1 levels are also inhibited by Compound 1 in multiple cancer cell lines (FIG. 191B).

To determine if Compound 1 down-regulation of PD-L1 enhances T cell activation, compound-treated KARPAS-299 cancer cells were co-cultured with PBMC-derived T cells stimulated with low concentrations of super antigen (SEB). KARPAS-299 cells were treated with DMSO (D) or Compound 1 at indicated concentrations for 48 h. PBMC from healthy donors were treated with or without 20 ng/ml SEB for 48 h. After wash with PBS, the PBMCs were incubated with the cancer cells for 24 h and the supernatants were collected to measure IL-2 and IFNγ using Mesoscale assays.

Figure 192B:
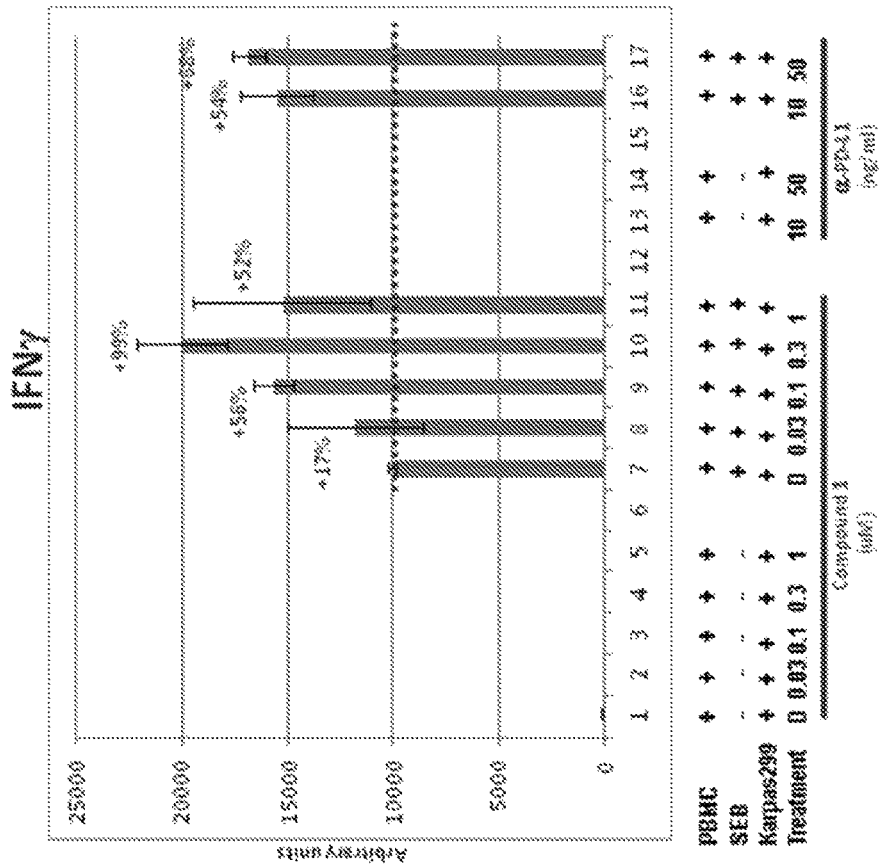
FIGS. 192A-192B illustrate Compound 1-treated KARPAS-299 cells increase production of IL-2 (FIG. 192A) and IFNγ (FIG. 192B) by PBMC-derived T cells stimulated with superantigen (SEB) in vitro. KARPAS-299 cells were treated with DMSO (D) or Compound 1 at indicated concentrations for 48 h. PBMC from healthy donors were treated with or without 20 ng/ml SEB for 48 h. After wash with PBS, the PBMCs were incubated with the cancer cells for 24 h and the supernatants were collected to measure IL-2 and IFNγ using MSD assays.
Figure 192A:
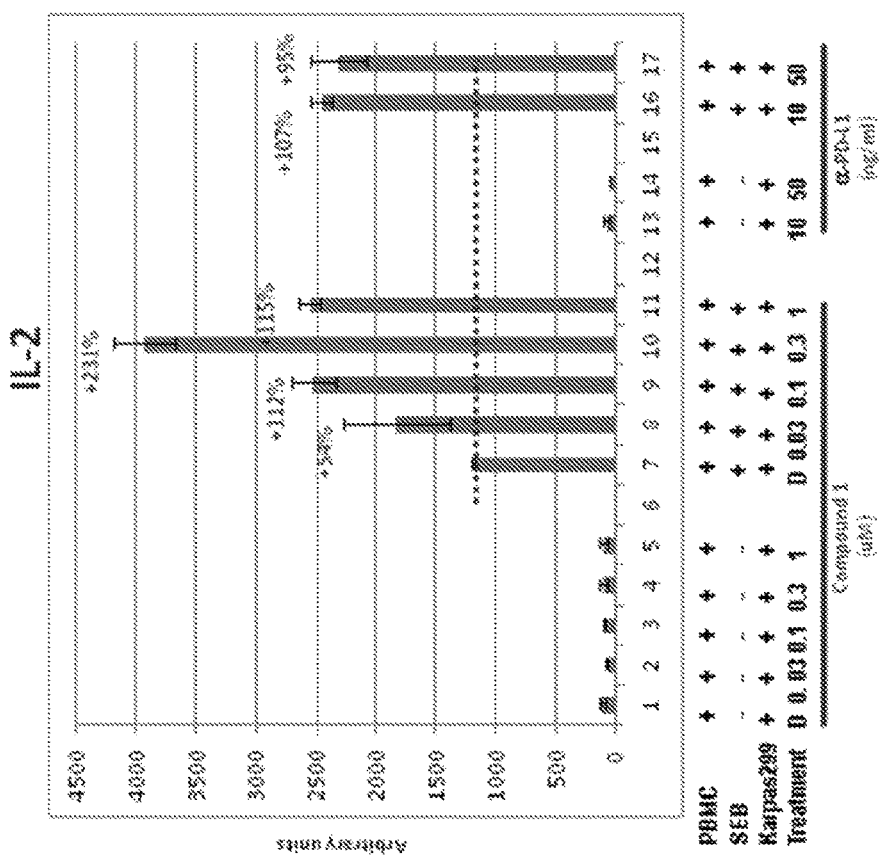

Supernatant levels of IL-2 and IFNγ were used as functional markers of T cell activation. In the absence of SEB, PBMC co-cultured with Compound-1-treated KARPAS-299 cells produced little IL-2 or IFNγ. In the presence of low concentrations of SEB (20 ng/ml), Compound 1-treated cancer cells co-cultured with PBMC demonstrated increased levels of both IL-2 and IFNγ production (FIGS. 192A-192B). The increased levels of IL-2 and IFNγ in Compound 1-treated cancer cells were similar to the levels observed with treatment of anti-PD-L1 (Ultra-LEAF™ from Biolegend).

Figure 192C:
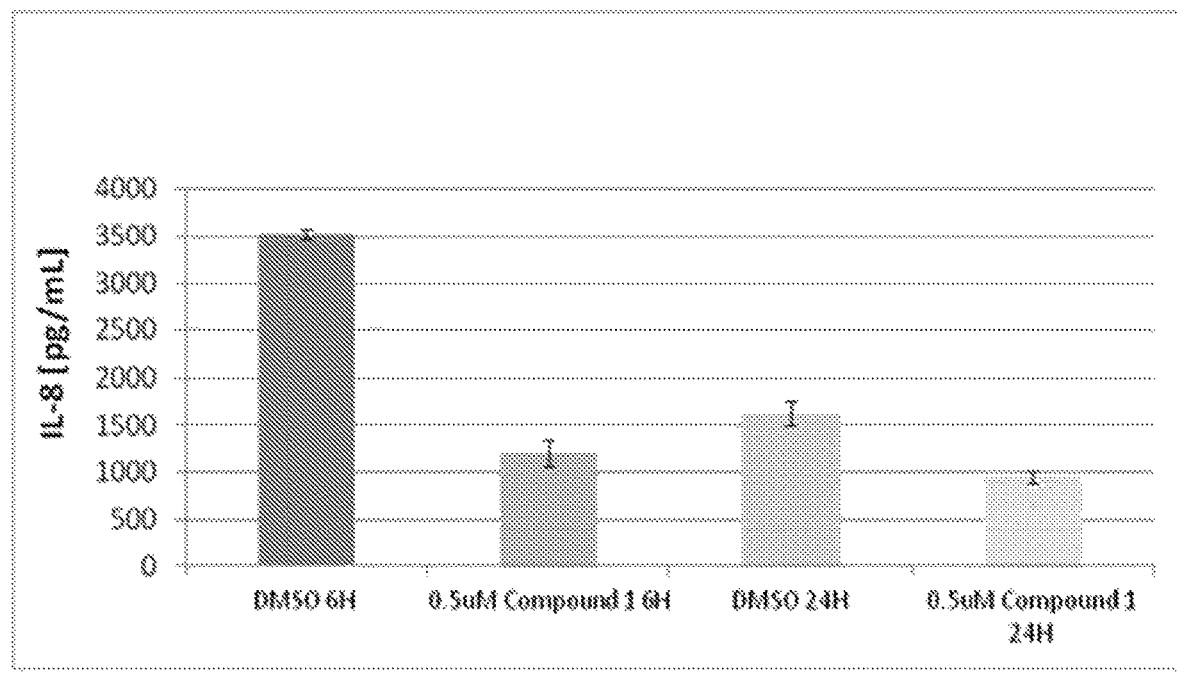
FIG. 192C illustrates the effect of Compound 1 treatment on levels of IL-8 were determined in PBMC culture media. PBMCs were isolated from whole blood and cultured in RPMI media plus 10% FBS. PBMCs were plated at 1×106 per milliliter in 10 cm2 dishes. The PBMCs were treated with 0.1% DMSO or 0.5 µM Compound 1. Treatments were taken down at designated time points. PBMCs were pelleted and used for Western blot analysis and 1 mL of culture media was taken for IL-8 analysis. The IL-8 analysis was performed with a Mesoscale V-Plex Human IL-8 kit according to the manufacturer's instructions. Compound 1 was shown to inhibit IL-8 levels at different time-points.

The effect of Compound 1 treatment on levels of IL-8 was determined in PBMC culture media. PBMCs were isolated from whole blood and cultured in RPMI media plus 10% FBS. PBMCs were plated at 1×10$^6$ per milliliter in 10 cm$^2$ dishes. The PBMCs were treated with 0.1% DMSO or 0.5 µM Compound 1. Treatments were taken down at the designated time points. The culture media (1 mL) was used for IL-8 analysis. The IL-8 analysis was performed with a Mesoscale V-Plex Human IL-8 kit according to the manufacturer's instructions. Compound 1 was shown to inhibit IL-8 levels at different time-points (FIG. 192C).

TEAD Reporter Assay.

Figure 212:
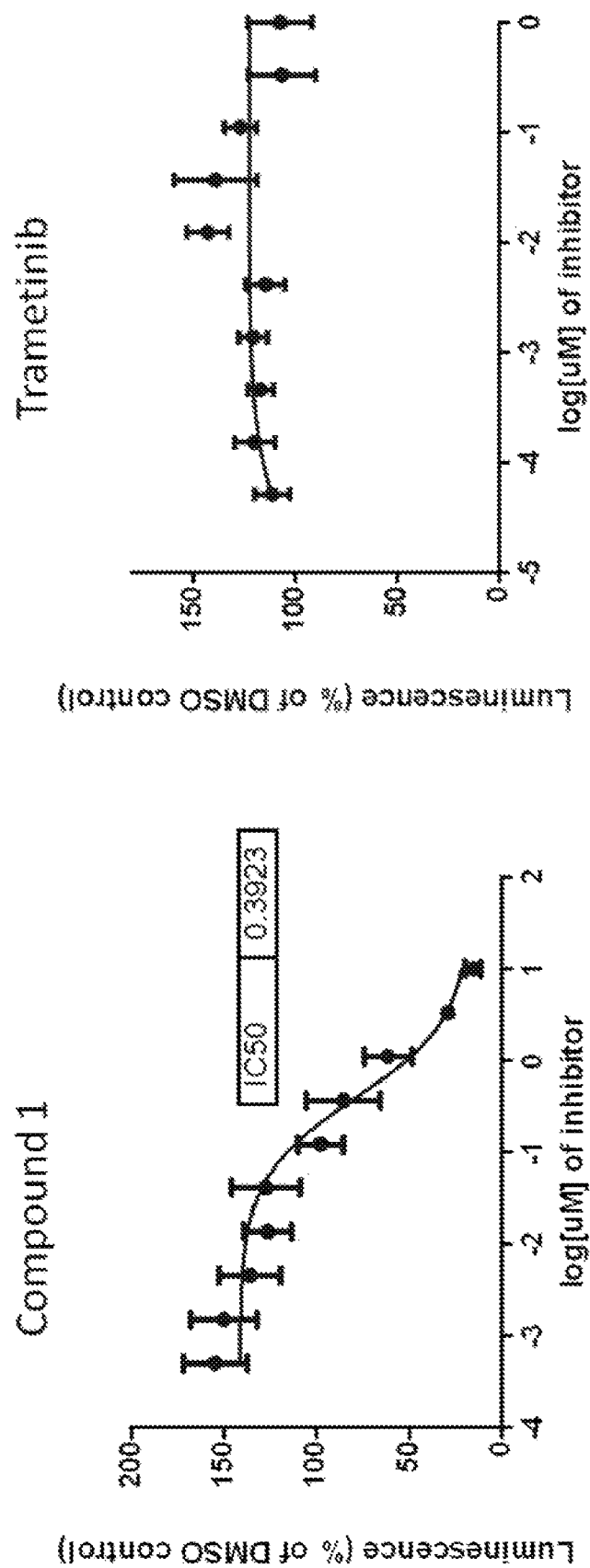
FIG. 212 illustrates TEAD reporter activity in 8×GTIIC-luciferase W138 VA13 cells treated with Compound 1 and trametinib for 72 hours. Luciferase activity was analyzed using the Bright Glo luciferase assay (Promega). Compound 1 inhibited TEAD reporter activity, with an average $IC_{50}$ of >10 μM in the 24 hour assay and an average $IC_{50}$ of 1.85 μM in the 72 hour assay (cumulative data of three experiments). Viability was not reproducibly affected by Compound 1 across the three assays. Trametinib did not inhibit TEAD reporter activity at 24 or 72 hours.

TEAD reporter activity was analyzed using WI38 VA13 cells stably expressing a YAP/TAZ responsive synthetic promoter driving luciferase expression (8×GTIIC-luciferase). 10,000 cells per well were seeded on a white-walled 96-well plate and left overnight. After 16-20 hours, cells were treated with compound and TEAD reporter activity was measured 24 or 72 hours later using Bright Glo luciferase assay (Promega) according to the manufacturer's instructions. This assay was performed 3 times for Compound 1 and twice for Trametinib. See FIG. 212.

Viability Assay.

In parallel 10,000 WI38 VA13 cells expressing 8×GTIIC-luciferase were seeded in each well of a black-walled 96-well plate. After 16-20 hours cells were treated with compound for 24 or 72 hours. At this time the serum and compound containing media was removed and replaced with 100 µl serum free media and 100 µl Cell Titer Fluor (Promega). The plate was incubated for 2 hours at 37° C. before reading fluorescence output. This assay is based on measurement of live-cell protease activity. The viability assay was performed to confirm that any effects of compounds on TEAD reporter were not the result of compound effects on viability. This assay was performed 3 times for Compound 1 and twice for Trametinib.

Conclusion.

These data provide an additional therapeutic hypothesis suggesting that treatment with Compound 1 will potentiate T cell activation. The in vitro data suggests that Compound 1 may enhance T cell immunity against cancer cells by inhibiting key oncogenic pathways such as the MAPK pathway and down-regulating the immune checkpoint molecule PD-L1 expression in tumor microenvironment. Cancer types that express high levels of PD-L1 (for example, melanoma, lung, RCC, or HCC) may therefore be sensitive to Compound 1.

Animal Models

Xenograft Models.

For xenograft model studies human cancer cell lines were injected into SCID (severe combined immunodeficiency) mice. Cancer cell lines were propagated in culture in vitro. Tumor bearing animals were generated by injecting precisely determined numbers of cells into mice. Following inoculation of animals, the tumors were allowed to grow to a certain size prior to randomization. The mice bearing xenograft tumors ranging between pre-determined sizes were pooled together and randomized into various treatment groups. A typical efficacy study design involved administering one or more compounds at various dose levels to tumor-bearing mice. Additionally, reference chemotherapeutic agents (positive control) and negative controls were similarly administered and maintained. Tumor measurements and body weights were taken over the course of the study.

Mice were anesthetized with inhaled isoflurane and then inoculated with LOX-IMVI tumor cells subcutaneously above the right hind leg with 0.1 mL of a single cell suspension in PBS using a sterile 1 mL syringe fitted with a 26-gauge needle. Following inoculation of the animals, tumors were allowed to grow to approximately 75-125 mm$^3$ or in some cases 250-400 mm$^3$ prior to randomization of the mice. The tumor of each animal was measured and animals with tumors in the appropriate range were included in the study. Animals from the study pool were then distributed randomly into various cages and the cages were randomly assigned to vehicle, positive control, or test article groups. All of the mice were tagged with metal ear tags on the right ear. A typical group consisted of 8-10 animals. For a typical xenograft study, SCID mice bearing tumors were randomized and dosed with compounds ranging from, for example, 100 mg/kg to 0.1 mg/kg with different dose scheduling, including, but not limited to, qd, q2d, q3d, q5d, q7d and bid. The mice were dosed for 1-4 weeks. Tumors were measured twice a week using calipers and tumor volumes were calculated using the formula of $W^2 \times L/2$.

The purpose of these studies was to test the efficacy of Compound 1 in the cell line-derived xenograft models, LOX-IMVI (melanoma) and Colo205 (colorectal) and the PDX1994060146 (patient-derived xenograft [PDX146]) colorectal xenograft model. These models were chosen because they harbor the V600E BRAF mutation. Additional PK/PD analysis was performed to examine the Compound 1-mediated inhibition of pathway biomarkers in the PDX146 xenograft model.

LOX-IMVI Subcutaneous Melanoma Xenograft Model.

Figure 193:
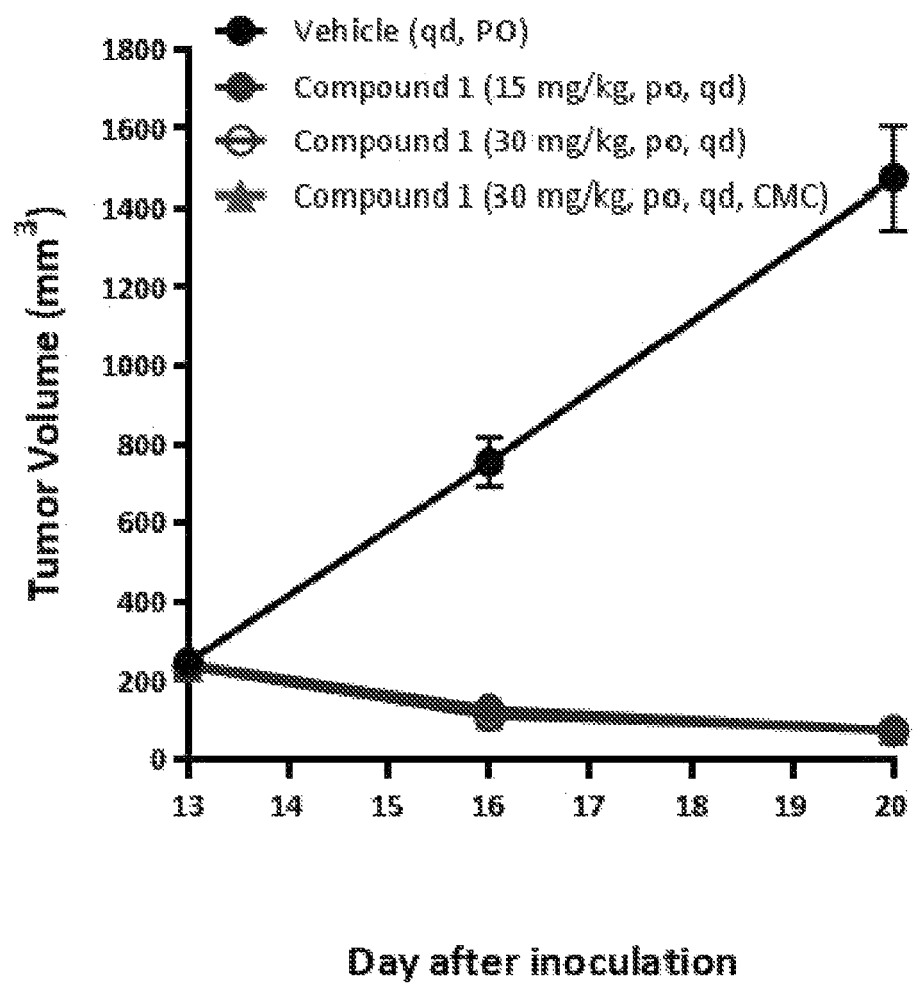
FIG. 193 illustrates antitumor activity of Compound 1 in the LOX-IMVI Xenograft Model. Female SCID mice were inoculated with 1×10⁶ LOX-IMVI tumor cells into the right flank. Mice were randomized into treatment groups (n=9/group) at the time of treatment initiation. Test article treatment started on Day 13 when the tumors were approximately 240 mm³.

The purpose of this study was to confirm the efficacy of Compound 1 in the LOX-IMVI melanoma xenograft model. One study (FIG. 193) in the LOX-IMVI xenograft model testing two dose levels of Compound 1 (15 and 30 mg/kg) demonstrated significant tumor volume reduction compared to the vehicle control (p<0.001 for both dose levels). Tumor regression was observed in 9 out of 9 animals for both dose levels and 1 out of 9 animals from each group was tumor free at study end.

Figure 194:
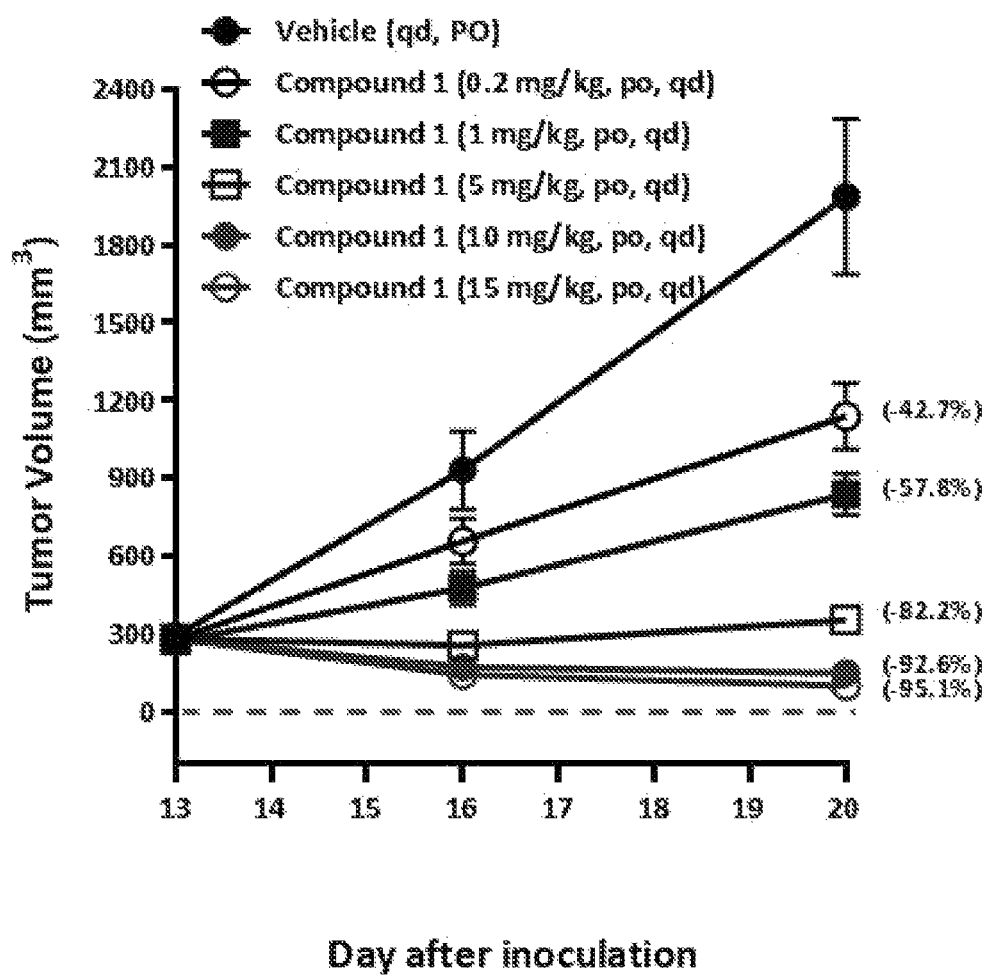
FIG. 194 illustrates antitumor activity of Compound 1 in the LOX IMVI Xenograft Model. Female severe-combined immunodeficient (SCID) mice were inoculated with 1×10⁶ LOX-IMVI tumor cells into the right flank. Mice were randomized into treatment groups (n=10/group) at the time of treatment initiation. Test article treatment started on Day 13 when the tumors were approximately 300 mm³. Percent inhibition is calculated relative to the vehicle control on the last study day and is in parentheses next to the respective tumor volume for the treatment groups. Dotted line is the tumor volume at the initiation of dosing.

In a separate experiment, Compound 1 was administered orally, QD for 8 days at 0.2, 1, 5, 10, and 15 mg/kg. Dose-dependent antitumor activity was observed with Compound 1 treatment in the LOX-IMVI xenograft model (FIG. 194). Tumor regression was observed at the 10 and 15 mg/kg dose levels.

Colo 205 Subcutaneous Colorectal Xenograft Model. Colo 205 Subcutaneous Colorectal Xenograft Model.

Figure 195:
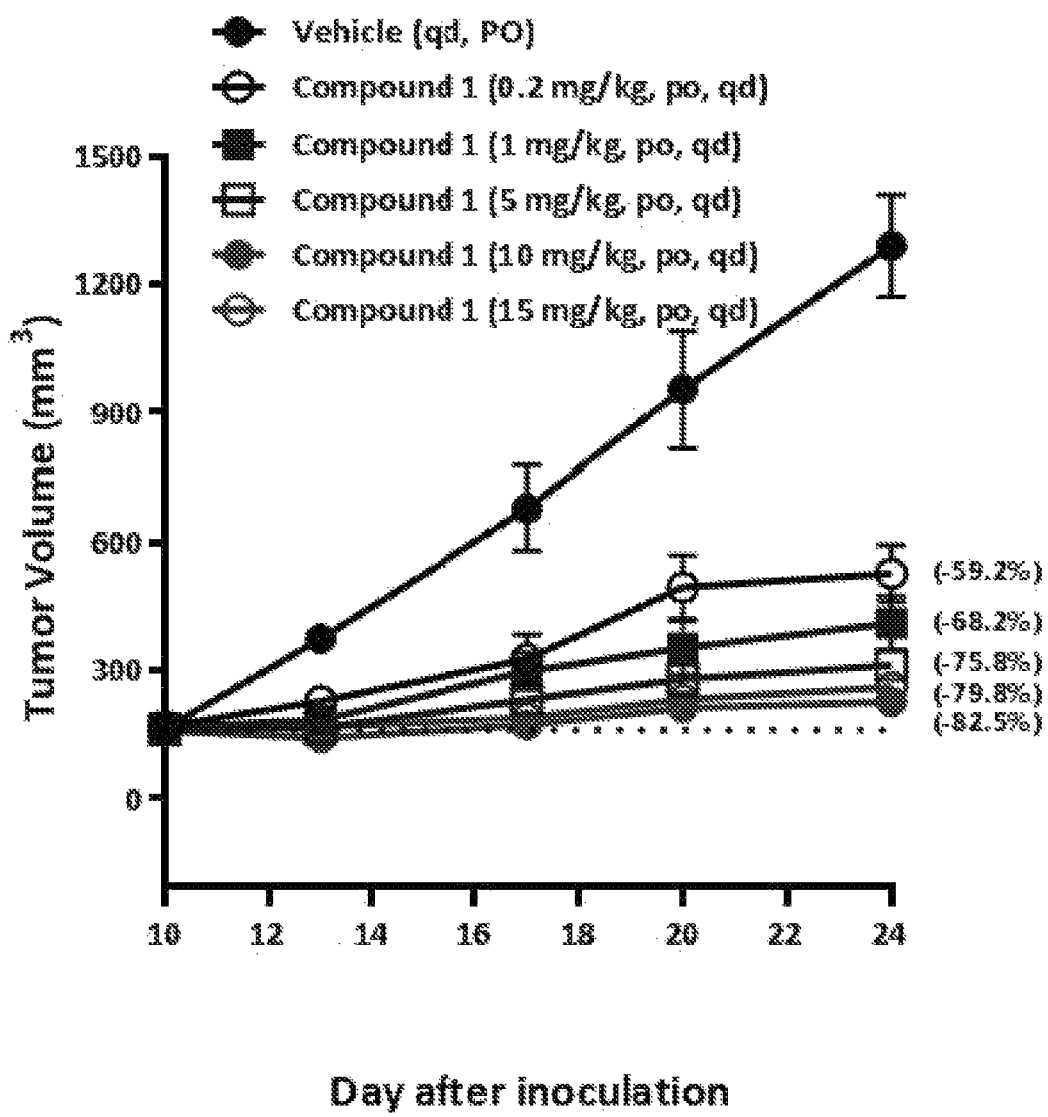
FIG. 195 illustrates antitumor activity of Compound 1 in the Colo 205 Xenograft Model. Female SCID mice were inoculated with 2×10⁶ Colo 205 tumor cells into the right flank. Mice were randomized into treatment groups (n=10/group) at the time of treatment initiation. Test article treatment started on Day 10 when the tumors were approximately 160 mm³. Percent inhibition is calculated relative to the vehicle control on the last study day and is in parentheses next to the respective tumor volume for the treatment groups. Dotted line is the tumor volume at the initiation of dosing.
Figure 196:
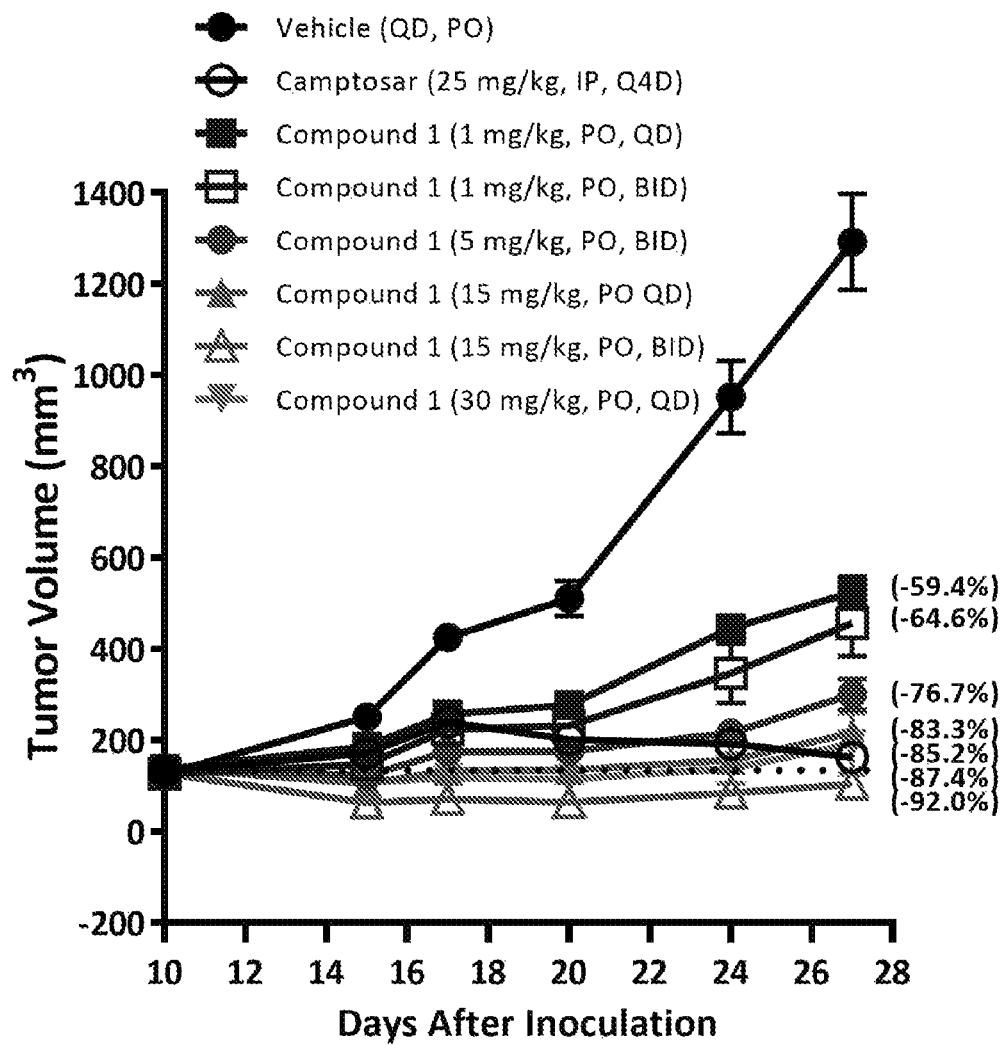
FIG. 196 illustrates antitumor activity of Compound 1 in the Colo 205 Xenograft Model. Female SCID mice were inoculated with 2×10⁶ Colo 205 tumor cells into the right flank. Mice were randomized into treatment groups (n=10/group) at the time of treatment initiation. Test article treatment started on Day 10 when the tumors were approximately 130 or 160 mm³. Percent inhibition is calculated relative to the vehicle control on the last study day and is in parentheses next to the respective tumor volume for the treatment groups. Dotted line is the tumor volume at the initiation of dosing.

The purpose of these studies was to test the efficacy of Compound 1 in the Colo 205 colorectal cancer xenograft model, and determine whether twice daily dosing (BID) had an impact on antitumor activity. In the first experiment Compound 1 was administered orally, QD for 15 days at 0.2, 1, 5, 10, and 15 mg/kg. Dose-dependent antitumor activity was observed with Compound 1 treatment in the Colo 205 xenograft model (FIG. 195). A scheduling study was conducted to determine whether BID dosing increased the antitumor activity of Compound 1. Dose-dependent antitumor activity was observed with Compound 1 treatment in the Colo 205 xenograft model (FIG. 196).

PDX1994060146 Subcutaneous Colorectal Patient-Derived Xenograft Model.

The purpose of these studies was to test the efficacy of Compound 1 in the PDX1994060146 (PDX146) colorectal cancer xenograft model and determine whether BID dosing had an impact on antitumor activity. A time to progression (TTP) study was performed to determine the effect of longer treatment duration on tumor growth.

Figures 197A, 197B:
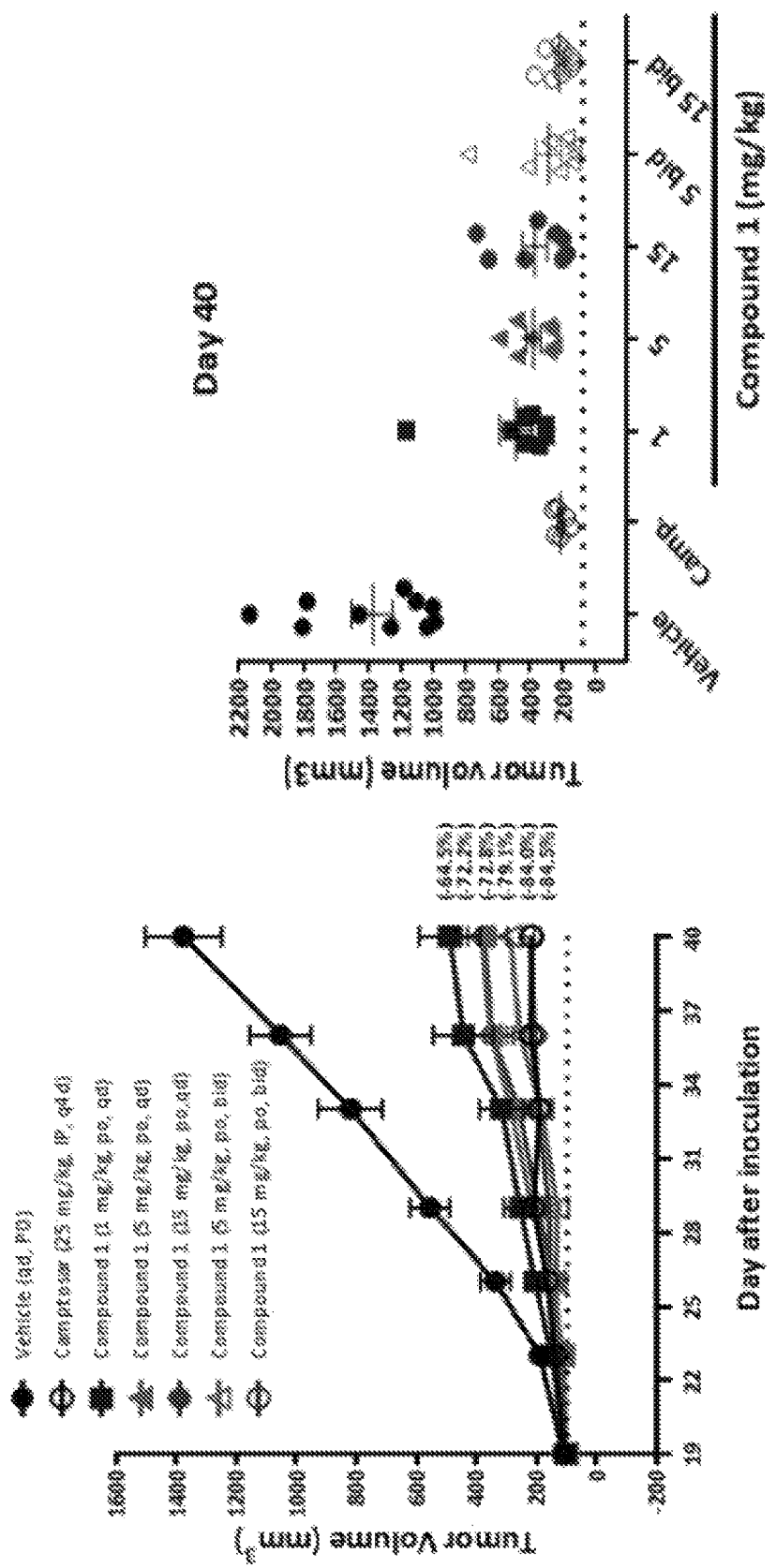
FIGS. 197A-197B illustrates antitumor activity of Compound 1 in the PDX146 Xenograft Model. Female NSG mice were inoculated with 25 μg of PDX146 tumor in a cell slurry into the right flank. Mice were randomized into treatment groups (n=8-10/group) at the time of treatment initiation. Test article treatment started on Day 19 when the tumors were approximately 100-110 mm$^3$.

In the first experiment Compound 1 was administered orally, QD at 1, 5, and 15 mg/kg or 5 and 15 mg/kg BID for 22 days. Dose-dependent antitumor activity was observed with Compound 1 treatment in the PDX146 xenograft model (FIGS. 197A-197B). Dosing 15 mg/kg BID appeared to increase the antitumor activity of Compound 1 compared to the administration of 15 mg/kg QD.

Figure 198:
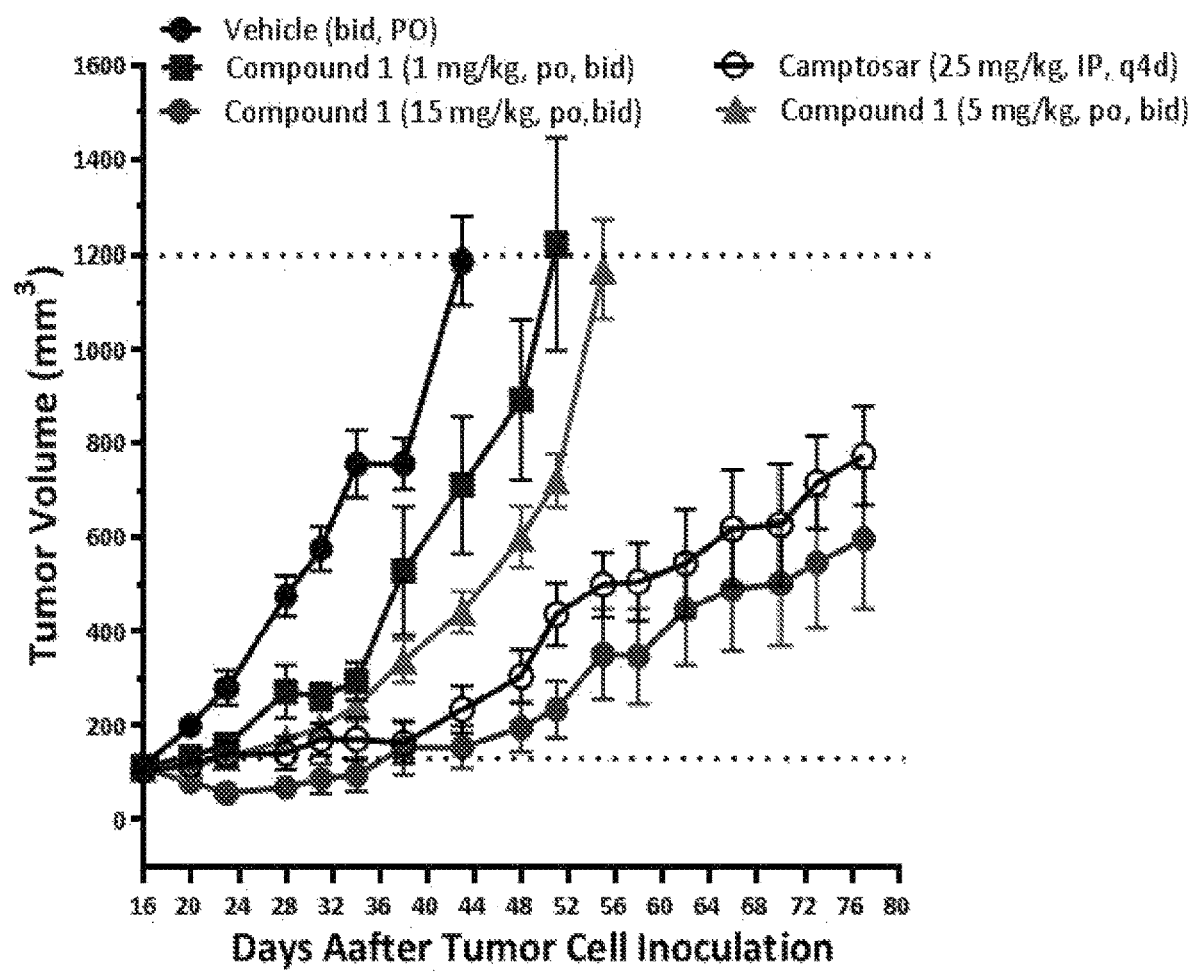
FIG. 198 illustrates tumor Growth Delay with Continuous Compound 1 Treatment in the PDX146 Xenograft Model. Female NSG mice were inoculated with 25 μg of PDX146 tumor in a cell slurry into the right flank. Mice were randomized into treatment groups (n=8-10/group) at the time of treatment initiation. Test article treatment started on Day 16 when the tumors were approximately 100-110 mm$^3$. Black dotted line is the tumor volume at the initiation of dosing and the red dotted line is the tumor volume on Day 43 when the vehicle control group was terminated.

In the TTP study, Compound 1 was administered orally, 1, 5, and 15 mg/kg BID for 49-77 days. Compound 1 treatment groups were dosed throughout the duration of the study until the group mean reached the predetermined endpoint of approximately 1200 mm³ or study termination. Tumor growth delay (TGD) was calculated as the time between the termination of the vehicle control group (on day 43) and the Compound 1 treatment groups. The TGD was 8, 12 and >37 days for the 1, 5 and 15 mg/kg treatment groups, respectively. (FIG. 198)

Biomarkers representing the activity of three different pathways, MAPK, Wnt, and Hippo, were inhibited in the PDX146 xenograft model. Sustained inhibition of these pathway biomarkers was observed through 24 h.

Antitumor Activity of Compound 1 in the β-catenin Mutant SW48 Colorectal Xenograft Model.

Figure 202A:
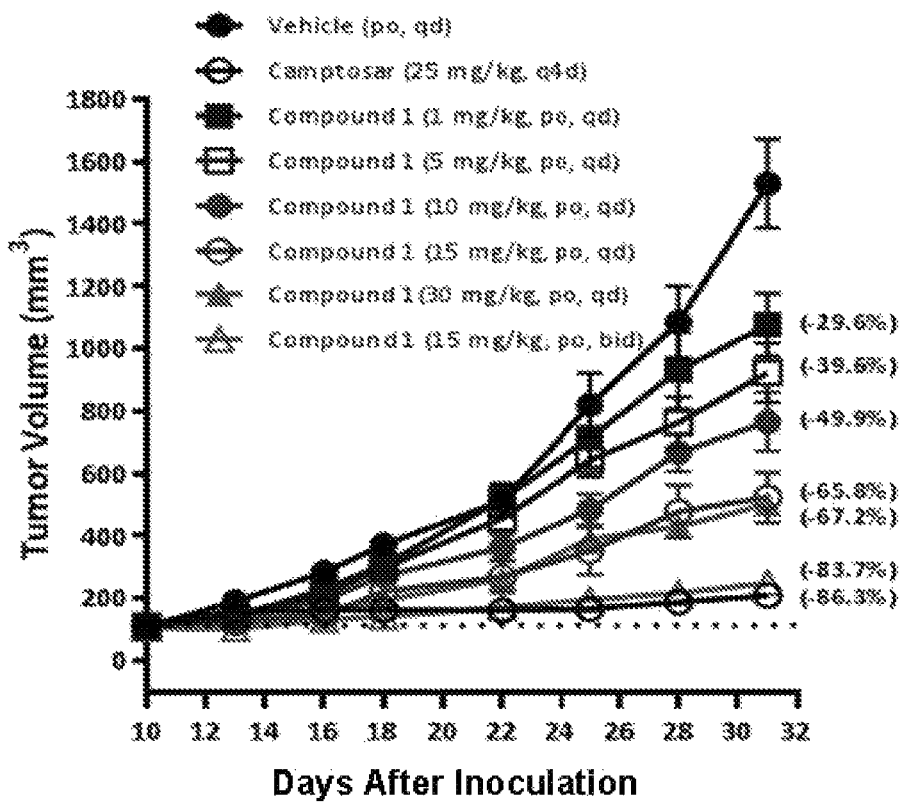
FIGS. 202A-202B illustrate antitumor activity of Compound 1 in the β-catenin mutant SW48 colorectal xenograft model. Female SCID mice were inoculated with 2×106 SW48 tumor cells into the right flank. Mice were randomized into treatment groups (n=10/group) at the time of treatment initiation. Test article treatment started on Day 10 when the tumors were approximately 110 and 105 mm$^3$ (FIG. 202A and FIG. 202B, respectively). Black dotted line is the tumor volume at the initiation of dosing. Graph on the left is a dose-response study (graph A). Graph on the right is a time to progression study where animals were maintained on drug during the course of the study (graph B). Dotted line is the tumor volume on Day 28 when the vehicle control group was terminated.
Figure 202B:
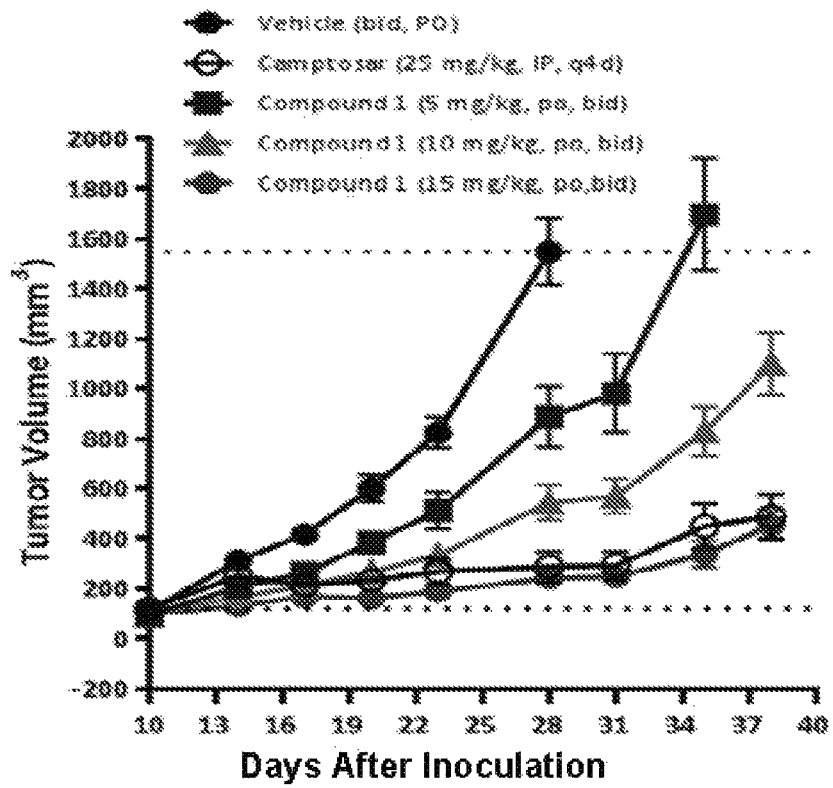

Female SCID mice were inoculated with $2 \times 10^6$ SW48 tumor cells into the right flank. Mice were randomized into treatment groups (n=10/group) at the time of treatment initiation. Test article treatment started on Day 10 when the tumors were approximately 110 and 105 mm³. (FIGS. 202A-202B) Black dotted line is the tumor volume at the initiation of dosing. Graph on the left is a dose-response study. Graph on the right is a time to progression study where animals were maintained on drug during the course of the study. Dotted line is the tumor volume on Day 28 when the vehicle control group was terminated.

Antitumor Activity in the Orthotopic Hep3B2.1-7 Hepatocellular Carcinoma Xenograft.

Figure 203:
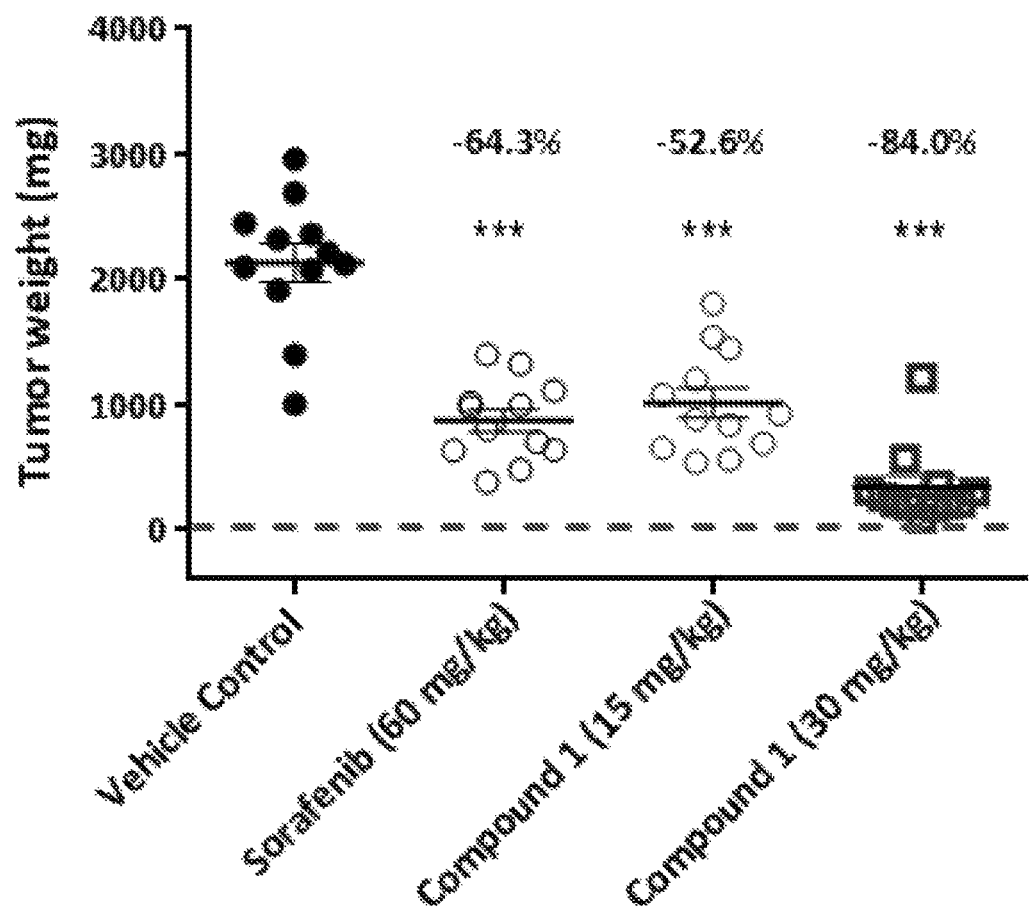
FIG. 203 illustrates antitumor activity in the orthotopic Hep3B2.1-7 hepatocellular carcinoma xenograft. Female SCID mice were orthotopically inoculated with 2×10$^6$ Hep3B2.1-7 tumor cells per animal. Seven days post-inoculation animals were randomized into treatment groups based on body weight and treatment commenced (Study day 0). Take rate assessment of a satellite group confirmed the presence of tumor in the liver in 100% of the animals. Compound 1 was dosed orally, QD for 21 days. On the day of study termination, tumors were removed and weighed. Individual tumor weights and the mean tumor weight±SEM of each group are plotted. Percent inhibition is calculated relative to the vehicle control and is above the respective tumor weight for the treatment groups. P values are derived from a one-way ANOVA with a Dunnet's post-hoc analysis. ***=p<0.001. Compound 1 showed a statistically significant reduction in tumor weight compared to vehicle controls.

Female SCID mice were orthotopically inoculated with $2 \times 10^6$ Hep3B2.1-7 tumor cells per animal. Seven days post-inoculation the animals were randomized into treatment groups based on body weight and the treatment commenced (Study day 0). Take rate assessment of a satellite group confirmed the presence of tumor in the liver in 100% of the animals. Treatment with Compound 1 was started and Compound 1 was dosed orally, QD for 21 days. Significant mean body weight loss expected with this model was observed in the vehicle control group. Animals treated with 15 mg/kg Compound 1 showed minimal body weight loss and a significant mean body weight gain was observed in the 30 mg/kg Compound 1 treatment group. On the day of study termination, the tumors were removed and weighed. Individual tumor weights and the mean tumor weight±SEM of each group was plotted (FIG. 203). Percent inhibition was calculated relative to the vehicle control. P values were derived from a one-way ANOVA with a Dunnet's post-hoc analysis. ***=p<0.001.

Antitumor Activity of Compound 1 in the C-Met Amplified Hepatocellular Carcinoma Patient-Derived Xenograft Model, LI0612.

Figure 204:
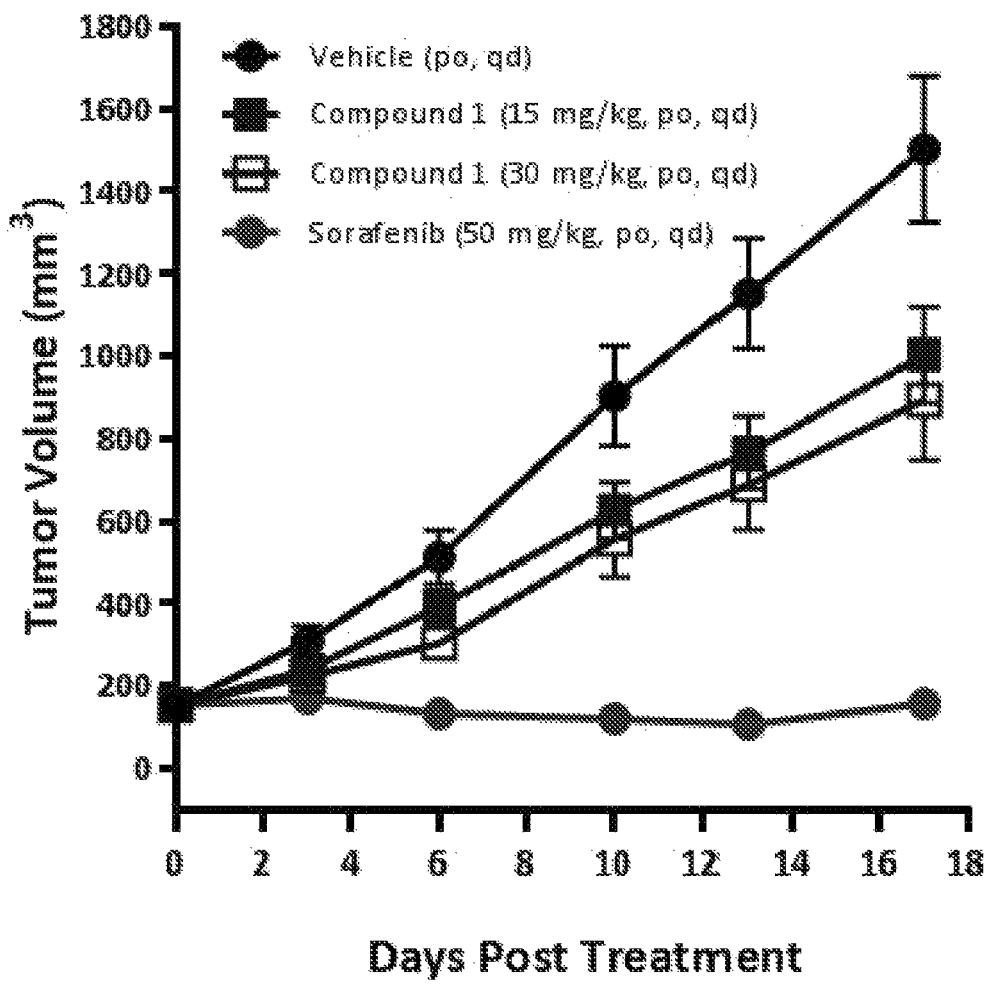
FIG. 204 illustrates antitumor activity of Compound 1 in the C-Met amplified hepatocellular carcinoma patient-derived xenograft model, LI0612. Female SCID mice were inoculated with hepatocellular carcinoma PDX model LI0612 tumor fragments (2-4 mm in diameter) into the right flank. Mice were randomized into treatment groups (n=10/group) at the time of treatment initiation. Test article treatment started on Day 18 when the tumors were approximately 150 mm$^3$. Tumor growth progressed in the vehicle control and Compound 1 treatment groups over the dosing period. A change in the growth kinetics was noted with Compound 1 administration resulting in significant tumor growth inhibition (TGI) with 30 mg/kg treatment (p=0.038, compared to the vehicle control).

Female SCID mice were inoculated with hepatocellular carcinoma PDX model LI0612 tumor fragments (2-4 mm in diameter) into the right flank. The mice were randomized into treatment groups (n=10/group) at the time of treatment initiation. Test article treatment started on Day 18 when the tumors were approximately 150 mm³ in size. Tumor growth progressed in the vehicle control and Compound 1 treatment groups over the dosing period. A change in the growth kinetics was noted with Compound 1 administration resulting in significant tumor growth inhibition (TGI) with 30 mg/kg treatment (p=0.038, compared to the vehicle control). See FIG. 204.

Pharmacokinetic/Pharmacodynamic Data in a BRAF Mutant Patient-Derived Xenograft Model.

Based on the known kinases (ERK 1/2, NLK and SIK) that are inhibited by Compound 1, the impact of compound treatment was evaluated on MAPK, β-catenin and Hippo pathway biomarkers in PDX146 tumors from xenografted mice. Tumor-bearing mice (tumors were ~400 mm³) were treated with a single dose of 1 or 5 mg/kg Compound 1. Tumor tissue was collected at 1, 2, 4, 8, and 24 h post-dose.

Figure 199B:
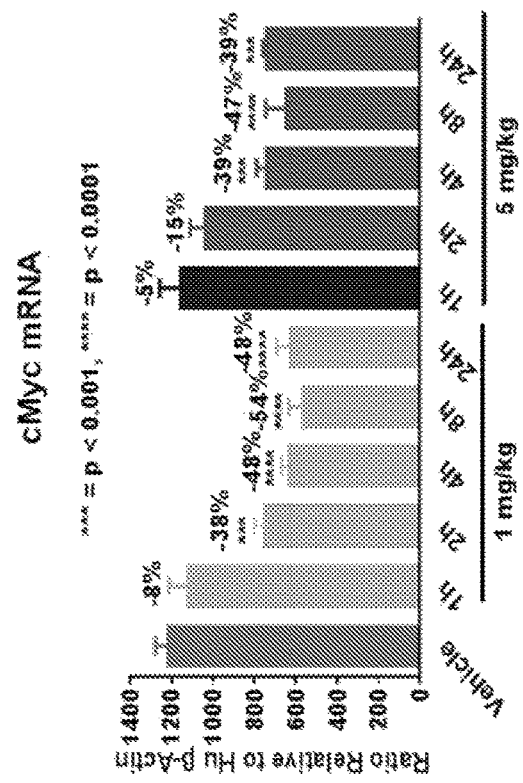
FIGS. 199A-199D illustrates Single doses of Compound 1 inhibit biomarkers in the MAPK, Wnt and Hippo signaling pathways in the PDX146 Xenograft Model: Modulation of MAPK, Wnt and Hippo pathways in PDX146 tumors treated with Compound 1. qRT-PCR assays were performed on RNA extracted from PDX146 tumors at the indicated time point post-dose. Data are expressed as mean±SEM. P values are derived from a one-way ANOVA with a Dunnet's post-hoc analysis.
Figure 199D:
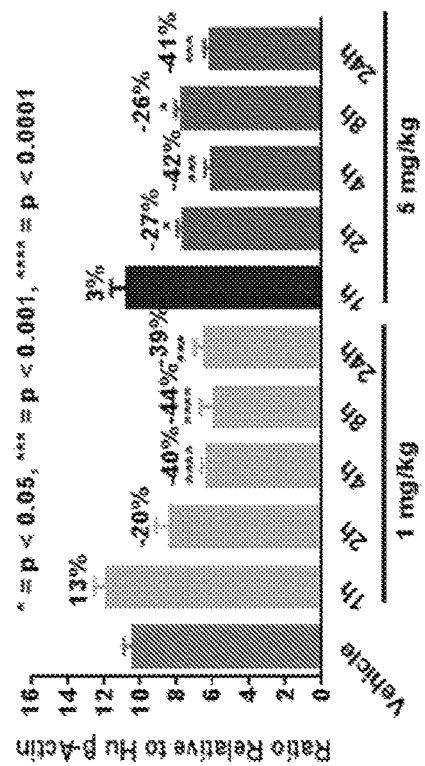
Figure 199A:
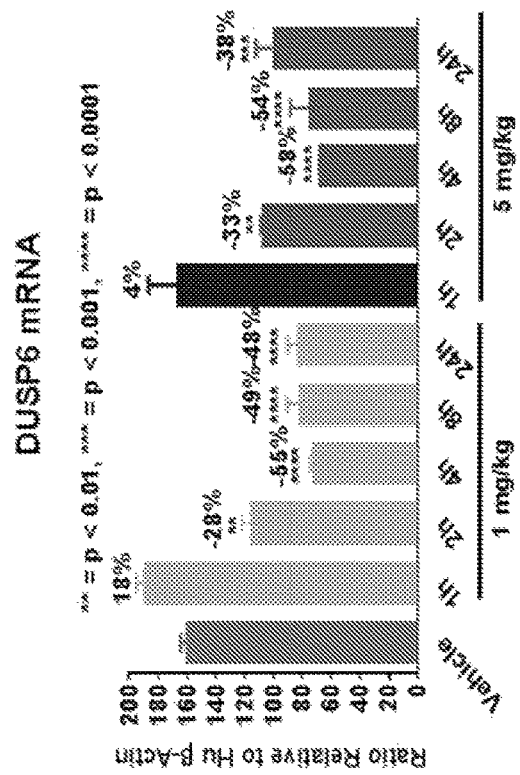
Figure 199C:
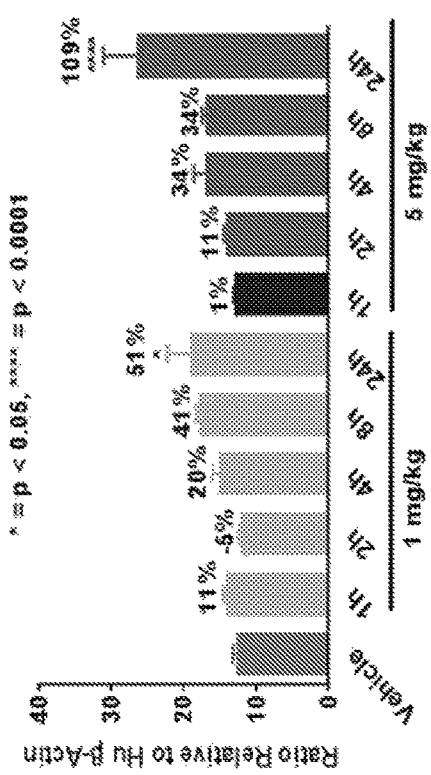
Figure 200A:
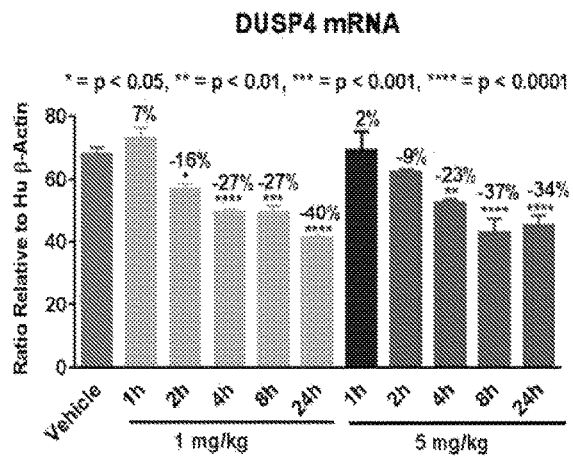
FIGS. 200A-200D illustrate Compound 1 inhibits biomarkers in the MAPK, Wnt and Hippo signalling pathways from PDX146 tumors following a single dose administration: Modulation of MAPK, Wnt and Hippo pathways in PDX146 tumors treated with Compound 1. qRT-PCR assays were performed on RNA extracted from PDX146 tumors at the indicated time point post-dose. YAP data is generated from western blot analysis of tumors from the 5 mg/kg treatment group and is expressed as a ratio of YAP to β-actin protein expression. Data are expressed as mean±SEM. P values are derived from a one-way ANOVA with a Dunnet's post-hoc analysis.
Figure 200B:
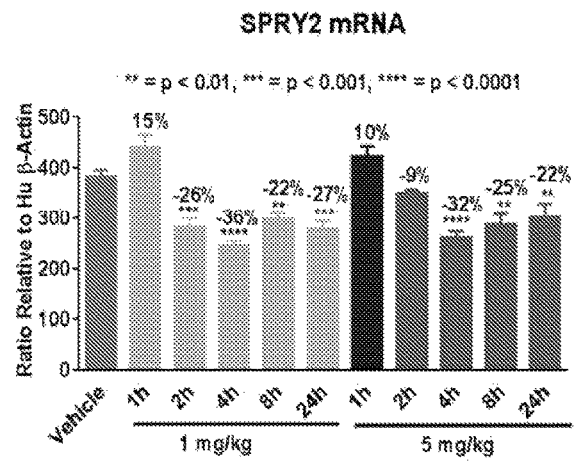
Figure 200C:
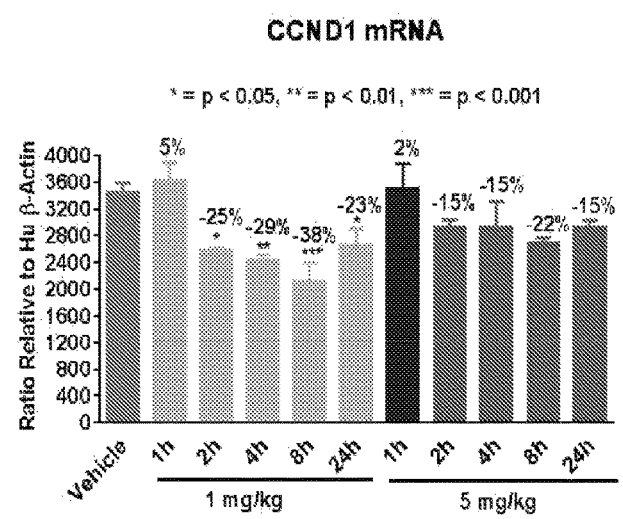
Figure 200D:
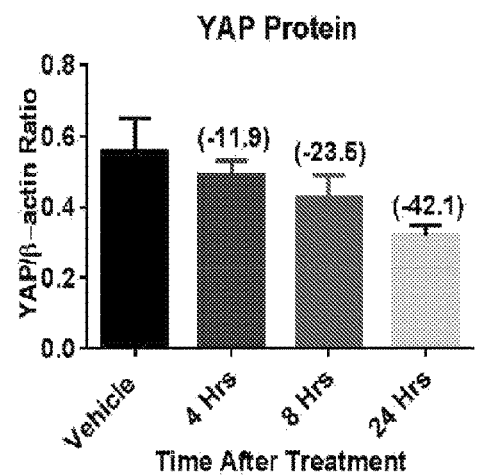
Figure 201A:
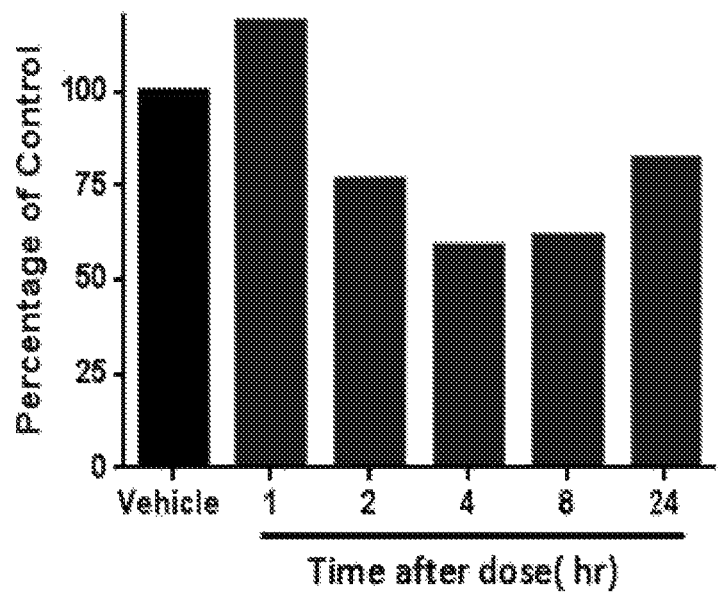
FIGS. 201A-201D illustrate phospho-RSK (pRSK) and phospho-ERK (pERK) protein levels, biomarkers of the MAPK signaling pathway, were modulated by a single dose administration of Compound 1. Western blot (pRSK) or Mesoscale (pERK) assays were performed on protein extracted from PDX146 tumors at the indicated time point post-dose. Phospho-RSK data is expressed as a % of the vehicle control. Phospho-ERK data is expressed as mean±SEM.
Figure 201B:
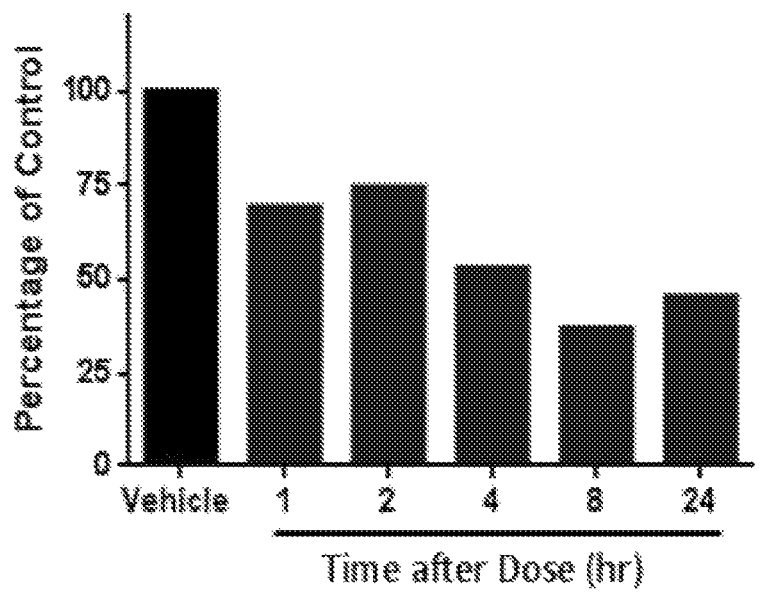
Figure 201C:
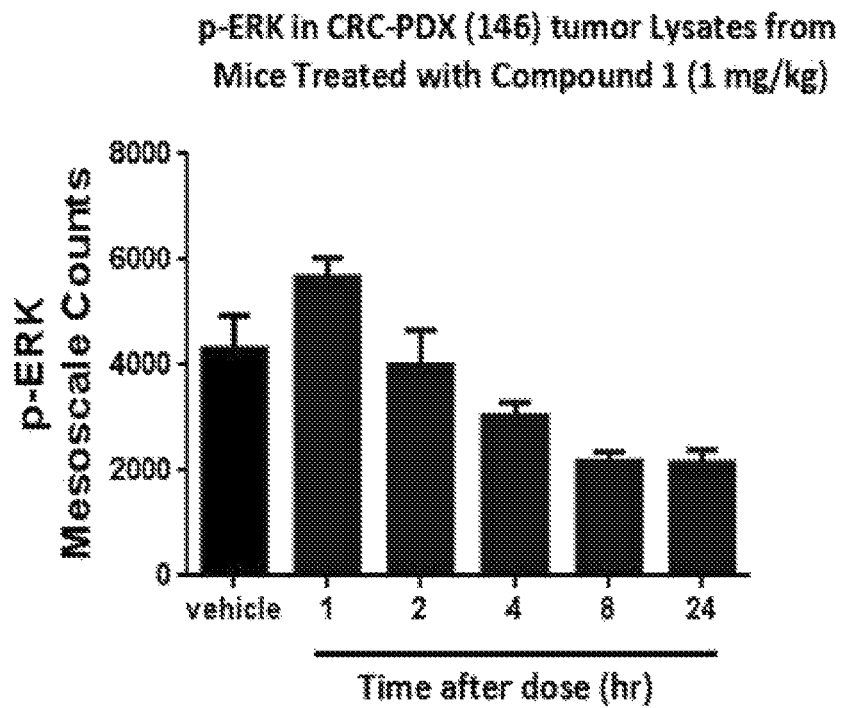
Figure 201D:
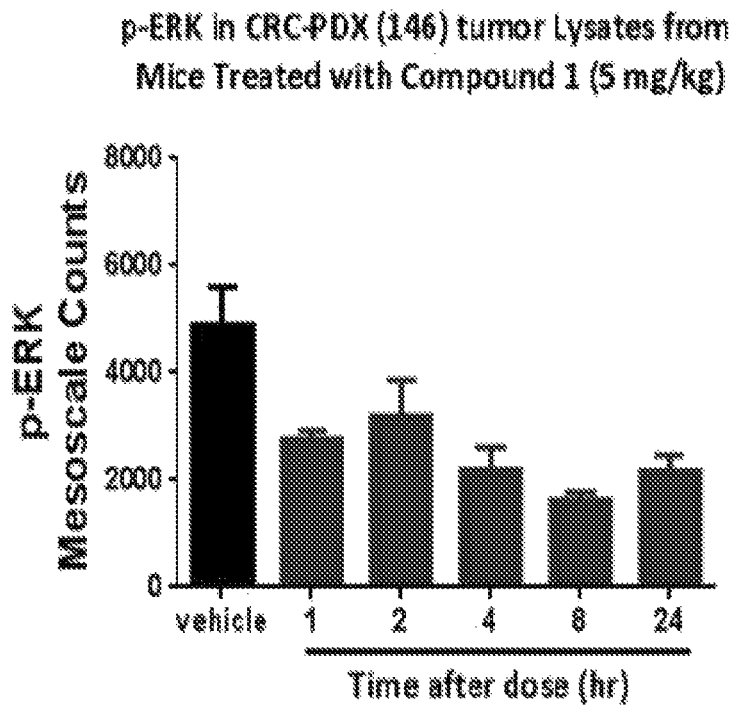

The modulation of the MAPK pathway was evaluated by examination of tumor DUSP4, DUSP6 and Sprouty (SPRY2) mRNA levels and pRSK and pERK protein levels. DUSP6 mRNA levels were significantly decreased with compound treatment starting 2 hr post-dose and remained suppressed through 24 h at both dose levels (FIG. 199A). A similar pattern was observed with DUSP4 and SPRY2 mRNA levels (FIGS. 200A-200B). Phospho-RSK (pRSK) and phospho-ERK (pERK) protein levels were modulated by Compound 1 treatment in a dose- and time-dependent manner (FIGS. 201A-201D). Levels of cMyc (FIG. 199B) and cyclin D1 (FIG. 200C), which are downstream of both the MAPK and Wnt signaling pathways, were inhibited with Compound 1 treatment. Compound 1 treatment upregulated the Wnt target gene, Axin2. Treatment with Compound 1 at both dose levels demonstrated a significant increase in Axin2 mRNA levels 24 h post-dose. Sustained inhibition of AREG (a downstream target gene in the Hippo pathway) mRNA levels was observed through 24 h. Additionally Compound 1 inhibited YAP protein levels in a time-dependent manner (not statistically significant (see FIG. 200D), which could be due to SIK inhibition and Hippo pathway regulation or an indirect effect as a result of MAPK inhibition.

These data suggest that Compound 1 impacts three different pathways, MAPK, Wnt and Hippo, in this BRAF mutant colorectal PDX model following a single dose administration.

Other Efficacy Model Data:

Compound 1 was profiled in additional xenograft models including β-catenin mutant (SW48, colorectal) and β-catenin activated models (orthotopic Hep3B, hepatocellular) and a c-met-amplified hepatocellular PDX model (LI0612). Significant antitumor activity was observed in all models.

Conclusion:

Significant dose-dependent antitumor activity was observed in all three BRAF mutant xenograft models (See FIGS. 202A-202B, FIG. 203, and FIG. 204). Tumor regression was observed with Compound 1 treatment across the models and there was a significant growth delay with long term treatment in the PDX146 model.

Patient Enrichment and Tumor Indications.

Based upon the in vitro and in vivo data of Compound 1, the patient enrichment hypotheses and tumor indications are outlined in Table 49 and Table 50.

TABLE 49

Patient enrichment biomarkers and tumor indications.

| Patient Enrichment Biomarkers | Tumor indications |
| --- | --- |
| BRAF mutant | CRC, Thyroid, Melanoma, Lung |
| NRAS mutant | Melanoma |
| KRAS mutant | Lung, CRC, Pancreas |
| CTNNB1 (β-catenin mutant and/or active) | CRC, Stomach, HCC, Sarcoma |

TABLE 50

| Molecular Alterations | Pathways | Clinical Indications |
| --- | --- | --- |
| CTNNB1 mutant, YAP amplification | Wnt/b-catenin//Hippo | HCC |
| BRAF mutant, CTNNB1 | MAPK//Wnt/b-catenin | CRC |
| CTNNB1 mutant | Wnt/b-catenin | Gastric |
| BRAF mutant, NRAS mutant | MAPK | Melanoma |

A number of references have been cited, the disclosures of which are incorporated herein by reference in their entirety.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A method for treating a cancer, comprising administering to a subject in need thereof an effective amount of a crystal form comprising Compound 1, or a tautomer thereof,

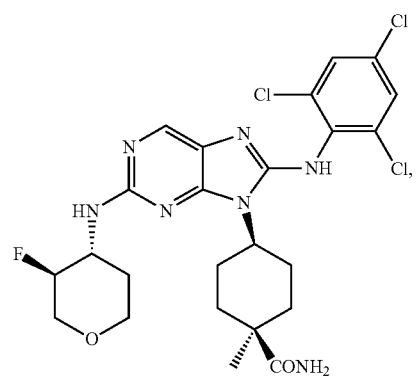

which has an X-ray powder diffraction pattern comprising peaks at
7.3, 8.5, 18.2, and 21.3° 2θ (±0.2° 2θ);
4.8, 9.6, 18.9, and 19.2° 2θ (±0.2° 2θ); or
9.0, 9.8, 9.9, and 16.7° 2θ (±0.2° 2θ);
wherein the cancer is a solid tumor or a hematological cancer.

2. The method of claim 1, wherein the solid tumor is melanoma, colorectal cancer, stomach cancer, head and neck cancer, thyroid cancer, bladder cancer, CNS cancer, lung cancer, pancreatic cancer, or soft tissue cancer.

3. The method of claim 1, wherein the cancer is bladder cancer, breast cancer, CNS cancer, colon cancer, gastrointestinal cancer, endocrine cancer, female genitoureal cancer, head and neck cancer, hematopoietic cancer, kidney cancer, liver cancer, lung cancer, melanoma, pancreas cancer, prostate cancer, or soft tissue cancer.

4. The method of claim 1, wherein the cancer is glioma, neuroblastoma, stomach cancer, thyroid cancer, adrenal gland cancer, cancer of the uterus, cervix, ovary clear cell, or vulva, leukemia, myeloma, NSCLC, SCLC, sarcoma or osteosarcoma.

5. The method of claim 1, wherein the cancer is hepatocellular carcinoma (HCC).

6. The method of claim 5, wherein the HCC is characterized by a beta-catenin mutation and/or increased YAP expression.

7. The method of claim 1, wherein the cancer is colorectal cancer (CRC), melanoma, gastric cancer, HCC, lung cancer, pancreatic cancer, leukemia, or multiple myeloma.

8. The method of claim 1, wherein the cancer is a cancer expressing PD-L1.

9. The method of claim 8, wherein the PD-L1 expressing cancer is melanoma, lung cancer, renal cell carcinoma (RCC), or HCC.

10. The method of claim 1, wherein the cancer is a cancer characterized by a BRAF mutation.

11. The method of claim 10, wherein the cancer characterized by a BRAF mutation is CRC, thyroid cancer, melanoma or lung cancer.

12. The method of claim 1, wherein the cancer is a cancer characterized by an NRAS mutation.

13. The method of claim 12, wherein the cancer characterized by an NRAS mutation is melanoma.

14. The method of claim 1, wherein the cancer is a cancer characterized by a KRAS mutation.

15. The method of claim 14, wherein the cancer characterized by a KRAS mutation is CRC, pancreas cancer or lung cancer.

16. The method of claim 1, wherein the cancer is a cancer characterized by a beta-catenin mutation.

17. The method of claim 16, wherein the beta-catenin mutation is one or more of beta-catenin S33Y, G34E, S45del, or S33C.

18. The method of claim 16, further comprising an EGFR mutation or increased EGFR activity.

19. The method of claim 16, further comprising a BRAF mutation.

20. The method of claim 16, wherein the cancer characterized by a beta-catenin mutation is CRC, stomach cancer, HCC or sarcoma.

21. The method of claim 1, wherein the cancer is a cancer characterized by an activated beta-catenin pathway.

22. The method of claim 21, wherein the cancer is CRC, stomach cancer, HCC or sarcoma.

23. The method of claim 1, wherein the cancer is gastric cancer.

24. The method of claim 23, wherein the gastric cancer is characterized by a beta-catenin mutation, or by an activated beta-catenin pathway.

25. The method of claim 1, wherein the cancer is melanoma.

26. The method of claim 25, wherein the melanoma is characterized by a BRAF mutation and/or NRAS mutation.

27. A method for modulating the levels of a biomarker in a subject having a cancer, comprising administering to said subject an effective amount of a crystal form comprising Compound 1, or a tautomer thereof:

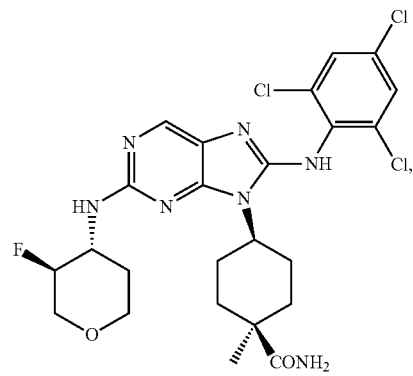

which has an X-ray powder diffraction pattern comprising peaks at
7.3, 8.5, 18.2, and 21.3° 2θ (±0.2° 2θ);
4.8, 9.6, 18.9, and 19.2° 2θ (±0.2° 2θ); or
9.0, 9.8, 9.9, and 16.7° 2θ (±0.2° 2θ).

28. The method of claim 27, wherein the biomarker is ERK, RSK1, DUSP4, DUSP5, DUSP6, BMF, EFNA1, EGR1, ETV5, FOS, FOSL1, GJA1, IL-8, cMyc, Cyclin D1, YAP, SPRY2, SPRY4, Axin2, CTGF, AREG, CYR61, CXCL1, HAS2, HES1, MAFF, CITED2, ELF3, or PD-L1.

29. The method of claim 27, wherein the modulation is measured by measurement of the reduction of phosphorylation levels of one or more of ERK and RSK1.

30. The method of claim 1, wherein the crystal form of Compound 1 is administered as a pharmaceutical composition comprising at least one pharmaceutically acceptable excipient.

* * * * *